US012698329B2

(12) United States Patent
Van Hoorick et al.

(10) Patent No.: US 12,698,329 B2
(45) Date of Patent: Aug. 4, 2026

(54) T CELL RECRUITING POLYPEPTIDES CAPABLE OF BINDING CD123 AND TCR α/β

(71) Applicant: Ablynx N.V., Zwijnaarde (BE)

(72) Inventors: Diane Van Hoorick, Zwijnaarde (BE); Annelies Roobrouck, Zwijnaarde (BE); Catelijne Stortelers, Ghent (BE); João Vieira, Didcot (GB); Edward McGowan, Royston (GB)

(73) Assignee: Ablynx NV, Zwijnaarde (BE)

( * ) Notice: Subject to any disclaimer, the term of this patent is extended or adjusted under 35 U.S.C. 154(b) by 0 days.

(21) Appl. No.: 18/486,205

(22) Filed: Oct. 13, 2023

(65) Prior Publication Data

US 2024/0199740 A1 Jun. 20, 2024

Related U.S. Application Data

(62) Division of application No. 16/348,544, filed as application No. PCT/EP2017/079507 on Nov. 16, 2017, now Pat. No. 11,840,569.

(60) Provisional application No. 62/422,770, filed on Nov. 16, 2016, provisional application No. 62/557,208, filed on Sep. 12, 2017.

(51) Int. Cl.
| | |
|---|---|
| *C07K 16/28* | (2006.01) |
| *A61K 39/00* | (2006.01) |
| *A61K 45/06* | (2006.01) |
| *C07K 16/46* | (2006.01) |

(52) U.S. Cl.
CPC ...... *C07K 16/2809* (2013.01); *A61K 39/0011* (2013.01); *A61K 39/001119* (2018.08); *C07K 16/2866* (2013.01); *C07K 16/468* (2013.01); *A61K 2039/5158* (2013.01); *A61K 45/06* (2013.01); *C07K 2317/22* (2013.01); *C07K 2317/24* (2013.01); *C07K 2317/31* (2013.01); *C07K 2317/565* (2013.01); *C07K 2317/569* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 9,193,780 B2 * | 11/2015 | Hultberg | ............ C07K 16/1027 |
| 10,927,186 B2 | 2/2021 | Roobrouck et al. | |
| 11,840,569 B2 * | 12/2023 | Van Hoorick | .......... A61P 25/00 |
| 2020/0157216 A1 | 5/2020 | Van Hoorick et al. | |

FOREIGN PATENT DOCUMENTS

| | | |
|---|---|---|
| KR | 10-1308771 B1 | 9/2013 |
| RU | 2556125 C2 | 7/2015 |
| WO | WO 2006/122786 A2 | 11/2006 |
| WO | WO 2009/100309 A2 | 8/2009 |
| WO | WO 2012/066058 A1 | 5/2012 |
| WO | WO 2013/173820 A2 | 11/2013 |
| WO | WO 2015/044386 A1 | 4/2015 |
| WO | WO 2016/028896 A1 | 2/2016 |
| WO | WO 2016/116626 A1 | 7/2016 |
| WO | WO 2016/180969 A1 | 11/2016 |

OTHER PUBLICATIONS

Rudikoff et al., Proc Natl Acad Sci USA 79: 1979 (Year: 1982).*
Piatesi et al., ChemBioChem 5: 460-466 (Year: 2004).*
Chen et al., J. Mol. Bio. 293: 865-881 (Year: 1999).*
Piche-Nicholas et al., MABS 10(1): 81-94 (Year: 2018).*
De Genst et al., Developmental and Comparative Immunology 30: 187-198 (Year: 2006).*
Tereshko et al., Protein Science. 17:1175-1187 (Year: 2008).*
Deschacht et al., The Journal of Immunology 184:5696-5704 (Year: 2010).*
Sircar et al., The Journal of Immunology 186:6357-6367 (Year: 2011).*
Diamond et al., Somatic mutation of the T15 heavy chain gives rise to an antibody with autoantibody specificity. Proc Natl Acad Sci U S A. Sep. 1984;81(18):5841-4. doi: 10.1073/pnas.81.18.5841.
Edwards et al., The remarkable flexibility of the human antibody repertoire; isolation of over one thousand different antibodies to a single protein, BLyS. J Mol Biol. Nov. 14, 2003;334(1):103-18. doi: 10.1016/j.jmb.2003.09.054.
Foote et al., Antibody framework residues affecting the conformation of the hypervariable loops. J Mol Biol. Mar. 20, 1992;224(2):487-99. doi: 10.1016/0022-2836(92)91010-m.
Kuo et al., Engineering a CD123xCD3 bispecific scFv immunofusion for the treatment of leukemia and elimination of leukemia stem cells. Prot Eng. Oct. 1, 2012; 25(10): 561-569.
Labrijn et al., Bispecific antibodies: a mechanistic review of the pipeline. Nat Rev Drug Discov. Aug. 2019;18(8):585-608. doi: 10.1038/s41573-019-0028-1.
Lloyd et al., Modelling the human immune response: performance of a 1011 human antibody repertoire against a broad panel of therapeutically relevant antigens. Protein Eng Des Sel. Mar. 2009;22(3):159-68. doi: 10.1093/protein/gzn058. Epub Oct. 29, 2008.
Ohno et al., Antigen-binding specificities of antibodies are primarily determined by seven residues of VH. Proc Natl Acad Sci U S A. May 1985;82(9):2945-9. doi: 10.1073/pnas.82.9.2945.
Padlan et al., Structure of an antibody-antigen complex: crystal structure of the HyHEL-10 Fab-lysozyme complex. Proc Natl Acad Sci U S A. Aug. 1989;86(15):5938-42. doi: 10.1073/pnas.86.15.5938.

(Continued)

*Primary Examiner* — Phuong Huynh
(74) *Attorney, Agent, or Firm* — Wolf, Greenfield & Sacks, P.C.

(57) ABSTRACT

Polypeptides are provided that bind CD123 on a target cell and the constant domain of TCR on a T cell. The polypeptides can be used in methods for treatment of CD123 associated cancers or inflammatory conditions.

19 Claims, 58 Drawing Sheets

Specification includes a Sequence Listing.

(56) References Cited

OTHER PUBLICATIONS

Piche-Nicholas et al., Changes in complementarity-determining regions significantly alter IgG binding to the neonatal Fc receptor (FcRn) and pharmacokinetics. MAbs. Jan. 2018;10(1):81-94. doi: 10.1080/19420862.2017.1389355. Epub Nov. 3, 2017.

Rudikoff et al., Single amino acid substitution altering antigen-binding specificity. Proc Natl Acad Sci U S A. Mar. 1982;79(6):1979-83.

Winter et al., Humanized Antibodies. Immunol Today. 1993;14(3):243-246.

PCT/EP2017/079507, Mar. 22, 2018, International Search Report and Written Opinion.

PCT/EP2017/079507, Mar. 31, 2019, International Preliminary Report on Patentability.

* cited by examiner

A.

B.

*Figure 3 cont':*
C.
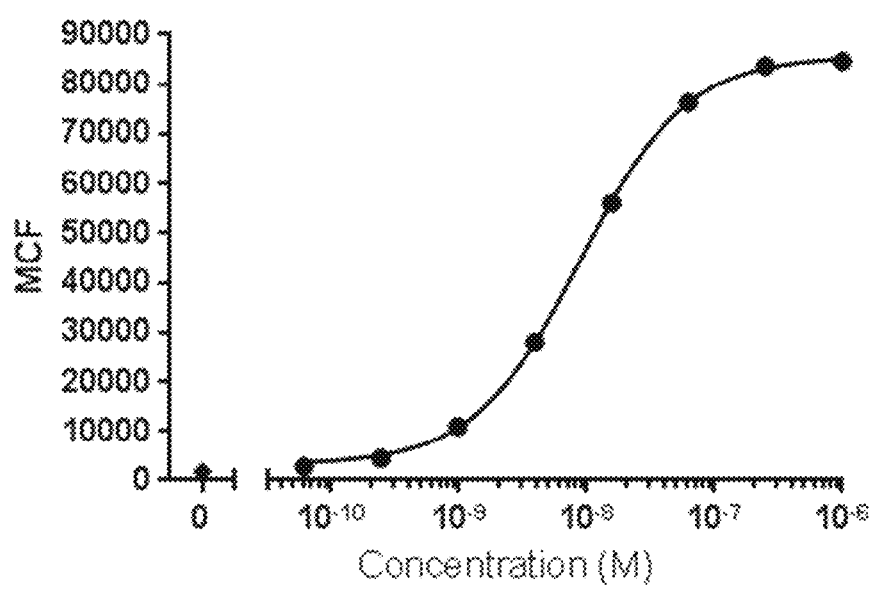
D.
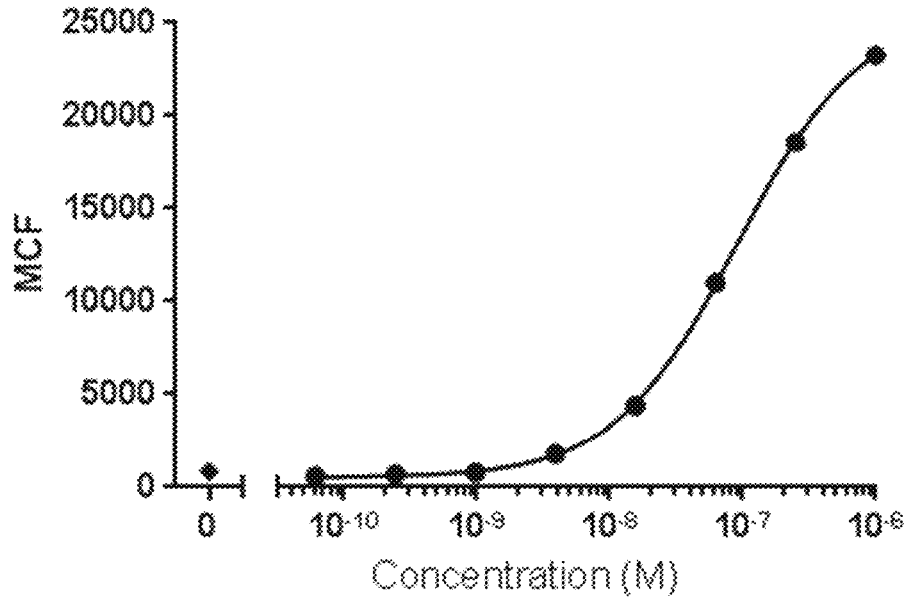

A.

T0170055A02

B.

T0170056G05

A.

B.

A.

T0170055A02

B.

T0170056G05

A.

B.

A.

B.

*Figure 12 cont':*
C.
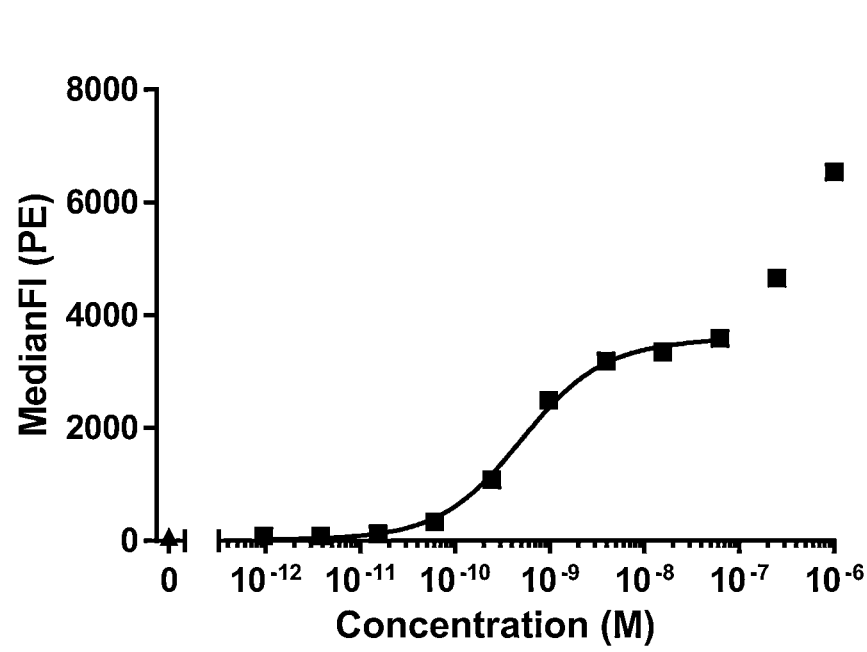
D.
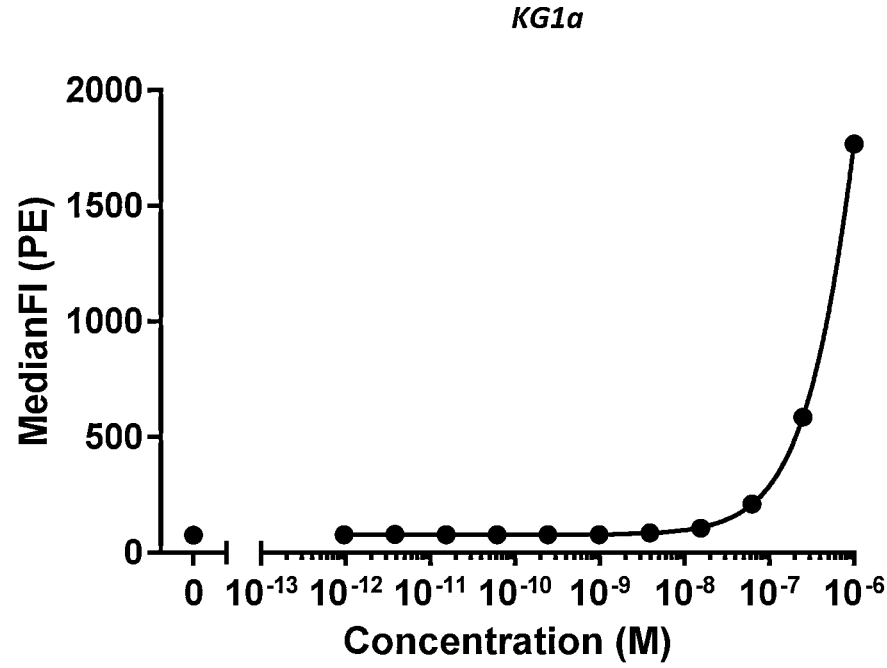

A.

Human CD123 CHO
Flp-In (closed symbol)

CHO Flp-In (open
symbol)

B.

Cynomolgus CD123 HEK Flp-In
(closed symbol)

HEK Flp-In (open symbol)

A.

Human CD123 CHO Flp-In (closed symbol)

CHO Flp-In (open symbol)

B.

Cynomolgus CD123 HEK Flp-In (closed symbol)

HEK Flp-In (open symbol)

A.

B.

A.

MOLM-13

B.

CHO Flp-In human CD123

A.

B.

A.

B.

A.

B.

A.

B.

*Figure 21 cont':*
C.
HEK Flp-In cynomolgus CD123
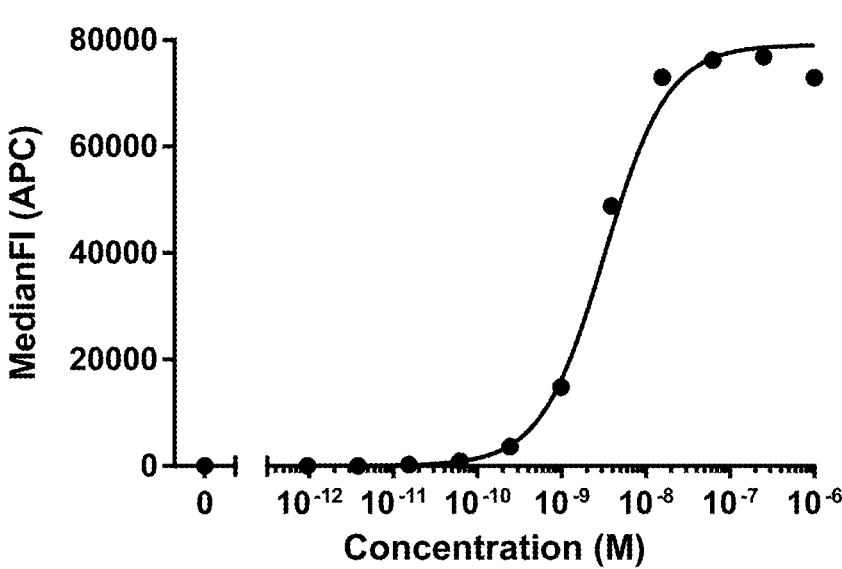
*Figure 22:*
A.
MOLM-13
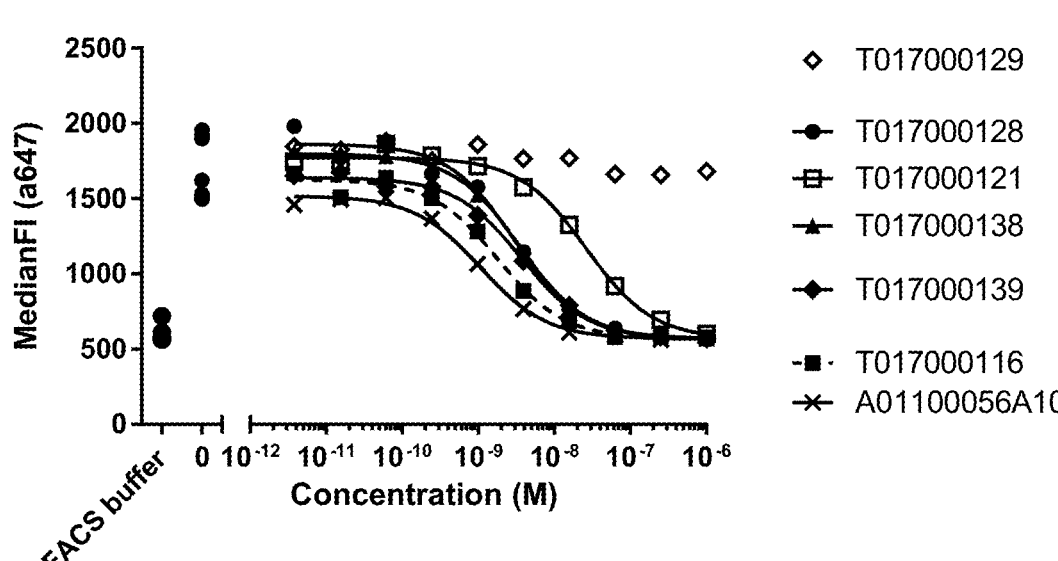

*Figure 22 cont':*
B.
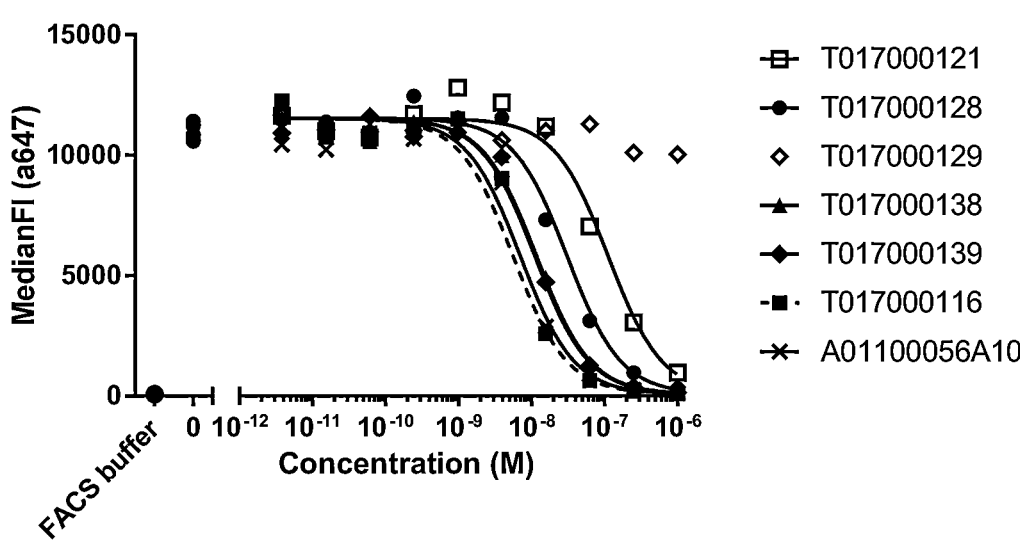
C.
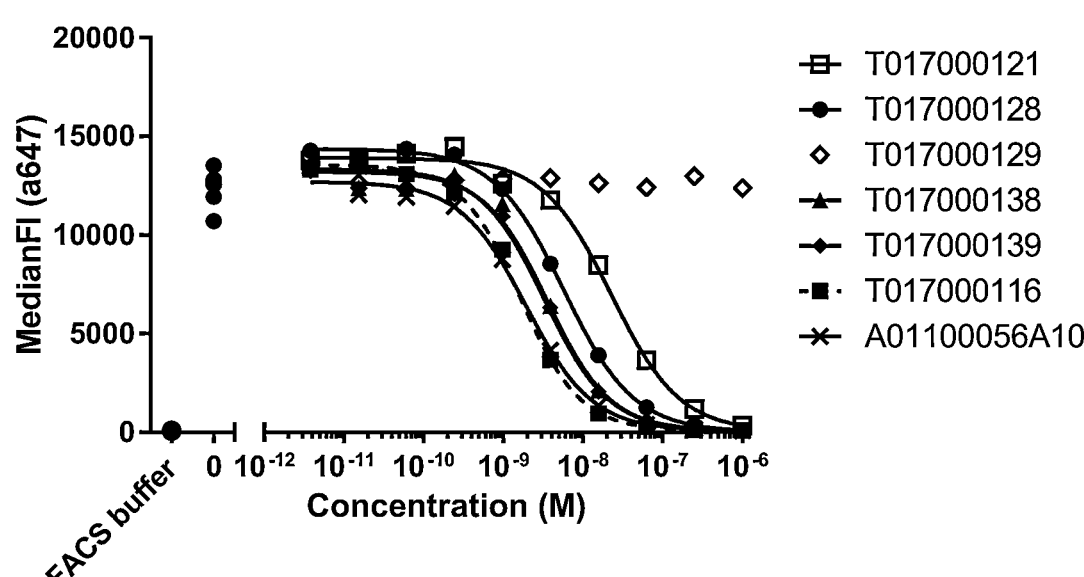

A.

CHO Flp-In human CD123

*Figure 32 cont':*
B.
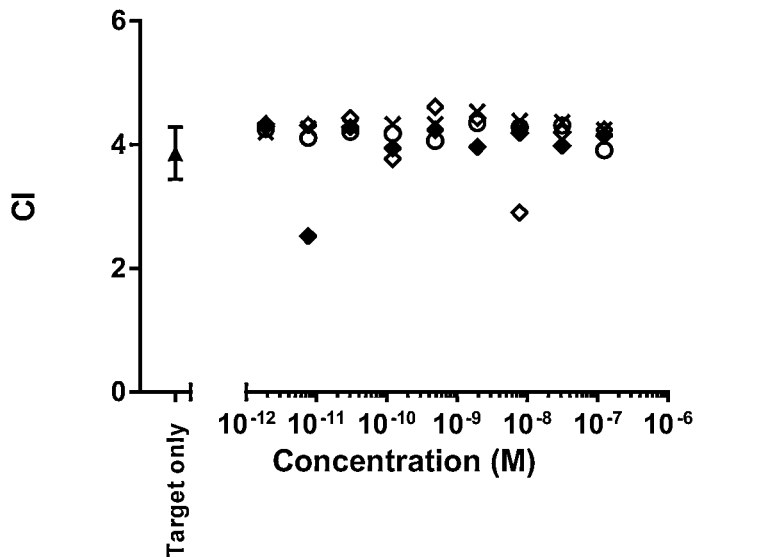
*Figure 33:*
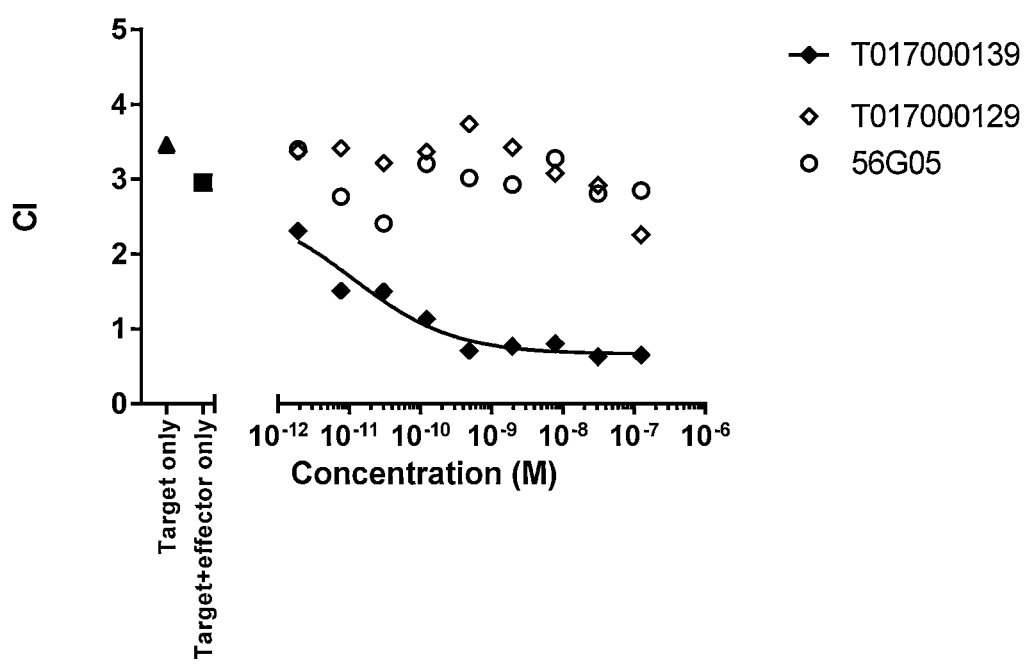

A.

HEK Flp-In cynomolgus CD123

*Figure 35 cont':*
B.
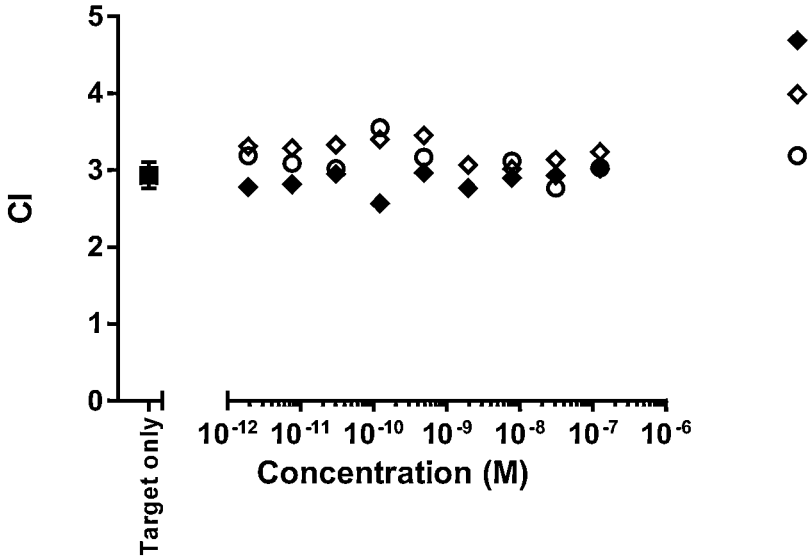
*Figure 36:*
A.
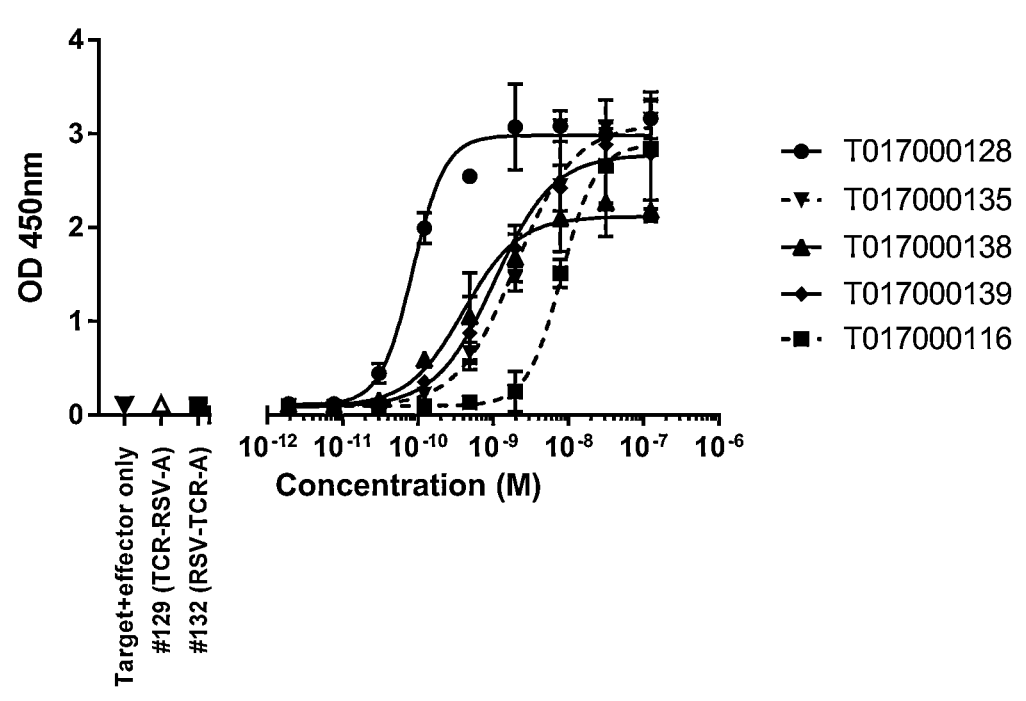

*Figure 36 cont':*
B.
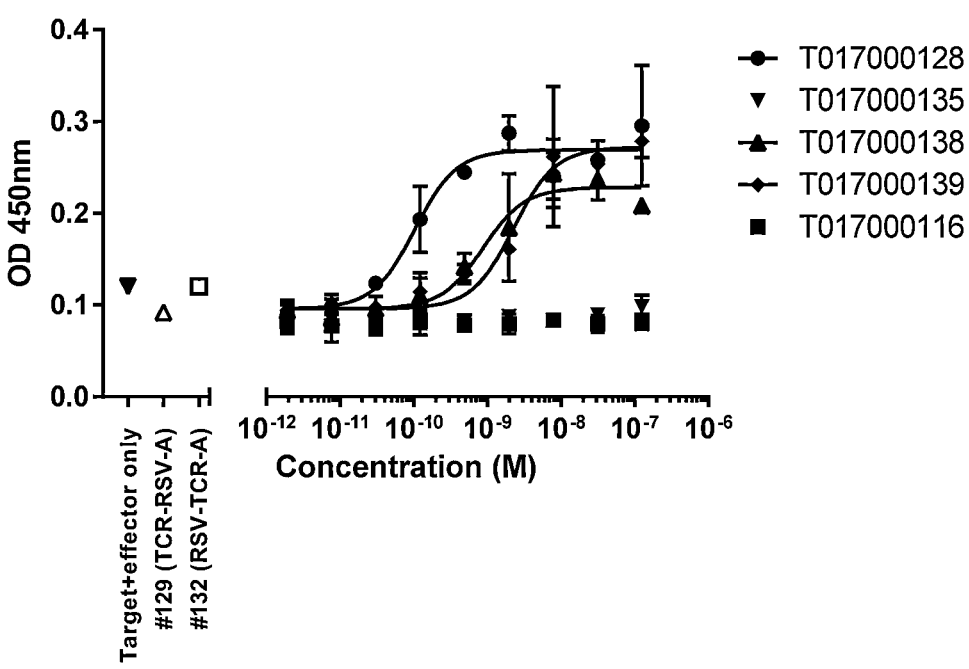
*Figure 37:*
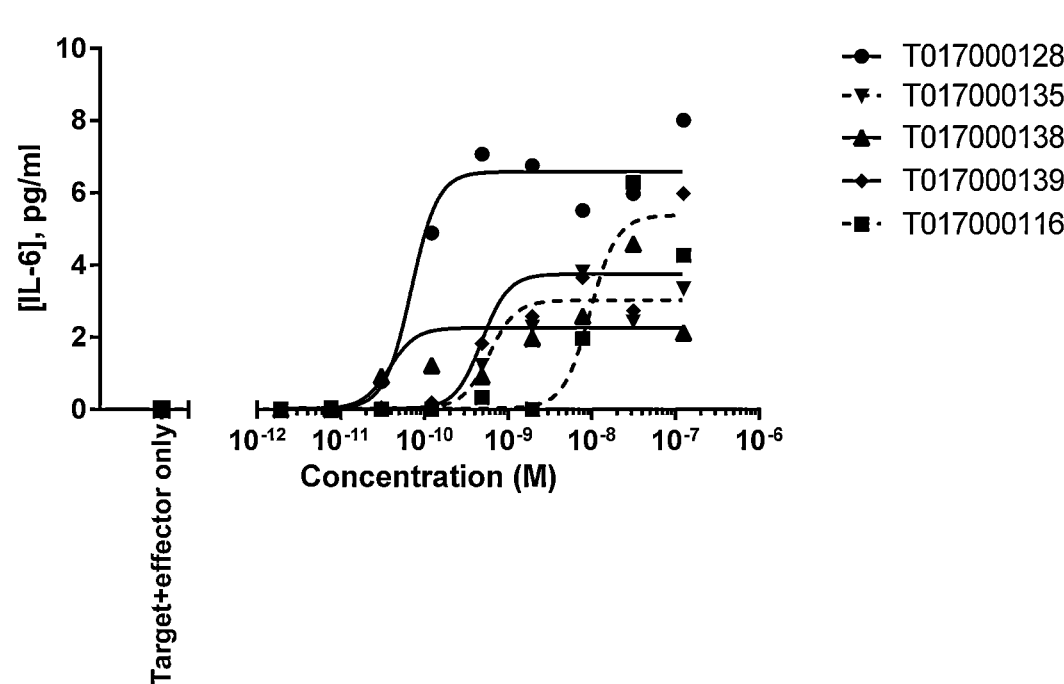

A.

B.

A.

B.

A.

B.

A.

B.

*Figure 42 cont':*
C.
Cynomolgus T cell redirected killing
Experiment 2
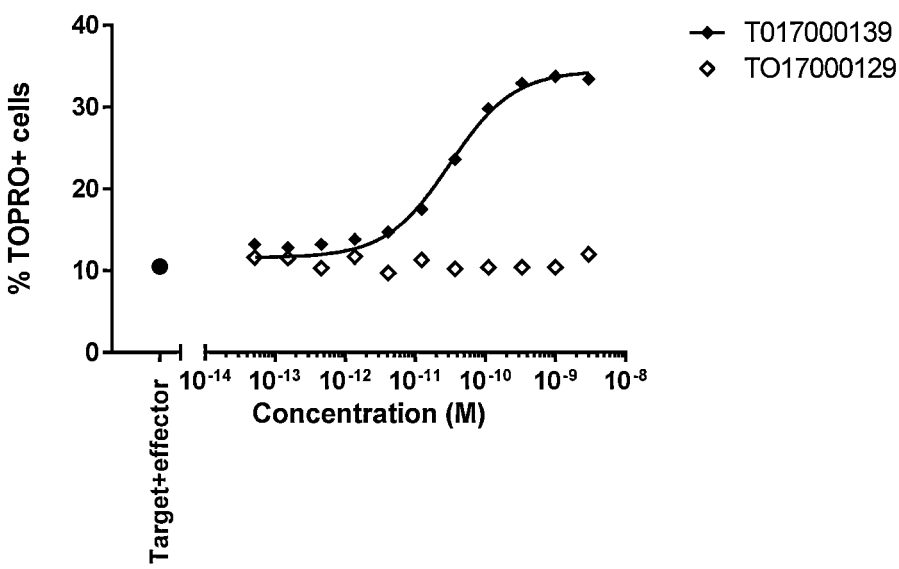
*Figure 43:*
A.
MOLM-13 (IFN-γ production)
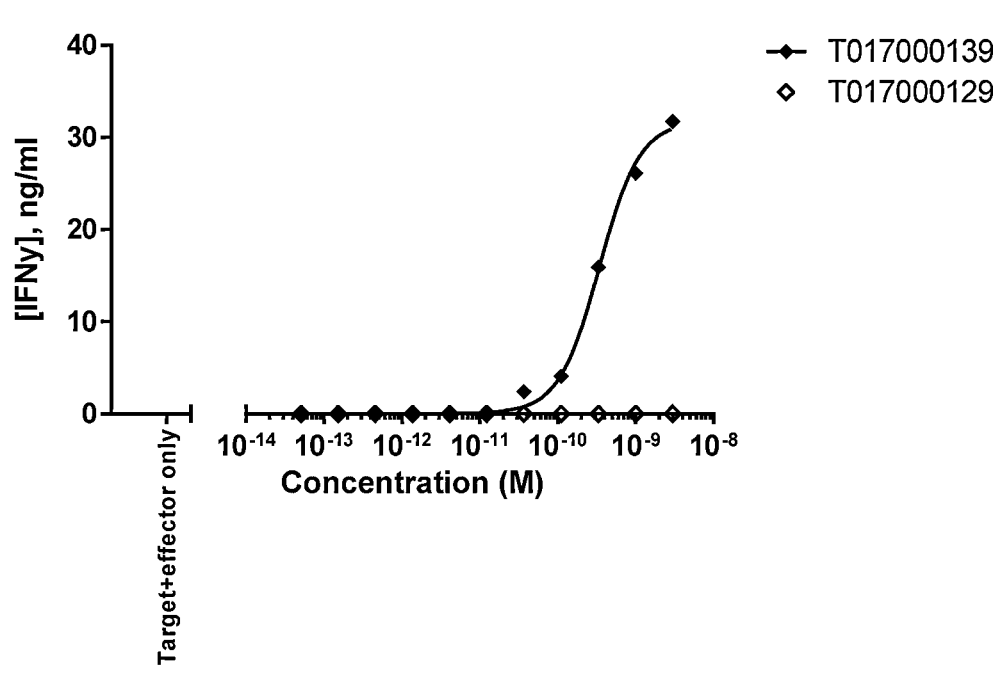

*Figure 43 cont':*
*B.*
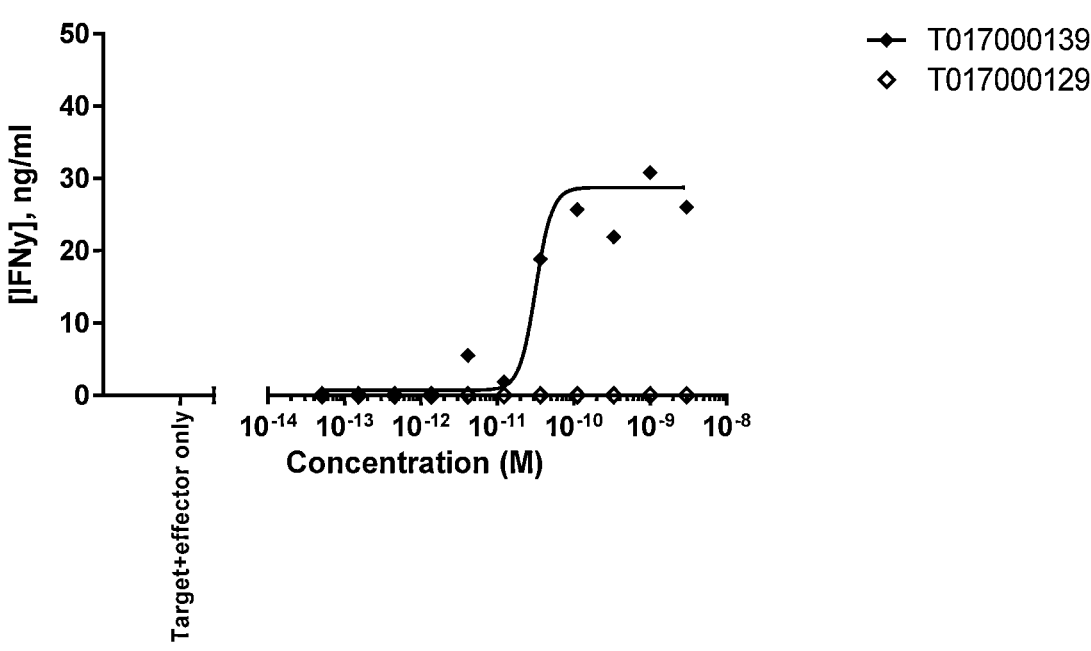
*C.*
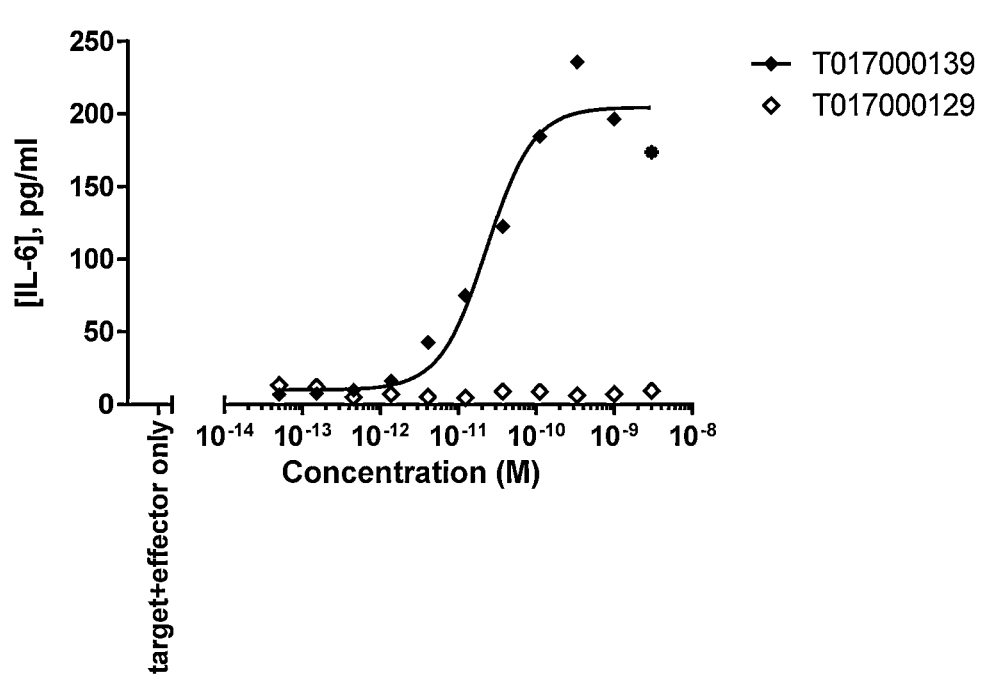

A.

▲   T017000138
◆   T017000139
●   T017000128

◆   T017000129
✕   A0110056A10
○   T0170056G05 (TCR)

B.

◆   T017000139
▲   T017000144

□   T017000129

A.

Human T cells

▲   T017000138

◆   T017000139

●   T017000128

■   T017000116

◇   T017000129

✖   A0110056A10

◯   T0170056G05

B.

Cynomolgus T cells

◆   T017000139

◇   T017000129

✖   T0170056G05

◯   A0110056A10

✚   A0110055F03

A.

B.

A.

B.

A.

B.

A.

B.

*Figure 52 cont':*
C.
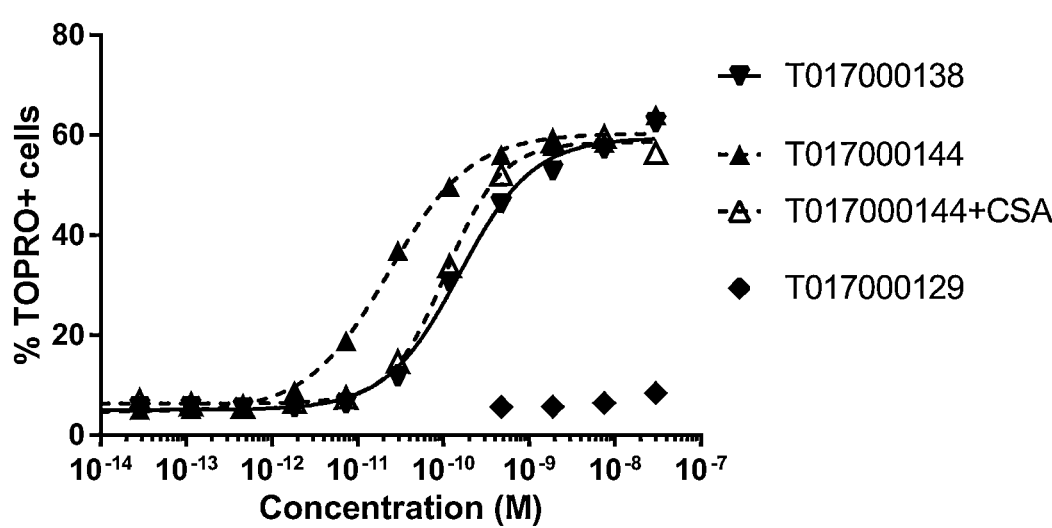
D.
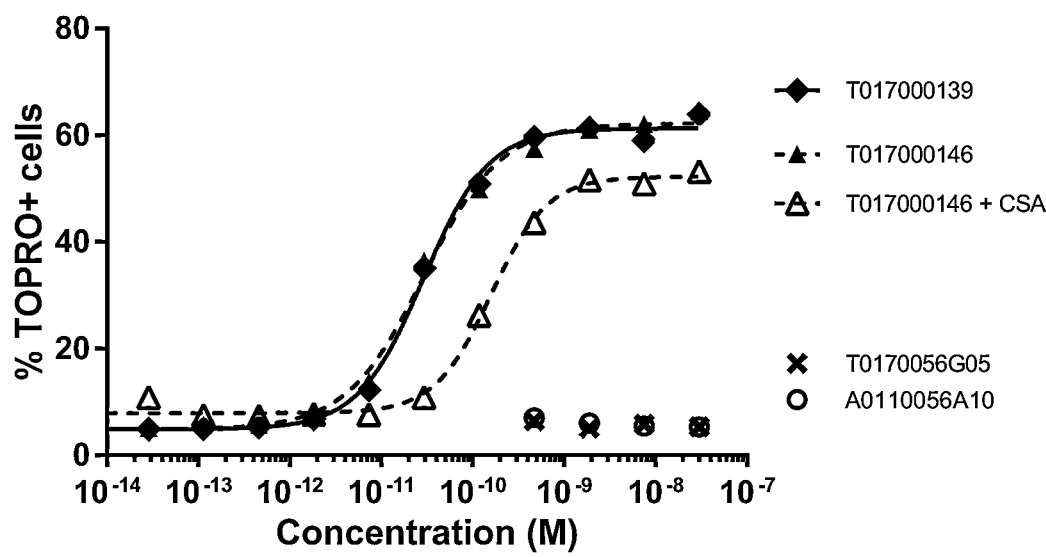

A.

B.

*Figure 53 cont':*
C.
Human T cell mediated killing
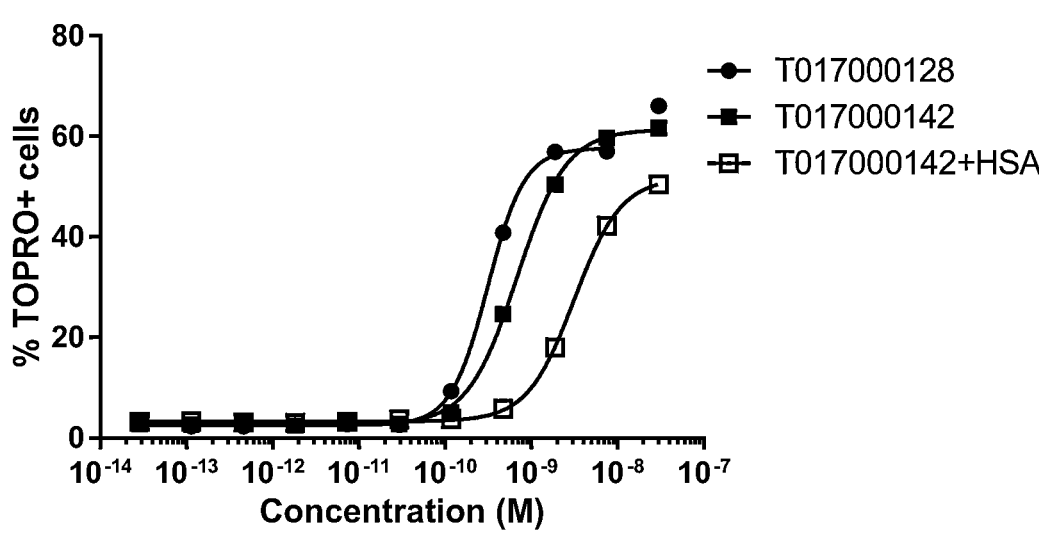
D.
Cynomolgus mediated killing
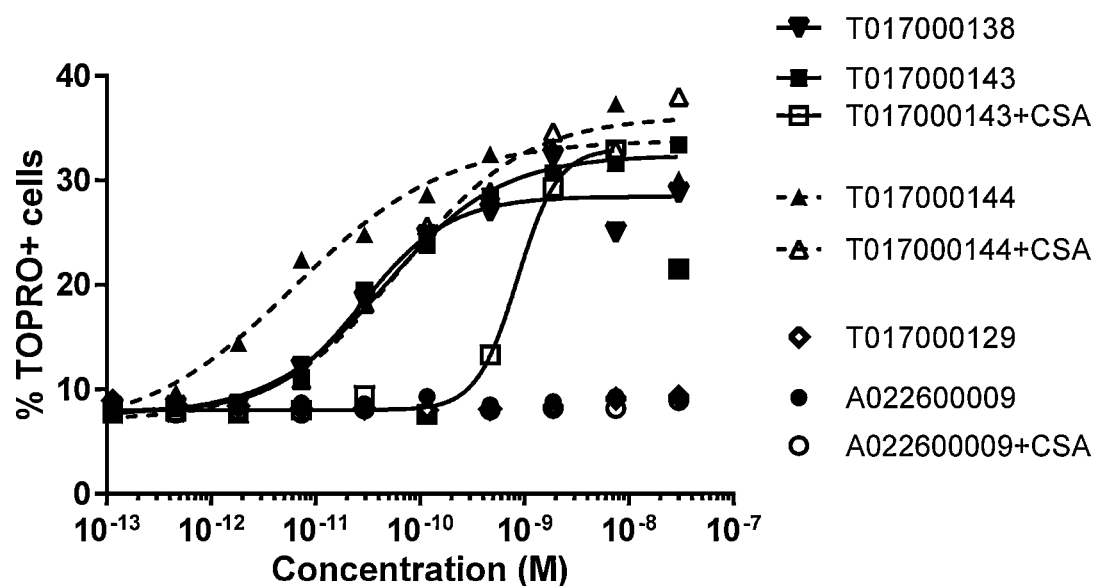

*Figure 53 cont':*
E.
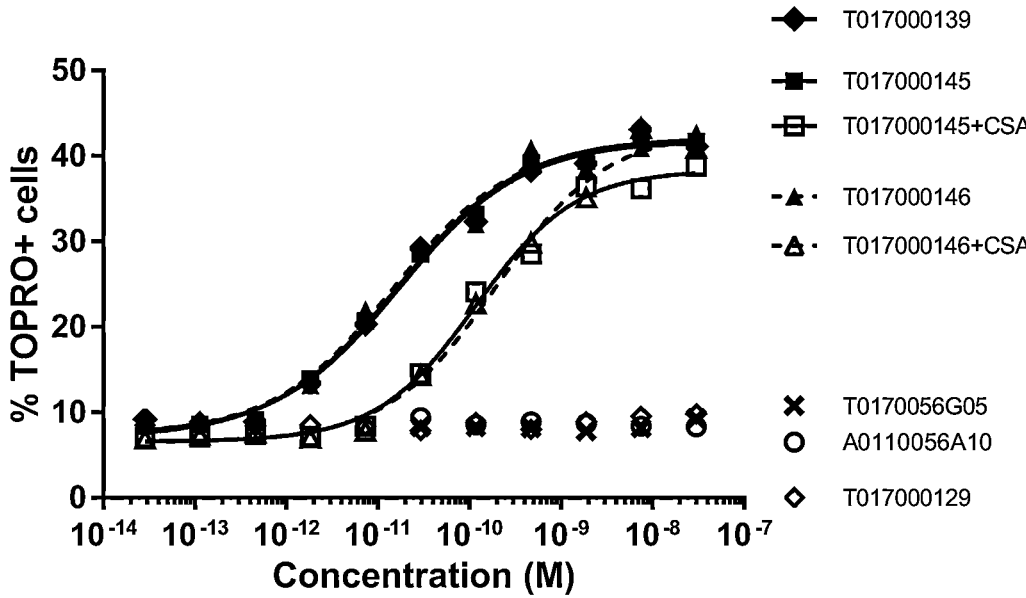
F.
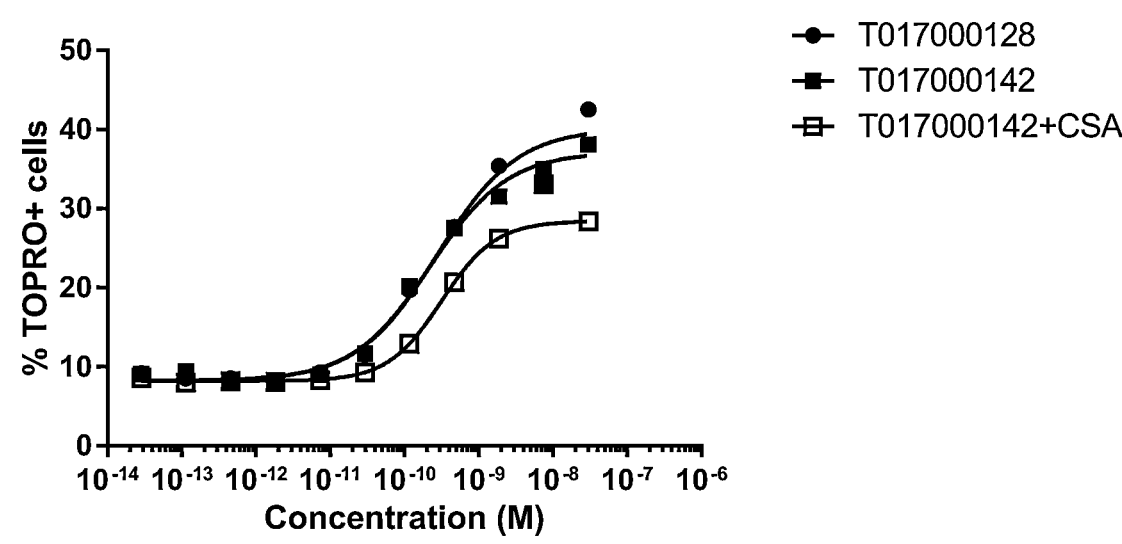

A.

B.

T CELL RECRUITING POLYPEPTIDES CAPABLE OF BINDING CD123 AND TCR α/β

RELATED APPLICATIONS

This application is a divisional of U.S. Ser. No. 16/348,544, now U.S. Pat. No. 11,840,569, filed on May 9, 2019, which is a national stage filing under 35 U.S.C. § 371 of International Patent Application PCT/EP2017/079507, filed Nov. 16, 2017, which claims priority under 35 U.S.C. § 119 (e) to U.S. Provisional Application Ser. No. 62/422,770, filed on Nov. 16, 2016 and U.S. Provisional Application Ser. No. 62/557,208, filed on Sep. 12, 2017, the contents of which are incorporated herein in their entirety.

REFERENCE TO AN ELECTRONIC SEQUENCE LISTING

The contents of the electronic sequence listing (A084870199US03-SEQ-CRP.xml; Size: 508,739 bytes; and Date of Creation: Oct. 12, 2023) is herein incorporated by reference in its entirety.

FIELD OF THE INVENTION

The present invention provides multispecific T cell recruiting polypeptides comprising one immunoglobulin single variable domain that specifically binds the constant domain of the T cell receptor (TCR) on a T cell and one or more immunoglobulin single variable domains that bind CD123 expressed on a target cell. The present invention also relates to the monovalent CD123 binding polypeptides for use in these multispecific polypeptides. The invention also provides nucleic acids encoding said polypeptides as well as vectors, hosts and methods for the production of the polypeptides of the invention. The invention also relates to methods for treatment making use of the polypeptides of the invention and kits providing the same.

BACKGROUND

CD123 (α subunit of the interleukin 3 receptor, IL-3Rα) is a 75 kDa glycoprotein, which becomes 43 kDa upon digestion with N-glycosidase (Sato et al. 1993, Blood 82: 752-761). CD123 consists of three extracellular domains, a transmembrane domain and a short intracellular region. The N-terminal extracellular domain contributes significantly to the interaction of CD123 with IL-3, while the intracellular region is necessary for signalling (Barry et al. 1997, Blood 89: 842-852). CD123 specifically binds IL3 with low affinity. Heterodimerisation of CD123 with the common β (βc) subunit, which on itself does not bind to IL-3, results in formation of IL-3R, a high-affinity receptor for IL-3. The βc subunit plays a significant role in signal transduction and as such triggers a range of biological functions. (Hara et al, 1996 Stem cells 14: 605-618)

While the βc subunit is expressed on the surface of various cells, CD123 expression is more restricted to IL-3 responsive cells, such as hematopoietic stem/progenitor cells, monocytes, megakaryocytes, B-lymphocytes and plasmacytoid dendritic cells. Binding of IL3 stimulates the proliferation and differentiation of hematopoietic cells. During maturation of these cells, CD123 expression gradually decreases and cannot be detected in mature lymphocytes and granulocytes.

CD123 is reported to be highly expressed on leukemia stem cells (LSC) and to be associated with the initiation and development of many diseases, such as acute myeloid leukemia (AML), acute lymphoblastic leukemia (ALL) and hairy cell leukemia (HCL). Reference is made to the review of Liu et al. (2015 Life Sciences 122: 59-64) for more details on CD123 and related clinal applications in leukemias. Given the difference in CD123 expression on normal hematopoietic stem cells and LSCs, CD123 is an interesting therapeutic target in hematological cancers.

AML is a clonal malignant disorder derived from a small population of LSC cells with overexpression of CD123. AML is characterised by proliferation of myeloid progenitor cells in the bone marrow and peripheral blood and results in the destruction of normal hematopoiesis. Although therapeutic regimens and supportive care for AML patients have improved over the years, no major changes occurred in the standard treatment options in the last three decades. Reference is made to Medinger et al. (2016 Leukemia Research Reports 6: 39-49) for an overview of novel approaches and therapeutic options in AML. Currently, only 35-40% of patients younger than 60 years cure from the disease. For elderly patients (>60 years), the overall prognosis remains adverse. Allogeneic hematopoietic stem cell transplantation currently provides the best chance for cure. Hence, there remains a need for novel therapeutics to cure AML.

A possible strategy for prevention of AML and treatment of relapse is the use of immunotherapy, which is a rapidly growing area of cancer research. Immunotherapy directs the body's immune surveillance system, and in particular T cells, to cancer cells.

Cytotoxic T cells (CTL) are T lymphocytes that kill cancer cells, cells that are infected (particularly with viruses), or cells that are damaged in other ways. T lymphocytes (or T cells) express the T cell receptor or TCR molecule and the CD3 receptor on the cell surface. The αβ TCR-CD3 complex (or "TCR complex") is composed of six different type I single-spanning transmembrane proteins: the TCRα and TCRβ chains that form the TCR heterodimer responsible for ligand recognition, and the non-covalently associated CD3γ, CD3δ, CD3ε and ζ chains, which bear cytoplasmic sequence motifs that are phosphorylated upon receptor activation and recruit a large number of signaling components (Call et al. 2004, Molecular Immunology 40: 1295-1305).

Both α and β chains of the T cell receptor consist of a constant domain and a variable domain. Physiologically, the αβ chains of the T cell receptor recognize the peptide loaded MHC complex and couple upon engagement to the CD3 chains. These CD3 chains subsequently transduce the engagement signal to the intracellular environment.

Considering the potential of naturally occurring cytotoxic T lymphocytes (CTLs) to mediate cell lysis, various strategies have been explored to recruit immune cells to mediate tumour cell killing. The elicitation of specific T cell responses however relies on the expression by cancer cells of MHC molecules and on the presence, generation, transport and display of specific peptide antigens. More recent developments have attempted an alternative approach by combining the advantages of immunotherapy with antibody therapy by engaging all T cells of a patient in a polyclonal fashion via recombinant antibody based technologies: "bispecifics".

Bispecific antibodies have been engineered that have a tumour recognition part on one arm (target-binding arm) whereas the other arm of the molecule has specificity for a T cell antigen (effector-binding arm), mostly CD3. Through the simultaneous binding of the two arms to their respective antigens, T lymphocytes are directed towards and activated at the tumour cell where they can exert their cytolytic function.

The concept of using bispecific antibodies to activate T cells against tumour cells was described more than 20 years ago, but manufacturing problems and clinical failures sent the field into stagnation. Further progress was made when smaller format bispecifics, resulting from the reduction of antibodies to their variable fragments, were developed.

Although a first T cell engaging format, Blinatumomab (a BiTE molecule recognizing CD19 and CD3), was approved in December 2014 for second line treatment by the FDA, many hurdles had to be overcome. The first clinical trials of Blinatumomab were prematurely stopped due to neurologic adverse events, cytokine release syndrome and infections on the one hand and the absence of objective clinical responses or robust signs of biological activity on the other hand.

As a treatment option for AML, MacroGenics recently developed MGD006, a CD3×CD123 bispecific DART (dual affinity retargeting molecules). As described in Hussaini et al. (2016 Blood 127: 122-131), MGD006 is able to recognize CD123 positive leukemia cells and to induce T cell activation resulting in killing of the CD123 overexpressing tumour cells in vitro and in vivo. However, the DART also upregulates the T cell activation marker CD25 on T cells upon incubation with the CD123 negative cell line K562$^{GFP}$ (FIG. 1D, Hussaini et al. 2016). Moreover, target independent killing was observed with two CD123 negative cell lines (FIG. 2B, Hussaini et al. 2016). Therefore, with this DART, safety issues may arise from this target independent T cell activation.

In order to minimise the risk for adverse events and systemic side effects, such as cytokine storms, utmost care must be taken upon selection of both the tumour and the T cell antigen arms. The latter must bind to a constant domain of the TCR complex in a monovalent fashion and may not trigger T cell signaling in the absence of the targeted cancer cells. Only the specific binding of both arms to their targets (the tumour and the T cell antigen) may trigger the formation of the cytolytic synapses and subsequent killing of the tumour cells. The specificity of the tumour recognition arm for its antigen is a requisite to avoid off-target binding, which would inevitably result in target-independent T cell activation.

Efficacy aside, MGD006, as well as blinatumomab, are very small in size and lack an Fc domain. Therefore, continuous intravenous infusion will be required for MGD006, which will not contribute to patient compliance. MacroGenics now attempts to solve this problem by fusing an Fc domain onto its next generation DARTs (WO2015026892), which makes the molecule not only bigger, but also may result in manufacturing problems and importation of other Fc functions. The larger format with Fc is expected to have a better PK, but re-introduces the risk of off-target activity.

Hence, there remains a need for alternative bispecific CD123×T cell antigen binding polypeptides with minimal target-independent T cell activation, wherein half-life can be tailored.

SUMMARY OF THE INVENTION

The invention solves this problem by providing multispecific polypeptides comprising one immunoglobulin single variable domain (ISV) that specifically binds to a constant domain of the T cell receptor (TCR) and one or more ISV that specifically bind CD123. In a particular aspect, the polypeptide redirects the T cells to the CD123 expressing cells and induces T cell mediated killing.

The combination of a T cell receptor binding ISV and CD123 binding ISV have been particularly selected to result in efficient T cell activation at (the site of) CD123 expressing cells, while target-independent T cell activation appears minimal.

Thus, in a first aspect the present invention provides a polypeptide that redirects T cells for killing of CD123 expressing cells, comprising one immunoglobulin single variable domain (ISV) that specifically binds T cell receptor (TCR) and one or more ISV that specifically bind CD123, wherein the ISV that specifically binds TCR (essentially) consists of 4 framework regions (FR1 to FR4, respectively) and 3 complementarity determining regions (CDR1 to CDR3, respectively), in which:

i) CDR1 is chosen from the group consisting of:
   a) SEQ ID NOs: 181-191; or
   b) amino acid sequences that have 4, 3, 2 or 1 amino acid(s) difference with the amino acid sequence of one of SEQ ID NOs: 181-191; provided that the ISV comprising the CDR1 with 4, 3, 2 or 1 amino acid(s) difference binds TCR with the same, about the same or a higher affinity compared to the binding by the ISV comprising the CDR1 without the 4, 3, 2 or 1 amino acid(s) difference, said affinity as measured by surface plasmon resonance;

and/or ii) CDR2 is chosen from the group consisting of:
   c) SEQ ID NOs: 192-217; or
   d) amino acid sequences that have 4, 3, 2 or 1 amino acid(s) difference with the amino acid sequence of one of SEQ ID NOs: 192-217; provided that the ISV comprising the CDR2 with 4, 3, 2 or 1 amino acid(s) difference binds TCR with the same, about the same or a higher affinity compared to the binding by the ISV comprising the CDR2 without the 4, 3, 2 or 1 amino acid(s) difference, said affinity as measured by surface plasmon resonance;

and/or iii) CDR3 is chosen from the group consisting of:
   e) SEQ ID NOs: 218-225; or
   f) amino acid sequences that have 4, 3, 2 or 1 amino acid(s) difference with the amino acid sequence of one of SEQ ID NOs: 218-225; provided that the ISV comprising the CDR3 with 4, 3, 2 or 1 amino acid(s) difference binds TCR with the same, about the same or a higher affinity compared to the binding by the ISV comprising the CDR3 without the 4, 3, 2 or 1 amino acid(s) difference, said affinity as measured by surface plasmon resonance;

and wherein the one or more ISV that specifically bind CD123 (essentially) consists of 4 framework regions (FR1 to FR4, respectively) and 3 complementarity determining regions (CDR1 to CDR3, respectively), in which:

i) CDR1 is chosen from the group consisting of:
   a) SEQ ID NOs: 11-16; or
   b) amino acid sequences that have 4, 3, 2 or 1 amino acid(s) difference with the amino acid sequence of one of SEQ ID NOs: 11-16; provided that the ISV comprising the CDR1 with 4, 3, 2 or 1 amino acid(s) difference binds CD123 with the same, about the same or a higher affinity compared to the binding by the ISV comprising the CDR1 without the 4, 3, 2 or 1 amino acid(s) difference, said affinity as measured by surface plasmon resonance;

and/or ii) CDR2 is chosen from the group consisting of:

c) SEQ ID NOs: 17-20; or d) amino acid sequences that have 4, 3, 2 or 1 amino acid(s) difference with the amino acid sequence of one of SEQ ID NOs: 17-20; provided that the ISV comprising the CDR2 with 4, 3, 2 or 1 amino acid(s) difference binds CD123 with the same, about the same or a higher affinity compared to the binding by the ISV comprising the CDR2 without the 4, 3, 2 or 1 amino acid(s) difference, said affinity as measured by surface plasmon resonance;

and/or iii) CDR3 is chosen from the group consisting of:

e) SEQ ID NOs: 21-25; or f) amino acid sequences that have 4, 3, 2 or 1 amino acid(s) difference with the amino acid sequence of one of SEQ ID NOs: 21-25; provided that the ISV comprising the CDR3 with 4, 3, 2 or 1 amino acid(s) difference binds CD123 with the same, about the same or a higher affinity compared to the binding by the ISV comprising the CDR3 without the 4, 3, 2 or 1 amino acid(s) difference, said affinity as measured by surface plasmon resonance.

In a further aspect, the present invention provides a polypeptide as described herein, wherein the ISV that specifically binds TCR (essentially) consists of 4 framework regions (FR1 to FR4, respectively) and 3 complementarity determining regions (CDR1 to CDR3, respectively), in which:

i) CDR1 is chosen from the group consisting of:

a) SEQ ID NOs: 181-191; or b) amino acid sequences that have 4, 3, 2 or 1 amino acid(s) difference with the amino acid sequence of one of SEQ ID NOs: 181-191; provided that the ISV comprising the CDR1 with 4, 3, 2 or 1 amino acid(s) difference binds TCR with the same, about the same or a higher affinity compared to the binding by the ISV comprising the CDR1 without the 4, 3, 2 or 1 amino acid(s) difference, said affinity as measured by surface plasmon resonance; and ii) CDR2 is chosen from the group consisting of:

c) SEQ ID NOs: 192-217; or d) amino acid sequences that have 4, 3, 2 or 1 amino acid(s) difference with the amino acid sequence of one of SEQ ID NOs: 192-217; provided that the ISV comprising the CDR2 with 4, 3, 2 or 1 amino acid(s) difference binds TCR with the same, about the same or a higher affinity compared to the binding by the ISV comprising the CDR2 without the 4, 3, 2 or 1 amino acid(s) difference, said affinity as measured by surface plasmon resonance; and iii) CDR3 is chosen from the group consisting of:

e) SEQ ID NOs: 218-225; or f) amino acid sequences that have 4, 3, 2 or 1 amino acid(s) difference with the amino acid sequence of one of SEQ ID NOs: 218-225; provided that the ISV comprising the CDR3 with 4, 3, 2 or 1 amino acid(s) difference binds TCR with the same, about the same or a higher affinity compared to the binding by the ISV comprising the CDR3 without the 4, 3, 2 or 1 amino acid(s) difference, said affinity as measured by surface plasmon resonance;

and wherein the one or more ISV that specifically bind CD123 (essentially) consists of 4 framework regions (FR1 to FR4, respectively) and 3 complementarity determining regions (CDR1 to CDR3, respectively), in which:

i) CDR1 is chosen from the group consisting of:

a) SEQ ID NOs: 11-16; or b) amino acid sequences that have 4, 3, 2 or 1 amino acid(s) difference with the amino acid sequence of one of SEQ ID NOs: 11-16; provided that the ISV comprising the CDR1 with 4, 3, 2 or 1 amino acid(s) difference binds CD123 with the same, about the same or a higher affinity compared to the binding by the ISV comprising the CDR1 without the 4, 3, 2 or 1 amino acid(s) difference, said affinity as measured by surface plasmon resonance; and ii) CDR2 is chosen from the group consisting of:

c) SEQ ID NOs: 17-20; or d) amino acid sequences that have 4, 3, 2 or 1 amino acid(s) difference with the amino acid sequence of one of SEQ ID NOs: 17-20; provided that the ISV comprising the CDR2 with 4, 3, 2 or 1 amino acid(s) difference binds CD123 with the same, about the same or a higher affinity compared to the binding by the ISV comprising the CDR2 without the 4, 3, 2 or 1 amino acid(s) difference, said affinity as measured by surface plasmon resonance; and iii) CDR3 is chosen from the group consisting of:

e) SEQ ID NOs: 21-25; or f) amino acid sequences that have 4, 3, 2 or 1 amino acid(s) difference with the amino acid sequence of one of SEQ ID NOs: 21-25; provided that the ISV comprising the CDR3 with 4, 3, 2 or 1 amino acid(s) difference binds CD123 with the same, about the same or a higher affinity compared to the binding by the ISV comprising the CDR3 without the 4, 3, 2 or 1 amino acid(s) difference, said affinity as measured by surface plasmon resonance.

In a further aspect, the present invention provides a polypeptide as described herein, wherein the ISV that specifically binds TCR (essentially) consists of 4 framework regions (FR1 to FR4, respectively) and 3 complementarity determining regions (CDR1 to CDR3, respectively), in which:

i) CDR1 is chosen from the group consisting of:

a) SEQ ID NOs: 181-191; or b) amino acid sequences that have 4, 3, 2 or 1 amino acid(s) difference with the amino acid sequence of one of SEQ ID NOs: 181-191, wherein the 4, 3, 2 or 1 amino acid(s) difference are present at position 2, 4, 5, 6, 8 and/or 10 of the CDR1 (position 27, 29, 30, 31, 33 and/or 35 according to Kabat numbering); provided that the ISV comprising the CDR1 with 4, 3, 2 or 1 amino acid(s) difference binds TCR with the same, about the same or a higher affinity compared to the binding by the ISV comprising the CDR1 without the 4, 3, 2 or 1 amino acid(s) difference, said affinity as measured by surface plasmon resonance; and ii) CDR2 is chosen from the group consisting of:

c) SEQ ID NOs: 192-217; or d) amino acid sequences that have 4, 3, 2 or 1 amino acid(s) difference with the amino acid sequence of one of SEQ ID NOs: 192-217, wherein the 4, 3, 2 or 1 amino acid(s) difference are present at position 1, 3, 5, 7, 8 and/or 9 of the CDR2 (position 50, 52, 54, 56, 57 and/or 58 according to Kabat numbering); provided that the ISV comprising the CDR2 with 4, 3, 2 or 1 amino acid(s) difference binds TCR with the same, about the same or a higher affinity compared to the binding by the ISV comprising the CDR2 without the 4, 3, 2 or 1 amino acid(s) difference, said affinity as measured by surface plasmon resonance; and iii) CDR3 is chosen from the group consisting of:

e) SEQ ID NOs: 218-225; or f) amino acid sequences that have 4, 3, 2 or 1 amino acid(s) difference with the amino acid sequence of one of SEQ ID NOs: 218-225, wherein the 4, 3, 2 or 1 amino acid(s) difference are present at position 1, 4, 5 and/or 8 of the CDR3 (position 95, 98, 99 and/or 101 according to Kabat numbering); provided that the ISV comprising the CDR3 with 4, 3, 2 or 1 amino acid(s) difference binds TCR with the same, about the same or a higher affinity compared to the binding by the ISV comprising the CDR3 without the 4, 3, 2 or 1 amino acid(s) difference, said affinity as measured by surface plasmon resonance;

and wherein the ISV that specifically binds CD123 is as further described herein.

In one aspect, the CDR1 encompassed in the ISV that specifically binds TCR may be chosen from the group consisting of:

a) SEQ ID NO: 181; or b) amino acid sequences that have 4, 3, 2 or 1 amino acid(s) difference with the amino acid sequence of SEQ ID NO: 181, wherein at position 2 the D has been changed into A, S, E or G;

at position 4 the H has been changed into Y;

at position 5 the K has been changed into L;

at position 6 the I has been changed into L;

at position 8 the F has been changed into I or V; and/or at position 10 the G has been changed into S;

provided that the ISV comprising the CDR1 with 4, 3, 2 or 1 amino acid(s) difference binds TCR with the same, about the same or a higher affinity compared to the binding by the ISV comprising the CDR1 without the 4, 3, 2 or 1 amino acid(s) difference, said affinity as measured by surface plasmon resonance.

Apart from this or in addition, CDR2 encompassed in the ISV that specifically binds TCR may be chosen from the group consisting of:

a) SEQ ID NO: 192; or b) amino acid sequences that have 4, 3, 2 or 1 amino acid(s) difference with the amino acid sequence of SEQ ID NO: 192, wherein at position 1 the H has been changed into T or R;

at position 3 the S has been changed into T or A;

at position 5 the G has been changed into S or A;

at position 7 the Q has been changed into D, E, T, A or V;

at position 8 the T has been changed into A or V; and/or at position 9 the D has been changed into A, Q, N, V or S;

provided that the ISV comprising the CDR2 with 4, 3, 2 or 1 amino acid(s) difference binds TCR with the same, about the same or a higher affinity compared to the binding by the ISV comprising the CDR2 without the 4, 3, 2 or 1 amino acid(s) difference, said affinity as measured by surface plasmon resonance.

Apart from this or in addition, the CDR3 encompassed in the ISV that specifically binds TCR may be chosen from the group consisting of:

a) SEQ ID NO:218; or b) amino acid sequences that have 4, 3, 2 or 1 amino acid(s) difference with the amino acid sequence of SEQ ID NO: 218, wherein at position 1 the F has been changed into Y, L or G;

at position 4 the I has been changed into L;

at position 5 the Y has been changed into W; and/or at position 8 the D has been changed into N or S;

provided that the ISV comprising the CDR3 with 4, 3, 2 or 1 amino acid(s) difference binds TCR with the same, about the same or a higher affinity compared to the binding by the ISV comprising the CDR3 without the 4, 3, 2 or 1 amino acid(s) difference, said affinity as measured by surface plasmon resonance.

Accordingly, the present invention provides a polypeptide as described herein, wherein the ISV that specifically binds TCR (essentially) consists of 4 framework regions (FR1 to FR4, respectively) and 3 complementarity determining regions (CDR1 to CDR3, respectively), in which:

i) CDR1 is chosen from the group consisting of:

a) SEQ ID NO: 181; or b) amino acid sequences that have 4, 3, 2 or 1 amino acid(s) difference with the amino acid sequence of SEQ ID NO: 181, wherein at position 2 the D has been changed into A, S, E or G;

at position 4 the H has been changed into Y;

at position 5 the K has been changed into L;

at position 6 the I has been changed into L;

at position 8 the F has been changed into I or V; and/or at position 10 the G has been changed into S;

provided that the polypeptide comprising the CDR1 with 4, 3, 2 or 1 amino acid(s) difference binds TCR with the same, about the same or a higher affinity compared to the binding by the polypeptide comprising the CDR1 without the 4, 3, 2 or 1 amino acid(s) difference, said affinity as measured by surface plasmon resonance; and ii) CDR2 is chosen from the group consisting of:

c) SEQ ID NOs: 192; or d) amino acid sequences that have 4, 3, 2 or 1 amino acid(s) difference with the amino acid sequence of SEQ ID NO: 192, wherein at position 1 the H has been changed into T or R;

at position 3 the S has been changed into T or A;

at position 5 the G has been changed into S or A;

at position 7 the Q has been changed into D, E, T, A or V;

at position 8 the T has been changed into A or V; and/or at position 9 the D has been changed into A, Q, N, V or S;

provided that the polypeptide comprising the CDR2 with 4, 3, 2 or 1 amino acid(s) difference binds TCR with the same, about the same or a higher affinity compared to the binding by the polypeptide comprising the CDR2 without the 4, 3, 2 or 1 amino acid(s) difference, said affinity as measured by surface plasmon resonance; and iii) CDR3 is chosen from the group consisting of:
   e) SEQ ID NOs: 218; or
   f) amino acid sequences that have 4, 3, 2 or 1 amino
      acid(s) difference with the amino acid sequence of
      SEQ ID NO: 218, wherein
   at position 1 the F has been changed into Y, L or G;
   at position 4 the I has been changed into L;
   at position 5 the Y has been changed into W; and/or
   at position 8 the D has been changed into N or S;
   provided that the polypeptide comprising the CDR3
      with 4, 3, 2 or 1 amino acid(s) difference binds TCR
      with the same, about the same or a higher affinity
      compared to the binding by the polypeptide com-
      prising the CDR3 without the 4, 3, 2 or 1 amino
      acid(s) difference, said affinity as measured by sur-
      face plasmon resonance;
   and wherein the ISV that specifically binds CD123 is as
      further described herein.

In a preferred aspect, the ISV that specifically binds TCR (essentially) consists of 4 framework regions (FR1 to FR4, respectively) and 3 complementarity determining regions (CDR1 to CDR3, respectively), in which CDR1 is chosen from the group consisting of SEQ ID NOs: 181-191, CDR2 is chosen from the group consisting of SEQ ID NOs: 192-217, and CDR3 is chosen from the group consisting of SEQ ID NOs: 218-225 Accordingly, the present invention provides a polypeptide comprising an ISV that specifically binds TCR (essentially) consisting of 4 framework regions (FR1 to FR4, respectively) and 3 complementarity deter-mining regions (CDR1 to CDR3, respectively), in which CDR1 is chosen from the group consisting of SEQ ID NOs: 181-191, CDR2 is chosen from the group consisting of SEQ ID NOs: 192-217, and CDR3 is chosen from the group consisting of SEQ ID NOs: 218-225 and comprising an ISV that specifically binds CD123 as further described herein.

In a further aspect, the present invention provides a polypeptide as described herein, wherein the ISV that spe-cifically binds TCR (essentially) consists of 4 framework regions (FR1 to FR4, respectively) and 3 complementarity determining regions (CDR1 to CDR3, respectively), in which CDR1 is SEQ ID NO: 181, CDR2 is SEQ ID NO: 192, and CDR3 is SEQ ID NO: 218 and wherein the ISV that specifically binds CD123 is as further described herein.

Preferred ISVs for use in the polypeptide of the invention may be chosen from the group consisting of SEQ ID NOs: 42 and 78-180 or from ISVs that have a sequence identity of more than 80%, more than 85%, more than 90%, more than 95%, or even more than 99% with one of SEQ ID NOs: 42 and 78-180. Accordingly, the present invention provides a polypeptide as described herein, wherein the ISV that spe-cifically binds TCR is chosen from the group consisting of SEQ ID NOs: 42 and 78-180 or from ISVs that have a sequence identity of more than 80%, more than 85%, more than 90%, more than 95%, or even more than 99% with one of SEQ ID NOs: 42 and 78-180, and wherein the ISV that specifically binds CD123 is as further described herein.

The ISV that specifically binds TCR may be present at any position in the polypeptide of the invention. Preferably, the ISV that specifically binds TCR is present at the N-ter-minus of the polypeptide of the invention. Accordingly, in a further aspect, the present invention provides a polypeptide as described herein, wherein the ISV that specifically binds TCR is located at the N-terminus of the polypeptide.

The polypeptide of the invention further encompasses one or more ISVs. The ISVs for use in the polypeptide of the invention have been particularly selected for their high specificity towards CD123 present on CD123 expressing target cells.

In a further aspect, therefore, the present invention pro-vides a polypeptide as described herein, wherein the ISV that specifically binds TCR is as described herein, and wherein the one or more ISV that specifically bind CD123 (essentially) consists of 4 framework regions (FR1 to FR4, respectively) and 3 complementarity determining regions (CDR1 to CDR3, respectively), in which:
   i) CDR1 is chosen from the group consisting of:
      a) SEQ ID NOs: 11-16; or
      b) amino acid sequences that have 4, 3, 2 or 1 amino
         acid(s) difference with the amino acid sequence of
         one of SEQ ID NOs: 11-16, wherein the 4, 3, 2 or 1
         amino acid(s) difference are present at position 3, 6,
         7 and/or 8 of the CDR1 (position 28, 31, 32 and/or
         33 according to Kabat numbering); provided that the
         ISV comprising the CDR1 with 4, 3, 2 or 1 amino
         acid(s) difference binds CD123 with the same, about
         the same or a higher affinity compared to the binding
         by the ISV comprising the CDR1 without the 4, 3, 2
         or 1 amino acid(s) difference, said affinity as mea-
         sured by surface plasmon resonance; and
   ii) CDR2 is chosen from the group consisting of:
      c) SEQ ID NOs: 17-20; or
      d) amino acid sequences that have 3, 2 or 1 amino
         acid(s) difference with the amino acid sequence of
         one of SEQ ID NOs: 17-20, wherein the 3, 2 or 1
         amino acid(s) difference are present at position 3, 6
         and/or 10 of the CDR2 (position 52, 54 and/or 58
         according to Kabat numbering); provided that the
         ISV comprising the CDR2 with 3, 2 or 1 amino
         acid(s) difference binds CD123 with the same, about
         the same or a higher affinity compared to the binding
         by the ISV comprising the CDR2 without the 3, 2 or
         1 amino acid(s) difference, said affinity as measured
         by surface plasmon resonance; and
   iii) CDR3 is chosen from the group consisting of:
      e) SEQ ID NOs: 21-25; or
      f) amino acid sequences that have 3, 2 or 1 amino
         acid(s) difference with the amino acid sequence of
         one of SEQ ID NOs: 21-25, wherein the 3, 2 or 1
         amino acid(s) difference are present at position 3, 4
         and/or 5 of the CDR3 (position 97, 98 and/or 99
         according to Kabat numbering); provided that the
         ISV comprising the CDR3 with 3, 2 or 1 amino
         acid(s) difference binds CD123 with the same, about
         the same or a higher affinity compared to the binding
         by the ISV comprising the CDR3 without the 3, 2 or
         1 amino acid(s) difference, said affinity as measured
         by surface plasmon resonance.

The present invention has identified ISVs that specifically bind CD123 with selected antigen binding sites or paratopes. In one aspect, the ISV that specifically binds CD123 binds to an epitope that is bound by the ISV 56A10 (i.e. an ISV that belongs to the same family as 56A10 or an ISV that is related to 56A10).

In one aspect, the CDR1 encompassed in the ISV that specifically binds CD123 may be chosen from the group consisting of:
   a) SEQ ID NO: 11; or
   b) amino acid sequences that have 4, 3, 2 or 1 amino
      acid(s) difference with the amino acid sequence of SEQ
      ID NO: 11, wherein
   at position 3 the T has been changed into S or P;
   at position 6 the I has been changed into S;

at position 7 the N has been changed into D; and/or at position 8 the D has been changed into V or A;

provided that the ISV comprising the CDR1 with 4, 3, 2 or 1 amino acid(s) difference binds CD123 with the same, about the same or a higher affinity compared to the binding by the ISV comprising the CDR1 without the 4, 3, 2 or 1 amino acid(s) difference, said affinity as measured by surface plasmon resonance.

Apart from this or in addition, the CDR2 encompassed in the ISV that specifically binds TCR may be SEQ ID NO: 17.

Apart from this or in addition, the CDR3 encompassed in the ISV that specifically binds TCR may be chosen from the group consisting of:

a) SEQ ID NO: 21; or b) amino acid sequences that have 1 amino acid difference with the amino acid sequence of SEQ ID NO: 21, wherein at position 3 the P has been changed into A;

provided that the ISV comprising the CDR3 with 1 amino acid(s) difference binds CD123 with the same, about the same or a higher affinity compared to the binding by the ISV comprising the CDR3 without the 1 amino acid(s) difference, said affinity as measured by surface plasmon resonance.

Accordingly, the present invention provides a polypeptide as described herein, wherein the ISV that specifically binds TCR is as described herein, and wherein the one or more ISV that specifically bind CD123 (essentially) consists of 4 framework regions (FR1 to FR4, respectively) and 3 complementarity determining regions (CDR1 to CDR3, respectively), in which:

i) CDR1 is chosen from the group consisting of:

a) SEQ ID NO: 11; or b) amino acid sequences that have 4, 3, 2 or 1 amino acid(s) difference with the amino acid sequence of SEQ ID NO: 11, wherein at position 3 the T has been changed into S or P;

at position 6 the I has been changed into S;

at position 7 the N has been changed into D; and/or at position 8 the D has been changed into V or A;

provided that the polypeptide comprising the CDR1 with 4, 3, 2 or 1 amino acid(s) difference binds CD123 with the same, about the same or a higher affinity compared to the binding by the polypeptide comprising the CDR1 without the 4, 3, 2 or 1 amino acid(s) difference, said affinity as measured by surface plasmon resonance; and ii) CDR2 is SEQ ID NO: 17; and iii) CDR3 is chosen from the group consisting of:

c) SEQ ID NOs: 21; or d) amino acid sequences that have 1 amino acid difference with the amino acid sequence of SEQ ID NO: 21, wherein at position 3 the P has been changed into A;

provided that the polypeptide comprising the CDR3 with 1 amino acid difference binds CD123 with the same, about the same or a higher affinity compared to the binding by the polypeptide comprising the CDR3 without the 1 amino acid difference, said affinity as measured by surface plasmon resonance.

In a preferred aspect, the ISV that specifically binds CD123 (essentially) consists of 4 framework regions (FR1 to FR4, respectively) and 3 complementarity determining regions (CDR1 to CDR3, respectively), in which CDR1 is chosen from the group consisting of SEQ ID NOs: 11-15, CDR2 is SEQ ID NO: 17, and CDR3 is chosen from the group consisting of SEQ ID NOs: 21-22.

Accordingly, the present invention provides a polypeptide comprising an ISV that specifically binds TCR as described herein, and comprising one or more ISV that specifically bind CD123 (essentially) consisting of 4 framework regions (FR1 to FR4, respectively) and 3 complementarity determining regions (CDR1 to CDR3, respectively), in which CDR1 is chosen from the group consisting of SEQ ID NOs: 11-15, CDR2 is SEQ ID NO: 17, and CDR3 is chosen from the group consisting of SEQ ID NOs: 21-22.

In a further aspect, the present invention provides a polypeptide as described herein, wherein the ISV that specifically binds TCR is as described herein and wherein the one or more ISV that specifically bind CD123 (essentially) consists of 4 framework regions (FR1 to FR4, respectively) and 3 complementarity determining regions (CDR1 to CDR3, respectively), in which CDR1 is SEQ ID NO: 11, CDR2 is SEQ ID NO: 17, and CDR3 is SEQ ID NO: 21.

Preferred ISVs for use in the polypeptide of the invention may be chosen from the group consisting SEQ ID NOs: 1-6 or from ISVs that have a sequence identity of more than 80%, more than 85%, more than 90%, more than 95%, or even more than 99% with one of SEQ ID NOs: 1-6. Accordingly, the present invention also provides a polypeptide as described herein, wherein the ISV that specifically binds TCR is as described herein and wherein the one or more ISV that specifically bind CD123 is chosen from the group consisting of SEQ ID NOs: 1-6 or from ISVs that have a sequence identity of more than 80%, more than 85%, more than 90%, more than 95%, or even more than 99% with one of SEQ ID NOs: 1-6.

In another aspect, the ISV that specifically binds CD123 binds to an epitope that is bound by the Nanobody 55F03 (i.e. an ISV that belongs to the same family as 55F03 or an ISV that is related to 55F03).

In one aspect, the CDR1 encompassed in the ISV that specifically binds CD123 is SEQ ID NO: 16.

Apart from this or in addition, the CDR2 encompassed in the ISV that specifically binds CD123 may be chosen from the group consisting of:

a) SEQ ID NO: 18; or b) amino acid sequences that have 3, 2 or 1 amino acid difference with the amino acid sequence of SEQ ID NO: 18, wherein at position 3 the Y has been changed into W;

at position 6 the N has been changed into S; and/or at position 10 the Q has been changed into E;

provided that the ISV comprising the CDR3 with 3, 2 or 1 amino acid(s) difference binds CD123 with the same, about the same or a higher affinity compared to the binding by the ISV comprising the CDR3 without the 3, 2 or 1 amino acid(s) difference, said affinity as measured by surface plasmon resonance.

Apart from this or in addition, the CDR3 encompassed in the ISV that specifically binds CD123 may be chosen from the group consisting of:

a) SEQ ID NO: 23; or b) amino acid sequences that have 2 or 1 amino acid difference with the amino acid sequence of SEQ ID NO: 23, wherein at position 4 the E has been changed into R; and/or at position 5 the T has been changed into D or Y;

provided that the ISV comprising the CDR3 with 2 or 1 amino acid(s) difference binds CD123 with the same, about the same or a higher affinity compared to the binding by the ISV comprising the CDR3 without the 2 or 1 amino acid(s) difference, said affinity as measured by surface plasmon resonance.

Accordingly, the present invention provides a polypeptide as described herein, wherein the ISV that specifically binds TCR is as described herein, and wherein the one or more ISV that specifically bind CD123 (essentially) consists of 4 framework regions (FR1 to FR4, respectively) and 3 complementarity determining regions (CDR1 to CDR3, respectively), in which:

i) CDR1 is SEQ ID NO: 16; and
  ii) CDR2 is chosen from the group consisting of:
    a) SEQ ID NO: 18; or
    b) amino acid sequences that have 3, 2 or 1 amino acid difference with the amino acid sequence of SEQ ID NO: 18, wherein
      at position 3 the Y has been changed into W;
      at position 6 the N has been changed into S; and/or
      at position 10 the Q has been changed into E;
      provided that the polypeptide comprising the CDR3 with 3, 2 or 1 amino acid(s) difference binds CD123 with the same, about the same or a higher affinity compared to the binding by the polypeptide comprising the CDR3 without the 3, 2 or 1 amino acid(s) difference, said affinity as measured by surface plasmon resonance; and
  iii) CDR3 is chosen from the group consisting of:
    c) SEQ ID NOs: 23; or
    d) amino acid sequences that have 2 or 1 amino acid difference with the amino acid sequence of SEQ ID NO: 23, wherein
      at position 4 the E has been changed into R; and/or
      at position 5 the T has been changed into D or Y;
      provided that the polypeptide comprising the CDR3 with 2 or 1 amino acid(s) difference binds CD123 with the same, about the same or a higher affinity compared to the binding by the polypeptide comprising the CDR3 without the 2 or 1 amino acid(s) difference, said affinity as measured by surface plasmon resonance.

In a preferred aspect, the ISV that specifically binds CD123 (essentially) consists of 4 framework regions (FR1 to FR4, respectively) and 3 complementarity determining regions (CDR1 to CDR3, respectively), in which CDR1 is SEQ ID NO: 16, CDR2 is chosen from the group consisting of SEQ ID NOs: 18-20, and CDR3 is chosen from the group consisting of SEQ ID NOs: 23-25.

Accordingly, the present invention provides a polypeptide comprising an ISV that specifically binds TCR as described herein, and comprising one or more ISV that specifically bind CD123 (essentially) consisting of 4 framework regions (FR1 to FR4, respectively) and 3 complementarity determining regions (CDR1 to CDR3, respectively), in which CDR1 is SEQ ID NO: 16, CDR2 is chosen from the group consisting of SEQ ID NOs: 18-20, and CDR3 is chosen from the group consisting of SEQ ID NOs: 23-25.

In a further aspect, the present invention provides a polypeptide as described herein, wherein the ISV that specifically binds TCR is as described herein, and wherein the one or more ISV that specifically bind CD123 (essentially) consists of 4 framework regions (FR1 to FR4, respectively) and 3 complementarity determining regions (CDR1 to CDR3, respectively), in which CDR1 is SEQ ID NO: 16, CDR2 is SEQ ID NO: 18, and CDR3 is SEQ ID NO: 23.

Preferred ISVs for use in the polypeptide of the invention may be chosen from the group consisting SEQ ID NOs: 7-10 or from ISVs that have a sequence identity of more than 80%, more than 85%, more than 90%, more than 95%, or even more than 99% with one of SEQ ID NOs: 7-10. Accordingly, in a further aspect, the present invention provides a polypeptide as described herein, wherein the ISV that specifically binds TCR is as described herein, and wherein the one or more ISV that specifically bind CD123 is chosen from the group consisting of SEQ ID NOs: 7-10 or from ISVs that have a sequence identity of more than 80%, more than 85%, more than 90%, more than 95%, or even more than 99% with one of SEQ ID NOs: 7-10.

The polypeptide of the invention may encompass one ISV that specifically binds CD123 or more than one ISV that specifically binds CD123, such as for example two, three or even more. In a further aspect, the present invention provides a polypeptide as described herein, comprising an ISV that specifically binds TCR as described herein, and comprising two or more ISVs that specifically bind CD123, preferably two.

The two or more, preferably two, ISVs encompassed in the polypeptide of the invention can be any ISV that specifically bind CD123 as described herein. The two or more, preferably two, ISVs encompassed in the polypeptide of the invention can be the same ISVs (i.e. with the same amino acid sequence) or they can be different ISVs (i.e. with a different amino acid sequence). In one aspect, the present invention provides a polypeptide as described in, wherein the two or more ISVs that specifically bind CD123 are biparatopic comprising a first ISV and a second ISV, wherein the first ISV binds to an epitope on CD123 that is different from the epitope on CD123 bound by the second ISV.

Preferably, the two or more, preferably two, ISVs that specifically bind CD123 are an ISV related to 56A10 and an ISV related to 55F03. Accordingly, in a one aspect, the present invention provides a polypeptide as described herein, wherein the first ISV is selected from the ISVs related to 56A10 and the second ISV is selected from the ISVs related to 55F03.

The two or more, preferably two, ISVs that specifically bind CD123 may be present at any position in the polypeptide of the invention. In one aspect, the present invention provides a polypeptide as described herein, wherein the second ISV is located N-terminally of the first ISV. In another aspect, the present invention provides a polypeptide as described herein, wherein the second ISV is located C-terminally of the first ISV.

The ISVs present in the polypeptide of the invention can be any ISV that is known in the art and as further described herein. In one aspect, the ISVs present in the polypeptide of the invention are selected from a single domain antibody, a dAb, a Nanobody, a VHH, a humanized VHH, a camelized VH or a VHH which has been obtained by affinity maturation. Accordingly, in a further aspect, the present invention provides a polypeptide as described herein, wherein the ISV that specifically binds TCR and the one or more ISV that specifically bind CD123 (essentially) consist of a single domain antibody, a dAb, a Nanobody, a VHH, a humanized VHH, a camelized VH or a VHH which has been obtained by affinity maturation.

Preferred polypeptides of the invention are chosen from the group consisting of SEQ ID NOs: 47, 49, 52, 53, 55, 56 and 58-61 or from polypeptides that have a sequence identity of more than 80%, more than 85%, more than 90%, more than 95%, or even more than 99% with one of SEQ ID NOs: 47, 49, 52, 53, 55, 56 and 58-61.

More preferably, the polypeptide is chosen from the group consisting of SEQ ID NOs: 47, 49, 52, 53, 55, 56 and 58-61.

As discussed above, the polypeptide of the invention redirects T cells for killing of CD123 expressing cells. In one aspect, the present invention provides a polypeptide as described herein, wherein said polypeptide induces T cell activation.

In a further aspect, the present invention provides a polypeptide as described herein, wherein said T cell activation is independent from MHC recognition.

In a further aspect, the present invention provides a polypeptide as described herein, wherein said T cell activation depends on presenting said polypeptide bound to CD123 on a target cell to a T cell.

In a further aspect, the present invention provides a polypeptide as described herein, wherein said T cell activation causes one or more cellular response by said T cell, wherein said cellular response is selected from the group consisting of proliferation, differentiation, cytokine secretion, cytotoxic effector molecule release, cytotoxic activity, expression of activation markers and redirected target cell lysis.

In a specific aspect, the T cell activation induced by the polypeptide of the invention causes killing of CD123 expressing cells with an average EC50 value of between 1 nM and 1 pM, such as at an average EC50 value of 500 pM or less, such as less than 400, 300, 200 or 100 pM or even less, such as less than 90, 80, 70, 60, 50, 40 or 30 pM or even less, said EC50 value preferably determined in a flow cytometry based assay with TOPRO3 read-out using MOLM-13 cells as target cells and human T cells as effector cells at an effector to target cell ratio of 10 to 1.

In another specific aspect, the T cell activation induced by the polypeptide of the invention causes lysis of CD123 expressing cells with an average lysis percentage of more than about 10%, such as 15%, 16%, 17%, 18%, 19% or 20% or even more, such as more than 25%, or even more than 30%, said lysis percentage preferably determined in a flow cytometry based assay with TOPRO3 read-out using MOLM-13 cells as target cells and human T cells as effector cells at an effector to target cell ratio of 10 to 1.

In another specific aspect, the present invention provides a polypeptide as described herein, wherein said T cell activation induced by the polypeptide of the invention causes IFN-γ secretion with an average EC50 value of between 100 nM and 10 pM, such as at an average EC50 value of 50 nM or less, such as less than 40, 30, 20, 10 or 9 nM or even less, such as less than 8, 7, 6, 5, 4, 3, 2 or 1 nM or even less, such as less than 500 pM or even less, such as less than 400, 300, 200 or 100 pM or even less, said EC50 value preferably determined in an ELISA based assay.

In a further aspect, the present invention provides a polypeptide as described herein, wherein said T cell activation causes proliferation of said T cells.

As discussed above, the polypeptides of the present invention are selected such that target-independent T cell activation should be minimal. In a further aspect, therefore, the present invention provides a polypeptide as described herein, wherein the T cell activation in the absence of CD123 positive cells is minimal.

More specifically, T cell activation induced lysis of CD123 negative cells by the polypeptides of the present invention is no more than about 10%, such as 9% or less, such as 8, 7, or 6% or even less, said lysis preferably determined as average lysis percentage in a flow cytometry based assay with TOPRO3 read-out using U-937 cells as target cells and human T cells as effector cells at an effector to target cell ratio of 10 to 1.

The present invention also relates to the building blocks, i.e. the ISVs that make up the polypeptides of the invention. Accordingly, the present invention also provides a polypeptide that is an ISV that specifically binds CD123 and that comprises or (essentially) consists of 4 framework regions (FR1 to FR4, respectively) and 3 complementarity determining regions (CDR1 to CDR3, respectively), in which:

i) CDR1 is chosen from the group consisting of:
   a) SEQ ID NOs: 11-16; or
   b) amino acid sequences that have 4, 3, 2 or 1 amino acid(s) difference with the amino acid sequence of one of SEQ ID NOs: 11-16; provided that the polypeptide comprising the CDR1 with 4, 3, 2 or 1 amino acid(s) difference binds CD123 with the same, about the same or a higher affinity compared to the binding by the polypeptide comprising the CDR1 without the 4, 3, 2 or 1 amino acid(s) difference, said affinity as measured by surface plasmon resonance;

and/or ii) CDR2 is chosen from the group consisting of:
   c) SEQ ID NOs: 17-20; or
   d) amino acid sequences that have 4, 3, 2 or 1 amino acid(s) difference with the amino acid sequence of one of SEQ ID NOs: 17-20; provided that the polypeptide comprising the CDR2 with 4, 3, 2 or 1 amino acid(s) difference binds CD123 with the same, about the same or a higher affinity compared to the binding by the polypeptide comprising the CDR2 without the 4, 3, 2 or 1 amino acid(s) difference, said affinity as measured by surface plasmon resonance;

and/or iii) CDR3 is chosen from the group consisting of:
   e) SEQ ID NOs: 21-25; or
   f) amino acid sequences that have 4, 3, 2 or 1 amino acid(s) difference with the amino acid sequence of one of SEQ ID NOs: 21-25; provided that the polypeptide comprising the CDR3 with 4, 3, 2 or 1 amino acid(s) difference binds CD123 with the same, about the same or a higher affinity compared to the binding by the polypeptide comprising the CDR3 without the 4, 3, 2 or 1 amino acid(s) difference, said affinity as measured by surface plasmon resonance.

More preferably, the polypeptide that is an ISV that specifically binds CD123 comprises or (essentially) consists of 4 framework regions (FR1 to FR4, respectively) and 3 complementarity determining regions (CDR1 to CDR3, respectively), in which:

i) CDR1 is chosen from the group consisting of:
   a) SEQ ID NOs: 11-16; or
   b) amino acid sequences that have 4, 3, 2 or 1 amino acid(s) difference with the amino acid sequence of one of SEQ ID NOs: 11-16; provided that the polypeptide comprising the CDR1 with 4, 3, 2 or 1 amino acid(s) difference binds CD123 with the same, about the same or a higher affinity compared to the binding by the polypeptide comprising the CDR1 without the 4, 3, 2 or 1 amino acid(s) difference, said affinity as measured by surface plasmon resonance;

and/or ii) CDR2 is chosen from the group consisting of:
   c) SEQ ID NOs: 17-20; or
   d) amino acid sequences that have 4, 3, 2 or 1 amino acid(s) difference with the amino acid sequence of one of SEQ ID NOs: 17-20; provided that the polypeptide comprising the CDR2 with 4, 3, 2 or 1 amino acid(s) difference binds CD123 with the same, about the same or a higher affinity compared to the binding by the polypeptide comprising the CDR2 without the 4, 3, 2 or 1 amino acid(s) difference, said affinity as measured by surface plasmon resonance;

and/or iii) CDR3 is chosen from the group consisting of:

e) SEQ ID NOs: 21-25; or f) amino acid sequences that have 4, 3, 2 or 1 amino acid(s) difference with the amino acid sequence of one of SEQ ID NOs: 21-25; provided that the polypeptide comprising the CDR3 with 4, 3, 2 or 1 amino acid(s) difference binds CD123 with the same, about the same or a higher affinity compared to the binding by the polypeptide comprising the CDR3 without the 4, 3, 2 or 1 amino acid(s) difference, said affinity as measured by surface plasmon resonance.

In a further aspect, the present invention also provides a polypeptide as described above, that comprises or (essentially) consists of 4 framework regions (FR1 to FR4, respectively) and 3 complementarity determining regions (CDR1 to CDR3, respectively), in which:

i) CDR1 is chosen from the group consisting of:

a) SEQ ID NOs: 11-16; or b) amino acid sequences that have 4, 3, 2 or 1 amino acid(s) difference with the amino acid sequence of one of SEQ ID NOs: 11-16, wherein the 4, 3, 2 or 1 amino acid(s) difference are present at position 3, 6, 7 and/or 8 of the CDR1 (position 28, 31, 32 and/or 33 according to Kabat numbering); provided that the polypeptide comprising the CDR1 with 4, 3, 2 or 1 amino acid(s) difference binds CD123 with the same, about the same or a higher affinity compared to the binding by the polypeptide comprising the CDR1 without the 4, 3, 2 or 1 amino acid(s) difference, said affinity as measured by surface plasmon resonance; and/or ii) CDR2 is chosen from the group consisting of:

c) SEQ ID NOs: 17-20; or d) amino acid sequences that have 3, 2 or 1 amino acid(s) difference with the amino acid sequence of one of SEQ ID NOs: 17-20, wherein the 3, 2 or 1 amino acid(s) difference are present at position 3, 6 and/or 10 of the CDR2 (position 52, 54 and/or 58 according to Kabat numbering); provided that the polypeptide comprising the CDR2 with 3, 2 or 1 amino acid(s) difference binds CD123 with the same, about the same or a higher affinity compared to the binding by the polypeptide comprising the CDR2 without the 3, 2 or 1 amino acid(s) difference, said affinity as measured by surface plasmon resonance; and/or iii) CDR3 is chosen from the group consisting of:

e) SEQ ID NOs: 21-25; or f) amino acid sequences that have 3, 2 or 1 amino acid(s) difference with the amino acid sequence of one of SEQ ID NOs: 21-25, wherein the 3, 2 or 1 amino acid(s) difference are present at position 3, 4 and/or 5 of the CDR3 (position 97, 98 and/or 99 according to Kabat numbering); provided that the polypeptide comprising the CDR3 with 3, 2 or 1 amino acid(s) difference binds CD123 with the same, about the same or a higher affinity compared to the binding by the polypeptide comprising the CDR3 without the 3, 2 or 1 amino acid(s) difference, said affinity as measured by surface plasmon resonance.

The present invention has identified ISVs that specifically bind CD123 with selected antigen binding sites or paratopes. In one aspect, the ISV that specifically binds CD123 binds to an epitope that is bound by the ISV 56A10 (i.e. an ISV that belongs to the same family as 56A10 or an ISV that is related to 56A10).

Accordingly, in one aspect, the CDR1 encompassed in the ISV that specifically binds CD123 may be chosen from the group consisting of:

a) SEQ ID NO: 11; or b) amino acid sequences that have 4, 3, 2 or 1 amino acid(s) difference with the amino acid sequence of SEQ ID NO: 11, wherein at position 3 the T has been changed into S or P;

at position 6 the I has been changed into S;

at position 7 the N has been changed into D; and/or at position 8 the D has been changed into V or A;

provided that the polypeptide comprising the CDR1 with 4, 3, 2 or 1 amino acid(s) difference binds CD123 with the same, about the same or a higher affinity compared to the binding by the polypeptide comprising the CDR1 without the 4, 3, 2 or 1 amino acid(s) difference, said affinity as measured by surface plasmon resonance.

Apart from this or in addition, the CDR2 encompassed in the ISV that specifically binds CD123 is SEQ ID NO: 17.

Apart from this or in addition, the CDR3 encompassed in the ISV that specifically binds CD123 may be chosen from the group consisting of:

a) SEQ ID NO: 21; or b) amino acid sequences that have 1 amino acid difference with the amino acid sequence of SEQ ID NO: 21, wherein at position 3 the P has been changed into A;

provided that the polypeptide comprising the CDR3 with 1 amino acid(s) difference binds CD123 with the same, about the same or a higher affinity compared to the binding by the polypeptide comprising the CDR3 without the 1 amino acid(s) difference, said affinity as measured by surface plasmon resonance.

Accordingly, the present invention also provides a polypeptide as described above, that comprises or (essentially) consists of 4 framework regions (FR1 to FR4, respectively) and 3 complementarity determining regions (CDR1 to CDR3, respectively), in which:

i) CDR1 is chosen from the group consisting of:

a) SEQ ID NO: 11; or b) amino acid sequences that have 4, 3, 2 or 1 amino acid(s) difference with the amino acid sequence of SEQ ID NO: 11, wherein at position 3 the T has been changed into S or P;

at position 6 the I has been changed into S;

at position 7 the N has been changed into D; and/or at position 8 the D has been changed into V or A;

provided that the polypeptide comprising the CDR1 with 4, 3, 2 or 1 amino acid(s) difference binds CD123 with the same, about the same or a higher affinity compared to the binding by the polypeptide comprising the CDR1 without the 4, 3, 2 or 1 amino acid(s) difference, said affinity as measured by surface plasmon resonance; and ii) CDR2 is SEQ ID NO: 17; and iii) CDR3 is chosen from the group consisting of:

c) SEQ ID NOs: 21; or d) amino acid sequences that have 1 amino acid difference with the amino acid sequence of SEQ ID NO: 21, wherein at position 3 the P has been changed into A;

provided that the polypeptide comprising the CDR3 with 1 amino acid difference binds CD123 with the same, about the same or a higher affinity compared to the binding by the polypeptide comprising the CDR3 without the 1 amino acid difference, said affinity as measured by surface plasmon resonance.

In a further aspect, the present invention provides a polypeptide as described herein, in which CDR1 is chosen from the group consisting of SEQ ID NOs: 11-15, CDR2 is SEQ ID NO: 17, and CDR3 is chosen from the group consisting of SEQ ID NOs: 21-22. Preferably, CDR1 is SEQ ID NO: 11, CDR2 is SEQ ID NO: 17, and CDR3 is SEQ ID NO: 21.

Preferred ISVs of the invention related to 56A10 may be chosen from the group consisting of SEQ ID NOs: 1-6 or from polypeptides that have a sequence identity of more than 80%, more than 85%, more than 90%, more than 95%, or even more than 99% with one of SEQ ID NOs: 1-6. Accordingly, in a further aspect, the present invention provides a polypeptide as described herein, wherein the polypeptide is chosen from the group consisting of SEQ ID NOs: 1-6 or from polypeptides that have a sequence identity of more than 80%, more than 85%, more than 90%, more than 95%, or even more than 99% with one of SEQ ID NOs: 1-6. Preferably, the polypeptide is chosen from the group consisting of SEQ ID NOs: 1-6.

In one aspect, the polypeptide of the invention binds to human CD123 expressed on MOLM-13 cells with an average EC50 value between 10 nM and 100 pM, such as at an average EC50 value of 5 nM or less, such as less than 4, 3, 2, or 1 nM or even less, preferably as measured by flow cytometry.

In another aspect, the polypeptide of the invention binds to human CD123 with an average KD value of between 10 nM and 100 pM, such as at an average KD value of 5 nM or less, such as less than 4, 3 or 2 nM or even less, said KD value preferably determined by surface plasmon resonance.

In yet another aspect, the ISV that specifically binds CD123 binds to an epitope that is bound by the ISV 55F03 (i.e. an ISV that belongs to the same family as 55F03 or an ISV that is related to 55F03). Accordingly, in one aspect, the CDR1 encompassed in the ISV that specifically binds CD123 is SEQ ID NO: 16.

Apart from this or in addition, the CDR2 encompassed in the ISV that specifically binds CD123 may be chosen from the group consisting of:
a) SEQ ID NO: 18; or
b) amino acid sequences that have 3, 2 or 1 amino acid difference with the amino acid sequence of SEQ ID NO: 18, wherein
at position 3 the Y has been changed into W;
at position 6 the N has been changed into S; and/or
at position 10 the Q has been changed into E;
provided that the polypeptide comprising the CDR3 with 3, 2 or 1 amino acid(s) difference binds CD123 with the same, about the same or a higher affinity compared to the binding by the polypeptide comprising the CDR3 without the 3, 2 or 1 amino acid(s) difference, said affinity as measured by surface plasmon resonance.

Apart from this or in addition, the CDR3 encompassed in the ISV that specifically binds CD123 may be chosen from the group consisting of:
a) SEQ ID NO: 23; or
b) amino acid sequences that have 2 or 1 amino acid difference with the amino acid sequence of SEQ ID NO: 23, wherein
at position 4 the E has been changed into R; and/or
at position 5 the T has been changed into D or Y;
provided that the polypeptide comprising the CDR3 with 2 or 1 amino acid(s) difference binds CD123 with the same, about the same or a higher affinity compared to the binding by the polypeptide comprising the CDR3 without the 2 or 1 amino acid(s) difference, said affinity as measured by surface plasmon resonance.

Accordingly, the present invention also provides a polypeptide as described above, that comprises or (essentially) consists of 4 framework regions (FR1 to FR4, respectively) and 3 complementarity determining regions (CDR1 to CDR3, respectively), in which:
i) CDR1 is SEQ ID NO: 16; and
ii) CDR2 is chosen from the group consisting of:
a) SEQ ID NO: 18; or
b) amino acid sequences that have 3, 2 or 1 amino acid difference with the amino acid sequence of SEQ ID NO: 18, wherein
at position 3 the Y has been changed into W;
at position 6 the N has been changed into S; and/or
at position 10 the Q has been changed into E;
provided that the polypeptide comprising the CDR3 with 3, 2 or 1 amino acid(s) difference binds CD123 with the same, about the same or a higher affinity compared to the binding by the polypeptide comprising the CDR3 without the 3, 2 or 1 amino acid(s) difference, said affinity as measured by surface plasmon resonance; and
iii) CDR3 is chosen from the group consisting of:
c) SEQ ID NOs: 23; or
d) amino acid sequences that have 2 or 1 amino acid difference with the amino acid sequence of SEQ ID NO: 23, wherein
at position 4 the E has been changed into R; and/or
at position 5 the T has been changed into D or Y;
provided that the polypeptide comprising the CDR3 with 2 or 1 amino acid(s) difference binds CD123 with the same, about the same or a higher affinity compared to the binding by the polypeptide comprising the CDR3 without the 2 or 1 amino acid(s) difference, said affinity as measured by surface plasmon resonance.

In a further aspect, the present invention provides a polypeptide as described herein, in which CDR1 is SEQ ID NO: 16, CDR2 is chosen from the group consisting of SEQ ID NOs: 18-20, and CDR3 is chosen from the group consisting of SEQ ID NOs: 23-25. Preferrably, CDR1 is SEQ ID NO: 16, CDR2 is SEQ ID NO: 18, and CDR3 is SEQ ID NO: 23.

Preferred ISVs of the invention related to 56A10 may be chosen from the group consisting of SEQ ID NOs: 7-10 or from polypeptides that have a sequence identity of more than 80%, more than 85%, more than 90%, more than 95%, or even more than 99% with one of SEQ ID NOs: 7-10. Accordingly, in a further aspect, the present invention provides a polypeptide as described herein, wherein the polypeptide is chosen from the group consisting of SEQ ID NOs: 7-10 or from polypeptides that have a sequence identity of more than 80%, more than 85%, more than 90%, more than 95%, or even more than 99% with one of SEQ ID NOs: 7-10. Preferably, the polypeptide is chosen from the group consisting of SEQ ID NOs: 7-10.

In one aspect, the polypeptide of the invention binds to human CD123 expressed on MOLM-13 cells with an average EC50 value between 10 pM and 100 nM, such as at an average EC50 value of 5 pM or less, such as less than 4, 3, 2, or 1 pM or even less, preferably as measured by flow cytometry.

In another aspect, the polypeptide of the invention binds to human CD123 with an average KD value of between 1 pM and 10 nM, such as at an average KD value of 500 nM or less, such as less than 400, 300 or 200 nM or even less, said KD value preferably determined by surface plasmon resonance.

In a further aspect, the present invention provides a polypeptide that cross-blocks the binding to CD123 of at least one of the polypeptides as described herein or that cross-blocks the binding to CD123 of one of the polypeptides with SEQ ID NOs: 1-10.

In a further aspect, the present invention provides a polypeptide that is cross-blocked from binding to CD123 by at least one of the polypeptides as described herein or that is cross-blocked from binding to CD123 by one of the polypeptides with SEQ ID NOs: 1-10.

The polypeptide that specifically binds CD123 as described herein, preferably (essentially) consists of a single domain antibody, a dAb, a Nanobody, a VHH, a humanized VHH, a camelized VH or a VHH which has been obtained by affinity maturation.

The polypeptide of the invention that specifically binds CD123 may contain one or more ISVs that specifically bind CD123. Accordingly, in a further aspect, the present invention provides a polypeptide comprising two or more ISVs, preferably two, that specifically bind CD123. In a preferred aspect, the two or more ISVs, preferably two ISVs, that specifically bind CD123, are chosen from the group of ISVs related to 56A10 or from the group of ISVs related to 55F03.

In a further aspect, the present invention provides a polypeptide that specifically binds CD123, comprising two ISVs that specifically bind CD123, wherein the ISVs are chosen from the group of ISVs related to 56A10 or from group of ISVs related to 55F03.

The polypeptide of the invention comprising two or more ISVs, preferably two ISVs, that specifically bind CD123 is preferably biparatopic comprising a first ISV and a second ISV, wherein the first ISV binds to an epitope on CD123 that is different from the epitope on CD123 bound by the second ISV. In a preferred aspect, the first ISV is selected from the group of ISVs related to 56A10 and the second ISV is selected from the group of ISVs related to 55F03.

The ISVs may be present at any position in the biparatopic polypeptide of the invention that binds CD123. In one aspect, the second ISV is located N-terminally of the first ISV. In another aspect, the second ISV is located C-terminally of the first ISV.

The ISVs present in the polypeptide of the invention may be directly linked to each other, or they can be linked via one or more linkers, preferably peptide linkers. Accordingly, in a further aspect, the present invention provides a polypeptide as described herein, wherein the ISVs are directly linked to each other or linked to each other via a linker. Preferred linkers for use in the polypeptides of the invention are shown in Table B-3 (SEQ ID NOs: 325). As such, in a further aspect, the present invention provides a polypeptide as described herein, in which the linker is selected from the group consisting of SEQ ID NOs: 325 to 336.

The present invention further encompasses constructs (also referred to herein as "construct(s) of the invention") that comprise a polypeptide as described herein, and further comprise one or more other groups, residues, moieties or binding units, optionally linked via one or more peptidic linkers.

In a further aspect, the said one or more other groups, residues, moieties or binding units may provide the construct with increased half-life, compared to the corresponding polypeptide without the one or more other groups, residues, moieties or binding units. Said one or more other groups, residues, moieties or binding units that provide the polypeptide with increased half-life can any molecule that provides for a retention of the polypeptide in the serum. In one aspect, the one or more other groups, residues, moieties or binding units that provide the polypeptide with increased half-life is chosen from the group consisting of a polyethylene glycol molecule, serum proteins or fragments thereof, binding units that can bind to serum proteins, an Fc portion and small proteins or peptides that can bind to serum proteins.

Accordingly, in one aspect, the present invention provides a construct as described herein, in which said one or more other groups, residues, moieties or binding units that provide the construct with increased half-life is chosen from the group consisting of serum albumin (such as human serum albumin) or a serum immunoglobulin (such as IgG).

In another aspect, the present invention provides a construct as described herein, in which said one or more other binding units that provide the construct with increased half-life is chosen from the group consisting of binding units that can bind to serum albumin (such as human serum albumin) or a serum immunoglobulin (such as IgG). Preferably, said one or more other binding units that provide the polypeptide with increased half-life is an ISV that binds serum albumin. In a further aspect, said ISV that binds serum albumin may (essentially) consist of a single domain antibody, a dAb, a Nanobody, a VHH, a humanized VHH or a camelized VH.

A preferred ISV for use in the constructs as described herein, is an ISV that binds serum albumin and that (essentially) consists of 4 framework regions (FR1 to FR4, respectively) and 3 complementary determining regions (CDR1 to CDR3, respectively), in which CDR1 is GFTFSSFGMS (SEQ ID NO: 363) or GFTFRSFGMS (SEQ ID NO: 364), CDR2 is SISGSGSDTL (SEQ ID NO: 365) and CDR3 is GGSLSR (SEQ ID NO: 366). Preferred ISVs that binds serum albumin are selected from the group consisting of SEQ ID NOs: 43 and 351 to 362.

As for the polypeptides of the invention, the other groups, residues, moieties or binding units, such as ISVs may be directly linked to each other or linked to each other via a linker. In a further aspect, the present invention provides a construct as described herein, in which the linker is selected from the group consisting of SEQ ID NOs: 325 to 336.

Preferred constructs of the invention may be chosen from the group consisting of SEQ ID NOs: 63-67 or constructs that have a sequence identity of more than 80%, more than 85%, more than 90%, more than 95%, or even more than 99% with one of SEQ ID NOs: 63-67, preferably, SEQ ID NOs: 63-67.

The constructs of the invention may be sequence optimized, e.g. to make the construct more human-like, to improve the expression of the constructs, to increased the stability of the constructs upon storage and/or to make the constructs less prone to binding by antibodies pre-existing in the serum.

In one aspect, the present invention provides a construct as described herein, further comprising a C-terminal extension (X)n, in which n is 1 to 5, such as 1, 2, 3, 4 or 5, and in which X is a naturally occurring amino acid, preferably no cysteine. Preferred constructs are chosen from the group consisting of SEQ ID NOs: 338-342.

The present invention also provides nucleic acids encoding the polypeptides and constructs (that are such that they can be obtained by expression of a nucleic acid encoding the same) as defined herein.

In one aspect, the nucleic acid as described herein, is in the form of a genetic construct.

The present invention also provides an expression vector comprising the nucleic acid as defined herein.

The present invention also provides a host or host cell comprising the nucleic acid as defined herein, or the expression vector as defined herein.

In a further aspect, the present invention provides a method for the production or construct (that is such that it can be obtained by expression of a nucleic acid encoding the same) of the polypeptide as defined herein, said method at least comprising the steps of:

a) expressing, in a suitable host cell or host organism or in another suitable expression system, the nucleic acid as defined herein; optionally followed by:

b) isolating and/or purifying the polypeptide or construct as defined herein.

In a further aspect, the present invention provides a composition comprising at least one polypeptide or construct as defined herein or a nucleic acid as defined herein. In one aspect, the composition is a pharmaceutical composition. In one aspect, the composition further comprises at least one pharmaceutically acceptable carrier, diluent or excipient and/or adjuvant, and optionally comprises one or more further pharmaceutically active polypeptides and/or compounds.

The present invention also provides a polypeptide as described herein, a construct as described herein, or a composition as described herein, for use as a medicament. In a further aspect, the present invention provides the use of a polypeptide as described herein, or a composition as described herein, for the manufacture of a medicament. In a further aspect, the present invention provides a polypeptide as described herein, a construct as described herein, or a composition as described herein, for use in the prevention, treatment and/or amelioration of a CD123 associated disease or condition. The present invention also provides a method for the prevention, treatment or and/or amelioration of a CD123 associated disease or condition, comprising the step of administering to a subject in need thereof, a pharmaceutically active amount of the polypeptide as described herein, a construct as described herein, or a composition as described herein. The present invention also provides the use of a polypeptide as described herein, a construct as described herein, or a composition as described herein, for the manufacture of a medicament for the prevention, treatment and/or amelioration of a CD123 associated disease or condition. Without being limiting, the CD123 associated disease or condition may be a proliferative disease or an inflammatory condition. Accordingly, in a further aspect, the present invention provides a polypeptide as described herein, a construct as described herein, or a composition as described herein, for use in the prevention, treatment and/or amelioration of a proliferative disease or an inflammatory condition. The present invention also provides a method for the prevention, treatment and/or amelioration of a proliferative disease or an inflammatory condition, comprising the step of administering to a subject in need thereof, a pharmaceutically active amount of the polypeptide as described herein, a construct as described herein, or a composition as described herein. The present invention also provides the use of a polypeptide as described herein, a construct as described herein, or a composition as described herein, for the manufacture of a medicament for the prevention, treatment and/or amelioration of a proliferative disease or an inflammatory condition.

Without being limiting, the proliferative disease may be cancer. Accordingly, in a further aspect, the present invention provides a polypeptide for described herein, a construct as described herein, or a composition as described herein, for use in the prevention, treatment and/or amelioration of cancer. The present invention also provides a method for the prevention, treatment and/or amelioration of cancer, comprising the step of administering to a subject in need thereof, a pharmaceutically active amount of the polypeptide as described herein, a construct as described herein, or a composition as described herein. The present invention also provides the use of a polypeptide as described herein, a construct as described herein, or a composition as described herein, for the manufacture of a medicament for the prevention, treatment and/or amelioration of cancer.

The cancer to be treated by the method of the invention can be any cancer known to be treated by CD123 target cell killing. Cancer known to involve CD123 expression on aberrantly proliferating cells include (without being limiting) lymphomas (including Burkitt's lymphoma, Hodgkin's lymphoma and non-Hodgkin's lymphoma), leukemias (including acute myeloid leukemia, chronic myeloid leukemia, acute B lymphoblastic leukemia, chronic lymphocytic leukemia and hairy cell leukemia), myelodysplastic syndrome, blastic plasmacytoid dendritic cell neoplasm, systemic mastocytosis and multiple myeloma. Accordingly, in a further aspect, the present invention provides a polypeptide as described herein, a construct as described herein, a composition as described herein, for use in the prevention, treatment and/or amelioration of a cancer selected from lymphomas (including Burkitt's lymphoma, Hodgkin's lymphoma and non-Hodgkin's lymphoma), leukemias (including acute myeloid leukemia, chronic myeloid leukemia, acute B lymphoblastic leukemia, chronic lymphocytic leukemia and hairy cell leukemia), myelodysplastic syndrome, blastic plasmacytoid dendritic cell neoplasm, systemic mastocytosis and multiple myeloma. The present invention also provides a method for the prevention, treatment and/or amelioration of cancer selected from lymphomas (including Burkitt's lymphoma, Hodgkin's lymphoma and non-Hodgkin's lymphoma), leukemias (including acute myeloid leukemia, chronic myeloid leukemia, acute B lymphoblastic leukemia, chronic lymphocytic leukemia and hairy cell leukemia), myelodysplastic syndrome, blastic plasmacytoid dendritic cell neoplasm, systemic mastocytosis and multiple myeloma, comprising the step of administering to a subject in need thereof, a pharmaceutically active amount of the polypeptide as described herein, a construct as described herein, or a composition as described herein. The present invention also provides the use of a polypeptide as described herein, a construct as described herein, or a composition as described herein, for the manufacture of a medicament for the prevention, treatment and/or amelioration of a cancer chosen from the group consisting of lymphomas (including Burkitt's lymphoma, Hodgkin's lymphoma and non-Hodgkin's lymphoma), leukemias (including acute myeloid leukemia, chronic myeloid leukemia, acute B lymphoblastic leukemia, chronic lymphocytic leukemia and hairy cell leukemia), myelodysplastic syndrome, blastic plasmacytoid dendritic cell neoplasm, systemic mastocytosis and multiple myeloma.

The inflammatory condition to be treated by the method of the invention can be any inflammatory condition known to be treated by CD123 target cell killing. Inflammatory conditions known to involve CD123 expression on cells include (without being limiting) Autoimmune Lupus (SLE), allergy, asthma and rheumatoid arthritis. Accordingly, in a further aspect, the present invention provides a polypeptide as described herein, a construct as described herein, a composition as described herein, for use in the prevention, treatment and/or amelioration of an inflammatory condition chosen from the group consisting of Autoimmune Lupus (SLE), allergy, asthma and rheumatoid arthritis. The present invention also provides a method for the prevention, treatment and/or amelioration of an inflammatory condition chosen from the group consisting of Autoimmune Lupus (SLE), allergy, asthma and rheumatoid arthritis, comprising the step of administering to a subject in need thereof, a pharmaceutically active amount of the polypeptide as described herein, a construct as described herein, or a composition as described herein. The present invention also provides the use of a polypeptide as described herein, a construct as described herein, or a composition as described herein, for the manufacture of a medicament for the prevention, treatment and/or amelioration of an inflammatory condition chosen from the group consisting of Autoimmune Lupus (SLE), allergy, asthma and rheumatoid arthritis.

The polypeptides, constructs and compositions of the present invention can also be used in combination with another therapeutic drug. Accordingly, in a further aspect, the present invention provides a polypeptide as described herein, a construct as described herein, a composition as described herein, for use in a combination treatment.

The present invention also provides a method as described herein, wherein the treatment is a combination treatment.

In a further aspect, the present invention provides the use of a polypeptide as described herein, a construct as described herein, or a composition as described herein, for the manufacture of a medicament for the prevention, treatment and/or amelioration as described herein, wherein the treatment is a combination treatment.

In a further aspect, the present invention provides a kit comprising a polypeptide as described herein, a construct as described herein, a nucleic acid as described herein, an expression vector as described herein or a host or host cell as described herein.

The MFI value (median channel fluorescence intensity) is plotted against the concentration.

Figure 14:
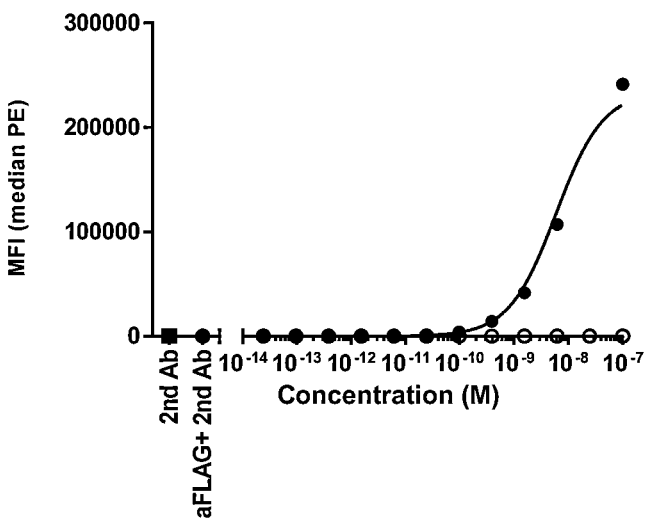
Figure 14:
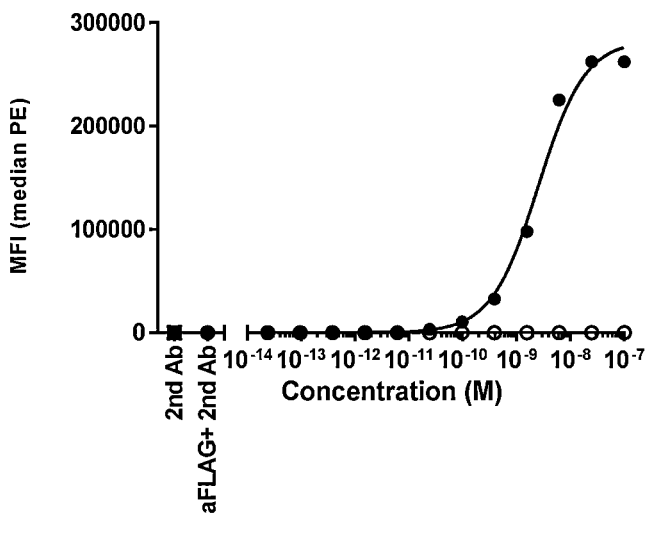

FIG. 14: Dose-dependent binding of A0110055F03 to Flp-In parental cells (open symbol) and CD123 transfected cells (closed symbol). The MFI value (median channel fluorescence intensity) is plotted against the concentration.

Figure 15:
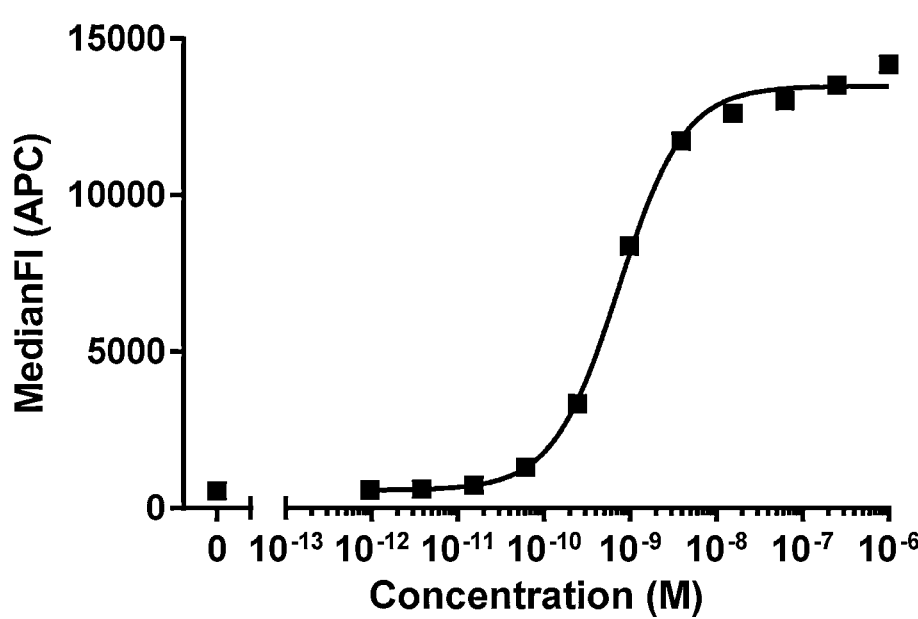
Figure 15:
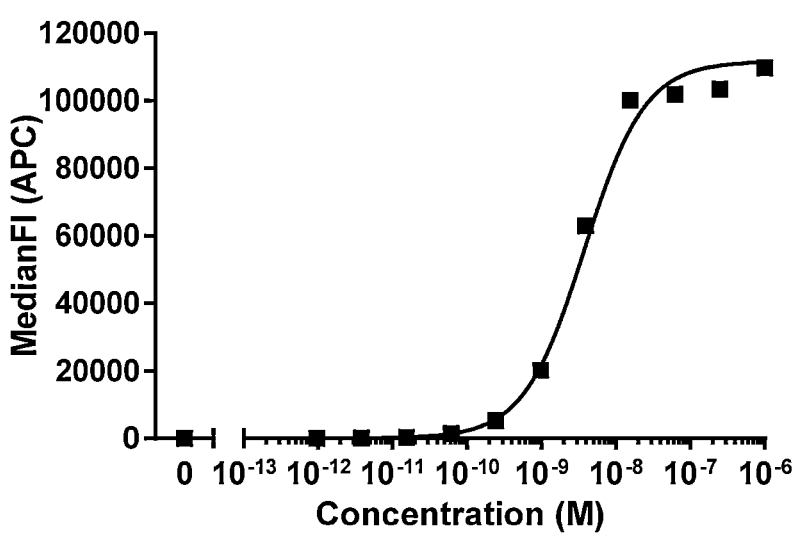

FIG. 15: Dose-dependent binding of the monovalent anti-CD123 Nanobody A0110056A10-Alexa 647 to MOLM-13 cells and on human CD123 transfected CHO Flp-In cells. The MFI value (median channel fluorescence intensity) is plotted against the concentration.

Figure 16:
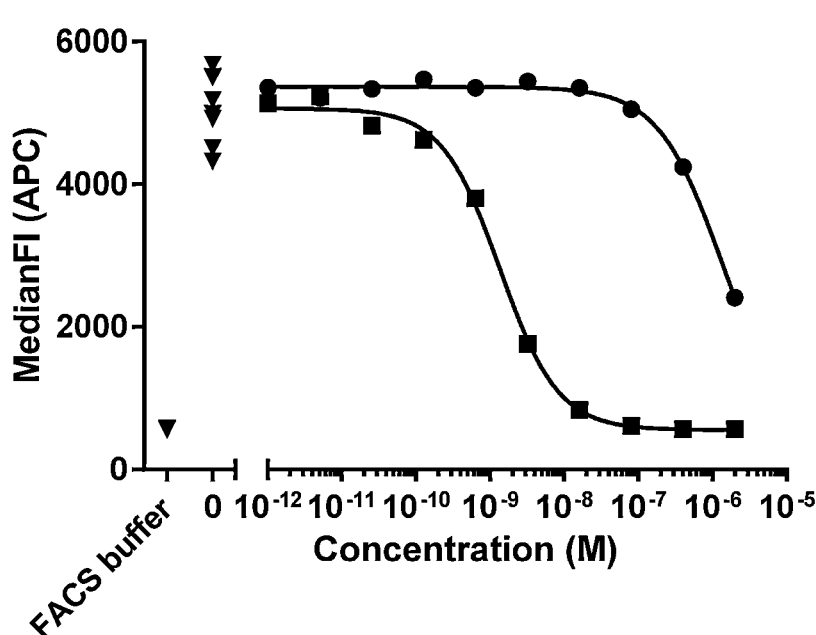
Figure 16:
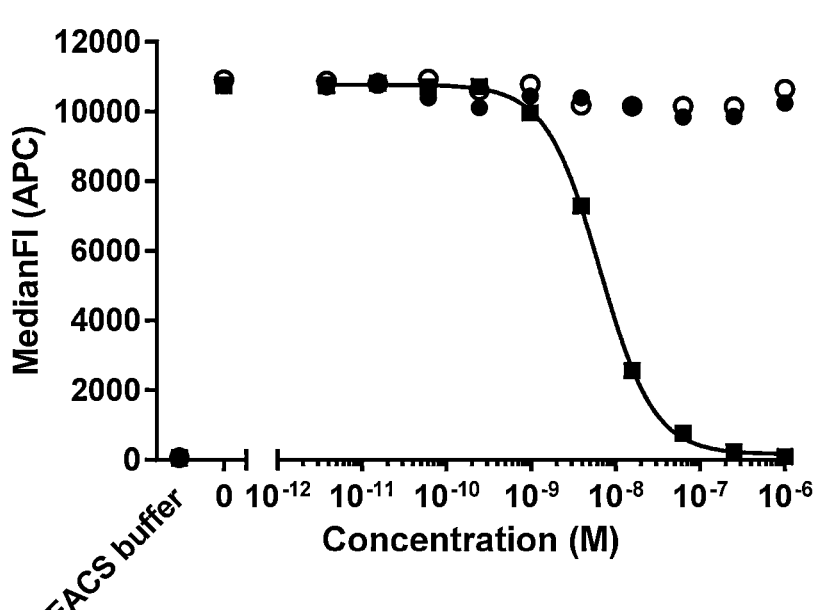

FIG. 16: Dose-dependent competition of the monovalent Nanobodies A0110056A10 (squares) and A0110055F03 (circles) with Alexa 647-labelled A0110056A10 for binding to human CD123 on MOLM-13 and on human CD123 transfected CHO Flp-In cells. The MFI value (median channel fluorescence intensity) is plotted against the concentration.

Figure 17:
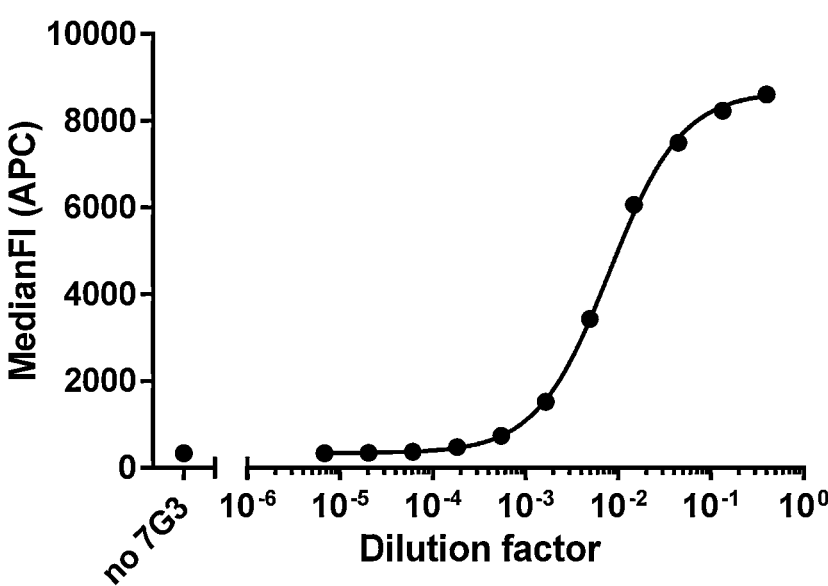
Figure 17:
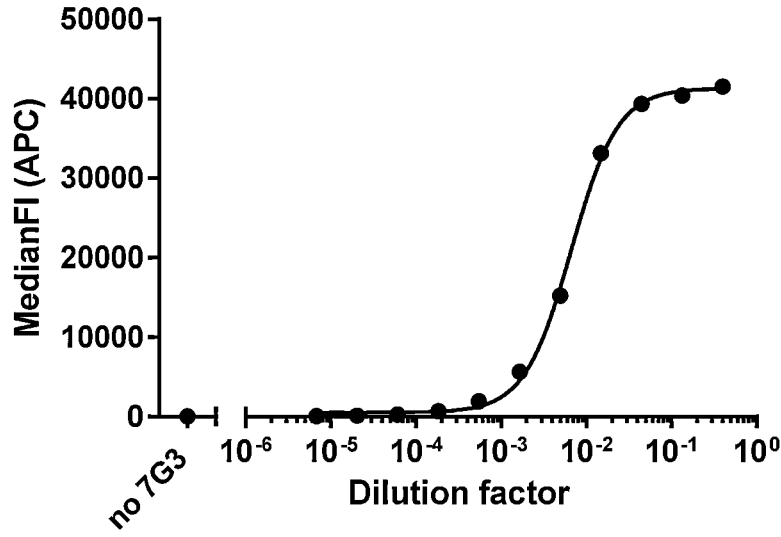

FIG. 17: Dose-dependent binding of the APC-labelled mouse anti-human CD123 (clone 7G3) antibody to human CD123 on MOLM-13 and on human CD123 transfected CHO Flp-In cells. The MFI value (median channel fluorescence intensity) is plotted against the concentration.

Figure 18:
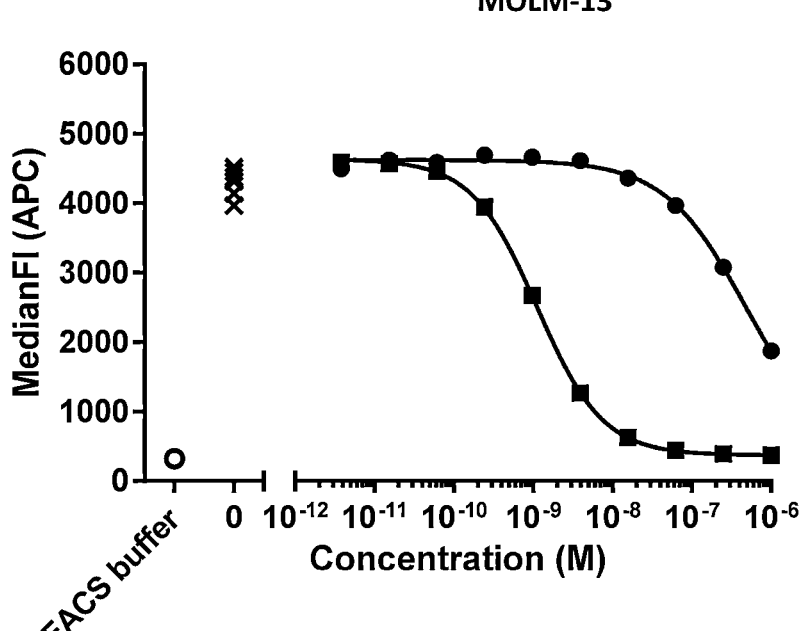
Figure 18:
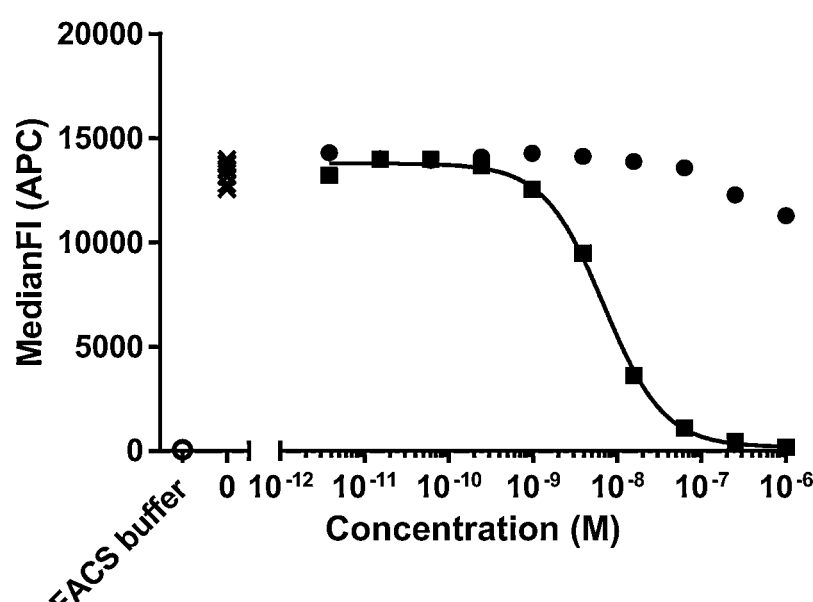

FIG. 18: Dose-dependent competition of the monovalent Nanobodies A0110056A10 (squares) and A0110055F03 (circles) with APC-labelled mouse anti-human CD123 (clone 7G3) antibody for binding to CD123 expressed on MOLM-13 or to CHO Flp-In cells transfected with huCD123. The MFI value (median channel fluorescence intensity) is plotted against the concentration.

Figure 19:
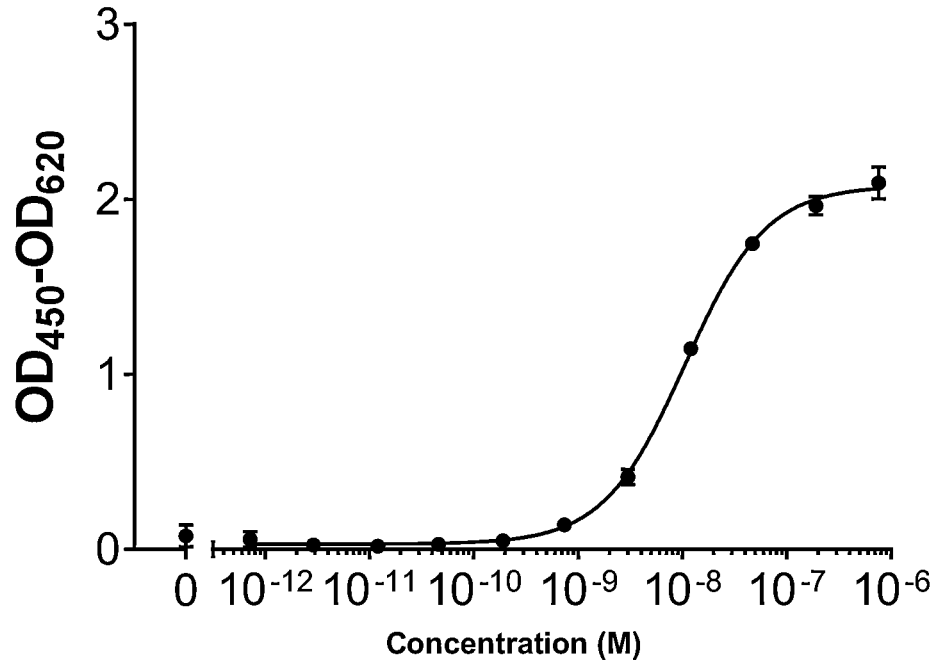

FIG. 19: Dose-dependent binding of the mouse anti-human CD123 (clone 7G3) antibody to in house biotinylated CD123 recombinant protein (R&D Systems, Cat. no. 301-R3/CF). The OD at 450 nm is plotted against the concentration.

Figure 20:
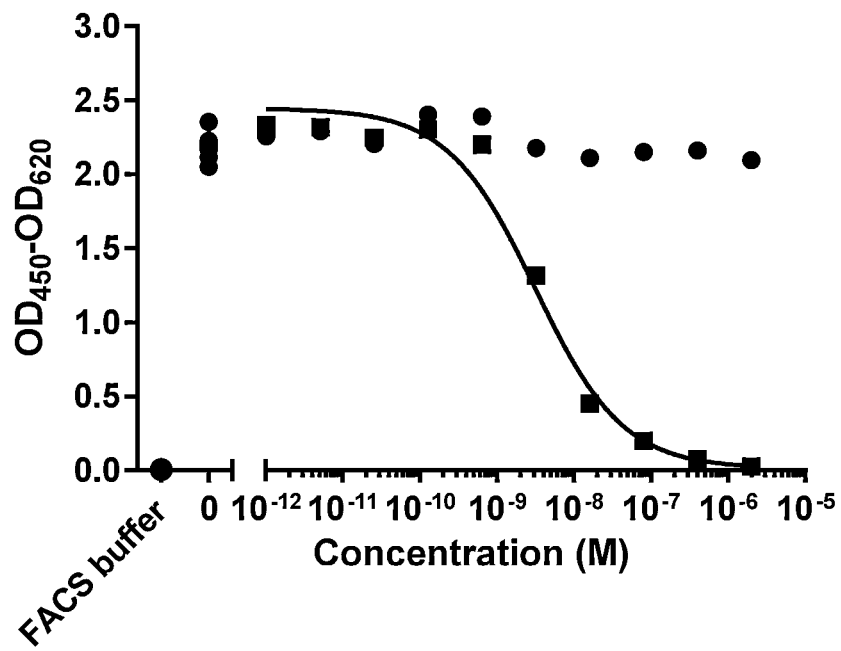
Figure 20:
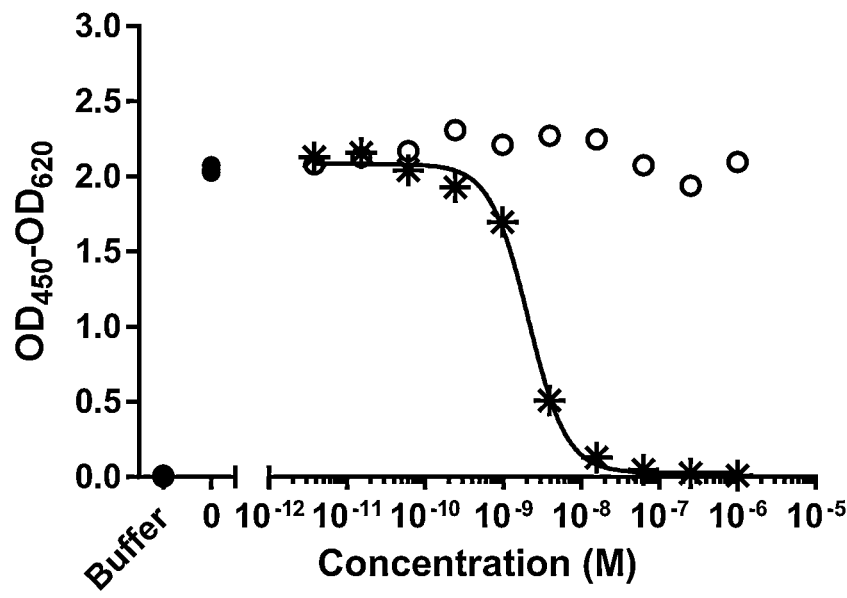

FIG. 20: Dose-dependent competition of the monovalent anti-CD123 Nanobodies A0110056A10 (squares) and A0110055F03 (closed circles) with mouse monoclonal anti-CD123 antibody (clone 7G3) (BD Biosciences, Cat no. 554527) for binding to the CD123 protein in ELISA. The irrelevant anti-egg lysozyme Nanobody cAbLys (open circles) and the mouse monoclonal anti-CD123 antibody (clone 7G3) in solution (stars) were taken along as negative and positive control, respectively. The OD at 450 nm is plotted against the concentration.

Figure 21:
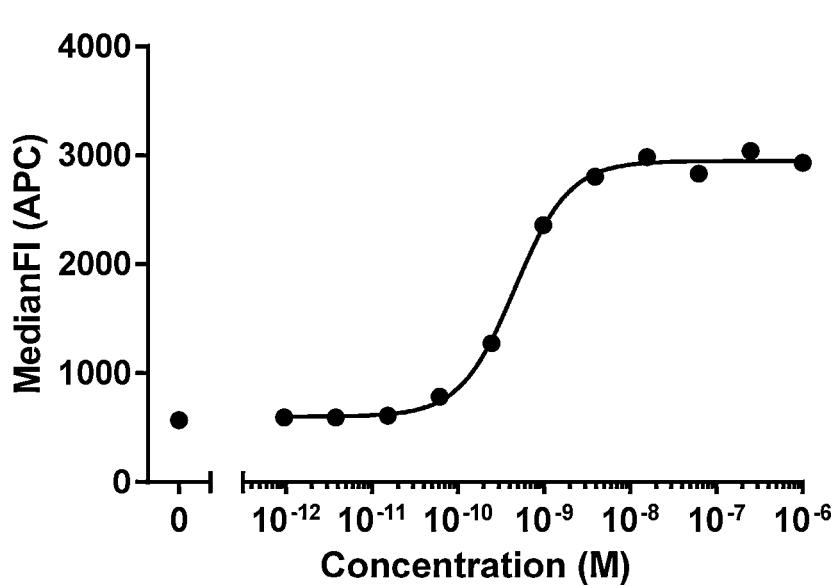
Figure 21:
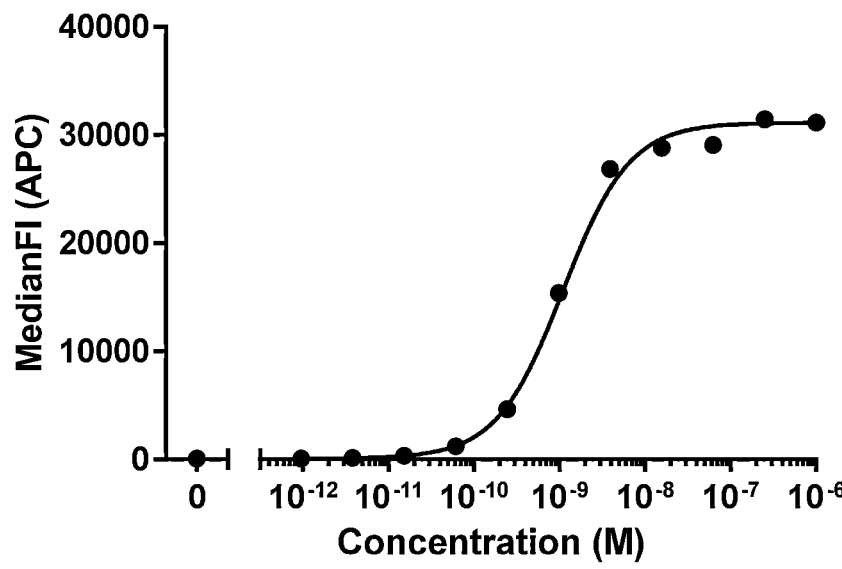

FIG. 21: Dose-dependent binding of the monovalent anti-CD123 Nanobody A0110056A10-Alexa 647 to MOLM-13 cells, to human CD123 transfected CHO Flp-In cells and to cyno CD123 transfected HEK Flp-In cells. The MFI value (median channel fluorescence intensity) is plotted against the concentration.

FIG. 22: Dose-dependent competition of the multivalent CD123/TCR binding polypeptides with Alexa647-A0110056A10 for binding to CD123 expressed on MOLM-13 cells and on huCD123 or cyCD123 transfected on CHO Flp-In or HEK Flp-In cells. The irrelevant multivalent polypeptide T017000129 was taken along as negative control. The MFI value (median channel fluorescence intensity) is plotted against the concentration.

Figure 23:
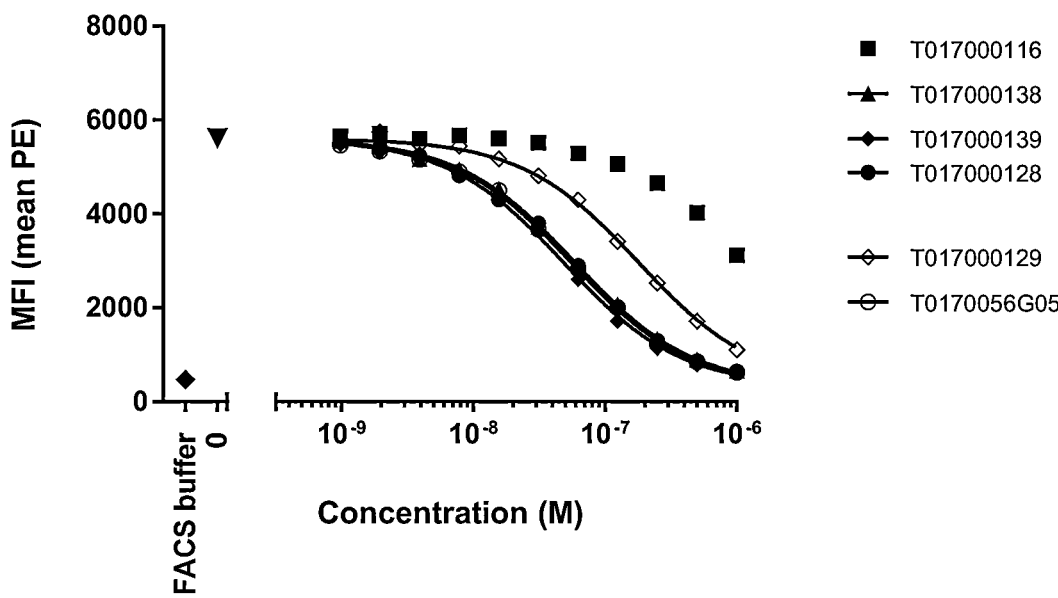

FIG. 23: Dose-dependent competition of the multivalent CD123/TCR binding polypeptides with biotinylated-T0170056G05 for binding to human TCR/CD3 expressed on CHO-K1 cells. The MFI value (median channel fluorescence intensity) is plotted against the concentration.

Figure 24:
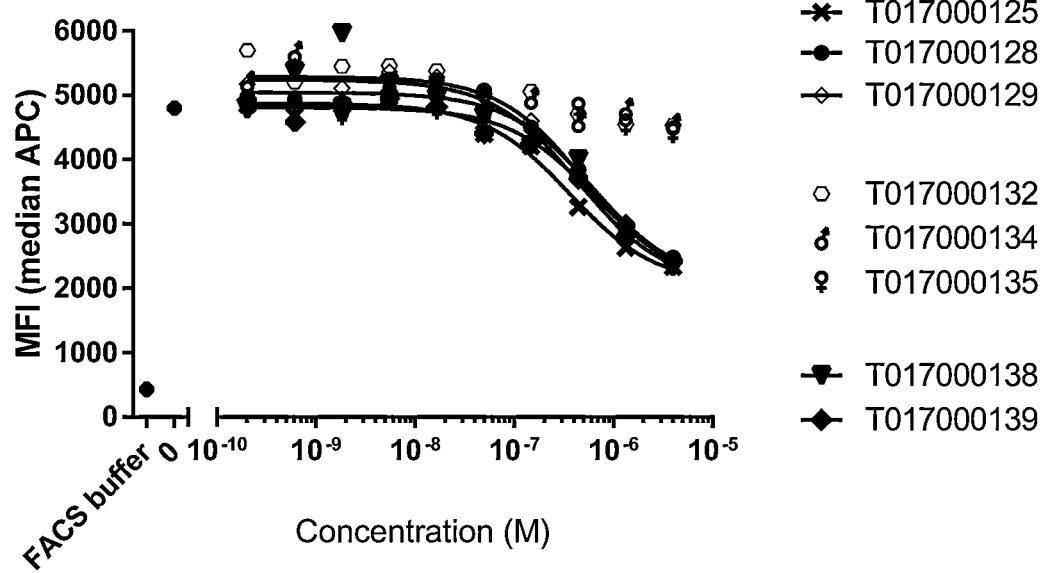

FIG. 24: Dose-dependent competition of the multivalent CD123/TCR binding polypeptides with T017000099 for binding to CD3/TCR expressed on HSC-F. The monovalent His tagged T017000125 was taken along as positive control. The MFI value (median channel fluorescence intensity) is plotted against the concentration.

Figure 25:
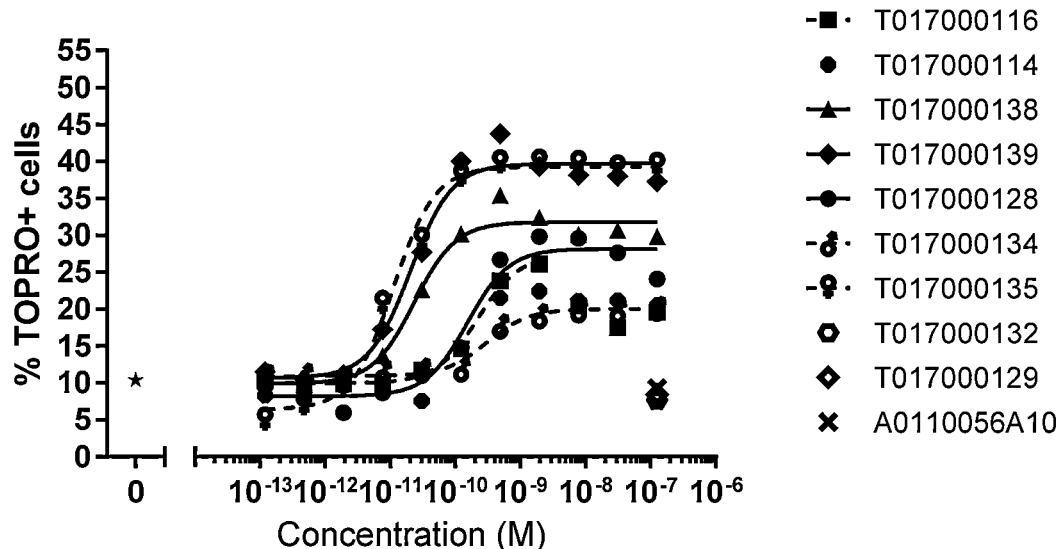

FIG. 25: Dose-dependent redirected human effector T cell killing of human CD123 expressing MOLM-13 cells in a flow cytometry based assay by multivalent CD123/TCR binding polypeptides using an effector to target ratio of 10:1. A0110056A10, T017000132 and T017000129 were taken along as negative control. The % cell death (% of TOPRO positive cells) was plotted against the concentration of the construct.

Figure 26:
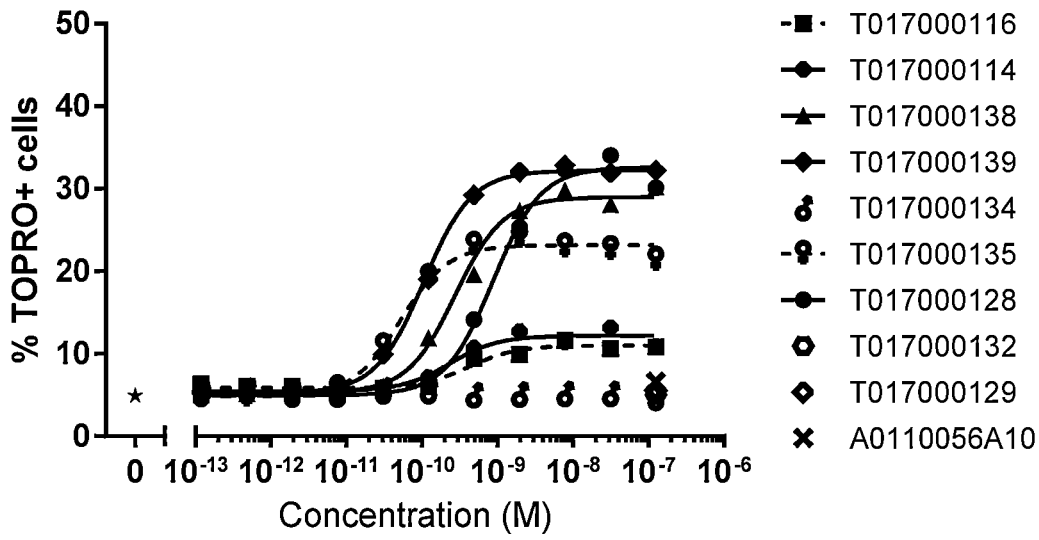

FIG. 26: Dose-dependent redirected human effector T cell killing of human CD123 expressing KG1a cells in a flow cytometry based assay by multivalent CD123/TCR binding polypeptides using an effector to target ratio of 10:1. A0110056A10, T017000129 and T017000132 were taken along as negative controls. The % cell death (% of TOPRO positive cells) was plotted against the concentration of the construct.

Figure 27:
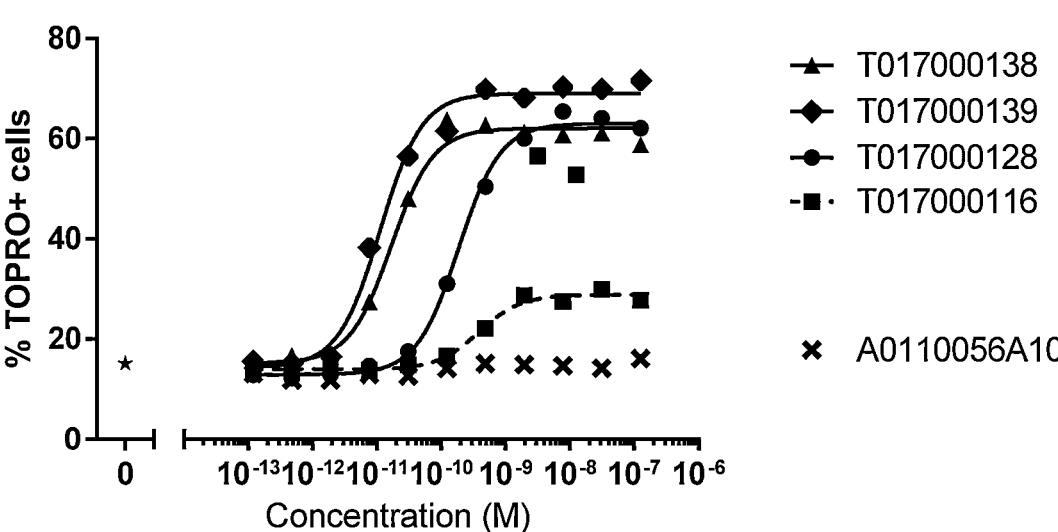

FIG. 27 Dose-dependent redirected cynomolgus effector T cell killing of human CD123 positive MOLM-13 cells in a flow cytometry based assay by multivalent CD123/TCR binding polypeptides using an effector to target ratio of 10:1. A0110056A10 was taken along as negative controls. The % cell death (% of TOPRO positive cells) was plotted against the concentration of the construct.

Figure 28:
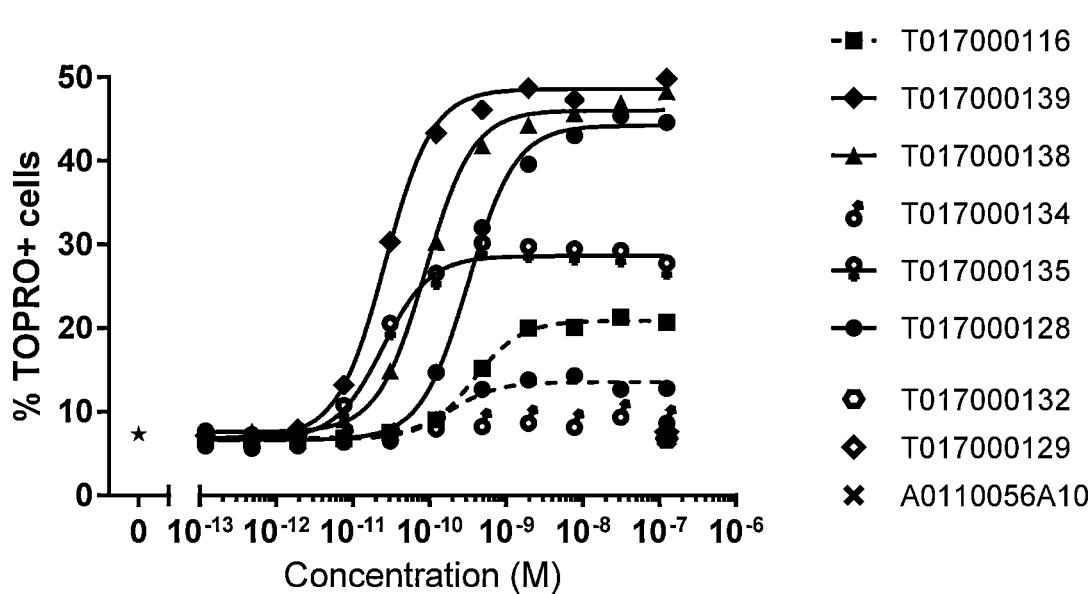

FIG. 28: Dose-dependent redirected cynomolgus effector T cell killing of human CD123 positive KG1a cells in a flow cytometry based assay by multivalent CD123/TCR binding polypeptides using an effector to target ratio of 8. Several irrelevant constructs were taken along as negative controls. The % cell death (% of TOPRO positive cells) was plotted against the concentration of the construct.

Figure 29:
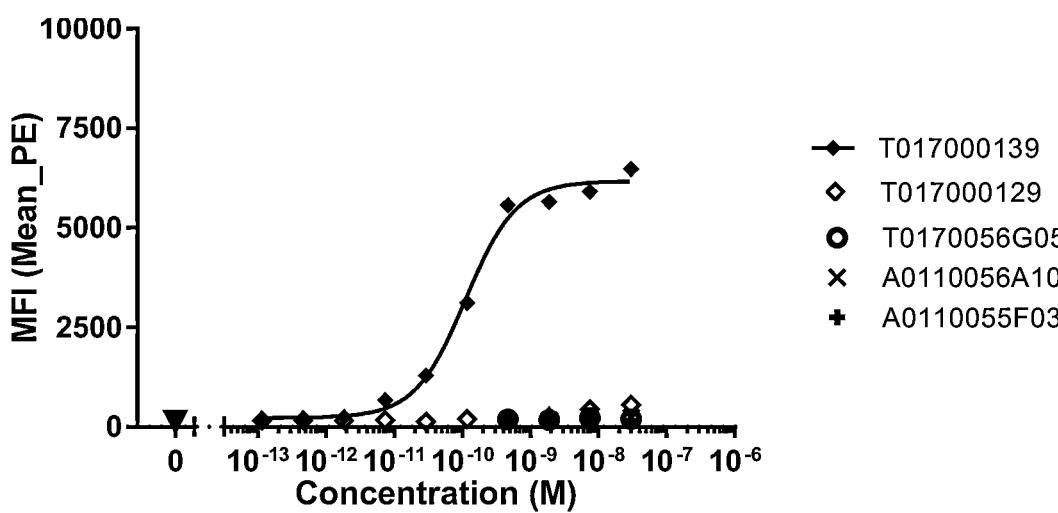

FIG. 29: Dose-dependent T cell activation (CD25 upregulation) by the multivalent CD123/TCR binding polypeptides on CD4/CD8+ gated T cell during the redirected cynomolgus effector T cell killing of human CD123 positive MOLM-13 cells after an incubation time of 72 h. The MFI (Mean fluorescence intensity) within CD4/CD8+ gated T cell was plotted against the concentration of the constructs.

Figure 30:
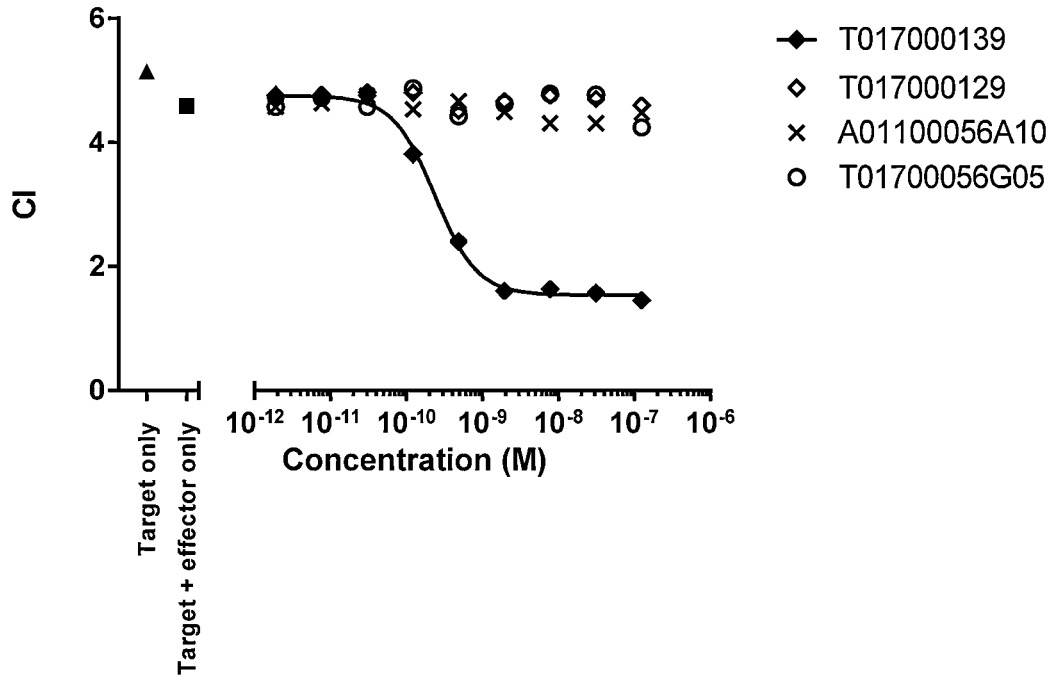

FIG. 30: Dose-dependent redirected human effector T cell killing of human CD123 transfected CHO Flp-In cells in an xCELLigence based assay by T017000139 (filled diamonds) using an effector to target ratio of 15:1. The monovalent Nanobodies A0110056A10, T0170056G05 and the irrelevant construct T017000129 were taken along as negative control. The Cell Index (CI) after an incubation time of 50 h was plotted against the concentration of the multispecific polypeptide.

Figure 31:
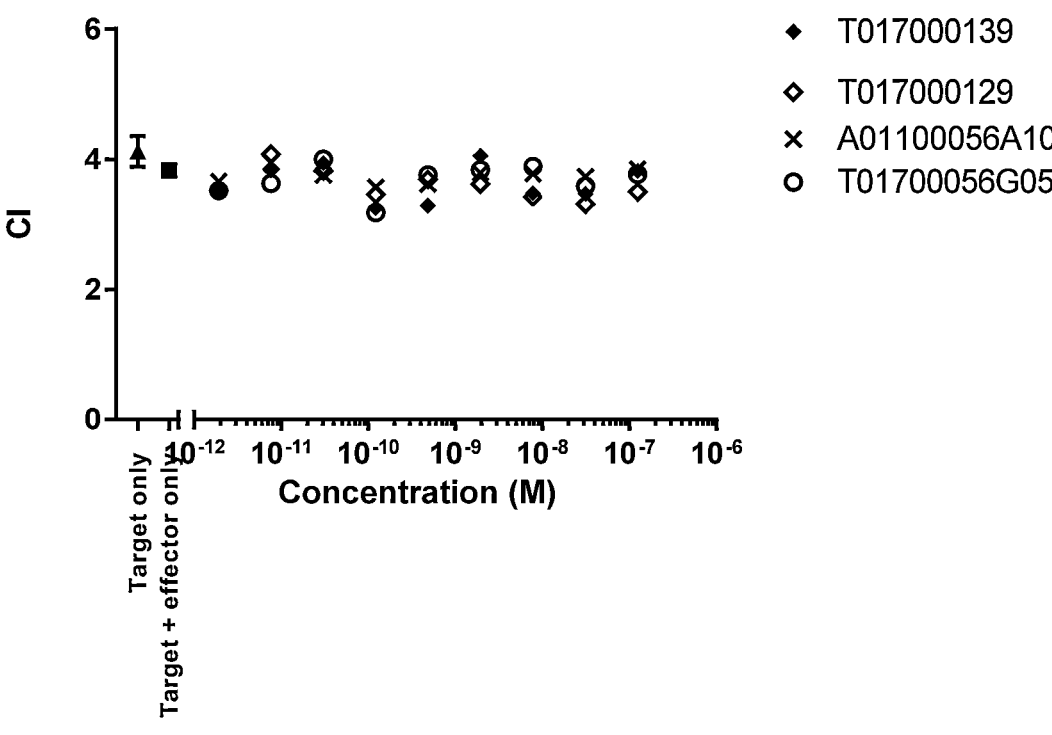

FIG. 31: Monovalent building blocks and multispecific polypeptides in the redirected human effector T cell killing assay using the CD123 negative CHO Flp-In reference cell line in an xCELLigence based assay using an effector to target ratio of 15:1. The CI after an incubation time of 50 h was plotted against the concentration of the multispecific polypeptide.

Figure 32:
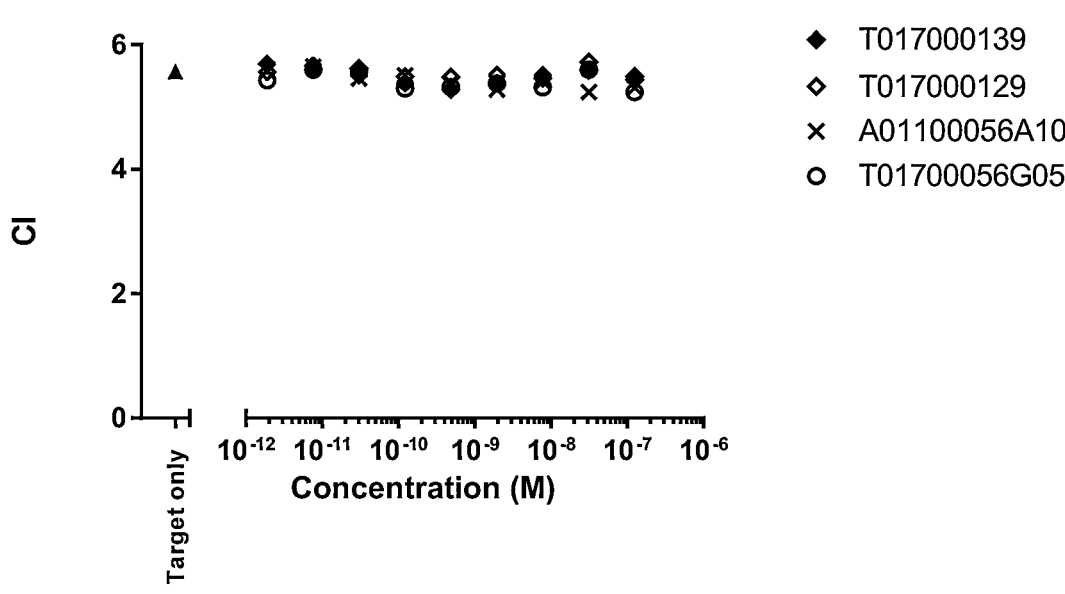

FIG. 32: Monovalent building blocks and multispecific CD123/TCR binding polypeptides on the growth of CD123 transfected and reference cell lines in the absence of T cells. The CI after an incubation time of 50 h was plotted against the concentration of the multispecific polypeptide.

FIG. 33: Dose-dependent redirected cynomolgus effector T cell killing of cynomolgus CD123 transfected HEK Flp-In cells in an xCELLigence based assay by T017000139 (filled diamonds) using an effector to target ratio of 15:1. The monovalent Nanobody, T0170056G05 and the irrelevant construct T017000129 were taken along as negative control.

The CI after an incubation time of 80 h was plotted against the concentration of the multispecific polypeptide.

Figure 34:
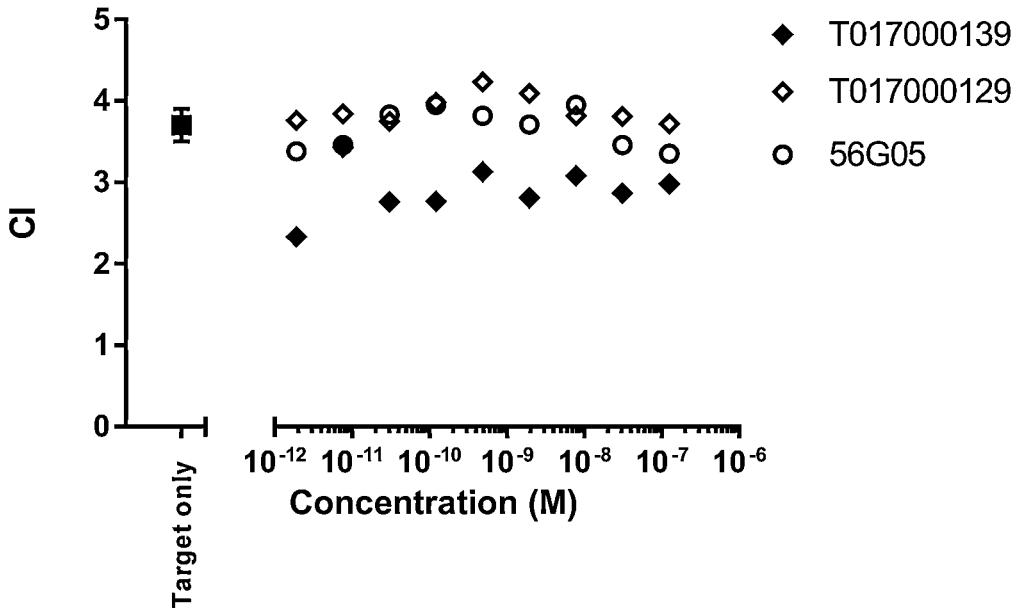

FIG. 34: Monovalent building block and multispecific polypeptides in the redirected cynomolgus T cell killing assay using the CD123 negative HEK Flp-In reference cell line. The CI after an incubation time of 80 h was plotted against the concentration of the multispecific polypeptide.

Figure 35:
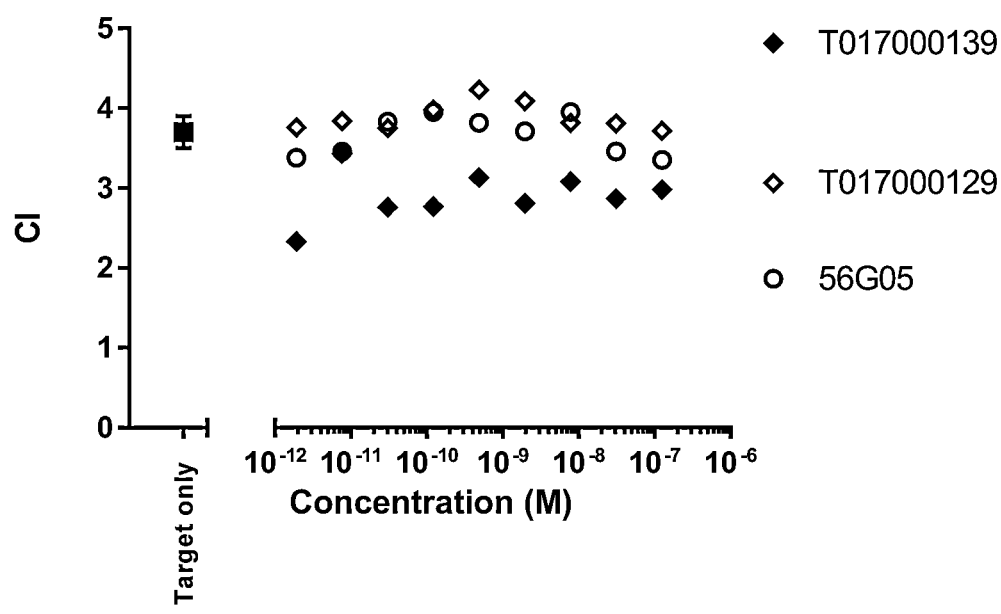

FIG. 35: Monovalent building block and multispecific CD123/TCR binding polypeptides on the growth of CD123 transfected and reference cell lines in the absence of T cells. The CI after an incubation time of 80 h was plotted against the concentration of the multispecific polypeptide.

FIG. 36: Dose-dependent cytokine production by effector T cells during multispecific CD123/TCR binding polypeptides dependent redirected T cell killing of human CD123 expressing CHO Flp-In target cells using an effector to target ratio of 10:1. INF-γ production was measured after 72 h. The OD value is plotted against the concentration.

FIG. 37: Dose-dependent cytokine production by effector T cells during multispecific CD123/TCR binding polypeptides dependent redirected T cell killing of human CD123 expressing CHO Flp-In target cells using an effector to target ratio of 10:1. IL-6 production was measured after 72 h. The pg/ml value is plotted against the concentration.

Figure 38:
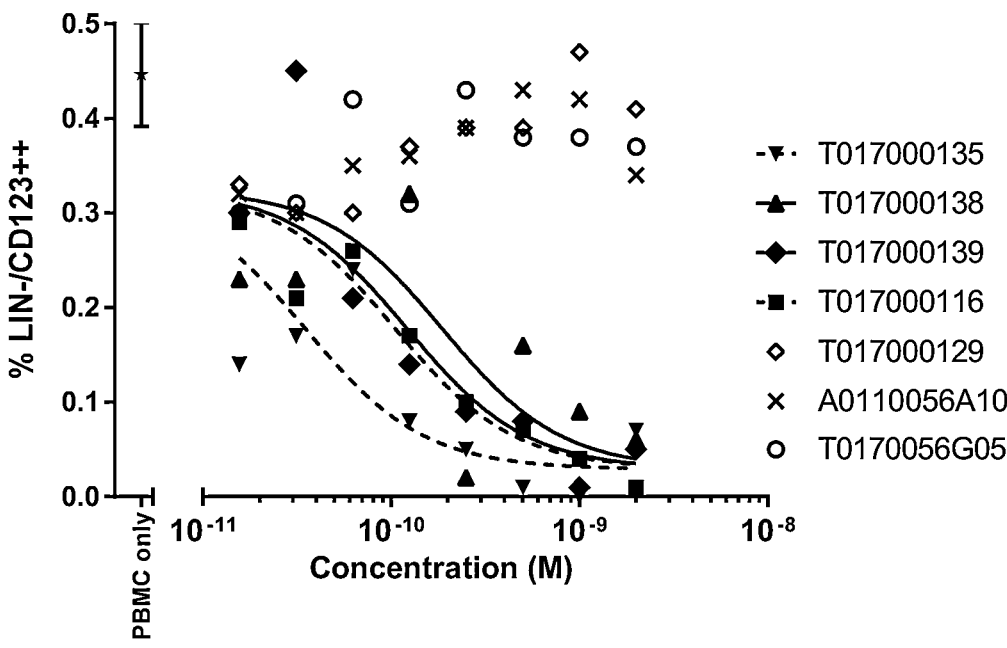
Figure 38:
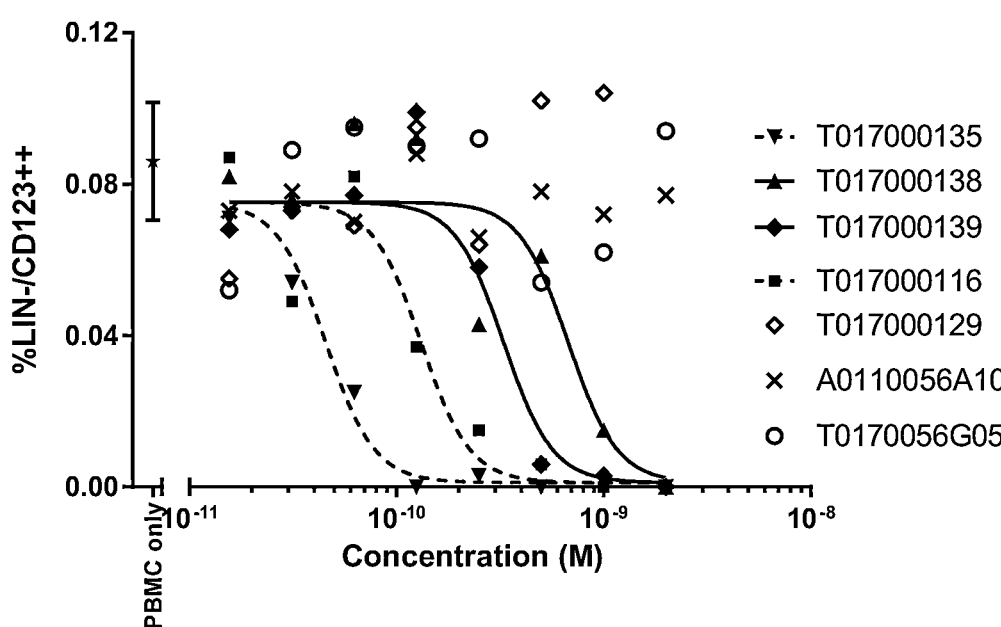

FIG. 38: Redirected autologous T cell mediated depletion of CD123+ pDCs and basophils by multivalent CD123/TCR binding polypeptides in healthy human and cynomolgus PBMC samples after an incubation time of 5 h. The percentage of Lin–/CD123+ cells (pDCs and basophils) was plotted against the concentration of the constructs.

Figure 39:
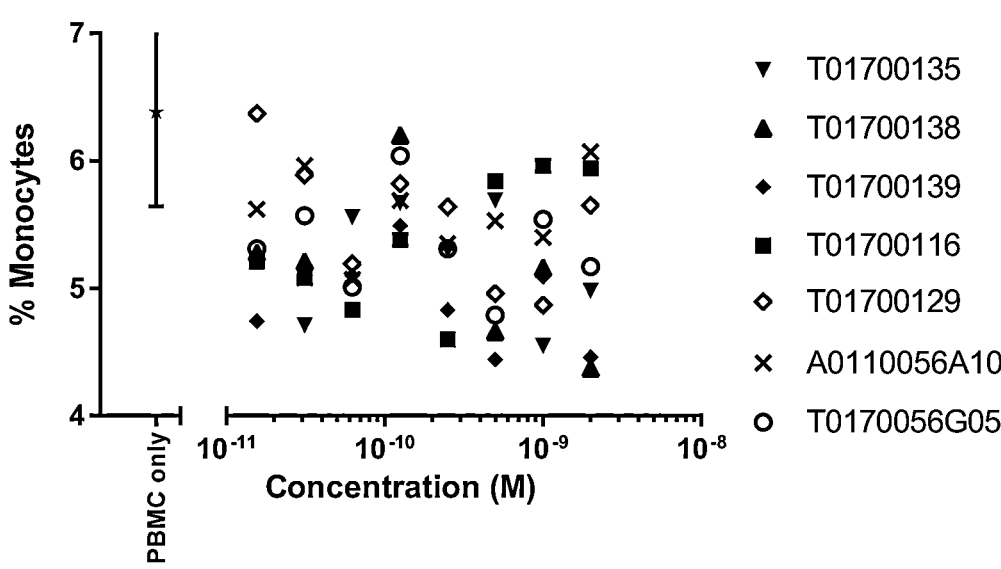
Figure 39:
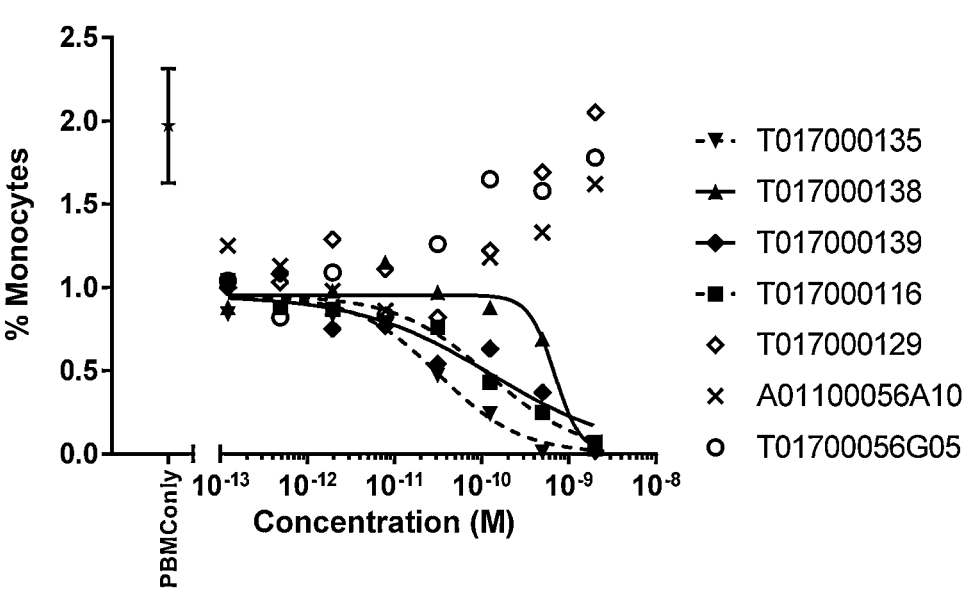

FIG. 39: Redirected autologous T cell monocyte depletion by multivalent CD123/TCR binding polypeptides in healthy human PBMC samples after an incubation time of 5 h (left) and 24 h (right). The percentage of monocytes (CD14+ cells) was plotted against the concentration of the constructs.

Figure 40:
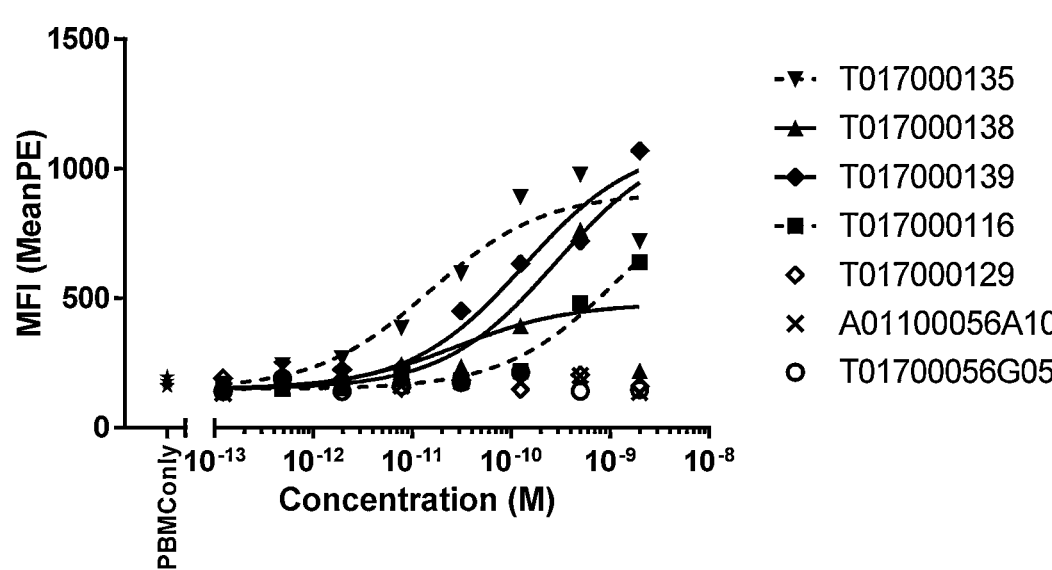

FIG. 40: Dose-dependent CD69 upregulation, human T cell activation by the multivalent CD123/TCR binding polypeptides on CD3+ gated T cell during redirected T cell killing of autologous CD123 positive cells after an incubation time of 24 h. The MFI (Mean fluorescence intensity) within CD3+ gated T cell was plotted against the concentration of the constructs.

Figure 41:
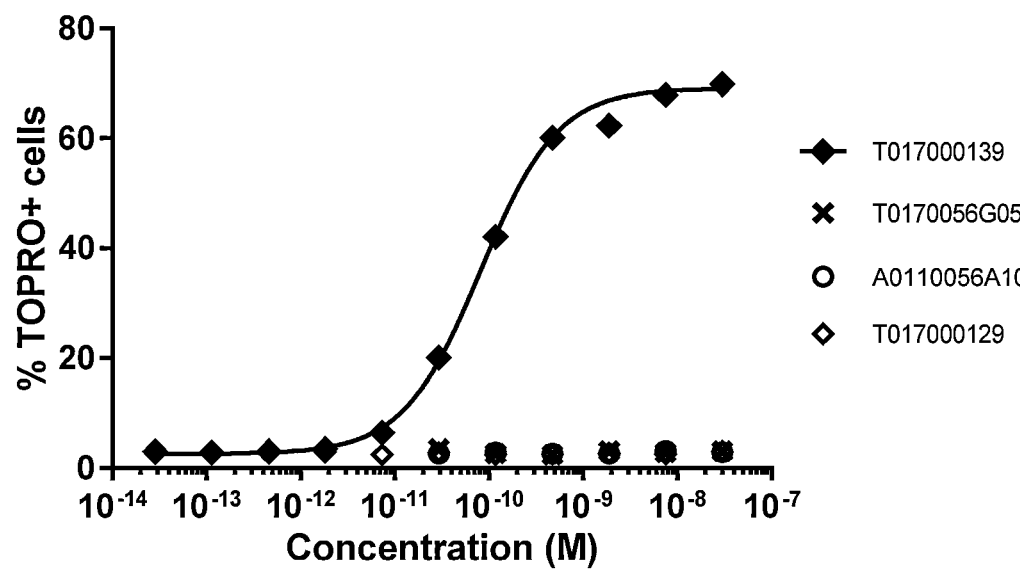
Figure 41:
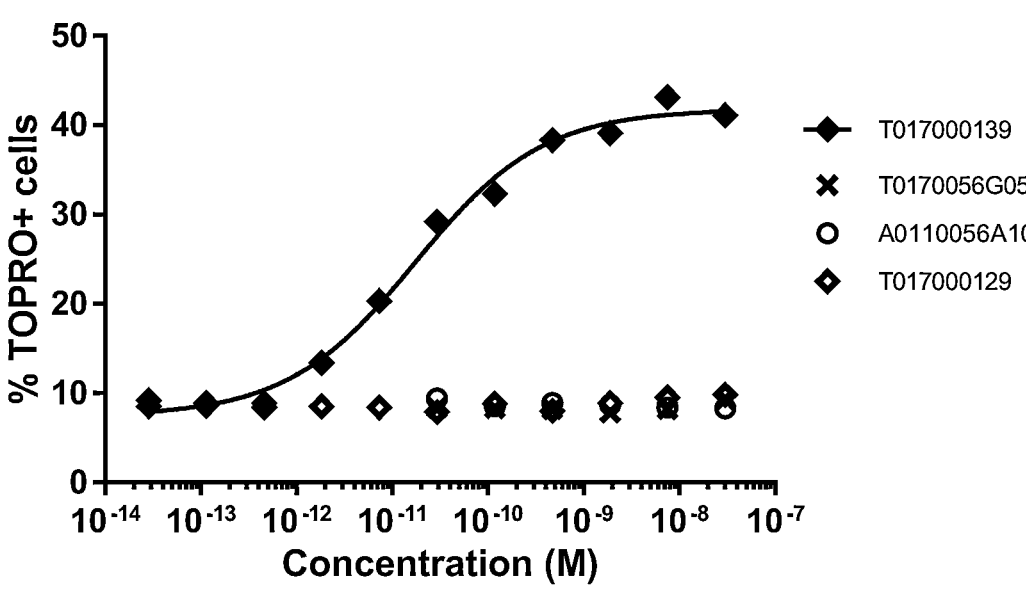

FIG. 41: Dose-dependent characterization of monovalent Nanobodies and the irrelevant multivalent polypeptide T017000129 for redirected human or cynomolgus effector T cell killing of human CD123 KG1a cells in a flow cytometry based assay using an effector to target ratio of 10:1. T017000139 (filled diamonds) was taken along as positive control. The % cell death (% of TOPRO positive cells) was plotted against the concentration of the construct.

Figure 42:
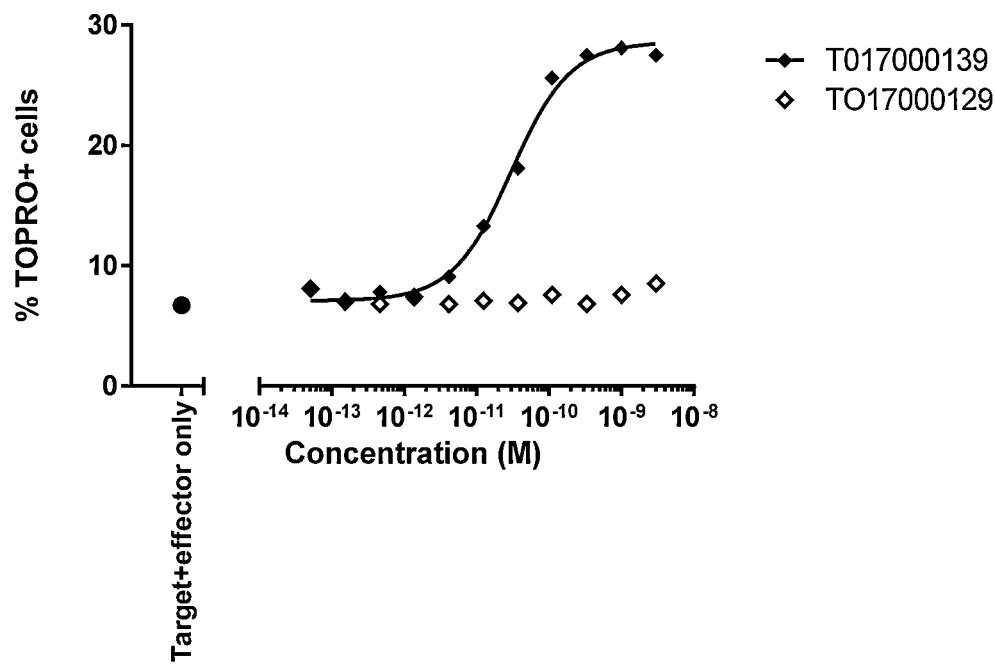
Figure 42:
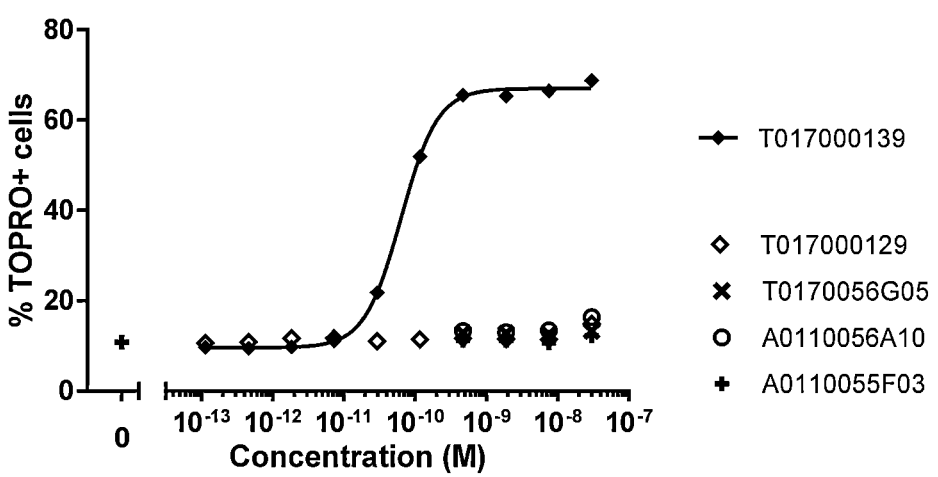

FIG. 42: Dose-dependent characterization of monovalent Nanobodies and the irrelevant multivalent polypeptide T017000129 for redirected human or cynomolgus effector T cell killing of human CD123 MOLM-13 cells in a flow cytometry based assay using an effector to target ratio of 10:1. T017000139 (filled diamonds) was taken along as positive control. The % cell death (% of TOPRO positive cells) was plotted against the concentration of the construct.

FIG. 43: Dose-dependent cytokine production by human effector T cells during multispecific CD123/TCR binding polypeptides dependent redirected T cell killing of MOLM-13 and KG1a target cells using an effector to target ratio of 10:1. Human IL-6 (FIG. 43C) and IFN-γ (FIGS. 43A and 43B) production was measured after 72 h. The concentration of cytokine is plotted against the concentration.

Figure 44:
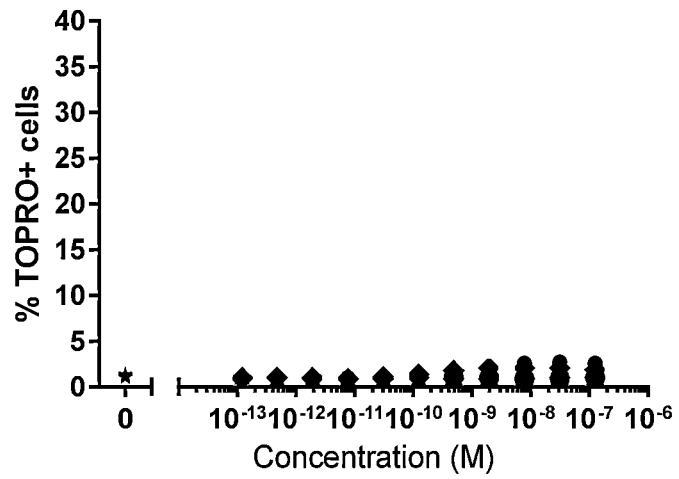
Figure 44:
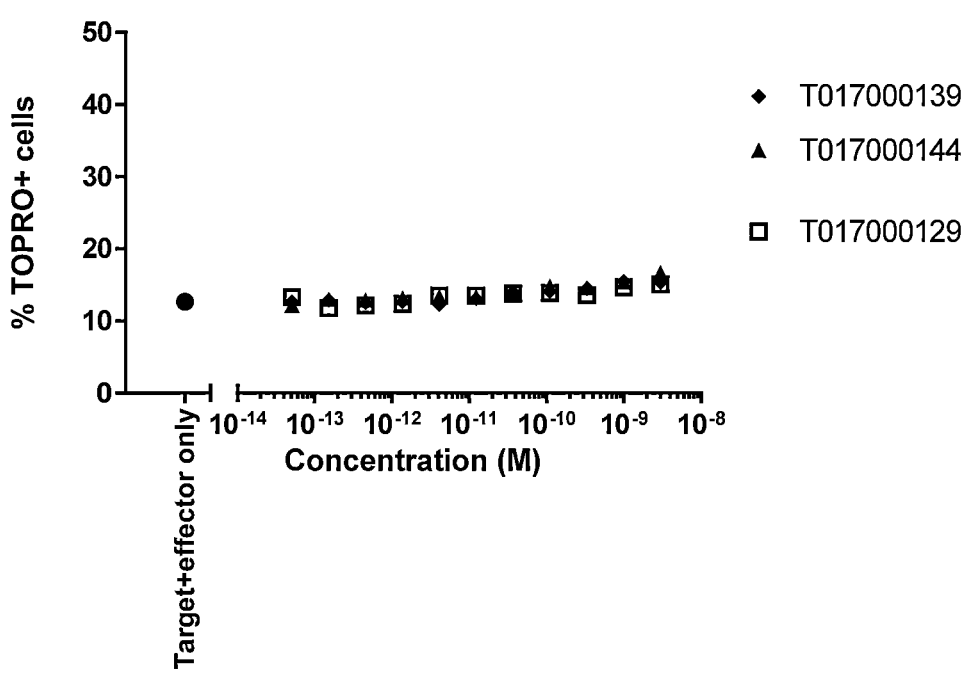

FIG. 44: Dose-dependent characterization of target independent redirected human effector T cell killing by multispecific CD123/TCR binding polypeptides in a flow cytometry based assay using CD123 negative NCI-H929 cell line. The % cell death (% of TOPRO positive cells) was plotted against the concentration of the construct.

Figure 45:
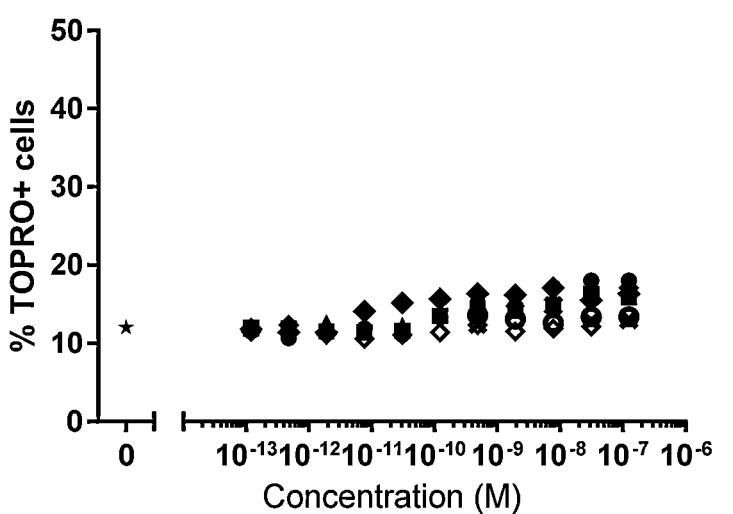
Figure 45:
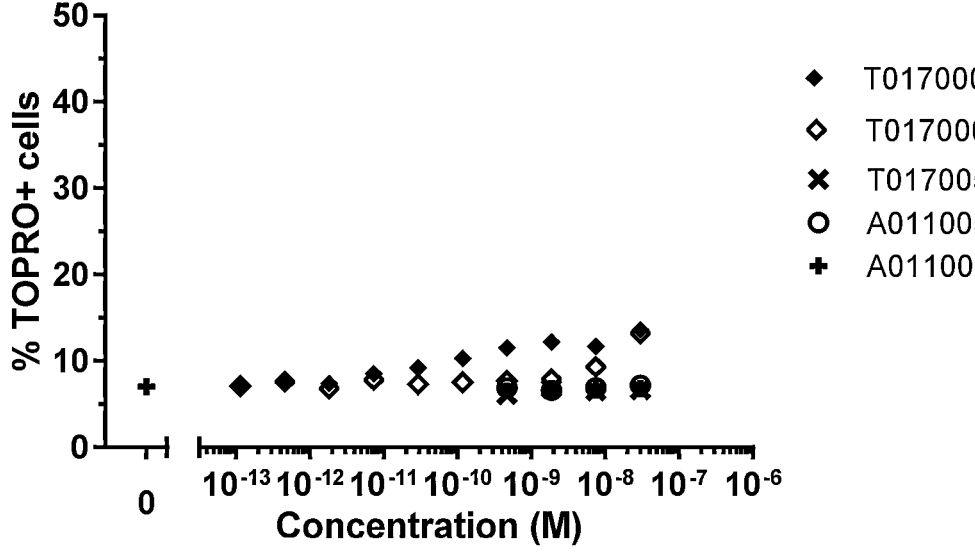

FIG. 45: Dose-dependent characterization of target independent redirected human or cynomolgus effector T cell killing by multispecific CD123/TCR binding polypeptides in a flow cytometry based assay using CD123 negative U937 cell line. The % cell death (% of TOPRO positive cells) was plotted against the concentration of the construct.

Figure 46:
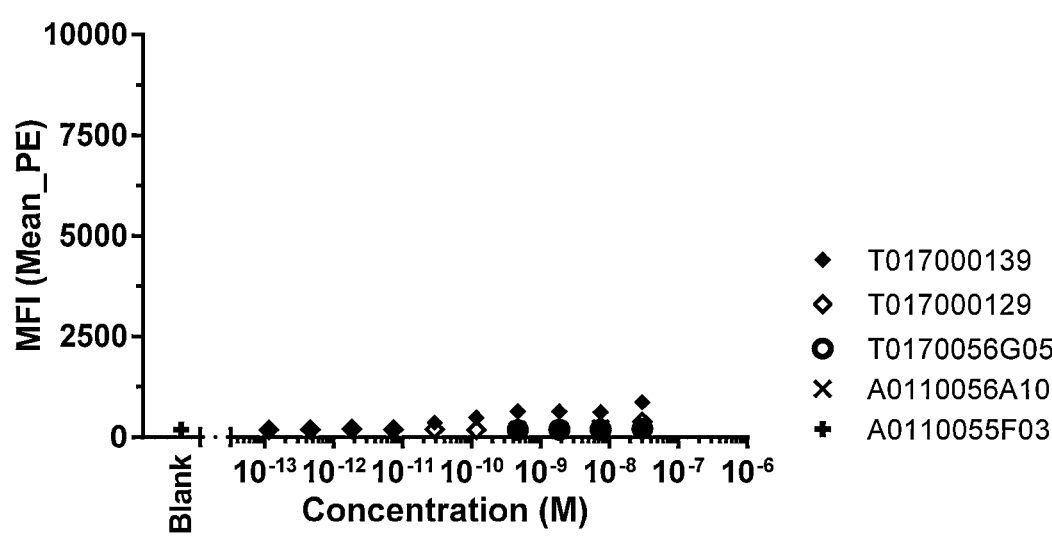
Figure 46:
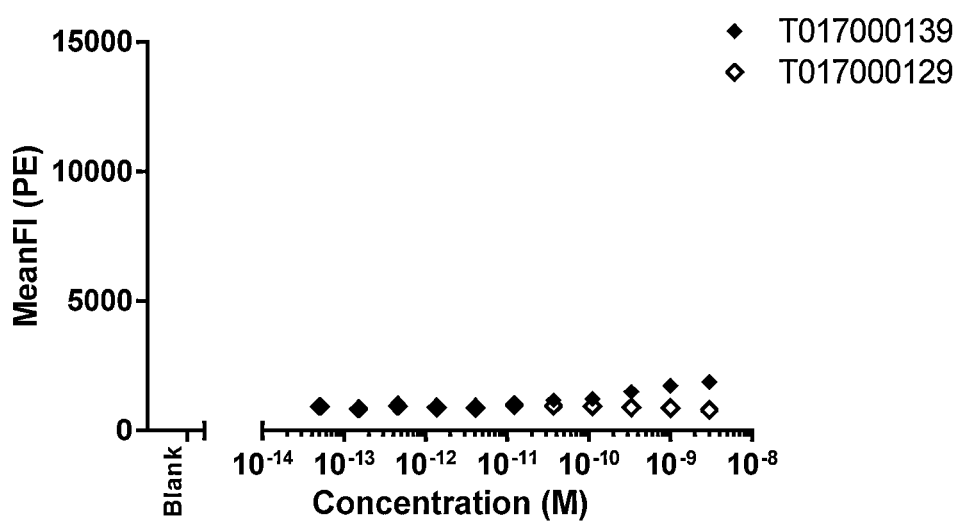

FIG. 46: Dose-dependent T cell activation readout by the multivalent CD123/TCR binding polypeptides on CD4/CD8+ gated T cell during the cynomolgus effector T cell killing of CD123 negative U-937 cells and during human effector T cell killing of CD123 negative NCI-H929 after an incubation time of 72 h. The MFI (Mean fluorescence intensity) within CD4/CD8+ gated T cell was plotted against the concentration of the constructs.

Figure 47:
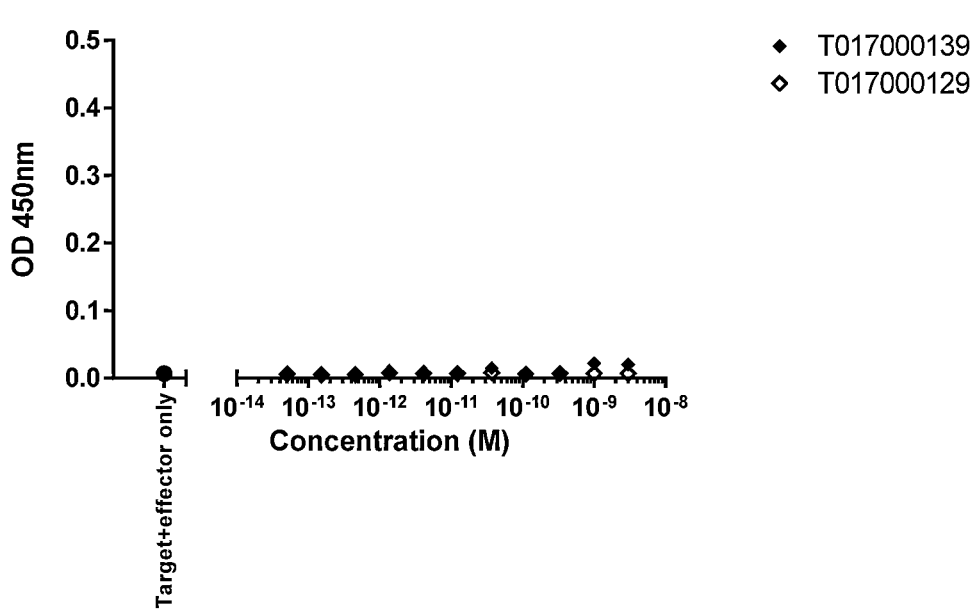
Figure 47:
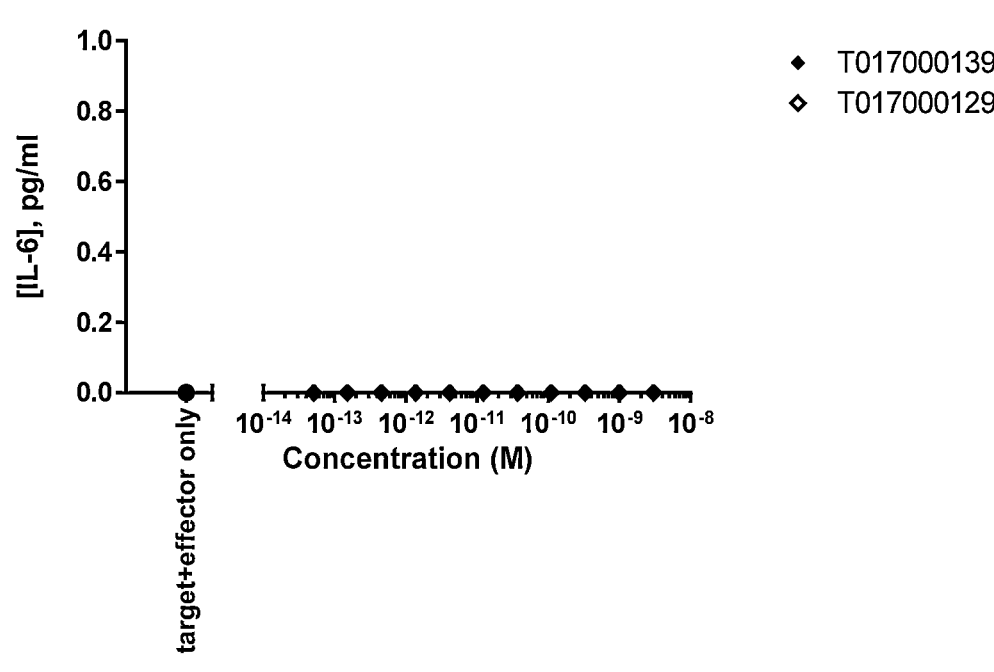

FIG. 47: Impact of multispecific CD123/TCR binding polypeptides on cytokine production using human effector T cells and NCI-H929 target cells using an effector to target ratio of 10:1. The OD value of amount of cytokine is plotted against the concentration.

Figure 48:
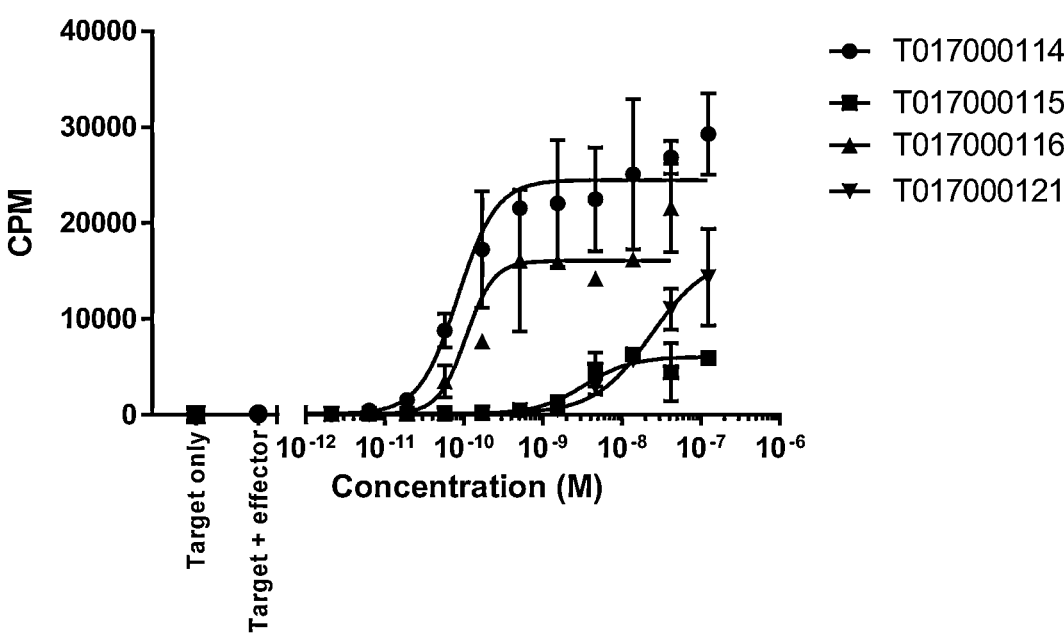
Figure 48:
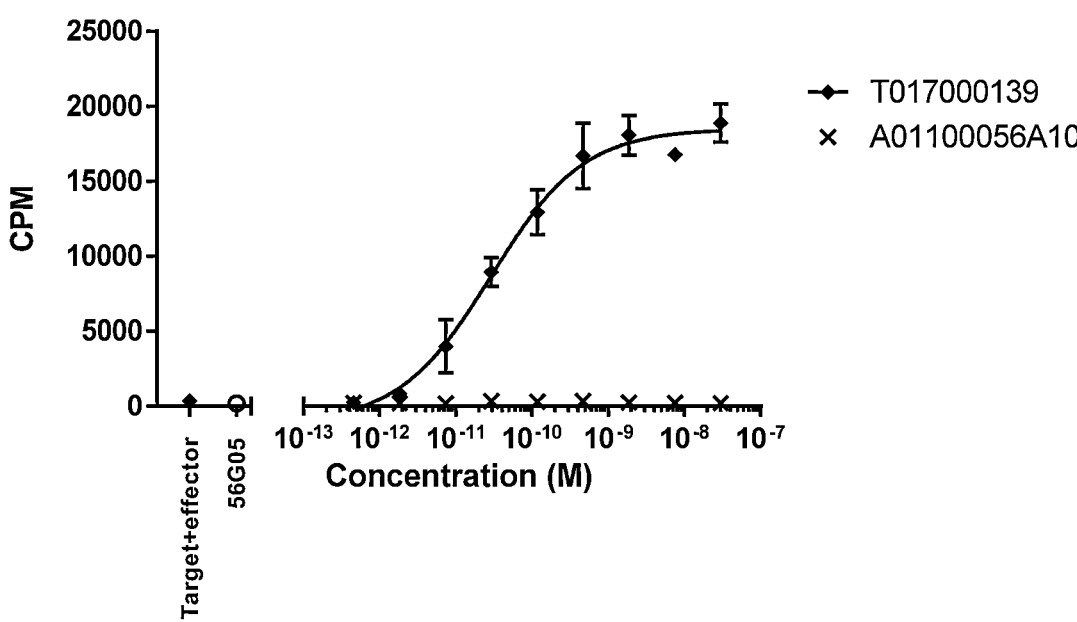

FIG. 48: Dose-dependent T cell proliferation of human effector T cells by multispecific polypeptides in a redirected MOLM-13 target cell killing setting using an effector to target ratio of 10:1. The CPM (count per minute) is plotted against the concentration.

Figure 49:
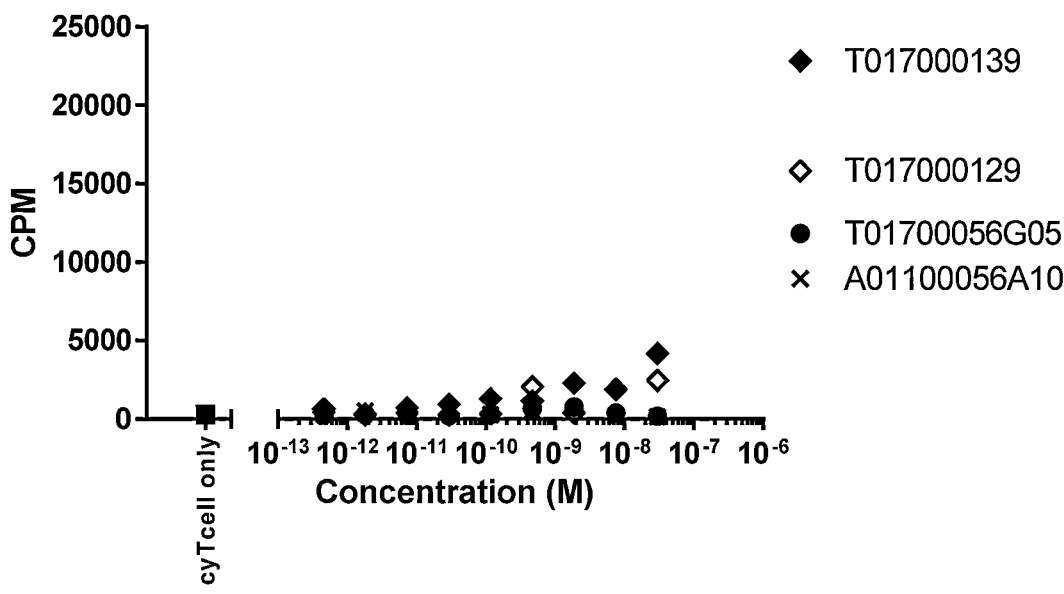

FIG. 49: Dose-dependent T cell proliferation of human effector T cells by multispecific polypeptides in absence of target cells. The CPM (count per minute) is plotted against the concentration.

Figure 50:
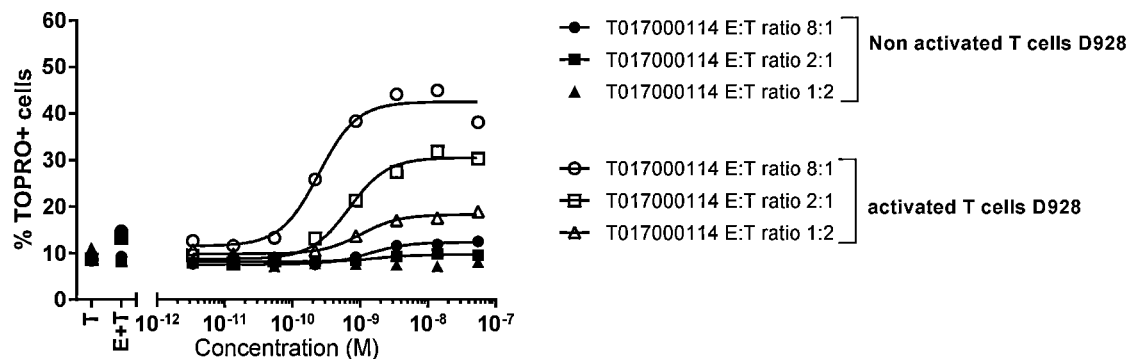

FIG. 50: Lytic potential of non-activated and pre-activated T cells in the presence of T017000114 and MOLM-13 cells at different E:T ratios.

Figure 51:
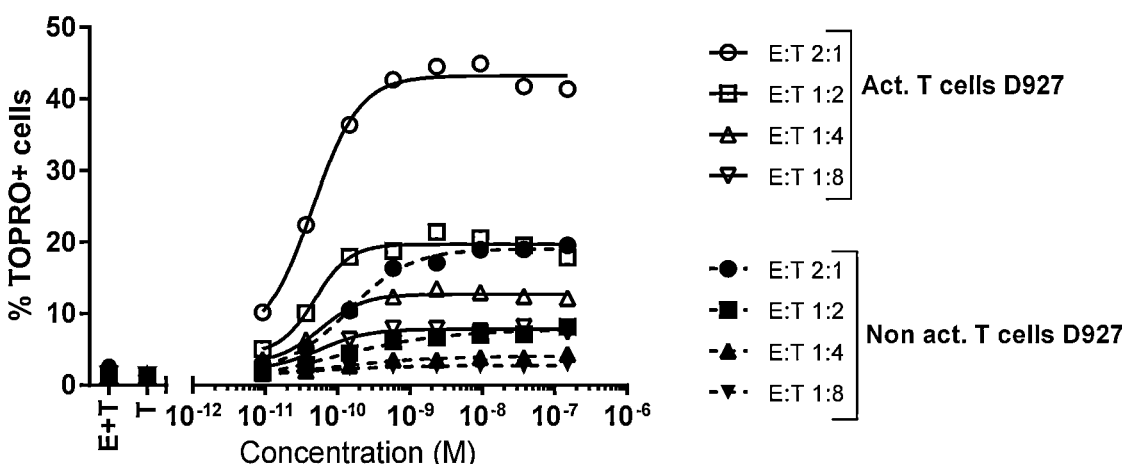

FIG. 51: Lytic potential of non-activated and pre-activated T cells in the presence of T017000139 and KG1a cells at different E:T ratios.

Figure 52:
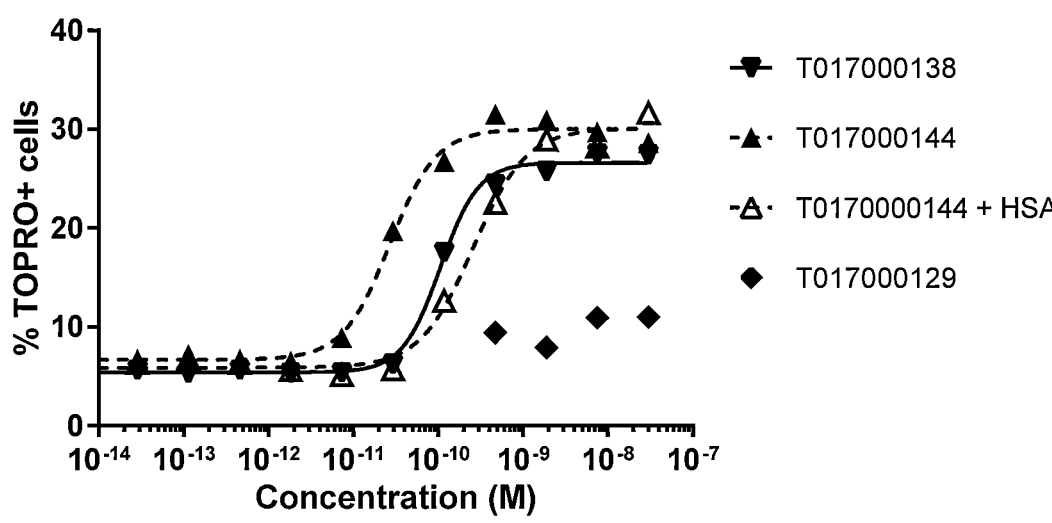
Figure 52:
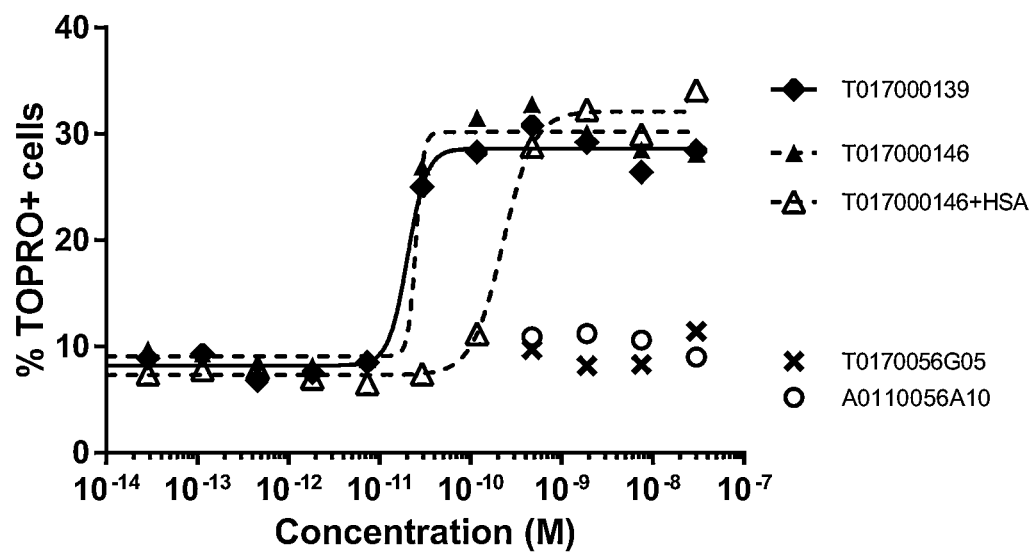

FIG. 52: Dose-dependent redirected T cell killing of MOLM-13 cells in the absence or presence of serum albumin in a flow cytometry based assay by multivalent CD123/TCR binding polypeptides, using an effector to target ratio of 10:1. The irrelevant multivalent polypeptide T017000129 and the monovalent building blocks A0110056A10 and T0170056G05 were taken along as negative control. The % cell death (% of TOPRO positive cells) was plotted against the concentration of the polypeptide.

Figure 53:
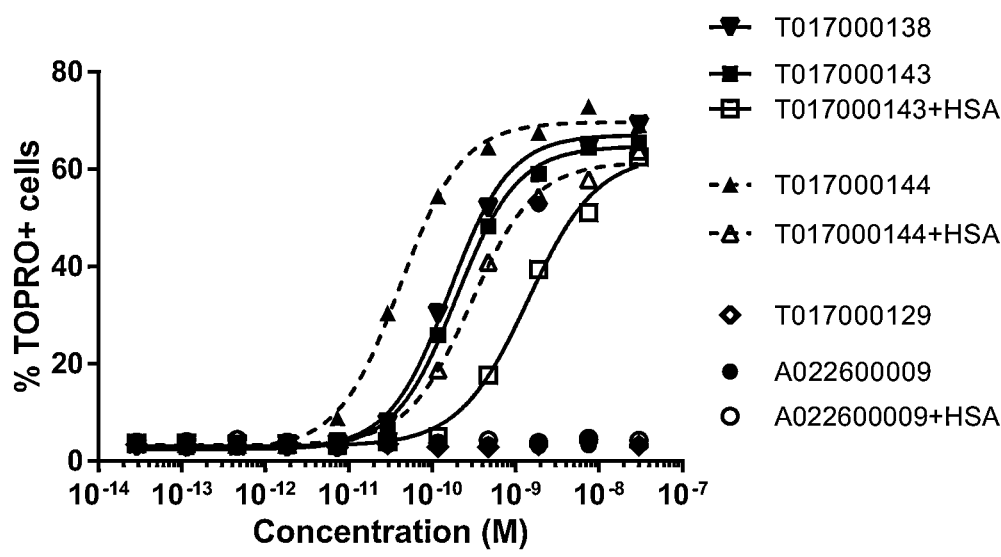
Figure 53:
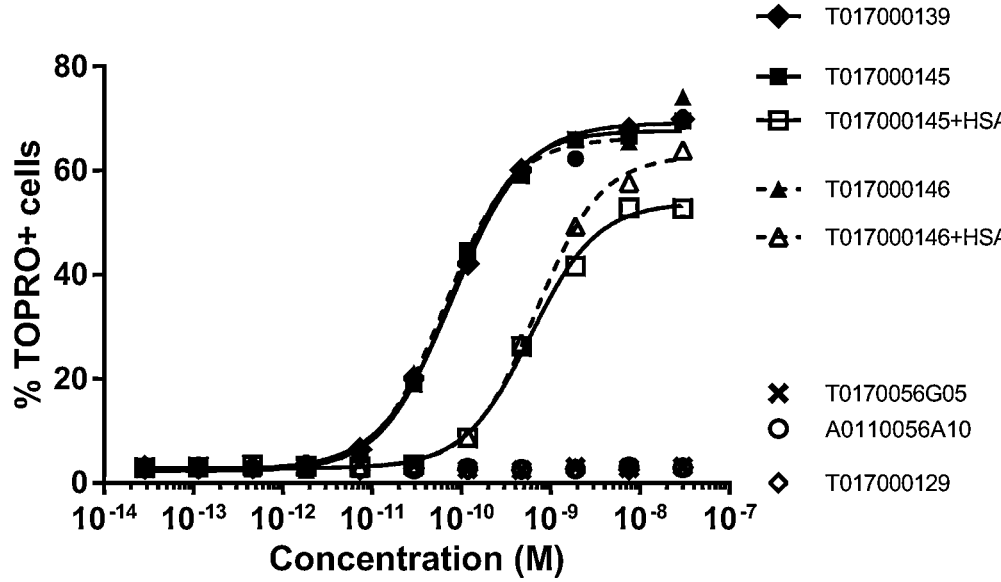

FIG. 53: Dose-dependent redirected T cell killing of KG1a cells in the absence or presence of serum albumin in a flow cytometry based assay by multivalent CD123/TCR binding polypeptides using an effector to target ratio of 10:1. The irrelevant multivalent polypeptides A022600009 (in the presence or absence of SA) and T017000129, and the monovalent building blocks A0110056A10 and T0170056G05 were taken along as negative control. The % cell death (% of TOPRO positive cells) was plotted against the concentration of the construct.

Figure 54:
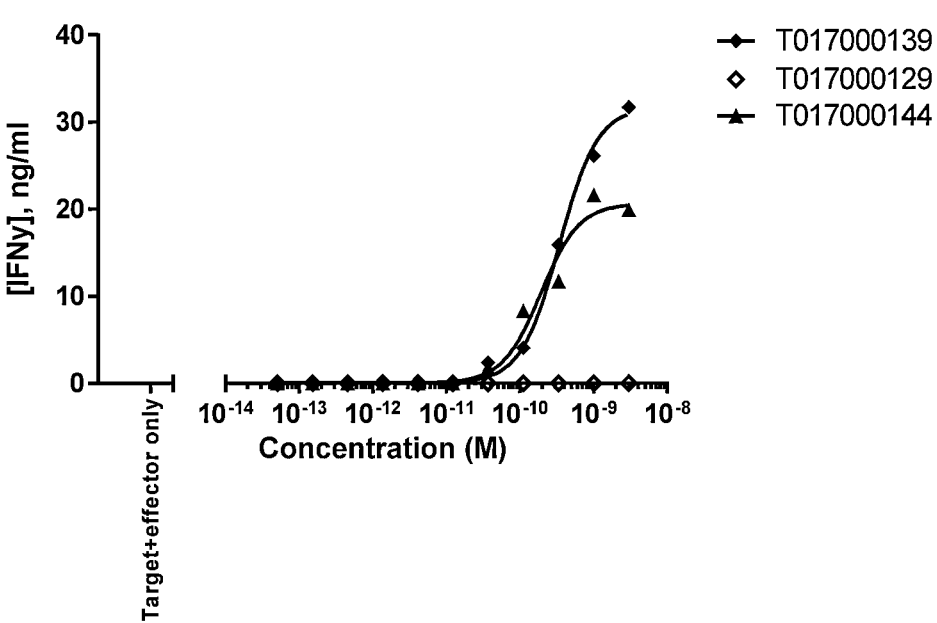
Figure 54:
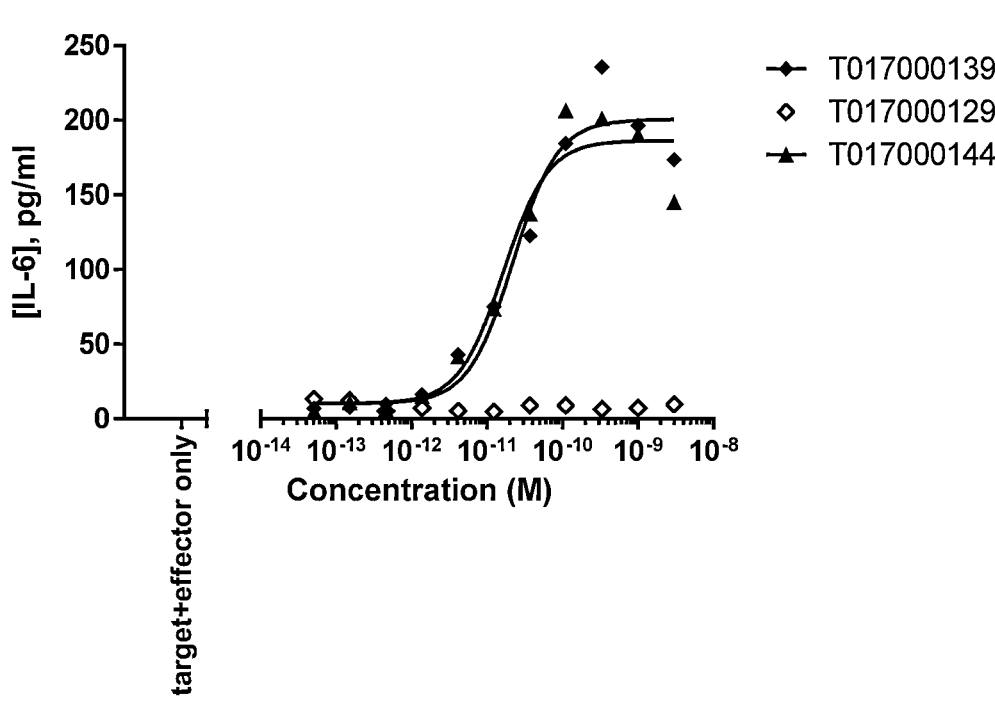

FIG. 54: Dose-dependent cytokine production by human T cells during redirected T cell killing of MOLM-13 by the HLE multispecific CD123/TCR binding polypeptides using an effector to target ratio of 10:1. The amount of cytokine is plotted against the concentration.

Figure 55:
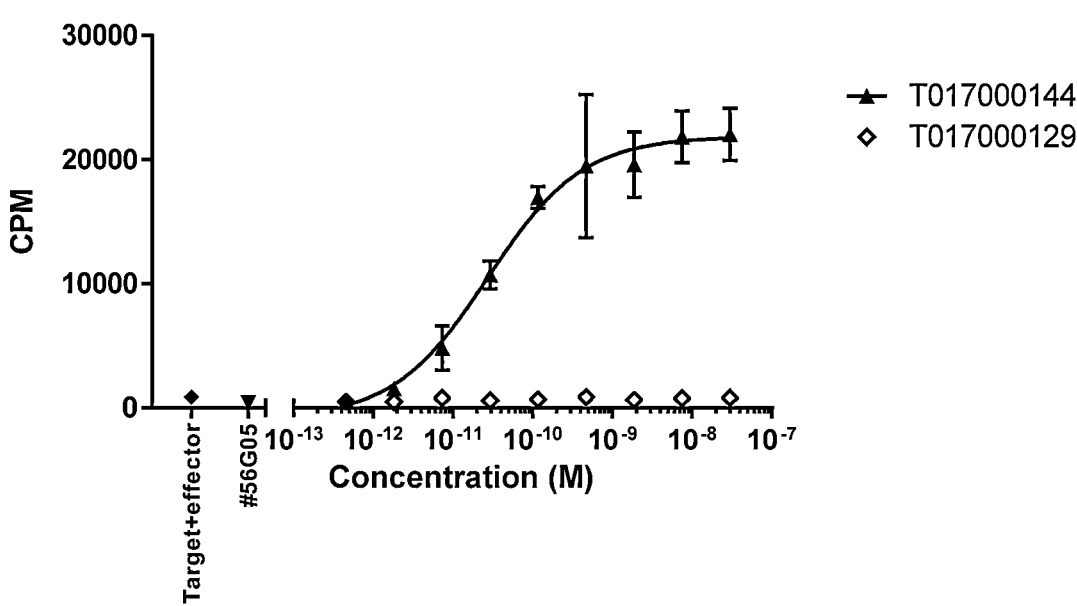

FIG. 55: Dose-dependent T cell proliferation of human effector T cells by HLE multispecific polypeptides in a redirected MOLM-13 target cell killing setting using an effector to target ratio of 10:1. The CPM (count per minute) is plotted against the concentration.

Figure 56:
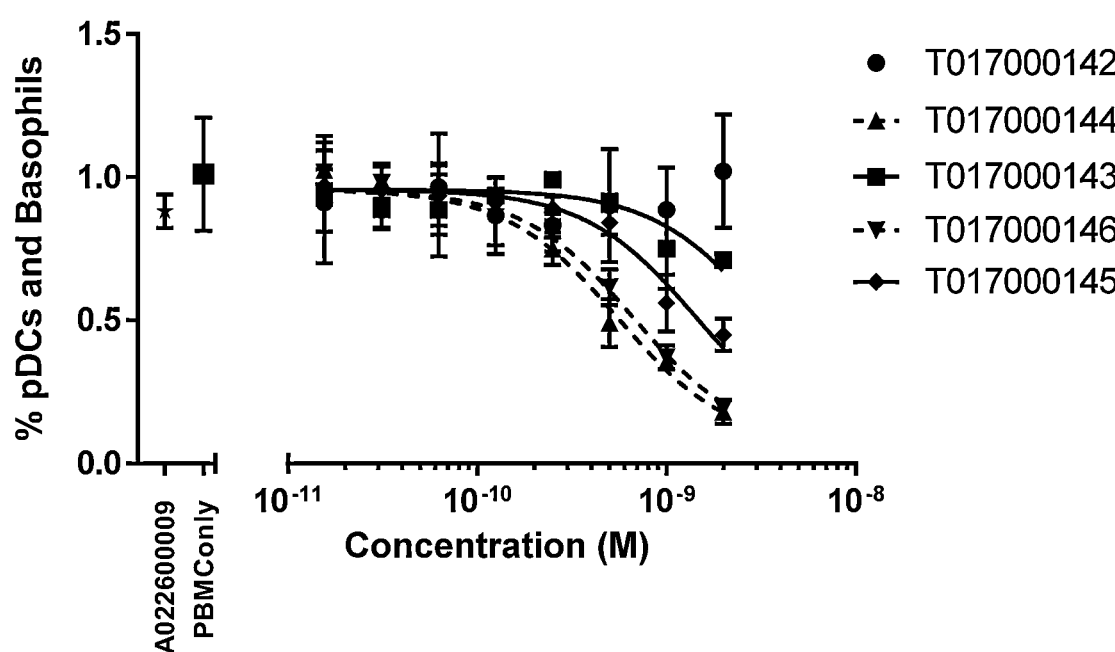

FIG. 56: Redirected autologous T cell redirected CD123+ pDC and basophil depletion by multivalent HLE CD123/TCR binding polypeptides in healthy human PBMC samples after an incubation time of 5 h. The percentage of Lin-/CD123+ cells (pDCs and basophils) was plotted against the concentration of the constructs.

Figure 57:
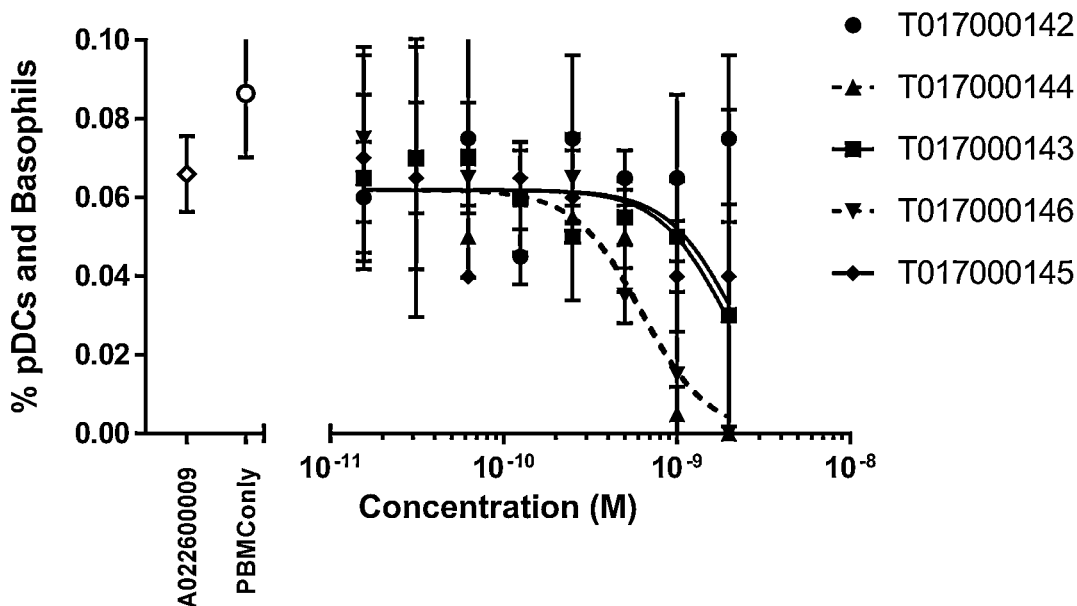

FIG. 57: Redirected autologous T cell redirected CD123+ pDC and basophil depletion by multivalent HLE CD123/TCR binding polypeptides in healthy cynomolgus PBMC samples in an in vitro setting after an incubation time of 5 h. The percentage of Lin-/CD123+ cells (pDCs and basophils) was plotted against the concentration of the constructs.

Figure 58:
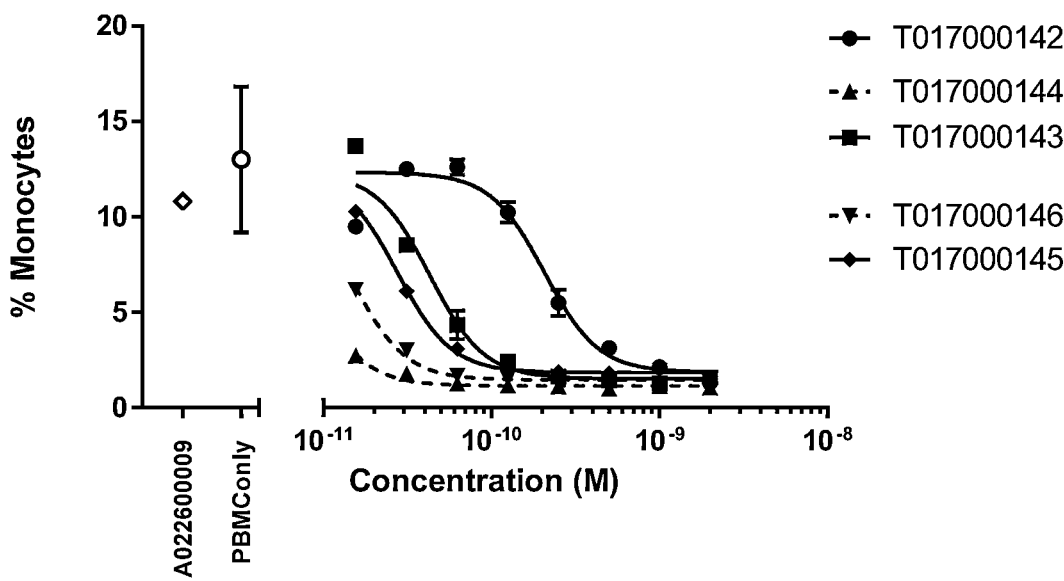

FIG. 58: Redirected autologous T cell redirected monocyte depletion by multivalent CD123/TCR binding polypeptides in healthy human PBMC samples after an incubation time of 24 h. The percentage of monocytes (CD14+ cells) was plotted against the concentration of the constructs.

Figure 59A:
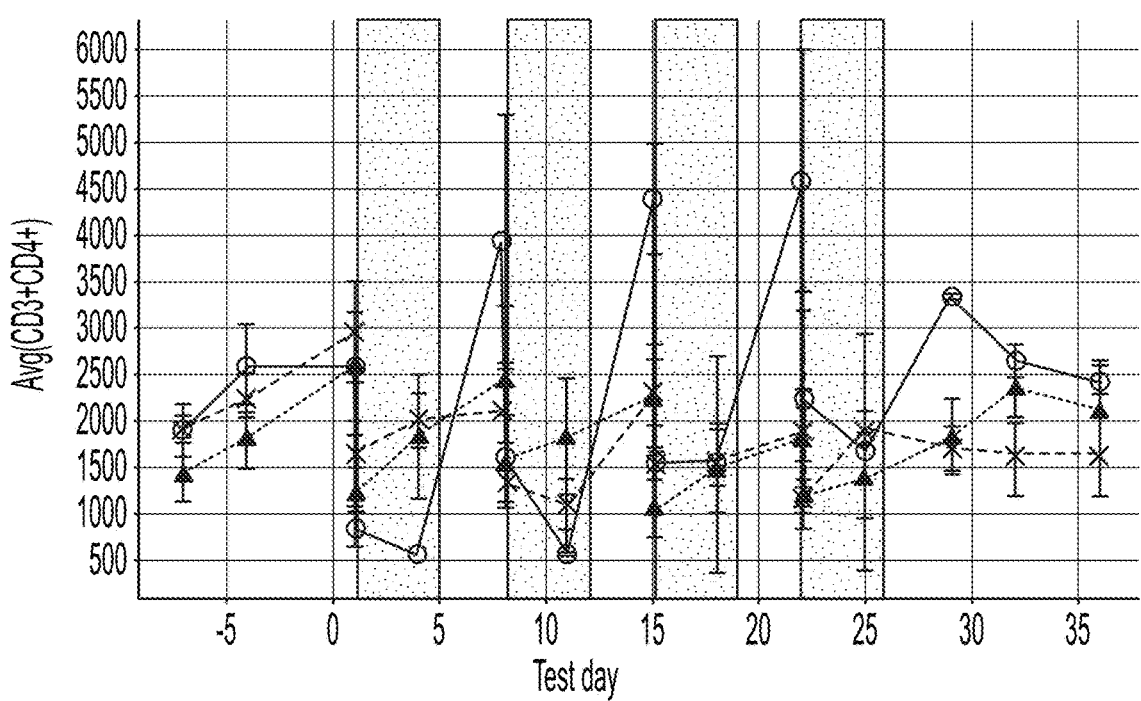
Figure 59B:
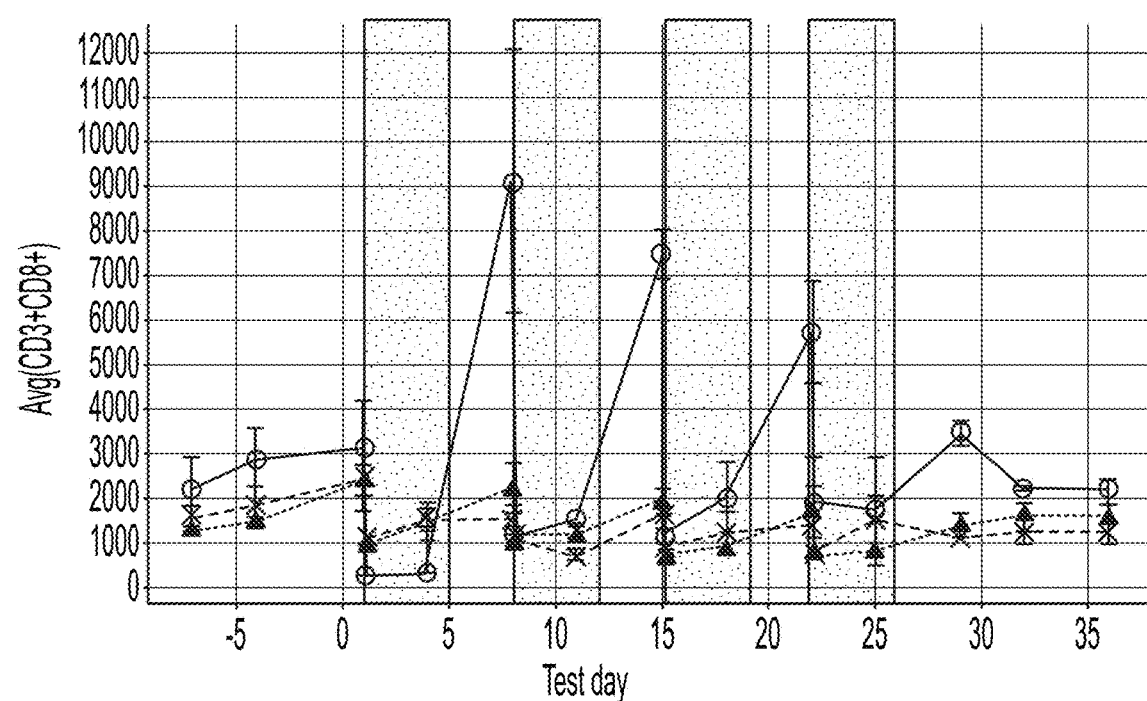

FIG. 59: T cell counts in peripheral blood of treated cynomolgus monkey over time. The absolute number of $CD4^+CD3^+$ T cells (top) and $CD8^+CD3^+$ T cells (bottom) per µL blood is expressed as average±SEM over time for the different treatment groups: positive control (open circles, n=2), irrelevant/TCR polypeptide (cross, n=4), CD123/TCR polypeptide (black triangle, n=4). Grey bars reflect continuous infusion treatment periods.

Figure 60:
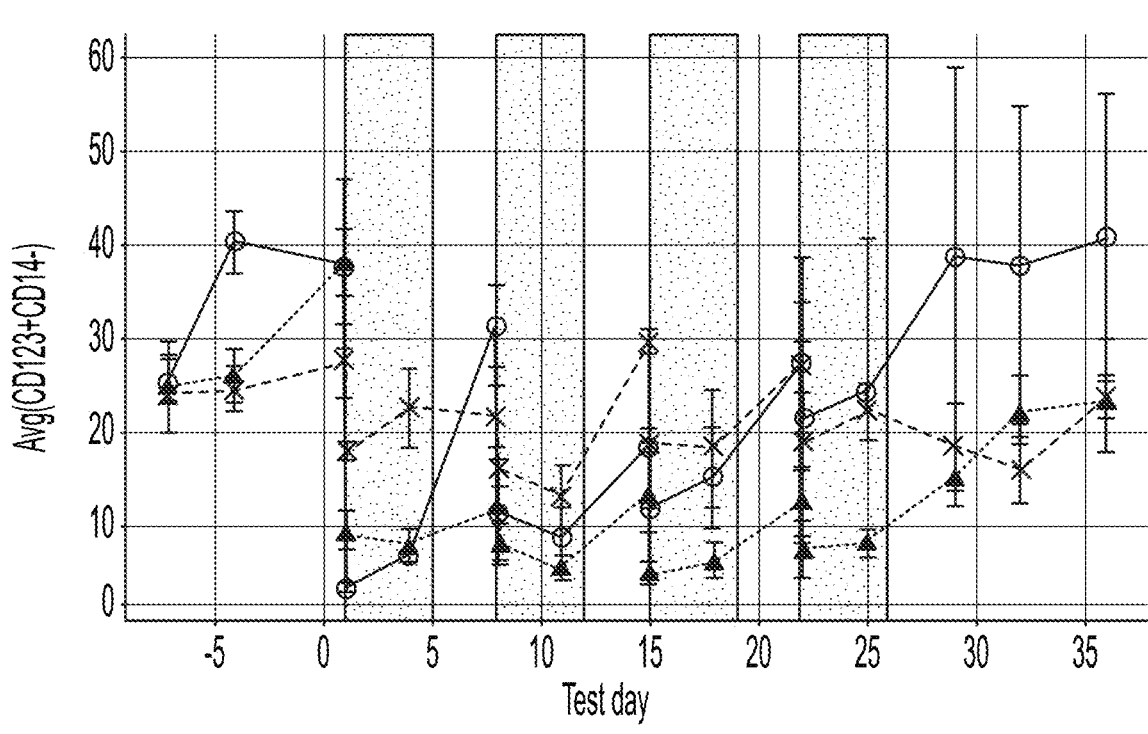

FIG. 60: $CD123^+CD14^-$ cell counts in peripheral blood of treated cynomolgus monkey over time. The absolute number of $CD123^+$ $CD14^-$ cells per µL blood is expressed as average±SEM for the different treatment groups: positive control (open circles, n=2), irrelevant/TCR polypeptide (cross, n=4), CD123/TCR polypeptide (black triangle, n=4). Grey bars reflect continuous infusion treatment periods.

Figure 61A:
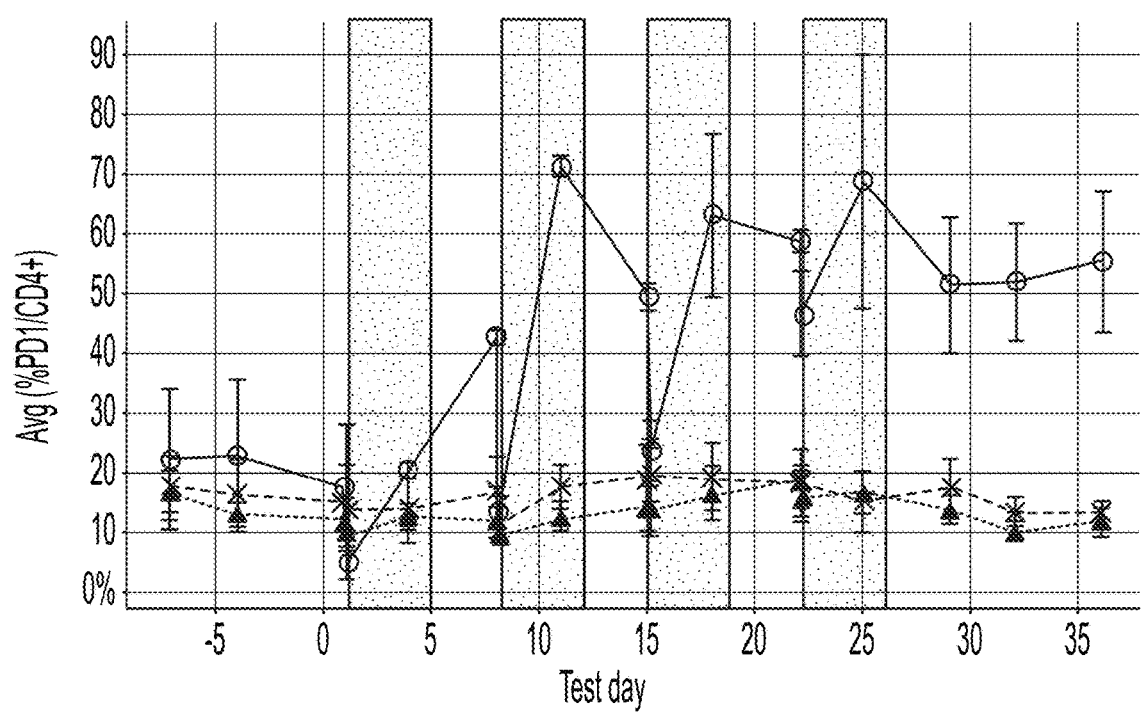
Figure 61B:
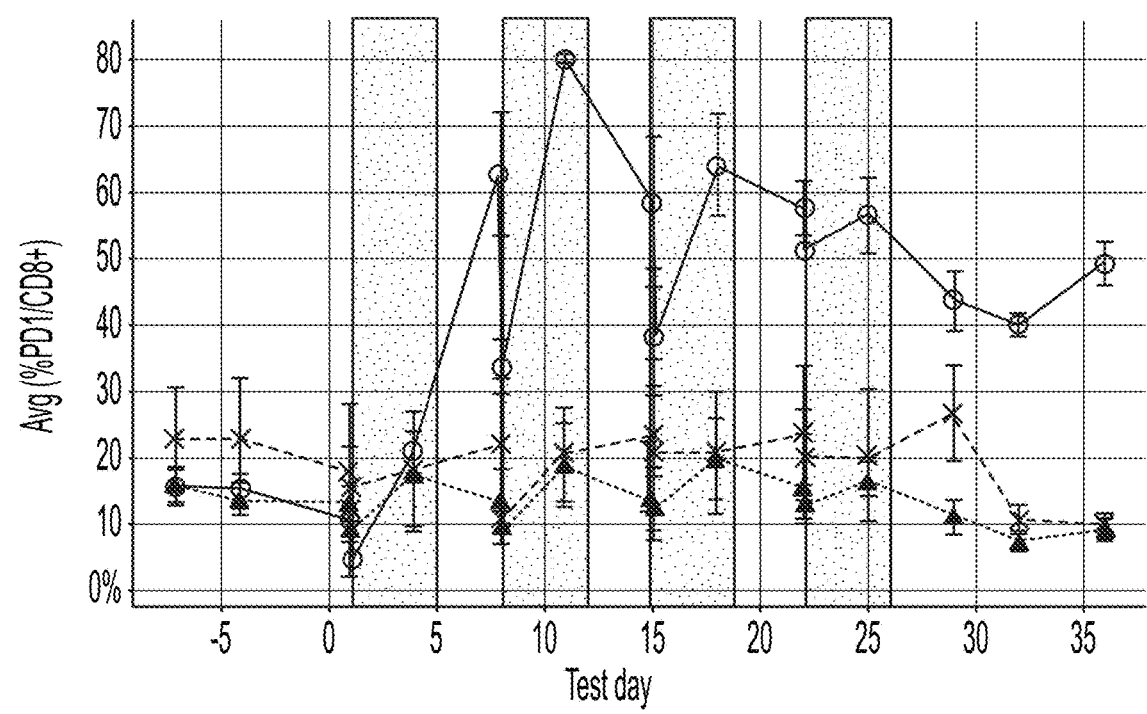

FIG. 61: PD-1 expression on $CD4^+CD3^+$ and $CD8^+CD3^+$ T cells over time. The frequency of $CD4^+CD3^+$ T cells (top) and $CD8^+$ $CD3^+$ T cells (bottom) in blood is expressed as average±SEM for the different treatment groups: positive control (open circles, n=2), irrelevant/TCR polypeptide (cross, n=4), CD123/TCR polypeptide (black triangle, n=4). Grey bars reflect continuous infusion treatment periods.

Figure 62:
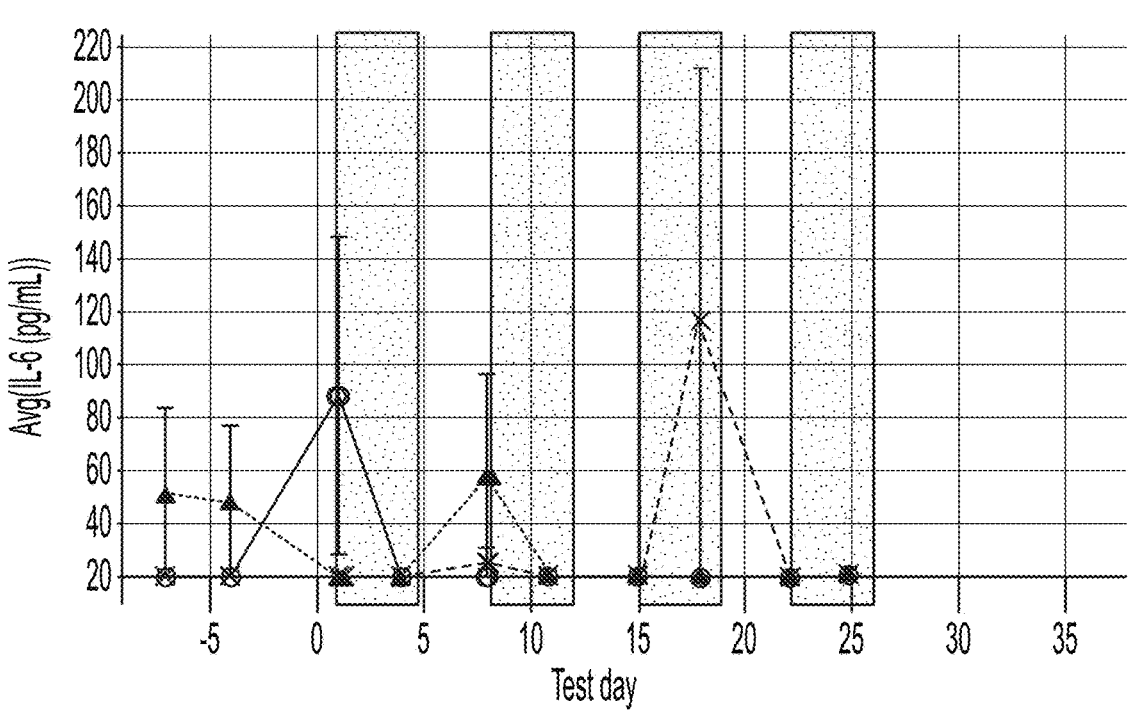

FIG. 62: Serum interleukin-6 in treated cynomolgus monkey over time. The concentration of IL-6 in serum is expressed as average±SEM (pg/mL) for the different treatment groups: positive control (open circles, n=2), irrelevant/TCR polypeptide (cross, n=4), CD123/TCR polypeptide (black triangle, n=4). Grey bars reflect continuous infusion treatment periods.

DETAILED DESCRIPTION

Definitions

Unless indicated or defined otherwise, all terms used have their usual meaning in the art, which will be clear to the skilled person. Reference is for example made to the standard handbooks, such as Sambrook et al. (1989, Molecular Cloning: A Laboratory Manual (2$^{nd}$ Ed.) Vols. 1-3, Cold Spring Harbor Laboratory Press), F. Ausubel et al. (1987, Current protocols in molecular biology, Green Publishing and Wiley Interscience, New York), Lewin (1985, Genes II, John Wiley & Sons, New York, N.Y.), Old et al. (1981, Principles of Gene Manipulation: An Introduction to Genetic Engineering (2nd Ed.) University of California Press, Berkeley, CA), Roitt et al. (2001, Immunology (6th Ed.) Mosby/Elsevier, Edinburgh), Roitt et al. (2001, Roitt's Essential Immunology (10th Ed.) Blackwell Publishing, UK), and Janeway et al. (2005, Immunobiology (6th Ed.) Garland Science Publishing/Churchill Livingstone, New York), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta (2006, Adv. Drug Deliv. Rev. 58 (5-6): 640-56), Levin and Weiss (2006, Mol. Biosyst. 2(1): 49-57), Irving et al. (2001, J. Immunol. Methods 248(1-2): 31-45), Schmitz et al. (2000, Placenta 21 Suppl. A: S106-12), Gonzales et al. (2005, Tumour Biol. 26(1): 31-43), which describe techniques for protein engineering, such as affinity maturation and other techniques for improving the specificity and other desired properties of proteins such as immunoglobulins.

The term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation.

Amino acid sequences are interpreted to mean a single amino acid or an unbranched sequence of two or more amino acids, depending on the context. Nucleotide sequences are interpreted to mean an unbranched sequence of 3 or more nucleotides.

Amino acids are those L-amino acids commonly found in naturally occurring proteins and are listed in Table B-1 below. Those amino acid sequences containing D-amino acids are not intended to be embraced by this definition. Any amino acid sequence that contains post-translationally modified amino acids may be described as the amino acid sequence that is initially translated using the symbols shown in the Table below with the modified positions; e.g., hydroxylations or glycosylations, but these modifications shall not be shown explicitly in the amino acid sequence. Any peptide or protein that can be expressed as a sequence modified linkages, cross links and end caps, non-peptidyl bonds, etc., is embraced by this definition.

TABLE B-1

| Common amino acids | | |
| --- | --- | --- |
| 1-Letter Code | 3-Letter Code | Name |
| A | Ala | Alanine |
| B | Asx | Aspartic acid or Asparagine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| J | Xle | Isoleucine or Leucine |
| K | Lys | Lysine |
| L | Leu | Leucine |
| M | Met | Methionine |
| N | Asn | Asparagine |
| O | Pyl | Pyrrolysine |
| P | Pro | Proline |
| Q | Gln | Glutamine |
| R | Arg | Arginine |
| S | Ser | Serine |
| T | Thr | Threonine |

TABLE B-1-continued

| Common amino acids | | |
|---|---|---|
| 1-Letter Code | 3-Letter Code | Name |
| U | Scy | Selenocysteine |
| V | Val | Valine |
| W | Trp | Tryptophan |
| X | Xxx | Uncommon or Unspecified |
| Y | Tyr | Tyrosine |
| Z | Glx | Glutamic acid or Glutamine |

The terms "protein", "peptide", "protein/peptide", and "polypeptide" are used interchangeably throughout the disclosure and each has the same meaning for purposes of this disclosure. Each term refers to an organic compound made of a linear chain of two or more amino acids. The compound may have ten or more amino acids; twenty-five or more amino acids; fifty or more amino acids; one hundred or more amino acids, two hundred or more amino acids, and even three hundred or more amino acids. The skilled artisan will appreciate that polypeptides generally comprise fewer amino acids than proteins, although there is no art-recognized cut-off point of the number of amino acids that distinguish a polypeptides and a protein; that polypeptides may be made by chemical synthesis or recombinant methods; and that proteins are generally made in vitro or in vivo by recombinant methods as known in the art.

Amino acid residues will be indicated according to the standard three-letter or one-letter amino acid code. Reference is made to Table A-2 on page 48 of WO 08/020079.

A nucleic acid or amino acid is considered to be "(in) (essentially) isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or amino acid is considered "(essentially) isolated" when it has been purified at least 2-fold, in particular at least 10-fold, more in particular at least 100-fold, and up to 1000-fold or more. A nucleic acid or amino acid that is "in (essentially) isolated form" is preferably essentially homogeneous, as determined using a suitable technique, such as a suitable chromatographical technique, such as polyacrylamide-gel electrophoresis.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

For instance, when a nucleotide sequence, amino acid sequence or polypeptide is said to "comprise" another nucleotide sequence, amino acid sequence or polypeptide, respectively, or to "essentially consist of" another nucleotide sequence, amino acid sequence or polypeptide, this may mean that the latter nucleotide sequence, amino acid sequence or polypeptide has been incorporated into the first mentioned nucleotide sequence, amino acid sequence or polypeptide, respectively, but more usually this generally means that the first mentioned nucleotide sequence, amino acid sequence or polypeptide comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a polypeptide of the invention is said to comprise an immunoglobulin single variable domain, this may mean that said immunoglobulin single variable domain sequence has been incorporated into the sequence of the polypeptide of the invention, but more usually this generally means that the polypeptide of the invention contains within its sequence the sequence of the immunoglobulin single variable domains irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleic acid or nucleotide sequence).

By "essentially consist of" is meant that the immunoglobulin single variable domain used in the method of the invention either is exactly the same as the polypeptide of the invention or corresponds to the polypeptide of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the immunoglobulin single variable domain.

By "consist of" is meant that the immunoglobulin single variable domain used in the method of the invention is exactly the same as the polypeptide of the invention.

For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position). Alternatively, the degree of sequence identity between two or more nucleotide sequences may be calculated using a known computer algorithm for sequence alignment such as NCBI Blast v2.0, using standard settings. Some other techniques, computer algorithms and settings for determining the degree of sequence identity are for example described in WO 04/037999, EP 0967284, EP 1085089, WO 00/55318, WO 00/78972, WO 98/49185 and GB 2357768. Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e., as an "amino acid difference" as defined herein. Alternatively, the degree of sequence identity between two amino acid sequences may be calculated using a known computer algorithm, such as those mentioned above for determining the degree of sequence identity for nucleotide sequences, again using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB 335768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, lie, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into lie or into Val; Lys into Arg, into Gln or into Glu; Met into Leu, into Tyr or into lie; Phe into Met, into Leu or into Tyr; Ser into Thr; Thr into Ser; Trp into Tyr; Tyr into Trp; and/or Phe into Val, into lie or into Leu.

Any amino acid substitutions applied to the polypeptides described herein may also be based on the analysis of the frequencies of amino acid variations between homologous proteins of different species developed by Schulz et al. (1978, Principles of Protein Structure, Springer-Verlag), on the analyses of structure forming potentials developed by Chou and Fasman (1974, Biochemistry 13: 211; 1978, Adv. Enzymol., 47: 45-149), and on the analysis of hydrophobicity patterns in proteins developed by Eisenberg et al. (1984, Proc. Natl. Acad Sci. USA 81: 140-144), Kyte and Doolittle (1981, J. Molec. Biol. 157: 105-132), and Goldman et al. (1986, Ann. Rev. Biophys. Chem. 15: 321-353), all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al. (1996, Nature Structural Biology, 3: 803), Spinelli et al. (1996, Natural Structural Biology, 3: 752-757) and Decanniere et al. (1999, Structure, 7 (4): 361). Further information about some of the amino acid residues that in conventional $V_H$ domains form the $V_H/V_L$ interface and potential camelizing substitutions on these positions can be found in the prior art cited above.

Amino acid sequences and nucleic acid sequences are said to be "exactly the same" if they have 100% sequence identity (as defined herein) over their entire length.

When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences. More particularly, in the amino acid sequences and/or polypeptides of the present invention, the term "amino acid difference" refers to an insertion, deletion or substitution of a single amino acid residue on a position of the CDR sequence specified in b), d) or f), compared to the CDR sequence of respectively a), c) or e); it being understood that the CDR sequence of b), d) and f) can contain one, two or maximal three such amino acid differences compared to the CDR sequence of respectively a), c) or e).

The "amino acid difference" can be any one, two, three or maximal four substitutions, deletions or insertions, or any combination thereof, that either improve the properties of the polypeptide of the invention or that at least do not detract too much from the desired properties or from the balance or combination of desired properties of the polypeptide of the invention. In this respect, the resulting polypeptide of the invention should at least bind CD123 or T cell receptor with the same, about the same, or a higher affinity compared to the polypeptide comprising the one or more CDR sequences without the one, two, three or maximal four substitutions, deletions or insertions, said affinity as measured by surface plasmon resonance.

In this respect, the amino acid sequence according to b), d) and/or f) may be an amino acid sequence that is derived from an amino acid sequence according to a), c) and/or e) respectively by means of affinity maturation using one or more techniques of affinity maturation known per se.

For example, and depending on the host organism used to express the polypeptide of the invention, such deletions and/or substitutions may be designed in such a way that one or more sites for post-translational modification (such as one or more glycosylation sites) are removed, as will be within the ability of the person skilled in the art.

The "affinity" denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of (mol/liter)$^{-1}$ (or M$^{-1}$). In the present specification, the stability of the interaction between two molecules will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the change of free energy (DG) of binding by the well-known relation $DG = RT \cdot \ln(K_D)$ (equivalently $DG = -RT \cdot \ln(K_A)$), where R equals the gas constant, T equals the absolute temperature and ln denotes the natural logarithm.

The $K_D$ for biological interactions which are considered meaningful (e.g. specific) are typically in the range of $10^{-12}$ M (0.001 nM) to $10^{-5}$ M (10000 nM). The stronger an interaction is, the lower is its $K_D$.

The $K_D$ can also be expressed as the ratio of the dissociation rate constant of a complex, denoted as $k_{off}$, to the rate of its association rate constant, denoted $k_{on}$ (so that $K_D = k_{off}/k_{on}$ and $K_A = k_{on}/k_{off}$). The off-rate $k_{off}$ has units $s^{-1}$ (where s is the SI unit notation of second). The on-rate $k_{on}$ has units $M^{-1}s^{-1}$. The on-rate may vary between $10^2$ $M^{-1}s^{-1}$ to about $10^7$ $M^{-1}s^{-1}$, approaching the diffusion-limited association rate constant for bimolecular interactions. The off-rate is related to the half-life of a given molecular interaction by the relation $t_{1/2} = \ln(2)/k_{off}$. The off-rate may vary between $10^{-6}$ $s^{-1}$ (near irreversible complex with a $t_{1/2}$ of multiple days) to 1 $s^{-1}$ ($t_{1/2} = 0.69$ s).

Specific binding of an antigen-binding protein, such as an ISV, to an antigen or antigenic determinant can be determined in any suitable manner known per se, including, for example, Scatchard analysis and/or competitive binding assays, such as radio-immunoassays (RIA), enzyme immunoassays (EIA) and sandwich competition assays, and the different variants thereof known per se in the art; as well as the other techniques mentioned herein.

The affinity of a molecular interaction between two molecules can be measured via different techniques known per se, such as the well-known surface plasmon resonance (SPR) biosensor technique (see for example Ober et al. 2001, Intern. Immunology 13: 1551-1559). The term "surface plasmon resonance", as used herein, refers to an optical phenomenon that allows for the analysis of real-time biospecific interactions by detection of alterations in protein concentrations within a biosensor matrix, where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIAcore® system (BIAcore International AB, a GE Healthcare company, Uppsala, Sweden and Piscataway, NJ). For further descriptions, see Jonsson et al. (1993, Ann. Biol. Clin. 51: 19-26), Jonsson et al. (1991 Biotechniques 11: 620-627), Johnsson et al. (1995, J. Mol. Recognit. 8: 125-131), and Johnnson et al. (1991, Anal. Biochem. 198: 268-277).

Another well-known biosensor technique to determine affinities of biomolecular interactions is bio-layer interferometry (BLI) (see for example Abdiche et al. 2008, Anal. Biochem. 377: 209-217). The term "bio-layer Interferometry" or "BLI", as used herein, refers to a label-free optical technique that analyzes the interference pattern of light reflected from two surfaces: an internal reference layer (reference beam) and a layer of immobilized protein on the biosensor tip (signal beam). A change in the number of molecules bound to the tip of the biosensor causes a shift in the interference pattern, reported as a wavelength shift (nm), the magnitude of which is a direct measure of the number of molecules bound to the biosensor tip surface. Since the interactions can be measured in real-time, association and dissociation rates and affinities can be determined. BLI can for example be performed using the well-known Octet® Systems (ForteBio, a division of Pall Life Sciences, Menlo Park, USA).

Alternatively, affinities can be measured in Kinetic Exclusion Assay (KinExA) (see for example Drake et al. 2004, Anal. Biochem., 328: 35-43), using the KinExA® platform (Sapidyne Instruments Inc, Boise, USA). The term "KinExA", as used herein, refers to a solution-based method to measure true equilibrium binding affinity and kinetics of unmodified molecules. Equilibrated solutions of an antibody/antigen complex are passed over a column with beads precoated with antigen (or antibody), allowing the free antibody (or antigen) to bind to the coated molecule. Detection of the antibody (or antigen) thus captured is accomplished with a fluorescently labeled protein binding the antibody (or antigen).

The GYROLAB® immunoassay system provides a platform for automated bioanalysis and rapid sample turnaround (Fraley et al. 2013, Bioanalysis 5: 1765-74).

It will also be clear to the skilled person that the measured $K_D$ may correspond to the apparent $K_D$ if the measuring process somehow influences the intrinsic binding affinity of the implied molecules for example by artifacts related to the coating on the biosensor of one molecule. Also, an apparent $K_D$ may be measured if one molecule contains more than one recognition sites for the other molecule. In such situation the measured affinity may be affected by the avidity of the interaction by the two molecules. As will be clear to the skilled person, and as described on pages 53-56 of WO 08/020079, the dissociation constant may be the actual or apparent dissociation constant. Methods for determining the dissociation constant will be clear to the skilled person, and for example include the techniques mentioned on pages 53-56 of WO 08/020079.

The terms "epitope" and "antigenic determinant", which can be used interchangeably, refer to the part of a macromolecule, such as a polypeptide or protein that is recognized by antigen-binding molecules, such as immunoglobulins, conventional antibodies, immunoglobulin single variable domains and/or polypeptides of the invention, and more particularly by the antigen-binding site of said molecules. Epitopes define the minimum binding site for an immunoglobulin, and thus represent the target of specificity of an immunoglobulin.

The part of an antigen-binding molecule (such as an immunoglobulin, a conventional antibody, an immunoglobulin single variable domain and/or a polypeptide of the invention) that recognizes the epitope is called a "paratope".

A polypeptide (such as an immunoglobulin, an antibody, an immunoglobulin single variable domain, a polypeptide of the invention, or generally an antigen binding molecule or a fragment thereof) that can "bind (to)" or "specifically bind (to)", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein, or is said to be "anti"-epitope, "anti"-antigen or "anti"-protein (e.g., "anti"-CD123 or "anti"-TCR).

The term "specificity" has the meaning given to it in paragraph n) on pages 53-56 of WO 08/020079; and as mentioned therein refers to the number of different types of antigens or antigenic determinants to which a particular antigen-binding molecule or antigen-binding protein (such as an immunoglobulin single variable domain and/or a polypeptide of the invention) can bind. The specificity of an antigen-binding protein can be determined based on affinity and/or avidity, as described on pages 53-56 of WO 08/020079 (incorporated herein by reference), which also describes some preferred techniques for measuring binding between an antigen-binding molecule (such as an immuno-globulin single variable domain and/or polypeptide of the invention) and the pertinent antigen. Typically, antigen-binding proteins (such as the immunoglobulin single vari-able domains and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4$ $M^{-1}$) is generally considered to indicate non-specific binding. Preferably, a monospecific polypeptide of the invention will bind to the desired antigen with an affinity less than 500 nM, preferably less than 200 nM, more preferably less than 10 nM, such as e.g., between 10 and 5 nM, such as less than 10 nM, less than 5 nM, less than 3 nM, less than 2 nM, such as 10 nM-1 nM, 5 nM-1 nM or even less. Specific binding of an antigen-binding protein to an antigen or antigenic determinant can be determined in any suitable manner known per se, including, for example, Scatchard analysis and/or competitive binding assays, such as radio-immunoassays (RIA), enzyme immunoassays (EIA) and sandwich competition assays, and the different variants thereof known per se in the art; as well as the other techniques mentioned herein.

As will be clear to the skilled person, and as described on pages 53-56 of WO 08/020079, the dissociation constant may be the actual or apparent dissociation constant. Meth-ods for determining the dissociation constant will be clear to the skilled person, and for example include the techniques mentioned on pages 53-56 of WO 08/020079.

One approach that may be used to assess affinity is the 2-step ELISA (Enzyme-Linked Immunosorbent Assay) pro-cedure of Friguet et al. (1985, J. Immunol. Methods 77: 305-19). This method establishes a solution phase binding equilibrium measurement and avoids possible artifacts relat-ing to adsorption of one of the molecules on a support such as plastic.

However, the accurate measurement of $K_D$ may be quite labor-intensive and as consequence, often apparent $K_D$ val-ues are determined to assess the binding strength of two molecules. It should be noted that as long all measurements are made in a consistent way (e.g. keeping the assay con-ditions unchanged) apparent $K_D$ measurements can be used as an approximation of the true $K_D$ and hence in the present document $K_D$ and apparent $K_D$ should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chro-mophore for light absorption detection, the biotin for streptavidin-mediated ELISA detection). Typically, the ref-erence molecule C is kept at a fixed concentration and the concentration of A is varied for a given concentration or amount of B. As a result an $IC_{50}$ value is obtained corre-sponding to the concentration of A at which the signal measured for C in absence of A is halved. Provided $K_{D\ ref}$, the $K_D$ of the reference molecule, is known, as well as the total concentration $c_{ref}$ of the reference molecule, the appar-ent $K_D$ for the interaction A-B can be obtained from fol-lowing formula: $K_D=IC_{50}/(1+c_{ref}/K_{Dref})$. Note that if $c_{ref}<<K_{D\ ref}$, $K_D\approx IC_{50}$. Provided the measurement of the $IC_{50}$ is performed in a consistent way (e.g. keeping $c_{ref}$ fixed) for the binders that are compared, the strength or stability of a molecular interaction can be assessed by the $IC_{50}$ and this measurement is judged as equivalent to $K_D$ or to apparent $K_D$ throughout this text.

The half maximal inhibitory concentration ($IC_{50}$) is a measure of the effectiveness of a compound in inhibiting a biological or biochemical function, e.g. a pharmacological effect. This quantitative measure indicates how much of the ISV (e.g. a Nanobody) (inhibitor) is needed to inhibit a given biological process (or component of a process, i.e. an enzyme, cell, cell receptor, chemotaxis, anaplasia, metasta-sis, invasiveness, etc.) by half. In other words, it is the half maximal (50%) inhibitory concentration (IC) of a substance (50% IC, or $IC_{50}$). The $IC_{50}$ of a drug can be determined by constructing a dose-response curve and examining the effect of different concentrations of antagonist such as the ISVD (e.g. a Nanobody) of the invention on reversing agonist activity. $IC_{50}$ values can be calculated for a given antagonist such as the ISVD (e.g. a Nanobody) of the invention by determining the concentration needed to inhibit half of the maximum biological response of the agonist.

The term half maximal effective concentration ($EC_{50}$) refers to the concentration of a compound which induces a response halfway between the baseline and maximum after a specified exposure time. In the present context it is used as a measure of a polypeptide's, ISV's (e.g. a Nanobody's) potency. The $EC_{50}$ of a graded dose response curve repre-sents the concentration of a compound where 50% of its maximal effect is observed. Concentration is preferably expressed in molar units.

In biological systems, small changes in ligand concentra-tion typically result in rapid changes in response, following a sigmoidal function. The inflection point at which the increase in response with increasing ligand concentration begins to slow is the $EC_{50}$. This can be determined math-ematically by derivation of the best-fit line. Relying on a graph for estimation is convenient in most cases. In case the $EC_{50}$ is provided in the examples section, the experiments were designed to reflect the $K_D$ as accurate as possible. In other words, the $EC_{50}$ values may then be considered as $K_D$ values.

It is also related to $IC_{50}$ which is a measure of a com-pound's inhibition (50% inhibition). For competition bind-ing assays and functional antagonist assays $IC_{50}$ is the most common summary measure of the dose-response curve. For agonist/stimulator assays the most common summary mea-sure is the $EC_{50}$.

The inhibitor constant, Ki, is an indication of how potent an inhibitor is; it is the concentration required to produce half maximum inhibition. The absolute inhibition constant $K_i$ can be calculated by using the Cheng-Prusoff equation:

$$K_i = \frac{IC50}{\frac{[L]}{K_D}+1}$$

in which [L] is the fixed concentration of the ligand.

An immunoglobulin single variable domain and/or poly-peptide is said to be "specific for" a first target or antigen compared to a second target or antigen when it binds to the first antigen with an affinity (as described above, and suitably expressed as a $K_D$ value, $K_A$ value, $k_{off}$ rate and/or $k_{on}$ rate) that is at least 10 times, such as at least 100 times, and preferably at least 1000 times, and up to 10000 times or more better than the affinity with which the immunoglobulin single variable domain and/or polypeptide binds to the second target or antigen. For example, the immunoglobulin single variable domain and/or polypeptide may bind to the first target or antigen with a $K_D$ value that is at least 10 times less, such as at least 100 times less, and preferably at least 1000 times less, such as 10000 times less or even less than that, than the $K_D$ with which said immunoglobulin single variable domain and/or polypeptide binds to the second target or antigen. Preferably, when an immunoglobulin single variable domain and/or polypeptide is "specific for" a first target or antigen compared to a second target or antigen, it is directed against (as defined herein) said first target or antigen, but not directed against said second target or antigen.

An amino acid sequence, such as e.g., an immunoglobulin single variable domain or polypeptide according to the invention, is said to be "cross-reactive" for two different antigens or antigenic determinants (such as e.g., serum albumin from two different species of mammal, such as e.g., human serum albumin and cyno serum albumin, such as e.g., CD123 from different species of mammal, such as e.g., human CD123 and cyno CD123, such as e.g., TCR from different species of mammal, such as e.g., human TCR and cyno TCR) if it is specific for (as defined herein) both these different antigens or antigenic determinants.

The terms "(cross)-block", "(cross)-blocked", "(cross)-blocking", "competitive binding", "(cross)-compete", "(cross)-competing" and "(cross)-competition" are used interchangeably herein to mean the ability of an immunoglobulin, antibody, immunoglobulin single variable domain, polypeptide or other binding agent to interfere with the binding of other immunoglobulins, antibodies, immunoglobulin single variable domains, polypeptides or binding agents to a given target. The extent to which an immunoglobulin, antibody, immunoglobulin single variable domain, polypeptide or other binding agent is able to interfere with the binding of another to the target, and therefore whether it can be said to cross-block according to the invention, can be determined using competition binding assays. One particularly suitable quantitative cross-blocking assay is described in the Examples and includes e.g. a fluorescence-activated cell sorting (FACS) binding assay with CD123 expressed on cells. The extent of (cross)-blocking can be measured by the (reduced) channel fluorescence. Another suitable quantitative cross-blocking assay uses a Biacore instrument which can measure the extent of interactions using surface plasmon resonance technology. Another suitable quantitative cross-blocking assay uses an ELISA-based approach to measure competition between immunoglobulins, antibodies, immunoglobulin single variable domains, polypeptides or other binding agents in terms of their binding to the target.

The following generally describes a suitable FACS assay for determining whether an immunoglobulin, antibody, immunoglobulin single variable domain, polypeptide or other binding agent cross-blocks or is capable of cross-blocking according to the invention. It will be appreciated that the assay can be used with any of the immunoglobulins, antibodies, immunoglobulin single variable domains, polypeptides or other binding agents described herein. The FACS instrument (e.g. FACSArray; Becton Dickinson) is operated in line with the manufacturer's recommendations.

To evaluate the "(cross)-blocking" or "(cross)-competition" between two binding agents (such as e.g., two immunoglobulin single variable domains and/or Nanobodies) for binding to CD123, a FACS competition experiment can be performed using cells (such as e.g., the endogenously CD123 expressing cell line MOLM-13 or Flp-In™-CHO cells overexpressing human CD123). Different detection reagents can be used including e.g. monoclonal ANTI-FLAG® M2 antibody (Sigma-Aldrich, cat #F1804), monoclonal anti-C-myc antibody (Sigma-Aldrich, cat #WH0004609M2), monoclonal ANTI-HIS TAG antibody (Sigma-Aldrich, cat #SAB1305538), each labeled differently. A wide range of fluorophores can be used as labels in flow cytometry (such as e.g PE (R-Phycoerythrin), 7-aminoactinomycin D (7-AAD), Acridine Orange, various forms of Alexa Fluor (such as e.g., Alexa647), Allophycocyanin (APC), AmCyan, Aminocoumarin, APC Cy5, APC Cy7, APC-H7, APC/Alexa Fluor 750, AsRed2, Azami-Green, Azurite, B ODIPY FL C5-ceramide, BCECF-AM, Bisoxonol DiBAC2(3), BODIPY-FL, Calcein, Calcein AM, Caroxy-H2DCFDA, Cascade Blue, Cascade Yellow, Cell Tracker Green, Cerulean, CFSE, Chromomycin A3, CM-H2DCFDA, Cy2, Cy3, Cy3.5, Cy3B, Cy5, Cy5.5, Cy7, CyPet, DAF-FM DAF-FM diacetate, DAPI, DCFH (2'7'Dichorodihydrofluorescein), DHR, Dihydrocalcein AM, Dihydrorhoadamine, Dihydrothidium, DiLC1(5), DiOC6(3), DiOC7(3), dKeima-Red, DRAQ5, Dronpa-Green, various forms of DsRed dTomato, various forms of DyLight, E. coli BioParticles AF488, E2-Crimson, E2-Orange, EBFP2, ECFP, various forms of eFluor, EGFP, EGFP*, Emerald, eqFP650, eqFP670, ER-Tracker Blue-White DPX, Ethidium Bromide, Express2, EYFP, Fc OxyBurst Green, Fc OxyBurst Green 123, FITC, Fluo-3, Fluo-4, Fluorescein, Fura-2, Fura-Red, GFPuv, H2DCFDA, HcRed1, Hoechst Blue (33258), Hoechst Red (33342), Hydroxycoumarin, HyPer, Indo-1, Indo-1 Blue (Low Ca2+), Indo-1 Violet (High Ca2+), iRFP, J-Red, JC-1, JC-9, Katushka (TurboFP635), Katushka2 Kusabira-Orange, LDS 751, Lissamine Rhodamine B, various forms of Live/Dead, Lucifer yellow, Lucifer Yellow CH, Lyso Tracker Blue, Lyso Tracker Green, Lyso Tracker Red, mAmertrine, Marina Blue, mBanana, mCFP, mCherry, mCitrine, Methoxycoumarin, mHoney-Dew, Midoriishi-Cyan, Mithramycin, Mito Tracker Deep Red, Mito Tracker Green, Mito Tracker Orange, Mito Tracker Red, MitoFluor Green, mKate (TagFP635), mKate2, mKeima, mKeima-Red, mKO, mKOk, mNeptune, Monochlorobimane, mOrange, mOrange2, mRaspberry, mPlum, mRFP1, mStrawberry, mTangerine, mTarquoise, mTFP1, mTFP1 (Teal), NBD, OxyBurst Green H2DCFDA, OxyBurst Green H2HFF BSA, Pacific Blue, PE (R-Phycoerythrin), PE Cy5, PE Cy5.5, PE Cy7, PE Texas Red, PE-Cy5 conjugates, PE-Cy7 conjugates, PerCP (Peridinin chlorphyll protein), PerCP Cy5.5, PhiYFP, PhiYFP-m, Propidium Iodide (PI), various forms of Qdot, Red 613, RFP Tomato, Rhod-2, S65A, S65C, S65L, S65T, Singlet Oxygen Sensor Green, Sirius, SNARF, Superfolder GFP, SYTOX Blue, SYTOX Green, SYTOX Orange, T-Sapphire, TagBFP, TagCFP, TagGFP, TagRFP, TagRFP657, TagYFP, tdTomato, Texas Red, Thiazole Orange, TMRE, TMRM, Topaz, TOTO-1, TO-PRO-1, TRITC, TRITC TruRed, TurboFP602, TurboFP635, TurboGFP, TurboRFP, TurboYFP, Venus, Vybrant CycleDye Violet, Wild Type GFP, X-Rhodamin, Y66F, Y66H, Y66W, YOYO-1, YPet, ZsGreen1, ZsYellow1, Zymosan A BioParticles AF488 (see more at: http://www.thefcn.org/flow-fluorochromes). Fluorophores, or simply "fluors", are typically attached to the antibody (e.g. the immunoglobulin single variable domains, such as Nanobodies) that recognizes CD123 or to the antibody that is used as detection reagent. Various conjugated antibodies are available, such as (without being limiting) for example antibodies conjugated to Alexa Fluor®, DyLight®, Rhodamine, PE, FITC, and Cy3. Each fluorophore has a characteristic peak excitation and emission wavelength. The combination of labels which can be used will depend on the wavelength of the lamp(s) or laser(s) used to excite the fluorophore and on the detectors available.

To evaluate the competition between two test binding agents (termed A and B*) for binding to CD123, a dilution series of cold (without any label) binding agent A is added to (e.g. 100 000) cells together with the labeled binding agent B*. The concentration of B* in the test mix should be high enough to readily saturate the binding sites on CD123 expressed on the cells. The concentration of binding agent B* that saturates the binding sites for that binding agent on CD123 expressed on the cells can be determined with a titration series of B* on the CD123 expressing cells and determination of the $EC_{50}$ value for binding. In order to work at saturating concentration, binding agent B* can be used at 100× the $EC_{50}$ concentration.

After incubation of the cells with the mixture of A and B* and washing of the cells, read out can be performed on a FACS. First a gate is set on the intact cells as determined from the scatter profile and the total amount of channel fluorescence is recorded.

A separate solution of binding agent B* is also prepared. The binding agent in this solutions should be in the same buffer and at the same concentration as in the test mix (with binding agents A and B*). This separate solution is also added to the cells. After incubation and cells wash, read out can be performed on a FACS. First a gate is set on the intact cells as determined from the scatter profile and the total amount of channel fluorescence is recorded.

A reduction of fluorescence for the cells incubated with the mixture of A and B* compared to the fluorescence for the cells incubated with the separate solution of B* indicates that binding agent A (cross)-blocks binding by binding agent B* for binding to CD123 expressed on the cells.

A cross-blocking immunoglobulin, antibody, immunoglobulin single variable domain, polypeptide or other binding agent according to the invention is one which will bind to the CD123 in the above FACS cross-blocking assay such that during the assay and in the presence of a second immunoglobulin, antibody, immunoglobulin single variable domain, polypeptide or other binding agent the recorded fluorescence is between 80% and 0.1% (e.g. 80% to 4%) of the maximum fluorescence (measured for the separate labelled immunoglobulin, antibody, immunoglobulin single variable domain, polypeptide or other binding agent), specifically between 75% and 0.1% (e.g. 75% to 4%) of the maximum fluorescence, and more specifically between 70% and 0.1% (e.g. 70% to 4%) of maximum fluorescence (as just defined above).

The competition between two test binding agents (termed A* and B*) for binding to CD123 can also be evaluated by adding both binding agents, each labeled with a different fluorophore, to the CD123 expressing cells. After incubation and cells wash, read out can be performed on a FACS. A gate is set for each fluorophore and the total amount of channel fluorescence is recorded. Reduction and/or absence of fluorescence of one of the fluorophore indicate (cross)-blocking by the binding agents for binding to CD123 expressed on the cells.

The following generally describes a suitable Biacore assay for determining whether an immunoglobulin, antibody, immunoglobulin single variable domain, polypeptide or other binding agent cross-blocks or is capable of cross-blocking according to the invention. It will be appreciated that the assay can be used with any of the immunoglobulins, antibodies, immunoglobulin single variable domains, polypeptides or other binding agents described herein. The Biacore instrument (for example the Biacore 3000) is operated in line with the manufacturer's recommendations. Thus in one cross-blocking assay, the target protein (e.g. CD123) is coupled to a CM5 Biacore chip using standard amine coupling chemistry to generate a surface that is coated with the target. Typically 200-800 resonance units of the target would be coupled to the chip (an amount that gives easily measurable levels of binding but that is readily saturable by the concentrations of test reagent being used). Two test binding agents (termed A* and B*) to be assessed for their ability to cross-block each other are mixed at a one to one molar ratio of binding sites in a suitable buffer to create the test mixture. When calculating the concentrations on a binding site basis the molecular weight of a binding agent is assumed to be the total molecular weight of the binding agent divided by the number of target binding sites on that binding agent. The concentration of each binding agent in the test mix should be high enough to readily saturate the binding sites for that binding agent on the target molecules captured on the Biacore chip. The binding agents in the mixture are at the same molar concentration (on a binding basis) and that concentration would typically be between 1.00 and 1.5 micromolar (on a binding site basis). Separate solutions containing A* alone and B* alone are also prepared. A* and B* in these solutions should be in the same buffer and at the same concentration as in the test mix. The test mixture is passed over the target-coated Biacore chip and the total amount of binding recorded. The chip is then treated in such a way as to remove the bound binding agents without damaging the chip-bound target. Typically this is done by treating the chip with 30 mM HCl for 60 seconds. The solution of A* alone is then passed over the target-coated surface and the amount of binding recorded. The chip is again treated to remove all of the bound binding agents without damaging the chip-bound target. The solution of B* alone is then passed over the target-coated surface and the amount of binding recorded. The maximum theoretical binding of the mixture of A* and B* is next calculated, and is the sum of the binding of each binding agent when passed over the target surface alone. If the actual recorded binding of the mixture is less than this theoretical maximum then the two binding agents are said to cross-block each other. Thus, in general, a cross-blocking immunoglobulin, antibody, immunoglobulin single variable domain, polypeptide or other binding agent according to the invention is one which will bind to the target in the above Biacore cross-blocking assay such that during the assay and in the presence of a second immunoglobulin, antibody, immunoglobulin single variable domain, polypeptide or other binding agent the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two immunoglobulins, antibodies, immunoglobulin single variable domains, polypeptides or binding agents in combination. The Biacore assay described above is a primary assay used to determine if immunoglobulins, antibodies, immunoglobulin single variable domains, polypeptide or other binding agents cross-block each other according to the invention. On rare occasions particular immunoglobulins, antibodies, immunoglobulin single variable domains, polypeptides or other binding agents may not bind to a target coupled via amine chemistry to a CM5 Biacore chip (this usually occurs when the relevant binding site on the target is masked or destroyed by the coupling to the chip). In such cases cross-blocking can be determined using a tagged version of the target, for example a N-terminal His-tagged version. In this particular format, an anti-His antibody would be coupled to the Biacore chip and then the His-tagged target would be passed over the surface of the chip and captured by the anti-His antibody. The cross blocking analysis would be carried out essentially as described above, except that after each chip regeneration cycle, new His-tagged target would be loaded back onto the anti-His antibody coated surface. In addition to the example given using N-terminal His-tagged target, C-terminal His-tagged target could alternatively be used. Furthermore, various other tags and tag binding protein combinations that are known in the art could be used for such a cross-blocking analysis (e.g. HA tag with anti-HA antibodies; FLAG tag with anti-FLAG antibodies; biotin tag with streptavidin).

The following generally describes an ELISA assay for determining whether an immunoglobulin, antibody, immunoglobulin single variable domain, polypeptide or other binding agent directed against a target (e.g., CD123) cross-blocks or is capable of cross-blocking as defined herein. It will be appreciated that the assay can be used with any of the immunoglobulins, antibodies, immunoglobulin single variable domains, polypeptides or other binding agents described herein. The general principal of the assay is to have an immunoglobulin, antibody, immunoglobulin single variable domain, polypeptide or binding agent that is directed against the target coated onto the wells of an ELISA plate. An excess amount of a second, potentially cross-blocking, anti-target immunoglobulin, antibody, immunoglobulin single variable domain, polypeptide or other binding agent is added in solution (i.e. not bound to the ELISA plate). A limited amount of the target is then added to the wells. The coated immunoglobulin, antibody, immunoglobulin single variable domain, polypeptide or other binding agent and the immunoglobulin, antibody, immunoglobulin single variable domain, polypeptide or other binding agent in solution compete for binding of the limited number of target molecules. The plate is washed to remove excess target that has not been bound by the coated immunoglobulin, antibody, immunoglobulin single variable domain, polypeptide or other binding agent and to also remove the second, solution phase immunoglobulin, antibody, immunoglobulin single variable domain, polypeptide or other binding agent as well as any complexes formed between the second, solution phase immunoglobulin, antibody, immunoglobulin single variable domain, polypeptide or other binding agent and target. The amount of bound target is then measured using a reagent that is appropriate to detect the target. An immunoglobulin, antibody, immunoglobulin single variable domain, polypeptide or other binding agent in solution that is able to cross-block the coated immunoglobulin, antibody, immunoglobulin single variable domain, polypeptide or other binding agent will be able to cause a decrease in the number of target molecules that the coated immunoglobulin, antibody, immunoglobulin single variable domain, polypeptide or other binding agent can bind relative to the number of target molecules that the coated immunoglobulin, antibody, immunoglobulin single variable domain, polypeptide or other binding agent can bind in the absence of the second, solution phase, immunoglobulin, antibody, immunoglobulin single variable domain, polypeptide or other binding agent. In the instance where the first immunoglobulin, antibody, immunoglobulin single variable domain, polypeptide or other binding agent, e.g., an Ab-X, is chosen to be the immobilized immunoglobulin, antibody, immunoglobulin single variable domain, polypeptide or other binding agent, it is coated onto the wells of the ELISA plate, after which the plates are blocked with a suitable blocking solution to minimize non-specific binding of reagents that are subsequently added. An excess amount of the second immunoglobulin, antibody, immunoglobulin single variable domain, polypeptide or other binding agent, i.e. Ab-Y, is then added to the ELISA plate such that the moles of Ab-Y target binding sites per well are at least 10 fold higher than the moles of Ab-X target binding sites that were used, per well, during the coating of the ELISA plate. Target is then added such that the moles of target added per well are at least 25-fold lower than the moles of Ab-X target binding sites that were used for coating each well. Following a suitable incubation period the ELISA plate is washed and a reagent for detecting the target is added to measure the amount of target specifically bound by the coated anti-target immunoglobulin, antibody, immunoglobulin single variable domain, polypeptide or other binding agent (in this case Ab-X). The background signal for the assay is defined as the signal obtained in wells with the coated immunoglobulin, antibody, immunoglobulin single variable domain, polypeptide or other binding agent (in this case Ab-X), second solution phase immunoglobulin single variable domain, polypeptide or other binding agent (in this case Ab-Y), target buffer only (i.e., without target) and target detection reagents. The positive control signal for the assay is defined as the signal obtained in wells with the coated immunoglobulin, antibody, immunoglobulin single variable domain, polypeptide or other binding agent (in this case Ab-X), second solution phase immunoglobulin, antibody, immunoglobulin single variable domain, polypeptide or other binding agent buffer only (i.e., without second solution phase immunoglobulin, antibody, immunoglobulin single variable domain, polypeptide or other binding agent), target and target detection reagents. The ELISA assay may be run in such a manner so as to have the positive control signal be at least 6 times the background signal. To avoid any artefacts (e.g. significantly different affinities between Ab-X and Ab-Y for the target) resulting from the choice of which immunoglobulin, antibody, immunoglobulin single variable domain, polypeptide or other binding agent to use as the coating immunoglobulin, antibody, immunoglobulin single variable domain, polypeptide or other binding agent and which to use as the second (competitor) immunoglobulin, antibody, immunoglobulin single variable domain, polypeptide or other binding agent, the cross-blocking assay may to be run in two formats: 1) format 1 is where Ab-X is the immunoglobulin, antibody, immunoglobulin single variable domain, polypeptide or other binding agent that is coated onto the ELISA plate and Ab-Y is the competitor immunoglobulin, antibody, immunoglobulin single variable domain, polypeptide or other binding agent that is in solution and 2) format 2 is where Ab-Y is the immunoglobulin, antibody, immunoglobulin single variable domain, polypeptide or other binding agent that is coated onto the ELISA plate and Ab-X is the competitor immunoglobulin, antibody, immunoglobulin single variable domain, polypeptide or other binding agent that is in solution. Ab-X and Ab-Y are defined as cross-blocking if, either in format 1 or in format 2, the solution phase anti-target immunoglobulin, antibody, immunoglobulin single variable domain, polypeptide or other binding agent is able to cause a reduction of between 60% and 100%, specifically between 70% and 100%, and more specifically between 80% and 100%, of the target detection signal (i.e., the amount of target bound by the coated immunoglobulin, antibody, immunoglobulin single variable domain, polypeptide or other binding agent) as compared to the target detection signal obtained in the absence of the solution phase anti-target immunoglobulin, antibody, immunoglobulin single variable domain, polypeptide or other binding agent (i.e., the positive control wells).

Other methods for determining whether an immunoglobulin, antibody, immunoglobulin single variable domain, polypeptide or other binding agent directed against a target (cross)-blocks, is capable of (cross)-blocking, competitively binds or is (cross)-competitive as defined herein are described e.g. in Xiao-Chi Jia et al. (2004, Journal of Immunological Methods 288: 91-98), Miller et al. (2011, Journal of Immunological Methods 365: 118-125) and/or the methods described herein (see e.g. Example 16).

The term "CD123" as used herein refers to the a subunit of the interleukin 3 receptor (IL-3Rα).

The term "TCR" as used herein refers to the T cell receptor, which consists of an TCRα and a TCRβ chain. Both α and β chains of the TCR consist of a constant domain and a variable domain. The polypeptides and immunoglobulin single variable domains of the present invention bind to the constant domain of TCR.

The "half-life" of a polypeptide of the invention can generally be defined as described in paragraph o) on page 57 of WO 08/020079 and as mentioned therein refers to the time taken for the serum concentration of the polypeptide to be reduced by 50%, in vivo, for example due to degradation of the polypeptide and/or clearance or sequestration of the polypeptide by natural mechanisms. The in vivo half-life of a polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t1/2-alpha, t1/2-beta and the area under the curve (AUC). Reference is for example made to the standard handbooks, such as Kenneth et al (1986, Chemical Stability of Pharmaceuticals: A Handbook for Pharmacists, John Wiley & Sons Inc) and M Gibaldi and D Perron (1982, Pharmacokinetics, Marcel Dekker, 2nd Rev. Ed., 1982). The terms "increase in half-life" or "increased half-life" are also as defined in paragraph o) on page 57 of WO 08/020079 and in particular refer to an increase in the t1/2-beta, either with or without an increase in the t1/2-alpha and/or the AUC or both.

Unless indicated otherwise, the term "immunoglobulin" and "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively).

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g., a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a two-layer sandwich of about seven antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confers specificity to an antibody for the antigen by carrying the antigen-binding site.

The term "immunoglobulin single variable domain" or "ISV", interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e., by a VH-VL pair of immunoglobulin domains, which jointly bind to an epitope of the respective antigen.

In contrast, immunoglobulin single variable domains are capable of specifically binding to an epitope of the antigen without pairing with an additional immunoglobulin variable domain. The binding site of an immunoglobulin single variable domain is formed by a single VH/VHH or VL domain. Hence, the antigen binding site of an immunoglobulin single variable domain is formed by no more than three CDRs.

As such, the single variable domain may be a light chain variable domain sequence (e.g., a VL-sequence) or a suitable fragment thereof; or a heavy chain variable domain sequence (e.g., a VH-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

In one aspect of the invention, the immunoglobulin single variable domains are heavy chain variable domain sequences (e.g., a VH-sequence); more specifically, the immunoglobulin single variable domains can be heavy chain variable domain sequences that are derived from a conventional four-chain antibody or heavy chain variable domain sequences that are derived from a heavy chain antibody.

For example, the immunoglobulin single variable domain may be a (single) domain antibody (or an amino acid that is suitable for use as a (single) domain antibody), a "dAb" or dAb (or an amino acid that is suitable for use as a dAb), a Nanobody (as defined herein, and including but not limited to a VHH), other single variable domains, or any suitable fragment of any one thereof.

In particular, the immunoglobulin single variable domain may be a Nanobody (as defined herein) or a suitable fragment thereof. [Note: Nanobody, Nanobodies and Nanoclone are registered trademarks of Ablynx N.V.] For a general description of Nanobodies, reference is made to the further description below, as well as to the prior art cited herein, such as e.g. described in WO 08/020079 (page 16).

"VHH domains", also known as VHHs, $V_HH$ domains, VHH antibody fragments, and VHH antibodies, have originally been described as the antigen binding immunoglobulin (variable) domain of "heavy chain antibodies" (i.e., of "antibodies devoid of light chains"; Hamers-Casterman et al. Nature 363: 446-448, 1993). The term "VHH domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "$V_L$ domains" or "VL domains"). For a further description of VHH's and Nanobodies, reference is made to the review article by Muyldermans (2001, Reviews in Molecular Biotechnology 74: 277-302), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164. For a further general description of Nanobodies, reference is made to the prior art cited herein, such as e.g., described in WO 08/020079 (page 16).

"Domain antibodies", also known as "Dab"s, "Domain Antibodies", and "dAbs" (the terms "Domain Antibodies" and "dAbs" being used as trademarks by the GlaxoSmithKline group of companies) have been described in e.g., EP 0368684, Ward et al. (1989, Nature 341: 544-546), Holt et al. (2003, Trends in Biotechnology 21: 484-490) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutical use in humans.

It should also be noted that, although less preferred in the context of the present invention because they are not of mammalian origin, single variable domains can be derived from certain species of shark (for example, the so-called "IgNAR domains", see for example WO 05/18629).

Thus, in the meaning of the present invention, the term "immunoglobulin single variable domain" or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as e.g., described in Davies and Riechmann (1994, FEBS 339: 285-290; 1995, Biotechnol. 13: 475-479; 1996, Prot. Eng. 9: 531-537) and Riechmann and Muyldermans (1999, J. Immunol. Methods 231: 25-38).

The amino acid residues of a VHH domain are numbered according to the general numbering for $V_H$ domains given by Kabat et al. ("Sequence of proteins of immunological interest", US Public Health Services, NIH Bethesda, MD, Publication No. 91), as applied to VHH domains from Camelids, as shown e.g., in FIG. 2 of Riechmann and Muyldermans (1999, J. Immunol. Methods 231: 25-38). Alternative methods for numbering the amino acid residues of $V_H$ domains, which methods can also be applied in an analogous manner to VHH domains, are known in the art. However, in the present description, claims and figures, the numbering according to Kabat applied to VHH domains as described above will be followed, unless indicated otherwise.

It should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a VH domain and a VHH domain will usually be in the range of from 110 to 120, often between 112 and 115. It should however be noted that smaller and longer sequences may also be suitable for the purposes described herein.

Determination of CDR regions may also be done according to different methods. In the CDR determination according to Kabat, FR1 of a VHH comprises the amino acid residues at positions 1-30, CDR1 of a VHH comprises the amino acid residues at positions 31-35, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113.

In the present application, however, CDR sequences were determined according to Kontermann and Dubel (2010, Eds., Antibody Engineering, vol 2, Springer Verlag Heidelberg Berlin, Martin, Chapter 3, pp. 33-51). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113 (according to Kabat numbering).

Immunoglobulin single variable domains such as Domain antibodies and Nanobodies (including VHH domains) can be subjected to humanization. In particular, humanized immunoglobulin single variable domains, such as Nanobodies (including VHH domains) may be immunoglobulin single variable domains that are as generally defined for in the previous paragraphs, but in which at least one amino acid residue is present (and in particular, in at least one of the framework residues) that is and/or that corresponds to a humanizing substitution (as defined herein). Potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) an immunoglobulin single variable domain, such as a Nanobody (including VHH domains) may be partially humanized or fully humanized.

Immunoglobulin single variable domains such as Domain antibodies and Nanobodies (including VHH domains and humanized VHH domains), can also be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al. (1992, Biotechnology 10: 779-783), Barbas, et al. (1994, Proc. Nat. Acad. Sci, USA 91: 3809-3813), Shier et al. (1995, Gene 169: 147-155), Yelton et al. (Immunol. 155: 1994-2004), Jackson et al. (J. Immunol. 154: 3310-9, 1995), Hawkins et al. (1995, J. Mol. Biol. 226: 889-896), Johnson and Hawkins (1996, Affinity maturation of antibodies using phage display, Oxford University Press).

The process of designing/selecting and/or preparing a polypeptide, starting from an immunoglobulin single variable domain such as a Domain antibody or a Nanobody, is also referred to herein as "formatting" said immunoglobulin single variable domain; and an immunoglobulin single variable domain that is made part of a polypeptide is said to be "formatted" or to be "in the format of" said polypeptide. Examples of ways in which an immunoglobulin single variable domain can be formatted and examples of such formats will be clear to the skilled person based on the disclosure herein; and such formatted immunoglobulin single variable domain form a further aspect of the invention.

For example, and without limitation, one or more immunoglobulin single variable domains may be used as a "binding unit", "binding domain" or "building block" (these terms are used interchangeable) for the preparation of a polypeptide, which may optionally contain one or more further immunoglobulin single variable domains that can serve as a binding unit (i.e., against the same or another epitope on CD123 and/or against one or more other antigens, proteins or targets than CD123, such as e.g., TCR).

Monovalent polypeptides comprise or essentially consist of only one binding unit (such as e.g., one immunoglobulin single variable domains). Polypeptides that comprise two or more binding units (such as e.g., two or more immunoglobulin single variable domains) will also be referred to herein as "multivalent" polypeptides, and the binding units/immunoglobulin single variable domains present in such polypeptides will also be referred to herein as being in a "multivalent format". For example a "bivalent" polypeptide may comprise two immunoglobulin single variable domains, optionally linked via a linker sequence, whereas a "trivalent" polypeptide may comprises three immunoglobulin single variable domains, optionally linked via two linker sequences, whereas a "tetravalent" polypeptide may comprise four immunoglobulin single variable domains, optionally linked via three linker sequences, etc.

In a multivalent polypeptide, the two or more immunoglobulin single variable domains may be the same or different, and may be directed against the same antigen or antigenic determinant (for example against the same part(s) or epitope(s) or against different parts or epitopes) or may alternatively be directed against different antigens or antigenic determinants; or any suitable combination thereof. Polypeptides that contain at least two binding units (such as e.g., at least two immunoglobulin single variable domains) in which at least one binding unit is directed against a first antigen (i.e., CD123) and at least one binding unit is directed against a second antigen (i.e., different from CD123) will also be referred to as "multispecific" polypeptides, and the binding units (such as e.g., immunoglobulin single variable domains) present in such polypeptides will also be referred to herein as being in a "multispecific format". Thus, for example, a "bispecific" polypeptide of the invention is a polypeptide that comprises at least one immunoglobulin single variable domain directed against a first antigen (i.e., CD123) and one further immunoglobulin single variable domain directed against a second antigen (i.e., different from CD123, such as e.g. TCR), whereas a "trispecific" polypeptide of the invention is a polypeptide that comprises at least one immunoglobulin single variable domain directed against a first antigen (i.e., CD123), one further immunoglobulin single variable domain directed against a second antigen (i.e., different from CD123, such as e.g., TCR) and at least one further immunoglobulin single variable domain directed against a third antigen (i.e., different from both CD123 and the second antigen); etc.

Polypeptides that are directed against one antigen will also be referred to as "monospecific" polypeptides. Such "monospecific" polypeptides may be monovalent polypeptides, containing only one binding unit (such as e.g., one immunoglobulin single variable domain) directed against one antigen (e.g. TCR or CD123). Such "monospecific" polypeptides may also be multivalent polypeptides, containing two or more immunoglobulin single variable domains directed against the same antigen. Such "monospecific" multivalent polypeptides can be directed against the same part(s) or epitope(s) of the same antigen or against different parts or epitopes of the same antigen) (e.g. CD123).

Polypeptides that comprise two or more binding units directed against different parts or epitopes on the same antigen are also referred to as "multiparatopic" polypeptides. As such, "multiparatopic" polypeptides, such as e.g., "biparatopic" polypeptides or "triparatopic" polypeptides, comprise or essentially consist of two or more binding units that each have a different paratope (as will be further described herein; see chapter on monospecific polypeptides of the invention).

Polypeptides of the Invention

The present invention provides polypeptides that redirect T cells for killing of CD123 expressing cells. The ability of these polypeptides to exert this function arises from their multispecific format. The multispecific polypeptides provided by the present invention (referred to as "multispecific polypeptide(s) of the invention") comprise one immunoglobulin single variable domain (ISV) that specifically binds T cell receptor (TCR) and one or more ISV that specifically bind CD123.

The invention also relates to monovalent polypeptides that may be used as a binding unit or building block in such a multispecific polypeptide of the invention. Accordingly, in one aspect, the invention provides ISVs that specifically bind TCR. In another aspect, the invention provides ISVs that specifically bind CD123. These monovalent polypeptides only bind to one antigen and will therefore be referred to as "monospecific polypeptide(s) of the invention".

The ISVs that specifically bind CD123 may further be formatted to form multivalent polypeptides, which are also encompassed in the invention. Such multivalent polypeptides comprise two or more ISVs that specifically bind CD123. These multivalent polypeptides only bind one antigen (i.e. CD123) and will therefore also be referred to as "monospecific polypeptide(s) of the invention".

The monospecific polypeptide(s) of the invention and multispecific polypeptide(s) of the invention are further described herein and are generally referred to as "polypeptide(s) of the invention".

1. Monospecific Polypeptides of the Invention 1.1 Monospecific Polypeptides that Bind TCR The present invention relates to a monospecific polypeptide that specifically binds TCR. Preferably, such monospecific polypeptide of the invention is monovalent. In a preferred aspect, the monospecifc polypeptide is an immunoglobulin single variable domain, which will be referred to herein as "immunoglobulin single variable domain(s) of the invention" or "ISV(s) of the invention".

The T cell receptor (also referred to herein as TCR) is a heterodimer that consists of a TCRα and a TCRβ chain. Both α and β chains of the TCR consist of a constant domain and a variable domain. The polypeptides of the invention specifically bind to the constant domain of the TCR.

The T cell receptor forms part of the TCR complex. As used herein, the terms "TCR complex" or "TCRαβ-CD3 complex" refers to the T cell receptor complex presented on the surface of T cells (see Kuhns et al. 2006, Immunity 24: 133-139). The TCR complex is composed of six different type I single-spanning transmembrane proteins: the TCRα and TCRβ chain that form the TCR heterodimer responsible for ligand recognition, and the non-covalently associated CD3γ, CD3δ, CD3ε and ζ chains, which bear cytoplasmic sequence motifs that are phosphorylated upon receptor activation and recruit a large number of signalling components. The sequences for the human CD3 and the human TCRα/β constant domains are provided in Table A-8 (SEQ ID NOs: 70-75; cf. UniProt identifiers: CD3 delta: P04234, CD3 gamma: P09693, CD3 epsilon: P07766, CD3 zeta: P20963, TCR alpha: P01848 and TCR beta: related to P01850).

In one aspect, the present invention relates to a polypeptide as described herein, that binds to the constant domain of the T cell receptor α (TCRα) (SEQ ID NO: 74) and/or the constant domain of the T cell receptor β (TCRβ) (SEQ ID NO: 75), or polymorphic variants or isoforms thereof.

Isoforms are alternative protein sequences that can be generated from the same gene by a single or by the combination of biological events such as alternative promoter usage, alternative splicing, alternative initiation and ribosomal frameshifting, all as known in the art.

Only after rigorous immunization, screening and selection methods, the present inventors were able to identify ISVs binding to the constant domains of TCR. A cluster of sequences, comprising 104 clones with similarities and differences in CDR1, CDR2 and CDR3 was identified (see Table A-5). A corresponding sequence alignment is provided (Table A-1).

Accordingly, the present invention relates to polypeptides that are ISVs chosen from the group consisting of SEQ ID NOs: 42 and 78-180 (cf. Table A-5). In a further aspect, the polypeptide is chosen from the group consisting of SEQ ID NOs: 42 and 78-180 or from polypeptides that have a sequence identity of more than 80%, more than 85%, more than 90%, more than 95%, or even more than 99% with one of SEQ ID NOs: 42 and 78-180.

Accordingly, the present invention relates to a polypeptide that binds TCR and comprises or (essentially) consists of 4 framework regions (FR1 to FR4, respectively) and 3 complementarity determining regions (CDR1 to CDR3, respectively), in which CDR1 has the amino acid sequence $GX_1VX_2X_3X_4NX_5LX_6$ (SEQ ID NO: 372), in which $X_1$ is D, A, S, E or G, $X_2$ is H or Y, $X_3$ is K or L, $X_4$ is I or L, $X_5$ is F, I or V, and $X_6$ is G or S.

In a further aspect, the present invention relates to a polypeptide that binds TCR and that comprises or (essentially) consists of 4 framework regions (FR1 to FR4, respectively) and 3 complementarity determining regions (CDR1 to CDR3, respectively), in which CDR2 has the amino acid sequence $X_1IX_2IX_3DX_4X_5X_6$ (SEQ ID NO: 371), in which $X_1$ is H, T or R, $X_2$ is S, T or A, $X_3$ is G, S or A, $X_4$ is Q, D, E, T, A or V, $X_5$ is T, A or V and $X_6$ is D, A, Q, N, V or S.

In a further aspect, the present invention relates to a polypeptide that binds TCR and that comprises or (essentially) consists of 4 framework regions (FR1 to FR4, respectively) and 3 complementarity determining regions (CDR1 to CDR3, respectively), in which CDR3 has the amino acid sequence $X_1$SR $X_2X_3$PYX$_4$Y (SEQ ID NO: 373), in which $X_1$ is F, Y, G, L or K, $X_2$ is I or L, $X_3$ is Y or W, and $X_4$ is D, N or S.

Preferred CDR sequences for use in the polypeptides of the invention, as well as preferred combinations of CDR sequences, are depicted in Table A-5.

Accordingly, the present invention relates to a polypeptide, preferably an ISV, that specifically binds TCR and that comprises or essentially consists of 4 framework regions (FR1 to FR4, respectively) and 3 complementarity determining regions (CDR1 to CDR3, respectively), in which:

i) CDR1 is chosen from the group consisting of:
   a) SEQ ID NOs: 181-191; or
   b) amino acid sequences that have 4, 3, 2 or 1 amino acid(s) difference with the amino acid sequence of one of SEQ ID NOs: 181-191; provided that the ISV comprising the CDR1 with 4, 3, 2 or 1 amino acid(s) difference binds TCR with about the same or a higher affinity compared to the binding by the ISV comprising the CDR1 without the 4, 3, 2 or 1 amino acid(s) difference, said affinity as measured by surface plasmon resonance;

and/or ii) CDR2 is chosen from the group consisting of:
   c) SEQ ID NOs: 192-217; or
   d) amino acid sequences that have 4, 3, 2 or 1 amino acid(s) difference with the amino acid sequence of one of SEQ ID NOs: 192-217; provided that the ISV comprising the CDR2 with 4, 3, 2 or 1 amino acid(s) difference binds TCR with about the same or a higher affinity compared to the binding by the ISV comprising the CDR2 without the 4, 3, 2 or 1 amino acid(s) difference, said affinity as measured by surface plasmon resonance;

and/or iii) CDR3 is chosen from the group consisting of:
   e) SEQ ID NOs: 218-225; or
   f) amino acid sequences that have 4, 3, 2 or 1 amino acid(s) difference with the amino acid sequence of one of SEQ ID NOs: 218-225; provided that the ISV comprising the CDR3 with 4, 3, 2 or 1 amino acid(s) difference binds TCR with about the same or a higher affinity compared to the binding by the ISV comprising the CDR3 without the 4, 3, 2 or 1 amino acid(s) difference, said affinity as measured by surface plasmon resonance.

In a further aspect, the present invention relates to a polypeptide, preferably an ISV, in which:

i) CDR1 is chosen from the group consisting of:
   a) SEQ ID NOs: 181-191; or
   b) amino acid sequences that have 4, 3, 2 or 1 amino acid(s) difference with the amino acid sequence of one of SEQ ID NOs: 181-191; provided that the polypeptide comprising the CDR1 with 4, 3, 2 or 1 amino acid(s) difference binds TCR with about the same or a higher affinity compared to the binding by the polypeptide comprising the CDR1 without the 4, 3, 2 or 1 amino acid(s) difference, said affinity as measured by surface plasmon resonance; and ii) CDR2 is chosen from the group consisting of:
   c) SEQ ID NOs: 192-217; or
   d) amino acid sequences that have 4, 3, 2 or 1 amino acid(s) difference with the amino acid sequence of one of SEQ ID NOs: 192-217; provided that the polypeptide comprising the CDR2 with 4, 3, 2 or 1 amino acid(s) difference binds TCR with about the same or a higher affinity compared to the binding by the polypeptide comprising the CDR2 without the 4, 3, 2 or 1 amino acid(s) difference, said affinity as measured by surface plasmon resonance; and iii) CDR3 is chosen from the group consisting of:
   e) SEQ ID NOs: 218-225; or
   f) amino acid sequences that have 4, 3, 2 or 1 amino acid(s) difference with the amino acid sequence of one of SEQ ID NOs: 218-225; provided that the polypeptide comprising the CDR3 with 4, 3, 2 or 1 amino acid(s) difference binds TCR with about the same or a higher affinity compared to the binding by the polypeptide comprising the CDR3 without the 4, 3, 2 or 1 amino acid(s) difference, said affinity as measured by surface plasmon resonance.

In particular, the present invention relates to a polypeptide, preferably an ISV, in which:

i) CDR1 is chosen from the group consisting of:
   a) SEQ ID NOs: 181-191; or
   b) amino acid sequences that have 4, 3, 2 or 1 amino acid(s) difference with the amino acid sequence of one of SEQ ID NOs: 181-191, wherein the 4, 3, 2 or 1 amino acid(s) difference are present at position 2, 4, 5, 6, 8 and/or 10 of the CDR1 (position 27, 29, 30, 31, 33 and/or 35 according to Kabat numbering); provided that the polypeptide comprising the CDR1 with 4, 3, 2 or 1 amino acid(s) difference binds TCR with about the same or a higher affinity compared to the binding by the polypeptide comprising the CDR1 without the 4, 3, 2 or 1 amino acid(s) difference, said affinity as measured by surface plasmon resonance; and ii) CDR2 is chosen from the group consisting of:
   c) SEQ ID NOs: 192-217; or
   d) amino acid sequences that have 4, 3, 2 or 1 amino acid(s) difference with the amino acid sequence of one of SEQ ID NOs: 192-217, wherein the 4, 3, 2 or 1 amino acid(s) difference are present at position 1, 3, 5, 7, 8 and/or 9 of the CDR2 (position 50, 52, 54, 56, 57 and/or 58 according to Kabat numbering); provided that the polypeptide comprising the CDR2 with 4, 3, 2 or 1 amino acid(s) difference binds TCR with about the same or a higher affinity compared to the binding by the polypeptide comprising the CDR2 without the 4, 3, 2 or 1 amino acid(s) difference, said affinity as measured by surface plasmon resonance; and iii) CDR3 is chosen from the group consisting of:
   e) SEQ ID NOs: 218-225; or
   f) amino acid sequences that have 4, 3, 2 or 1 amino acid(s) difference with the amino acid sequence of one of SEQ ID NOs: 218-225, wherein the 4, 3, 2 or 1 amino acid(s) difference are present at position 1, 4, 5 and/or 8 of the CDR3 (position 95, 98, 99 and/or 101 according to Kabat numbering); provided that the polypeptide comprising the CDR3 with 4, 3, 2 or 1 amino acid(s) difference binds TCR with about the same or a higher affinity compared to the binding by the polypeptide comprising the CDR3 without the 4, 3, 2 or 1 amino acid(s) difference, said affinity as measured by surface plasmon resonance.

In another aspect, the present invention relates to a polypeptide, preferably an ISV, in which CDR1 is chosen from the group consisting of:

a) SEQ ID NO: 181; or b) amino acid sequences that have 4, 3, 2 or 1 amino acid(s) difference with the amino acid sequence of SEQ ID NO: 181, wherein at position 2 the D has been changed into A, S, E or G;

at position 4 the H has been changed into Y;

at position 5 the K has been changed into L;

at position 6 the I has been changed into L;

at position 8 the F has been changed into I or V; and/or at position 10 the G has been changed into S;

provided that the polypeptide comprising the CDR1 with 4, 3, 2 or 1 amino acid(s) difference binds TCR with about the same or a higher affinity compared to the binding by the polypeptide comprising the CDR1 without the 4, 3, 2 or 1 amino acid(s) difference, said affinity as measured by surface plasmon resonance.

In another aspect, the present invention relates to a polypeptide, preferably an ISV, in which CDR2 is chosen from the group consisting of:

a) SEQ ID NO: 192; or b) amino acid sequences that have 4, 3, 2 or 1 amino acid(s) difference with the amino acid sequence of SEQ ID NO: 192, wherein at position 1 the H has been changed into T or R;

at position 3 the S has been changed into T or A;

at position 5 the G has been changed into S or A;

at position 7 the Q has been changed into D, E, T, A or V;

at position 8 the T has been changed into A or V; and/or at position 9 the D has been changed into A, Q, N, V or S;

provided that the polypeptide comprising the CDR2 with 4, 3, 2 or 1 amino acid(s) difference binds TCR with about the same or a higher affinity compared to the binding by the polypeptide comprising the CDR2 without the 4, 3, 2 or 1 amino acid(s) difference, said affinity as measured by surface plasmon resonance.

In another aspect, the present invention relates to a polypeptide, preferably an ISV, in which CDR3 is chosen from the group consisting of:

a) SEQ ID NO:218; or b) amino acid sequences that have 4, 3, 2 or 1 amino acid(s) difference with the amino acid sequence of SEQ ID NO: 218, wherein at position 1 the F has been changed into Y, L or G;

at position 4 the I has been changed into L;

at position 5 the Y has been changed into W; and/or at position 8 the D has been changed into N or S;

provided that the polypeptide comprising the CDR3 with 4, 3, 2 or 1 amino acid(s) difference binds TCR with about the same or a higher affinity compared to the binding by the polypeptide comprising the CDR3 without the 4, 3, 2 or 1 amino acid(s) difference, said affinity as measured by surface plasmon resonance.

Accordingly, the present invention relates to a polypeptide, preferably an ISV, in which:

i) CDR1 is chosen from the group consisting of:

a) SEQ ID NO: 181; or b) amino acid sequences that have 4, 3, 2 or 1 amino acid(s) difference with the amino acid sequence of SEQ ID NO: 181, wherein at position 2 the D has been changed into A, S, E or G;

at position 4 the H has been changed into Y;

at position 5 the K has been changed into L;

at position 6 the I has been changed into L;

at position 8 the F has been changed into I or V; and/or at position 10 the G has been changed into S;

provided that the polypeptide comprising the CDR1 with 4, 3, 2 or 1 amino acid(s) difference binds TCR with about the same or a higher affinity compared to the binding by the polypeptide comprising the CDR1 without the 4, 3, 2 or 1 amino acid(s) difference, said affinity as measured by surface plasmon resonance; and ii) CDR2 is chosen from the group consisting of:

c) SEQ ID NOs: 192; or d) amino acid sequences that have 4, 3, 2 or 1 amino acid(s) difference with the amino acid sequence of SEQ ID NO: 192, wherein at position 1 the H has been changed into T or R;

at position 3 the S has been changed into T or A;

at position 5 the G has been changed into S or A;

at position 7 the Q has been changed into D, E, T, A or V;

at position 8 the T has been changed into A or V; and/or at position 9 the D has been changed into A, Q, N, V or S;

provided that the polypeptide comprising the CDR2 with 4, 3, 2 or 1 amino acid(s) difference binds TCR with about the same or a higher affinity compared to the binding by the polypeptide comprising the CDR2 without the 4, 3, 2 or 1 amino acid(s) difference, said affinity as measured by surface plasmon resonance; and iii) CDR3 is chosen from the group consisting of:

e) SEQ ID NOs: 218; or f) amino acid sequences that have 4, 3, 2 or 1 amino acid(s) difference with the amino acid sequence of SEQ ID NO: 218, wherein at position 1 the F has been changed into Y, L or G;

at position 4 the I has been changed into L;

at position 5 the Y has been changed into W; and/or at position 8 the D has been changed into N or S;

provided that the polypeptide comprising the CDR3 with 4, 3, 2 or 1 amino acid(s) difference binds TCR with about the same or a higher affinity compared to the binding by the polypeptide comprising the CDR3 without the 4, 3, 2 or 1 amino acid(s) difference, said affinity as measured by surface plasmon resonance.

In another aspect, the present invention relates to a polypeptide, preferably an ISV, in which CDR1 is chosen from the group consisting of SEQ ID NOs: 181-191, CDR2 is chosen from the group consisting of SEQ ID NOs: 192-217, and CDR3 is chosen from the group consisting of SEQ ID NOs: 218-225.

Accordingly, in a preferred aspect, the present invention relates to a polypeptide, preferably an ISV, in which CDR1 is SEQ ID NO: 181, CDR2 is SEQ ID NO: 192, and CDR3 is SEQ ID NO: 218.

Generally, the combinations of CDRs listed in Table A-5 (i.e. those mentioned on the same line in Table A-5) are preferred. Thus, it is generally preferred that, when a CDR in an ISV is a CDR sequence mentioned in Table A-5 or suitably chosen from the group consisting of CDR sequences that have 4, 3, 2 or only 1 amino acid difference(s) with a CDR sequence listed in Table A-5, that at least one and preferably both of the other CDR's are suitably chosen from the CDR sequences that belong to the same combination in Table A-5 (i.e. mentioned on the same line in Table A-5) or are suitably chosen from the group consisting of CDR sequences that have 4, 3, 2 or only 1 amino acid difference(s) with the CDR sequence(s) belonging to the same combination.

The present invention also relates to a polypeptide, preferably an ISV, that cross-blocks the binding to TCR of at least one of the polypeptides as described herein and/or that is cross-blocked from binding to TCR by at least one of the polypeptides as described herein.

The polypeptides of the present invention specifically bind TCR on the surface of effector cells, such as T cells. In "monovalent" format, the monovalent polypeptides of the invention that bind TCR cause minimal to no T cell activation.

As used herein, the term "an effector cell" is a cell comprising a TCR complex, preferably an immune cell, such as a T cell, preferably a CD4$^+$ T-helper cell (also known as CD4 cell, T-helper cell or T4 cell), more preferably a Cytotoxic T cell (also known as $T_c$ cell, CTL or CD8$^+$ T cells) or Natural Killer T cells (NKT cells). In some aspects, the cell is present in vivo. In some aspects, the cell is present in vitro. The effector cell of the invention relates in particular to mammalian cells, preferably to primate cells, and even more preferably to human cells.

"T cell activation" as used herein refers to one or more cellular response(s) of a T cell, e.g. a cytotoxic T cell, such as selected from: proliferation, differentiation, cytokine secretion, cytotoxic effector molecule release, cytotoxic activity, expression of activation markers, and redirected target cell lysis.

The monospecific polypeptide of the invention binds to the constant domain of the T cell receptor (TCR) with an average $K_D$ value of between 100 nM and 10 pM, such as at an average $K_D$ value of 90 nM or less, even more preferably at an average $K_D$ value of 80 nM or less, such as less than 70, 60, 50, 40, 30, 20, 10, 5 nM or even less, such as less than 4, 3, 2, or 1 nM, such as less than 500, 400, 300, 200, 100, 90, 80, 70, 60, 50, 40, 30, 20 pM, or even less, such as less than 10 pM. Preferably, the $K_D$ is determined by Kinexa, BLI or SPR, for instance as determined by Proteon. For instance, said $K_D$ is determined as set out in the Examples section.

The monospecific polypeptide of the invention binds to TCR with an EC50 value of between 100 nM and 1 pM, such as at an average EC50 value of 100 nM or less, even more preferably at an average EC50 value of 90 nM or less, such as less than 80, 70, 60, 50, 40, 30, 20, 10, 5 nM or even less, such as less than 4, 3, 2, or 1 nM or even less, such as less than 500, 400, 300, 200, 100, 90, 80, 70, 60, 50, 40, 30, 20, 10, 5 pM, or even less, such as less than 4 pM. Said average EC50 is preferably determined by FACS, Biacore or ELISA, for instance, said EC50 is determined as set out in the Examples section.

It has been shown in the examples that the $K_D$ correlates well with the EC50.

In a further aspect, the monospecific polypeptide as described herein, has an on rate constant ($k_{on}$) to (or for binding) TCR selected from the group consisting of at least about $10^2$ M$^{-1}$s$^{-1}$, at least about $10^3$ M$^{-1}$s$^{-1}$, at least about $10^4$ M$^{-1}$s$^{-1}$, at least about $10^5$ M$^{-1}$s$^{-1}$, at least about $10^6$ M$^{-1}$s$^{-1}$, $10^7$ M$^{-1}$s$^{-1}$, at least about $10^8$ M$^{-1}$s$^{-1}$, at least about $10^9$ M$^{-1}$s$^{-1}$, and at least about $10^{10}$ M$^{-1}$s$^{-1}$, preferably as measured by surface plasmon resonance or as performed in the examples section.

In a further aspect, the monospecific polypeptide as described herein, has an off rate constant ($k_{off}$) to (or for binding) TCR selected from the group consisting of at most about $10^{-3}$ s$^{-1}$, at most about $10^{-4}$ s$^{-1}$, at most about $10^{-5}$ s$^{-1}$, at most about $10^{-6}$ s$^{-1}$, at most about $10^{-7}$ s$^{-1}$, at most about $10^{-8}$ s$^{-1}$, at most about $10^{-9}$ s$^{-1}$, and at most about $10^{-10}$ s$^{-1}$, preferably as measured by surface plasmon resonance or as performed in the examples section.

The monospecific polypeptides and/or immunoglobulin single variable domains of the invention that bind TCR may have framework sequences that are preferably (a suitable combination of) immunoglobulin framework sequences or framework sequences that have been derived from immunoglobulin framework sequences (for example, by sequence optimization such as humanization or camelization). For example, the framework sequences may be framework sequences derived from an immunoglobulin single variable domain such as a light chain variable domain (e.g., a $V_L$-sequence) and/or from a heavy chain variable domain (e.g., a $V_H$-sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized.

The framework sequences may preferably be such that the monospecific polypeptide and/or immunoglobulin single variable domain is a Domain antibody (or an amino acid sequence that is suitable for use as a Domain antibody); a single domain antibody (or an amino acid that is suitable for use as a single domain antibody); a "dAb" (or an amino acid that is suitable for use as a dAb); a Nanobody; a $V_{HH}$; a humanized $V_{HH}$; a camelized $V_H$; or a $V_{HH}$ that has been obtained by affinity maturation. Again, suitable framework sequences will be clear to the skilled person, for example on the basis of the standard handbooks and the further disclosure and prior art mentioned herein.

In particular, the framework sequences present in the monospecific polypeptides of the invention may contain one or more of Hallmark residues (as defined in WO 08/020079 (Tables A-3 to A-8)), such that the monospecific polypeptide of the invention is a Nanobody. Some preferred, but non-limiting examples of (suitable combinations of) such framework sequences will become clear from the further disclosure herein (see e.g., Table A-5). Generally, Nanobodies (in particular $V_{HH}$s, partially or fully humanized $V_{HH}$s and camelized $V_H$s) can in particular be characterized by the presence of one or more "Hallmark residues" in one or more of the framework sequences (as e.g., further described in WO 08/020079, page 61, line 24 to page 98, line 3).

More in particular, the invention provides polypeptides comprising or (essentially) consisting of at least one immunoglobulin single variable domain that is an amino acid sequence with the (general) structure

```
FR1 - CDR1 - FR2 - CDR2 - FR3 - CDR3 - FR4
``` in which FR1 to FR4 refer to framework regions 1 to 4, respectively, and in which CDR1 to CDR3 refer to the complementarity determining regions 1 to 3, respectively, and which:

i) have at least 80%, more preferably 90%, even more preferably 95% amino acid identity with at least one of the amino acid sequences of SEQ ID NOs: 42 and 78-180 (see Table A-5), in which for the purposes of determining the degree of amino acid identity, the amino acid residues that form the CDR sequences are disregarded. In this respect, reference is also made to Table A-5, which lists the framework 1 sequences (SEQ ID NOs: 226-250), framework 2 sequences (SEQ ID NOs: 251-276), framework 3 sequences (SEQ ID NOs: 277-319) and framework 4 sequences (SEQ ID NOs: 320-324) of the immunoglobulin single variable domains of SEQ ID NOs: 42 and 78-180 (see Table A-5); or and in which:

ii) preferably one or more of the amino acid residues at positions 11, 37, 44, 45, 47, 83, 84, 103, 104 and 108 according to the Kabat numbering are chosen from the Hallmark residues mentioned in Table A-3 to Table A-8 of WO 08/020079.

The present invention also provides a number of sequence optimized polypeptides and/or immunoglobulin single variable domains.

In particular, sequence optimized polypeptides and/or immunoglobulin single variable domains of the invention may be amino acid sequences that are as generally defined for immunoglobulin single variable domains in the previous paragraphs, but in which at least one amino acid residue is present (and in particular, in at least one of the framework residues) that is and/or that corresponds to a humanizing substitution (as defined herein). Some preferred, but non-limiting humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring VHH sequence with the corresponding framework sequence of one or more closely related human VH sequences, after which one or more of the potentially useful humanizing substitutions (or combinations thereof) thus determined can be introduced into said VHH sequence (in any manner known per se, as further described herein) and the resulting humanized VHH sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) an immunoglobulin single variable domains may be partially humanized or fully humanized.

The present invention also relates to sequence optimized polypeptides and/or immunoglobulin single variable domains that may show improved expression and/or increased stability upon storage during stability studies. The sequence optimized polypeptides and/or ISVs of the present invention may show reduced pyroglutamate post-translational modification of the N-terminus and hence have increased product stability. In addition, the sequence optimized polypeptides and/or ISVs of the present invention may show other improved properties such as e.g. less immunogenicity, improved binding characteristics (suitably measured and/or expressed as a $K_D$-value (actual or apparent), a $K_A$-value (actual or apparent), a $k_{on}$-rate and/or a $k_{off}$-rate, or alternatively as an $EC_{50}$ value, as further described herein) for TCR, improved affinity and/or improved avidity for TCR.

Some particularly preferred sequence optimized immunoglobulin single variable domains of the invention are sequence optimized variants of the immunoglobulin single variable domains of SEQ ID NOs: 42 and 78-180.

Thus, some other preferred immunoglobulin single variable domains of the invention are Nanobodies which can bind (as defined herein) to TCR and which:

i) are a sequence optimized variant of one of the immunoglobulin single variable domains of SEQ ID NOs: 42 and 78-180; and/or ii) have at least 80% amino acid identity with at least one of the immunoglobulin single variable domains of SEQ ID NOs: 42 and 78-180 (see Table A-5), in which for the purposes of determining the degree of amino acid identity, the amino acid residues that form the CDR sequences are disregarded; In this respect, reference is also made to Table A-5, which lists the framework 1 sequences (SEQ ID NOs: 226-250), framework 2 sequences (SEQ ID NOs: 251-276), framework 3 sequences (SEQ ID NOs: 277-319) and framework 4 sequences (SEQ ID NOs: 320-324) of the immunoglobulin single variable domains of SEQ ID NOs: 42 and 78-180 (see Table A-5);

and in which:

iii) preferably one or more of the amino acid residues at positions 11, 37, 44, 45, 47, 83, 84, 103, 104 and 108 according to the Kabat numbering are chosen from the Hallmark residues mentioned in Table A-3 to Table A-8 of WO 08/020079.

The sequence optimized polypeptides and/or immunoglobulin single variable domains of the invention may also contain the specific mutations/amino acid residues described in the following co-pending US provisional applications, all entitled "Improved immunoglobulin variable domains": U.S. 61/994,552 filed May 16, 2014; U.S. 61/014,015 filed Jun. 18, 2014; U.S. 62/040,167 filed Aug. 21, 2014; and U.S. 62/047,560, filed Sep. 8, 2014 (all assigned to Ablynx N.V.) as well as the International application WO 2015/173325 which was based on these provisional applications and which was published on Nov. 19, 2015.

In particular, the sequence optimized polypeptides and/or immunoglobulin single variable domains of the invention may suitably contain (i) a K or Q at position 112; or (ii) a K or Q at position 110 in combination with a V at position 11; or (iii) a T at position 89; or (iv) an L on position 89 with a K or Q at position 110; or (v) a V at position 11 and an L at position 89; or any suitable combination of (i) to (v).

As also described in said co-pending US provisional applications, when the polypeptides and/or immunoglobulin single variable domains of the invention contain the mutations according to one of (i) to (v) above (or a suitable combination thereof):

the amino acid residue at position 11 is preferably chosen from L, V or K (and is most preferably V); and the amino acid residue at position 14 is preferably suitably chosen from A or P; and the amino acid residue at position 41 is preferably suitably chosen from A or P; and the amino acid residue at position 89 is preferably suitably chosen from T, V or L; and the amino acid residue at position 108 is preferably suitably chosen from Q or L; and the amino acid residue at position 110 is preferably suitably chosen from T, K or Q; and the amino acid residue at position 112 is preferably suitably chosen from S, K or Q.

As mentioned in said co-pending US provisional applications, said mutations are effective in preventing or reducing binding of so-called "pre-existing antibodies" to the polypeptides, immunoglobulin single variable domains and/or constructs of the invention. For this purpose, the polypeptides and/or immunoglobulin single variable domains of the invention may also contain (optionally in combination with said mutations) a C-terminal extension (X)n (in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (1)), for which reference is again made to said US provisional applications as well as to WO 12/175741. In particular, a polypeptide and/or immunoglobulin single variable domain of the invention may contain such a C-terminal extension when it forms the C-terminal end of a protein, polypeptide or other construct comprising the same (again, as further described in said US provisional applications as well as WO 12/175741).

Accordingly, the present invention relates to a polypeptide as described herein, further comprising a C-terminal extension (X)n, in which n is 1 to 5, such as 1, 2, 3, 4 or 5, and in which X is a naturally occurring amino acid, preferably no cysteine.

These polypeptides of the invention, and in particular the immunoglobulin single variable domains comprising the CDR sequences of the invention are particularly suited for use as building block or binding unit for the preparation of multispecific polypeptides, such as the multispecific polypeptides of the invention.

Accordingly, the monospecific polypeptides of the invention that bind TCR can be in essentially isolated form (as defined herein), or they may form part of a protein or polypeptide, which may comprise or essentially consist of one polypeptide or ISV that binds TCR and which may optionally further comprise one or more further amino acid sequences (all optionally linked via one or more suitable linkers).

Accordingly, the present invention also relates to a protein or polypeptide that comprises or essentially consists of one monospecific polypeptide of the invention (or suitable fragments thereof). In a further aspect, the monospecific polypeptides of the invention that bind TCR may form part of a multispecific polypeptide, which may comprise or essentially consist of one ISV that binds TCR and which may optionally further comprise one or more further ISV that specifically binds another target, such as CD123, and which may optionally further comprise one or more further amino acid sequences (all optionally linked via one or more suitable linkers).

The monospecific polypeptides of the invention are thus used as a binding unit or building block in such a protein or polypeptide, so as to provide a multispecific polypeptide of the invention, as described herein (for multispecific polypeptides containing one or more VHH domains and their preparation, reference is also made to Conrath et al. (2001, J. Biol. Chem. 276: 7346-7350), as well as to for example WO 96/34103, WO 99/23221 and WO 2010/115998). The present invention thus also relates to a polypeptide which is a monovalent construct comprising or essentially consisting of one monovalent polypeptide that binds TCR.

1.2 CD123 Binding Polypeptides

The present invention relates to a monospecific polypeptide that specifically binds CD123, preferably human and/or cyno CD123. In a preferred aspect, the monospecific polypeptide is an immunoglobulin single variable domain, also referred to herein as "immunoglobulin single variable domain(s) of the invention" or "ISV(s) of the invention".

CD123 is also known as the α subunit of the interleukin 3 receptor (IL-3Rα). The sequences of the human CD123 and cyno CD123 are provided in Table A-8 (SEQ ID NOs: 68-69; cf. human CD123: NCBI RefSeq NP_002174 and cyno CD123: NCBI genbank no. EHH61867.1).

In one aspect, the present invention relates to a monospecific polypeptide as described herein, that binds to human CD123 (SEQ ID NO: 68).

The monospecific polypeptides that bind CD123 have been carefully selected for their specificity towards CD123. The polypeptides of the invention exhibit highly specific binding to CD123 upon formatting into a multispecific format of the invention (i.e. a format comprising one ISV that binds TCR and one or more ISVs that bind CD123). As such, off-target binding is avoided and target independent T cell activation is minimal, as further exemplified herein.

The inventors identified 2 clusters of Nanobodies (Example 12), that exhibited highly specific binding to CD123. Upon formatting of representatives of the clusters into a multispecific polypeptide of the invention (as further described), only minimal target-independent T cell activation was observed indicating the high specificity of the cluster representatives. Corresponding alignments are provided (see Table A-2 for the Nanobodies related to (family members of) Nanobody 56A10 (i.e., Nanobodies belonging to the same family as Nanobody 56A10) and Table A-3 for the Nanobodies related to (family members of) Nanobody 55F03 (i.e. Nanobodies belonging to the same family as Nanobody 55F03)).

A "Nanobody family", "V$_{HH}$ family" or "family" as used in the present specification refers to a group of Nanobodies and/or V$_{HH}$ sequences that have identical lengths (i.e. they have the same number of amino acids within their sequence) and of which the amino acid sequence between position 8 and position 106 (according to Kabat numbering) has an amino acid sequence identity of 89% or more.

Accordingly, the present invention relates to polypeptides, preferably ISVs, chosen from the group consisting of SEQ ID NOs: 1-10 (cf. Table A-4). In a further aspect, the polypeptide is chosen from the group consisting of SEQ ID NOs: 1-10 or from polypeptides that have a sequence identity of more than 80%, more than 85%, more than 90%, more than 95%, or even more than 99% with one of SEQ ID NOs: 1-10.

Accordingly, the present invention relates to a polypeptide, preferably an ISV, that specifically binds CD123 and that comprises or essentially consists of 4 framework regions (FR1 to FR4, respectively) and 3 complementarity determining regions (CDR1 to CDR3, respectively), in which:

i) CDR1 is chosen from the group consisting of:
  a) SEQ ID NOs: 11-16; or
  b) amino acid sequences that have 4, 3, 2 or 1 amino acid(s) difference with the amino acid sequence of one of SEQ ID NOs: 11-16; provided that the polypeptide comprising the CDR1 with 4, 3, 2 or 1 amino acid(s) difference binds CD123 with about the same or a higher affinity compared to the binding by the polypeptide comprising the CDR1 without the 4, 3, 2 or 1 amino acid(s) difference, said affinity as measured by surface plasmon resonance;

and/or
ii) CDR2 is chosen from the group consisting of:
  c) SEQ ID NOs: 17-20; or
  d) amino acid sequences that have 4, 3, 2 or 1 amino acid(s) difference with the amino acid sequence of one of SEQ ID NOs: 17-20; provided that the polypeptide comprising the CDR2 with 4, 3, 2 or 1 amino acid(s) difference binds CD123 with about the same or a higher affinity compared to the binding by the polypeptide comprising the CDR2 without the 4, 3, 2 or 1 amino acid(s) difference, said affinity as measured by surface plasmon resonance;

and/or iii) CDR3 is chosen from the group consisting of:
   e) SEQ ID NOs: 21-25; or
   f) amino acid sequences that have 4, 3, 2 or 1 amino acid(s) difference with the amino acid sequence of one of SEQ ID NOs: 21-25; provided that the polypeptide comprising the CDR3 with 4, 3, 2 or 1 amino acid(s) difference binds CD123 with about the same or a higher affinity compared to the binding by the polypeptide comprising the CDR3 without the 4, 3, 2 or 1 amino acid(s) difference, said affinity as measured by surface plasmon resonance.

In a further aspect, the present invention relates to a polypeptide, preferably an ISV, that specifically binds CD123 and that comprises or essentially consists of 4 framework regions (FR1 to FR4, respectively) and 3 complementarity determining regions (CDR1 to CDR3, respectively), in which:

i) CDR1 is chosen from the group consisting of:
   a) SEQ ID NOs: 11-16; or
   b) amino acid sequences that have 4, 3, 2 or 1 amino acid(s) difference with the amino acid sequence of one of SEQ ID NOs: 11-16; provided that the polypeptide comprising the CDR1 with 4, 3, 2 or 1 amino acid(s) difference binds CD123 with about the same or a higher affinity compared to the binding by the polypeptide comprising the CDR1 without the 4, 3, 2 or 1 amino acid(s) difference, said affinity as measured by surface plasmon resonance; and ii) CDR2 is chosen from the group consisting of:
   c) SEQ ID NOs: 17-20; or
   d) amino acid sequences that have 4, 3, 2 or 1 amino acid(s) difference with the amino acid sequence of one of SEQ ID NOs: 17-20; provided that the polypeptide comprising the CDR2 with 4, 3, 2 or 1 amino acid(s) difference binds CD123 with about the same or a higher affinity compared to the binding by the polypeptide comprising the CDR2 without the 4, 3, 2 or 1 amino acid(s) difference, said affinity as measured by surface plasmon resonance; and iii) CDR3 is chosen from the group consisting of:
   e) SEQ ID NOs: 21-25; or
   f) amino acid sequences that have 4, 3, 2 or 1 amino acid(s) difference with the amino acid sequence of one of SEQ ID NOs: 21-25; provided that the polypeptide comprising the CDR3 with 4, 3, 2 or 1 amino acid(s) difference binds CD123 with about the same or a higher affinity compared to the binding by the polypeptide comprising the CDR3 without the 4, 3, 2 or 1 amino acid(s) difference, said affinity as measured by surface plasmon resonance.

In a further aspect, the polypeptide of the invention, preferably an ISV, comprises or essentially consists of 4 framework regions (FR1 to FR4, respectively) and 3 complementarity determining regions (CDR1 to CDR3, respectively), in which:

i) CDR1 is chosen from the group consisting of:
   a) SEQ ID NOs: 11-16; or
   b) amino acid sequences that have 4, 3, 2 or 1 amino acid(s) difference with the amino acid sequence of one of SEQ ID NOs: 11-16, wherein the 4, 3, 2 or 1 amino acid(s) difference are present at position 3, 6, 7 and/or 8 of the CDR1 (position 28, 31, 32 and/or 33 according to Kabat numbering); provided that the polypeptide comprising the CDR1 with 4, 3, 2 or 1 amino acid(s) difference binds CD123 with about the same or a higher affinity compared to the binding by the polypeptide comprising the CDR1 without the 4, 3, 2 or 1 amino acid(s) difference, said affinity as measured by surface plasmon resonance;

and/or ii) CDR2 is chosen from the group consisting of:
   c) SEQ ID NOs: 17-20; or
   d) amino acid sequences that have 3, 2 or 1 amino acid(s) difference with the amino acid sequence of one of SEQ ID NOs: 17-20, wherein the 3, 2 or 1 amino acid(s) difference are present at position 3, 6 and/or 10 of the CDR2 (position 52, 54 and/or 58 according to Kabat numbering); provided that the polypeptide comprising the CDR2 with 3, 2 or 1 amino acid(s) difference binds CD123 with about the same or a higher affinity compared to the binding by the polypeptide comprising the CDR2 without the 3, 2 or 1 amino acid(s) difference, said affinity as measured by surface plasmon resonance;

and/or iii) CDR3 is chosen from the group consisting of:
   e) SEQ ID NOs: 21-25; or
   f) amino acid sequences that have 3, 2 or 1 amino acid(s) difference with the amino acid sequence of one of SEQ ID NOs: 21-25, wherein the 3, 2 or 1 amino acid(s) difference are present at position 3, 4 and/or 5 of the CDR3 (position 97, 98 and/or 99 according to Kabat numbering); provided that the polypeptide comprising the CDR3 with 3, 2 or 1 amino acid(s) difference binds CD123 with about the same or a higher affinity compared to the binding by the polypeptide comprising the CDR3 without the 3, 2 or 1 amino acid(s) difference, said affinity as measured by surface plasmon resonance.

In a further aspect, the polypeptide of the invention, preferably an ISV, comprises or essentially consists of 4 framework regions (FR1 to FR4, respectively) and 3 complementarity determining regions (CDR1 to CDR3, respectively), in which:

i) CDR1 is chosen from the group consisting of:
   a) SEQ ID NOs: 11-16; or
   b) amino acid sequences that have 4, 3, 2 or 1 amino acid(s) difference with the amino acid sequence of one of SEQ ID NOs: 11-16, wherein the 4, 3, 2 or 1 amino acid(s) difference are present at position 3, 6, 7 and/or 8 of the CDR1 (position 28, 31, 32 and/or 33 according to Kabat numbering); provided that the polypeptide comprising the CDR1 with 4, 3, 2 or 1 amino acid(s) difference binds CD123 with about the same or a higher affinity compared to the binding by the polypeptide comprising the CDR1 without the 4, 3, 2 or 1 amino acid(s) difference, said affinity as measured by surface plasmon resonance; and ii) CDR2 is chosen from the group consisting of:
   c) SEQ ID NOs: 17-20; or
   d) amino acid sequences that have 3, 2 or 1 amino acid(s) difference with the amino acid sequence of one of SEQ ID NOs: 17-20, wherein the 3, 2 or 1 amino acid(s) difference are present at position 3, 6 and/or 10 of the CDR2 (position 52, 54 and/or 58 according to Kabat numbering); provided that the polypeptide comprising the CDR2 with 3, 2 or 1 amino acid(s) difference binds CD123 with about the same or a higher affinity compared to the binding by the polypeptide comprising the CDR2 without the 3, 2 or 1 amino acid(s) difference, said affinity as measured by surface plasmon resonance; and iii) CDR3 is chosen from the group consisting of:
   e) SEQ ID NOs: 21-25; or
   f) amino acid sequences that have 3, 2 or 1 amino acid(s) difference with the amino acid sequence of one of SEQ ID NOs: 21-25, wherein the 3, 2 or 1 amino acid(s) difference are present at position 3, 4 and/or 5 of the CDR3 (position 97, 98 and/or 99 according to Kabat numbering); provided that the polypeptide comprising the CDR3 with 3, 2 or 1 amino acid(s) difference binds CD123 with about the same or a higher affinity compared to the binding by the polypeptide comprising the CDR3 without the 3, 2 or 1 amino acid(s) difference, said affinity as measured by surface plasmon resonance.

In one aspect, the polypeptides, preferably ISVs, of the invention may have a sequence identity of more than 80%, more than 85%, more than 90%, more than 95%, or even more than 99% with one of SEQ ID NOs: 1-6 (cf. Table A-4). These polypeptides are referred to herein as "polypeptide(s) related to 56A10" or "ISV(s) related to 56A10".

Accordingly, the present invention relates to a polypeptide, preferably an ISV, in which CDR1 is chosen from the group consisting of:
   a) SEQ ID NO: 11; or
   b) amino acid sequences that have 4, 3, 2 or 1 amino acid(s) difference with the amino acid sequence of SEQ ID NO: 11, wherein
      at position 3 the T has been changed into S or P;
      at position 6 the I has been changed into S;
      at position 7 the N has been changed into D; and/or
      at position 8 the D has been changed into V or A;
      provided that the polypeptide comprising the CDR1 with 4, 3, 2 or 1 amino acid(s) difference binds CD123 with about the same or a higher affinity compared to the binding by the polypeptide comprising the CDR1 without the 4, 3, 2 or 1 amino acid(s) difference, said affinity as measured by surface plasmon resonance.

In a further aspect, the present invention relates to a polypeptide, preferably an ISV, in which CDR2 is SEQ ID NO: 17.

In a further aspect, the present invention relates to a polypeptide, preferably an ISV, in which CDR3 is chosen from the group consisting of:
   a) SEQ ID NO: 21; or
   b) amino acid sequences that have 1 amino acid difference with the amino acid sequence of SEQ ID NO: 21, wherein
      at position 3 the P has been changed into A;
      provided that the polypeptide comprising the CDR3 with 1 amino acid(s) difference binds CD123 with about the same or a higher affinity compared to the binding by the polypeptide comprising the CDR3 without the 1 amino acid(s) difference, said affinity as measured by surface plasmon resonance.

Accordingly, the present invention relates to a polypeptide, preferably an ISV, in which:
   i) CDR1 is chosen from the group consisting of:
      a) SEQ ID NO: 11; or
      b) amino acid sequences that have 4, 3, 2 or 1 amino acid(s) difference with the amino acid sequence of SEQ ID NO: 11, wherein
         at position 3 the T has been changed into S or P;
         at position 6 the I has been changed into S;

at position 7 the N has been changed into D; and/or
         at position 8 the D has been changed into V or A;
         provided that the polypeptide comprising the CDR1 with 4, 3, 2 or 1 amino acid(s) difference binds CD123 with about the same or a higher affinity compared to the binding by the polypeptide comprising the CDR1 without the 4, 3, 2 or 1 amino acid(s) difference, said affinity as measured by surface plasmon resonance; and
   ii) CDR2 is SEQ ID NO: 17; and
   iii) CDR3 is chosen from the group consisting of:
      c) SEQ ID NOs: 21; or
      d) amino acid sequences that have 1 amino acid difference with the amino acid sequence of SEQ ID NO: 21, wherein
         at position 3 the P has been changed into A;
         provided that the polypeptide comprising the CDR3 with 1 amino acid difference binds CD123 with about the same or a higher affinity compared to the binding by the polypeptide comprising the CDR3 without the 1 amino acid difference, said affinity as measured by surface plasmon resonance.

In another aspect, the present invention relates to a polypeptide, preferably an ISV, as described herein, in which CDR1 is chosen from the group consisting of SEQ ID NOs: 11-15, CDR2 is SEQ ID NO: 17, and CDR3 is chosen from the group consisting of SEQ ID NOs: 21-22.

Accordingly, in a preferred aspect, the present invention relates to a polypeptide, preferably an ISV, as described herein, in which CDR1 is SEQ ID NO: 11, CDR2 is SEQ ID NO: 17, and CDR3 is SEQ ID NO: 21.

Accordingly, the present invention relates to polypeptides that are ISVs chosen from the group consisting of SEQ ID NOs: 1-6.

The polypeptides or ISVs related to 56A10 were selected for their exquisite specificity for CD123. Binding of the polypeptides of the invention can be measured in suitable binding assays, including but not limited a flow cytometry assay. In such flow cytometry assay, cells may be used that endogenously express CD123 (such as e.g. MOLM-13 or KG1a cells). Alternatively, cells may be used that are transfected to overexpress CD123 (such as e.g. CHO-K1 huCD123 or HEK293 cyno CD123). Suitable cell lines will become clear from the examples herein.

The polypeptide, preferably ISV, of the invention may bind to CD123 expressed on cells or CD123 expressing cells with an average EC50 value between 10 nM and 100 pM.

More specifically, the polypeptide, preferably ISV, of the invention binds to human CD123 expressed on MOLM-13 cells with an average EC50 value between 10 nM and 100 pM, such as at an average EC50 value of 5 nM or less, such as less than 4, 3, 2, or 1 nM or even less, preferably as measured by flow cytometry.

The polypeptide, preferably ISV, of the invention binds to human CD123 expressed on CHO-K1 cells with an average EC50 value between 10 nM and 100 pM, such as at an average EC50 value of 5 nM or less, such as less than 4, 3, 2, or 1 nM or even less, preferably as measured by flow cytometry.

The polypeptide, preferably ISV, of the invention binds to cyno CD123 expressed on HEK293 cells with an average EC50 value between 10 nM and 100 pM, such as at an average EC50 value of 5 nM or less, such as less than 4, or 3 nM or even less, preferably as measured by flow cytometry.

Binding of the polypeptides, preferably ISVs, of the invention can also be measured by SPR.

As such, the polypeptide, preferably ISV, of the invention may bind to human CD123 with an average $K_D$ value of between 10 nM and 100 pM, such as at an average $K_D$ value of 5 nM or less, such as less than 4, 3 or 2 nM or even less, said $K_D$ value preferably determined by surface plasmon resonance.

Accordingly, the present invention relates to a polypeptide or ISV as described herein, wherein said average $K_D$ or EC50 is determined by flow cytometry or SPR, for instance said $K_D$ or EC50 is determined as set out in the Examples section.

It has been shown in the examples that the $K_D$ as measured in SPR correlates well with the EC50 as measured in flow cytometry.

In another aspect, the polypeptides of the invention may have a sequence identity of more than 80%, more than 85%, more than 90%, more than 95%, or even more than 99% with one of SEQ ID NOs: 7-10 (cf. Table A-4). These polypeptides are referred to herein as "polypeptide(s) related to 55F03" or "ISV(s) related to 55F03".

Accordingly, the present invention relates to a polypeptide, preferably an ISV, in which CDR1 is SEQ ID NO: 16.

In a further aspect, the present invention relates to a polypeptide, preferably an ISV, in which CDR2 is chosen from the group consisting of:
a) SEQ ID NO: 18; or
b) amino acid sequences that have 3, 2 or 1 amino acid difference with the amino acid sequence of SEQ ID NO: 18, wherein
at position 3 the Y has been changed into W;
at position 6 the N has been changed into S; and/or
at position 10 the Q has been changed into E;
provided that the polypeptide comprising the CDR3 with 3, 2 or 1 amino acid(s) difference binds CD123 with about the same or a higher affinity compared to the binding by the polypeptide comprising the CDR3 without the 3, 2 or 1 amino acid(s) difference, said affinity as measured by surface plasmon resonance.

In a further aspect, the present invention relates to a polypeptide, preferably an ISV, in which CDR3 is chosen from the group consisting of:
a) SEQ ID NO: 23; or
b) amino acid sequences that have 2 or 1 amino acid difference with the amino acid sequence of SEQ ID NO: 23, wherein
at position 4 the E has been changed into R; and/or
at position 5 the T has been changed into D or Y;
provided that the polypeptide comprising the CDR3 with 2 or 1 amino acid(s) difference binds CD123 with about the same or a higher affinity compared to the binding by the polypeptide comprising the CDR3 without the 2 or 1 amino acid(s) difference, said affinity as measured by surface plasmon resonance.

Accordingly, the present invention relates to a polypeptide, preferably an ISV, in which:
i) CDR1 is SEQ ID NO: 16; and
ii) CDR2 is chosen from the group consisting of:
a) SEQ ID NO: 18; or
b) amino acid sequences that have 3, 2 or 1 amino acid difference with the amino acid sequence of SEQ ID NO: 18, wherein
at position 3 the Y has been changed into W;
at position 6 the N has been changed into S; and/or
at position 10 the Q has been changed into E;
provided that the polypeptide comprising the CDR3 with 3, 2 or 1 amino acid(s) difference binds CD123 with about the same or a higher affinity compared to the binding by the polypeptide comprising the CDR3 without the 3, 2 or 1 amino acid(s) difference, said affinity as measured by surface plasmon resonance; and
iii) CDR3 is chosen from the group consisting of:
c) SEQ ID NOs: 23; or
d) amino acid sequences that have 2 or 1 amino acid difference with the amino acid sequence of SEQ ID NO: 23, wherein
at position 4 the E has been changed into R; and/or
at position 5 the T has been changed into D or Y;
provided that the polypeptide comprising the CDR3 with 2 or 1 amino acid(s) difference binds CD123 with about the same or a higher affinity compared to the binding by the polypeptide comprising the CDR3 without the 2 or 1 amino acid(s) difference, said affinity as measured by surface plasmon resonance.

In another aspect, the present invention relates to a polypeptide, preferably an ISV, as described herein, in which CDR1 is SEQ ID NO: 16, CDR2 is chosen from the group consisting of SEQ ID NOs: 18-20, and CDR3 is chosen from the group consisting of SEQ ID NOs: 23-25.

Accordingly, in a preferred aspect, the present invention relates to a polypeptide, preferably an ISV, as described herein, in which CDR1 is SEQ ID NO: 16, CDR2 is SEQ ID NO: 18, and CDR3 is SEQ ID NO: 23.

Preferred polypeptides and/or ISVs are chosen from the group consisting of SEQ ID NOs: 7-10.

The polypeptides or ISVs related to 55F03 were selected for their exquisite specificity for CD123. Binding of the polypeptides of the invention can be measured in suitable binding assays, including but not-limited to a flow cytometry assay and SPR, as described herein.

The polypeptide, preferably ISV, of the invention may bind to CD123 expressed on cells or CD123 expressing cells with an average EC50 value between 10 µM and 100 nM.

More specifically, the polypeptide, preferably ISV, of the invention binds to human CD123 expressed on MOLM-13 cells with an average EC50 value between 10 µM and 100 nM, such as at an average EC50 value of 5 µM or less, such as less than 4, 3, 2, or 1 µM or even less, preferably as measured by flow cytometry.

The polypeptide, preferably ISV, of the invention binds to human CD123 expressed on CHO-K1 cells with an average EC50 value between 100 nM and 1 nM, such as at an average EC50 value of 50 nM or less, such as less than 40, 30, 20, or 10 nM or even less, such as less than 9, 8 or 7 nM or even less, preferably as measured by flow cytometry.

The polypeptide, preferably ISV, of the invention binds to cyno CD123 expressed on HEK293 cells with an average EC50 value between 10 nM and 100 pM, such as at an average EC50 value of 5 nM or less, such as less than 4, or 3 nM or even less, preferably as measured by flow cytometry.

In a further aspect, the present invention relates to a polypeptide or ISV that binds to human CD123 with an average $K_D$ value of between 1 µM and 10 nM, such as at an average $K_D$ value of 500 nM or less, such as less than 400, 300 or 200 nM or even less, said $K_D$ value preferably determined by surface plasmon resonance.

Accordingly, the present invention relates to a polypeptide or ISV as described herein, wherein said average $K_D$ or EC50 is determined by flow cytometry or SPR, for instance said $K_D$ or EC50 is determined as set out in the Examples section.

It has been shown in the examples that the $K_D$, as measured in SPR, correlates well with the EC50, as determined in a flow cytometry based assay using MOLM-13 cells.

Generally, the combinations of CDRs listed in Table A-4 (i.e. those mentioned on the same line in Table A-4) are preferred. Thus, it is generally preferred that, when a CDR in an ISV is a CDR sequence mentioned in Table A-4 or suitably chosen from the group consisting of CDR sequences that have 4, 3, 2 or only 1 amino acid difference(s) with a CDR sequence listed in Table A-4, that at least one and preferably both of the other CDR's are suitably chosen from the CDR sequences that belong to the same combination in Table A-4 (i.e. mentioned on the same line in Table A-4) or are suitably chosen from the group consisting of CDR sequences that have 4, 3, 2 or only 1 amino acid difference(s) with the CDR sequence(s) belonging to the same combination. Representative polypeptides of the present invention having the CDRs described above are shown in Table A-4.

The present invention also relates to a polypeptide, preferably ISV, that specifically binds CD123 that cross-blocks the binding to CD123 of at least one of the polypeptides as described herein and/or selected from SEQ ID NOs: 1-10 and/or that is cross-blocked from binding to CD123 by at least one of the polypeptides as described herein and/or selected from SEQ ID NOs: 1-10.

The invention further relates to a monospecific polypeptide that comprises or (essentially) consists of two or more ISVs that bind CD123. In such a multivalent (monospecific) polypeptide, also referred to herein as "multivalent polypeptide(s) of the invention", the two or more ISVs that bind CD123 may optionally be lined via one or more peptidic linkers, as further described herein.

Accordingly, the present invention relates to a polypeptide comprising two or more ISVs that specifically bind CD123, wherein the ISVs are chosen from the group of ISVs related to 56A10 or from the group of ISVs related to 55F03.

In a more specific aspect, the present invention relates to polypeptides comprising two ISVs that specifically bind CD123, wherein the ISVs are chosen from the group of ISVs related to 56A10 or from group of ISVs related to 55F03.

In such a multivalent monospecific polypeptide of the invention, the two or more immunoglobulin single variable domains may be the same or different, and may be directed against the same antigenic determinant of CD123 (for example against the same part(s) or epitope(s) of CD123) or may alternatively be directed against different antigenic determinants of CD123 or against different parts or epitopes of CD123; or any suitable combination thereof. For example, a bivalent polypeptide of the invention may comprise (a) two identical immunoglobulin single variable domains; (b) a first immunoglobulin single variable domain directed against a first antigenic determinant of CD123 and a second immunoglobulin single variable domain directed against the same antigenic determinant of CD123 which is different from the first immunoglobulin single variable domain; or (c) a first immunoglobulin single variable domain directed against a first antigenic determinant of CD123 and a second immunoglobulin single variable domain directed against another antigenic determinant of CD123.

A trivalent polypeptide of the invention may be any of the above, further comprising (a) an identical immunoglobulin single variable domain; (b) a different immunoglobulin single variable domain directed against the same antigenic determinant of CD123; or (c) a different immunoglobulin single variable domain directed against another antigenic determinant of CD123.

As such, in one aspect, the monospecific polypeptide of the invention may be a multiparatopic polypeptide, such as e.g., a biparatopic polypeptide. The term "biparatopic" (antigen-)binding molecule or "biparatopic" polypeptide as used herein shall mean a polypeptide comprising at least two (i.e. two or more) immunoglobulin single variable domains, wherein a "first" immunoglobulin single variable domain is directed against CD123 and a "second" immunoglobulin single variable domain is directed against CD123, and wherein these "first" and "second" immunoglobulin single variable domains have a different paratope. Accordingly, the biparatopic polypeptide comprises or consists of two or more immunoglobulin single variable domains that are directed against CD123, wherein at least one "first" immunoglobulin single variable domain is directed against a first epitope on CD123 and at least one "second" immunoglobulin single variable domain is directed against a second epitope on CD123 different from the first epitope on CD123.

Accordingly, the present invention relates to polypeptides, wherein the two or more ISVs that specifically bind CD123 are biparatopic comprising a first ISV and a second ISV, wherein the first ISV binds to an epitope on CD123 that is different from the epitope on CD123 bound by the second ISV. Such polypeptide(s) are also referred to herein as "biparatopic polypeptide(s) of the invention".

In a further aspect, the present invention provides a (biparatopic) polypeptide as described herein, wherein the first ISV is selected from the group of ISVs related to 56A10 and the second ISV is selected from the group of ISVs related to 55F03.

In a further aspect, the present invention provides a polypeptide as described herein, wherein the second ISV is located N-terminally of the first ISV. Such a polypeptide comprises an ISV related to 55F03 N-terminally of an ISV related to 56A10.

In a further aspect, the present invention provides a polypeptide as described herein, wherein the second ISV is located C-terminally of the first ISV. Such a polypeptide comprises an ISV related to 55F03 C-terminally of an ISV related to 56A10.

The biparatopic polypeptides of the invention may have an improved affinity for binding to CD123 compared to the corresponding monovalent polypeptide, due to avid binding, also referred to as "avidity".

Avidity is the affinity of the polypeptide, i.e. the ligand is able to bind via two (or more) pharmacophores (ISV) in which the multiple interactions synergize to enhance the "apparent" affinity. Avidity is the measure of the strength of binding between the polypeptide of the invention and the pertinent antigens or antigenic determinants. The polypeptide of the invention is able to bind via its two (or more) building blocks, such as ISVs, to the at least two targets or antigenic determinants, in which the multiple interactions, e.g. the first building block or ISV binding to the first target or first antigenic determinant and the second building block or ISV binding to the second target or second antigenic determinant, synergize to enhance the "apparent" affinity. Avidity is related to both the affinity between an antigenic determinant and its antigen binding site on the antigen-binding molecule and the number of pertinent binding sites present on the antigen-binding molecules. For example, and without limitation, polypeptides that contain two or more building blocks, such as ISVs directed against different targets on a cell or different antigenic determinants may (and usually will) bind with higher avidity than each of the individual monomers or individual building blocks, such as, for instance, the monovalent ISVs, comprised in the polypeptides of the invention.

The monospecific polypeptides of the invention comprise or (essentially) consist of one or more immunoglobulin single variable domains. The framework sequences of these ISVs are preferably (a suitable combination of) immunoglobulin framework sequences or framework sequences that have been derived from immunoglobulin framework sequences (for example, by sequence optimization such as humanization or camelization). For example, the framework sequences may be framework sequences derived from an immunoglobulin single variable domain such as a light chain variable domain (e.g., a $V_L$-sequence) and/or from a heavy chain variable domain (e.g., a $V_H$-sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized.

The framework sequences may preferably be such that the ISV encompassed in the monospecific polypeptide of the invention is a Domain antibody (or an amino acid sequence that is suitable for use as a Domain antibody); a single domain antibody (or an amino acid that is suitable for use as a single domain antibody); a "dAb" (or an amino acid that is suitable for use as a dAb); a Nanobody; a $V_{HH}$; a humanized $V_{HH}$; a camelized $V_H$; or a $V_{HH}$ that has been obtained by affinity maturation. Again, suitable framework sequences will be clear to the skilled person, for example on the basis of the standard handbooks and the further disclosure and prior art mentioned herein.

In particular, the framework sequences present in the monospecific polypeptides of the invention may contain one or more of Hallmark residues (as defined in WO 08/020079 (Tables A-3 to A-8)), such that the monospecific polypeptide of the invention is a Nanobody. Some preferred, but non-limiting examples of (suitable combinations of) such framework sequences will become clear from the further disclosure herein (see e.g., Table A-4). Generally, Nanobodies (in particular $V_{HH}$s, partially or fully humanized $V_{HH}$s and camelized $V_H$s) can in particular be characterized by the presence of one or more "Hallmark residues" in one or more of the framework sequences (as e.g., further described in WO 08/020079, page 61, line 24 to page 98, line 3).

More in particular, the invention provides polypeptides comprising at least one immunoglobulin single variable domain that is an amino acid sequence with the (general) structure

```
FR1 - CDR1 - FR2 - CDR2 - FR3 - CDR3 - FR4
``` in which FR1 to FR4 refer to framework regions 1 to 4, respectively, and in which CDR1 to CDR3 refer to the complementarity determining regions 1 to 3, respectively, and which:

i) have at least 80%, more preferably 90%, even more preferably 95% amino acid identity with at least one of the amino acid sequences of SEQ ID NOs: 1-10 (see Table A-4), in which for the purposes of determining the degree of amino acid identity, the amino acid residues that form the CDR sequences are disregarded. In this respect, reference is also made to Table A-4, which lists the framework 1 sequences (SEQ ID NOs: 26-29), framework 2 sequences (SEQ ID NOs: 30-33), framework 3 sequences (SEQ ID NOs: 36-39) and framework 4 sequences (SEQ ID NOs: 40-41) of the immunoglobulin single variable domains of SEQ ID NOs: 1-10 (see Table A-4); or and in which:

ii) preferably one or more of the amino acid residues at positions 11, 37, 44, 45, 47, 83, 84, 103, 104 and 108 according to the Kabat numbering are chosen from the Hallmark residues mentioned in Table A-3 to Table A-8 of WO 08/020079.

The present invention also provides a number of sequence optimized polypeptides and/or immunoglobulin single variable domains.

In particular, sequence optimized polypeptides and/or immunoglobulin single variable domains of the invention may be amino acid sequences that are as generally defined for immunoglobulin single variable domains in the previous paragraphs, but in which at least one amino acid residue is present (and in particular, in at least one of the framework residues) that is and/or that corresponds to a humanizing substitution (as defined herein). Some preferred, but non-limiting humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring VHH sequence with the corresponding framework sequence of one or more closely related human VH sequences, after which one or more of the potentially useful humanizing substitutions (or combinations thereof) thus determined can be introduced into said VHH sequence (in any manner known per se, as further described herein) and the resulting humanized VHH sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) an immunoglobulin single variable domains may be partially humanized or fully humanized.

The present invention also relates to sequence optimized polypeptides and/or immunoglobulin single variable domains that may show improved expression and/or increased stability upon storage during stability studies. The sequence optimized polypeptides and/or ISVs of the present invention may show reduced pyroglutamate post-translational modification of the N-terminus and hence have increased product stability. In addition, the sequence optimized polypeptides and/or ISVs of the present invention may show other improved properties such as e.g. less immunogenicity, improved binding characteristics (suitably measured and/or expressed as a $K_D$-value (actual or apparent), a $K_A$-value (actual or apparent), a $k_{on}$-rate and/or a $k_{off}$-rate, or alternatively as an $EC_{50}$ value, as further described herein) for CD123, improved affinity and/or improved avidity for CD123.

Some particularly preferred sequence optimized immunoglobulin single variable domains of the invention are sequence optimized variants of the immunoglobulin single variable domains of SEQ ID NOs: 1-10.

Thus, some other preferred immunoglobulin single variable domains of the invention are Nanobodies which can bind (as defined herein) to CD123 and which:

i) are a sequence optimized variant of one of the immu-
noglobulin single variable domains of SEQ ID NOs:
1-10; and/or ii) have at least 80% amino acid identity with at least one
of the immunoglobulin single variable domains of SEQ
ID NOs: 1-10 (see Table A-4), in which for the pur-
poses of determining the degree of amino acid identity,
the amino acid residues that form the CDR sequences
are disregarded; In this respect, reference is also made
to Table A-4, which lists the framework 1 sequences
(SEQ ID NOs: 26-29), framework 2 sequences (SEQ
ID NOs: 30-32), framework 3 sequences (SEQ ID
NOs: 34-39) and framework 4 sequences (SEQ ID
NOs: 40-41) of the immunoglobulin single variable
domains of SEQ ID NOs: 1-10 (see Table A-4;
and in which:

iii) preferably one or more of the amino acid residues at
positions 11, 37, 44, 45, 47, 83, 84, 103, 104 and 108
according to the Kabat numbering are chosen from the
Hallmark residues mentioned in Table A-3 to Table A-8
of WO 08/020079.

The polypeptides and/or immunoglobulin single variable
domains of the invention may also contain the specific
mutations/amino acid residues described in the following
co-pending US provisional applications, all entitled
"Improved immunoglobulin variable domains": U.S.
61/994,552 filed May 16, 2014; U.S. 61/014,015 filed Jun.
18, 2014; U.S. 62/040,167 filed Aug. 21, 2014; and U.S.
62/047,560, filed Sep. 8, 2014 (all assigned to Ablynx N.V.)
as well as the International application WO 2015/173325
which was based on these provisional applications and
which was published on Nov. 19, 2015.

In particular, the polypeptides and/or immunoglobulin
single variable domains of the invention may suitably con-
tain (i) a K or Q at position 112; or (ii) a K or Q at position
110 in combination with a V at position 11; or (iii) a T at
position 89; or (iv) an L on position 89 with a K or Q at
position 110; or (v) a V at position 11 and an L at position
89; or any suitable combination of (i) to (v).

As also described in said co-pending US provisional
applications, when the polypeptide and/or immunoglobulin
single variable domains of the invention contain the muta-
tions according to one of (i) to (v) above (or a suitable
combination thereof):

the amino acid residue at position 11 is preferably chosen
from L, V or K (and is most preferably V); and the amino acid residue at position 14 is preferably suitably
chosen from A or P; and the amino acid residue at position 41 is preferably suitably
chosen from A or P; and the amino acid residue at position 89 is preferably suitably
chosen from T, V or L; and the amino acid residue at position 108 is preferably
suitably chosen from Q or L; and the amino acid residue at position 110 is preferably
suitably chosen from T, K or Q; and the amino acid residue at position 112 is preferably
suitably chosen from S, K or Q.

As mentioned in said co-pending US provisional appli-
cations, said mutations are effective in preventing or reduc-
ing binding of so-called "pre-existing antibodies" to the
polypeptides and/or immunoglobulin single variable
domains, and/or constructs of the invention. For this pur-
pose, the polypeptides and/or immunoglobulin single vari-
able domains of the invention may also contain (optionally
in combination with said mutations) a C-terminal extension
(X)n (in which n is 1 to 10, preferably 1 to 5, such as 1, 2, 3, 4 or 5 (and preferably 1 or 2, such as 1); and each X is an
(preferably naturally occurring) amino acid residue that is
independently chosen, and preferably independently chosen
from the group consisting of alanine (A), glycine (G), valine
(V), leucine (L) or isoleucine (I)), for which reference is
again made to said US provisional applications as well as to
WO 12/175741. In particular, a polypeptide and/or immu-
noglobulin single variable domain of the invention may
contain such a C-terminal extension when it forms the
C-terminal end of a protein, polypeptide or other construct
comprising the same (again, as further described in said US
provisional applications as well as WO 12/175741).

Accordingly, the present invention relates to a polypep-
tide as described herein, further comprising a C-terminal
extension (X)n, in which n is 1 to 5, such as 1, 2, 3, 4 or 5,
and in which X is a naturally occurring amino acid, prefer-
ably no cysteine.

These polypeptides of the invention, and in particular the
immunoglobulin single variable domains comprising the
CDR sequences of the invention are particularly suited for
use as building block or binding unit for the preparation of
multivalent or multispecific polypeptides.

Accordingly, the monospecific polypeptides of the inven-
tion that bind CD123 can be in essentially isolated form (as
defined herein), or they may form part of a protein or
polypeptide, which may comprise or essentially consist of
one or more ISV that bind CD123 and which may optionally
further comprise one or more further amino acid sequences
(all optionally linked via one or more suitable linkers).

Accordingly, the present invention also relates to a protein
or polypeptide that comprises or essentially consists of one
or more monospecific polypeptide of the invention (or
suitable fragments thereof). In a further aspect, the mono-
specific polypeptides of the invention that bind CD123 may
form part of a multispecific polypeptide, which may com-
prise or essentially consist of one or more ISV that binds
CD123 and which may optionally further comprise one ISV
that specifically binds another target, such as e.g., TCR, and
which may optionally further comprise one or more further
amino acid sequences (all optionally linked via one or more
suitable linkers).

The monospecific polypeptides of the invention are thus
used as a binding unit or building block in such a protein or
polypeptide, so as to provide a multispecific polypeptide of
the invention, as described herein (for multispecific poly-
peptides containing one or more VHH domains and their
preparation, reference is also made to Conrath et al. (2001,
J. Biol. Chem. 276: 7346-7350), as well as to for example
WO 96/34103, WO 99/23221 and WO 2010/115998).

2. Multispecific Polypeptides

The invention further relates to multispecific polypeptides
comprising or (essentially) consisting of two or more build-
ing blocks (such as at least two monospecific polypeptides
or ISVs of the invention), in which at least one building
block is directed against a first antigen (i.e., CD123) and at
least one building block is directed against a second antigen
(i.e., TCR). These multispecific polypeptide are also referred
to herein as "multispecific polypeptide(s) of the invention".
Preferred immunoglobulin single variable domains for use
in these multispecific polypeptides of the invention are the
monospecific polypeptides of the invention (as described
earlier).

As described further herein, additional binding units, such
as immunoglobulin single variable domains, having differ-
ent antigen specificity (i.e., different from CD123 and TCR)
may be linked the multispecific polypeptides of the inven-
tion. By combining immunoglobulin single variable domains of three or more specificities, trispecific, tetraspecific etc. constructs can be formed. These multispecific polypeptide are also referred to herein as "(multispecific) polypeptide(s) of the invention" or "construct(s) of the invention".

Thus, for example, a "bispecific polypeptide of the invention" is a polypeptide that comprises or (essentially) consists of at least one immunoglobulin single variable domain against a first antigen (i.e., CD123) and at least one further immunoglobulin single variable domain against a second antigen (i.e., TCR), whereas a "trispecific polypeptide of the invention" is a polypeptide that comprises or (essentially) consists of at least one immunoglobulin single variable domain against a first antigen (i.e., CD123), at least one further immunoglobulin single variable domain against a second antigen (i.e., TCR) and at least one further immunoglobulin single variable domain against a third antigen (i.e., different from CD123 and TCR), etc. The immunoglobulin single variable domains may optionally be linked via one or more peptidic linkers, as further described herein.

Accordingly, the present invention relates to polypeptides comprising or (essentially) consisting of one immunoglobulin single variable domain that specifically binds TCR and one or more ISV that specifically binds CD123. In a further aspect, the present invention also provides polypeptides comprising or (essentially) consisting of one immunoglobulin single variable domain that specifically binds TCR and two or more ISVs that specifically bind CD123. Some non-limiting examples of such multispecific polypeptides or constructs thereof will become clear from the further description herein.

It will be appreciated (as is also demonstrated in the Example section) that the ISV that specifically binds TCR and the one or more ISV that specifically bind CD123 can be positioned in any order in the polypeptide of the invention. More particularly, in one aspect, the ISV binding TCR is positioned N-terminally and the one or more ISV binding CD123 is positioned C-terminally. In another aspect, the one or more ISV binding CD123 is positional N-terminally and the ISV binding TCR is positioned C-terminally. In another aspect, one or more ISV that bind CD123 is positioned N-terminally, the ISV that binds TCR is positioned centrally and one or more further ISV that bind CD123 is positioned C-terminally. In a preferred aspect, the invention relates to a polypeptide, wherein the ISV that specifically binds TCR is located at the N-terminus of the polypeptide.

In some aspects, the multispecific polypeptides of the invention comprise two or more ISVs that specifically bind CD123. In one aspect, the two or more ISVs that specifically bind CD123 bind to the same epitope on CD123. In one aspect, such multispecific polypeptides of the invention may comprise two or more ISVs related to 56A10. In another aspect, such polypeptides of the invention comprise two or more ISVs related to 55F03.

In a more preferred aspect, the two or more ISVs that specifically bind CD123 bind to a different epitope. Accordingly, the present invention relates to a multispecific polypeptide, wherein the two or more ISVs that specifically bind CD123 are biparatopic comprising a first ISV and a second ISV, wherein the first ISV binds to an epitope on CD123 that is different from the epitope on CD123 bound by the second ISV.

More specifically, the present invention relates to a multispecific polypeptide of the invention, wherein the first ISV that binds CD123 is selected from the ISVs related to 56A10 and the second ISV that binds CD123 is selected from the ISVs related to 55F03. As discussed earlier, these biparatopic polypeptides of the invention have an improved affinity for binding to CD123 compared to the monospecific polypeptides of the invention, due to avid binding, also referred to as avidity.

It will be appreciated (as is also demonstrated in the Example section) that the ISVs that bind CD123 can be positioned in any order in the multispecific polypeptide of the invention. More particularly, in one aspect, the second ISV (i.e., the ISV related to 55F03) is located N-terminally of the first ISV (i.e., the ISV related to 56A10). In another aspect, the second ISV (i.e., the ISV related to 55F03) is located C-terminally of the first ISV (i.e., the ISV related to 56A10). Some non-limiting examples of such multispecific constructs will become clear from the further description herein.

Typically, the multispecific polypeptides of the invention combine high affinity and high specificity antigen recognition on the target cell with T cell activation, resulting in an activation that is independent of the T cells' natural specificity.

A "target cell" as referred to herein, is a cell that presents a particular antigen (i.e., CD123) on its surface. In one aspect, the "target cell" is a cell that is characterized by overexpression of CD123. In a preferred aspect, such target cell is associated with a CD123 associated disease. In an even more preferred aspect, the target cell is a cancer cell that (over)expresses CD123. The term "cancer" refers to the pathological condition in mammals that is typically characterized by dysregulated cellular proliferation or survival.

"T cell activation" as used herein refers to one or more cellular response(s) of a T cell, e.g. a cytotoxic T cell, such as selected from: proliferation, differentiation, cytokine secretion, cytotoxic effector molecule release, cytotoxic activity, expression of activation markers, and redirected target cell lysis. The term "cellular response(s)" a used herein, refers to a response of a cell as a result of intracellular signalling upon assembly of the TCR complex.

The mode of action of polypeptides that bind both to a cell surface molecule (such as e.g., CD123) on a target cell and to the T cell TCR is commonly known. Bringing a T cell in close vicinity to a target cell (such as e.g., a CD123 expressing cell), i.e., engaging said T cell and clustering of the TCR complex results in T cell activation and subsequent killing of the target cell by the T cell. In the present invention this process is exploited in fighting against a CD123 associated disease, such as a proliferative disease or an inflammatory condition. Generally, T cells are equipped with granules containing a deadly combination of pore-forming proteins, called perforins, and cell death-inducing proteases, called granzymes. Preferably, these proteins are delivered into target cells (such as e.g., CD123 expressing cells) via a cytolytic synapse that forms if T cells are in close vicinity with a target cell that is aimed to be killed. Normally, close vicinity between a T cell and a target cell is achieved by the T cell binding to an MHC/peptide complex using its matching T cell receptor. The polypeptides of the invention bring a T cell into such close vicinity to a target cell in the absence of the T cell receptor/MHC interaction.

Accordingly, the present invention relates to a multispecific polypeptide as described herein, wherein said polypeptide directs the T cell to the target cell. Accordingly, the polypeptide(s) of the present invention "redirect(s) T cells for killing of CD123 expressing cells", which means that the polypeptide(s) of the invention bring(s) a T cell in such close proximity to a CD123 expressing cell that it is killed.

With one arm (an ISV that binds TCR), the multispecific polypeptide of the invention binds to the constant domain of the TCR subunit, a protein component of the signal-transducing complex of the T cell receptor on T cells. With the other arm (one or more ISV that binds CD123), the multispecific polypeptide binds to CD123 on target cells. Preferably, T cell activation is only seen when the multispecific polypeptides are presented to T cells at (the site of) CD123 expressing cells. Antigen dependence on target cells (i.e., CD123 expressing cells) for activation results in a favourable safety profile. The multispecific polypeptides of the invention exhibit highly specific binding to CD123. As such, off-target binding is avoided and target independent T cell activation is minimal, as exemplified herein. In one aspect, the multispecific polypeptides transiently tether T cells and target cells. Preferably, the multispecific polypeptide can induce resting polyclonal T cells, such as CD4+ and/or CD8+ T cells into activation, for highly potent redirected lysis of target cells (i.e., CD123 expressing cells). Preferably, the T cell is directed to a next target cell after lysis of the first target cell.

In one aspect, the present invention relates to a multispecific polypeptide as described herein, wherein said multispecific polypeptide induces T cell activation.

In a further aspect, the present invention relates to a multispecific polypeptide, wherein said T cell activation is independent from MHC recognition.

"T cell activation independent from MHC recognition" as used herein, refers to T cell activation that is independent of the binding of an MHC/peptide complex on a target cell to its matching T cell receptor on a T cell. By bringing a T cell in close proximity to a target cell, the target cell will get killed. Normally, close vicinity between a T cell and a target cell is achieved by the T cell binding to an MHC/peptide complex using its matching T cell receptor. The multispecific polypeptides of the invention bring a T cell into such close vicinity to a target cell in the absence of the T cell receptor/MHC interaction. The multispecific polypeptides bind to CD123 on a target cell and are as such presented and bound to T cells, resulting in T cell activation and killing of the target cell.

Accordingly, in a further aspect, the present invention relates to a multispecific polypeptide, wherein said T cell activation depends on presenting said polypeptide bound to CD123 on a target cell to a T cell.

In a further aspect, the present invention relates to a multispecific polypeptide, wherein said T cell activation causes one or more cellular response by said T cell, wherein said cellular response is selected from the group consisting of proliferation, differentiation, cytokine secretion, cytotoxic effector molecule release, cytotoxic activity, expression of activation markers and redirected target cell lysis.

Suitable assays to measure T cell activation are known in the art, for instance as described in WO 99/54440 or by Schlereth et al. (2005, Cancer Immunol. Immunother. 20: 1-12), or as exemplified in the examples or below.

Without being limited, T cell activation by the polypeptides of the invention can be measured by monitoring upregulation of CD69, CD25 and various cell adhesion molecules, de novo expression and/or release of cytokines (e.g., IFN-$\gamma$, TNF-$\alpha$, IL-6, IL-2, IL-4 and IL-10), upregulation of granzyme and perforin expression, and/or cell proliferation, membrane blebbing, activation of procaspases 3 and/or 7, fragmentation of nuclear DNA and/or cleavage of caspase substrate poly (ADPribose) polymerase. Preferably, redirected lysis of target cells by the multispecific polypeptides is independent of T cell receptor specificity, presence of MHC class I and/or $\beta$2 microglobulin, and/or of any co-stimulatory stimuli.

The polypeptides of the invention show redirected lysis in vitro with previously unstimulated (i.e. non activated) peripheral polyclonal CD8+- and CD4+-positive T cells, as exemplified further herein. The redirected lysis of target cells via the recruitment of T cells by the polypeptides of the invention involves cytolytic synapse formation and delivery of perforin and granzymes. Cell lysis by T cells has been described, e.g. by Atkinson and Bleackley (1995, Crit. Rev. Immunol 15 (3-4): 359-384). Preferably, the polypeptide of the invention mediates killing of target cells, e.g. cancer cells, by stimulating T cells in pore formation and delivering pro-apoptotic components of cytotoxic T cell granules. Preferably, the engaged T cells are capable of serial target cell lysis. In vitro, with the polypeptides of the invention, redirected lysis is seen at low picomolar concentrations, suggesting that very low numbers of the polypeptides of the invention need to be bound to target cells for triggering T cells. As demonstrated in the examples, the low effector to target ratio might be indicative for serial target cell lysis and demonstrated the high potency of the polypeptides of the invention.

As used herein, the term "potency" is a measure of the biological activity of an agent, such as a monospecific or multispecific polypeptide, ISV or Nanobody. Potency is a function of the amount of polypeptide of the invention required for its specific effect to occur. It is measured simply as the inverse of the $IC_{50}$ for that polypeptide. For the multispecific polypeptides of the invention, it refers to the capacity of said polypeptide of the invention to induce T cell activation. Potency of an agent can be determined by any suitable method known in the art, such as for instance as described in the experimental section. Cell culture based potency assays are often the preferred format for determining biological activity since they measure the physiological response elicited by the agent and can generate results within a relatively short period of time. Various types of cell based assays, based on the mechanism of action of the product, can be used, including but not limited to proliferation assays, cytotoxicity assays, cell killing assays, reporter gene assays, cell surface receptor binding assays, and assays to measure induction/inhibition of functionally essential proteins or other signal molecules (such as phosphorylated proteins, enzymes, cytokines, cAMP and the like), T cell mediated tumour cell killing assay (for instance as set out in the Examples section), all well known in the art. Results from cell based potency assays can be expressed as "relative potency" as determined by comparison of the multispecific polypeptide of the invention to the response obtained for the corresponding reference monovalent ISV, e.g. a polypeptide comprising only one ISV or one Nanobody, optionally further comprising an irrelevant Nanobody (cf. experimental section).

The "efficacy" (of the polypeptide of the invention) measures the maximum strength of the effect itself, at saturating polypeptide concentrations. Efficacy indicates the maximum response achievable by the polypeptide of the invention. It refers to the ability of a polypeptide to produce the desired (therapeutic) effect.

In one aspect, the multispecific polypeptide of the invention activates T cells, resulting in killing of CD123 expressing cells (such as MOLM-13 or KG1a cells) with an average EC50 value between 10 nM and 1 pM, as determined in a flow cytometry based assay. (cf. Example 25)

More specifically, the polypeptide of the invention induces T cell activation, wherein said T cell activation causes killing of CD123 expressing cells (such as MOLM-13 cells) with an average EC50 value of between 1 nM and 1 pM, such as at an average EC50 value of 500 pM or less, such as less than 400, 300, 200 or 100 pM or even less, such as less than 90, 80, 70, 60, 50, 40 or 30 pM or even less, said EC50 value for example determined in a flow cytometry based assay with TOPRO3 read-out using MOLM-13 cells as target cells and human T cells as effector cells at an effector to target cell ratio of 10 to 1.

More specifically, the polypeptide of the invention induces T cell activation, wherein said T cell activation causes lysis of CD123 expressing cells (such as MOLM-13 cells) with an average lysis percentage of more than about 10%, such as 15%, 16%, 17%, 18%, 19% or 20% or even more, such as more than 25%, or even more than 30%, said lysis percentage for example determined in a flow cytometry based assay with TOPRO3 read-out using MOLM-13 cells as target cells and human T cells as effector cells at an effector to target cell ratio of 10 to 1.

More specifically, the polypeptide of the invention induces T cell activation, wherein said T cell activation causes killing of CD123 expressing cells (such as KG1a cells) with an average EC50 value of between 10 nM and 10 pM, such as at an average EC50 value of 5 nM or less, such as less than 4, 3, 2 or 1 nM or even less, such as less than 90, 80, 70 or 60 pM or even less, said EC50 value for example determined in a flow cytometry based assay with TOPRO3 read-out using KG1a cells as target cells and human T cells as effector cells at an effector to target cell ratio of 10 to 1.

More specifically, the polypeptide of the invention induces T cell activation, wherein said T cell activation causes lysis of CD123 expressing cells (such as KG1a cells) with an average lysis percentage of more than about 10%, such as 15%, 16%, 17% or 18% or even more, such as more than 24%, said lysis percentage for example determined in a flow cytometry based assay with TOPRO3 read-out using KG1a cells as target cells and human T cells as effector cells at an effector to target cell ratio of to 1.

In another aspect, the multispecific polypeptides of the invention activate T cells and may as such induce cytokine secretion. Accordingly, the polypeptides cause IFN-γ or IL-6 secretion with an average EC50 value of between 100 nM and 10 pM. (cf. Example 30)

More specifically, the polypeptide of the invention induces T cell activation, wherein said T cell activation cause IFN-γ secretion with an average EC50 value of between 100 nM and 10 pM, such as at an average EC50 value of 50 nM or less, such as less than 40, 30, 20, 10 or 9 nM or even less, such as less than 8, 7, 6, 5, 4, 3, 2 or 1 nM or even less, such as less than 500 pM or even less, such as less than 400, 300, 200 or 100 pM or even less, said EC50 value for example determined in an ELISA based assay, as for example further explained in Example 30.

More specifically, the polypeptide of the invention induces T cell activation, wherein said T cell activation cause IL-6 secretion with an average EC50 value of between 100 nM and 10 pM, such as at an average EC50 value of 50 nM or less, such as less than 40, 30, 20 or 10 nM or even less, such as less than 9, 8, 7, 6, 5, 4, 3, 2 or 1 nM or even less, such as less than 500 pM or even less, such as less than 400, 300, 200 or 100 pM or even less, said EC50 value for example determined in an ELISA based assay, as for example further explained in Example 30.

In another aspect, the multispecific polypeptides of the invention cause depletion of plasmacytoid cells (pDCs) and basophils. (cf. Example 31)

Accordingly, the present invention relates to a polypeptide, wherein said T cell activation causes depletion of plasmacytoid cells (pDCs) and basophils.

In another aspect, the multispecific polypeptides of the invention may further cause T cell proliferation. (cf. Example 39)

Accordingly, the present invention relates to a polypeptide, wherein said T cell activation causes proliferation of said T cells.

The multispecific polypeptides of the invention comprise on or more ISV that specifically binds CD123, which has been carefully selected for their specificity. As such, the multispecific polypeptides of the invention exhibit highly specific binding to CD123, which enables them to kill CD123 expressing target cells. In contrast, only minimal killing was observed in the absence of CD123 expressing cells, which underscores the safety of the polypeptides of the invention.

Accordingly, in another aspect, the present invention relates to a polypeptide, wherein the T cell activation in the absence of CD123 positive cells is minimal. (cf. Example 36 to 38)

More specifically, the present invention relates to a polypeptide, wherein the T cell activation induced lysis of CD123 negative cells is no more than about 10%, such as 9% or less, such as 8, 7, or 6% or even less, said lysis for example determined as average lysis percentage in a flow cytometry based assay with TOPRO3 read-out using CD123 negative cells, such as U-937 or NCI-H929 cells, as target cells and human T cells as effector cells at an effector to target cell ratio of 10 to 1.

More specifically, the present invention relates to a polypeptide, which does not induce secretion of IFN-γ and IL-6 in the presence of CD123 negative cells, said secretion for example determined in an ELISA based assay.

The inventors observed that certain multispecific polypeptides of the invention, comprising a TCR binding ISV of the invention and one or more CD123 binding ISV of the invention, were particularly suited to redirect T cells for killing of CD123 expressing cells. With these multispecific polypeptides of the invention, activation of T cells was minimal in the absence of CD123 expressing cells.

Accordingly, the present invention relates to a multispecific polypeptide that redirects T cells for killing of CD123 expressing cells, comprising one immunoglobulin single variable domain (ISV) that specifically binds T cell receptor (TCR) and one or more ISV that specifically bind CD123, wherein the ISV that specifically binds TCR essentially consists of 4 framework regions (FR1 to FR4, respectively) and 3 complementarity determining regions (CDR1 to CDR3, respectively), in which:
  i) CDR1 is chosen from the group consisting of:
    a) SEQ ID NOs: 181-191; or
    b) amino acid sequences that have 4, 3, 2 or 1 amino acid(s) difference with the amino acid sequence of one of SEQ ID NOs: 181-191; provided that the ISV comprising the CDR1 with 4, 3, 2 or 1 amino acid(s) difference binds TCR with about the same or a higher affinity compared to the binding by the ISV comprising the CDR1 without the 4, 3, 2 or 1 amino acid(s) difference, said affinity as measured by surface plasmon resonance;
  and/or
  ii) CDR2 is chosen from the group consisting of:
    c) SEQ ID NOs: 192-217; or
    d) amino acid sequences that have 4, 3, 2 or 1 amino acid(s) difference with the amino acid sequence of one of SEQ ID NOs: 192-217; provided that the ISV comprising the CDR2 with 4, 3, 2 or 1 amino acid(s) difference binds TCR with about the same or a higher affinity compared to the binding by the ISV comprising the CDR2 without the 4, 3, 2 or 1 amino acid(s) difference, said affinity as measured by surface plasmon resonance;

and/or iii) CDR3 is chosen from the group consisting of:

e) SEQ ID NOs: 218-225; or f) amino acid sequences that have 4, 3, 2 or 1 amino acid(s) difference with the amino acid sequence of one of SEQ ID NOs: 218-225; provided that the ISV comprising the CDR3 with 4, 3, 2 or 1 amino acid(s) difference binds TCR with about the same or a higher affinity compared to the binding by the ISV comprising the CDR3 without the 4, 3, 2 or 1 amino acid(s) difference, said affinity as measured by surface plasmon resonance;

and wherein the one or more ISV that specifically bind CD123 essentially consists of 4 framework regions (FR1 to FR4, respectively) and 3 complementarity determining regions (CDR1 to CDR3, respectively), in which:

i) CDR1 is chosen from the group consisting of:

a) SEQ ID NOs: 11-16; or b) amino acid sequences that have 4, 3, 2 or 1 amino acid(s) difference with the amino acid sequence of one of SEQ ID NOs: 11-16; provided that the ISV comprising the CDR1 with 4, 3, 2 or 1 amino acid(s) difference binds CD123 with about the same or a higher affinity compared to the binding by the ISV comprising the CDR1 without the 4, 3, 2 or 1 amino acid(s) difference, said affinity as measured by surface plasmon resonance;

and/or ii) CDR2 is chosen from the group consisting of:

c) SEQ ID NOs: 17-20; or d) amino acid sequences that have 4, 3, 2 or 1 amino acid(s) difference with the amino acid sequence of one of SEQ ID NOs: 17-20; provided that the ISV comprising the CDR2 with 4, 3, 2 or 1 amino acid(s) difference binds CD123 with about the same or a higher affinity compared to the binding by the ISV comprising the CDR2 without the 4, 3, 2 or 1 amino acid(s) difference, said affinity as measured by surface plasmon resonance;

and/or iii) CDR3 is chosen from the group consisting of:

e) SEQ ID NOs: 21-25; or f) amino acid sequences that have 4, 3, 2 or 1 amino acid(s) difference with the amino acid sequence of one of SEQ ID NOs: 21-25; provided that the ISV comprising the CDR3 with 4, 3, 2 or 1 amino acid(s) difference binds CD123 with about the same or a higher affinity compared to the binding by the ISV comprising the CDR3 without the 4, 3, 2 or 1 amino acid(s) difference, said affinity as measured by surface plasmon resonance.

In a further aspect, the present invention relates to a multispecific polypeptide, wherein the ISV that specifically binds TCR essentially consists of 4 framework regions (FR1 to FR4, respectively) and 3 complementarity determining regions (CDR1 to CDR3, respectively), in which:

i) CDR1 is chosen from the group consisting of:

a) SEQ ID NOs: 181-191; or b) amino acid sequences that have 4, 3, 2 or 1 amino acid(s) difference with the amino acid sequence of one of SEQ ID NOs: 181-191; provided that the ISV comprising the CDR1 with 4, 3, 2 or 1 amino acid(s) difference binds TCR with about the same or a higher affinity compared to the binding by the ISV comprising the CDR1 without the 4, 3, 2 or 1 amino acid(s) difference, said affinity as measured by surface plasmon resonance; and ii) CDR2 is chosen from the group consisting of:

c) SEQ ID NOs: 192-217; or d) amino acid sequences that have 4, 3, 2 or 1 amino acid(s) difference with the amino acid sequence of one of SEQ ID NOs: 192-217; provided that the ISV comprising the CDR2 with 4, 3, 2 or 1 amino acid(s) difference binds TCR with about the same or a higher affinity compared to the binding by the ISV comprising the CDR2 without the 4, 3, 2 or 1 amino acid(s) difference, said affinity as measured by surface plasmon resonance; and iii) CDR3 is chosen from the group consisting of:

e) SEQ ID NOs: 218-225; or f) amino acid sequences that have 4, 3, 2 or 1 amino acid(s) difference with the amino acid sequence of one of SEQ ID NOs: 218-225; provided that the ISV comprising the CDR3 with 4, 3, 2 or 1 amino acid(s) difference binds TCR with about the same or a higher affinity compared to the binding by the ISV comprising the CDR3 without the 4, 3, 2 or 1 amino acid(s) difference, said affinity as measured by surface plasmon resonance;

and wherein the one or more ISV that specifically bind CD123 essentially consists of 4 framework regions (FR1 to FR4, respectively) and 3 complementarity determining regions (CDR1 to CDR3, respectively), in which:

i) CDR1 is chosen from the group consisting of:

a) SEQ ID NOs: 11-16; or b) amino acid sequences that have 4, 3, 2 or 1 amino acid(s) difference with the amino acid sequence of one of SEQ ID NOs: 11-16; provided that the ISV comprising the CDR1 with 4, 3, 2 or 1 amino acid(s) difference binds CD123 with about the same or a higher affinity compared to the binding by the ISV comprising the CDR1 without the 4, 3, 2 or 1 amino acid(s) difference, said affinity as measured by surface plasmon resonance; and ii) CDR2 is chosen from the group consisting of:

c) SEQ ID NOs: 17-20; or d) amino acid sequences that have 4, 3, 2 or 1 amino acid(s) difference with the amino acid sequence of one of SEQ ID NOs: 17-20; provided that the ISV comprising the CDR2 with 4, 3, 2 or 1 amino acid(s) difference binds CD123 with about the same or a higher affinity compared to the binding by the ISV comprising the CDR2 without the 4, 3, 2 or 1 amino acid(s) difference, said affinity as measured by surface plasmon resonance; and iii) CDR3 is chosen from the group consisting of:

e) SEQ ID NOs: 21-25; or f) amino acid sequences that have 4, 3, 2 or 1 amino acid(s) difference with the amino acid sequence of one of SEQ ID NOs: 21-25; provided that the ISV comprising the CDR3 with 4, 3, 2 or 1 amino acid(s) difference binds CD123 with about the same or a higher affinity compared to the binding by the ISV comprising the CDR3 without the 4, 3, 2 or 1 amino acid(s) difference, said affinity as measured by surface plasmon resonance.

In a particular aspect, the present invention relates to a multispecific polypeptide, wherein the ISV that specifically binds TCR essentially consists of 4 framework regions (FR1 to FR4, respectively) and 3 complementarity determining regions (CDR1 to CDR3, respectively), in which:

i) CDR1 is chosen from the group consisting of:

a) SEQ ID NOs: 181-191; or b) amino acid sequences that have 4, 3, 2 or 1 amino acid(s) difference with the amino acid sequence of one of SEQ ID NOs: 181-191, wherein the 4, 3, 2 or 1 amino acid(s) difference are present at position 2, 4, 5, 6, 8 and/or 10 of the CDR1 (position 27, 29, 30, 31, 33 and/or 35 according to Kabat numbering); provided that the ISV comprising the CDR1 with 4, 3, 2 or 1 amino acid(s) difference binds TCR with about the same or a higher affinity compared to the binding by the ISV comprising the CDR1 without the 4, 3, 2 or 1 amino acid(s) difference, said affinity as measured by surface plasmon resonance; and ii) CDR2 is chosen from the group consisting of:

c) SEQ ID NOs: 192-217; or d) amino acid sequences that have 4, 3, 2 or 1 amino acid(s) difference with the amino acid sequence of one of SEQ ID NOs: 192-217, wherein the 4, 3, 2 or 1 amino acid(s) difference are present at position 1, 3, 5, 7, 8 and/or 9 of the CDR2 (position 50, 52, 54, 56, 57 and/or 58 according to Kabat numbering); provided that the ISV comprising the CDR2 with 4, 3, 2 or 1 amino acid(s) difference binds TCR with about the same or a higher affinity compared to the binding by the ISV comprising the CDR2 without the 4, 3, 2 or 1 amino acid(s) difference, said affinity as measured by surface plasmon resonance; and iii) CDR3 is chosen from the group consisting of:

e) SEQ ID NOs: 218-225; or f) amino acid sequences that have 4, 3, 2 or 1 amino acid(s) difference with the amino acid sequence of one of SEQ ID NOs: 218-225, wherein the 4, 3, 2 or 1 amino acid(s) difference are present at position 1, 4, 5 and/or 8 of the CDR3 (position 95, 98, 99 and/or 101 according to Kabat numbering); provided that the ISV comprising the CDR3 with 4, 3, 2 or 1 amino acid(s) difference binds TCR with about the same or a higher affinity compared to the binding by the ISV comprising the CDR3 without the 4, 3, 2 or 1 amino acid(s) difference, said affinity as measured by surface plasmon resonance;

and wherein the ISV that specifically binds CD123 is as described further herein.

In another aspect, the present invention relates to a multispecific polypeptide as described above, wherein the ISV that specifically binds TCR essentially consists of 4 framework regions (FR1 to FR4, respectively) and 3 complementarity determining regions (CDR1 to CDR3, respectively), in which CDR1 is chosen from the group consisting of:

a) SEQ ID NO: 181; or b) amino acid sequences that have 4, 3, 2 or 1 amino acid(s) difference with the amino acid sequence of SEQ ID NO: 181, wherein at position 2 the D has been changed into A, S, E or G;

at position 4 the H has been changed into Y;

at position 5 the K has been changed into L;

at position 6 the I has been changed into L;

at position 8 the F has been changed into I or V; and/or at position 10 the G has been changed into S;

provided that the ISV comprising the CDR1 with 4, 3, 2 or 1 amino acid(s) difference binds TCR with about the same or a higher affinity compared to the binding by the ISV comprising the CDR1 without the 4, 3, 2 or 1 amino acid(s) difference, said affinity as measured by surface plasmon resonance.

In another aspect, the present invention relates to a multispecific polypeptide as described above, wherein the ISV that specifically binds TCR essentially consists of 4 framework regions (FR1 to FR4, respectively) and 3 complementarity determining regions (CDR1 to CDR3, respectively), in which CDR2 is chosen from the group consisting of:

a) SEQ ID NO: 192; or b) amino acid sequences that have 4, 3, 2 or 1 amino acid(s) difference with the amino acid sequence of SEQ ID NO: 192, wherein at position 1 the H has been changed into T or R;

at position 3 the S has been changed into T or A;

at position 5 the G has been changed into S or A;

at position 7 the Q has been changed into D, E, T, A or V;

at position 8 the T has been changed into A or V; and/or at position 9 the D has been changed into A, Q, N, V or S;

provided that the ISV comprising the CDR2 with 4, 3, 2 or 1 amino acid(s) difference binds TCR with about the same or a higher affinity compared to the binding by the ISV comprising the CDR2 without the 4, 3, 2 or 1 amino acid(s) difference, said affinity as measured by surface plasmon resonance.

In another aspect, the present invention relates to a multispecific polypeptide as described above, wherein the ISV that specifically binds TCR essentially consists of 4 framework regions (FR1 to FR4, respectively) and 3 complementarity determining regions (CDR1 to CDR3, respectively), in which CDR3 is chosen from the group consisting of:

a) SEQ ID NO:218; or b) amino acid sequences that have 4, 3, 2 or 1 amino acid(s) difference with the amino acid sequence of SEQ ID NO: 218, wherein at position 1 the F has been changed into Y, L or G;

at position 4 the I has been changed into L;

at position 5 the Y has been changed into W; and/or at position 8 the D has been changed into N or S;

provided that the ISV comprising the CDR3 with 4, 3, 2 or 1 amino acid(s) difference binds TCR with about the same or a higher affinity compared to the binding by the ISV comprising the CDR3 without the 4, 3, 2 or 1 amino acid(s) difference, said affinity as measured by surface plasmon resonance.

Accordingly, the present invention relates to a multispecific polypeptide as described above, wherein the ISV that specifically binds TCR essentially consists of 4 framework regions (FR1 to FR4, respectively) and 3 complementarity determining regions (CDR1 to CDR3, respectively), in which:

i) CDR1 is chosen from the group consisting of:

a) SEQ ID NO: 181; or b) amino acid sequences that have 4, 3, 2 or 1 amino acid(s) difference with the amino acid sequence of SEQ ID NO: 181, wherein at position 2 the D has been changed into A, S, E or G;

at position 4 the H has been changed into Y;

at position 5 the K has been changed into L;

at position 6 the I has been changed into L;

at position 8 the F has been changed into I or V; and/or at position 10 the G has been changed into S;

provided that the ISV comprising the CDR1 with 4, 3, 2 or 1 amino acid(s) difference binds TCR with about the same or a higher affinity compared to the binding by the ISV comprising the CDR1 without the 4, 3, 2 or 1 amino acid(s) difference, said affinity as measured by surface plasmon resonance; and ii) CDR2 is chosen from the group consisting of:

c) SEQ ID NOs: 192; or d) amino acid sequences that have 4, 3, 2 or 1 amino acid(s) difference with the amino acid sequence of SEQ ID NO: 192, wherein at position 1 the H has been changed into T or R;

at position 3 the S has been changed into T or A;

at position 5 the G has been changed into S or A;

at position 7 the Q has been changed into D, E, T, A or V;

at position 8 the T has been changed into A or V; and/or at position 9 the D has been changed into A, Q, N, V or S;

provided that the ISV comprising the CDR2 with 4, 3, 2 or 1 amino acid(s) difference binds TCR with about the same or a higher affinity compared to the binding by the ISV comprising the CDR2 without the 4, 3, 2 or 1 amino acid(s) difference, said affinity as measured by surface plasmon resonance; and iii) CDR3 is chosen from the group consisting of:

e) SEQ ID NOs: 218; or f) amino acid sequences that have 4, 3, 2 or 1 amino acid(s) difference with the amino acid sequence of SEQ ID NO: 218, wherein at position 1 the F has been changed into Y, L or G;

at position 4 the I has been changed into L;

at position 5 the Y has been changed into W; and/or at position 8 the D has been changed into N or S;

provided that the ISV comprising the CDR3 with 4, 3, 2 or 1 amino acid(s) difference binds TCR with about the same or a higher affinity compared to the binding by the ISV comprising the CDR3 without the 4, 3, 2 or 1 amino acid(s) difference, said affinity as measured by surface plasmon resonance;

and wherein the ISV that specifically binds CD123 is as described further herein.

In another aspect, the present invention relates to a multispecific polypeptide, wherein the ISV that specifically binds TCR essentially consists of 4 framework regions (FR1 to FR4, respectively) and 3 complementarity determining regions (CDR1 to CDR3, respectively), in which CDR1 is chosen from the group consisting of SEQ ID NOs: 181-191, CDR2 is chosen from the group consisting of SEQ ID NOs: 192-217, and CDR3 is chosen from the group consisting of SEQ ID NOs: 218-225 and wherein the ISV that specifically binds CD123 is as described further herein.

Accordingly, the present invention relates to a multispecific polypeptide, wherein the ISV that specifically binds TCR essentially consists of 4 framework regions (FR1 to FR4, respectively) and 3 complementarity determining regions (CDR1 to CDR3, respectively), in which CDR1 is SEQ ID NO: 181, CDR2 is SEQ ID NO: 192, and CDR3 is SEQ ID NO: 218 and wherein the ISV that specifically binds CD123 is as described further herein.

In a preferred aspect, the present invention relates to a multispecific polypeptide, wherein the ISV that specifically binds TCR is chosen from the group consisting of SEQ ID NOs: 42 and 78-180 or from ISVs that have a sequence identity of more than 80%, more than 85%, more than 90%, more than 95%, or even more than 99% with one of SEQ ID NOs: 42 and 78-180 and wherein the ISV that specifically binds CD123 is as described further herein.

Apart from the TCR binding ISV as described above, in the multispecific polypeptides of the invention, the one or more ISV that specifically bind CD123 are related to 56A10 and/or 55F03.

Accordingly, the present invention relates to a multispecific polypeptide wherein the ISV that specifically binds TCR is as described herein and wherein the one or more ISV that specifically bind CD123 essentially consists of 4 framework regions (FR1 to FR4, respectively) and 3 complementarity determining regions (CDR1 to CDR3, respectively), in which:

i) CDR1 is chosen from the group consisting of:

a) SEQ ID NOs: 11-16; or b) amino acid sequences that have 4, 3, 2 or 1 amino acid(s) difference with the amino acid sequence of one of SEQ ID NOs: 11-16, wherein the 4, 3, 2 or 1 amino acid(s) difference are present at position 3, 6, 7 and/or 8 of the CDR1 (position 28, 31, 32 and/or 33 according to Kabat numbering); provided that the ISV comprising the CDR1 with 4, 3, 2 or 1 amino acid(s) difference binds CD123 with about the same or a higher affinity compared to the binding by the ISV comprising the CDR1 without the 4, 3, 2 or 1 amino acid(s) difference, said affinity as measured by surface plasmon resonance; and ii) CDR2 is chosen from the group consisting of:

c) SEQ ID NOs: 17-20; or d) amino acid sequences that have 3, 2 or 1 amino acid(s) difference with the amino acid sequence of one of SEQ ID NOs: 17-20, wherein the 3, 2 or 1 amino acid(s) difference are present at position 3, 6 and/or 10 of the CDR2 (position 52, 54 and/or 58 according to Kabat numbering); provided that the ISV comprising the CDR2 with 3, 2 or 1 amino acid(s) difference binds CD123 with about the same or a higher affinity compared to the binding by the ISV comprising the CDR2 without the 3, 2 or 1 amino acid(s) difference, said affinity as measured by surface plasmon resonance; and iii) CDR3 is chosen from the group consisting of:

e) SEQ ID NOs: 21-25; or f) amino acid sequences that have 3, 2 or 1 amino acid(s) difference with the amino acid sequence of one of SEQ ID NOs: 21-25, wherein the 3, 2 or 1 amino acid(s) difference are present at position 3, 4 and/or 5 of the CDR3 (position 97, 98 and/or 99 according to Kabat numbering); provided that the ISV comprising the CDR3 with 3, 2 or 1 amino acid(s) difference binds CD123 with about the same or a higher affinity compared to the binding by the ISV comprising the CDR3 without the 3, 2 or 1 amino acid(s) difference, said affinity as measured by surface plasmon resonance.

In one aspect, the one or more ISV that specifically binds CD123 may be an ISV related to 56A10. Accordingly, the present invention relates to a multispecific polypeptide as described above, wherein the one or more ISV that specifically bind CD123 essentially consists of 4 framework regions (FR1 to FR4, respectively) and 3 complementarity determining regions (CDR1 to CDR3, respectively), in which CDR1 is chosen from the group consisting of:

a) SEQ ID NO: 11; or b) amino acid sequences that have 4, 3, 2 or 1 amino acid(s) difference with the amino acid sequence of SEQ ID NO: 11, wherein at position 3 the T has been changed into S or P;

at position 6 the I has been changed into S;

at position 7 the N has been changed into D; and/or at position 8 the D has been changed into V or A;

provided that the ISV comprising the CDR1 with 4, 3, 2 or 1 amino acid(s) difference binds CD123 with about the same or a higher affinity compared to the binding by the ISV comprising the CDR1 without the 4, 3, 2 or 1 amino acid(s) difference, said affinity as measured by surface plasmon resonance.

In another aspect, the present invention relates to a multispecific polypeptide as described above, wherein the one or more ISV that specifically bind CD123 essentially consists of 4 framework regions (FR1 to FR4, respectively) and 3 complementarity determining regions (CDR1 to CDR3, respectively), in which CDR2 is SEQ ID NO: 17.

In another aspect, the present invention relates to a multispecific polypeptide as described above, wherein the one or more ISV that specifically bind CD123 essentially consists of 4 framework regions (FR1 to FR4, respectively) and 3 complementarity determining regions (CDR1 to CDR3, respectively), in which CDR3 is chosen from the group consisting of:

a) SEQ ID NO: 21; or b) amino acid sequences that have 1 amino acid difference with the amino acid sequence of SEQ ID NO: 21, wherein at position 3 the P has been changed into A;

provided that the ISV comprising the CDR3 with 1 amino acid(s) difference binds CD123 with about the same or a higher affinity compared to the binding by the ISV comprising the CDR3 without the 1 amino acid(s) difference, said affinity as measured by surface plasmon resonance.

Accordingly, the present invention relates to a multispecific polypeptide wherein the ISV that specifically binds TCR is as described herein and wherein the one or more ISV that specifically bind CD123 essentially consists of 4 framework regions (FR1 to FR4, respectively) and 3 complementarity determining regions (CDR1 to CDR3, respectively), in which:

i) CDR1 is chosen from the group consisting of:

a) SEQ ID NO: 11; or b) amino acid sequences that have 4, 3, 2 or 1 amino acid(s) difference with the amino acid sequence of SEQ ID NO: 11, wherein at position 3 the T has been changed into S or P;

at position 6 the I has been changed into S;

at position 7 the N has been changed into D; and/or at position 8 the D has been changed into V or A;

provided that the polypeptide comprising the CDR1 with 4, 3, 2 or 1 amino acid(s) difference binds CD123 with about the same or a higher affinity compared to the binding by the polypeptide comprising the CDR1 without the 4, 3, 2 or 1 amino acid(s) difference, said affinity as measured by surface plasmon resonance; and ii) CDR2 is SEQ ID NO: 17; and iii) CDR3 is chosen from the group consisting of:

c) SEQ ID NOs: 21; or d) amino acid sequences that have 1 amino acid difference with the amino acid sequence of SEQ ID NO: 21, wherein at position 3 the P has been changed into A;

provided that the polypeptide comprising the CDR3 with 1 amino acid difference binds CD123 with about the same or a higher affinity compared to the binding by the polypeptide comprising the CDR3 without the 1 amino acid difference, said affinity as measured by surface plasmon resonance.

In another aspect, the present invention relates to a multispecific polypeptide wherein the ISV that specifically binds TCR is as described herein and wherein the one or more ISV that specifically bind CD123 essentially consists of 4 framework regions (FR1 to FR4, respectively) and 3 complementarity determining regions (CDR1 to CDR3, respectively), in which CDR1 is chosen from the group consisting of SEQ ID NOs: 11-15, CDR2 is SEQ ID NO: 17, and CDR3 is chosen from the group consisting of SEQ ID NOs: 21-22.

Accordingly, the present invention relates to a multispecific polypeptide wherein the ISV that specifically binds TCR is as described herein and wherein the one or more ISV that specifically bind CD123 essentially consists of 4 framework regions (FR1 to FR4, respectively) and 3 complementarity determining regions (CDR1 to CDR3, respectively), in which CDR1 is SEQ ID NO: 11, CDR2 is SEQ ID NO: 17, and CDR3 is SEQ ID NO: 21.

In a preferred aspect, the present invention relates to a multispecific polypeptide wherein the ISV that specifically binds TCR is as described herein and wherein the one or more ISV that specifically bind CD123 is chosen from the group consisting of SEQ ID NOs: 1-6 or from ISVs that have a sequence identity of more than 80%, more than 85%, more than 90%, more than 95%, or even more than 99% with one of SEQ ID NOs: 1-6.

Apart from the above, or in addition, the ISV that specifically binds CD123 may be an ISV related to 55F03.

Accordingly, the present invention also relates to a multispecific polypeptide as described above, wherein the one or more ISV that specifically bind CD123 essentially consists of 4 framework regions (FR1 to FR4, respectively) and 3 complementarity determining regions (CDR1 to CDR3, respectively), in which CDR1 is SEQ ID NO: 16.

In another aspect, the present invention relates to a multispecific polypeptide as described above, wherein the one or more ISV that specifically bind CD123 essentially consists of 4 framework regions (FR1 to FR4, respectively) and 3 complementarity determining regions (CDR1 to CDR3, respectively), in which CDR2 is chosen from the group consisting of:

a) SEQ ID NO: 18; or b) amino acid sequences that have 3, 2 or 1 amino acid difference with the amino acid sequence of SEQ ID NO: 18, wherein at position 3 the Y has been changed into W;

at position 6 the N has been changed into S; and/or at position 10 the Q has been changed into E;

provided that the ISV comprising the CDR3 with 3, 2 or 1 amino acid(s) difference binds CD123 with about the same or a higher affinity compared to the binding by the ISV comprising the CDR3 without the 3, 2 or 1 amino acid(s) difference, said affinity as measured by surface plasmon resonance.

In another aspect, the present invention relates to a multispecific polypeptide as described above, wherein the one or more ISV that specifically bind CD123 essentially consists of 4 framework regions (FR1 to FR4, respectively)

and 3 complementarity determining regions (CDR1 to CDR3, respectively), in which CDR3 is chosen from the group consisting of:

a) SEQ ID NO: 23; or b) amino acid sequences that have 2 or 1 amino acid difference with the amino acid sequence of SEQ ID NO: 23, wherein at position 4 the E has been changed into R; and/or at position 5 the T has been changed into D or Y;

provided that the ISV comprising the CDR3 with 2 or 1 amino acid(s) difference binds CD123 with about the same or a higher affinity compared to the binding by the ISV comprising the CDR3 without the 2 or 1 amino acid(s) difference, said affinity as measured by surface plasmon resonance.

Accordingly, the present invention relates to a multispecific polypeptide wherein the ISV that specifically binds TCR is as described herein and wherein the one or more ISV that specifically bind CD123 essentially consists of 4 framework regions (FR1 to FR4, respectively) and 3 complementarity determining regions (CDR1 to CDR3, respectively), in which:

i) CDR1 is SEQ ID NO: 16; and ii) CDR2 is chosen from the group consisting of:

a) SEQ ID NO: 18; or b) amino acid sequences that have 3, 2 or 1 amino acid difference with the amino acid sequence of SEQ ID NO: 18, wherein at position 3 the Y has been changed into W;

at position 6 the N has been changed into S; and/or at position 10 the Q has been changed into E;

provided that the polypeptide comprising the CDR3 with 3, 2 or 1 amino acid(s) difference binds CD123 with about the same or a higher affinity compared to the binding by the polypeptide comprising the CDR3 without the 3, 2 or 1 amino acid(s) difference, said affinity as measured by surface plasmon resonance; and iii) CDR3 is chosen from the group consisting of:

c) SEQ ID NOs: 23; or d) amino acid sequences that have 2 or 1 amino acid difference with the amino acid sequence of SEQ ID NO: 23, wherein at position 4 the E has been changed into R; and/or at position 5 the T has been changed into D or Y;

provided that the polypeptide comprising the CDR3 with 2 or 1 amino acid(s) difference binds CD123 with about the same or a higher affinity compared to the binding by the polypeptide comprising the CDR3 without the 2 or 1 amino acid(s) difference, said affinity as measured by surface plasmon resonance.

In another aspect, the present invention relates to a multispecific polypeptide wherein the ISV that specifically binds TCR is as described herein and wherein the one or more ISV that specifically bind CD123 essentially consists of 4 framework regions (FR1 to FR4, respectively) and 3 complementarity determining regions (CDR1 to CDR3, respectively), in which CDR1 is SEQ ID NO: 16, CDR2 is chosen from the group consisting of SEQ ID NOs: 18-20, and CDR3 is chosen from the group consisting of SEQ ID NOs: 23-25.

Accordingly, the present invention relates to a multispecific polypeptide wherein the ISV that specifically binds TCR is as described herein and wherein the one or more ISV that specifically bind CD123 essentially consists of 4 framework regions (FR1 to FR4, respectively) and 3 complementarity determining regions (CDR1 to CDR3, respectively), in which CDR1 is SEQ ID NO: 16, CDR2 is SEQ ID NO: 18, and CDR3 is SEQ ID NO: 23.

In a preferred aspect, the present invention relates to a multispecific polypeptide wherein the ISV that specifically binds TCR is as described herein and, wherein the one or more ISV that specifically bind CD123 is chosen from the group consisting of SEQ ID NOs: 7-10 or from ISVs that have a sequence identity of more than 80%, more than 85%, more than 90%, more than 95%, or even more than 99% with one of SEQ ID NOs: 7-10.

As extensively described for the monospecific polypeptides, the immunoglobulin single variable domains present in the multispecific polypeptide of the invention may consist of a light chain variable domain sequence (e.g., a $V_L$-sequence) or of a heavy chain variable domain sequence (e.g., a $V_H$-sequence); they may consist of a heavy chain variable domain sequence that is derived from a conventional four-chain antibody or of a heavy chain variable domain sequence that is derived from heavy chain antibody. In a preferred aspect, they consist of a Domain antibody (or an amino acid that is suitable for use as a Domain antibody), of a single domain antibody (or an amino acid that is suitable for use as a single domain antibody), of a "dAb" (or an amino acid that is suitable for use as a dAb), of a Nanobody (including but not limited to a $V_{HH}$), a humanized VHH, a camelized VH, or of a VHH sequence that has been obtained by affinity maturation. The immunoglobulin single variable domains may consist of a partially or fully humanized Nanobody or a partially or fully humanized VHH. The immunoglobulin single variable domains may also contain mutations (as described herein) that are effective in preventing or reducing binding of so-called "pre-existing antibodies" to the immunoglobulin single variable domains and constructs of the invention. In a preferred aspect of the invention, the immunoglobulin single variable domains encompassed in the multispecific polypeptide of the invention are one or more monospecific polypeptides of the invention, as defined herein.

Preferred polypeptides of the invention may be chosen from the group consisting of SEQ ID NOs: 47, 49, 52, 53, 55, 56 and 58-61 (cf. Table A-7). In a further aspect, the polypeptide is chosen from the group consisting of SEQ ID NOs: 47, 49, 52, 53, 55, 56 and 58-61 or from polypeptides that have a sequence identity of more than 80%, more than 85%, more than 90%, more than 95%, or even more than 99% with one of SEQ ID NOs: 47, 49, 52, 53, 55, 56 and 58-61.

The multispecific polypeptides of the invention may comprise one or more other groups, residues, moieties or binding units as to form "polypeptide(s) of the invention" or construct(s) of the invention", as further described herein. For example, such a binding unit may be an amino acid sequence that increases the half-life (also referred to herein as "half-life extension" and "half-life extended construct") of the polypeptide. According to a specific, but non-limiting aspect of the invention, the polypeptides of the invention may thus contain, besides the one or more immunoglobulin single variable domains against CD123, and the one immunoglobulin single variable domain against TCR, at least one immunoglobulin single variable domain against serum albumin (such as human serum albumin). Accordingly, the present invention relates to a construct as described herein, wherein said binding unit that provides the polypeptide with an increased half-life is an immunoglobulin single variable domain that binds serum albumin. In a further aspect, the present invention relates to a construct as described herein, wherein said ISV that binds serum albumin essentially consists of a single domain antibody, a dAb, a Nanobody, a VHH, a humanized VHH or a camelized VH.

In a preferred aspect, the ISV that binds serum albumin is selected from the group consisting of SEQ ID NOs 43 or 351 to 362.

In a preferred aspect, the ISVs are directly linked to each or linked to each other via a linker.

Preferred constructs of the invention may be chosen from the group of constructs consisting of SEQ ID NOs: 63-67 or constructs that have a sequence identity of more than 80%, more than 85%, more than 90%, more than 95%, or even more than 99% with one of SEQ ID NOs: 63-67.

In a preferred aspect, the construct is selected from the group consisting of SEQ ID NOs: 63-67.

Upon their administration, the half-life extended constructs of the invention will not be removed instantaneous by renal clearance. As such the half-life extension will contribute to a favourable PK profile. Accordingly, there will be no need for continuous intravenous infusion and, as such, patient compliance will be improved. In a specific aspect, the constructs of the present invention do not require continuous infusion.

Also as extensively described for the monospecific polypeptides, the multispecific polypeptides of the invention or constructs of the invention may further comprise mutations that are effective in preventing or reducing binding of so-called "pre-existing antibodies" to the polypeptides and constructs of the invention. For this purpose, the polypeptides and constructs of the invention may contain a C-terminal extension $(X)n$ (in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (1)), as described herein.

Accordingly, the present invention relates to a polypeptide or construct of the invention, further comprising a C-terminal extension $(X)n$, in which n is 1 to 5, such as 1, 2, 3, 4 or 5, and in which X is a naturally occurring amino acid, preferably no cysteine.

More specifically, the present invention relates to a polypeptide or construct, wherein said polypeptide or construct is chosen from the group consisting of SEQ ID NOs: 338-342.

A method for preparing the multivalent or multispecific polypeptides of the invention may comprise at least the steps of linking two or more immunoglobulin single variable domains, monovalent polypeptides and/or monospecific polypeptides of the invention and for example one or more linkers together in a suitable manner. The immunoglobulin single variable domains, monovalent polypeptides and/or monospecific polypeptides of the invention (and linkers) can be coupled by any method known in the art and as further described herein. Preferred techniques include the linking of the nucleic acid sequences that encode the immunoglobulin single variable domains, monovalent polypeptides and/or monospecific polypeptides of the invention (and linkers) to prepare a genetic construct that expresses the multivalent or multispecific polypeptide. Techniques for linking amino acids or nucleic acids will be clear to the skilled person, and reference is again made to the standard handbooks, such as Sambrook et al. and Ausubel et al., mentioned above, as well as the Examples below.

Accordingly, the present invention also relates to the use of an immunoglobulin single variable domain, monovalent polypeptide and/or monospecific polypeptide of the invention in preparing a multivalent polypeptide or multispecific polypeptide of the invention. The method for the preparation of a multivalent or multispecific polypeptide will comprise the linking of one or more immunoglobulin single variable domains and/or polypeptides of the invention to at least one further immunoglobulin single variable domain, monovalent polypeptide and/or monospecific polypeptide of the invention, optionally via one or more linkers. The immunoglobulin single variable domain, monovalent polypeptide and/or monospecific polypeptide of the invention is then used as a binding domain or binding unit in providing and/or preparing the multivalent or multispecific polypeptide comprising two (e.g., in a bivalent polypeptide), three (e.g., in a trivalent polypeptide) or more (e.g., in a multivalent polypeptide) binding units. In this respect, the immunoglobulin singe variable domain, the monovalent polypeptide and/or the monospecific polypeptide of the invention may be used as a binding domain or binding unit in providing and/or preparing a multivalent or multispecific, such as bispecific or trispecific polypeptide comprising two, three or more binding units.

Accordingly, the present invention also relates to the use of an immunoglobulin single variable domain and/or particularly, a monovalent or monospecific polypeptide of the invention (as described herein) in preparing a multivalent or multispecific polypeptide. The method for the preparation of the multivalent or multispecific polypeptide will comprise the linking of the immunoglobulin single variable domain, monovalent polypeptide and/or monospecific polypeptide of the invention to at least one further immunoglobulin single variable domain, monovalent polypeptide and/or monospecific polypeptide of the invention, optionally via one or more linkers (as further described herein).

Constructs of the Invention

The monospecific polypeptide of the invention and the multispecific polypeptide of the invention, may or may not further comprise one or more other groups, residues, moieties or binding units (these monovalent polypeptides as well as multivalent polypeptides (with or without additional groups, residues, moieties or binding units) are all referred to as "construct(s) of the invention"). If present, such further groups, residues, moieties or binding units may or may not provide further functionality to the immunoglobulin single variable domain (and/or to the polypeptide in which it is present) and may or may not modify the properties of the immunoglobulin single variable domain.

For example, such further groups, residues, moieties or binding units may be one or more additional amino acid sequences, such that the polypeptide is a (fusion) protein or (fusion) polypeptide. In a preferred but non-limiting aspect, said one or more other groups, residues, moieties or binding units are immunoglobulins. Even more preferably, said one or more other groups, residues, moieties or binding units are immunoglobulin single variable domains chosen from the group consisting of Domain antibodies, amino acids that are suitable for use as a Domain antibody, single domain antibodies, amino acids that are suitable for use as a single domain antibody, "dAb" 's, amino acids that are suitable for use as a dAb, or Nanobodies (such as e.g. VHH, humanized VHH or a camelized VH).

As described above, additional binding units, such as immunoglobulin single variable domains having different antigen specificity can be linked to form multispecific constructs. By combining immunoglobulin single variable domains of two or more specificities, bispecific, trispecific etc. constructs can be formed. For example, a polypeptide according to the invention may comprise a monospecific or multispecific polypeptide of the invention and one or more immunoglobulin single variable domain(s) against another target (i.e., different from CD123 or TCR). Such constructs and modifications thereof, which the skilled person can readily envisage, are all encompassed by the term "construct of the invention" as used herein.

In the constructs described above, the one, two or more immunoglobulin single variable domains and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting construct is a fusion (protein) or fusion (polypeptide).

The one or more further groups, residues, moieties or binding units may be any suitable and/or desired amino acid sequences. The further amino acid sequences may or may not change, alter or otherwise influence the (biological) properties of the polypeptide of the invention, and may or may not add further functionality to the polypeptide of the invention. Preferably, the further amino acid sequence is such that it confers one or more desired properties or functionalities to the polypeptide of the invention.

Example of such amino acid sequences will be clear to the skilled person, and may generally comprise all amino acid sequences that are used in peptide fusions based on conventional antibodies and fragments thereof (including but not limited to ScFv's and single domain antibodies). Reference is for example made to the review by Holliger and Hudson (2005, Nature Biotechnology 23: 1126-1136).

For example, such an amino acid sequence may be an amino acid sequence that increases the half-life, the solubility, or the absorption, reduces the immunogenicity or the toxicity, eliminates or attenuates undesirable side effects, and/or confers other advantageous properties to and/or reduces the undesired properties of the construct of the invention, compared to polypeptide of the invention per se. Some non-limiting examples of such amino acid sequences are serum proteins, such as human serum albumin (see for example WO 00/27435) or haptenic molecules (for example haptens that are recognized by circulating antibodies, see for example WO 98/22141).

In a specific, but non-limiting aspect of the invention, which will be further described herein, the construct of the invention may have an increased half-life in serum (as further described herein) compared to the immunoglobulin single variable domain or polypeptide from which they have been derived. For example, an immunoglobulin single variable domain or polypeptide of the invention may be linked (chemically or otherwise) to one or more groups or moieties that extend the half-life (such as polyethylene glycol molecule (PEG)), so as to provide a derivative of the polypeptide of the invention with increased half-life.

In one specific aspect of the invention, a construct is prepared that has an increased half-life, compared to the corresponding polypeptide of the invention. Examples of constructs of the invention that comprise such half-life extending moieties for example include, without limitation, constructs in which the immunoglobulin single variable domains are suitable linked to one or more serum proteins or fragments thereof (such as (human) serum albumin or suitable fragments thereof) or to one or more binding units (such as, for example, Domain antibodies, amino acids that are suitable for use as a Domain antibody, single domain antibodies, amino acids that are suitable for use as a single domain antibody, "dAb" 's, amino acids that are suitable for use as a dAb, Nanobodies, VHHs, humanized VHHs or camelized VHs) that can bind to serum proteins (such as serum albumin (such as human serum albumin)), serum immunoglobulins (such as IgG), transferrin or one of the other serum proteins listed in WO 04/003019; polypeptides in which the immunoglobulin single variable domain is linked to an Fc portion (such as a human Fc) or a suitable part or fragment thereof; or constructs in which the one or more immunoglobulin single variable domains are suitably linked to one or more small proteins or peptides that can bind to serum proteins (such as, without limitation, the proteins and peptides described in WO 91/01743, WO 01/45746 or WO 02/076489). Reference is also made to the dAb's described in WO 03/002609 and WO 04/003019 and to Harmsen et al. (2005, Vaccine 23: 4926-4942); to EP 0368684, as well as to WO 08/028977, WO 08/043821, WO 08/043822, WO 08/068280, WO 09/127691 and WO 11/095545 by Ablynx N.V.

According to a specific, but non-limiting aspect of the invention, the constructs of the invention may contain, besides the one or more immunoglobulin single variable domains against CD123, and/or the one immunoglobulin single variable domain against TCR, at least one immunoglobulin single variable domain that binds serum albumin (such as human serum albumin). Accordingly, the present invention relates to a construct as described herein, wherein said binding unit that provides the construct with an increased half-life is an immunoglobulin single variable domain that binds serum albumin. In a further aspect, the present invention relates to a construct as described herein, wherein said ISV that binds serum albumin essentially consists of a single domain antibody, a dAb, a Nanobody, a VHH, a humanized VHH or a camelized VH.

The ISV that binds serum albumin may be any ISV as described in the art.

In one aspect, the immunoglobulin single variable domain that binds human serum albumin may be as generally described in the applications by Ablynx N.V. cited above (see for example WO 04/062551). Some preferred Nanobodies that provide for increased half-life and that can be used in the constructs of the invention include the Nanobodies ALB-1 to ALB-10 disclosed in WO 06/122787 (see Tables II and Ill), as well as the Nanobodies disclosed in WO 2012/175400 or WO 2015/173325 (e.g., SEQ ID NOs: 1-11 of WO 2012/175400, SEQ ID NO: 19 of WO 2015/173325) and Nanobodies from the provisional applications U.S. 62/256,841, U.S. 62/335,746, U.S. 62/349,294 and the corresponding International application by Assignee entitled "Improved serum albumin binders" that invokes the priority of these three US provisional applications."

In one aspect, the present invention relates to a polypeptide as described herein, wherein said ISV that binds serum albumin essentially consists of 4 framework regions (FR1 to FR4, respectively) and 3 complementarity determining regions (CDR1 to CDR3 respectively), in which CDR1 is GFTFSSFGMS (SEQ ID NO: 363) or GFTFRSFGMS (SEQ ID NO: 364), CDR2 is SISGSGSDTL (SEQ ID NO: 365) and CDR3 is GGSLSR (SEQ ID NO: 366).

Some particularly preferred Nanobodies that provide for increased half-life and that can be used in the constructs of the invention include immunoglobulin single variable domains also referred to as Alb, Alb23, Alb129, Alb132, Alb11, Alb11 (S112K)-A, Alb82, Alb82-A, Alb82-AA, Alb82-AAA, Alb82-G, Alb82-GG, Alb82-GGG (Table B-2).

Accordingly, the present invention relates to a construct as described herein, wherein said ISV that binds serum albumin is selected from the group consisting of SEQ ID NOs 43 or 351 to 362.

have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days),

TABLE B-2

| ISV | SEQ ID NO | Sequence |
|---|---|---|
| Alb8 | 43 | EVQLVESGGGLVQPGNSLRLSCAASGFTFSSFGMSWVRQAPGKGLEWVSSISGSGSD TLYADSVKGRFTISRDNAKTTLYLQMNSLRPEDTAVYYCTIGGSLSRSSQGTLVTVSS |
| Alb23 | 351 | EVQLLESGGGLVQPGGSLRLSCAASGFTFRSFGMSWVRQAPGKGPEWVSSISGSGSD TLYADSVKGRFTISRDNSKNTLYLQMNSLRPEDTAVYYCTIGGSLSRSSQGTLVTVSS |
| Alb129 | 352 | EVQLVESGGGVVQPGNSLRLSCAASGFTFSSFGMSWVRQAPGKGLEWVSSISGSGS DTLYADSVKGRFTISRDNAKTTLYLQMNSLRPEDTATYYCTIGGSLSRSSQGTLVTVSSA |
| Alb132 | 353 | EVQLVESGGGVVQPGGSLRLSCAASGFTFRSFGMSWVRQAPGKGPEWVSSISGSGS DTLYADSVKGRFTISRDNSKNTLYLQMNSLRPEDTATYYCTIGGSLSRSSQGTLVTVSS A |
| Alb11 | 354 | EVQLVESGGGLVQPGNSLRLSCAASGFTFSSFGMSWVRQAPGKGLEWVSSISGSGSD TLYADSVKGRFTISRDNAKTTLYLQMNSLRPEDTAVYYCTIGGSLSRSSQGTLVTVSS |
| Alb11 (S112K)-A | 355 | EVQLVESGGGLVQPGNSLRLSCAASGFTFSSFGMSWVRQAPGKGLEWVSSISGSGSD TLYADSVKGRFTISRDNAKTTLYLQMNSLRPEDTAVYYCTIGGSLSRSSQGTLVKVSSA |
| Alb82 | 356 | EVQLVESGGGVVQPGNSLRLSCAASGFTFSSFGMSWVRQAPGKGLEWVSSISGSGS DTLYADSVKGRFTISRDNAKTTLYLQMNSLRPEDTALYYCTIGGSLSRSSQGTLVTVSS |
| Alb82-A | 357 | EVQLVESGGGVVQPGNSLRLSCAASGFTFSSFGMSWVRQAPGKGLEWVSSISGSGS DTLYADSVKGRFTISRDNAKTTLYLQMNSLRPEDTALYYCTIGGSLSRSSQGTLVTVSSA |
| Alb82-AA | 358 | EVQLVESGGGVVQPGNSLRLSCAASGFTFSSFGMSWVRQAPGKGLEWVSSISGSGS DTLYADSVKGRFTISRDNAKTTLYLQMNSLRPEDTALYYCTIGGSLSRSSQGTLVTVSSA A |
| Alb82-AAA | 359 | EVQLVESGGGVVQPGNSLRLSCAASGFTFSSFGMSWVRQAPGKGLEWVSSISGSGS DTLYADSVKGRFTISRDNAKTTLYLQMNSLRPEDTALYYCTIGGSLSRSSQGTLVTVSSA AA |
| Alb82-G | 360 | EVQLVESGGGVVQPGNSLRLSCAASGFTFSSFGMSWVRQAPGKGLEWVSSISGSGS DTLYADSVKGRFTISRDNAKTTLYLQMNSLRPEDTALYYCTIGGSLSRSSQGTLVTVSSG |
| Alb82-GG | 361 | EVQLVESGGGVVQPGNSLRLSCAASGFTFSSFGMSWVRQAPGKGLEWVSSISGSGS DTLYADSVKGRFTISRDNAKTTLYLQMNSLRPEDTALYYCTIGGSLSRSSQGTLVTVSSG G |
| Alb82-GGG | 362 | EVQLVESGGGVVQPGNSLRLSCAASGFTFSSFGMSWVRQAPGKGLEWVSSISGSGS DTLYADSVKGRFTISRDNAKTTLYLQMNSLRPEDTALYYCTIGGSLSRSSQGTLVTVSSG GG |

Generally, the constructs of the invention with increased half-life preferably have a half-life that is at least 1.5 times, preferably at least 2 times, such as at least 5 times, for example at least 10 times or more than 20 times, greater than the half-life of the corresponding immunoglobulin single variable domain or polypeptide of the invention per se.

Generally, the constructs of the invention with increased half-life preferably have a half-life that is increased with more than 1 hours, preferably more than 2 hours, more preferably more than 6 hours, such as more than 12 hours, or even more than 24, 48 or 72 hours, compared to the half-life of the corresponding immunoglobulin single variable domain or polypeptide of the invention per se.

In another preferred, but non-limiting aspect, such constructs of the invention exhibit a serum half-life in human of at least about 12 hours, preferably at least 24 hours, more preferably at least 48 hours, even more preferably at least 72 hours or more. For example, constructs of the invention may more preferably at least about 12 days (such as about 12 to 18 days or more), or more than 14 days (such as about 14 to 19 days).

In the present invention, it was demonstrated that the inclusion of an albumin targeting binding unit in the construct as such did not have an essential impact on the obtained potency or efficacy. Although a minor loss of efficacy/potency was observed in the presence of HSA, the half-life extended TCR binding multispecific polypeptides were still potent in killing of CD123 expressing cells. Albumin-based drug delivery has been demonstrated to be useful for achieving improved cancer therapy, largely due to its passive target toward tumour via the enhanced permeability and retention effect and the increased demand for albumin by tumour cells as source of energy and amino acids.

According to one specific aspect, one or more polypeptides of the invention may be linked (optionally via a suitable linker or hinge region) to one or more constant domains (for example, 2 or 3 constant domains that can be used as part of/to form an Fc portion), to an Fc portion and/or to one or more antibody parts, fragments or domains that confer one or more effector functions to the polypeptide of the invention and/or may confer the ability to bind to one or more Fc receptors. For example, for this purpose, and without being limited thereto, the one or more further amino acid sequences may comprise one or more $C_H2$ and/or $C_H3$ domains of an antibody, such as from a heavy chain antibody (as described herein) and more preferably from a conventional human 4-chain antibody; and/or may form (part of) and Fc region, for example from IgG (e.g. from IgG1, IgG2, IgG3 or IgG4), from IgE or from another human Ig such as IgA, IgD or IgM. For example, WO 94/04678 describes heavy chain antibodies comprising a Camelid $V_{HH}$ domain or a humanized derivative thereof (i.e. a Nanobody), in which the Camelidae $C_H2$ and/or $C_H3$ domain have been replaced by human $C_H2$ and $C_H3$ domains, so as to provide an immunoglobulin that consists of 2 heavy chains each comprising a Nanobody and human $C_H2$ and $C_H3$ domains (but no $C_H1$ domain), which immunoglobulin has the effector function provided by the $C_H2$ and $C_H3$ domains and which immunoglobulin can function without the presence of any light chains. Other amino acid sequences that can be suitably linked to the polypeptides of the invention so as to provide an effector function will be clear to the skilled person, and may be chosen on the basis of the desired effector function(s). Reference is for example made to WO 04/058820, WO 99/42077, WO 02/056910 and WO 05/017148, as well as the review by Holliger and Hudson, supra; and to WO 09/068628. Coupling of a polypeptide of the invention to an Fc portion may also lead to an increased half-life, compared to the corresponding polypeptide of the invention. For some applications, the use of an Fc portion and/or of constant domains (i.e., $C_H2$ and/or $C_H3$ domains) that confer increased half-life without any biologically significant effector function may also be suitable or even preferred. Other suitable constructs comprising one or more polypeptides of the invention and one or more constant domains with increased half-life in vivo will be clear to the skilled person, and may for example comprise polypeptides linked to a $C_H3$ domain, optionally via a linker sequence. Generally, any fusion protein or derivatives with increased half-life will preferably have a molecular weight of more than 50 kDa, the cut-off value for renal absorption.

In another specific, but non-limiting, aspect, the polypeptides of the invention may be linked (optionally via a suitable linker or hinge region) to naturally occurring, synthetic or semi-synthetic constant domains (or analogs, variants, mutants, parts or fragments thereof) that have a reduced (or essentially no) tendency to self-associate into dimers (i.e. compared to constant domains that naturally occur in conventional 4-chain antibodies). Such monomeric (i.e. not self-associating) Fc chain variants, or fragments thereof, will be clear to the skilled person. For example, Helm et al. (J. Biol. Chem. 271: 7494, 1996), describe monomeric Fc chain variants that can be used in the polypeptide chains of the invention.

Also, such monomeric Fc chain variants are preferably such that they are still capable of binding to the complement or the relevant Fc receptor(s) (depending on the Fc portion from which they are derived), and/or such that they still have some or all of the effector functions of the Fc portion from which they are derived (or at a reduced level still suitable for the intended use). Alternatively, in such a polypeptide chain of the invention, the monomeric Fc chain may be used to confer increased half-life upon the polypeptide chain, in which case the monomeric Fc chain may also have no or essentially no effector functions.

The further amino acid residues may or may not change, alter or otherwise influence other (biological) properties of the polypeptide of the invention and may or may not add further functionality to the polypeptide of the invention. For example, such amino acid residues:

a) can comprise an N-terminal Met residue, for example as result of expression in a heterologous host cell or host organism.

b) may form a signal sequence or leader sequence that directs secretion of the polypeptide from a host cell upon synthesis (for example to provide a pre-, pro- or prepro-form of the polypeptide of the invention, depending on the host cell used to express the polypeptide of the invention). Suitable secretory leader peptides will be clear to the skilled person, and may be as further described herein. Usually, such a leader sequence will be linked to the N-terminus of the polypeptide, although the invention in its broadest sense is not limited thereto;

c) may form a "tag", for example an amino acid sequence or residue that allows or facilitates the purification of the polypeptide, for example using affinity techniques directed against said sequence or residue. Thereafter, said sequence or residue may be removed (e.g. by chemical or enzymatical cleavage) to provide the polypeptide (for this purpose, the tag may optionally be linked to the amino acid sequence or polypeptide sequence via a cleavable linker sequence or contain a cleavable motif). Some preferred, but non-limiting examples of such residues are multiple histidine residues, glutathione residues and a myc-tag such as AAAEQKLISEEDLNGAA (SEQ ID NO: 206);

d) may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the polypeptides of the invention.

In the constructs of the invention, the two or more building blocks, ISVs or Nanobodies and the optionally one or more polypeptides, one or more other groups, drugs, agents, residues, moieties or binding units may be directly linked to each other (as for example described in WO 99/23221) and/or may be linked to each other via one or more suitable spacers or linkers, or any combination thereof.

Suitable spacers or linkers for use in the constructs of the invention will be clear to the skilled person, and may generally be any linker or spacer used in the art to link amino acid sequences, and/or other groups, drugs, agents, residues, moieties or binding units. Preferably, said linker or spacer is suitable for use in constructing polypeptides and/or construct that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each immunoglobulin single variable domain by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_x ser_y)_z$, such as (for example $(gly_4 ser)_3$ or $(gly_3 ser_2)_3$, as described in WO 99/42077, and the GS30, GS15, GS9 and GS7 linkers described in the applications by Ablynx mentioned herein (see for example WO 06/040153 and WO 06/122825), as well as hinge-like regions such as the hinge regions of naturally occurring heavy chain antibodies or similar sequences (such as described in WO 94/04678).

Some other particularly preferred linkers are mentioned in Table B-3, of which 35GS (SEQ ID NO: 334) is particularly preferred.

Accordingly, the invention relates to polypeptides wherein the ISVs are linked to each other via a linker selected from the group consisting of SEQ ID NOs: 325 to 336.

TABLE B-3

Linkers

| Link-er | SEQ ID NO | Sequence |
|---|---|---|
| 5GS | 325 | GGGGS |
| 7GS | 326 | SGGSGGS |
| 9GS | 327 | GGGGSGGGS |
| 10GS | 328 | GGGGSGGGGS |
| 15GS | 329 | GGGGSGGGGSGGGGS |
| 18GS | 330 | GGGGSGGGGSGGGGGGS |
| 20GS | 331 | GGGGSGGGGSGGGGSGGGGS |
| 25GS | 332 | GGGGSGGGGSGGGGSGGGGSGGGGS |
| 30GS | 333 | GGGGSGGGGSGGGGSGGGGSGGGGSGGGGS |
| 35GS | 334 | GGGGSGGGGSGGGGSGGGGSGGGGSGGGGSGGGGS |
| 40GS | 335 | GGGGSGGGGSGGGGSGGGGSGGGGSGGGGSGGGGSGGGGS |
| Poly-A | 336 | AAA |

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final polypeptide of the invention, including but not limited to the affinity, specificity or avidity for CD123 and/or TCR, or for one or more of the other antigens. Based on the disclosure herein, the skilled person will be able to determine the optimal linker(s) for use in a specific polypeptide of the invention, optionally after some limited routine experiments.

For example, in multivalent or multispecifc polypeptides of the invention that comprise building blocks, ISVs or Nanobodies directed against a first and second target, the length and flexibility of the linker are preferably such that it allows each building block, ISV or Nanobody of the invention present in the polypeptide to bind to its cognate target, e.g. the antigenic determinant on each of the targets. Again, based on the disclosure herein, the skilled person will be able to determine the optimal linker(s) for use in a specific polypeptide of the invention, optionally after some limited routine experiments.

It is also within the scope of the invention that the linker(s) used confer one or more other favourable properties or functionality to the polypeptides or constructs of the invention, and/or provide one or more sites for the formation of derivatives and/or for the attachment of functional groups (e.g., as described herein for the derivatives of the polypeptides of the invention). For example, linkers containing one or more charged amino acid residues can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide or construct of the invention, optionally after some limited routine experiments.

Finally, when two or more linkers are used in the polypeptides or contructs of the invention, these linkers may be the same or different. Again, based on the disclosure herein, the skilled person will be able to determine the optimal linkers for use in a specific polypeptide or construct of the invention, optionally after some limited routine experiments.

Usually, for ease of expression and production, a polypeptide or construct of the invention will be a linear polypeptide. However, the invention in its broadest sense is not limited thereto. For example, when a polypeptide of the invention comprises three of more amino acid sequences, ISVs or Nanobodies, it is possible to link them by use of a linker with three or more "arms", which each "arm" being linked to an amino acid sequence, ISV or Nanobody, so as to provide a "star-shaped" construct. It is also possible, although usually less preferred, to use circular constructs.

Accordingly, the present invention relates to a polypeptide as described herein, wherein said first ISV and said second ISV and possibly said third ISV and/or said ISV binding serum albumin are directly linked to each other or are linked via a linker.

Also encompassed in the present invention are constructs that comprise an immunoglobulin single variable domain or polypeptide of the invention and further comprising tags or other functional moieties, e.g., toxins, labels, radiochemicals, etc.

Alternatively, the additional groups, residues, moieties or binding units may for example be chemical groups, residues, moieties, which may or may not by themselves be biologically and/or pharmacologically active. For example, and without limitation, such groups may be linked to the two or more immunoglobulin single variable domains or monovalent polypeptides so as to provide a "derivative" of the polypeptide of the invention.

Accordingly, the invention in its broadest sense also comprises derivatives of the polypeptides of the invention. Such derivatives can generally be obtained by modification, and in particular by chemical and/or biological (e.g., enzymatical) modification, of the polypeptides of the invention and/or of one or more of the amino acid residues that form a polypeptide of the invention.

Examples of such modifications, as well as examples of amino acid residues within the polypeptide sequences that can be modified in such a manner (i.e. either on the protein backbone but preferably on a side chain), methods and techniques that can be used to introduce such modifications and the potential uses and advantages of such modifications will be clear to the skilled person (see also Zangi et al. 2013, Nat. biotechnol. 31: 898-907).

For example, such a modification may involve the introduction (e.g., by covalent linking or in any other suitable manner) of one or more functional groups, residues or moieties into or onto the polypeptide of the invention, and in particular of one or more functional groups, residues or moieties that confer one or more desired properties or functionalities to the polypeptide of the invention. Example of such functional groups will be clear to the skilled person.

For example, such modification may comprise the introduction (e.g., by covalent binding or in any other suitable manner) of one or more functional groups that that increase the half-life, the solubility and/or the absorption of the polypeptide of the invention, that reduce the immunogenicity and/or the toxicity of the polypeptide of the invention, that eliminate or attenuate any undesirable side effects of the polypeptide of the invention, and/or that confer other advantageous properties to and/or reduce the undesired properties of the polypeptide of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington (1980, Pharmaceutical Sciences, 16th ed., Mack Publishing Co., Easton, PA, 1980). Such functional groups may for example be linked directly (for example covalently) to a polypeptide of the invention, or optionally via a suitable linker or spacer, as will again be clear to the skilled person.

One specific example is a derivative polypeptide of the invention wherein the polypeptide of the invention has been chemically modified to increase the half-life thereof (for example, by means of pegylation). This is one of the most widely used techniques for increasing the half-life and/or reducing the immunogenicity of pharmaceutical proteins and comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman (2002, Nat. Biotechnol. 54: 531-545), Veronese and Harris (2003, Adv. Drug Deliv. Rev. 54: 453-456), Harris and Chess (2003, Nat. Rev. Drug. Discov. 2: 214-221) and WO 04/060965. Various reagents for pegylation of proteins are also commercially available, for example from Nektar Therapeutics, USA.

Preferably, site-directed pegylation is used, in particular via a cysteine-residue (see for example Yang et al. (2003, Protein Engineering 16: 761-770)). For example, for this purpose, PEG may be attached to a cysteine residue that naturally occurs in a polypeptide of the invention, a poly-peptide of the invention may be modified so as to suitably introduce one or more cysteine residues for attachment of PEG, or an amino acid sequence comprising one or more cysteine residues for attachment of PEG may be fused to the N- and/or C-terminus of a polypeptide of the invention, all using techniques of protein engineering known per se to the skilled person.

Preferably, for the polypeptides of the invention, a PEG is used with a molecular weight of more than 5000, such as more than 10,000 and less than 200,000, such as less than 100,000; for example in the range of 20,000-80,000.

Another, usually less preferred modification comprises N-linked or O-linked glycosylation, usually as part of co-translational and/or post-translational modification, depending on the host cell used for expressing the polypeptide of the invention.

Yet another modification may comprise the introduction of one or more detectable labels or other signal-generating groups or moieties, depending on the intended use of the labelled polypeptide of the invention. Suitable labels and techniques for attaching, using and detecting them will be clear to the skilled person, and for example include, but are not limited to, fluorescent labels (such as fluorescein, iso-thiocyanate, rhodamine, phycoerythrin, phycocyanin, allo-phycocyanin, o-phthaldehyde, and fluorescamine and fluo-rescent metals such as $^{152}$Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes (such as $^3$H, $^{125}$I, $^{32}$P, $^{35}$S, $^{14}$C, $^{51}$Cr, $^{36}$Cl, $^{57}$Co, $^{58}$Co, $^{59}$Fe, and $^{75}$Se), metals, metals chelates or metallic cations (for example metallic cations such as $^{99m}$Tc, $^{123}$I, $^{111}$In, $^{131}$I, $^{97}$Ru, $^{67}$Cu, $^{67}$Ga, and $^{68}$Ga or other metals or metallic cations that are particularly suited for use in in vivo, in vitro or in situ diagnosis and imaging, such as ($^{157}$Gd, $^{55}$Mn, $^{162}$Dy, $^{52}$Cr, and $^{56}$Fe)), as well as chromophores and enzymes (such as malate dehydrogenase, staphylococcal nuclease, delta-V-steroid isomerase, yeast alcohol dehydro-genase, alpha-glycerophosphate dehydrogenase, triose phosphate isomerase, biotinavidin peroxidase, horseradish peroxidase, alkaline phosphatase, asparaginase, glucose oxi-dase, β-galactosidase, ribonuclease, urease, catalase, glu-cose-VI-phosphate dehydrogenase, glucoamylase and ace-tylcholine esterase). Other suitable labels will be clear to the skilled person, and for example include moieties that can be detected using NMR or ESR spectroscopy.

Such labelled polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the polypeptide of the invention to another protein, polypeptide or chemical compound that is bound to the other half of the binding pair, i.e. through formation of the binding pair. For example, a polypeptide of the invention may be conjugated to biotin, and linked to another protein, polypeptide, compound or carrier conjugated to avidin or streptavidin. For example, such a conjugated polypeptide of the invention may be used as a reporter, for example in a diagnostic system where a detectable signal-producing agent is conjugated to avidin or streptavidin. Such binding pairs may for example also be used to bind the polypeptide of the invention to a carrier, including carriers suitable for pharmaceutical purposes. One non-limiting example are the liposomal formulations described by Cao and Suresh (2000, Journal of Drug Targeting 8: 257). Such binding pairs may also be used to link a therapeutically active agent to the polypeptide of the invention.

Other potential chemical and enzymatical modifications will be clear to the skilled person. Such modifications may also be introduced for research purposes (e.g. to study function-activity relationships). Reference is for example made to Lundblad and Bradshaw (1997, Biotechnol. Appl. Biochem. 26: 143-151).

Preferably, the derivatives are such that they bind to CD123 and/or TCR, with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein (i.e. as defined for the polypeptides of the invention).

Such polypeptides of the invention and derivatives thereof may also be in essentially isolated form (as defined herein).

The invention further relates to methods for preparing the polypeptides, nucleic acids, host cells, and compositions described herein.

The polypeptides and constructs of the invention can be prepared in a manner known per se, as will be clear to the skilled person from the further description herein. For example, the polypeptides and constructs of the invention can be prepared in any manner known per se for the preparation of antibodies and in particular for the preparation of antibody fragments (including but not limited to (single) domain antibodies and ScFv fragments). Some preferred, but non-limiting methods for preparing the polypeptides, constructs and nucleic acids include the methods and techniques described herein.

The method for producing a polypeptide or construct (that is such that it can be obtained by expression of a nucleic acid encoding the same) of the invention may comprise the following steps:

expressing, in a suitable host cell or host organism (also referred to herein as a "host of the invention") or in another suitable expression system a nucleic acid that encodes said polypeptide or construct of the invention (also referred to herein as a "nucleic acid of the invention"), optionally followed by:

isolating and/or purifying the polypeptide or construct of the invention thus obtained.

In particular, such a method may comprise the steps of:

cultivating and/or maintaining a host of the invention under conditions that are such that said host of the invention expresses and/or produces at least one polypeptide or construct (that is such that it can be obtained by expression of a nucleic acid encoding the same) of the invention;

optionally followed by:

isolating and/or purifying the polypeptide or construct of the invention thus obtained.

Accordingly, the present invention also relates to a nucleic acid or nucleotide sequence that encodes a polypeptide or construct (that is such that it can be obtained by expression of a nucleic acid encoding the same) of the invention (also referred to as "nucleic acid of the invention"). A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one aspect of the invention, the nucleic acid of the invention is in essentially isolated from, as defined herein. The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the polypeptides or constructs (that are such that they can be obtained by expression of a nucleic acid encoding the same) of the invention given herein, and/or can be isolated from a suitable natural source. Also, as will be clear to the skilled person, to prepare a nucleic acid of the invention, also several nucleotide sequences, such as at least one nucleotide seqence encoding an immunoglobulin single variable domain of the invention and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct of the invention comprises a) at least one nucleic acid of the invention; operably connected to b) one or more regulatory elements, such as a promoter and optionally a suitable terminator; and optionally also c) one or more further elements of genetic constructs known per se;

in which the terms "regulatory element", "promoter", "terminator" and "operably connected" have their usual meaning in the art (as further described herein); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used; the intended host cell or host organism; the manner in which the nucleotide sequences of the invention of interest are to be expressed (e.g. via constitutive, transient or inducible expression); and/or the transformation technique to be used. For example, regulatory sequences, promoters and terminators known per se for the expression and production of antibodies and antibody fragments (including but not limited to (single) domain antibodies and ScFv fragments) may be used in an essentially analogous manner.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promoter). Generally, when two nucleotide sequences are operably linked, they will be in the same orientation and usually also in the same reading frame. They will usually also be essentially contiguous, although this may also not be required.

Preferably, the regulatory and further elements of the genetic constructs of the invention are such that they are capable of providing their intended biological function in the intended host cell or host organism.

For instance, a promoter, enhancer or terminator should be "operable" in the intended host cell or host organism, by which is meant that (for example) said promoter should be capable of initiating or otherwise controlling/regulating the transcription and/or the expression of a nucleotide sequence—e.g., a coding sequence—to which it is operably linked (as defined herein).

Some particularly preferred promoters include, but are not limited to, promoters known per se for the expression in the host cells mentioned herein; and in particular promoters for the expression in the bacterial or yeast cells, such as those mentioned herein and/or those used in the Examples.

A selection marker should be such that it allows—i.e., under appropriate selection conditions—host cells and/or host organisms that have been (successfully) transformed with the nucleotide sequence of the invention to be distinguished from host cells/organisms that have not been (successfully) transformed. Some preferred, but non-limiting examples of such markers are genes that provide resistance against antibiotics (such as kanamycin or ampicillin), genes that provide for temperature resistance, or genes that allow the host cell or host organism to be maintained in the absence of certain factors, compounds and/or (food) components in the medium that are essential for survival of the non-transformed cells or organisms.

A leader sequence should be such that—in the intended host cell or host organism—it allows for the desired post-translational modifications and/or such that it directs the transcribed mRNA to a desired part or organelle of a cell. A leader sequence may also allow for secretion of the expression product from said cell. As such, the leader sequence may be any pro-, pre-, or prepro-sequence operable in the host cell or host organism. Leader sequences may not be required for expression in a bacterial cell. For example, leader sequences known per se for the expression and production of antibodies and antibody fragments (including but not limited to single domain antibodies and ScFv fragments) may be used in an essentially analogous manner.

An expression marker or reporter gene should be such that—in the host cell or host organism—it allows for detection of the expression of (a gene or nucleotide sequence present on) the genetic construct. An expression marker may optionally also allow for the localisation of the expressed product, e.g., in a specific part or organelle of a cell and/or in (a) specific cell(s), tissue(s), organ(s) or part(s) of a multicellular organism. Such reporter genes may also be expressed as a protein fusion with the ISV, polypeptide or construct of the invention. Some preferred, but non-limiting examples include fluorescent proteins such as GFP.

Some preferred, but non-limiting examples of suitable promoters, terminator and further elements include those that can be used for the expression in the host cells mentioned herein; and in particular those that are suitable for expression in bacterial or yeast cells, such as those mentioned herein and/or those used in the Examples below. For some (further) non-limiting examples of the promoters, selection markers, leader sequences, expression markers and further elements that may be present/used in the genetic constructs of the invention—such as terminators, transcriptional and/or translational enhancers and/or integration factors—reference is made to the general handbooks such as Sambrook et al. and Ausubel et al. mentioned above, as well as to the examples that are given in WO 95/07463, WO 96/23810, WO 95/07463, WO 95/21191, WO 97/11094, WO 97/42320, WO 98/06737, WO 98/21355, U.S. Pat. Nos. 7,207,410, 5,693,492 and EP 1085089. Other examples will be clear to the skilled person. Reference is also made to the general background art cited above and the further references cited herein.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

Often, the genetic constructs of the invention will be obtained by inserting a nucleotide sequence of the invention in a suitable (expression) vector known per se. Some preferred, but non-limiting examples of suitable expression vectors are those used in the Examples below, as well as those mentioned herein.

The nucleic acids of the invention and/or the genetic constructs of the invention may be used to transform a host cell or host organism, i.e., for expression and/or production of the polypeptide or construct (that is such that it can be obtained by expression of a nucleic acid encoding the same) of the invention. The host is preferably a non-human host. Suitable hosts or host cells will be clear to the skilled person, and may for example be any suitable fungal, prokaryotic or eukaryotic cell or cell line or any suitable fungal, prokaryotic or (non-human) eukaryotic organism, for example:

a bacterial strain, including but not limited to gram-negative strains such as strains of *Escherichia coli*; of *Proteus*, for example of *Proteus mirabilis*; of *Pseudomonas*, for example of *Pseudomonas fluorescens*; and gram-positive strains such as strains of *Bacillus*, for example of *Bacillus subtilis* or of *Bacillus brevis*; of *Streptomyces*, for example of *Streptomyces lividans*; of *Staphylococcus*, for example of *Staphylococcus carnosus*; and of *Lactococcus*, for example of *Lactococcus lactis;* a fungal cell, including but not limited to cells from species of *Trichoderma*, for example from *Trichoderma reesei*; of *Neurospora*, for example from *Neurospora crassa*; of *Sordaria*, for example from *Sordaria macrospora*; of *Aspergillus*, for example from *Aspergillus niger* or from *Aspergillus sojae*; or from other filamentous fungi;

a yeast cell, including but not limited to cells from species of *Saccharomyces*, for example of *Saccharomyces cerevisiae*; of *Schizosaccharomyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of Arxula, for example of Arxula adeninivorans; of *Yarrowia*, for example of *Yarrowia lipolytica;* an amphibian cell or cell line, such as *Xenopus* oocytes;

an insect-derived cell or cell line, such as cells/cell lines derived from lepidoptera, including but not limited to *Spodoptera* SF9 and Sf21 cells or cells/cell lines derived from *Drosophila*, such as Schneider and Kc cells;

a plant or plant cell, for example in tobacco plants; and/or a mammalian cell or cell line, for example a cell or cell line derived from a human, a cell or a cell line from mammals including but not limited to CHO-cells, BHK-cells (for example BHK-21 cells) and human cells or cell lines such as HeLa, COS (for example COS-7) and PER.C6 cells;

as well as all other host cells or (non-human) hosts known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al. (1998, Res Immunol. 149: 589-599); Riechmann and Muyldermans (1999), supra; van der Linden (2000, J. Biotechnol. 80: 261-270); Joosten et al. (2003, Microb. Cell Fact. 2: 1); Joosten et al. 2005, (Appl. Microbiol. Biotechnol. 66: 384-392); and the further references cited herein.

The polypeptides or constructs of the invention may also be expressed as so-called "intrabodies", as for example described in WO 94/02610, WO 95/22618 and U.S. Pat. No. 7,004,940; WO 03/014960; in Cattaneo and Biocca (1997, Intracellular Antibodies: Development and Applications" Landes and Springer-Verlag); and in Kontermann (2004, Methods 34: 163-170).

The polypeptides or constructs of the invention can for example also be produced in the milk of transgenic mammals, for example in the milk of rabbits, cows, goats or sheep (see for example U.S. Pat. Nos. 6,741,957, 6,304,489 and 6,849,992 for general techniques for introducing transgenes into mammals), in plants or parts of plants including but not limited to their leaves, flowers, fruits, seed, roots or tubers (for example in tobacco, maize, soybean or alfalfa) or in for example pupae of the silkworm *Bombix mori*.

Furthermore, the polypeptides or the constructs of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the *E. coli* Zubay system.

Preferably, in the invention, an (in vivo or in vitro) expression system, such as a bacterial expression system, is used that provides the polypeptides or constructs of the invention in a form that is suitable for pharmaceutical use, and such expression systems will again be clear to the skilled person. As also will be clear to the skilled person, polypeptides or constructs of the invention suitable for pharmaceutical use can be prepared using techniques for peptide synthesis.

For production on industrial scale, preferred heterologous hosts for the (industrial) production of immunoglobulin single variable domains or immunoglobulin single variable domain-containing polypeptide therapeutics include strains of *E. coli, Pichia pastoris, S. cerevisiae* that are suitable for large scale expression/production/fermentation, and in particular for large scale pharmaceutical expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

The choice of the specific expression system would depend in part on the requirement for certain post-translational modifications, more specifically glycosylation. The production of an immunoglobulin single variable domain-containing recombinant protein for which glycosylation is desired or required would necessitate the use of mammalian expression hosts that have the ability to glycosylate the expressed protein. In this respect, it will be clear to the skilled person that the glycosylation pattern obtained (i.e., the kind, number and position of residues attached) will depend on the cell or cell line that is used for the expression. Preferably, either a human cell or cell line is used (i.e., leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast usually leads to a glycosylation pattern that differs from human glycosylation. Nevertheless, it should be understood that all the foregoing host cells and expression systems can be used in the invention, depending on the desired polypeptide or construct to be obtained.

Thus, according to one non-limiting aspect of the invention, the polypeptide or construct of the invention is glycosylated. According to another non-limiting aspect of the invention, the polypeptide or construct of the invention is non-glycosylated.

According to one preferred, but non-limiting aspect of the invention, the polypeptide or construct of the invention is produced in a bacterial cell, in particular a bacterial cell suitable for large scale pharmaceutical production, such as cells of the strains mentioned above.

According to another preferred, but non-limiting aspect of the invention, the polypeptide or construct of the invention is produced in a yeast cell, in particular a yeast cell suitable for large scale pharmaceutical production, such as cells of the species mentioned above.

According to yet another preferred, but non-limiting aspect of the invention, the polypeptide or construct of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

When expression in a host cell is used to produce the polypeptides or constructs of the invention, the polypeptides or constructs of the invention can be produced either intracellularly (e.g., in the cytosol, in the periplasma or in inclusion bodies) and then isolated from the host cells and optionally further purified; or can be produced extracellularly (e.g., in the medium in which the host cells are cultured) and then isolated from the culture medium and optionally further purified. When eukaryotic host cells are used, extracellular production is usually preferred since this considerably facilitates the further isolation and downstream processing of the polypeptides or constructs obtained. Bacterial cells such as the strains of E. coli mentioned above normally do not secrete proteins extracellularly, except for a few classes of proteins such as toxins and hemolysin, and secretory production in E. coli refers to the translocation of proteins across the inner membrane to the periplasmic space. Periplasmic production provides several advantages over cytosolic production. For example, the N-terminal amino acid sequence of the secreted product can be identical to the natural gene product after cleavage of the secretion signal sequence by a specific signal peptidase. Also, there appears to be much less protease activity in the periplasm than in the cytoplasm. In addition, protein purification is simpler due to fewer contaminating proteins in the periplasm. Another advantage is that correct disulfide bonds may form because the periplasm provides a more oxidative environment than the cytoplasm. Proteins overexpressed in E. coli are often found in insoluble aggregates, so-called inclusion bodies. These inclusion bodies may be located in the cytosol or in the periplasm; the recovery of biologically active proteins from these inclusion bodies requires a denaturation/refolding process. Many recombinant proteins, including therapeutic proteins, are recovered from inclusion bodies. Alternatively, as will be clear to the skilled person, recombinant strains of bacteria that have been genetically modified so as to secrete a desired protein, and in particular a polypeptide or construct of the invention, can be used.

Thus, according to one non-limiting aspect of the invention, the polypeptide or construct of the invention is a polypeptide or construct that has been produced intracellularly and that has been isolated from the host cell, and in particular from a bacterial cell or from an inclusion body in a bacterial cell. According to another non-limiting aspect of the invention, the polypeptide or construct of the invention is a polypeptide or construct that has been produced extracellularly, and that has been isolated from the medium in which the host cell is cultivated.

Some preferred, but non-limiting promoters for use with these host cells include:

for expression in E. coli: lac promoter (and derivatives thereof such as the lacUV5 promoter); arabinose promoter; left- (PL) and rightward (PR) promoter of phage lambda; promoter of the trp operon; hybrid lac/trp promoters (tac and trc); T7-promoter (more specifically that of T7-phage gene 10) and other T-phage promoters; promoter of the Tn10 tetracycline resistance gene; engineered variants of the above promoters that include one or more copies of an extraneous regulatory operator sequence;

for expression in S. cerevisiae: constitutive: ADH1 (alcohol dehydrogenase 1), ENO (enolase), CYC1 (cytochrome c iso-1), GAPDH (glyceraldehydes-3-phosphate dehydrogenase), PGK1 (phosphoglycerate kinase), PYK1 (pyruvate kinase); regulated: GAL1, 10,7 (galactose metabolic enzymes), ADH2 (alcohol dehydrogenase 2), PHO5 (acid phosphatase), CUP1 (copper metallothionein); heterologous: CaMV (cauliflower mosaic virus 35S promoter);

for expression in Pichia pastoris: the AOX1 promoter (alcohol oxidase 1);

for expression in mammalian cells: human cytomegalovirus (hCMV) immediate early enhancer/promoter; human cytomegalovirus (hCMV) immediate early promoter variant that contains two tetracycline operator sequences such that the promoter can be regulated by the Tet repressor; Herpes Simplex Virus thymidine kinase (TK) promoter; Rous Sarcoma Virus long terminal repeat (RSV LTR) enhancer/promoter; elongation factor 1α (hEF-1α) promoter from human, chimpanzee, mouse or rat; the SV40 early promoter; HIV-1 long terminal repeat promoter; β-actin promoter.

Some preferred, but non-limiting vectors for use with these host cells include:

vectors for expression in mammalian cells: pMAMneo (Clontech), pcDNA3 (Invitrogen), pMC1neo (Stratagene), pSG5 (Stratagene), EBO-pSV2-neo (ATCC 37593), pBPV-1 (8-2) (ATCC 37110), pdBPV-MMTneo (342-12) (ATCC 37224), pRSVgpt (ATCC37199), pRSVneo (ATCC37198), pSV2-dhfr (ATCC 37146), pUCTag (ATCC 37460) and 1ZD35 (ATCC 37565), as well as viral-based expression systems, such as those based on adenovirus;

vectors for expression in bacterial cells: pET vectors (Novagen) and pQE vectors (Qiagen);

vectors for expression in yeast or other fungal cells: pYES2 (Invitrogen) and Pichia expression vectors (Invitrogen);

vectors for expression in insect cells: pBlueBacII (Invitrogen) and other baculovirus vectors;

vectors for expression in plants or plant cells: for example vectors based on cauliflower mosaic virus or tobacco mosaic virus, suitable strains of Agrobacterium, or Ti-plasmid based vectors.

Some preferred, but non-limiting secretory sequences for use with these host cells include:

for use in bacterial cells such as E. coli: PelB, Bla, OmpA, OmpC, OmpF, OmpT, StII, PhoA, PhoE, MalE, Lpp, LamB, and the like; TAT signal peptide, hemolysin C-terminal secretion signal;

for use in yeast: α-mating factor prepro-sequence, phosphatase (pho1), invertase (Suc), etc.;

for use in mammalian cells: indigenous signal in case the target protein is of eukaryotic origin; murine Ig κ-chain V-J2-C signal peptide; etc.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the polypeptide or construct of the invention, e.g., using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g., under suitable conditions), a polypeptide or construct of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

Accordingly, in another aspect, the invention relates to a host or host cell that expresses (or that under suitable circumstances is capable of expressing) a polypeptide or construct of the invention; and/or that contains a nucleic acid encoding the same. Some preferred but non-limiting examples of such hosts or host cells can be as generally described in WO 04/041867, WO 04/041865 or WO 09/068627. For example, polypeptides or constructs of the invention may with advantage be expressed, produced or manufactured in a yeast strain, such as a strain of *Pichia pastoris*. Reference is also made to WO 04/25591, WO 10/125187, WO 11/003622, and WO 12/056000 which also describes the expression/production in *Pichia* and other hosts/host cells of immunoglobulin single variable domains and polypeptides comprising the same.

To produce/obtain expression of the polypeptides or constructs of the invention, the transformed host cell or transformed host organism may generally be kept, maintained and/or cultured under conditions such that the (desired) polypeptide or construct of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g., when the nucleotide sequences of the invention are under the control of an inducible promoter); all of which may be selected by the skilled person. Again, under such conditions, the polypeptides or construct of the invention may be expressed in a constitutive manner, in a transient manner, or only when suitably induced.

It will also be clear to the skilled person that the polypeptide or construct of the invention may (first) be generated in an immature form (as mentioned above), which may then be subjected to post-translational modification, depending on the host cell/host organism used. Also, the polypeptide or construct of the invention may be glycosylated, again depending on the host cell/host organism used.

The polypeptide or construct of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g., using a specific, cleavable amino acid sequence fused with the polypeptide or construct of the invention) and/or preparative immunological techniques (i.e. using antibodies against the polypeptide or construct to be isolated).

Compositions of the Invention

The invention further relates to a product or composition containing or comprising at least one polypeptide or construct of the invention, and/or at least one nucleic acid of the invention, and optionally one or more further components of such compositions known per se, i.e. depending on the intended use of the composition.

Generally, for pharmaceutical use, the polypeptides or constructs of the invention may be formulated as a pharmaceutical preparation or composition comprising at least one polypeptide or construct of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (for example intravenous, intraperitoneal, subcutaneous, intramuscular, intraluminal, intra-arterial or intrathecal administration), for topical administration, for administration by inhalation, by a skin patch, by an implant, by a suppository, etc, wherein the parenteral administration is preferred. Such suitable administration forms—which may be solid, semi-solid or liquid, depending on the manner of administration—as well as methods and carriers for use in the preparation thereof, will be clear to the skilled person, and are further described herein. Such a pharmaceutical preparation or composition will generally be referred to herein as a "pharmaceutical composition". A pharmaceutical preparation of composition for use in a non-human organism will generally be referred to herein as a "veterinary composition". Some preferred but non-limiting examples of such compositions will become clear from the further description herein.

Thus, in a further aspect, the invention relates to a pharmaceutical composition that contains at least one polypeptide or construct of the invention and at least one suitable carrier, diluent or excipient (i.e., suitable for pharmaceutical use), and optionally one or more further active substances. In a particular aspect, the invention relates to a pharmaceutical composition that contains a polypeptide or construct of the invention selected from any of SEQ ID NOs: 1-10, 47, 49, 52, 53, 55, 56, 58-61, 63-67, and 338-342 and at least one suitable carrier, diluent or excipient (i.e. suitable for pharmaceutical use), and optionally one or more further active substances.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Generally, the polypeptides and constructs of the invention can be formulated and administered in any suitable manner known per se. Reference is for example made to the general background art cited above (and in particular to WO 04/041862, WO 04/041863, WO 04/041865, WO 04/041867 and WO 08/020079) as well as to the standard handbooks, such as Remington's Pharmaceutical Sciences, 18th Ed., Mack Publishing Company, USA (1990), Remington, the Science and Practice of Pharmacy, 21st Ed., Lippincott Williams and Wilkins (2005); or the Handbook of Therapeutic Antibodies (S. Dubel, Ed.), Wiley, Weinheim, 2007 (see for example pages 252-255).

For example, the polypeptides or construct of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (e.g., intravenous, intraperitoneal, subcutaneous, intramuscular, intraluminal, intra-arterial or intrathecal administration).

Preparations for parenteral administration may for example be sterile solutions, suspensions, dispersions or emulsions that are suitable for infusion or injection. Suitable carriers or diluents for such preparations for example include, without limitation, those mentioned on page 143 of WO 08/020079. Usually, aqueous solutions or suspensions will be preferred.

The polypeptides or constructs of the invention may be administered intravenously or intraperitoneally by infusion or injection. Solutions of the polypeptides or constructs of the invention can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical compositions suitable for parenteral administration comprise one or more immunoglobulin single variable domain, polypeptide or construct in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers, which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol, sorbic acid, thimerosal, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly-(anhydrides). Depot injectable formulations are also prepared by entrapping the drug in liposomes or microemulsions, which are compatible with body tissue.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage.

Sterile injectable solutions are prepared by incorporating the polypeptides or constructs of the invention in the required amount in the appropriate solvent with several of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

The amount of the polypeptides or constructs of the invention required for use in treatment will vary not only with the particular polypeptide or construct selected but also with the route of administration, the nature of the condition being treated and the age and condition of the patient and will be ultimately at the discretion of the attendant physician or clinician. Also the dosage of the polypeptides or constructs of the invention will vary.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, PA. The dosage can also be adjusted by the individual physician in the event of any complication.

In another aspect, kits are provided comprising a polypeptide or construct of the invention, a nucleic acid of the invention, an expression vector of the invention, or a host or host cell of the invention. The kit may also comprise one or more vials containing the polypeptide or construct and instructions for use. The kit may also contain means for administering the polypeptide or construct of the invention such as a syringe, infuser or the like.

Uses of the Polypeptides, Construct or Compositions of the Invention

The invention further relates to applications and uses of the polypeptides, constructs, nucleic acids, host cells, and compositions described herein, as well as to methods for the prevention and/or treatment of CD123 associated diseases or conditions. Some preferred but non-limiting applications and uses will become clear from the further description herein.

The polypeptides, constructs, and compositions of the present invention can generally be used to activate T cells at (the site of) CD123 expressing cells; such as to lyse the CD123 expressing cells. The simultaneous binding by the polypeptides and constructs of the present invention to TCR on T cells and CD123 on tumour cells induces the activation of the cells and the subsequent lysis (killing) of the CD123 expressing cells. When not bound to CD123 expressing cells, the polypeptides and constructs of the invention show hardly any T cell activation. As such, target-independent lysis (i.e., lysis of cells without CD123 expression) by the polypeptides and constructs of the present invention is minimal.

Accordingly, in one aspect, the polypeptides, constructs and compositions of the present invention cause lysis of CD123 expressing cells with an average lysis percentage of at least 10%, preferably at least 15%, such as at least 16%, 17%, 18%, 19% or 20% or more, such as 30% or more of compared to the number of CD123 expressing cells under the same conditions but without the presence of the polypeptide or construct of the invention, measured in any suitable manner known per se, for example using one of the assays described herein (such as the redirected human T cell mediated killing flow-cytometry based assays, as described in the Example section).

Apart from this or at the same time, the T cell activation induced lysis of CD123 negative cells by the polypeptides, constructs and compositions of the present invention, is no more than about 10%, such as 9% or less, such as 8, 7, or 6% or even less, of the number of CD123 negative cells under the same conditions but without the presence of the polypeptide or construct of the invention, measured in any suitable manner known per se, for example using one of the assays described herein (such as the redirected human T cell mediated killing flow-cytometry based assays, as described in the Example section).

This killing of CD123 expressing cells can be advantageous in diseases or conditions in which the presence of such CD123 expressing cells is abundant and/or not desired.

Accordingly, in one aspect, the present invention provides a polypeptide, construct or a composition, for use as a medicament.

In a further aspect, the present invention provides a polypeptide or construct of the invention or a composition comprising the same, for use in the prevention, treatment and/or amelioration of a CD123 associated disease or condition.

More particularly, the present invention provides a polypeptide or construct of the invention or a composition comprising the same, for use in the prevention, treatment and/or amelioration of a CD123 associated disease or condition, wherein the CD123 associated disease or condition is a proliferative disease or an inflammatory condition.

The invention also relates to a method for the prevention, treatment and/or amelioration of a CD123 associated disease or condition, said method comprising administering, to a subject in need thereof, a pharmaceutically active amount of a polypeptide or construct of the invention, and/or of a composition comprising the same.

In particular, the present invention relates to a method as described above, wherein the CD123 associated disease or condition is a proliferative disease or an inflammatory condition.

The inflammatory condition can be any inflammatory condition prevented, treated and/or ameliorated by killing of CD123 expressing cells.

In one aspect, the inflammatory condition is chosen from the group consisting of Autoimmune Lupus (SLE), allergy, asthma and rheumatoid arthritis.

Accordingly, the present invention relates to a polypeptide, construct or a composition for use in the prevention, treatment and/or amelioration of an inflammatory condition, wherein said inflammatory condition is chosen from the group consisting of Autoimmune Lupus (SLE), allergy, asthma and rheumatoid arthritis.

Accordingly, the present invention also relates to methods for the prevention, treatment and/or amelioration of an inflammatory condition, wherein said inflammatory condition is chosen from the group consisting of Autoimmune Lupus (SLE), allergy, asthma and rheumatoid arthritis, said method comprising administering, to a subject in need thereof, a pharmaceutically active amount of at least one polypeptide or construct of the invention or a composition of the invention.

The proliferative disease can be any proliferative disease prevented, treated and/or ameliorated by killing of CD123 expressing cells.

In one aspect, said proliferative disease is cancer. Examples of cancers associated with CD123 overexpression will be clear to the skilled person based on the disclosure herein, and for example include (without being limiting) the following cancers: lymphomas (including Burkitt's lymphoma, Hodgkin's lymphoma and non-Hodgkin's lymphoma), leukemias (including acute myeloid leukemia, chronic myeloid leukemia, acute B lymphoblastic leukemia, chronic lymphocytic leukemia and hairy cell leukemia), myelodysplastic syndrome, blastic plasmacytoid dendritic cell neoplasm, systemic mastocytosis and multiple myeloma.

Accordingly, the present invention relates to a polypeptide, construct or a composition for use in the prevention, treatment and/or amelioration of cancer, wherein said cancer is chosen from the group consisting of lymphomas (including Burkitt's lymphoma, Hodgkin's lymphoma and non-Hodgkin's lymphoma), leukemias (including acute myeloid leukemia, chronic myeloid leukemia, acute B lymphoblastic leukemia, chronic lymphocytic leukemia and hairy cell leukemia), myelodysplastic syndrome, blastic plasmacytoid dendritic cell neoplasm, systemic mastocytosis and multiple myeloma.

Accordingly, the present invention also relates to methods for the prevention, treatment and/or amelioration of cancer, wherein said cancer is chosen from the group consisting of lymphomas (including Burkitt's lymphoma, Hodgkin's lymphoma and non-Hodgkin's lymphoma), leukemias (including acute myeloid leukemia, chronic myeloid leukemia, acute B lymphoblastic leukemia, chronic lymphocytic leukemia and hairy cell leukemia), myelodysplastic syndrome, blastic plasmacytoid dendritic cell neoplasm, systemic mastocytosis and multiple myeloma, said method comprising administering, to a subject in need thereof, a pharmaceutically active amount of at least one polypeptide or construct of the invention or a composition of the invention.

The invention also relates to the use of a polypeptide or construct of the invention, or a composition of the invention, for the manufacture of a medicament.

In a further aspect, the present invention relates to the use of a polypeptide or construct of the invention or a composition comprising the same, for the manufacture of a medicament for the prevention, treatment and/or amelioration of a CD123 associated disease or condition.

More particularly, the present invention relates to the use of a polypeptide or construct of the invention or a composition comprising the same, for the manufacture of a medicament for the prevention, treatment and/or amelioration of a CD123 associated disease or condition, wherein the CD123 associated disease or condition is a proliferative disease or an inflammatory condition.

In one aspect, the invention relates to the use of a polypeptide or construct of the invention, or a composition comprising the same, for the manufacture of a medicament for the prevention, treatment and/or amelioration of an inflammatory condition, wherein said inflammatory condition is chosen from the group consisting of Autoimmune Lupus (SLE), allergy, asthma and rheumatoid arthritis.

In another aspect, the invention relates to the use of a polypeptide or construct of the invention, or a composition comprising the same, for the manufacture of a medicament for the prevention, treatment and/or amelioration of a proliferative disease, wherein said proliferative disease is cancer. Examples of cancers associated with CD123 overexpression will be clear to the skilled person based on the disclosure herein, and for example include (without being limiting) the following cancers: lymphomas (including Burkitt's lymphoma, Hodgkin's lymphoma and non-Hodgkin's lymphoma), leukemias (including acute myeloid leukemia, chronic myeloid leukemia, acute B lymphoblastic leukemia, chronic lymphocytic leukemia and hairy cell leukemia), myelodysplastic syndrome, blastic plasmacytoid dendritic cell neoplasm, systemic mastocytosis and multiple myeloma.

Accordingly, the present invention also relates the use of a polypeptide or construct of the invention, or a composition comprising the same, for the manufacture of a medicament for the prevention, treatment and/or amelioration of cancer, wherein said cancer is chosen from the group consisting of lymphomas (including Burkitt's lymphoma, Hodgkin's lymphoma and non-Hodgkin's lymphoma), leukemias (including acute myeloid leukemia, chronic myeloid leukemia, acute B lymphoblastic leukemia, chronic lymphocytic leukemia and hairy cell leukemia), myelodysplastic syndrome, blastic plasmacytoid dendritic cell neoplasm, systemic mastocytosis and multiple myeloma.

In the context of the present invention, the term "prevention, treatment and/or amelioration" not only comprises preventing, treating and/or ameliorating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

As used interchangeably herein, the term "pharmaceutically effective amount" or "pharmaceutically active amount" refers to an amount that is sufficient to activate T cells in the presence of CD123 expressing cells. In the context of a CD123 associated disease, it refers to the amount of a polypeptide, construct or pharmaceutical composition alone, or in combination with another therapy, that provides a therapeutic benefit in the prevention, treatment and/or amelioration of the CD123 associated disease. Used in connection with an amount of a multispecific polypeptide or construct of the invention, the term can encompass an amount that improves overall therapy, reduces or avoids unwanted effects, or enhances the therapeutic efficacy of or synergies with another therapy.

As used herein, the term "therapy" refers to any protocol, method and/or agent that can be used in the treatment, prevention and/or management of a CD123 associated disease, e.g., an inflammatory condition or proliferative disease. In certain embodiments, the terms "therapies" and "therapy" refer to a biological therapy, supportive therapy, and/or other therapies useful in the treatment, prevention and/or management of a CD123 associated disease, e.g., an inflammatory condition or proliferative disease, or one or more symptoms thereof known to one of skill in the art such as medical personnel.

In another aspect, the invention relates to a method for immunotherapy, and in particular for passive immunotherapy, which method comprises administering, to a subject suffering from or at risk of a CD123 associated disease, a pharmaceutically active amount of a polypeptide or construct of the invention, and/or of a pharmaceutical composition comprising the same.

The subject to be treated may be any warm-blooded animal, but is in particular a mammal, and more in particular a human being. As will be clear to the skilled person, the subject to be treated will in particular be a person suffering from, or at risk of the diseases and conditions mentioned herein.

In general, the polypeptides or construct according to the invention and/or the compositions comprising the same can be administered in any suitable manner. For example (but not limited thereto) the polypeptides according to the invention and compositions comprising the same can be administered orally, parenterally (e.g., intravenously, intraperitoneally, subcutaneously, intramuscularly, intraluminally, intra-arterially or intrathecally or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

In a preferred aspect, the polypeptides or constructs of the invention or the compositions comprising the same are administered intravenously (e.g., (but not limited thereto), by infusion or a bolus) or subcutaneously.

The polypeptides or constructs of the invention and/or the compositions comprising the same are administered according to a regime of treatment that is suitable for preventing, treating and/or ameliorating a CD123 associated disease. The clinician will generally be able to determine a suitable treatment regimen, depending on factors such as the type of disease to be treated, the stage of the disease, the severity of the disease and/or the severity of the symptoms thereof, the specific polypeptide or construct of the invention to be used, the specific route of administration and pharmaceutical formulation or composition to be used, the age, gender, weight, diet, general condition of the patient, and similar factors well known to the clinician.

Generally, the treatment regimen will comprise the administration of one or more polypeptides or constructs of the invention, or of one or more compositions comprising the same, in one or more pharmaceutically effective amounts or doses. The specific amount(s) or doses to administered can be determined by the clinician, again based on the factors cited above.

Generally, for the prevention, treatment and/or amelioration of a CD123 associated disease and depending on the type of CD123 associated disease (e.g., a proliferative disorder (including cancer) or inflammatory condition) to be treated, the stage of the disease to be treated, the potency of the polypeptide or construct of the invention to be used, the specific route of administration and the specific pharmaceutical formulation or composition used, the polypeptides of the invention will generally be administered in an amount between 1 gram and 1 microgram per kg body weight per day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies of antibody fragments against the same target via essentially the same route, taking into account however differences in affinity/avidity, efficacy, biodistribution, half-life and similar factors well known to the skilled person.

Usually, in the above method, a single polypeptide or construct of the invention will be used. It is however within the scope of the invention to use two or more polypeptides or constructs of the invention in combination.

The polypeptides or constructs of the invention, or compositions comprising the same may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgement.

In particular, the polypeptides, constructs and compositions of the invention may be used in combination with other pharmaceutically active compounds or principles that are or can be used for the prevention, treatment and/or amelioration of a CD123 associated disease (e.g., a proliferative disorder (including cancer) or inflammatory condition), as a result of which a synergistic effect may or may not be obtained. Examples of such compounds and principles, as well as routes, methods and pharmaceutical formulations or compositions for administering them will be clear to the clinician.

Examples of such compounds and principles, as well as routes, methods and pharmaceutical formulations or compositions for administering them will be clear to the clinician and include (without being limiting): Anthracyclines (daunurubicin, doxorubicin, idarubicine, mitoxantrone, rubidazone), Cytarabine (AML), haematopoietic growth factors, demethylating agents (such as decitabine or azacytidine), all-trans retinoic acid, arsenic trioxide, DNA methyltransferase inhibitors, Melphalan, Prednisone, Lenalidomide, Cyclophosphamide, Thalidomide, Dexamethasone, Bortezomib, fludarabine, corticosteroids, vincristine, rasburicase, L-Asparaginase, pegylated asparaginase, Cladribine, Pentostatin, Adriamycin, Bleomycin, Vinblastine, Dacarbazine; or any combination thereof.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

Further uses of the polypeptides or constructs, nucleic acids, genetic constructs and hosts and host cells of the invention will be clear to the skilled person based on the disclosure herein.

The aspects illustrated and discussed in this specification are intended only to teach those skilled in the art the best way known to the inventors to make and use the invention. Modifications and variations of the above-described aspects of the invention are possible without departing from the invention, as appreciated by those skilled in the art in light of the above teachings. It is therefore understood that, within the scope of the claims and their equivalents, the invention may be practiced otherwise than as specifically described.

The invention will now be further described by means of the following non-limiting preferred aspects, examples and figures.

The entire contents of all of the references (including literature references, issued patents, published patent applications, and co-pending patent applications) cited throughout this application are hereby expressly incorporated by reference, in particular for the teaching that is referenced hereinabove.

EXAMPLES

Example 1: Material and Methods Related to TCR 1.1 TCR αβ/CD3 Transfected Cell Lines Transient and stable CHO-K1 (ATCC: CCL-61), HEK293H (Life technologies, 11631-017), Llana (Fibroblast cells from llama Navel cord cells) cell lines with recombinant overexpression of all 6 chains of the full human T cell Receptor (TCR) complex were generated. For this, the coding sequences of the TCR alpha (α) and TCR beta (β) chain were cloned in a pcDNA3.1-derived vector, downstream of a CMV promotor and a 2A-like viral peptide sequence was inserted between both chains to induce ribosomal skipping during translation of the polyprotein. In the same vector, the coding sequences of the epsilon, delta, gamma and zeta chains of the CD3 complex were cloned downstream of an additional CMV promotor, also using 2A-like viral peptide sequences between the respective chains. In addition, a stable HEK293H clone with recombinant overexpression of the 4 chains of the human CD3 was generated as described above using a single gene vector.

The used sequences for the human CD3 and the human TCRα/β constant domains were derived from UniProtKB (CD3 delta: P04234, CD3 gamma: P09693, CD3 epsilon: P07766, CD3 zeta: P20963, TCR α: P01848 and TCR 1: P01850; SEQ ID NOs: 70 to 75, respectively). The sequences for the human TCRα/β variable domains were derived from crystal structure sequences (PDB codes: 2IAN, 2XN9 and 3TOE) (human TCR α variable domains derived from 2IAN, 2XN9 and 3TOE with SEQ ID NOs: 343, 76 and 345, respectively; human TCR 1 variable domains derived from 2IAN, 2XN9 and 3TOE with SEQ ID NOs: 344, 77 and 346, respectively).

Figure 1:
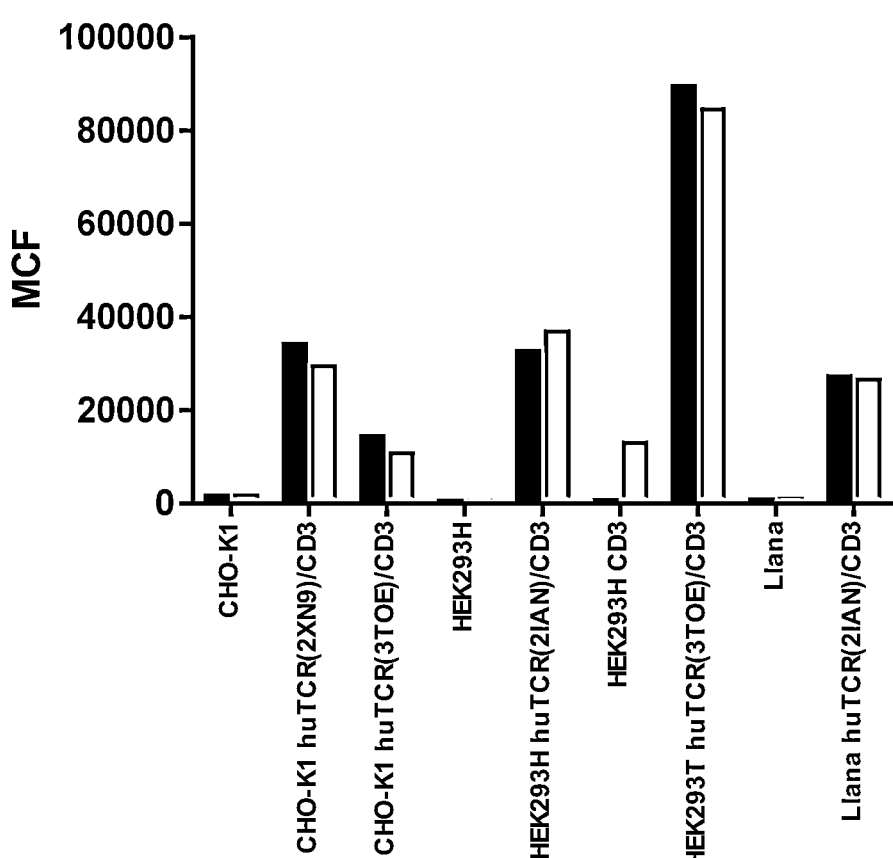
FIG. 1: Assessment of the expression of human TCR/CD3 and human CD3 on transfected CHO, HEK293 and Llana cell lines using 100 nM anti-human TCR $\alpha/\beta$ antibody (clone BW242/412) (black) and 100 nM anti-human CD3 antibody (clone OKT-3) (grey). The MCF value (mean channel fluorescence) was plotted for each cell line. The X-axis depicts the cell type and the transfected genes; CD3 indicates transfection with the CD3 complex (epsilon, delta, gamma and zeta chains), huTCR indicates transfection with the TCR $\alpha/\beta$ chains, wherein the variable domain used is between brackets.

The cell surface expression of the human T cell receptor complex was confirmed by flow cytometry using a functional mouse IgG2b anti-human TCRα/β antibody, clone BW242/412 (Miltenyi, 130-098-219) and a functional mouse IgG2a anti-CD3 PE labelled antibody, clone OKT-3 (eBioscience, 12-0037) (FIG. 1).

1.2 Soluble Recombinant TCR α/β Proteins

Soluble human and cynomolgus/rhesus monkey TCR α/β proteins were generated in house. The sequences for the extracellular part of the human TCRα/β constant domain were derived from UniProtKB (TCR α: P01848 and TCR β: P01850; SEQ ID NOs: 74 and 75, respectively). The human TCR α/β variable domains were derived from crystal structure sequence (PDB code: 2XN9; SEQ ID NOs: 76 and 77, respectively for α and β chain).

The sequences for the extracellular part of the cynomolgus/rhesus monkey TCR α/β constant domains were derived from GenBank files EHH63463 and AEA41868 respectively (SEQ ID NOs: 347 and 348). The sequences for the cynomolgus/rhesus monkey TCR α/β variable domains were derived from AEA41865 and AEA41866 (SEQ ID NOs: 349 and 350, respectively for α and β chain).

The extracellular domains of human TCRα/β (2XN9) or cynomolgus/rhesus monkey TCR α/β were fused to a zipper protein coding sequence (O'Shea et al. 1993 Curr. Biol. 3(10): 658-667), produced by CHOK1SV cells (Lonza) using Lonza's GS Gene Expression System™ and subsequently purified.

Figure 2:
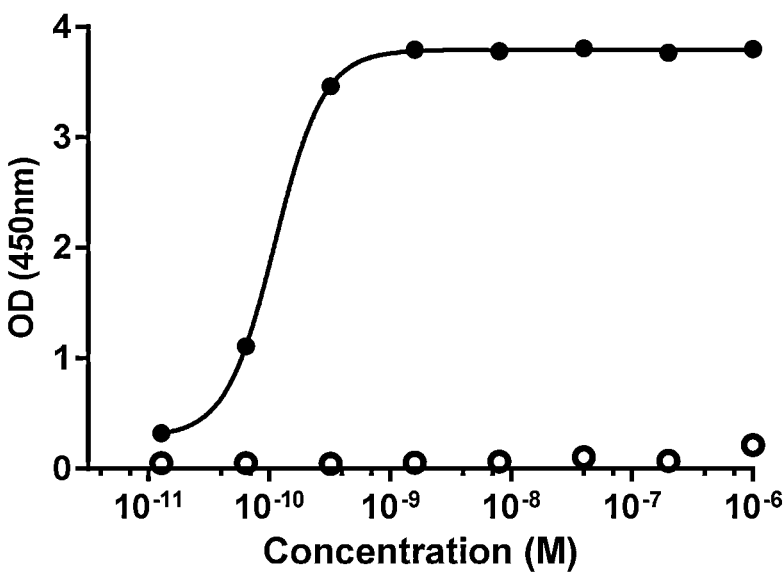
FIG. 2: Quality assessment of soluble recombinant cynomolgus TCR $\alpha/\beta$ proteins using anti-non-human primate/ Rat TCR$\alpha/\beta$ antibody clone R73; anti-human TCR ($\alpha/\beta$) antibodies (solid circles) and an irrelevant anti-egg lysozyme Nanobody (cAblys) (open circles). The OD value was plotted against the concentration of the Nanobody.

Quality of the TCR α/β zipper proteins was assessed in an ELISA binding assay. Maxisorp 96-well ELISA plates (Nunc) were coated with 2 μg/mL soluble recombinant human TCRα/β (2XN9)-zipper protein or soluble recombinant cynomolgus TCR α/β-zipper protein. After an overnight incubation, plates were washed and blocked with PBS+1% casein for 1 h at room temperature. Next, plates were incubated with serial dilutions of either a functional flag tagged Nanobody or the functional mouse IgG anti-non-human primate/Rat TCRα/β antibody, clone R73 (eBioscience, 16-5960) for 1 h at room temperature while shaking, washed again and incubated with Monoclonal ANTI-FLAG M2-Peroxidase (HRP) (Sigma, A8592), respectively Peroxidase-Conjugated Rabbit Anti-Mouse Immunoglobulins (Dako, P0260). After 1 h, TMB One Solution (Promega, G7431) was added. The reaction was stopped with 2M $H_2SO_4$ and the dose dependent binding was determined by measuring the OD at 450 nm using the Tecan sunrise 4 (FIG. 2).

Example 2: Immunization of Llamas with TCR/CD3, Cloning of the Heavy Chain-Only Antibody Fragment Repertoires and Preparation of Phages 2.1 Immunization It was set out to generate heavy chain only antibodies in camelidae (e.g. llama and alpaca) against T cell receptor (TCR) a and/or 3 constant chains. Although the native T cell receptor complex consists of both CD3 (gamma, delta, epsilon and zeta) chains, as well as TCR α- and β-chains, it was hypothesized that the absence of CD3 chains would facilitate access to the constant domains of the TCR. Especially since the CD3 chains laterally surround, and limit access to the constant domains of the TCR α- and β-chains. Contrary to our experience with other targets, the obtaining of an immune response against TCR α- or β-chains was not as straight forward as expected.

In a final approach, after approval of the Ethical Committee (CRIA, LA1400575, Belgium-EC2012 #1), the inventors attempted a complex immunization protocol with DNA encoding for T cell complex. In short, 3 additional llamas were immunized with a pVAX1-human TCR(2IAN)/CD3 (described in Example 1.1) plasmid vector (Invitrogen, Carlsbad, CA, USA) and with a pVAX1-human TCRα/β (2XN9)/CD3 (described in Example 1.1) plasmid vector (Invitrogen, Carlsbad, CA, USA) according to standard protocols. Two llamas received additionally 1 subcutaneous injection of primary human T cells. Human T cells were collected from Buffy Coat blood, from healthy volunteers (Blood bank Gent) using RosetteSep (StemCell Technologies, 15061) followed by enriching on Ficoll-Paque™ PLUS (GE Healthcare, 17-1440-03) according to manufactures instructions and stored in liquid nitrogen. After thawing, cells were washed, and re-suspended in D-PBS from Gibco and kept on ice prior to injection.

2.2 Cloning of the Heavy Chain-Only Antibody Fragment Repertoires and Preparation of Phages Per animal, blood samples were collected after the injection of one type of immunization antigen. From these blood samples, PBMC were prepared using Ficoll-Hypaque according to the manufacturer's instructions (Amersham Biosciences, Piscataway, NJ, USA). For each immunized llama, libraries were constructed by pooling the total RNA isolated from samples originating from a certain subset of the immunization schedule, i.e. after one type of immunization antigen.

In short, the PCR-amplified VHH repertoire was cloned via specific restriction sites into a vector designed to facilitate phage display of the VHH library. The vector was derived from pUC119. In frame with the VHH coding sequence, the vector encodes a C-terminal 3×FLAG and His6 tag. Phages were prepared according to standard protocols (see for example WO 04/041865, WO 04/041863, WO 04/062551, WO 05/044858 and other prior art and applications filed by Ablynx N.V. cited herein).

Example 3: Selection of TCR/CD3 Specific VHHs Via Phage Display

The vast majority of selected VHHs were directed against the variable regions of either the TCR α or TCR β chain. Therefore different selection and counter-selection strategies had to be devised by the inventors.

In short, VHH repertoires obtained from all llamas and cloned as phage library were used in different selection strategies, applying a multiplicity of selection conditions. Selections using human TCR/CD3 transfected cell lines with the same variable domain as used during immunization resulted in only variable domain binders. Therefore, tools containing a different variable TCRα/β domain (transfected cells (described in Example 1.1), soluble protein (described in Example 1.2), or human primary T cells (isolated as described in Example 2.1)) were used during selections and proved to be crucial in identification of constant domain binders. Additional variables during selections included the antigen presentation method (in solution when using cells or coated onto plates when proteins), the antigen concentration, the orthologue used (human or cynomolgus recombinant TCR α/β protein), and the number of selection rounds. All solid coated phase selections were done in Maxisorp 96-well plates (Nunc, Wiesbaden, Germany).

Selections were performed as follows: TCRα/β-CD3 antigen preparations for solid and solution phase selection formats were presented as described above at multiple concentrations. After 2 h incubation with the phage libraries, followed by extensive washing, bound phages were eluted with trypsin (1 mg/mL) for 15 minutes. The trypsin protease activity was immediately neutralized by applying 0.8 mM protease inhibitor ABSF. As control, selections without antigen were performed in parallel.

Phage outputs were used to infect *E. coli* for analysis of individual VHH clones. Periplasmic extracts were prepared according to standard protocols (see for example WO 03/035694, WO 04/041865, WO 04/041863, WO 04/062551 and other prior art and applications filed by Ablynx N.V. cited herein).

Example 4: Screening, Sequence Analysis and Purification 4.1 Screening for TCR/CD3 Binding Nanobodies in a Flow Cytometry Assay Periplasmic extracts were screened for cell expressed TCR/CD3 binding using human TCR/CD3 transfected CHO-K1 or HEK293H cells and the respective CHO-K1 or HEK293H reference cell line in a mixed cell line setup. To this end, a large batch of the reference cell lines were labelled with 8 μM PKH26 and frozen. $5\times10^4$ PKH labelled reference cells were mixed with $5\times10^4$ target cells and incubated with periplasmic extracts for 30 min at 4° C., and washed 3 times. Next, cells were incubated with 1 μg/ml monoclonal ANTI-FLAG® M2 antibody (Sigma-Aldrich, F1804) for 30 min at 4° C., washed again, and incubated for 30 min at 4° C. with 5 pg/ml Allophycocyanin (APC) AffiniPure Goat Anti-Mouse IgG (Jackson Immunoresearch, 115-135-164). Samples were washed, resuspended in FACS Buffer (D-PBS from Gibco, with 10% FBS from Sigma and 0.05% sodium azide from Merck) and then analysed via a BD FACSArray. First a P1 population which represented more than 80% of the total cell population was selected based on FSC-SSC distribution. In this gate, 20,000 cells were counted during acquisition. Based on PKH26-SSC distribution, the PKH labelled parental population and the human TCR/CD3 unlabelled target population was selected. For these 2 populations the mean APC value was calculated.

4.2 Screening for TCR/CD3 Binding Nanobodies in a Human T Cell Activation Assay

After several attempts, it turned out that activation of purified human T cells by antibodies or Nanobodies according to standard protocols, i.e. coated onto a 96 well plate, was not sensitive enough (data not shown).

In order to assess activity, a different assay was developed, based on bead coupled T cell activation. In short, Dynabeads® Goat Anti-Mouse IgG (ThermoFisher Scientific, 11033) were coated with monoclonal mouse ANTI-FLAG® M2 antibody (Sigma-Aldrich, F1804) (15 μg/1E7 beads). After an incubation period of 2 h at 4° C., Dynabeads® were washed and incubated with 80 μl periplasmic extract for 20 min at 4° C. while shaking. Non-coupled Nanobodies were washed away before adding the bead complex together with soluble mouse anti-CD28 antibody (Pelicluster CD28—Sanquin, M1650) to purified primary human T cells (isolated as described in Example 2.1). As control condition, non-stimulated human T cells were used. In brief, Dynabeads® Goat Anti-Mouse IgG (ThermoFisher Scientific, 11033) coupled to monoclonal mouse ANTI-FLAG® M2 antibodies were incubated in 80 μl periplasmic extract containing irrelevant Nanobodies. After removal of the non-coupled Nanobodies during a wash step, the irrelevant Nanobody-bead complex was added to purified primary human T cells. After an incubation of 24 h at 37° and 5% $CO_2$ the activation status of the human T cells was determined by measuring the CD69 expression level in flow cytometry using monoclonal mouse anti-human CD69PE (BD Biosciences, 557050).

4.3 Sequence Analysis of the Obtained Nanobodies

Nanobodies which scored positive in the flow cytometric binding screen and the T cell activation assay were sequenced.

The sequence analysis resulted in the identification of Nanobody T0170056G05 and different family members thereof, representing a total of 104 different clones (SEQ ID NOs: 42 and 78 to 180). Corresponding alignment is provided (Table A-1).

The sequence variability of the CDRs of the family members against T0170056G05, is depicted in the tables below.

TABLE B-4

| (SEQ ID NO: 374) | | | | | | | | | |
|---|---|---|---|---|---|---|---|---|---|
| 56G05 | | | | CDR1 | | | | | |
| Kabat numbering | 26 | 27 | 28 | 29 | 30 | 31 | 32 | 33 | 34 | 35 |
| absolute numbering | 1 | 2 | 3 | 4 | 5* | 6 | 7 | 8 | 9 | 10 |
| 56G05 sequence | G | D | V | H | K | I | N | F | L | G |
| variations | | | A | | Y | L | L | | I | | S |
| variations | | | S | | | | | | V | |
| variations | | | E | | | | | | | |
| variations | | | G | | | | | | | |

*in case position 5 is an L, then position 6 is also L

TABLE B-5

| (SEQ ID NO: 375) | | | | | | | | | |
|---|---|---|---|---|---|---|---|---|---|
| 56G05 | | | | CDR2 | | | | | |
| Kabat numbering | 50 | 51 | 52 | 53 | 54 | 55 | 56 | 57 | 58 |
| absolute numbering | 1 | 2 | 3 | 4 | 5 | 6 | 7 | 8 | 9 |
| 56G05 sequence | H | I | S | I | G | D | Q | T | D |
| variations | T | | T | | S | | D | V | A |
| variations | R | | A | | A | | E | A | Q |
| variations | | | | | | | T | | N |
| variations | | | | | | | A | | V |
| variations | | | | | | | V | | S |

TABLE B-6

| (SEQ ID NO: 376) | | | | | | | | |
|---|---|---|---|---|---|---|---|---|
| 56G05 | | | | CDR3 | | | | |
| Kabat numbering | 95 | 96 | 97 | 98 | 99 | 100 | 100a | 101 | 102 |
| absolute numbering | 1 | 2 | 3 | 4 | 5 | 6 | 7 | 8 | 9 |
| 56G05 sequence | F | S | R | I | Y | P | Y | D | Y |
| variations | Y | | | L | W | | | N | |

TABLE B-6-continued

| (SEQ ID NO: 376) | | |
|---|---|---|
| variations | G | S |
| variations | L | |

4.4 Purification of Monovalent Nanobodies

Two representative Nanobodies of the identified family were selected and expressed in *E. coli* TG1 as triple Flag, His6-tagged proteins. Expression was induced by addition of 1 mM IPTG and allowed to continue for 4 hours at 37° C. After spinning the cell cultures, periplasmic extracts were prepared by freeze-thawing the pellets. These extracts were used as starting material and Nanobodies were purified via IMAC and size exclusion chromatography (SEC).

The Nanobodies were purified to 95% purity as assessed via SDS-PAGE (data not shown).

Example 5: Binding of Anti-TCR Nanobodies to Human TCR/CD3 Expressed on CHO-K1 Cells and to Purified Primary Human T Cells Dose-dependent binding of the purified monovalent anti-TCR Nanobodies to human TCRα/β (2XN9)/CD3 expressed on CHO-K1 cells and to purified primary human T cells was evaluated by flow cytometry. In brief, cells were harvested and transferred to a V-bottom 96-well plate ($1\times10^5$ cells/well) and serial dilutions of Nanobodies (starting from 1 pM) were allowed to associate for 30 minutes at 4° C. in FACS buffer. Cells were washed three times by centrifugation and probed with 1 µg/ml monoclonal mouse ANTI-FLAG® M2 antibodies (Sigma-Aldrich, F1804) for 30 minutes at 4° C., washed again, and incubated for 30 min at 4° C. with 5 µg/ml R-Phycoerythrin AffiniPure F(ab')$_2$ Fragment Goat Anti-Mouse IgG (Jackson Immunoresearch 115-116-071). After incubation, cells were washed 3 times with FACS Buffer. Subsequently, cells were resuspended in FACS buffer supplemented with 5 nM TOPRO3 (Molecular Probes, T3605) to distinguish live from dead cells, which are removed during the gating procedure. Cells were analysed using a FACS Array flow cytometer (BD Biosciences) and Flowing Software. First a P1 population which represented more than 80% of the total cell population was selected based on FSC-SSC distribution. In this gate, 10000 cells were counted during acquisition. From this population the TOPRO+ cells (dead cells) were excluded and the median PE value was calculated.

Figure 3:
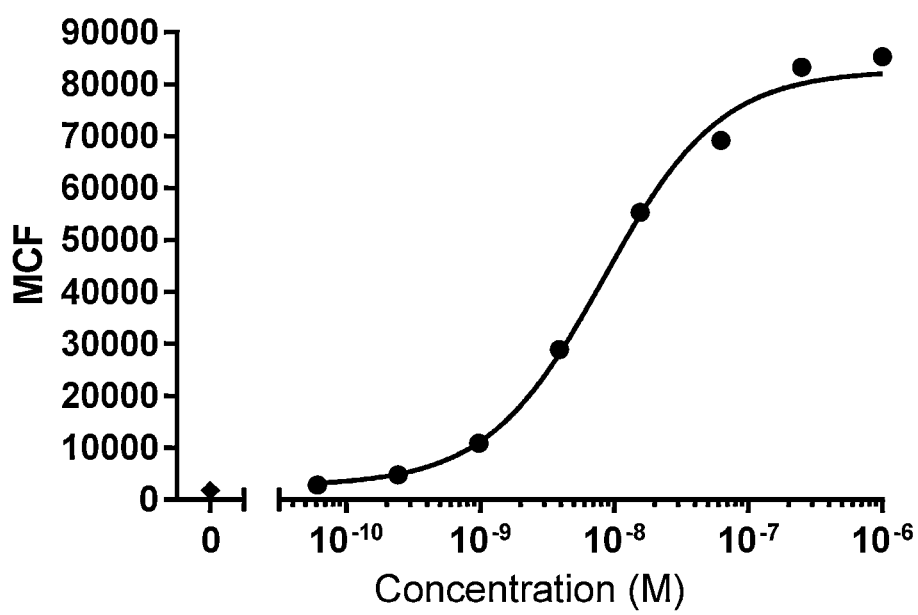
FIG. 3: Dose dependent binding of monovalent anti-TCR Nanobodies to human TCR/CD3 expressed on CHO-K1 cells (FIGS. 3A and 3C) and to primary human T cells (FIGS. 3B and 3D). The MCF value (mean channel fluorescence) was plotted against the concentration of the Nanobody.
Figure 3:
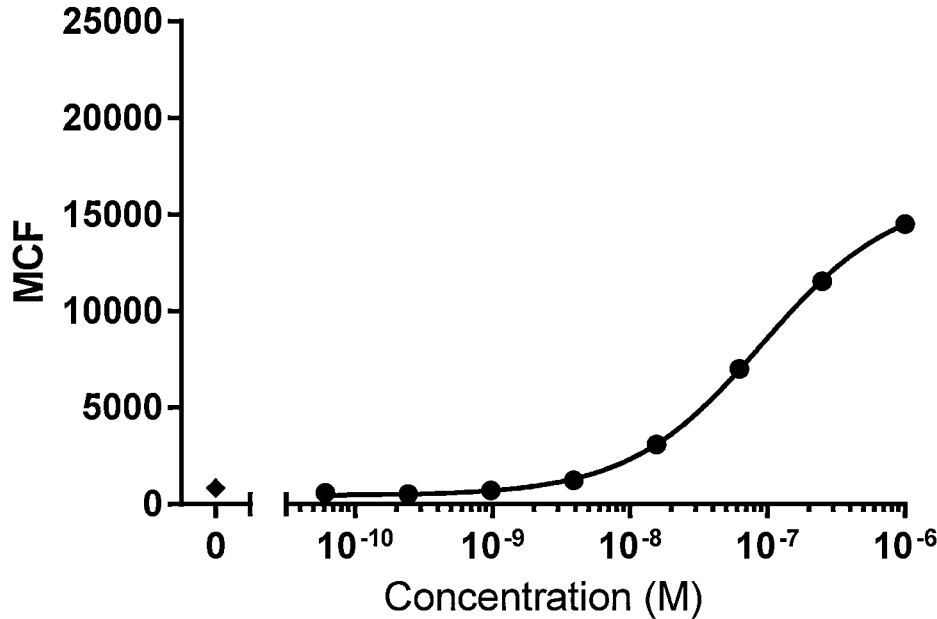

The results are shown in FIG. 3. The EC50 values obtained from the dose response curve are represented in Table C-1.

TABLE C-1

| EC50 (M) of anti-TCR monovalent Nanobodies for binding CHO-K1 human TCRα/β(2XN9)−/CD3 cells and for binding purified primary T cells as determined in flow cytometry. | | | | | | |
|---|---|---|---|---|---|---|
| | CHO-K1 TCRα/β(2XN9)/CD3 | | | Primary human T cells | | |
| sample ID | EC50 (M) | 95% LCI | 95% UCI | EC50 (M) | 95% LCI | 95% UCI |
| T0170055A02 | 8.4E−09 | 7.2E−09 | 9.7E−09 | 9.1E−08 | 8.1E−08 | 1.0E−07 |
| T0170056G05 | 8.9E−09 | 8.3E−09 | 9.4E−09 | 9.1E−08 | 8.3E−08 | 9.9E−08 |

The Nanobodies clearly bound to human TCR/CD3 expressed on CHO-K1 cells. The Nanobodies also bound to purified primary human T cells, although with slightly lower potency compared to the CHO-K1 human TCRα/β (2XN9)/CD3 cells.

Example 6: Determination of Binding Epitope

Binding of the purified monovalent anti-TCR Nanobodies to human TCRα/β (2IAN)/CD3 expressed on HEK293H cells was evaluated and compared with the binding to HEK293H cells transfected with human CD3 in flow cytometry, as outlined in Example 5. Dilution series of T0170055A02 and T0170056G05 starting from 1 μM were applied to the cells. The parental HEK293H cell line was included as TCR/CD3 negative cell line.

Figure 4:
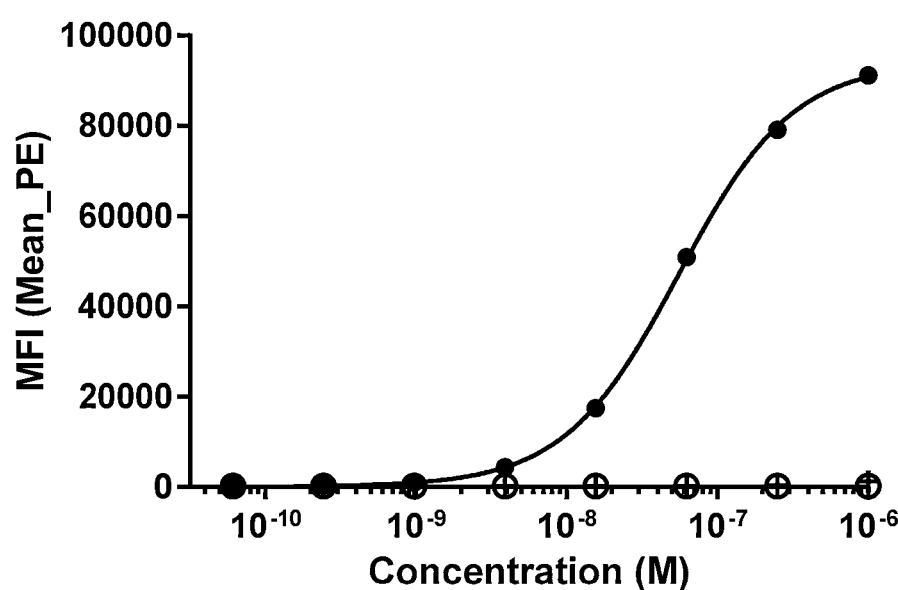
FIG. 4: Dose dependent binding of monovalent anti-TCR Nanobodies to HEK293H human TCR(2IAN)/CD3 (closed circle), HEK293H human CD3 (cross) and to HEK293H reference cell line (open circles). The MCF value (mean channel fluorescence) was plotted against the concentration of the Nanobody.
Figure 4:
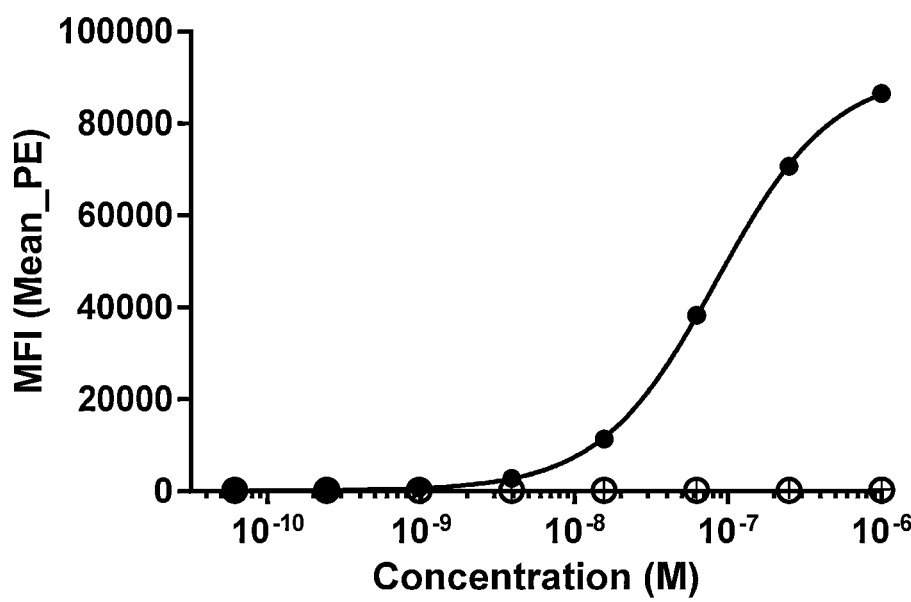

The results are shown in FIG. 4. The EC50 values obtained from the dose response curve are depicted in Table C-2.

ForteBio Corp.). Recombinant human soluble TCRα/β (2XN9)-zipper protein was covalently immobilized on amine-reactive sensors (ForteBio) via NHS/EDC coupling chemistry. For kinetic analysis, sensors were first dipped into running buffer (10 mM Hepes, 150 mM NaCl, 0.05% p20, pH7.4 from GE Healthcare Life Sciences) to determine baseline setting. Subsequently, sensors were dipped into wells containing different concentrations of purified Nanobodies (range between 1.4 nM and 1 mM) for the association step (180s) and transferred to wells containing running buffer for the dissociation (15 min) step. Affinity constants (KD) were calculated applying a 1:1 interaction model using the ForteBio Data Analysis software.

Figure 6A:
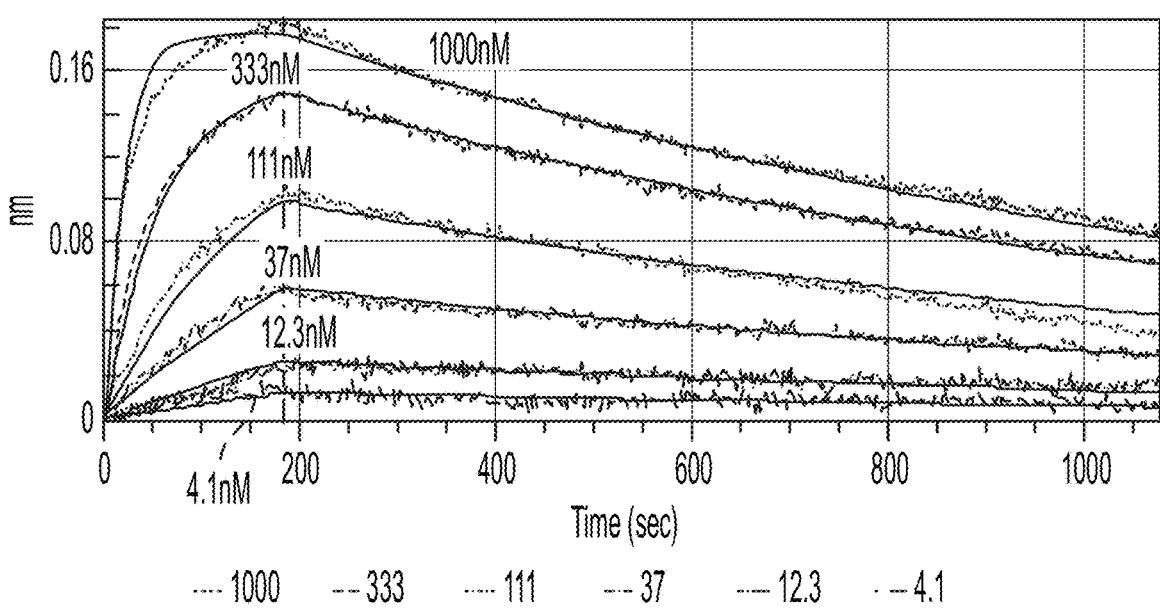
FIG. 6: Kinetic analysis of T01700055A02 (FIG. 6A) and T01700056G05 (FIG. 6B) on soluble recombinant human TCR $\alpha/\beta$ (2XN9)-zipper protein interaction via BioLayer Interferometry on an Octet RED384 instrument. Applied analyte concentrations were: 1000, 333, 111, 37, 12.3, 4.1 and 1.4 nM. Langmuir fits to the kinetic data are indicated with the black lines, whereas sensorgrams are presented by the grey lines.
Figure 6B:
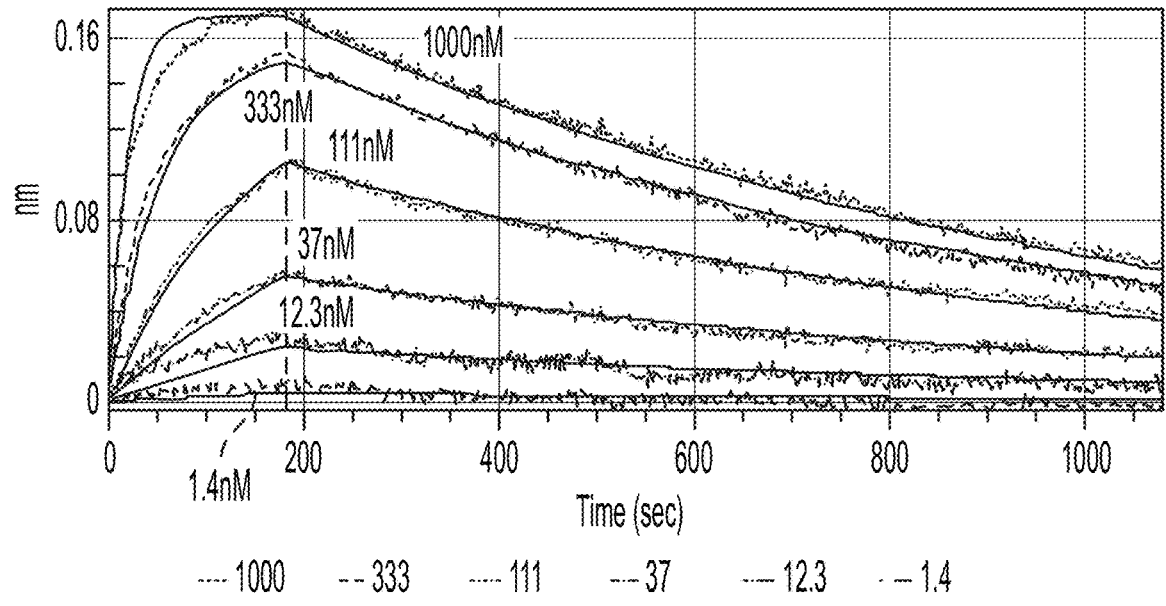

The results are depicted in FIG. 6. The binding characteristics are listed in Table C-4.

TABLE C-2

EC50 (M) of anti-TCR monovalent Nanobodies for binding human TCRα/β (2IAN)/CD3 or human CD3 expressed on HEK293H cells, as determined in flow cytometry.

| | HEK293H wt | | HEK293H CD3 | | HEK293H TCR/CD3 | |
|---|---|---|---|---|---|---|
| Sample ID | EC50 | MCF at 1 μM | EC50 | MCF at 1 μM | EC50 | MCF at 1 μM |
| T0170055A02 | No fit | 246 | No fit | 1194 | 5.5E−08 | 91229 |
| T0170056G05 | No fit | 299 | No fit | 352 | 8.4E−08 | 86510 |

The Nanobodies clearly bound to human TCR(2IAN)/CD3 expressed on HEK293H but not to the HEK293H cells transfected with human CD3 only, nor to the HEK293H parental cell line. In conclusion, the 2 clones were specific for binding to human TCR α/β. No binding was observed to human CD3.

Example 7: Binding of Anti-TCR Nanobodies to Soluble Recombinant Human TCR α/β Protein

7.1 Binding of Anti-TCR Nanobodies to Human T Cell Receptor Protein in ELISA Binding of the purified monovalent TCR Nanobodies to soluble recombinant human TCR α/β protein was evaluated in ELISA (as described in Example 1.2) using 2 μg/ml directly coated soluble recombinant human TCR α/β protein.

Figure 5:
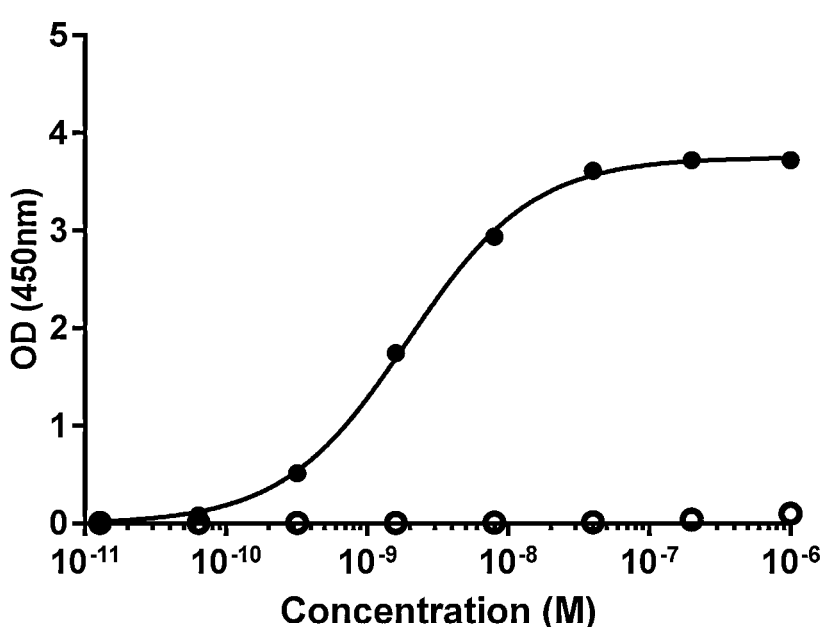
FIG. 5: Dose dependent binding of monovalent anti-TCR Nanobodies (closed circles) and an irrelevant Nanobody (open circles) to soluble recombinant human TCR $\alpha/\beta$ (2XN9)-zipper protein. The OD at 450 nm was plotted against the concentration of the Nanobody.
Figure 5:
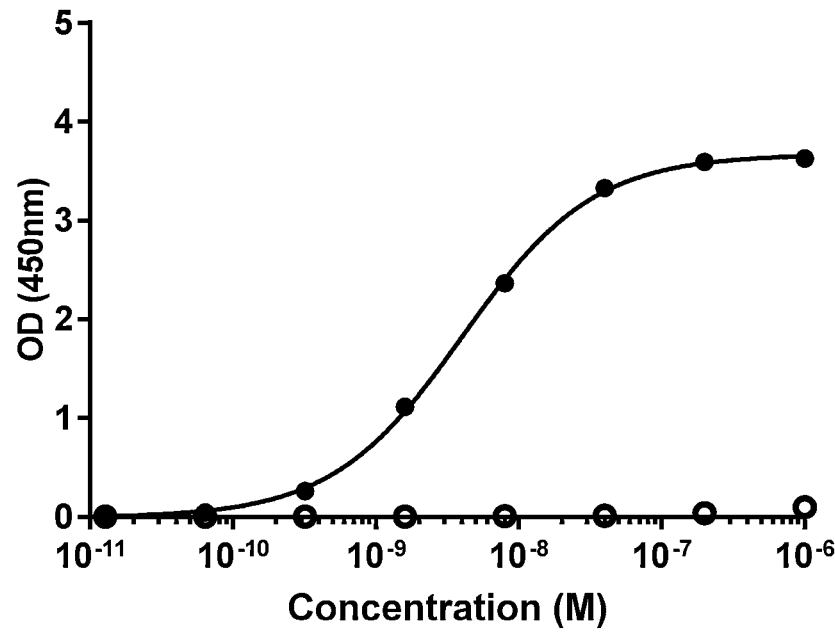

The results are shown in FIG. 5. The EC50 values obtained from the dose response curve are depicted in Table C-3.

TABLE C-3

EC50 (M) of anti-TCR monovalent Nanobodies for binding soluble recombinant human TCRα/β(2XN9) protein, as determined in ELISA.

| sample ID | EC50 (M) | 95% LCI | 95% UCI |
|---|---|---|---|
| T0170055A02 | 1.9E−09 | 1.7E−09 | 2.2E−09 |
| T0170056G05 | 4.0E−09 | 3.5E−09 | 4.6E−09 |

The anti-TCR Nanobodies bound to soluble recombinant human TCR α/β protein.

7.2 Binding of Anti-TCR Nanobodies to Human T Cell Receptor Protein in BLI

Binding affinities were measured using Bio-Layer Interferometry (BLI) on an Octet RED384 instrument (Pall

TABLE C-4

Kinetic analysis of anti-TCR monovalent Nanobodies for binding soluble recombinant human TCRα/β(2XN9) protein as determined with the Octet RED384 instrument.

| | human soluble TCRα/β(2XN9)-zipper protein | | |
|---|---|---|---|
| sample ID | kon (1/Ms) | koff (1/s) | KD (M) |
| T0170055A02 | 4.9E+04 | 8.4E−04 | 1.7E−08 |
| T0170056G05 | 5.0E+04 | 1.2E−03 | 2.4E−08 |

The binding affinities determined using BLI on human soluble TCRα/β (2XN9)-zipper protein showed correlation with the affinities determined on CHO-K1 human TCRα/β (2XN9)/CD3 cells in flow cytometry (cf. Example 5).

Example 8: Binding of Anti-TCR Nanobodies to Recombinant Cynomolgus Soluble TCR α/β Protein

8.1 Binding of Anti-TCR Nanobodies to Cynomolgus T Cell Receptor Protein in ELISA Binding of purified monovalent anti-TCR Nanobodies to recombinant cynomolgus soluble TCRα/β protein was evaluated in ELISA (as described in Example 1.2) using 2.1 g/ml directly coated recombinant cynomolgus soluble TCRα/β zipper protein.

Figure 7:
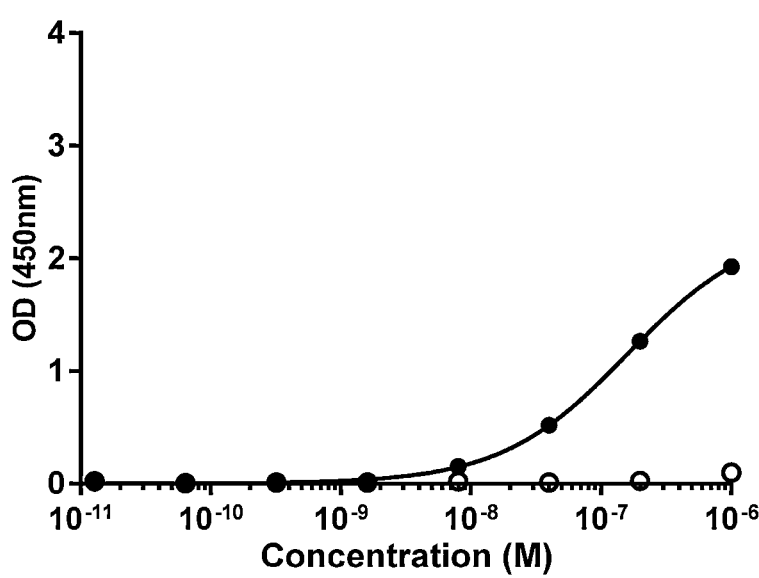
FIG. 7: Dose dependent binding of monovalent anti-TCR Nanobodies (closed circles) and an irrelevant Nanobody (open circles) to soluble recombinant cynomolgus TCR $\alpha/\beta$-zipper protein. The OD at 450 nm was plotted against the concentration of the Nanobody.
Figure 7:
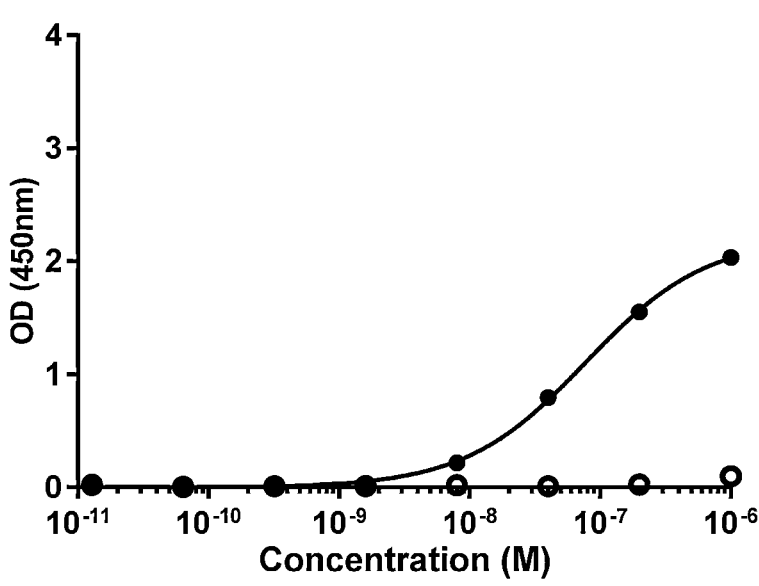

The EC50 values obtained from the dose response curve are depicted in Table C-5. An exemplary result is shown in FIG. 7.

TABLE C-5

EC50 (M) of anti-TCR monovalent Nanobodies for binding to
recombinant cynomolgus soluble TCRα/β-zipper protein as
determined in ELISA.

| sample ID | EC50 (M) | 95% LCI | 95% UCI |
|---|---|---|---|
| T0170055A02 | 1.6E-07 | 1.5E-07 | 1.7E-07 |
| T0170056G05 | 7.7E-08 | 6.6E-08 | 9.1E-08 |

The results indicated that the anti-TCR Nanobodies bind to the recombinant cynomolgus soluble TCRα/β-zipper protein.

8.2 Binding of Anti-TCR Nanobodies to Cynomolgus T Cell Receptor Protein in BLI

Binding affinities of the monovalent anti-TCR Nanobodies were measured using Bio-Layer Interferometry (BLI) on an Octet RED384 instrument (Pall ForteBio Corp.) essentially as described in Example 7.2 using recombinant cynomolgus soluble TCRα/β protein.

Figure 8A:
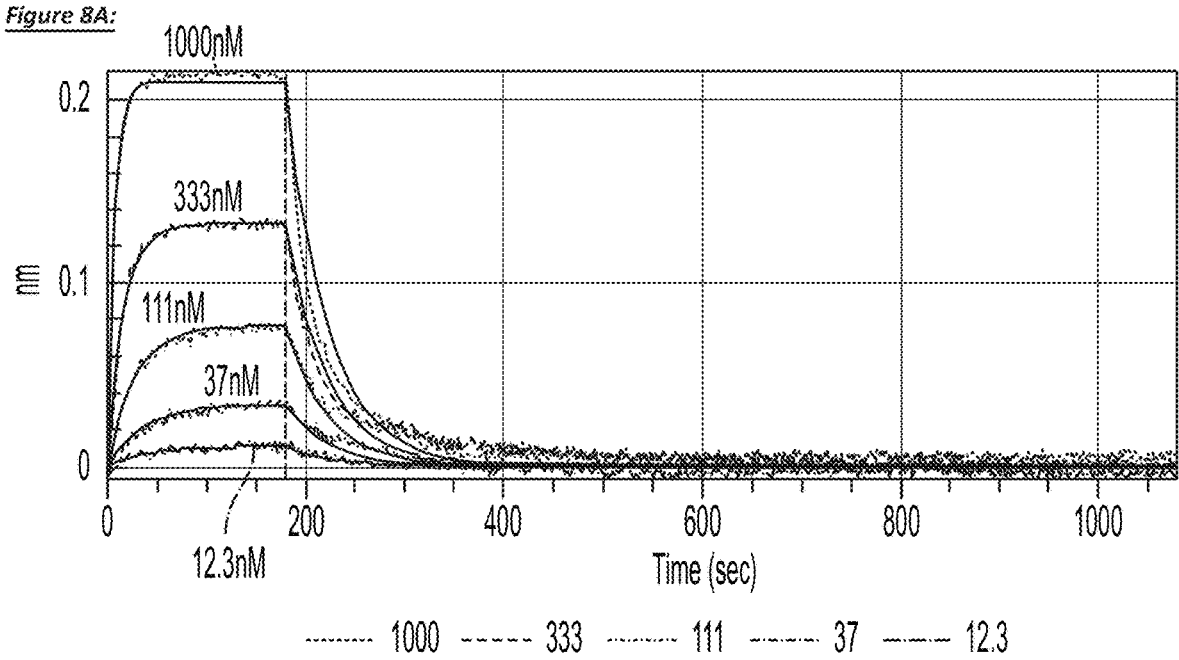
FIG. 8: Kinetic analysis of T0170055A02 (FIG. 8A) and T0170056G05 (FIG. 8B) on soluble recombinant cynomolgus TCR$\alpha/\beta$-zipper protein interaction via BioLayer Interferometry on an Octet RED384 instrument. Applied analyte concentrations were: 1000, 333, 111, 37, 12.3, 4.1 and 1.4 nM. Langmuir fits to the kinetic data are indicated with the black lines, whereas sensorgrams are presented by the grey lines.
Figure 8B:
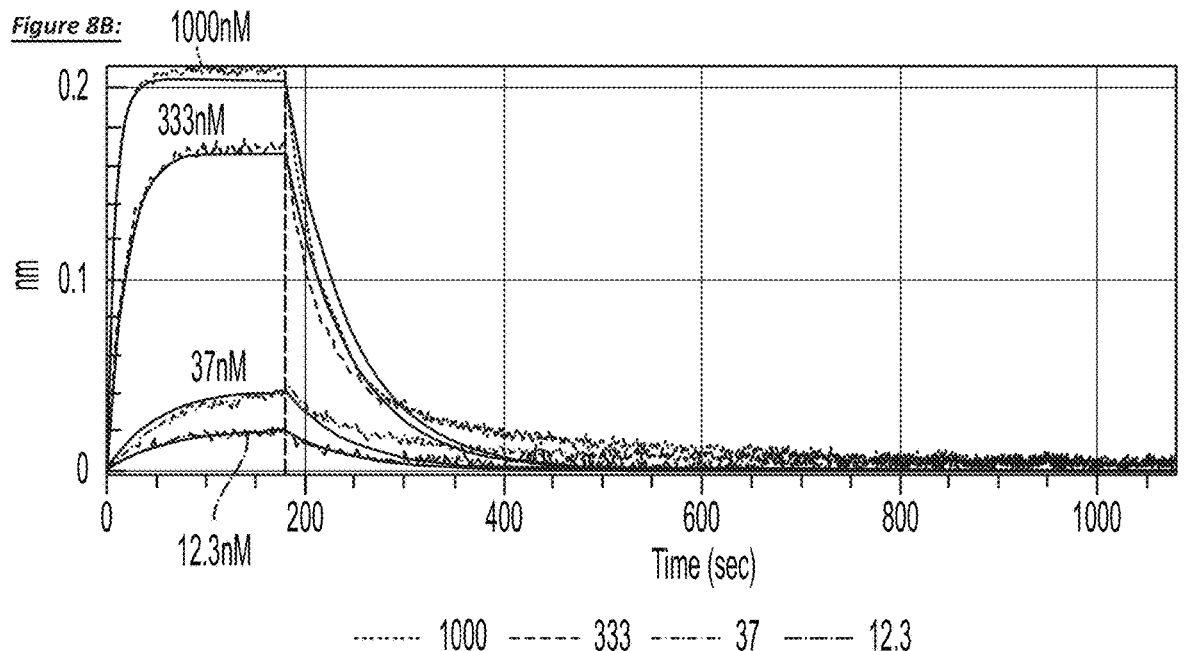

The results are depicted in FIG. 8. The binding characteristics of the anti-TCR Nanobodies are listed in Table C-6.

TABLE C-6

Kinetic analysis of anti-TCR monovalent Nanobodies for binding
recombinant cynomolgus soluble TCRα/β-zipper protein as
determined with the Octet RED384 instrument.

| sample ID | kon (1/Ms) | koff (1/s) | KD (M) |
|---|---|---|---|
| T0170055A02 | 1.1E+05 | 2.4E-02 | 2.1E-07 |
| T0170056G05 | 1.1E+05 | 1.6E-02 | 1.5E-07 |

The Nanobodies bind to the recombinant cynomolgus soluble TCRα/β protein with a 10 fold lower affinity compared to recombinant human soluble TCRα/β (2XN9)-zipper protein.

Example 9: Determination of Purified Primary Human T Cell Activation Capacity Functionality of purified monovalent anti-TCR Nanobodies was evaluated in the human T cell activation assay. Dynabeads® Goat Anti-Mouse IgG (ThermoFisher Scientific, 11033) were coated with monoclonal mouse ANTI-FLAG® M2 antibody (Sigma-Aldrich, F1804, 15 μg/1E7 beads). After an incubation period of 2 h at 4° C., Dynabeads® were washed and incubated with a fixed (1 μg) amount of purified Flag tagged Nanobody for 20 min at 4° C. while shaking. Non-coupled Nanobodies were washed away before adding the bead complex together with soluble mouse anti-CD28 antibody (Pelicluster CD28—Sanquin, M1650) to purified primary human T cells isolated (isolated as described in Example 2.1) from distinct healthy donors. In addition, the effect of monovalent TCR binding by the Nanobodies was evaluated by the incubation of the Nanobody with the purified primary human T cells without prior capture onto anti-mouse IgG Dynabeads®, in the presence of anti-CD28 antibody. The activation status of the purified primary human T cells was monitored by measuring the CD69 expression in flow cytometry using monoclonal mouse anti-human CD69PE (BD Biosciences, 557050) after an incubation of 24 h at 37° C. and 5% $CO_2$.

Figure 9:
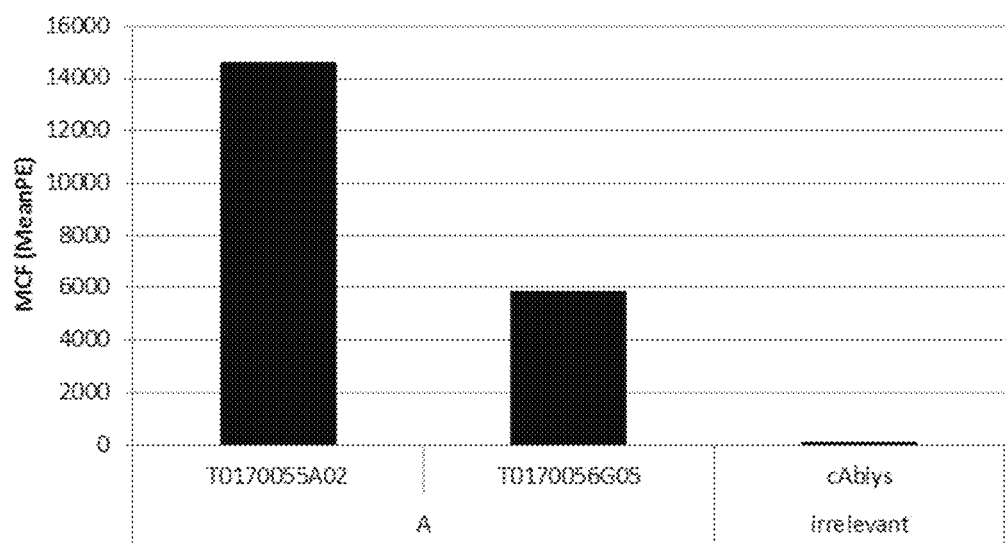
FIG. 9: T cell activation data of bead coupled monovalent anti-TCR Nanobodies (FIG. 9A). T cell activation data of monovalent anti-TCR Nanobodies presented in solution (FIG. 9B). Activation was measured by monitoring the CD69 upregulation on primary human T cells. The MCF value (mean channel fluorescence) was plotted for each Nanobody.
Figure 9:
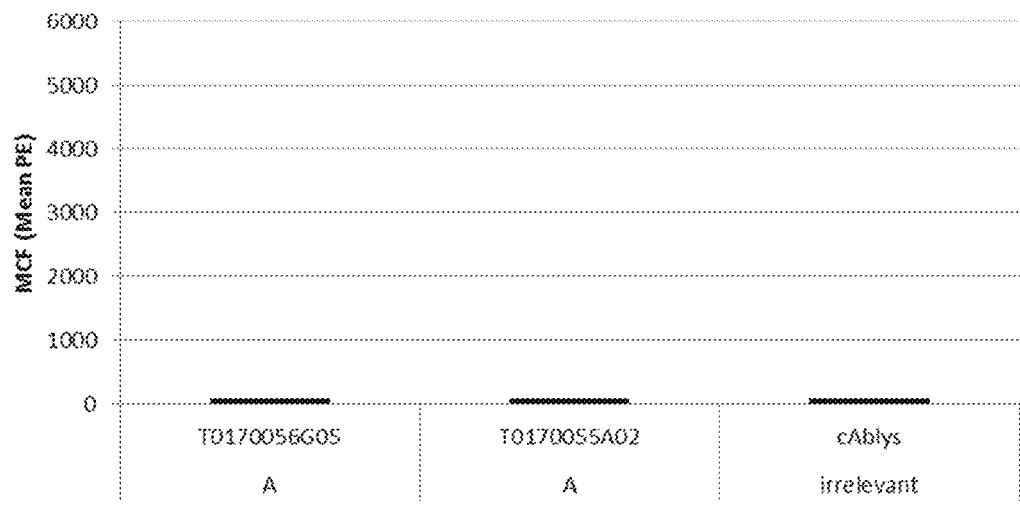

In conclusion, the anti-TCR Nanobodies showed clear CD69 upregulation after capturing onto anti-mouse IgG dynabeads. The irrelevant Nanobody did not show any CD69 upregulation (FIG. 9A). In addition, none of the Nanobodies presented in solution were able to activate purified primary human T cells as measured by increased expression of CD69 (FIG. 9B).

Example 10: Immunization of Llamas with CD123, Cloning of the Heavy Chain-Only Antibody Fragment Repertoires and Preparation of Phage 10.1 Immunization Three llamas were immunized, according to standard protocols, with recombinant His-tagged extracellular domain of human CD123 (R&D Systems, 301-R3/CF) via an intramuscular injection in the neck using Stimune as adjuvant (Cedi Diagnostics, Lelystad, The Netherlands).

Three llamas were immunized with recombinant His-tagged extracellular domain of human CD123 (R&D Systems, 301-R3/CF) for four times with two week intervals via an intramuscular injection in the neck using Stimune as adjuvant (Cedi Diagnostics, Lelystad, The Netherlands). Immune serum samples taken at day 35 were analysed for antigen-specific binding by ELISA to adsorbed hCD123. All llamas show an excellent IgG 1 mediated serum response, and a good to moderate heavy chain mediated response against hCD123.

10.2 Cloning of the Heavy Chain-Only Antibody Fragment Repertoires and Preparation of Phage Per animal, 100 mL blood samples were collected four and eight days after the last injection of the immunization antigen. From these blood samples, PBMC were prepared using Ficoll-Hypaque according to the manufacturer's instructions (Amersham Biosciences, Piscataway, NJ, USA). For each immunized llama, libraries were constructed by pooling the total RNA isolated from different blood samples.

In short, the PCR-amplified VHH repertoire was cloned via specific restriction sites into a phagemid vector designed to facilitate phage display of the VHH library. The vector was derived from pUC119. In frame with the VHH coding sequence, the vector encodes a C-terminal 3×FLAG and HIS6 tag. Phages were prepared according to standard protocols (see for example WO 04/041865, WO 04/041863, WO 04/062551, WO 05/044858 and other prior art and applications filed by Ablynx N.V. cited herein).

Example 11: Selection of CD123 Specific VHHs Via Phage Display

VHH repertoires obtained from all llamas and cloned as phagemid library were used in different selection strategies, applying a multiplicity of selection conditions. Variables included: i) the source of CD123 antigen (recombinant protein produced in human cells or full length protein overexpressed on cells), ii) antigen presentation (in solution when using biotinylated recombinant ectodomain, direct coated onto plates for non-biotinylated Fc-fused ectodomain), and iii) the antigen concentration.

In brief, HEK293T cells overexpressing CD123 (generated in house), biotinylated human CD123 (R&D Systems, 301-R3/CF, biotinylated in house) and plate-coated human CD123-Fc (Sino Biologicals, 10518-H08H) were incubated for 1 h-2 h with $2×E^{11}$ phage particles of the different libraries followed by extensive washing; bound phages were eluted with trypsin (1 mg/mL) for 15 minutes and then the protease activity was immediately neutralized by applying 0.8 mM protease inhibitor ABSF. As control, selections with parental cell line or without antigen were performed in parallel.

Phage outputs were used to infect *E. coli* for analysis of individual VHH clones. Periplasmic extracts were prepared according to standard protocols (see for example WO 03/035694, WO 04/041865, WO 04/041863, WO 04/062551 and other prior art and applications filed by Ablynx N.V. cited herein).

Example 12: Screening for CD123 Binding Nanobodies

12.1 Screening in Binding ELISA

Periplasmic extracts were screened in a binding ELISA on human CD123 (R&D Systems, 301-R3). To this end, a microtiter plate was coated with human CD123 (1 μg/ml) and incubated overnight at 4° C. Plates were blocked for one hour at room temperature with 4% Marvel in PBS. The plates were washed with PBS-Tween. The periplasmic extracts (1/10 diluted in PBS with 2% Marvel) were incubated for at least 1 hour at RT. Plates were washed with PBS-Tween, after which binding of VHH was detected with Monoclonal ANTI-FLAG M2-Peroxidase (HRP), (Sigma, A8592, 1/5000) in PBS with 1% Marvel. Staining was performed with the substrate esTMB (Nalgene) and the signals were measured after 15 minutes at 450 nm.

12.2 Screening in Flow Cytometry

Periplasmic extracts were screened in a flow cytometry assay on transient transfected HEK293T-hCD123 cells in 96-wells format. In addition, binding was assessed to endogeneously IL-3R expressing MOLM-13 cells, to confirm binding to IL-3Rα in the presence of the IL-3Rβ partner in the heterodimeric receptor complex. To this end, the cells (1×10^5 cells/well/0.1 mL) were incubated with the periplasmic extracts (1:10 dilutions) for 30 min at 4° C. in FACS buffer (D-PBS from Invitrogen, with 10% FBS from Sigma and 0.05% sodium azide from Merck). Cells were washed 3 times, and incubated with 1 μg/ml monoclonal ANTI-FLAG® M2 antibody (Sigma-Aldrich, F1804) for 30 min at 4° C., washed again, and incubated for 30 min at 4° C. with goat anti-mouse RPE labelled antibody (Jackson Immunoresearch, 115-116-071, 1:100). Samples were washed, incubated with TOPRO3 to stain for dead cells in FACS Buffer and fluorescence was assessed on a FACSArray device (BD).

12.3 Sequencing Analysis of Nanobodies

Nanobodies which scored positive in the binding ELISA and the flow cytometry assay were sequenced. The sequence analysis resulted in the identification of Nanobodies A0110056A10 and A0110055F03 and different family members thereof. Corresponding alignments are provided in Table A-2 and Table A-3, respectively.

The sequence variability of the CDRs of the family members against A0110056A10, is depicted in the tables below.

TABLE B-7

(SEQ ID NO: 377)

| 56A10 | | | | | | CDR1 | | | | |
|---|---|---|---|---|---|---|---|---|---|---|
| Kabat numbering | 26 | 27 | 28 | 29 | 30 | 31 | 32 | 33 | 34 | 35 |
| absolute numbering | 1 | 2 | 3* | 4 | 5 | 6** | 7 | 8 | 9 | 10 |
| 56A10 sequence | G | I | T | S | K | I | N | D | M | G |
| variations | | | S | | | S | D | V | | |
| variations | | | P | | | | | A | | |

*in case position 3 is an S, then position 7 is an D.

**in case position 6 is an I, then position 8 is an D.

TABLE B-8

| (SEQ ID NO: 378) | | | | | | | | | |
|---|---|---|---|---|---|---|---|---|---|
| 56A10 | CDR2 | | | | | | | | |
| Kabat numbering | 50 | 51 | 52 | 53 | 54 | 55 | 56 | 57 | 58 |
| absolute numbering | 1 | 2 | 3 | 4 | 5 | 6 | 7 | 8 | 9 |
| 56A10 sequence variations | S | I | T | A | T | G | T | T | N |

TABLE B-9

| (SEQ ID NO: 379) | | | | | | | |
|---|---|---|---|---|---|---|---|
| 56A10 | CDR3 | | | | | | |
| Kabat numbering | 95 | 96 | 97 | 98 | 99 | 100 | 101 |
| absolute numbering | 1 | 2 | 3 | 4 | 5 | 6 | 7 |
| 56A10 sequence variations | F | P | P | I | S | N | F |
| | | | A | | | | |

The sequence variability of the CDRs of the family members against A011005F03, is depicted in the tables below.

TABLE B-10

| (SEQ ID NO: 380) | | | | | | | | | | |
|---|---|---|---|---|---|---|---|---|---|---|
| 55F03 | CDR1 | | | | | | | | | |
| Kabat numbering | 26 | 27 | 28 | 29 | 30 | 31 | 32 | 33 | 34 | 35 |
| absolute numbering | 1 | 2 | 3* | 4 | 5 | 6** | 7 | 8 | 9 | 10 |
| 55F03 sequence variations | G | R | T | F | S | S | Y | V | M | G |

TABLE B-11

| (SEQ ID NOs: 381) | | | | | | | | | | |
|---|---|---|---|---|---|---|---|---|---|---|
| 55F03 | CDR2 | | | | | | | | | |
| Kabat numbering | 50 | 51 | 52 | 52a | 53 | 54 | 55 | 56 | 57 | 58 |
| absolute numbering | 1 | 2 | 3 | 4 | 5 | 6* | 7 | 8 | 9 | 10 |
| 55F03 sequence variations | A | I | Y | W | S | N | G | K | T | Q |
| | | | W | | | S | | | | E |

*in case position 6 is an S, then position 10 is an E.

TABLE B-12

| (SEQ ID NOs: 382) | | | | | | | | | | | | | | | | |
|---|---|---|---|---|---|---|---|---|---|---|---|---|---|---|---|---|
| 55F03 | CDR3 | | | | | | | | | | | | | | | |
| Kabat numbering | 95 | 96 | 97 | 98 | 99 | 100 | 100a | 100b | 100c | 100d | 100e | 100f | 100g | 100h | 101 | 102 |
| absolute numbering | 1 | 2 | 3 | 4* | 5 | 6 | 7 | 8 | 9 | 10 | 11 | 12 | 13 | 14 | 15 | 16 |
| 55F03 sequence variations | D | K | D | E | T | G | F | R | T | L | P | I | A | Y | D | Y |
| variations | | | | R | D | | | | | | | | | | | |
| variations | | | | | Y | | | | | | | | | | | |

*in case position 4 is an R, then position 5 is a D or Y.

12.4 Purification of Monovalent Nanobodies

Representative Nanobodies for each family were selected and expressed in *E. coli* TG1 as triple Flag, His6-tagged proteins. Expression was induced by addition of 1 mM IPTG and allowed to continue for 4 hours at 37° C. After spinning the cell cultures, periplasmic extracts were prepared by freeze-thawing the pellets. These extracts were used as starting material and Nanobodies were purified via IMAC and size exclusion chromatography (SEC). The Nanobodies were purified to 95% purity as assessed via SDS-PAGE (data not shown).

Figure 10:
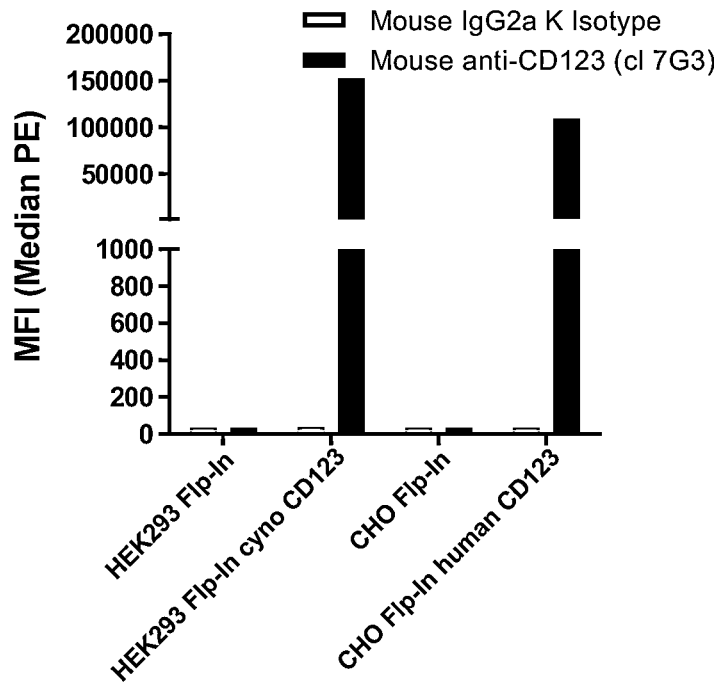
FIG. 10: Assessment the expression of human CD123 expression on HEK293 Flp-In, HEK293 Flp-In cyno CD123, CHO Flp-In and CHO Flp-In human CD123 using the anti-CD123 antibody (BD Biosciences, Cat. no. 554527) (black) and the isotype control (eBioscience, Cat. no. 16-4724-85) followed by PE-labelled goat anti-mouse (Jackson Immunoresearch lab. Inc., Cat. no. 115-116-071) (grey) in flow cytometry. The MFI value (median channel fluorescence intensity) is plotted for each cell line.

Example 13: Additional Cell Lines for Characterisation 13.1 CD123 Transfected Cell Lines Stable HEK293 Flp-In (Invitrogen, R750-07) and CHO Flp-In (Invitrogen, R758-07) cell lines with recombinant overexpression of CD123 were generated using the Flp-In™ site-directed recombination technology (Flp-In™ System For Generating Stable Mammalian Expression Cell Lines by Flp Recombinase-Mediated Integration (Invitrogen, K601001, K601002)). Hereby, DNA integration occurs at a specific genomic location at an FRT (Flp Recombination Target) site by the Flp recombinase (pOG44) derived from *Saccharomyces cerevisiae*. The Flp-In™ host cell line and expression plasmid (pcDNA5) both contain this FRT site, thereby allowing a single homologous DNA recombination. The sequence for human CD123 was derived from NCBI RefSeq NP_002174, the sequence of cynomolgus CD123 was derived from NCBI genbank no. EHH61867.1 (SEQ ID NOs: 68 and 69, respectively). The cell surface expression of human and cynomolgus CD123 was confirmed by flow cytometry using the mouse monoclonal anti-CD123 antibody (BD Biosciences, 554527) and the mouse IgG2a isotype control (BD Bioscience, 16-4724-85). In brief, cells ($1\times10^5$ cells/well) were harvested and transferred to a V-bottom 96-well plate (Greiner Bio-one, 651 180) and stained at 4° C. with mouse monoclonal anti-CD123 antibody (0.25 µg/ml) and with mouse IgG2a isotype control (0.25 µg/ml). After 30 min of incubation, cells were pelleted by centrifugation and washed 3 times with FACS Buffer (D-PBS from Gibco with 10% FBS (Sigma, F7524) and 0.05% sodium azide (Acros organics, 190380050)). Next, cells were incubated with 5 µg/ml R-Phycoerythrin AffiniPure F(ab')₂ Fragment Goat Anti-Mouse IgG (Jackson Immunoresearch, 115-116-071) for 30 minutes at 4° C. After incubation, cells were washed 3 times with FACS Buffer. Subsequently, cells were resuspended in FACS buffer supplemented with 5 nM TOPRO3 (Molecular Probes, T3605) to distinguish live from dead cells. Cells were analysed using a FACS Array flow cytometer (BD Biosciences) and Flowing Software. First a P1 population which represented more than 80% of the total cell population was selected based on FSC-SSC distribution. In this gate, 10000 cells were counted during acquisition. From this population the TOPRO+ cells (dead cells) were excluded and the median PE value was calculated. The data are shown in FIG. 10.

13.2 U937, MOLM-13, KG1a and NCI-H929 Cell Lines

Figure 11:
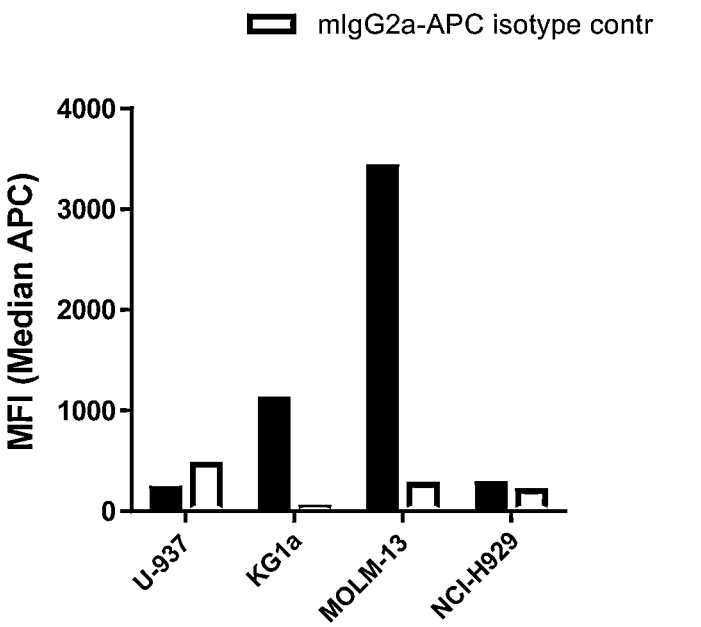
FIG. 11: Assessment of human CD123 expression on U-937, MOLM-13, KG1a and NCI-H929 cells using the APC-labelled anti-CD123 antibody (BD Biosciences, Cat. no. 560087) (black) and the APC-labelled isotype control (Biolegend, Cat. no. 400220) (grey) in flow cytometry. The MFI value (median channel fluorescence intensity) is plotted for each cell line.

The expression level of human CD123 on MOLM-13 (DSMZ, ACC-554), U-937 (ATCC®, CRL-1593.2™), KG1a (ATCC®, CCL246.1™) and NCI-H929 (DSMZ, ACC-163) was determined using the APC-labelled mouse monoclonal anti-CD123 antibody (BD Biosciences, 560087) and the APC-labelled isotype control (Biolegend, 400220) in flow cytometry. In brief, cells were harvested and suspended at a density of $1\times10^7$ cells/ml in FACS buffer with 25 µg human Fc block (BD Biosciences, 564220) and incubated for 10 min at RT. Next, cells were diluted to a cell concentration of $1\times10^6$ cells/ml and transferred to a V-bottom 96-well plate ($1\times10^5$ cells/well). Cells were stained at 4° C. with APC-labelled mouse monoclonal anti-CD123 antibody (diluted 10 times) and the APC-labelled isotype control (diluted 10 times). After 30 min of incubation, cells were washed 3 times and resuspended in FACS Buffer supplemented with 1 µg/ml Propidium iodine (PI) (Sigma, P4170) for 30 min at 4° C. and then analysed via a BD FACSCanto and Flowing software. First a P1 population which represented more than 80% of the total cell population was selected based on FSC-SSC distribution. 10000 cells were counted within P1. From this population the PI+ cells (dead cells) were excluded and the median APC value was calculated. The data are shown in FIG. 11.

In addition, the number of receptors per cell was determined using the QIFIKIT (Dako, K0078) according to manufacturer's instructions. The data are shown in Table C-7.

TABLE C-7

| Number of CD123 molecules per cell. | | |
| --- | --- | --- |
| | MOLM-13 | KG1a |
| CD123 molecules/cell | 6543 | 3353 |

Example 14: Binding of Monovalent Anti-CD123 Nanobodies to Endogenously CD123 Expressing Cell Lines Dose-dependent binding of the purified monovalent anti-CD123 Nanobodies to endogenously CD123 expressing cell lines MOLM-13 and KG1a was evaluated by flow cytometry. In brief, cells were harvested and transferred to a V-bottom 96-well plate ($1\times10^5$ cells/well) and serial dilutions of Nanobodies (starting from 1 µM) were allowed to associate for 30 minutes at 4° C. in FACS buffer. Cells were washed three times by centrifugation and probed with monoclonal mouse ANTI-FLAG® M2 antibody (Sigma-Aldrich, F1804) for 30 minutes at 4° C., washed again, and incubated for 30 min at 4° C. with 5 µg/ml R-Phycoerythrin AffiniPure F(ab')₂ Fragment Goat Anti-Mouse IgG (Jackson Immunoresearch, 115-116-071). After incubation, cells were washed 3 times with FACS Buffer. Subsequently, cells were resuspended in FACS buffer supplemented with 5 nM TOPRO3 (Molecular Probes, T3605) to distinguish live from dead cells, which are removed during the gating procedure. Cells were analysed using a FACS Array flow cytometer (BD Biosciences) and Flowing Software. First a P1 population which represented more than 80% of the total cell population was selected based on FSC-SSC distribution. In this gate, 10000 cells were counted during acquisition. From this population the TOPRO+ cells (dead cells) were excluded and the median PE value was calculated.

Figure 12:
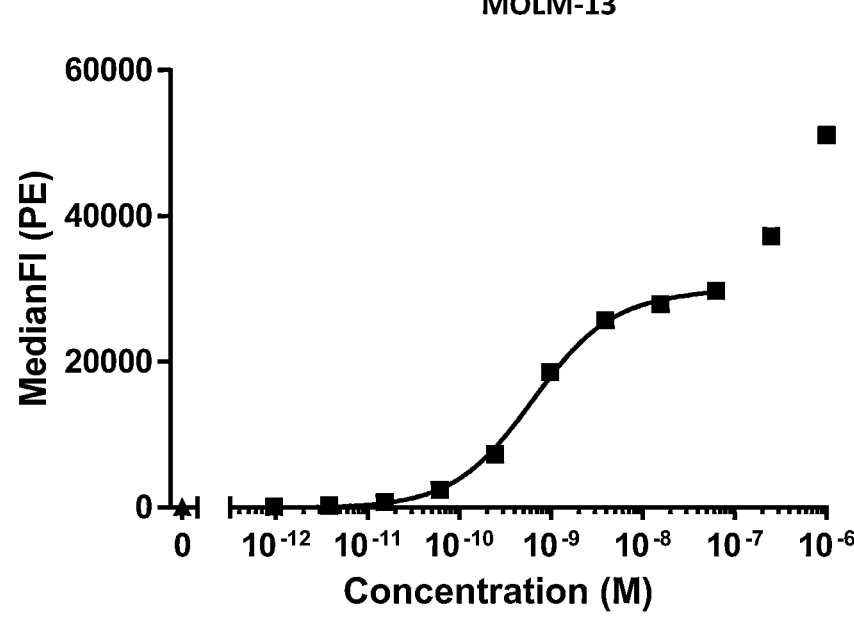
FIG. 12: Dose-dependent binding of the monovalent anti-CD123 Nanobodies A0110056A10 (squares) and A0110055F03 (circles) to MOLM-13 and KG1a cells. The MFI value (median channel fluorescence intensity) is plotted against the concentration.
Figure 12:
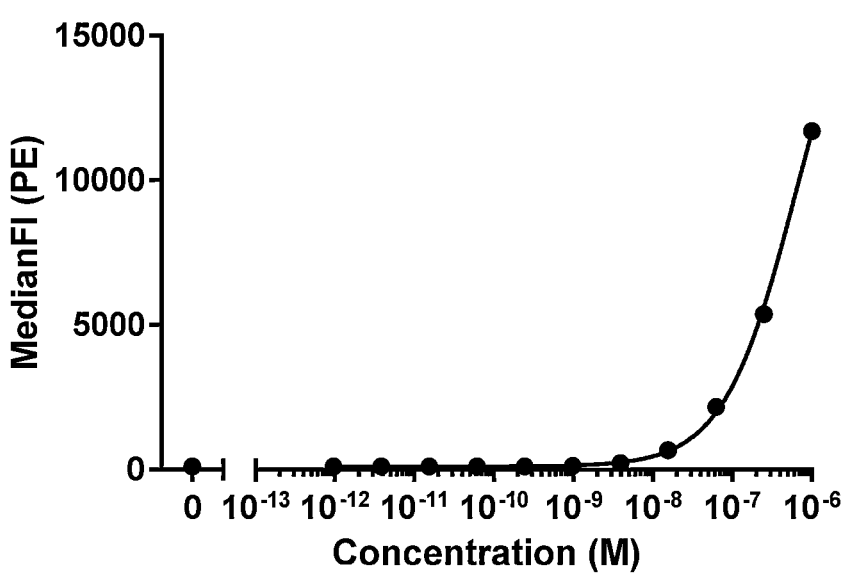

Binding of the Nanobodies to MOLM-13 and KG1a is presented in FIG. 12. The EC50 values obtained from the dose response curves are depicted in Table C-8.

TABLE C-8

| | MOLM-13 | | | KG1a | | |
|---|---|---|---|---|---|---|
| Sample ID | EC50 (M) | 95% LCI | 95% UCI | EC50 (M) | 95% LCI | 95% UCI |
| A0110056A10 | 6.3E–10 | 3.8E–10 | 8.8E–10 | 5.0E–10 | 2.4E–10 | 7.6E–10 |
| A0110055F03 | >1E–07 | | | >1E–07 | | |

EC50 (M) of monovalent anti-CD123 Nanobodies for binding to MOLM-13 and KG1a as determined in flow cytometry.

There was binding of both Nanobodies to the CD123 endogenously expressing cells (MOLM-13, KG1a).

Example 15: Binding of Monovalent Anti-CD123 Nanobodies to CD123 on Transfected Cells Dose-dependent binding of the purified monovalent anti-CD123 Nanobodies to human CD123 overexpressing CHO-K1 and cynomolgus CD123 overexpressing HEK293 cells was evaluated by flow cytometry.

To detect the binding of A0110055F03, cells were harvested and transferred to a V-bottom 96-well plate (1×10^5 cells/well). Serial dilutions of A0110055F03 (starting from 100 nM) were allowed to associate for 30 minutes at 4° C. in FACS buffer. Cells were washed 3 times with FACS buffer by centrifugation and probed with 1 µg/ml monoclonal mouse ANTI-FLAG® M2 antibody (Sigma-Aldrich, F1804) for 30 minutes at 4° C. to detect bound Nanobody. Detection was done with 0.5 µg/ml R-Phycoerythrin Affi-niPure F(ab')$_2$ Fragment Goat Anti-Mouse IgG (Jackson Immunoresearch, 115-116-071) for 30 minutes at 4° C. Cells were washed and incubated with TOPRO3 to stain for dead cells, which are then removed during the gating procedure. The cells were then analysed via a BD FACSArray. First a P1 population which represented more than 80% of the total cell population was selected based on FSC-SSC distribution. In this gate, 10000 cells were counted during acquisition. From this population the TOPRO+ cells (dead cells) were excluded and the median PE value was calculated.

To detect the binding of A0110056A10, cells were harvested and transferred to a V-bottom 96-well plate (1×10^5 cells/well). Serial dilutions of Alexa647-labelled A0110056A10 (starting from 100 nM) were allowed to associate for 30 minutes at 4° C. in FACS buffer. After 30 min of incubation, cells were pelleted by centrifugation and washed 3 times with FACS Buffer. Subsequently, cells were resuspended in FACS buffer supplemented with 1 µg/ml Propidium iodine to distinguish live from dead cells. Cells were analysed using a FACS Array flow cytometer (BD Biosciences) and Flowing Software. First a P1 population which represented more than 80% of the total cell population was selected based on FSC-SSC distribution. In this gate, 10000 cells were counted during acquisition. From this population the PI+ cells (dead cells) were excluded and the median APC-value was calculated.

Figure 13:
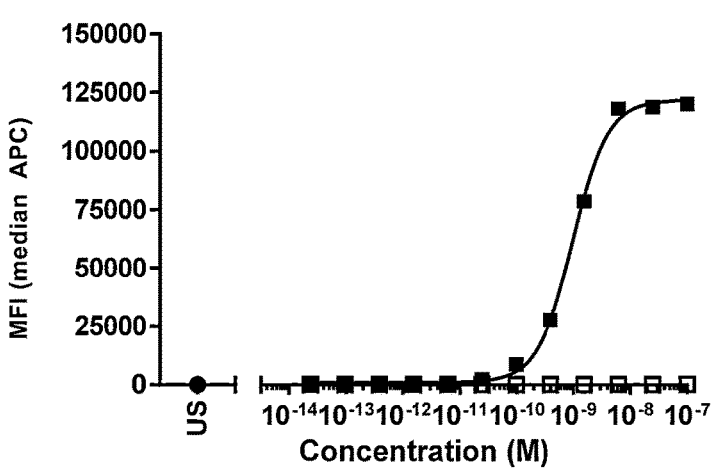
FIG. 13: Dose-dependent binding of Alexa647-labelled A0110056A10 to Flp-In parental cells (open symbol) and CD123 transfected cells (closed symbol) transfected cells.
Figure 13:
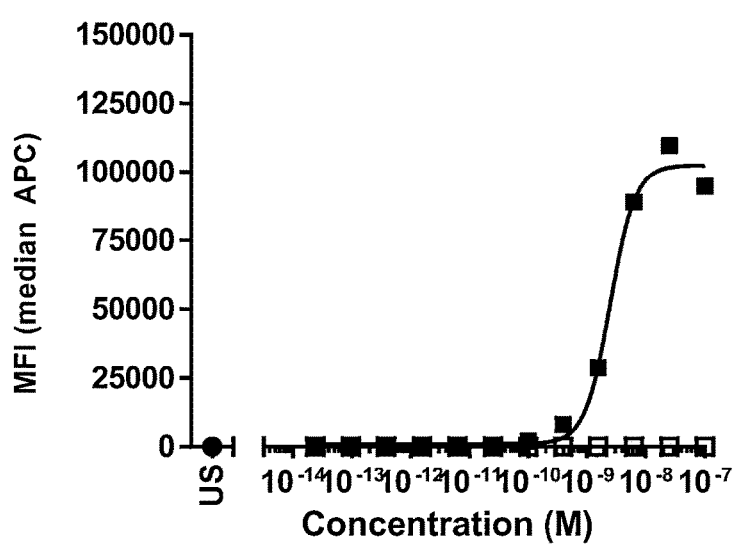

Binding of the Nanobodies to the CD123 transfected cell lines and reference cell line is presented in FIG. 13 and FIG. 14, for Nanobody A0110056A10 and A0110055F03 respectively. The EC50 values obtained from the dose response curves are depicted in and Table C-9.

TABLE C-9

| | HEK Flp-In cyCD123 transfected cells | | | CHO Flp-In huCD123 transfected cells | | |
|---|---|---|---|---|---|---|
| Sample ID | EC50 (M) | 95% LCI | 95% UCI | EC50 (M) | 95% LCI | 95% UCI |
| A0110056A10 | 2.48E–09 | 1.90E–09 | 3.20E–09 | 9.74E–10 | 8.50E–10 | 1.11E–09 |
| A0110055F03 | 2.53E–09 | 2.04E–09 | 3.14E–09 | 5.94E–09 | 1.00E–09 | 3.52E–08 |

EC50 (M) of monovalent anti-CD123 Nanobodies for binding to huCD123 and cyCD123 transfected cells as determined in flow cytometry.

There was binding of both Nanobodies to the CD123 transfected cell lines. Both Nanobodies are human—cynomolgus CD123 cross-reactive.

Example 16: Nanobody Competition for Binding to CD123 Expressed on Cells in Flow Cytometry To investigate whether the CD123 Nanobodies compete with each other, a Nanobody competition assay was set up. To this end, a large batch of A0110056A10 was labelled with Alexa647 and frozen. Next, cells were harvested and transferred to a V-bottom 96-well plate ($1\times10^5$ cells/well) and mixed with a serial dilution of the Nanobodies and a fixed concentration of A0110056A10-Alexa647 (0.7 nM for MOLM-13, 0.5 nM for CHO Flp-In human CD123). The A0110056A10-Alexa647 concentrations used in the assay were below the EC50 value for binding of A0110056A10-Alexa647 to the respective cells (binding curves are depicted in FIG. 15). After an incubation period of 90 min at 4° C., the binding of A0110056A10-Alexa647 was determined in flow cytometry. Thereto, cells were washed 3 times and resuspended in FACS Buffer supplemented with 1 μg/ml Propidium iodine, incubated for 30 min at 4° C. and then analysed via a BD FACSArray. First a P1 population which represented more than 80% of the total cell population was selected based on FSC-SSC distribution. 10000 cells were counted within P1. From this population the PI+ cells (dead cells) were excluded and the median APC value was calculated.

The results are presented in FIG. 16. The IC50 values obtained from the dose response curves are depicted in Table C-10.

TABLE C-10

| | IC50 (M) of monovalent anti-CD123 Nanobodies in the A0110056A10 Nanobody competition assay. | | | | | |
|---|---|---|---|---|---|---|
| | MOLM-13 | | | CHO Flp-In human CD123 | | |
| Sample ID | IC50 (M) | 95% LCI | 95% UCI | IC50 (M) | 95% LCI | 95% UCI |
| A0110056A10 | 1.4E−09 | 1.1E−09 | 1.8E−09 | 6.7E−09 | 5.3E−09 | 8.5E−09 |
| A0110055F03 | >1E−07 | | | / | / | / |

The non-labelled A0110056A10 competed with A0110056A10-Alexa647 for binding to CD123 on MOLM-13 cells and to human CD123 expressed on transfected CHO Flp-In cells, as expected. Nanobody A0110055F03 did not compete with A0110056A10-Alexa647 for binding to CD123 on the human CD123 transfected CHO Flp-In cells. On the MOLM-13 cell line, A0110055F03 did only compete with A0110056A10-Alexa647 at the highest concentrations tested.

Example 17: Competition with Mouse Monoclonal Anti-CD123 Antibody (Clone 7G3) for Binding to CD123 Expressed on Cells in Flow Cytometry To examine whether the anti-CD123 Nanobodies compete with the mouse monoclonal anti-CD123 antibody (clone 7G3) for binding to human CD123 on cells, a mouse monoclonal anti-CD123 antibody (clone 7G3) competition assay was performed using a flow cytometry based methodology as described in Example 16. To this end, serial dilutions of Nanobodies and an EC30 concentration of the APC-labelled mouse monoclonal anti-CD123 antibody (clone 7G3) (BD Biosciences, 560087) were incubated for 90 min with the cells after which antibody binding was determined in flow cytometry. Binding curves of APC-labelled mouse monoclonal anti-CD123 antibody (clone 7G3) to MOLM-13 and human CD123 transfected CHO Flp-In cells are depicted in FIG. 17.

The results from the competition experiments are pre-sented in FIG. 18. The IC50 values obtained from the dose response curves are depicted in Table C-11.

TABLE C-11

| IC50 (M) of monovalent anti-CD123 Nanobodies in the mouse monoclonal anti-CD123 antibody (clone 7G3) competition assay. | | | | | |
|---|---|---|---|---|---|
| | MOLM-13 | | | CHO Flp-In human CD123 | | |
| Sample ID | IC50 (M) | 95% LCI | 95% UCI | IC50 (M) | 95% LCI | 95% UCI |
| A0110056A10 | 1.1E–09 | 1.1E–09 | 1.2E–09 | 6.5E–09 | 6.1E–09 | 6.9E–09 |
| A0110055F03 | 4.8E–07 | 1.8E–07 | 1.2E–06 | | | |

Nanobody A0110056A10 showed competition with mouse monoclonal anti-CD123 antibody (clone 7G3) on the MOLM-13 and the human CD123 transfected CHO Flp-In cells; therefore the epitopes of mouse monoclonal anti-CD123 antibody (clone 7G3) and Nanobody A0110056A10 are at least partially overlapping. A0110055F03 competed with mouse monoclonal anti-CD123 antibody (clone 7G3) on the MOLM-13 cells. The absence of competition with mouse monoclonal anti-CD123 antibody (clone 7G3) on the human CD123 transfected CHO Flp-In cell line might be the result of the lower affinity of Nanobody A0110055F03 for human CD123.

Example 18: Competition with Mouse Monoclonal Anti-CD123 Antibody (Clone 7G3) for Binding to Recombinant Human CD123 in ELISA To investigate whether the anti-CD123 Nanobodies compete with the mouse monoclonal anti-CD123 antibody (clone 7G3) for binding to recombinant human CD123 protein, a competition assay was performed using an ELISA based methodology. Briefly, mouse monoclonal anti-CD123 antibody (clone 7G3) (BD Biosciences, 554527) was coated at 1 ug/ml in PBS. After an overnight incubation at 4° C., plates were blocked with casein (1% in PBS) at room temperature. Next, a serial dilution of the monovalent anti-CD123 Nanobodies and 4 nM of in house biotinylated-CD123 recombinant protein (R&D Systems, 301-R3/CF) was added and incubated for 1 h at room temperature in PBS+0.1% Casein+0.05% Tween. The concentration of the in house biotinylated-CD123 recombinant protein was based on the EC30 value obtained from the binding of in house biotinylated-CD123 recombinant protein to the mouse monoclonal anti-CD123 antibody (clone 7G3) (binding curve is depicted in FIG. 19). The non-coated mouse mono-clonal anti-CD123 antibody, (clone 7G3) was taken along as positive control, the irrelevant anti-egg lysozyme Nanobody cAbLys was taken along as negative control. The plates were washed with PBS+0.05% Tween using the Tecan Hydrospeed washer and 7G3 associated biotinylated-CD123 was detected via 1 µg/ml extravidine peroxidise (Sigma, E2886) in PBS+0.1% Casein+0.05% Tween, followed by development with esTMB substrate. The reaction was stopped with 1M HCl and the absorption at OD450 nm was measured using the Tecan Infinite M1000.

The results are presented in FIG. 20. The $IC_{50}$ value obtained from the dose response curve are depicted in Table C-12.

TABLE C-12

| IC50 (M) of monovalent Nanobody A010056A10 in the 7G3 competition ELISA. | | | |
|---|---|---|---|
| Sample ID | IC50 (M) | 95% LCI | 95% UCI |
| A0110056A10 | 3.1E–09 | 1.5E–09 | 6.5E–09 |

Competition was observed between A0110056A10 and the mouse monoclonal anti-CD123 antibody (clone 7G3) for binding to the recombinant human CD123 protein. A0110055F03 did not compete with mouse monoclonal anti-CD123 antibody (clone 7G3) for binding to the recombinant human CD123 protein.

Example 19: Binding of Monovalent Anti-CD123 Nanobodies to Human CD123 Protein (SPR)

Binding affinities of the purified CD123 specific Nano-bodies for human CD123 were evaluated by means of an SPR based assay on a ProteOn XPR36 instrument. Thereto, recombinant CD123 (R&D Systems, 301-R3-025/CF) was immobilized on a CM5 chip via amine coupling, using EDC and NHS chemistry. Purified Nanobodies were injected for 2 minutes at different concentrations (between 4.2 nM and 1000 nM) for kinetic analysis via a one-shot kinetics approach. Flow rate was 45 µl/min and ProteOn running buffer (PBS, pH 7.4, 0.005% Tween 20) was used as running buffer. The dissociation time of the 1000 nM sample was 15 min. Evaluation of the association/dissociation data was performed by fitting a 1:1 interaction model (Langmuir binding model).

TABLE C-13

| Binding characteristics of monovalent anti-CD123 Nanobodies determined in Proteon using directly coated human CD123 protein. | | | |
|---|---|---|---|
| Sample ID | ka (1/Ms) | kd (1/s) | KD (M) |
| A0110056A10 | 5.3E+05 | 7.9E–04 | 1.5E–09 |
| A0110055F03 | 2.5E+04 | 3.9E–03 | 1.6E–07 |

The $K_D$ values of the monovalent anti-CD123 Nanobodies for binding to human CD123 correlated with the binding data on cells. A0110056A10 has a better affinity compared to the A0110055F03.

Example 20: Construction of CD123/TCR Multispecific Polypeptides and Control Constructs In order to obtain polypeptides capable of engaging T cells, the CD123 Nanobodies were linked with the anti-TCR (T cell receptor) Nanobody T0170056G05 (SEQ ID NO: 42). The latter is a Nanobody specifically binding the TCR α/β constant domain. (see PCT/EP2016/060859, entitled "T cell recruiting polypeptides based on TCR alpha/beta reactivity", filed on May 13, 2016 by Ablynx N.V)

The therapeutic activity of T cell engaging polypeptides can be improved by the simultaneous targeting of multiple epitopes on a tumour associated antigen. Not only can tumour cells create an escape mechanism by the down-regulation of targeted antigens within a therapy, but also by introducing (point-)mutations. Simultaneous targeting of multiple epitopes on an antigen is likely to reduce the probability of generating tumour escape variants. Furthermore, targeting multiple epitopes on a single antigen can increase the affinity of binding (avidity effect). For this multivalent tumour antigen targeting concept, the two Nanobodies reactive towards the CD123 antigen were linked with Nanobody T0170056G05 against the TCR/CD3 complex.

The specific order of the respective Nanobodies was varied within the format. The effector and tumour Nanobodies were genetically linked with a 35GS linker and subsequently expressed in the yeast *Pichia* according to standard protocols (multispecific polypeptides). In parallel, irrelevant constructs were generated by replacing one or both of the tumour reactive Nanobodies with the irrelevant anti-egg lysozyme Nanobody cAbLys or anti-RSV Nanobody RSV007B02(Q108L).

The generated polypeptides are listed in Table C-14.

TABLE C-14

Sample ID and description of multispecific polypeptides.

| Sample ID | SEQ. ID NO* | Description |
|---|---|---|
| T017000113 | 46 | A0110055F03-35GS-cAbLys3(D1E,Q5V,A6E,Q108L)-35GS-T0170056G05-FLAG3-HIS6 |
| T017000114 | 47 | A0110055F03-35GS-A0110056A10-35GS-T0170056G05-FLAG3-HIS6 |
| T017000115 | 48 | A0110056A10-35GS-cAbLys3(D1E,Q5V,A6E,Q108L)-35GS-T0170056G05-FLAG3-HIS6 |
| T017000116 | 49 | A0110056A10-35GS-A0110055F03-35GS-T0170056G05-FLAG3-HIS6 |
| T017000120 | 50 | cAbLys3(D1E,Q5V,A6E,Q108L)-35GS-A0110055F03-35GS-T0170056G05-FLAG3-HIS6 |
| T017000121 | 51 | cAbLys3(D1E,Q5V,A6E,Q108L)-35GS-A0110056A10-35GS-T0170056G05-FLAG3-HIS6 |
| T017000125 | 42 | T0170056G05-HIS6 |
| T017000126 | 52 | A0110055F03(E1D)-35GS-A0110056A10-35GS-T0170056G05-A |
| T017000128 | 53 | T0170056G05(E1D)-35GS-A0110056A10-A |
| T017000129 | 54 | T0170056G05(E1D)-35GS-RSV007B02(Q108L)-A |
| T017000130 | 55 | A0110056A10(E1D)-35GS-A0110055F03-35GS-T0170056G05-A |
| T017000131 | 56 | A0110056A10(E1D)-35GS-T0170056G05-A |
| T017000132 | 57 | RSV007B02(E1D,Q108L)-35GS-T0170056G05-A |
| T017000134 | 58 | A0110056A10(E1D)-35GS-T0170056G05-35GS-A0110055F03-A |
| T017000135 | 59 | A0110055F03(E1D)-35GS-T0170056G05-35GS-A0110056A10-A |

TABLE C-14-continued

Sample ID and description of multispecific polypeptides.

| Sample ID | SEQ. ID NO* | Description |
|---|---|---|
| T017000138 | 60 | T0170056G05(E1D)-35GS-A0110056A10-35GS-A0110055F03-A |
| T017000139 | 61 | T0170056G05(E1D)-35GS-A0110055F03-35GS-A0110056A10-A |

*SEQ ID NOs correspond to the sequence of the multispecific polypeptides without C-terminal tags or Ala-extension

Example 21: Competition Between A0110056A10 and the Multispecific CD123/TCR Constructs for Binding to CD123 Expressed on Cells in Flow Cytometry The binding of the CD123/TCR multispecific polypeptides to human or cynomolgus CD123 was evaluated in the A0110056A10 competition assay as described in Example 16. Next to binding to the MOLM-13 and CHO Flp-In huCD123 cells, binding to cyno CD123 transfected HEK Flp-In cells was assessed.

To this end, a batch of A0110056A10 was labelled with Alexa647 and frozen. Next, cells were harvested and transferred to a V-bottom 96-well plate ($1 \times 10^5$ cells/well) and mixed with a serial dilution of the multispecific binding polypeptides (starting from 1 μM) and a fixed concentration of A0110056A10-Alexa647. The concentrations used in the assay (0.4 nM for MOLM-13, 0.9 nM for CHO Flp-In human CD123 and for HEK Flp-In cynomolgus CD123) were below the EC50 value for binding of A0110056A10-Alexa647 to the respective cells (binding curves are depicted in FIG. 21). After an incubation period of 90 min at 4° C., the binding of A0110056A10-Alexa647 was determined in flow cytometry as described in Example 16. A0110056A10 and T017000129 were taken along as a positive and negative control, respectively.

The results are presented in FIG. 22. The $IC_{50}$ values obtained from the dose response curves are depicted in Table C-15 and Table C-16.

TABLE C-15

IC50 (M) of CD123/TCR multispecific polypeptides and controls in the A0110056A10 Nanobody competition assay on MOLM-13 cells.

| Sample ID | MOLM-13 | | |
|---|---|---|---|
| | IC50 (M) | 95% LCI | 95% UCI |
| T017000121 | 2.6E−08 | 2.2E−08 | 3.1E−08 |
| T017000128 | 3.1E−09 | 2.6E−09 | 3.6E−09 |
| T017000138 | 3.5E−09 | 3.0E−09 | 4.1E−09 |
| T017000139 | 3.7E−09 | 3.1E−09 | 4.4E−09 |
| T017000116 | 1.8E−09 | 1.5E−09 | 2.2E−09 |
| A0110056A10 | 1.1E−09 | 8.7E−10 | 1.3E−09 |

TABLE C-16

| | | | | | | |
|---|---|---|---|---|---|---|
| IC50 (M) of CD123/TCR multispecific polypeptides and controls in the A0110056A10 Nanobody competition assay on CD123 transfected cells. | | | | | | |
| | HEK Flp-In cyCD123 transfected cells | | | CHO Flp-In huCD123 transfected cells | | |
| Sample ID | IC50 (M) | 95% LCI | 95% UCI | IC50 (M) | 95% LCI | 95% UCI |
| T017000121 | 1.1E–07 | 9.6E–08 | 1.3E–07 | 2.3E–08 | 1.9E–08 | 2.7E–08 |
| T017000128 | 3.1E–08 | 2.6E–08 | 3.6E–08 | 5.8E–09 | 5.4E–09 | 6.2E–09 |
| T017000138 | 1.2E–08 | 1.0E–08 | 1.4E–08 | 3.6E–09 | 2.8E–09 | 4.6E–09 |
| T017000139 | 1.1E–08 | 9.6E–09 | 1.3E–08 | 3.3E–09 | 2.7E–09 | 4.1E–09 |
| T017000116 | 5.6E–09 | 4.8E–09 | 6.4E–09 | 1.6E–09 | 1.4E–09 | 1.9E–09 |
| A0110056A10 | 7.0E–09 | 6.1E–09 | 8.1E–09 | 1.9E–09 | 1.7E–09 | 2.3E–09 |

All tested multispecific constructs showed binding to human and cynomolgus CD123 expressing cells confirming human cynomolgus CD123 crossreactivity. A small drop in affinity was observed for the polypeptides where the A0110056A10 is not at the N-terminal position.

Example 22: Competition Between T0170056G05 and CD123/TCR Multispecific Polypeptides for Binding to Human TCR/CD3 Expressed on Cells in Flow Cytometry The binding of the CD123/TCR multispecific polypeptides to human TCR/CD3 was evaluated in a T0170056G05 competition assay by flow cytometry. To this end, a large batch of T0170056G05 was labelled with biotin and frozen. Next, CHO-K1 human TCR/CD3 expressing cells were harvested and transferred to a V-bottom 96-well plate ($1 \times 10^5$ cells/well) and mixed with a serial dilution of the multispecific binding polypeptides (starting from 1 μM) and a fixed concentration of biotinylated T0170056G05 in FACS buffer. The concentration of biotinylated T0170056G05 used in the assay (30 nM) was below the EC50 value for binding to the cells (data not shown). After an incubation period of 90 min at 4° C., the binding of the biotinylated T01700056G05 Nanobody was determined in flow cytometry. Thereto, cells were washed 3 times and resuspended in streptavidin-PE (ebioscience, 12-4317-87, 1000 fold diluted) in FACS buffer and incubated for 30 min at 4° C. Afterwards, cells were washed 3 times and resuspended in FACS Buffer+1 μg/ml TOPRO (Molecular Probes, T3605) for 30 min at 4° C. and then analysed via a BD FACSCanto. First a P1 population which represented more than 80% of the total cell population was selected based on FSC-SSC distribution. 10000 cells were counted within P1. From this population the TOPRO+ cells (dead cells) were excluded and the median PE value was calculated. T0170056G05 was taken along as a positive control.

The results are presented in FIG. 23. The $IC_{50}$ values obtained from the dose response curves are depicted in Table C-17.

TABLE C-17

| | | | |
|---|---|---|---|
| IC50 (M) of CD123/TCR multispecific polypeptides and control Nanobody in the T0170056G05 competition assay. | | | |
| | CHO-K1 huTCR/CD3 | | |
| Sample ID | IC50 (M) | 95% LCI | 95% UCI |
| T017000138 | 5.9E–08 | 5.5E–08 | 6.4E–08 |
| T017000139 | 4.9E–08 | 4.5E–08 | 5.2E–08 |
| T017000129 | 1.8E–07 | 1.7E–07 | 1.9E–07 |

TABLE C-17-continued

| | | | |
|---|---|---|---|
| IC50 (M) of CD123/TCR multispecific polypeptides and control Nanobody in the T0170056G05 competition assay. | | | |
| | CHO-K1 huTCR/CD3 | | |
| Sample ID | IC50 (M) | 95% LCI | 95% UCI |
| T017000128 | 5.7E–08 | 5.3E–08 | 6.1E–08 |
| T017000116 | >1E–07 | | |
| T0170056G05 | 5.5E–08 | 5.2E–08 | 5.9E–08 |

The binding of the CD123/TCR multispecific polypeptides to human TCR/CD3 expressed on cells was confirmed. A drop in affinity of the CD123/TCR multispecific polypeptide T017000116 versus the monovalent TCR Nanobody was observed due to the C-terminal position of the TCR Nanobody.

Example 23: Competition Between T017000099 and the CD123/TCR Multispecific Polypeptides for Binding to Cynomolgus TCR/CD3 Expressed on Cells in Flow Cytometry The binding of the CD123/TCR multispecific polypeptides to cyno TCR/CD3 was evaluated in a T01700099 (bivalent T0170056G01, SEQ ID NO: 337) competition assay in flow cytometry. To this end, HSC-F (JCRB, JCRB1164) cynomolgus TCR/CD3 expressing cells were harvested and transferred to a V-bottom 96-well plate ($1 \times 10^5$ cells/well) and mixed with a serial dilution of the CD123/TCR multispecific polypeptides (starting from 1 μM) and 500 nM of T01700099 in FACS buffer. After an incubation period of 90 min at 4° C., cells were washed 3 times with FACS buffer by centrifugation and probed with 1 μg/ml monoclonal mouse ANTI-FLAG® M2 antibodies (Sigma-Aldrich, F1804) for 30 minutes at 4° C., to detect bound T01700099. Detection was done with 5 μg/ml Allophyco-cyanin (APC) AffiniPure Goat Anti-Mouse IgG (Jackson Immunoresearch, 115-135-164) for 30 minutes at 4° C. Cells were washed and incubated with Propidium Iodine to stain for dead cells, which are then removed during the gating procedure. The cells were then analysed via a BD FACSAr-ray. First a P1 population which represented more than 80% of the total cell population was selected based on FSC-SSC distribution. In this gate, 10000 cells were counted during acquisition. From this population the PI+ cells (dead cells) were excluded and the median APC value was calculated. T017000125 was taken along as a positive control.

The results are presented in FIG. 24. The $IC_{50}$ values obtained from the dose response curves are depicted in Table C-18.

TABLE C-18

IC50 (M) of CD123/TCR multispecific polypeptides and control
Nanobody in the T017000099 competition assay.

| Sample ID | HSC-F | | |
| | IC50 (M) | 95% LCI | 95% UCI |
| --- | --- | --- | --- |
| T017000125 | 3.7E–07 | 2.5E–07 | 5.3E–07 |
| T017000128 | 6.3E–07 | 4.4E–07 | 8.8E–07 |
| T017000129 | 5.2E–07 | 3.7E–07 | 7.2E–07 |
| T017000138 | 4.4E–07 | 3.2E–07 | 6.2E–07 |
| T017000139 | 6.4E–07 | 4.5E–07 | 9.2E–07 |

For all CD123/TCR multispecific constructs with the TCR binding Nanobody at the N-terminus, binding to cynomolgus TCR/CD3 was observed.

Example 24: Binding of Monovalent Nanobodies and Multispecific Polypeptides to Human CD123 Protein (SPR)

Binding affinities for the CD123/TCR multispecific polypeptides were evaluated by means of an SPR based affinity determination on a ProteOn XPR36 instrument. Thereto, recombinant CD123 (R&D Systems, 301-R3-025/CF) was immobilized on a CM5 chip via amine coupling, using EDC and NHS chemistry. Purified Nanobodies were injected for 2 minutes at different concentrations (between 4.2 nM and 1000 nM) via a one-shot kinetics approach for kinetic analysis. The dissociation time of the 1000 nM sample was 15 min. Flow rate was 45 µl/min and ProteOn running buffer (PBS, pH 7.4, 0.005% Tween 20) was used as running buffer. Evaluation of the association/dissociation data was performed by fitting a 1:1 interaction model (Langmuir binding model). The binding characteristics are listed in Table C-19.

TABLE C-19

Binding characteristics of multispecific polypeptides determined
in Proteon using directly coated human CD123 protein

| sample ID | ka (1/Ms) | kd (1/s) | KD (M) | |
| --- | --- | --- | --- | --- |
| T017000120 | 1.5E+04 | 2.5E–03 | 1.7E–07 | Values only indicative due to incomplete regeneration of previous Nb (116) |
| T017000121 | 4.0E+04 | 8.6E–04 | 2.2E–08 | — |
| T017000113 | 2.0E+04 | 3.2E–03 | 1.6E–07 | |
| T017000115 | 3.3E+05 | 5.1E–04 | 1.5E–09 | Values only indicative due to incomplete regeneration of previous Nb (114) |
| T017000114 | 8.4E+04 | 1.9E–04 | 2.3E–09 | |
| T017000116 | 2.4E+05 | 2.1E–04 | 8.8E–10 | |

The KD of the monovalent Nanobodies and multispecific polypeptides to human IL3Ra correlates with the binding data on cells. The construct, T017000116 containing the two IL3Ra building blocks had the best KD.

Example 25: Redirected Human T Cell Mediated Killing of CD123 Target Cells by CD123/TCR Multispecific Polypeptides in a Flow Cytometry Based Assay In order to assess whether the CD123/TCR multispecific polypeptides were able to kill tumour cells, cytotoxicity assays were performed with isolated human T cells as effector cells.

Thereto, human T cells were collected from Buffy Coat blood from healthy volunteers (Blood bank Gent) using RosetteSep (StemCell Technologies, 15061) followed by enriching on Ficoll-Paque™ PLUS (GE Healthcare, 17-1440-03) according to manufacturer's instructions. The quality and purity of the purified human T cells was checked with anti-CD3 (eBioscience, 12-0037-73), anti-CD8 (BD-Biosciences, 555367), anti-CD4 (BD Biosciences, 345771), anti-CD45RO (BD Biosciences, 555493), anti-CD45RA (BDBiosciences, 550855), anti-CD19 (BDBiosciences, 555413), anti-CD25 (BDBiosciences, 557138) and anti-CD69 (BDBiosciences, 557050) fluorescently labelled antibodies in a flow cytometric assay. Cells were frozen in liquid nitrogen.

Human CD123 expressing MOLM-13 and KG1a cells were labelled with 81 µM PKH-26 membrane dye using the PKH26 red fluorescent cell linker kit (Sigma, PKH26GL-1KT) according to manufacturer's instruction and used as target cells. $2.5 \times 10^5$ effector (i.e. human primary T cells) and $2.5 \times 10^4$ target cells (i.e. PKH-labelled MOLM-13 or KG1a cells) were co-incubated in 96-well V-bottom plates (effector versus target ratio of 10:1). For measurement of the concentration-dependent cell lysis, serial dilutions of the CD123/TCR multispecific polypeptides were added to the cells and incubated for 18 h in a 5% $CO_2$ atmosphere at 37° C. Nanobody A0110056A10 and constructs T017000129 and T017000132 were taken along as negative control. After incubation, cells were pelleted by centrifugation and washed with FACS buffer. Subsequently, cells were resuspended in FACS buffer supplemented with 5 nM TOPRO3 (Molecular Probes, T3605) to distinguish live from dead cells. Cells were analysed using a FACS Array flow cytometer (BD Biosciences). Per sample, a total sample volume of 80 µl was acquired. Gating was set on PKH26 positive cells, and within this population the TOPRO3 positive cells were determined. T017000129, T017000132 and A0110056A10 were taken along as a negative control.

Exemplary results are shown in FIG. 25 and FIG. 26 for the MOLM-13 and KG1a cells, respectively. The $EC_{50}$ values are depicted in Table C-20 and Table C-21 for the MOLM-13 and KG1a cells, respectively.

TABLE C-20

EC50 (M) and % lysis of CD123/TCR multispecific
polypeptides for redirected human T cell mediated killing
of MOLM-13 cells in a flow cytometry based assay.

| Sample ID | EC50 (M) | 95% LCI | 95% UCI | % lysis |
| --- | --- | --- | --- | --- |
| T017000116 | 2.2E–10 | 1.1E–10 | 4.5E–10 | 17 |
| T017000128 | 1.5E–10 | 9.4E–11 | 2.5E–10 | 20 |
| T017000135 | 1.1E–11 | 8.1E–12 | 1.5E–11 | 33 |
| T017000138 | 2.3E–11 | 1.5E–11 | 3.7E–11 | 22 |
| T017000139 | 2E–11 | 1.4E–11 | 2.9E–11 | 29 |
| T017000134 | 3E–10 | 1E–10 | 9.2E–10 | 9 |

TABLE C-21

EC50 (M) and % lysis of CD123/TCR multispecific
polypeptides for redirected human T cell mediated killing
of KG1a cells in a flow cytometry based assay.

| Sample ID | EC50 (M) | 95% LCI | 95% UCI | % lysis |
| --- | --- | --- | --- | --- |
| T017000114 | 2.4E–10 | 1.5E–10 | 3.6E–10 | 7 |
| T017000116 | 4.2E–10 | 2.4E–10 | 7.3E–10 | 5 |
| T017000128 | 8.7E–10 | 7.0E–10 | 1.1E–09 | 28 |
| T017000135 | 5.1E–11 | 4.1E–11 | 6.5E–11 | 18 |

TABLE C-21-continued

EC50 (M) and % lysis of CD123/TCR multispecific
polypeptides for redirected human T cell mediated killing
of KG1a cells in a flow cytometry based assay.

| Sample ID | EC50 (M) | 95% LCI | 95% UCI | % lysis |
|---|---|---|---|---|
| T017000138 | 2.8E-10 | 2.2E-10 | 3.4E-10 | 24 |
| T017000139 | 1.1E-10 | 8.5E-11 | 1.3E-10 | 27 |

The CD123/TCR multispecific polypeptides induced human T cell mediated killing of CD123 positive cell lines. There was clear preference for the position of the TCR Nanobody in the multispecific polypeptide. In general, the constructs with the anti-TCR Nanobody at the N-terminal position showed best killing potential. The constructs T017000135, T017000138 and T013700139 with two CD123 reactive Nanobodies showed improved potency compared to construct T017000128 with only one CD123 Nanobody. These results demonstrated that the CD123/TCR multispecific polypeptides can induce T cell mediated killing of tumour target positive cell lines and that targeting multiple epitopes on a single antigen improves functionality (avidity effect).

In addition, comparison of constructs T017000138 and T017000139, both trivalent Nanobodies with the TCR reactive Nanobody at the N terminal position, showed that there is an impact of the orientation of the CD123 Nanobodies on potency and efficacy.

The monovalent CD123 building block and the irrelevant constructs containing the TCR building block did not induce any target cell killing, confirming the requirement of cross-linking the T cell and target cell with the multispecific CD123/TCR polypeptides to induce killing.

The results were confirmed using purified T cells from different donors (data not shown).

Example 26: Redirected Cynomolgus T Cell Mediated Killing of CD123 Target Cells by Multispecific CD123/TCR Polypeptides in a Flow Cytometry Based Assay To confirm the human-cyno TCR cross-reactivity of the CD123/TCR multispecific polypeptides, the constructs were evaluated in a cynomolgus T cell mediated CD123 positive tumour cell killing assay. In brief, multispecific polypeptides were incubated with $2.5 \times 10^4$ PKH labelled target cells (i.e. MOLM-13 or KG1a cells) in the presence of $2.5 \times 10^5$ effector cells (i.e. cynomolgus primary T cells (E:T=10:1), as described in Example 25. T cells were isolated by LPT Laboratory of Pharmacology and Toxicology GmbH & Co. KG, using the Pan T Cell Isolation Kit (MACS, 130-091-993). Nanobody A0110056A10 and constructs T017000129 and T017000132 were taken along as negative control.

Exemplary results are shown in FIG. 27 and FIG. 28 for the MOLM-13 and KG1a cells, respectively. The $EC_{50}$ values are depicted in Table C-22 and Table C-23 for the MOLM-13 and KG1a cells, respectively.

TABLE C-22

EC50 (M) and % lysis of CD123/TCR multispecific
polypeptides for redirected cyno T cell mediated
killing of MOLM-13 cells in a flow cytometry based assay.

| Sample ID | EC50 (M) | 95% LCI | 95% UCI | % lysis |
|---|---|---|---|---|
| T017000116 | 3.9E-10 | 2.4E-10 | 6.2E-10 | 15 |
| T017000128 | 1.8E-10 | 1.5E-10 | 2.3E-10 | 50 |
| T017000138 | 1.7E-11 | 1.3E-11 | 2.2E-11 | 47 |
| T017000139 | 1.1E-11 | 8.9E-12 | 1.4E-11 | 55 |

TABLE C-23

EC50 (M) and % lysis of CD123/TCR multispecific
polypeptides for redirected cyno T cell mediated
killing of KG1a cells in a flow cytometry based assay.

| Sample ID | EC50 (M) | 95% LCI | 95% UCI | % lysis |
|---|---|---|---|---|
| T017000114 | 1.9E-10 | 1.3E-10 | 2.8E-10 | 7 |
| T017000116 | 3.7E-10 | 2.9E-10 | 4.7E-10 | 14 |
| T017000128 | 3.2E-10 | 2.7E-10 | 3.7E-10 | 38 |
| T017000135 | 2.4E-11 | 2.0E-11 | 2.9E-11 | 22 |
| T017000138 | 8.8E-11 | 7.6E-11 | 1.0E-10 | 38 |
| T017000139 | 2.6E-11 | 2.3E-11 | 3.0E-11 | 42 |

All CD123/TCR multispecific polypeptides, except for T017000134, induced cynomolgus T cell mediated killing of CD123 positive MOLM-13 or KG1a cell lines. Constructs with the TCR reactive Nanobody at the N terminal position were most potent and efficacious. Constructs T017000138 and T017000139, both trivalent Nanobodies with two CD123 reactive Nanobodies showed improved potency compared to the construct T017000128, which contains only one CD123 reactive Nanobody. The monovalent anti-CD123 Nanobody and the irrelevant constructs containing the TCR building block did not induce any target cell killing, confirming the requirement of cross-linking the T cell and target cell with the multispecific CD123/TCR polypeptides to induce killing.

The results were confirmed using purified T cells from different cynomolgus monkeys (data not shown).

Example 27: Cynomolgus T Cell Activation by the CD123/TCR Multispecific Polypeptides During Redirected Cynomolgus T Cell Mediated Killing of CD123 Target Cells To monitor T cell activation following the treatment of the cynomolgus T cells and CD123 positive MOLM-13 cells with multispecific CD123/TCR polypeptides, the polypeptides were incubated for 72 h at 37° C. with $2.5 \times 10^4$ target cells in the presence of $2.5 \times 10^5$ primary T cells (E:T=10:1), as described in Example 26. Cynomolgus T cell activation was measured by monitoring the CD25 upregulation on the CD4/CD8 T cell population in flow cytometry.

Thereto, after the incubation of 72 h, effector and target cells were collected by centrifugation and suspended in FACS buffer with 25 μg/ml human Fc block (BD Bioscience, 564220) and incubated for 10 min at room temperature (RT). Next, cells were stained with monoclonal mouse anti-CD4-APC (Biolegend, 300505) (200-fold diluted), monoclonal mouse anti-CD8 APC (BDBiosciences, 555366) (50-fold diluted) and monoclonal anti-CD25 PE (BD Biosciences, 557138) (50-fold diluted) antibodies in FACS buffer for 30 min at 4° C. After incubation, cells were pelleted by centrifugation and washed with FACS buffer. Subsequently, cells were resuspended in FACS buffer and analysed using a FACS Canto flow cytometer (BD Biosciences). Per sample, a total sample volume of 30 µl was acquired. T cells were gated based on the SSC-APC plot. From this population the mean PE value was calculated.

The data is shown in FIG. 29. The $EC_{50}$ value obtained for T017000139 is depicted in Table C-24.

TABLE C-24

| EC50 (M) of CD25 upregulation on cynomolgus T cell by T017000139 during the redirected cynomolgus T cell mediated killing of MOLM-13 cells in a flow cytometry based assay. | | | |
|---|---|---|---|
| Sample ID | EC50 (M) | 95% LCI | 95% UCI |
| T017000139 | 6.0E-11 | 5.1E-11 | 7.1E-11 |

No CD25 upregulation was observed when T cells were incubated with CD123 positive MOLM-13 target cells and the monovalent TCR or CD123 binding building blocks T0170056G05, A0110055F03 or A0110056A10 or the irrelevant multivalent polypeptide T017000129. The data showed CD25 upregulation on cynomolgus primary T cells after incubation with CD123 positive MOLM-13 target cells and the T017000139 multispecific polypeptide.

MOLM-13 cells were killed in a dose-dependent manner (FIG. 25, Table C-22), indicating that the multispecific CD123/TCR binding polypeptide induced T cell activation in the process of redirected killing.

Likewise, T cells were not activated when incubated with target cells and the monovalent building blocks and irrelevant multispecific polypeptide, indicating the requirement of cross-linking the T cell and target cell with the TCR/CD123 multispecific polypeptides to induce CD25 upregulation.

Example 28: Redirected Human T Cell Mediated Killing of CD123 Transfected Adherent Target Cells by Multispecific CD123/TCR Binding Polypeptides in an xCELLigence Based Assay The TCR/CD123 binding polypeptides were characterized for redirected human T cell mediated killing of human CD123 transfected adherent target cells in an xCELLigence based assay. In this assay, fluctuations in impedance induced by the adherence of target cells to the surface of an electrode are measured. T cells are non-adherent and therefore do not impact the impedance measurements. The xCELLigence instrument (Roche) quantifies the changes in electrical impedance, displaying them as a dimensionless parameter termed cell-index, which is directly proportional to the total area of tissue-culture well that is covered by cells. In brief, an xCELLigence station was placed in a 37° C. incubator at 5% $Co_2$. 50 µl of assay medium was added to each well of E-plate 96 (ACEA Biosciences; 05 232 368 001) and a blank reading on the xCELLigence system was performed to measure background impedance in absence of cells. Subsequently, $2\times10^4$ human CD123 transfected CHO Flp-In or CHO Flp-In reference cells were seeded onto the E-plate 96, and 50 µl serial diluted multispecific polypeptide was added. After 30 min at RT, 50 µl of human T cells $(3\times10^5)$ was added per well to have an effector to target ratio of 15:1. The plate was placed in the xCELLigence station and impedance was measured every 15 min for 3 days. The data were analysed using a fixed time point indicated in the results.

The IC50 values obtained in this assay are listed in Table C-25. The results are depicted in FIG. 30, FIG. 31 and FIG. 32.

154

TABLE C-25

| IC50 (M) of T013700139 for redirected human T cell mediated killing of human CD123 transfected adherent target cells in an xCELLigence based assay, using an effector to target ratio of 15 to 1, analysed at 50 h after seeding. | | | |
|---|---|---|---|
| Sample ID | IC50 (M) | 95% LCI | 95% UCI |
| T017000139 | 2.4E-10 | 2.0E-10 | 2.8E-10 |

The obtained data confirmed the results obtained in the flow cytometry based killing assay, i.e. CD123/TCR multispecific polypeptides can induce human T cell mediated killing of CD123 positive cell lines (FIG. 30) and no killing activity is observed in the absence of T cells (FIG. 32). In addition, only when the CD123 tumour target antigen was present T cell mediated killing was observed (see FIG. 31 for absence of killing with reference cell line), indicating that the multispecific polypeptides are critically dependent on their target for induction of cytotoxicity.

The monovalent Nanobodies A0110056A10 and T0170056G05 and the irrelevant construct T017000129 did not induce target cell killing, confirming the requirement of cross-linking the T cell and target cell with the multispecific CD123/TCR binding polypeptide to induce killing.

The results were confirmed using purified T cells from different donors (data not shown).

Example 29: Redirected Cynomolgus T Cell Mediated Killing of CD123 Transfected Adherent Target Cells by Multispecific CD123/TCR Binding Polypeptides in an xCELLigence Based Assay To confirm the cross-reactivity of the multispecific polypeptides, the constructs were evaluated in a redirected cynomolgus T cell mediated killing of cynomolgus CD123 transfected adherent target cells in an xCELLigence based assay as described in Example 28.

The IC50 values obtained in this assay are listed in Table C-26. The results are depicted in FIG. 33, FIG. 34 and FIG. 35.

TABLE C-26

| IC50 (M) of T013700139 for redirected cynomolgus T cell mediated killing of cynomolgus CD123 transfected adherent target cells in an xCELLigence based assay, using an effector to target ratio of 15 to 1, analysed at 80 h after seeding. | | | |
|---|---|---|---|
| Sample ID | IC50 (M) | 95% LCI | 95% UCI |
| T017000139 | 1.1E-11 | 2.7E-12 | 4.8E-11 |

CD123/TCR multispecific polypeptide T017000139 could induce cynomolgus T cell mediated killing of CD123 positive cell lines (FIG. 33) and no killing activity was observed in the absence of T cells (FIG. 35). In addition, only when the cynomolgus CD123 tumour target antigen was present T cell mediated killing was observed (FIG. 34), indicating that the multispecific polypeptides are critically dependent on their target for induction of cytotoxicity.

The monovalent Nanobodies A0110056A10 and T0170056G05 and the irrelevant construct T017000129 did not induce target cell killing, confirming the requirement of cross-linking the T cell and target cell with the multispecific CD123/TCR binding polypeptide to induce killing.

The human-cynomolgus CD123 and TCR cross-reactivity of the multispecific polypeptide T017000139 was confirmed in an xCELLigence based killing assay.

The results were confirmed using purified T cells from different donors (data not shown).

Example 30: Impact of Multispecific CD123/TCR Binding Polypeptides on Cytokine Production During Redirected Killing The induction of cytokine release was monitored during the human and cyno T cell mediated CD123 killing based on the xCELLigence assay. The release of the cytokine IFN-γ and IL-6 was measured by ELISA. Briefly, human CD123 transfected CHO-K1 cells ($2 \times 10^4$ cells/well) were seeded in E-plate 96 in the presence of purified human or cynomolgus primary T cells ($3 \times 10E^5$ cells/well) with a serial dilution of multispecific TCR/CD123 binding polypeptides (starting at 125 nM) or a fixed concentration (125 nM) of irrelevant polypeptides, as described in Example 28. 72 h after the addition of the human or cyno primary T cells/polypeptides to the plates, human IFN-γ and human IL-6 production by the human primary T cells and cynomolgus IFN-γ by the cynomolgus primary T cells in the supernatant was measured.

The release of human IL-6 was measured in ELISA using the Human IL-6 Quantikine ELISA Kit (R&D systems, D6050), according to the manufacturer's instructions. The release of IFN-γ was determined as follows: Maxisorp 96-well ELISA plates (Nunc) were coated with anti-human IFN-γ antibody (BDBiosciences, 551221) respectively anti-cynomolgus IFN-γ antibody (Biolegend, 507502). After overnight incubation, plates were washed and blocked with PBS+2% BSA for 1 h at room temperature. Next, plates were incubated with 100 μl of the supernatants (2 fold diluted) and 1 μg/ml biotinylated anti-IFN-γ antibody (BD Biosciences, 554550) for 2 h 30 min while shaking, washed again and incubated with streptavidin-HRP (Dakocytomation, P0397). After 30 min, TMB One Solution (Promega, G7431) was added. The reaction was stopped with 2M $H_2SO_4$ and the polypeptide dose dependent production of IFN-γ was determined by measurement of the OD at 405 nm using the Tecan sunrise 4.

The results for IFN-γ are shown in FIG. 36. The results for IL-6 are shown in FIG. 37. The EC50 values obtained in these assays are listed in Table C-27 and Table C-28.

TABLE C-27

EC50 (M) of the TCR/CD123 binding polypeptides for IFN-γ secretion during the redirected T cell mediated killing of CD123 transfected adherent target cells in the xCELLigence based assay.

| Sample ID | human T cells | | | cynomolgus T cells | | |
|---|---|---|---|---|---|---|
| | EC50 (M) | 95% LCI | 95% UCI | EC50 (M) | 95% LCI | 95% UCI |
| T017000128 | 8.6E−11 | 6.6E−11 | 1.1E−10 | 1.0E−10 | 3.7E−11 | 2.9E−10 |
| T017000135 | 2.0E−09 | 1.3E−09 | 3.1E−09 | / | / | / |
| T017000138 | 4.0E−10 | 2.3E−10 | 7.0E−10 | 8.7E−10 | 2.1E−10 | 3.6E−09 |
| T017000139 | 1.0E−09 | 5.9E−10 | 1.9E−09 | 2.3E−09 | 7.8E−10 | 6.6E−09 |
| T017000116 | 8.1E−09 | 4.6E−09 | 1.4E−08 | / | / | / |

157

TABLE C-28

EC50 (M) of the TCR/CD123 binding polypeptides
for human IL-6 secretion during the redirected
human T cell mediated killing of CD123 transfected
adherent target cells in the xCELLigence based assay.

| | human T cells | | |
|---|---|---|---|
| Sample ID | EC50 (M) | 95% LCI | 95% UCI |
| T017000128 | 6.9E−11 | 3.8E−11 | 1.3E−10 |
| T017000135 | 5.9E−10 | 3.0E−10 | 1.2E−09 |
| T017000138 | 3.8E−11 | 1.8E−11 | 8.1E−11 |
| T017000139 | 4.8E−10 | 2.6E−10 | 9.0E−10 |
| T017000116 | 9.6E−09 | 5.6E−09 | 1.6E−08 |

Cytokine production was observed when the CD123 overexpressing CHO Flp-In cells and primary T cells were incubated with the CD123/TCR binding constructs. The irrelevant constructs T017000129 and T017000132 did not induce cytokine production.

Example 31: Redirected Autologous T Cell
Plasmacytoid Dendritic Cells (pDCs) and Basophil
Depletion by Multispecific CD123/TCR
Polypeptides in Healthy PBMC Cryopreserved peripheral blood mononucleocytes (PBMC) were thawed and washed with assay medium (RMPI 1640+10% FBS). 2×10^5 PBMCs were incubated with serial dilutions of multispecific polypeptides in 200 µL assay medium in a 96-well V-bottom plate and incubated at 37° C. in a 5% CO2 incubator. At indicated time points, cells were stained at 4° C. with monoclonal mouse anti-CD14-APC (Biolegend, 301808), anti-CD16-APC (Biolegend, 302012), anti-CD19-APC (Biolegend, 302212), anti-CD20-APC (Biolegend, 302312), anti-CD56-APC (Biolegend, 318310), anti-CD123-PE (Biolegend, 306006) and anti-HLA-DR-FITC (Biolegend, 307603) antibodies. In brief, cells were harvested and washed one time with FACS Buffer (D-PBS from Gibco, with 10% FBS from Sigma and 0.05% sodium azide from Merck) and resuspended in 25 µl human BD Fc Block, 0.5 µg/ml (BD Biosciences, 564220, 1000× diluted) for 10 minutes at RT. Next, 25 µl of the antibodies were added and incubated for 30 min at 4° C. according to the manufacturer's instructions. A separate well containing PBMC was resuspended in FACS buffer supplemented with 5 nM TOPRO3 (Molecular Probes, T3605) to distinguish live from dead cell population. Samples were washed 3 times, resuspended in FACS Buffer (D-PBS from Gibco, with 10% FBS from Sigma and 0.05% sodium azide from Merck) and then analysed via a FACS Canto (BD) cytometer equipped with FACS Diva software. Per sample, a total sample volume of 75 µl was acquired. Data analysis was performed using FACS Diva and Flowing software.

Based on the well containing the TOPRO stain, gating was set to exclude the dead cells. Human and cynomolgus pDC and basophils were identified as the Lineage marker (CD16, CD20, CD19, CD56) negative/CD123 positive population.

The results are depicted in FIG. 38.

Depletion of the human respectively cynomolgus CD123 positive population by the CD123/TCR multispecific polypeptides was observed after an incubation time of 5 h. When the targeting Nanobody was replaced by an irrelevant Nanobody, no depletion of the CD123 positive population was observed, indicating the requirement of cross-linking the T cell and target cell with the TCR/CD123 multispecific polypeptides to induce depletion.

The assay was repeated using PBMC from 3 different human donors and PBMC from 2 different cynomolgus monkeys, confirming the functionality of the TCR/CD123 multispecific polypeptides.

Example 32: Redirected Autologous Human T Cell
Monocyte Depletion by Multispecific CD123/TCR
Binding Polypeptides in Healthy Human PBMC
Samples To evaluate to depletion of monocytes, the assay was performed as described above, using Cryopreserved human PBMC that were thawed and washed with assay medium (RMPI 1640+10% FBS) and incubated with serial dilutions of multispecific polypeptide for either 5 h or 24 h. Staining of the cells was performed as described above. Monocytes were identified as the CD14+ population.

The results are depicted in FIG. 39.

After 5 h of incubation, no monocyte depletion was observed for the TCR/CD123 multispecific polypeptide and irrelevant Nanobodies. After 24 h, monocyte depletion was observed for the TCR/CD123 multispecific polypeptides and not for the irrelevant constructs. The assay was repeated using PBMC from 3 different donors, confirming the functionality of the TCR/CD123 multispecific polypeptides.

Example 33: Human T Cell Activation by the
Multispecific CD123/TCR Binding Polypeptides
During Redirected T Cell Killing of Autologous
CD123 Positive Cells in Healthy Human PBMC
Samples To characterize T cell activation during the TCR/CD123 multispecific polypeptides mediated depletion process, the autologous PBMC assay was performed as described above and the activation status of human T cells was monitored by measurement of the upregulation of CD69 after 24 h incubation. In brief, after the incubation time of 24 h, cells were stained 30 min at 4° C. with monoclonal mouse anti-CD3-FITC antibody (BD Biosciences, 555332) to identify the human T cells, and monoclonal mouse anti-human CD69-PE antibody (BD Biosciences, 557050) to evaluate T cell activation. Cells were washed 3 times, resuspended in FACS Buffer (D-PBS from Gibco, with 10% FBS from Sigma and 0.05% sodium azide from Merck) and then analysed via a FACS Canto (BD) cytometer equipped with FACS Diva software. Per sample, a total sample volume of 75 µl was acquired. Data analysis was performed using FACS Diva and Flowing software.

Exemplary results are shown in FIG. 40.

The data showed dose dependent upregulation of CD69 on human CD3+ T cells when PBMC were incubated with the multispecific CD123/TCR binding polypeptides. Incubation with the monovalent Nanobodies or irrelevant constructs did not result in CD69 upregulation.

Example 34: Characterization of Irrelevant
Constructs for Redirected T Cell Mediated Killing
of CD123 Target Cells in a Flow Cytometry Based
Assay To evaluate the safety of the TCR Nanobody T0170056G05, an in depth analysis of the irrelevant constructs (the monovalent Nanobodies and the multivalent polypeptide T017000129) was performed in the redirected T cell mediated target killing assay using an E:T ratio of 10:1 as described in Example 25 and 26. Construct T017000139 was taken along as positive control.

The results using the KG1a target cells are shown in FIG. 41, the results using the MOLM-13 are show in and FIG. 42. The EC50 values obtained are listed in Table C-29 and Table C-30.

TABLE C-29

EC50 (M) of T017000139 for redirected T cell mediated killing of CD123 positive KG1a cells in a flow cytometry based assay.

| | Human T cells | | | Cynomolgus T cells | | |
|---|---|---|---|---|---|---|
| Sample ID | EC50 (M) | 95% LCI | 95% UCI | EC50 (M) | 95% LCI | 95% UCI |
| T017000139 | 8.1E–11 | 7.4E–11 | 8.9E–11 | 1.7E–11 | 9.7E–12 | 3.1E–11 |

TABLE C-30

EC50 (M) of T017000139 for redirected T cell mediated killing of CD123 positive MOLM-13 cells in a flow cytometry based assay.

| Experiment 1 | | |
|---|---|---|
| | Cynomolgus T cells | |
| Sample ID | EC50 (M) | 95% LCI | 95% UCI |
| T017000139 | 6E–11 | 5.1E–11 | 7.1E–11 |

| Experiment 2 | | | | | |
|---|---|---|---|---|---|
| | Human T cells | | | Cynomolgus T cells | | |
| Sample ID | EC50 (M) | 95% LCI | 95% UCI | EC50 (M) | 95% LCI | 95% UCI |
| T017000139 | 3.0E–11 | 1.9E–11 | 4.7E–11 | 3.1E–11 | 1.9E–11 | 5.1E–11 |

The positive control T017000139 behaved as expected when using human and cynomolgus T cells. Neither the monovalent building blocks nor the irrelevant polypeptide T017000129 (CD123 building blocks were replaced with an irrelevant building block) induced killing of CD123 positive cells, confirming the specificity of the TCR/CD123 multi-specific polypeptides.

Example 35: Impact of Multispecific CD123/TCR Binding Polypeptides on Cytokine Production During Human Redirected Killing The induction of cytokine release was monitored during the human T cell mediated CD123 killing assay based on the FACS based readout. The release of the human cytokine IFN-γ and IL-6 was measured by ELISA. Briefly, MOLM-13 or KG1a were seeded in V-bottom 96-well plate ($2 \times 10^4$ cells/well) in the presence of purified human primary T cells ($3 \times 10^5$ cells/well) with a serial dilution of multispecific TCR/CD123 binding polypeptides irrelevant polypeptides, as described in Example 25. 72 h after the addition of the human primary T cells/polypeptides to the plates, human IFN-γ and IL-6 production by the human primary T cells in the supernatant was measured as described in Example 30.

The results are shown in FIGS. 43A and 43B. The EC50 values obtained in this assay are listed in Table C-31 and Table C-32.

TABLE C-31

EC50 (M) of the TCR/CD123 binding polypeptides for human IFN-γ secretion during the redirected human T cell mediated killing of CD123 positive MOLM-13 or KG1a cells in the flow cytometry based assay.

| | MOLM-13 | | | KG1a | | |
|---|---|---|---|---|---|---|
| Sample ID | EC50 (M) | 95% LCI | 95% UCI | EC50 (M) | 95% LCI | 95% UCI |
| T017000139 | 3.4E–10 | 2.5E–10 | 4.6E–10 | 3.2E–11 | 1.9E–11 | 5.4E–11 |

TABLE C-32

EC50 (M) of the TCR/CD123 binding polypeptides
for human IL-6 secretion during the redirected
human T cell mediated killing of CD123 positive
MOLM-13 cells in the flow cytometry based assay.

| Sample ID | EC50 (M) | 95% LCI | 95% UCI |
|---|---|---|---|
| T017000139 | 2.3E–11 | 1.5E–11 | 3.5E–11 |

Cytokine production was observed when the MOLM-13 of KG1a cells and human primary T cells were incubated with the CD123/TCR binding constructs. The irrelevant constructs T017000129 did not induce cytokine production.

Example 36: Characterisation of Target Independent Redirected Human or Cynomolgus Effector T Cell Killing for Multispecific CD123/TCR Binding Polypeptides in a Flow Cytometry Based Assay Using CD123 Negative Cell Lines To evaluate the CD123 independent redirected killing of multispecific polypeptides, the CD123 negative U-937 and NCI-H929 cell lines were evaluated in a flow cytometry based killing assay. U-937 and NCI-H929 cells were labelled with 8 μM PKH-26 membrane dye using the PKH26 red fluorescent cell linker kit (Sigma, PKH26GL-1KT) according to manufacturer's instruction and used as target cells. The assay was performed as described in Example 25 and 26 using primary human or cynomolgus T cells (E:T=10:1).

Exemplary results are shown in FIG. 44 and FIG. 45, for the NCI-H929 and U-937 cells, respectively.

The TCR/CD123 multispecific polypeptides and the irrelevant constructs showed only minimal T cell redirected U-937 killing activity (less than 6%), indicating that the multispecific polypeptides have good specificity for binding to CD123.

Example 37: Characterization of T Cell Activation for Multispecific CD123/TCR Binding Polypeptides During Redirected Effector T Cell Killing Assay Using CD123 Negative Cell Lines To monitor T cell activation following the treatment of T cells and CD123 negative cells with multispecific CD123/TCR binding polypeptides, the polypeptides were incubated for 24 h at 37° C. with $2.5 \times 10^4$ U-937 respectively NCI-H929 target cells in the presence of $2.5 \times 10^5$ primary T cells (E:T=10:1), as described in Example 25 and 26. T cell activation was evaluated as described before by monitoring the CD25 upregulation after 72 h of incubation on the CD4/CD8 T cell population was measured in flow cytometry as described in Example 27, using monoclonal mouse anti-CD4-APC (Biolegend, 300505), monoclonal mouse anti-CD8 APC (BD Biosciences, 555366) and monoclonal anti-CD25 (BD Biosciences, 557138) antibodies.

Exemplary results are shown in FIG. 46.

Evaluation of the T cell activation after incubation with the multispecific polypeptides and the U-937 or NCI-929 CD123 negative cell lines showed only minimal upregulation of CD25 for any of the multispecific polypeptides. So, in the presence of CD123 negative target cells there was only minimal T cell activation or killing by the T cells.

Example 38: Characterisation of Cytokine Production for Multispecific CD123/TCR Binding Polypeptides During Human Redirected Killing The aspecific induction of cytokine release was monitored during the human T cell mediated killing assay based on the FACS based readout. The release of the cytokine IFN-γ and IL-6 was measured by ELISA. Briefly, NCI-H929 were seeded in V-bottom 96-well plate ($2 \times 10^4$ cells/well) in the presence of purified human primary T cells ($3 \times 10E^5$ cells/well) with a serial dilution of multispecific TCR/CD123 binding polypeptides or irrelevant polypeptides, as described in Example 25. 72 h after the addition of the human primary T cells/polypeptides to the plates, IFN-γ and IL-6 production by the human primary T cells was measured in the supernatant as described in Example 30. The results are shown in FIG. 47.

Cytokine production was not observed when CD123 negative NCI-H929 cell line and human primary T cells were incubated with the CD123/TCR binding constructs.

Example 39: Impact of Multispecific CD123/TCR Binding Polypeptides on T Cell Proliferation During Redirected Killing To investigate the effect of the multispecific CD123/TCR binding polypeptides on the proliferation of the human T cells, gamma-irradiated (100 Gy) MOLM-13 cells were seeded in 96-well flat bottom microtiter plates (Greiner bio-one, 655 180, $2 \times 10^4$ cells/well) together with the multispecific polypeptides and the human primary T cells ($2 \times 10^5$ cells/well) and incubated for 72 hours at 37° C. in a humidified atmosphere of 5× CO2 in air. Next, cells were pulsed for approximately 18 hours with 3H-thymidine (3H-Tdr, New England Nuclear, Boston, MA, 20 Ci/mM specific activities), harvested on glass fiber filter strips, and then counted by liquid scintillation counting.

Exemplary results are shown in FIG. 48.

The CD123/TCR multispecific polypeptides induced T cell proliferation in a dose-dependent manner. No T cell proliferation was observed for the irrelevant construct T017000129.

In parallel, the effect of the multispecific CD123/TCR binding polypeptides on the proliferation of the human T cells in the absence of target cells was evaluated. Thereto, the multispecific polypeptides and the human primary T cells ($2 \times 10^5$ cells/well) were incubated for 72 hours at 37° C. in a humidified atmosphere of 5× CO2 in air. The proliferation was measured as described above. Data are shown in FIG. 49.

Example 40: Lytic Performance of Pre-Activated T Cells Versus Non-Activated T Cells To test the lytic performance of T cells in response to a multiple day-incubation period under stimulatory conditions, primary human T cells (isolated as described in Example 25) were thawed and pre-activated using Dynabeads® Human T-Activator CD3/CD28 (Gibco—Technologies, 11132D) using a T cell to beads ratio of 2:1. After 3 days, beads were replaced by fresh beads for an additional three days. Next, beads were removed and pre-activated and non-activated T cells were evaluated in a MOLM-13 target killing assay. In brief, non-activated or CD3/CD28 pre-activated primary T cells from the same donor were mixed with PKH labelled MOLM-13 cells at different E:T ratios (8:1, 2:1, 1:2, 1:4) and with serial dilutions of T017000114 or with PKH labelled KG1A cells at different E:T ratios (2:1, 1:2, 1:4, 1:8) and with serial dilutions of T017000139. Cytotoxicity readout after 24 h of incubation was performed as described above in Example 25.

The results are shown in FIG. 50 and FIG. 51, for the MOLM-13 and KG1a cells respectively. The EC50 values obtained in this assay are listed in Table C-33 and Table C-34, for the MOLM-13 and KG1a cells respectively.

TABLE C-33

EC50 (M) and % lysis for T017000114 for redirected human T cell mediated killing of MOLM-13 cells in a flow cytometry based assay, using pre-activated and non-activated T cells.

| | non-activated T cells | | | | pre-activated T cells | | | |
|---|---|---|---|---|---|---|---|---|
| Sample ID | EC50 (M) | 95% LCI | 95% UCI | % lysis | EC50 (M) | 95% LCI | 95% UCI | % lysis |
| T017000114 E:T ratio 8:1 | 1.4E−09 | 2.4E−10 | 7.8E−09 | 12 | 2.4E−10 | 1.9E−10 | 3.2E−10 | 43 |
| T017000114 E:T ratio 2:1 | 1.9E−09 | 6.2E−12 | 6.0E−07 | 10 | 6.8E−10 | 4.7E−10 | 9.9E−10 | 31 |
| T017000114 E:T ratio 1:2 | | | | | 1.0E−09 | 4.0E−10 | 2.6E−09 | 18 |

TABLE C-34

EC50 (M) and % lysis for T017000139 for redirected human T cell mediated killing KG1a cells in a flow cytometry based assay, using pre-activated and non-activated T cells.

| | non-activated T cells | | | | pre-activated T cells | | | |
|---|---|---|---|---|---|---|---|---|
| Sample ID | EC50 (M) | 95% LCI | 95% UCI | % lysis | EC50 (M) | 95% LCI | 95% UCI | % lysis |
| T017000139 E:T ratio 2:1 | 1.4E−10 | 8.1E−11 | 2.5E−10 | 19 | 4.5E−11 | 2.2E−11 | 9.1E−11 | 43 |
| T017000139 E:T ratio 1:2 | 7.7E−11 | 3.0E−12 | 2.0E−09 | 8 | 4.9E−11 | 2.2E−11 | 1.1E−10 | 20 |
| T017000139 E:T ratio 1:4 | 9.2E−11 | 2.8E−12 | 3.0E−09 | 4 | 5.8E−11 | 3.1E−11 | 1.1E−10 | 13 |
| T017000139 E:T ratio 1:8 | 3.4E−11 | 1.9E−13 | 6.1E−09 | 3 | 5.6E−11 | 2.3E−11 | 1.4E−10 | 8 |

Pre-activated T cells lysed the target cells more potently than the non-activated T cells at all E:T ratios tested. Pre-stimulation of effector cells with anti-CD3/anti-CD28 resulted in the higher lysis rates.

Example 41: Construction of Half-Life Extended (HLE) Multispecific CD123/TCR Binding Polypeptides and Control Polypeptides ALB11 (SEQ ID NO: 43), a Nanobody binding to human serum albumin (HSA), was linked to the CD123/TCR binding polypeptides to increase the in vivo half-life of the formatted molecules (WO 06/122787). A number of formats were generated with the TCR α/β recruiting Nanobody at the N-terminus and the CD123 tumour targeting Nanobodies or the albumin targeting Nanobody at the C-terminus using a 35GS linker and expressed as indicated above. Irrelevant constructs were generated by replacing the tumour antigen binding Nanobodies with an irrelevant anti-RSV Nanobody. An overview of the explored formats is shown in Table C-35.

TABLE C-35

Sample ID and description of HLE constructs.

| Sample ID | SEQ ID NO* | Description |
|---|---|---|
| A022600009 | 62 | T0170056G05-35GS-RSV007B02(Q108L)-35GS-ALB11 |
| T017000142 | 63 | T0170056G05(E1D)-35GS-A0110056A10-35GS-ALB11-A |
| T017000143 | 64 | T0170056G05(E1D)-35GS-A0110056A10-35GS-A0110055F03-35GS-ALB11-A |
| T017000144 | 65 | T0170056G05(E1D)-35GS-A0110056A10-35GS-ALB11-35GS-A0110055F03-A |
| T017000145 | 66 | T0170056G05(E1D)-35GS-A0110055F03-35GS-A0110056A10-35GS-ALB11-A |
| T017000146 | 67 | T0170056G05(E1D)-35GS-A0110055F03-35GS-ALB11-35GS-A0110056A10-A |

*SEQ ID NOs correspond to the sequence of the multispecific polypeptides without C-terminal tags or Ala-extension

Example 42: Albumin Binding Properties of ALB11 in the Multispecific Recruitment Polypeptides The binding affinities of the half-life extended multispe- [5] cific polypeptides to human, respectively cynomolgus serum albumin (SA) were measured by means of an SPR based affinity determination on a Biacore T100 instrument. Thereto, human (Sigma, A3782), respectively cynomolgus SA (produced in house) was immobilized onto a CM5 chip [10] via amine coupling, using EDC and NHS chemistry. TCR/ CD123 binding polypeptides were injected for 2 minutes at different concentrations (between 6.2 and 500 nM) and allowed to dissociate for 15 min at a flow rate of 45 µl/min. In between sample injections, the surfaces were regenerated [15] with 10 mM Glycine-HCl pH1.5. HBS-EP+ was used as running buffer. The kinetic constants were calculated from the sensorgrams using the BIAEvaluation software with an algorithm using a single cycle kinetics 1:1 binding model. The affinity constant KD was calculated from resulting [20] association and dissociation rate constants ka and kd, and is shown in Table C-36.

TABLE C-36

| Albumin binding properties of ALB11 in the HLE multispecific polypeptides. | | | | | |
|---|---|---|---|---|---|
| Human SA | | | Cynomolgus SA | | |
| $k_a$ (1/MS) | $k_d$ (1/s) | $K_D$ (M) | $k_a$ (1/MS) | $k_d$ (1/s) | $K_D$ (M) |
| T017000142 | 1.1E+05 | 7.2E–03 | 6.9E–08 | 9.0E+04 | 7.3E–03 | 8.1E–08 |
| T017000143 | 1.6E+05 | 9.5E–03 | 5.9E–08 | 1.2E+05 | 9.4E–03 | 7.6E–08 |
| T017000144 | 9.1E+04 | 7.8E–03 | 8.5E–08 | 7.4E+04 | 8.1E–03 | 1.1E–07 |

TABLE C-36-continued

| Albumin binding properties of ALB11 in the HLE multispecific polypeptides. | | | | | |
|---|---|---|---|---|---|
| Human SA | | | Cynomolgus SA | | |
| $k_a$ (1/MS) | $k_d$ (1/s) | $K_D$ (M) | $k_a$ (1/MS) | $k_d$ (1/s) | $K_D$ (M) |
| T017000145 | 1.1E+05 | 8.5E–03 | 7.6E–08 | 1.0E+05 | 9.9E–03 | 9.8E–08 |
| T017000146 | 8.4E+04 | 8.5E–03 | 1.0E–07 | 6.8E+04 | 8.8E–03 | 1.3E–07 |
| A022600009 | 1.1E+05 | 8.0E–03 | 7.5E–08 | 8.5E+04 | 8.0E–03 | 9.4E–08 |
| ALB11 | 5.3E+05 | 1.6E–03 | 3.0E–09 | 5.1E+05 | 1.6E–03 | 3.2E–09 |

Formatting of the ALB11 building block into the multi-specific recruitment polypeptides resulted in an allowable drop in affinity for binding to human and cynomolgus serum albumin.

Example 43: Redirected T Cell Mediated Killing of MOLM-13 Target Cells by HLE CD123/TCR Binding Polypeptides in a Flow Cytometry Based Assay Since the addition of the ALB11 Nanobody, and the binding to serum albumin (SA) might influence the potency of the polypeptides, the HLE CD123/TCR binding polypeptides were evaluated for redirected human and cynomolgus [30] T cell mediated killing of CD123 positive MOLM-13 target cells based on flow cytometry assay as described in Example 25 and 26 in the absence or presence of 30 µM SA.

The EC50 values obtained in this assay are listed in Table C-37. The results are depicted in FIG. 52.

TABLE C-37

| | EC50 (M) and % lysis of HLE CD123/TCR binding polypeptides for redirected T cell mediated killing of MOLM-13 cells in a flow cytometry based assay using an E:T ratio of 10:1. | | | | | | | |
|---|---|---|---|---|---|---|---|---|
| | human T cells | | | | cynomolgus T cells | | | |
| Sample ID | % lysis | EC50 (M) | 95% LCI | 95% UCI | % lysis | EC50 (M) | 95% LCI | 95% UCI |
| T017000138 | 21 | 1.1E–10 | 8.8E–11 | 1.3E–10 | 54 | 1.5E–10 | 1.1E–10 | 2.1E–10 |
| T017000144 | 23 | 2.7E–11 | 2.0E–11 | 3.6E–11 | 56 | 2.3E–11 | 1.7E–11 | 3.0E–11 |
| T017000144 + SA | 24 | 2.6E–10 | 1.9E–10 | 3.5E–10 | 52 | 1.1E–10 | 9.3E–11 | 1.2E–10 |
| T017000139 | 20 | 2.0E–11 | 9.3E–12 | 4.4E–11 | 56 | 2.9E–11 | 2.3E–11 | 3.5E–11 |
| T017000146 | 21 | 2.5E–11 | | | 57 | 2.9E–11 | 2.3E–11 | 3.7E–11 |
| T017000146 + SA | 25 | 2.3E–10 | 1.7E–10 | 2.9E–10 | 44 | 1.6E–10 | 1.3E–10 | 1.9E–10 |

All the HLE multispecific CD123/TCR binding polypeptides showed dose dependent killing of the MOLM-13 cells both by human and by cynomolgus T cells. The inclusion of ALB11 in the construct did not decrease the potency. Upon addition of HSA or CSA, a small drop in potency was observed while the efficacy was not affected.

Example 44: Redirected T Cell Mediated Killing of KG1a Target Cells by HIE CD123/TCR Binding Polypeptides in a Flow Cytometry Based Assay The half-life extended TCR/CD123 binding polypeptides were also evaluated for redirected human and cynomolgus T cell mediated killing of CD123 KG1a target cells based on a flow cytometry assay as described in Example 24 and 25, in the absence or presence of 30 µM serum albumin.

The EC50 values obtained in this assay are listed in Table C-38. The results are depicted in FIG. 53.

TABLE C-38

EC50 (M) and % lysis of HLE CD123/TCR binding polypeptides for redirected T cell mediated killing of KG1a cells in a flow cytometry based assay using an E:T ratio of 10:1.

| | | human T cells | | | cynomolgus T cells | | | |
|---|---|---|---|---|---|---|---|---|
| Sample ID | % lysis | EC50 (M) | 95% LCI | 95% UCI | % lysis | EC50 (M) | 95% LCI | 95% UCI |
| T017000138 | 64 | 1.6E–10 | 1.3E–10 | 2.0E–10 | 21 | 2.8E–11 | 2.3E–11 | 3.4E–11 |
| T017000143 | 62 | 1.9E–10 | 1.6E–10 | 2.3E–10 | 25 | 4.7E–11 | 2.9E–11 | 7.5E–11 |
| T017000144 | 67 | 4.1E–11 | 3.4E–11 | 5.0E–11 | 28 | 6.3E–12 | 9.3E–13 | 4.3E–11 |
| T017000143 + SA | 60 | 1.4E–09 | 1.0E–09 | 1.9E–09 | 25 | 8.6E–10 | 7.1E–10 | 1.0E–09 |
| T017000144 + SA | 58 | 2.9E–10 | 2.4E–10 | 3.6E–10 | 29 | 6.6E–11 | 3.4E–11 | 1.3E–10 |
| T017000139 | 67 | 8.1E–11 | 7.4E–11 | 8.9E–11 | 34 | 1.7E–11 | 9.7E–12 | 3.1E–11 |
| T017000145 | 65 | 7.4E–11 | 6.4E–11 | 8.6E–11 | 35 | 1.6E–11 | 1.1E–11 | 2.4E–11 |
| T017000146 | 64 | 6.6E–11 | 5.9E–11 | 7.4E–11 | 34 | 1.5E–11 | 7.2E–12 | 3.0E–11 |
| T017000145 + SA | 51 | 5.9E–10 | 4.9E–10 | 7.2E–10 | 32 | 1.2E–10 | 7.4E–11 | 1.9E–10 |
| T017000146 + SA | 60 | 6.8E–10 | 5.8E–10 | 8.0E–10 | 36 | 2.0E–10 | 1.1E–10 | 3.5E–10 |
| T017000128 | 55 | 3.1E–10 | 3.0E–10 | 3.3E–10 | 32 | 2.8E–10 | 1.3E–10 | 6.1E–10 |
| T017000142 | 59 | 6.8E–10 | 6.2E–10 | 7.5E–10 | 29 | 2.2E–10 | 1.4E–10 | 3.6E–10 |
| T017000142 + SA | 48 | 3.1E–09 | 3.0E–09 | 3.3E–09 | 20 | 3.2E–10 | 2.9E–10 | 3.5E–10 |

All the HLE multispecific CD123/TCR binding polypeptides showed dose dependent killing of the KG1a cells both by human and by cynomolgus T cells. The inclusion of ALB11 in the construct did not decrease the potency. Upon addition of HSA or CSA, a small drop in potency was observed while the efficacy was not affected.

Example 45: Impact of HLE Multispecific CD123/TCR Binding Polypeptide T017000144 on Cytokine Production During Redirected Killing The induction of cytokine release was monitored during human T cell mediated killing assay based on the FACS based readout. The release of IFN-γ and IL-6 was measured by ELISA. Briefly, MOLM-13 ($2\times10^4$ cells/well) were seeded in V-bottom 96-well plate in the presence of purified human primary T cells ($3\times10^5$ cells/well) with a serial dilution of multispecific TCR/CD123 binding polypeptides or irrelevant polypeptides, as described in Example 35. 72 h after the addition of the human primary T cells/polypeptides to the plates, IFN-γ and IL-6 production by the human primary T cells in the supernatant was measured as described in Example 30.

The EC50 values obtained in this assay are listed in Table C-39 and Table C-40. The results are depicted in FIG. 54.

TABLE C-39

| EC50 (M) of the TCR/CD123 binding polypeptides for human IFN-γ secretion during the redirected human T cell mediated killing of CD123 positive MOLM-13 cells in the flow cytometry based assay. | | | |
|---|---|---|---|
| Sample ID | EC50 (M) | 95% LCI | 95% UCI |
| T017000139 | 3.4E–10 | 2.5E–10 | 4.6E–10 |
| T017000144 | 1.9E–10 | 1.3E–10 | 2.9E–10 |

TABLE C-40

| EC50 (M) of the TCR/CD123 binding polypeptides for human IL-6 secretion during the redirected human T cell mediated killing of CD123 positive MOLM-13 cells in the flow cytometry based assay. | | | |
|---|---|---|---|
| Sample ID | EC50 (M) | 95% LCI | 95% UCI |
| T017000139 | 2.3E–11 | 1.5E–11 | 3.5E–11 |
| T017000144 | 1.6E–11 | 9.9E–12 | 2.7E–11 |

Cytokine production was observed when the MOLM-13 cells and human primary T cells were incubated with the HLE CD123/TCR binding construct T017000144. The irrelevant construct T017000129 did not induce cytokine production.

Example 46: Impact of HLE Multispecific CD123/TCR Binding Polypeptides on T Cell Proliferation During Redirected Killing To investigate the effect of the HLE multispecific CD123/TCR binding polypeptides on the proliferation of the human T cells, gamma-irradiated (100 Gy) MOLM-13 cells were seeded in 96-well flat bottom microtiter plates ($2\times10^4$ cells/well) together with the HLE multispecific polypeptide T017000144 and the human primary T cells ($2\times10^5$ cells/well) and incubated for 72 hours at 37° C. in a humidified atmosphere of 5× CO2 in air in the absence of SA.

T017000129 was taken along as negative control. Next, cells were pulsed for approximately 18 hours with 3H-thymidine (3H-Tdr, New England Nuclear, Boston, MA, 20 Ci/mM specific activities), harvested on glass fiber filter strips, and then counted by liquid scintillation counting.

Exemplary results are shown in FIG. 55.

The HLE CD123/TCR multispecific polypeptide T017000144 induced T cell proliferation in a dose-dependent manner. No T cell proliferation was observed for the irrelevant construct T017000129.

Example 47: Redirected Autologous T Cell Plasmacytoid Dendritic Cells (pDCs) and Basophil Depletion by HLE CD123/TCR Multispecific Polypeptides in Healthy Human PBMC Samples and Healthy Cynomolgus PBMC The HLE constructs were further evaluated in the human and cynomolgus autologous PBMC assay in the absence of SA, as described in Example 31. The depletion of CD123 positive cells (pDC: Lineage negative, CD123 positive, HLA-DR positive and basophils: Lineage negative, CD123 positive, HLA-DR negative) by multispecific polypeptides was evaluated after an incubation time of 5 h.

The results are depicted in FIG. 56 and FIG. 57, for the human and cynomolgus PBMC respectively.

The HLE CD123/TCR multispecific polypeptides were able to deplete CD123+ pDCs and basophils within human and cynomolgus PBMC by redirected T cells. Construct T017000144 was the most potent polypeptide. Construct T017000142, composed of one TCR building block, ALB11 and only one CD123 building block did not show functionality in the PBMC assay after 5 h. The human cynomolgus cross-reactivity of the HLE CD123/TCR multispecific polypeptides was confirmed in the autologous setting.

Example 48: Redirected Autologous T Cell Monocyte Depletion by HLE CD123/TCR Multispecific Polypeptides in Healthy Human PBMC Samples The depletion of monocytes (CD14+ cells) by the HLE multispecific polypeptides in an autologous human PBMC setting was evaluated after an incubation time of 24 h in the absence of SA. The assay was performed as described in Example 32.

The results are depicted in FIG. 58.

The HLE multispecific polypeptides were able to deplete CD123+ monocytes within human PBMC by redirected T cells. Construct T017000144 was the most potent polypeptide. Construct T017000142, composed of one TCR building block, ALB11 and only one CD123 building block showed functionality in the autologous monocyte depletion assay after 24 h.

Example 49: In Vivo Efficacy and Safety in a Non-Human Primate Model

In vivo efficacy and safety of non-HLE and HLE multispecific CD123/TCR binding Nanobodies are evaluated in a non-human primate model.

Animals treated with a reference compound are included as positive control. Treatment with non-HLE IRR/TCR binding polypeptides is used as specificity control for the CD123-targeting moiety of the multispecific polypeptides. The reference compound and the non-HLE multispecific CD123/TCR binding polypeptides are administered via continuous i.v. infusion after a 7-day NaCl infusion 'pre-treatment' of cynomolgus monkeys. The non-HLE multispecific CD123/TCR binding polypeptides are administered for 4 weeks as 4-day on/3-day off infusion at equimolar doses to the reference compound in a weekly dose escalation scheme according to Table C-41. The HLE multispecific CD123/TCR binding polypeptide is administered to cynomolgus monkeys via bolus i.v. injections on days 1, 2, 3, 8, 15, and 22 in a weekly dose escalation scheme according to Table C-41.

TABLE C-41

Treatment regimen.

| Group | Compound | Dose levels (ng/kg/day) | | | | Route of administration |
|---|---|---|---|---|---|---|
| | | Test week 1 | Test week 2 | Test week 3 | Test week 4 | |
| 1 | Reference | D1-5: 100 | D8-12: 300 | D15-19: 600 | D22-26: 1000 | continuous 24 h infusion |
| 2 | Irrelevant/TCR polypeptide | D1-5: 49.5 | D8-12: 148.4 | D15-19: 296.8 | D22-26: 494.6 | continuous 24 h infusion |
| 3 | Non-HLE CD123/TCR polypeptide | D1-5: 74.0 | D8-12: 222.1 | D15-19: 444.3 | D22-26: 740.4 | continuous 24 h infusion |
| 4 | HLE CD123/TCR polypeptide | D1: 0.6 D2: 0.4 D3: 0.34 | D8: 2.21 | D15: 4.42 | D22: 7.13 | i.v. bolus injection |

T cell redistribution from the blood is monitored by measuring T cell subsets, as described in Table C-42, using flow cytometry and differential blood count on test days −7, d-4, d1 (pre-dose+4 hrs post-dose), d4, d8 (pre-dose+4 hrs post-dose), d11, d15 (pre-dose+4 hrs post-dose), d18, d22 (pre-dose+4 hrs post-dose), d25, d29, d32, and d36.

TABLE C-42

Marker combinations for blood T cell phenotyping.

| Marker | Cells | Unit |
|---|---|---|
| CD3+CD4+ | T-helper cells (Th) | % of PBMC and cells/μL |
| CD3+CD8+ | Cytotoxic T-cells (Tc) | % of PBMC and cells/μL |
| CD25+CD3+CD4+ | activated Th | % of CD3+CD4+ and cells/μL |
| CD25+CD3+CD8+ | activated Tc | % of CD3+CD8+ and cells/μL |
| PD1+CD3+CD4+ | PD (programmed cell death protein) upregulation on Th | % of CD3+CD4+ and cells/μL |
| PD1+CD3+CD8+ | PD upregulation on Tc | % of CD3+CD8+ and cells/μL |
| CD25+PD1+CD3+CD4+ | PD upregulation on activated Th | % of CD3+CD4+CD25+ and cells/μL |
| CD25+PD1+CD3+CD8+ | PD upregulation on activated Tc | % of CD3+CD8+CD25+ and cells/μL |

In vivo efficacy is assessed by evaluation of the percentage and number of CD123+ cells in PBMC, as detailed in Table C-43, using flow cytometry and differential blood count in the blood on test days −7, d-4, d1 (pre-dose+4 hrs post-dose), d4, d8 (pre-dose+4 hrs post-dose), d11, d15 (pre-dose+4 hrs post-dose), d18, d22 (pre-dose+4 hrs post-dose), d25, d29, d32, and d36.

TABLE C-43

Marker combinations for assessment of depletion of CD123+ cells.

| Marker | Cells | Unit |
|---|---|---|
| CD14−$^{low}$CD123+ | pDC (plamacytoid dendritic cells) based on CD123 marker and basophils and mDCs (myeloid dendritic cells) | % of PBMC and cells/μL |
| CD14−$^{low}$CD303+ | pDC based on CD303 marker | % of PBMC and cells/μL |
| CD14−$^{low}$CD123+CD303+ | overlap between CD123 and CD303 | % of PBMC and cells/μL |

TABLE C-43-continued

Marker combinations for assessment of depletion of CD123+ cells.

| Marker | Cells | Unit |
|---|---|---|
| CD14+ | monocytes | % of PBMC and cells/μL |
| CD14+CD123+ | CD123+ monocytes | % of CD14+ and cells/μL |
| CD123+ | absolute no. of target cells based on CD123 | % of PBMC and cells/μL |
| CD303+ | absolut no. of CD303 cells | % of PBMC and cells/μL |

Safety is assessed by evaluation of cytokines (IL-1β, IL-2, IL-4, IL-5, IL-6, IL-8, IL-10, IL-12(p70), TNF-α, TNF-β, IFN-γ) in the serum on test days −7, d-4, d1 (4 hrs post-dose), d4, d8 (4 hrs post-dose), d11, d15 (4 hrs post-dose), d18, d22 (4 hrs post-dose), d25, d29, d32, and d36.

Serum samples for PK analysis are collected on days −7, d-4, d1 (pre-dose+4 hrs post-dose), d4, d8 (pre-dose+4 hrs post-dose), d11, d15 (pre-dose+4 hrs post-dose), d18, d22 (pre-dose+4 hrs post-dose), d25, d29, d32, and d36.

Serum samples for ADA analysis are collected on days −7, d1 (pre-dose), d8 (pre-dose), d15 (pre-dose), d22 (pre-dose), d29, and d36.

On day 4 and day 25, blood T cells are isolated from all animals and tested in an exhaustion test as described in Example 25.

On day 29, necropsy is performed on the group 2 animals. On day 36, necropsy is performed on all remaining animals.

Example 50: In Vivo Efficacy and Safety in a Non-Human Primate Model—Multispecific CD123/TCR Binding Nanobody, Experimental Results In vivo efficacy and safety of the multispecific CD123/TCR binding polypeptide T017000139 was evaluated in a non-human primate model.

Animals treated with the reference compound (MGD006, Macrogenics) were included as positive control. Treatment with the irrelevant/TCR binding polypeptide T017000129 was used as specificity control for the CD123-targeting moiety of the multispecific polypeptide. The reference compound, the irrelevant/TCR binding polypeptide and the multispecific CD123/TCR binding polypeptide were administered via continuous i.v. infusion after a 7-day NaCl infusion 'pre-treatment' of cynomolgus monkeys. The irrelevant/TCR binding polypeptide and the multispecific CD123/TCR binding polypeptide were administered for 4 weeks as 4-day on/3-day off infusion at equimolar doses to the reference compound in a weekly dose escalation scheme according to Table C-44.

TABLE C-44

Treatment regimen.

| | | Dose levels (ng/kg/day) | | | | |
|---|---|---|---|---|---|---|
| Group | Compound | Test week 1 (D1-5) | Test week 2 (D8-12) | Test week 3 (D15-19) | Test week 4 (D22-26) | Route of administration |
| 1 | Reference compound MGD006 | 100 | 300 | 600 | 1000 | continuous 24 h infusion |
| 2 | Irrelevant/TCR polypeptide | 49.5 | 148.4 | 296.8 | 494.6 | continuous 24 h infusion |

TABLE C-44-continued

|  | | Treatment regimen. | | | | |
|--|--|--|--|--|--|--|
|  | | Dose levels (ng/kg/day) | | | | |
| Group | Compound | Test week 1 (D1-5) | Test week 2 (D8-12) | Test week 3 (D15-19) | Test week 4 (D22-26) | Route of administration |
| 3 | (T017000129) CD123/TCR polypeptide T017000139 | 74.0 | 222.1 | 444.3 | 740.4 | continuous 24 h infusion |

T cell redistribution from the blood was monitored by measuring T cell subsets using flow cytometry on test days −7, d-4, d1 (pre-dose+4 hrs post-dose), d4, d8 (pre-dose+4 hrs post-dose), d11, d15 (pre-dose+4 hrs post-dose), d18, d22 (pre-dose+4 hrs post-dose), d25, d29, d32, and d36.

As shown in FIG. 59, in the positive control group treated with the reference compound, the numbers of circulating CD4+CD3+ and CD8+ CD3+ T cells fluctuated during the different dosing cycles, suggesting a trafficking and/or margination, rather than depletion. In contrast, treatment with CD123/TCR polypeptide or with the irrelevant/TCR polypeptide did not results in a strong fluctuation of CD4+CD3+ or CD8+ CD3+ T cell numbers.

The circulating CD123+ CD14− cell numbers were explored as a pharmacodynamic endpoint to asses in vivo efficacy by measuring the number of CD123+CD14− cells in PBMC using flow cytometry in the blood on test days −7, d-4, d1 (pre-dose+4 hrs post-dose), d4, d8 (pre-dose+4 hrs post-dose), d11, d15 (pre-dose+4 hrs post-dose), d18, d22 (pre-dose+4 hrs post-dose), d25, d29, d32, and d36.

The results are depicted in FIG. 60. CD123+ CD14− cells were depleted in the animals treated with the reference compound MGD006 (positive control), although a loss of efficacy was observed towards the 4th dosing cycle. Treatment with CD123/TCR polypeptide caused a depletion of CD123+CD14− cells in the blood already from the first dosing cycle, that persisted through the 4th and final dosing cycle. In animals treated with the irrelevant/TCR polypeptide, no significant depletion of CD123+CD14− cells was observed.

Next, the expression of PD-1 on circulating CD4+CD3+ T cells and CD8+CD3+ T cells was explored as a surrogate marker to assess T cell exhaustion in vivo. For this, PD-1 expression was measured in PBMC using flow cytometry in the blood on test days −7, d-4, d1 (pre-dose+4 hrs post-dose), d4, d8 (pre-dose+4 hrs post-dose), d11, d15 (pre-dose+4 hrs post-dose), d18, d22 (pre-dose+4 hrs post-dose), d25, d29, d32, and d36.

The results are depicted in FIG. 61. PD-1 expression was strongly increased on the majority of CD4+CD3+ T cells and CD8+CD3+ T cells in the animals treated with the reference compound MGD006 (positive control) and remained on approximately half of the CD4+CD3+ T cells and CD8+CD3+ T cells after termination of dosing. In contrast, PD-1 expression remained at baseline upon treatment with CD123/TCR polypeptide or with the irrelevant/TCR polypeptide throughout the dosing cycles.

Safety was assessed by evaluation of cytokines (IL-1β, IL-2, IL-4, IL-5, IL-6, IL-10, IL-12(p70), TNF-α, TNF-β, IFN-γ) in the serum on test days −7, d-4, d1 (4 hrs post-dose), d4, d8 (4 hrs post-dose), d11, d15 (4 hrs post-dose), d18, d22 (4 hrs post-dose), and d25.

The levels of the following cytokines remained below detection limit of the assay: IL-1β, IL-2, IL-4, IL-5, IL-10, IL-12(p70), TNF-α, TNF-β and IFN-γ. Interleukin-6 was detected in low concentrations in the positive control group at the beginning of the first dosing cycle. This increase was transient and only in one animal. In the group treated with CD123/TCR polypeptide, one animal showed detectable IL-6 concentrations pre-dose and one animal showed a transient small increase at the beginning of the second dosing cycle, suggesting manipulative stress. In the group treated with irrelevant/TCR polypeptide, one animal showed a transient small increase in IL-6 in the third dosing cycle, again suggesting manipulative stress. The results from the IL-6 measurements are depicted in FIG. 62.

TABLE A-1

Sequence alignment of TCR cluster A binders-part 1

```
                                        1         10        20        30        40        50        60        70    78

SEQ ID NO: 42   T0170PMP056G05:   EVQLVESGGGLVQPGGSLRLSCVASGDVHKINFLGWYRQAPGKEREKVAHISIGDQTDYADSAKGRFTISRDESKNMV
SEQ ID NO: 85   T0170PMP053D01:   ...........................K...A....A...............T.E....M.T.T....DV..........A....
SEQ ID NO: 136  T0170PMP067D01:   ...........................K...A....A...............T.E....M.T.T....EV..........A....
SEQ ID NO: 124  T0170PMP056F01:   ...........................K.P.A....A...............T.E....M.T.T....EV..........A....
SEQ ID NO: 152  T0170PMP069A06:   ...........................K...A....A...............T.E....M.T.T....EV.E........A....
SEQ ID NO: 141  T0170PMP067F02:   ...........................K...A....A...............T.E....M.T.T....EV.H........A....
SEQ ID NO: 142  T0170PMP068C03:   ...........................K...A....A...............T.E....M.T.T....EVA.........A....
SEQ ID NO: 103  T0170PMP055E05:   ...........................K...A....A................E....M.T.T....EV..........A....
SEQ ID NO: 96   T0170PMP055C02:   ...........................K...A....A...............T.E....M..T....EV..........A....
SEQ ID NO: 137  T0170PMP067D06:   ...........................K...A....A................E....M.T.T....EV..........AT...
SEQ ID NO: 105  T0170PMP055F03:   .................................................I..............S..........E........
SEQ ID NO: 130  T0170PMP061A02:   .................................................I............A.S..........E........
SEQ ID NO: 122  T0170PMP056D11:   .................................................I............R.S..........E........
SEQ ID NO: 153  T0170PMP069B02:   .............R...................................I..............S..........E........
SEQ ID NO: 172  T0170PMP070G02:   .................................................I..............S..........E........
SEQ ID NO: 79   T0170PMP028B01:   ...................................A...S................GL.T.T..T.......Y......AR...
SEQ ID NO: 81   T0170PMP028G06:   ...................................A...S...............L.T.T..T.......Y......AR...
SEQ ID NO: 106  T0170PMP055F06:   ...................................A...S...............L.T.T..A.......Y......AR...
SEQ ID NO: 78   T0170PMP027A05:   ...................................A...S...............L.T.T..T...............A....
SEQ ID NO: 83   T0170PMP040C01:   ...................................A...S...............L.T.T..T...............A....
SEQ ID NO: 80   T0170PMP028F10:   ...........R.....P.A...S................M.T.T..A...............A....
SEQ ID NO: 82   T0170PMP029F08:   ...................................A...S...............M.T.T..A...............A....
SEQ ID NO: 90   T0170PMP055A08:   .............S.....................A...S...............M.T.T..A...............A....
```

TABLE A-1-continued

```
SEQ ID NO: 109   T0170PMP055G09:  ..............S.......A..S..............V.T.T..A........
SEQ ID NO: 145   T0170PMP068D05:  ..............S....P.A..S..............M.T.T..A........
SEQ ID NO: 151   T0170PMP068F08:  ..............S.......A..S.............GM.T.T..A........
SEQ ID NO: 171   T0170PMP070F11:  ..............S.......A..S....C........M.T.T..A........
SEQ ID NO: 163   T0170PMP069E11:  .....................A..E...I...C....DM.T.T..A........
SEQ ID NO: 175   T0170PMP084B07:  .....................A..E...I........DM.T.T..E.Q......
SEQ ID NO: 87    T0170PMP055A01:  ...........R.........A......I.....A....M.T.T..A........
SEQ ID NO: 88    T0170PMP055A02:  .....................A......I.....A....M.T.T..A........
SEQ ID NO: 99    T0170PMP055D03:  .....................A......I.....A....M.T.T..A.N......
SEQ ID NO: 101   T0170PMP055D10:  .....................A......I.....A....M.T.T..A....G...
SEQ ID NO: 147   T0170PMP068E01:  ................E....A......I.....A....M.T.T..A........
SEQ ID NO: 177   T0170PMP084E03:  .....................A......I.....A....M.T.T..A........
```

Sequence alignment of TCR cluster A binders-part 1 continued

```
                   79        90        100       110
                   | ab      |         | a        |
Kabat #:
SEQ ID NO: 42    T0170PMP056G05:  YLQMNSLKPEDTAVYFCRAFSRIYPYDYWGQGTLVTVSS
SEQ ID NO: 85    T0170PMP053D01:  ...T.........V...G.L..N................
SEQ ID NO: 136   T0170PMP067D01:  ...T.........V...G.L..N................
SEQ ID NO: 124   T0170PMP056F01:  ...T.........V...G.L..N................
SEQ ID NO: 152   T0170PMP069A06:  ...TG........V...G.L..N................
SEQ ID NO: 141   T0170PMP067F02:  ...T.........V...G.L..N.....Q..........
SEQ ID NO: 142   T0170PMP068C03:  ...T.........V...G.L..N.....Q..........
SEQ ID NO: 103   T0170PMP055E05:  ...T.T.......V...G.L..N.....Q..........
SEQ ID NO: 96    T0170PMP055C02:  ...T.T.......V...G.L..N.....Q..........
SEQ ID NO: 137   T0170PMP067D06:  ...T.........G........N....N..........
SEQ ID NO: 105   T0170PMP055F03:  ......................L................
SEQ ID NO: 130   T0170PMP061A02:  ......................L................
```

TABLE A-1-continued

| SEQ ID NO: | Identifier | Sequence |
|---|---|---|
| SEQ ID NO: 122 | T0170PMP056D11: | ...........L.................. |
| SEQ ID NO: 153 | T0170PMP069B02: | ...........L.......Q.......... |
| SEQ ID NO: 172 | T0170PMP070G02: | ......A....L.......Q.......... |
| SEQ ID NO: 79 | T0170PMP028B01: | ...........G..L...N....Q...... |
| SEQ ID NO: 81 | T0170PMP028G06: | ...........G..L...N........... |
| SEQ ID NO: 106 | T0170PMP055F06: | ...........G..L...N........... |
| SEQ ID NO: 78 | T0170PMP027A05: | ......H....G..L...N....Q...... |
| SEQ ID NO: 83 | T0170PMP040C01: | ...........G..L...N....Q...... |
| SEQ ID NO: 80 | T0170PMP028F10: | ...........G..L...N....Q...... |
| SEQ ID NO: 82 | T0170PMP029F08: | ...........G..L...N........... |
| SEQ ID NO: 90 | T0170PMP055A08: | ...S.......G..L...N........... |
| SEQ ID NO: 109 | T0170PMP055G09: | ...S.......G..L...N....Q...... |
| SEQ ID NO: 145 | T0170PMP068D05: | ...S.......G..L...N....Q...... |
| SEQ ID NO: 151 | T0170PMP068F08: | ...S.......G..L...N....Q...... |
| SEQ ID NO: 171 | T0170PMP070F11: | ...S.......G..L...N....Q...... |
| SEQ ID NO: 163 | T0170PMP069E11: | ...........L..L...N........... |
| SEQ ID NO: 175 | T0170PMP084B07: | ...........L..L...N........... |
| SEQ ID NO: 87 | T0170PMP055A01: | ..............Y...N........... |
| SEQ ID NO: 88 | T0170PMP055A02: | ..............Y...N........... |
| SEQ ID NO: 99 | T0170PMP055D03: | ..............Y...N........... |
| SEQ ID NO: 101 | T0170PMP055D10: | ..............Y...N........... |
| SEQ ID NO: 147 | T0170PMP068E01: | ..............Y...N........... |
| SEQ ID NO: 177 | T0170PMP084E03: | .........G....Y...N........... |

TABLE A-1-continued

Sequence alignment of TCR cluster A binders-part 2

```
                          1        10        20        30        40        50        60        70   78
                          |         |         |         |         |         |         |         |    |
Kabat #:                  EVQLVESGGGLVQPGGSLRLSCVASGDVHKINFLGWYRQAPGKEREKVAHISIGDQTDYADSAKGRFTISRDESKNMV SEQ ID NO: 42   T0170PMP056G05:  EVQLVESGGGLVQPGGSLRLSCVASGDVHKINFLGWYRQAPGKEREKVAHISIGDQTDYADSAKGRFTISRDESKNMV
SEQ ID NO: 178  T0170PMP084E05:  ......................................A.........H....A...M...T..A.......A
SEQ ID NO: 107  T0170PMP055F08:  ......................................A.........I....A...M.T..A.......A
SEQ ID NO: 114  T0170PMP056C01:  ......................................A.G.......I....A...M...T..A.......A
SEQ ID NO: 126  T0170PMP056G02:  .................A....................A.........I....A...M...T..A.......A
SEQ ID NO: 133  T0170PMP067A03:  ......................................A.........I....A.H.M...T..A.......A
SEQ ID NO: 135  T0170PMP067C09:  ......................................A.........I....A...M...T..A.......AE.
SEQ ID NO: 150  T0170PMP068F06:  ......................................A.........I....A...M...T..A....A.V
SEQ ID NO: 158  T0170PMP069D02:  .................M....................A.........I....A...M...T..A.......A
SEQ ID NO: 169  T0170PMP070D07:  ......................................A.........I....A...M...T..A.......A
SEQ ID NO: 176  T0170PMP084C02:  ......................................A.........I....A...M...T..A.......A
SEQ ID NO: 131  T0170PMP061B04:  ......................................A.........I....A...M...T..A.......A
SEQ ID NO: 159  T0170PMP069D07:  ......................................A.........I.V.A...M...T..A.......A
SEQ ID NO: 113  T0170PMP056B11:  .........................A.T.A........A.........I....A...M...T..A.......A
SEQ ID NO: 180  T0170PMP084F10:  .................W.A..................A.........I....A...M...T..T.......A
SEQ ID NO: 116  T0170PMP056C03:  ......................................A.........I....A...M...T..A.......A
SEQ ID NO: 156  T0170PMP069C04:  ......................................A.........I.A.G.M...T..A.......A
SEQ ID NO: 121  T0170PMP056D02:  ......................................A.........I....A...M...T..A.......A
SEQ ID NO: 132  T0170PMP067A01:  ......................................A.........I....A.GM.T..A.......A
SEQ ID NO: 134  T0170PMP067B06:  ......................................A.........I.AR.M...T..A.......A
SEQ ID NO: 164  T0170PMP069F05:  ......................................A.........I.H..A...M...T..A.......A
SEQ ID NO: 179  T0170PMP084F04:  ......................................A.........I.V..A...M...T..A.......A
SEQ ID NO: 98   T0170PMP055C10:  ......................................A.........V....A...M...T..A.......A
SEQ ID NO: 86   T0170PMP053E10:  ......................................R.........I....A...M...T..A.E.....A
```

TABLE A-1-continued

```
SEQ ID NO: 92    T0170PMP055B01:  .........R......I......A...M..T..A.V.E........A....
SEQ ID NO: 155   T0170PMP069C01:  .........R......I......A..MI..T..A...E........A....
SEQ ID NO: 138   T0170PMP067D09:  ..........A...I......A...M..T..A.S.G........A....
SEQ ID NO: 139   T0170PMP067E03:  ............A......I......A...M..T..A.S.........A....
SEQ ID NO: 120   T0170PMP056D01:  ..........D..........A......M..T.A.A...EF........P....
SEQ ID NO: 140   T0170PMP067E06:  ..........D..........A......M..T.A.A...EF........P....
SEQ ID NO: 162   T0170PMP069E09:  ....................A......M..T.A.A...EF........P....
SEQ ID NO: 157   T0170PMP069C05:  ..........D..........A......M..T.A.A...EF........P....
SEQ ID NO: 166   T0170PMP070B08:  ..........D..........A......M..T.A.A...EF........P....
SEQ ID NO: 89    T0170PMP055A03:  ................................T..A.........A....
SEQ ID NO: 118   T0170PMP056C07:  ................................T..A.........A....
```

Sequence alignment of TCR cluster A binders-part 2 continued

```
                          79       90    100    110
                          | ab      |     | a     |
Kabat #:
SEQ ID NO: 42    T0170PMP056G05:  YLQMNSLKPEDTAVYFCRAFSRIYPYDYWGQGTLVTVSS
SEQ ID NO: 178   T0170PMP084E05:  .................Y......N..............
SEQ ID NO: 107   T0170PMP055F08:  .................Y......N..............
SEQ ID NO: 114   T0170PMP056C01:  .................Y......N..............
SEQ ID NO: 126   T0170PMP056G02:  .................Y......N..............
SEQ ID NO: 133   T0170PMP067A03:  .................Y......N..............
SEQ ID NO: 135   T0170PMP067C09:  .................Y......N..............
SEQ ID NO: 150   T0170PMP068F06:  .................Y......N..............
SEQ ID NO: 158   T0170PMP069D02:  .................Y......N..............
SEQ ID NO: 169   T0170PMP070D07:  .........A.......Y......N..............
SEQ ID NO: 176   T0170PMP084C02:  ....D....A.......Y......N..............
SEQ ID NO: 131   T0170PMP061B04:  .................Y......N..............
SEQ ID NO: 159   T0170PMP069D07:  .........A.......Y......N..............
```

TABLE A-1-continued

| SEQ ID NO: | | Sequence |
|---|---|---|
| SEQ ID NO: 113 | T0170PMP056B11: | ..........Y......N............ |
| SEQ ID NO: 180 | T0170PMP084F10: | ..........Y......N............ |
| SEQ ID NO: 116 | T0170PMP056C03: | ..........Y......N....Q....... |
| SEQ ID NO: 156 | T0170PMP069C04: | ..........Y......N....Q....... |
| SEQ ID NO: 121 | T0170PMP056D02: | ..........Y......N..R..Q...... |
| SEQ ID NO: 132 | T0170PMP067A01: | ..........Y......N....Q....... |
| SEQ ID NO: 134 | T0170PMP067B06: | ..........Y......N....Q....... |
| SEQ ID NO: 164 | T0170PMP069F05: | ......L....Y......N....Q...... |
| SEQ ID NO: 179 | T0170PMP084F04: | ......A......Y......N....Q.... |
| SEQ ID NO: 98 | T0170PMP055C10: | H.........Y......N....Q....... |
| SEQ ID NO: 86 | T0170PMP053E10: | ..........Y......N....Q....... |
| SEQ ID NO: 92 | T0170PMP055B01: | ..........Y......N....Q....... |
| SEQ ID NO: 155 | T0170PMP069C01: | ..........Y......N....Q....... |
| SEQ ID NO: 138 | T0170PMP067D09: | ..L.N.......Y......N.......... |
| SEQ ID NO: 139 | T0170PMP067E03: | ..L.N.......Y......N.......... |
| SEQ ID NO: 120 | T0170PMP056D01: | H........L..G......N....Q..... |
| SEQ ID NO: 140 | T0170PMP067E06: | .........L..G......N....Q..... |
| SEQ ID NO: 162 | T0170PMP069E09: | .........L..G......N....Q..... |
| SEQ ID NO: 157 | T0170PMP069C05: | .........L..G......S....Q..... |
| SEQ ID NO: 166 | T0170PMP070B08: | ...V.....L..G......N....Q..... |
| SEQ ID NO: 89 | T0170PMP055A03: | ............G..........Q...... |
| SEQ ID NO: 118 | T0170PMP056C07: | ............G........R........ |

Sequence alignment of TCR cluster A binders-part 3

```
Kabat #:              1    10   20   30   40   50   60   70 78
SEQ ID NO: 42  T0170PMP056G05: EVQLVESGGGLVQPGGSLRLSCVASGDVHKINFLGWYRQAPGKEREKVAHISIGDQTDYADSAKGRFTISRDESKNMV
SEQ ID NO: 168 T0170PMP070C09: .............................P...................................T...A.........
```

TABLE A-1-continued

| SEQ ID NO | Clone ID | Sequence |
|---|---|---|
| SEQ ID NO: 174 | T0170PMP082B04: | .....P..............T.A.A.........A.... |
| SEQ ID NO: 110 | T0170PMP056A02: | ....A...............T............A.... |
| SEQ ID NO: 108 | T0170PMP055G05: | .....H.....A........T..A..........A.... |
| SEQ ID NO: 154 | T0170PMP069B08: | .......Y....A........T..A..........A.... |
| SEQ ID NO: 97 | T0170PMP055C06: | ..H.......H.....A........H.P.T..V..........A.... |
| SEQ ID NO: 100 | T0170PMP055D06: | .......H....A........T..V..........A.... |
| SEQ ID NO: 102 | T0170PMP055E01: | .....E.Y....A........T.A.VA....F.....A.... |
| SEQ ID NO: 104 | T0170PMP055F02: | .....E.Y....A........T.A.VA....F.....A.... |
| SEQ ID NO: 115 | T0170PMP056C02: | .....E.Y..P.A........T.A.VA....F.Q...A.... |
| SEQ ID NO: 173 | T0170PMP070G06: | .....E.Y..P.A........T.A.VA....F.....A.... |
| SEQ ID NO: 165 | T0170PMP069G08: | ....Q.....E.Y....A........T.A.VA....F.....A.... |
| SEQ ID NO: 170 | T0170PMP070E07: | .....E.Y....A........T.A.VA....F.....GA.. |
| SEQ ID NO: 146 | T0170PMP068D07: | .....E.Y....A........T.A.VA....F.....V.. |
| SEQ ID NO: 127 | T0170PMP056G11: | .....E.Y....A........T.A.VA....F.....GA.. |
| SEQ ID NO: 143 | T0170PMP068C07: | .....E.Y....A........T.A.AA....F.....A.... |
| SEQ ID NO: 160 | T0170PMP069E02: | .....E.Y....A........T.A.AA....F.....A.... |
| SEQ ID NO: 144 | T0170PMP068C11: | .....E.Y....A........T.A.AA....F.....A.... |
| SEQ ID NO: 148 | T0170PMP068E08: | .....E.Y....A........T.A.AA....F.....A.... |
| SEQ ID NO: 123 | T0170PMP056E02: | ..E......E.Y..A........T.A.VA....F..L..A.... |
| SEQ ID NO: 112 | T0170PMP056A10: | .....S.LL...AV.....GV.T.A.A..SHF.....A.... |
| SEQ ID NO: 116 | T0170PMP056C10: | .....S.LL...AV....M.T.T.A.A..SHF.....A.... |
| SEQ ID NO: 93 | T0170PMP055B02: | .....S.LL...A....C..M..T.A.A..SHF.....A.... |
| SEQ ID NO: 111 | T0170PMP056A08: | .....S.LL...A......M..T.A.A..SHF.....A.... |
| SEQ ID NO: 117 | T0170PMP056C04: | .....S.LL...A......M..T.A.A..SHF.....A.... |
| SEQ ID NO: 129 | T0170PMP057D06: | .....S.LL...A......M..T.A.A..SHF.....A.... |
| SEQ ID NO: 84 | T0170PMP053A03: | .....S.LL...AV.....M..T.A.A..SHF.....A.... |
| SEQ ID NO: 161 | T0170PMP069E07: | .....S.LL...A......M..T.A.A..SHF.....A.... |

TABLE A-1-continued

```
SEQ ID NO: 95   T0170PMP055B11:  ..................M...T.A.A...HF..........A.....
SEQ ID NO: 125  T0170PMP056F08:  .........G...A...S.LL.M...T.A.A...HF..........A.....
SEQ ID NO: 167  T0170PMP070B09:  .........A...S.LL.....T.A.A...SHF.........A.....
SEQ ID NO: 149  T0170PMP068F04:  .........A...S.LL.M...T.A.V...SYF.........A.....
SEQ ID NO: 91   T0170PMP055A10:  .........A...S.LL.M...A.A.A...HF..........A.....
SEQ ID NO: 94   T0170PMP055B03:  ......P.A...S.LL.M...T.A.A...HF..........A.....
SEQ ID NO: 128  T0170PMP057B02:  ..W......A..S.Y.....S....H.L.T.T.AA.......AR...
```

Sequence alignment of TCR cluster A binders-part 3 continued

```
                Kabat #:         79         90        100        110
                                 |          |         |a         |
                                 ab         ab SEQ ID NO: 42   T0170PMP056G05:  YLQMNSLKPEDTAVYFCRAFSRIYPYDYWGQGTLVTVSS
SEQ ID NO: 168  T0170PMP070C09:  ...................G..................
SEQ ID NO: 174  T0170PMP082B04:  ...................G..................
SEQ ID NO: 110  T0170PMP056A02:  ...................G...W..........Q...
SEQ ID NO: 108  T0170PMP055G05:  ...................G..............Q...
SEQ ID NO: 154  T0170PMP069B08:  ...................G..................
SEQ ID NO: 97   T0170PMP055C06:  .....N.............G..............Q...
SEQ ID NO: 100  T0170PMP055D06:  F....N.............G..............Q...
SEQ ID NO: 102  T0170PMP055E01:  ...................G...W..........Q...
SEQ ID NO: 104  T0170PMP055F02:  ...................G...W..........Q...
SEQ ID NO: 115  T0170PMP056C02:  ...................G...W..........Q...
SEQ ID NO: 173  T0170PMP070G06:  ...................G...W..........Q...
SEQ ID NO: 165  T0170PMP069G08:  ...................G...W..........Q...
SEQ ID NO: 170  T0170PMP070E07:  ...................G...W..........Q...
SEQ ID NO: 146  T0170PMP068D07:  ...................G...W..........Q...
SEQ ID NO: 127  T0170PMP056G11:  ...................G...W..........Q...
SEQ ID NO: 143  T0170PMP068C07:  ...................G...W..........Q...
```

TABLE A-1-continued

| SEQ ID NO: 160 | T0170PMP069E02: | ................................................................G..W.......... |
| SEQ ID NO: 144 | T0170PMP068C11: | ................................................................G............Q..... |
| SEQ ID NO: 148 | T0170PMP068E08: | ..............................R.................................G..W...........Q..... |
| SEQ ID NO: 123 | T0170PMP056E02: | ..............................R.................................G..W........... |
| SEQ ID NO: 112 | T0170PMP056A10: | ..............................R.................................G...........Q..... |
| SEQ ID NO: 119 | T0170PMP056C10: | ..............................R.................................G...........Q..... |
| SEQ ID NO: 93  | T0170PMP055B02: | ..............................R.................................G.............. |
| SEQ ID NO: 111 | T0170PMP056A08: | ..............................R.................................G.............. |
| SEQ ID NO: 117 | T0170PMP056C04: | ..............................R.................................G......H....... |
| SEQ ID NO: 129 | T0170PMP057D06: | ..............................R.................................G...........Q..... |
| SEQ ID NO: 84  | T0170PMP053A03: | ..........................G.R..................................G.............. |
| SEQ ID NO: 161 | T0170PMP069E07: | ..............................R.................................G.............. |
| SEQ ID NO: 95  | T0170PMP055B11: | ..............................R.................................G.............. |
| SEQ ID NO: 125 | T0170PMP056F08: | ..............................R.................................G.............. |
| SEQ ID NO: 167 | T0170PMP070B09: | ........................N.R....................................G.............. |
| SEQ ID NO: 149 | T0170PMP068F04: | ..............................R.................................G...........Q..... |
| SEQ ID NO: 91  | T0170PMP055A10: | ..............................R.................................G........R..Q..... |
| SEQ ID NO: 94  | T0170PMP055B03: | ..............................R.................................G...........Q..... |
| SEQ ID NO: 128 | T0170PMP057B02: | ..............................L..H.G..L..N............Q..... |

TABLE A-2

Sequence alignment of CD123 binding Nanobody A0110056A10 and family members thereof.

|  |  | Kabat #: | 1 | 10 | 20 | 30 | 40 | 50 | 60 | 70 |
|---|---|---|---|---|---|---|---|---|---|---|
| SEQ ID NO: 1 | A0110PMP056A10: | | EVQLVKSGGGLVQAGGSLRLSCAASGITSKINDMGWYRQTPGNYREWVASITATGTTNYRDSVKGRFTISRDNAKSTVY | | | | | | | |
| SEQ ID NO: 2 | A0110PMP055A10: | | .....E.........................N.S..SDA.......K...............N... | | | | | | | |
| SEQ ID NO: 3 | A0110PMP055B11: | | .....E.........................N....S.A.......K...............N... | | | | | | | |
| SEQ ID NO: 3 | A0110PMP055B12: | | .....E.........................N....S.A.......K...............N... | | | | | | | |
| SEQ ID NO: 4 | A0110PMP056D09: | | .....E....................P.......F...........................N... | | | | | | | |
| SEQ ID NO: 5 | A0110PMP056G10: | | .....E................................................N... | | | | | | | |
| SEQ ID NO: 6 | A0110PMP057B09: | | .....E......................S.V...............K...............N... | | | | | | | |
| SEQ ID NO: 2 | A0110PMP057D11: | | .....E.........................N.S..SDA.......K...............N... | | | | | | | |

|  |  | Kabat #: | 80 abc | 90 | 100 | 110 |
|---|---|---|---|---|---|---|
| SEQ ID NO: 1 | T0170PMP056G05: | | LQMNSLKPEDTTVYYCNTFPPISNF-WGQGTLVTVSS | | | |
| SEQ ID NO: 2 | A0110PMP055A10: | | ..................A......-......Q...... | | | |
| SEQ ID NO: 3 | A0110PMP055B11: | | ..................A......-......Q...... | | | |
| SEQ ID NO: 3 | A0110PMP055B12: | | ..................A......-............ | | | |
| SEQ ID NO: 4 | A0110PMP056D09: | | ..................-.................. | | | |
| SEQ ID NO: 5 | A0110PMP056G10: | | .................................... | | | |
| SEQ ID NO: 6 | A0110PMP057B09: | | ..................A......-......Q...... | | | |
| SEQ ID NO: 2 | A0110PMP057D11: | | ..................A......-......Q...... | | | |

TABLE A-3

Sequence alignment of CD123 binding Nanobody A0110055F03 and family members thereof.

```
                          1        10        20        30        40        50        60        70
Kabat #:                  |         |         |         |         |         |    a    |         |
SEQ ID NO: 7  A0110PMP055F03: EVQLVESGGGLVQAGGPLRLSCAASGRTFSSYVMGWFRQAPGKEREFVAAIYWSNGKTQYTDSVKGRFTISGDNAKNTVY
SEQ ID NO: 8  A0110PMP055A04: .............................S....................S...E.........L............
SEQ ID NO: 9  A0110PMP056C03: .............................S..................S..E..E.........L............
SEQ ID NO: 10 A0110PMP056G01: .............................S.................W.S..E.........L............
```

```
                          80        90        100       110
Kabat #:                  | abc     |         | abcdefgh |
SEQ ID NO: 7  A0110PMP055F03: LQMNSLNPEDTAVYYCVADKDETGFRTLPIAYDYWGQGTQVTVSS
SEQ ID NO: 8  A0110PMP055A04: ..............................RD.............
SEQ ID NO: 9  A0110PMP056C03: ..............................RY.............
SEQ ID NO: 10 A0110PMP056G01: ...N..........................RD.............
```

TABLE A-4

CDRs and framework sequences of CD123 binding building blocks, plus preferred combinations as provided in formula I, namely FR1-CDR1-FR2-CDR2-FR3-CDR3-FR4. "SEQ" refers to the given SEQ ID NO. The first column refers to the SEQ ID NO of the complete ISV, i.e. FR1-CDR1-FR2-CDR2-FR3-CDR3-FR4. CDR1, CDR2 and CDR3 were determined according to Kontermann, 2010.

| SEQ | Nanobody | SEQ | FR1 | SEQ | CDR1 | SEQ | FR2 | SEQ | CDR2 | SEQ | FR3 | SEQ | CDR3 | SEQ | FR4 |
|---|---|---|---|---|---|---|---|---|---|---|---|---|---|---|---|
| 1 | A0110PMP 056A10 | 26 | EVQLVKSGGGLVQ AGGSLRLSCAAS | 11 | GITSKIN DMG | 30 | WYRQTPGNY REWVA | 17 | SITATG TTN | 34 | YRDSVKGRFTISRDNAKSTV YLQMNSLKPEDTTVYYCNT | 21 | FPPISNF | 40 | WGQGTL VTVSS |
| 2 | A0110PMP 055A10/ A0110PMP 057D11 | 27 | EVQLVESGGGLVQ AGGSLRLSCAAN | 12 | GISSKSD AMG | 31 | WYRQTPGKY REWVA | 17 | SITATG TTN | 35 | YRDSVKGRFTISRDNAKNTV YLQMNSLKPEDTTVYYCNT | 22 | FPAISNF | 41 | WGQGTQ VTVSS |
| 3 | A0110PMP 055B11/ A0110PMP 055B12 | 27 | EVQLVESGGGLVQ AGGSLRLSCAAN | 13 | GITSKSN AMG | 31 | WYRQTPGKY REWVA | 17 | SITATG TTN | 35 | YRDSVKGRFTISRDNAKNTV YLQMNSLKPEDTTVYYCNT | 22 | FPAISNF | 41 | WGQGTQ VTVSS |
| 4 | A0110PMP 056D09 | 28 | EVQLVESGGGLVQ AGGSLRLSCAAS | 14 | GIPSKIN DMG | 32 | WFRQTPGNY REWVA | 17 | SITATG TTN | 35 | YRDSVKGRFTISRDNAKNTV YLQMNSLKPEDTTVYYCNT | 21 | FPPISNF | 40 | WGQGTL VTVSS |
| 5 | A0110PMP 056G10 | 28 | EVQLVESGGGLVQ AGGSLRLSCAAS | 11 | GITSKIN DMG | 30 | WYRQTPGNY REWVA | 17 | SITATG TTN | 34 | YRDSVKGRFTISRDNAKSTV YLQMNSLKPEDTTVYYCNT | 21 | FPPISNF | 40 | WGQGTL VTVSS |
| 6 | A0110PMP 057B09 | 28 | EVQLVESGGGLVQ AGGSLRLSCAAS | 15 | GITSKSN VMG | 31 | WYRQTPGKY REWVA | 17 | SITATG TTN | 35 | YRDSVKGRFTISRDNAKNTV YLQMNSLKPEDTTVYYCNT | 22 | FPAISNF | 41 | WGQGTQ VTVSS |
| 7 | A0110PMP 055F03 | 29 | EVQLVESGGGLVQ AGGPLRLSCAAS | 16 | GRTFSSY VMG | 33 | WFRQAPGKE REFVA | 18 | AIYWSN GKTQ | 36 | YTDSVKGRFTISGDNAKNTV YLQMNSLNPEDTAVYYCVA | 23 | DKDETGFRTL PIAYDY | 41 | WGQGTQ VTVSS |
| 8 | A0110PMP 055A04 | 28 | EVQLVESGGGLVQ AGGSLRLSCAAS | 16 | GRTFSSY VMG | 33 | WFRQAPGKE REFVA | 19 | AIYWSS GKTE | 37 | YTDSVKGRFTLSGDNAKNTV YLQMNSLNPEDTAVYYCVA | 24 | DKDRDGFRTL PIAYDY | 41 | WGQGTQ VTVSS |
| 9 | A0110PMP 056C03 | 28 | EVQLVESGGGLVQ AGGSLRLSCAAS | 16 | GRTFSSY VMG | 33 | WFRQAPGKE REFVA | 19 | AIYWSS GKTE | 38 | YTESVKGRFTLSGDNAKNTV YLQMNSLNPEDTAVYYCVA | 25 | DKDRYGFRTL PIAYDY | 41 | WGQGTQ VTVSS |
| 10 | A0110PMP 056G01 | 28 | EVQLVESGGGLVQ AGGSLRLSCAAS | 16 | GRTFSSY VMG | 33 | WFRQAPGKE REFVA | 20 | AIWWSS GKTE | 39 | YTDSVKGRFTLSGDNAKNTV YLQMNNILNPEDTAVYYCVA | 24 | DKDRDGFRTL PIAYDY | 41 | WGQGTQ VTVSS |

TABLE A-5

CDRs and framework sequences of TCR binding building blocks, plus preferred combinations as provided in formula I, namely FR1-CDR1-FR2-CDR2-FR3-CDR3-FR4. "SEQ" refers to the given SEQ ID NO. The first column refers to the SEQ ID NO of the complete ISV, i.e. FR1-CDR1-FR2-CDR2-FR3-CDR3-FR4. CDR1, CDR2 and CDR3 were determined according to Kontermann, 2010.

| SEQ | Nanobody | SEQ | FR1 | SEQ | CDR1 | SEQ | FR2 | SEQ | CDR2 | SEQ | FR3 | SEQ | CDR3 | SEQ | FR4 |
|---|---|---|---|---|---|---|---|---|---|---|---|---|---|---|---|
| 42 | T0170PMP 056G05 | 226 | EVQLVESGGGLVQP GGSLRLSCVAS | 181 | GDVHKIN FLG | 251 | WYRQAPGKE REKVA | 192 | HISIGD QTD | 277 | YADSAKGRFTISRDESKNMV YLQMNSLKPEDTAVYFCRA | 218 | FSRIYPYDY | 320 | WGQGTL VTVSS |
| 78 | T0170PMP 027A05 | 227 | EVQLVESGGGLVQP GGSLRLSCAAS | 182 | GSVHKIN FLG | 252 | WYRQAPGKE RELVA | 193 | TITIGD TTD | 278 | YADSAKGRFTISRDEAKNMV YLQMNSLKPEDTAVHFCRA | 219 | GSRLYPYNY | 321 | WGQGTQ VTVSS |
| 79 | T0170PMP 028B01 | 227 | EVQLVESGGGLVQP GGSLRLSCAAS | 182 | GSVHKIN FLG | 253 | WYRQAPGKE RGLVA | 193 | TITIGD TTD | 279 | YADYAKGRFTISRDEARNMV YLQMNSLKPEDTAVYFCRA | 219 | GSRLYPYNY | 321 | WGQGTQ VTVSS |
| 80 | T0170PMP 028F10 | 228 | EVQLVESGGGLVQP GRSLRLPCAAS | 182 | GSVHKIN FLG | 254 | WYRQAPGKE REMVA | 194 | TITIGD ATD | 280 | YADSAKGRFTISRDEAKNMV YLQMNSLKPEDTAVYFCRA | 219 | GSRLYPYNY | 321 | WGQGTQ VTVSS |
| 81 | T0170PMP 028G06 | 227 | EVQLVESGGGLVQP GGSLRLSCAAS | 182 | GSVHKIN FLG | 252 | WYRQAPGKE RELVA | 193 | TITIGD TTD | 279 | YADYAKGRFTISRDEARNMV YLQMNSLKPEDTAVYFCRA | 219 | GSRLYPYNY | 320 | WGQGTL VTVSS |
| 82 | T0170PMP 029F08 | 227 | EVQLVESGGGLVQP GGSLRLSCAAS | 182 | GSVHKIN FLG | 254 | WYRQAPGKE REMVA | 194 | TITIGD ATD | 280 | YADSAKGRFTISRDEAKNMV YLQMNSLKPEDTAVYFCRA | 219 | GSRLYPYNY | 320 | WGQGTL VTVSS |
| 83 | T0170PMP 040001 | 227 | EVQLVESGGGLVQP GGSLRLSCAAS | 182 | GSVHKIN FLG | 252 | WYRQAPGKE RELVA | 193 | TITIGD TTD | 280 | YADSAKGRFTISRDEAKNMV YLQMNSLKPEDTAVYFCRA | 219 | GSRLYPYNY | 321 | WGQGTQ VTVSS |
| 84 | T0170PMP 053A03 | 229 | EVQLVESGGGLVQP GGSLRLSCAVS | 183 | GSVHLLN FLG | 254 | WYRQAPGKE REMVA | 195 | HITIAD ATD | 281 | YSHFAKGRFTISRDEAKNMV YLQMNSLRPEDTAVYFCRA | 220 | GSRIYPYDY | 320 | WGQGTL VTVSS |
| 85 | T0170PMP 053D01 | 230 | EVQLVESGGGLVQP GGSLRLSCAAS | 184 | GAVHKIN FLG | 255 | WYRQTPEKE REMVA | 196 | TITIGD DVD | 282 | YADSAKGRFTISRDEAKNMV YLQMTSLKPEDTAVYVCRA | 219 | GSRLYPYNY | 320 | WGQGTL VTVSS |
| 86 | T0170PMP 053E10 | 231 | EVQLVESGGGLVQP GGSLRLSCRAS | 185 | GDVHKIN ILG | 256 | WYRQAPAKE REMVA | 197 | HITIGD ATD | 283 | YAESAKGRFTISRDEAKNMV YLQMNSLKPEDTAVYFCRA | 221 | YSRIYPYNY | 321 | WGQGTQ VTVSS |
| 87 | T0170PMP 055A01 | 232 | EVQLVESGGGLVRP GGSLRLSCAAS | 185 | GDVHKIN ILG | 256 | WYRQAPGKE REMVA | 197 | HITIGD ATD | 280 | YADSAKGRFTISRDEAKNMV YLQMNSLKPEDTAVYFCRA | 221 | YSRIYPYNY | 320 | WGQGTL VTVSS |
| 88 | T0170PMP 055A02 | 227 | EVQLVESGGGLVQP GGSLRLSCAAS | 185 | GDVHKIN ILG | 256 | WYRQAPAKE REMVA | 197 | HITIGD ATD | 280 | YADSAKGRFTISRDEAKNMV YLQMNSLKPEDTAVYFCRA | 221 | YSRIYPYNY | 320 | WGQGTL VTVSS |
| 89 | T0170PMP 055A03 | 226 | EVQLVESGGGLVQP GGSLRLSCVAS | 181 | GHVHKIN FLG | 251 | WYRQAPGKE REKVA | 198 | HITIGD QAD | 280 | YADSAKGRFTISRDEAKNMV YLQMNSLKPEDTAVYFCRA | 220 | GSRIYPYDY | 321 | WGQGTQ VTVSS |
| 90 | T0170PMP 055A08 | 233 | EVQLVESGGGSVQP GGSLRLSCAAS | 182 | GSVHKIN FLG | 254 | WYRQAPGKE REMVA | 194 | TITIGD ATD | 284 | YADSAKGRFTISRDEAKNMV YLQMNSLSPEDTAVYFCRA | 219 | GSRLYPYNY | 320 | WGQGTL VTVSS |
| 91 | T0170PMP 055A10 | 227 | EVQLVESGGGLVQP GGSLRLSCAAS | 183 | GSVHLLN FLG | 254 | WYRQAPGKE REMVA | 199 | HISIAD ATD | 285 | YAHFAKGRFTISRDEAKNMV YLQMNSLRPEDTAVYFCRA | 220 | GSRIYPYDY | 322 | WGRGTQ VTVSS |

TABLE A-5-continued

CDRs and framework sequences of TCR binding building blocks, plus preferred combinations as provided in formula I, namely FR1-CDR1-FR2-CDR2-FR3-CDR3-FR4. "SEQ" refers to the given SEQ ID NO. The first column refers to the SEQ ID NO of the complete ISV, i.e. FR1-CDR1-FR2-CDR2-FR3-CDR3-FR4. CDR1, CDR2 and CDR3 were determined according to Kontermann, 2010.

| SEQ | Nanobody | SEQ | FR1 | SEQ | CDR1 | SEQ | FR2 | SEQ | CDR2 | SEQ | FR3 | SEQ | CDR3 | SEQ | FR4 |
|---|---|---|---|---|---|---|---|---|---|---|---|---|---|---|---|
| 92 | T0170PMP 055B01 | 231 | EVQLVESGGGLVQP GGSLRLSCRAS | 185 | GDVHKIN ILG | 256 | WYRQAPAKE REMVA | 200 | HITTIGD ATV | 283 | YAESAKGRFTISRDEAKNMV YLQMNSLKPEDTAVYFCRA | 221 | YSRIYPYNY | 321 | WGQGTQ VTVSS |
| 93 | T0170PMP 055B02 | 227 | EVQLVESGGGLVQP GGSLRLSCAAS | 183 | GSVHLLN FLG | 257 | WYRQCPGKE REMVA | 195 | HITIAD ATD | 281 | YSHFAKGRFTISRDEAKNMV YLQMNSLRPEDTAVYFCRA | 220 | GSRIYPYDY | 320 | WGQGTL VTVSS |
| 94 | T0170PMP 055B03 | 234 | EVQLVESGGGLVQP GGSLRPSCAAS | 183 | GSVHLLN FLG | 254 | WYRQAPGKE REMVA | 195 | HITIAD ATD | 285 | YAHFAKGRFTISRDEAKNMV YLQMNSLRPEDTAVYFCRA | 220 | GSRIYPYDY | 321 | WGQGTQ VTVSS |
| 95 | T0170PMP 055B11 | 227 | EVQLVESGGGLVQP GGSLRLSCAAS | 183 | GSVHLLN FLG | 254 | WYRQAPGKE REMVA | 195 | HITIAD ATD | 285 | YAHFAKGRFTISRDEAKNMV YLQMNSLRPEDTAVYFCRA | 220 | GSRIYPYDY | 320 | WGQGTL VTVSS |
| 96 | T0170PMP 055C02 | 230 | EVQLVESGGGLVQP GGSLKLSCAAS | 184 | GAVHKIN FLG | 255 | WYRQTPEKE REMVA | 201 | HITIGD EVD | 286 | YADSAKGRFTISRDEAKNMV YLQMTSLTPEDTAVYVCRA | 219 | GSRLYPYNY | 321 | WGQGTQ VTVSS |
| 97 | T0170PMP 055C06 | 235 | EVQLVESGGGLVHP GGSLRLSCAAS | 181 | GDVHKIN FLG | 258 | WHRQPPGKE REKVA | 202 | HITIGD VTD | 287 | YADSAKGRFTISRDEAKNMV YLQMNNLKPEDTAVYFCRA | 220 | GSRIYPYDY | 321 | WGQGTQ VTVSS |
| 98 | T0170PMP 055C10 | 227 | EVQLVESGGGLVQP GGSLRLSCAAS | 186 | GDVHKIN VLG | 256 | WYRQAPAKE REMVA | 197 | HITIGD ATD | 288 | YADSAKGRFTISRDEAKNMV HLQMNSLKPEDTAVYFCRA | 221 | YSRIYPYNY | 321 | WGQGTQ VTVSS |
| 99 | T0170PMP 055D03 | 227 | EVQLVESGGGLVQP GGSLRLSCAAS | 185 | GDVHKIN ILG | 256 | WYRQAPGKE REMVA | 203 | HITIGD ATN | 280 | YADSAKGRFTISRDEAKNMV YLQMNSLKPEDTAVYFCRA | 221 | YSRIYPYNY | 320 | WGQGTL VTVSS |
| 100 | T0170PMP 055D06 | 227 | EVQLVESGGGLVQP GGSLRLSCAAS | 181 | GDVHKIN FLG | 259 | WHRQAPGKE REKVA | 202 | HITIGD VTD | 289 | YADSAKGRFTISRDEAKNMV FLQMNNLKPEDTAVYFCRA | 220 | GSRIYPYDY | 321 | WGQGTQ VTVSS |
| 101 | T0170PMP 055D10 | 227 | EVQLVESGGGLVQP GGSLRLSCAAS | 185 | GDVHKIN ILG | 256 | WYRQAPAKE REMVA | 197 | HITIGD ATD | 290 | YAGSAKGRFTISRDEAKNMV YLQMNSLKPEDTAVYFCRA | 221 | YSRIYPYNY | 320 | WGQGTL VTVSS |
| 102 | T0170PMP 055E01 | 227 | EVQLVESGGGLVQP GGSLRLSCAAS | 187 | GEVYKIN FLG | 251 | WYRQAPGKE REKVA | 204 | HITIAD VAD | 291 | YADFAKGRFTISRDEAKNMV YLQMNSLKPEDTAVYFCRA | 222 | GSRIWPYDY | 321 | WGQGTQ VTVSS |
| 103 | T0170PMP 055E05 | 230 | EVQLVESGGGLVQP GGSLKLSCAAS | 184 | GAVHKIN FLG | 260 | WYRQAPEKE REMVA | 205 | TITIGD EVD | 292 | YADFAKGRFTISRDEAKNMV YLQMTSLKPEDTTVYVCRA | 219 | GSRLYPYNY | 321 | WGQGTQ VTVSS |
| 104 | T0170PMP 055F02 | 227 | EVQLVESGGGLVQP GGSLRLSCAAS | 187 | GEVYKIN FLG | 251 | WYRQAPGKE REKVA | 204 | HITIAD VAD | 291 | YADFAKGRFTISRDEAKNMV YLQMNSLKPEDTAVYFCRA | 222 | GSRIWPYDY | 320 | WGQGTL VTVSS |
| 105 | T0170PMP 055F03 | 226 | EVQLVESGGGLVQP GGSLRLSCVAS | 185 | GDVHKIN ILG | 206 | WYRQAPGKE REKVA | 251 | HISISD QTD | 293 | YAESAKGRFTISRDESKNMV YLQMNSLKPEDTAVYLCRA | 218 | FSRIYPYDY | 320 | WGQGTL VTVSS |
| 106 | T0170PMP 055F06 | 227 | EVQLVESGGGLVQP GGSLRLSCAAS | 182 | GSVHKIN FLG | 252 | WYRQAPGKE RELVA | 194 | TITIGD ATD | 279 | YADYAKGRFTISRDEAKNMV YLQMNSLKPEDTAVYFCRA | 219 | GSRLYPYNY | 320 | WGQGTL VTVSS |

TABLE A-5-continued

CDRs and framework sequences of TCR binding building blocks, plus preferred combinations as provided in formula I, namely FR1-CDR1-FR2-CDR2-FR3-CDR3-FR4. "SEQ" refers to the given SEQ ID NO. The first column refers to the SEQ ID NO of the complete ISV, i.e. FR1-CDR1-FR2-CDR2-FR3-CDR3-FR4. CDR1, CDR2 and CDR3 were determined according to Kontermann, 2010.

| SEQ | Nanobody | SEQ | FR1 | SEQ | CDR1 | SEQ | FR2 | SEQ | CDR2 | SEQ | FR3 | SEQ | CDR3 | SEQ | FR4 |
|---|---|---|---|---|---|---|---|---|---|---|---|---|---|---|---|
| 107 | T0170PMP 055F08 | 227 | EVQLVESGGGLVQP GGSLRLSCAAS | 185 | GDVHKIN ILG | 256 | WYRQAPAKE REMVA | 197 | HITIGD ATD | 294 | YADSAKGRFAISRDEAKNMV YLQMNSLKPEDTAVYFCRA | 221 | YSRIYPYNY | 320 | WGQGTL VTVSS |
| 108 | T0170PMP 055G05 | 227 | EVQLVESGGGLVQP GGSLRLSCAAS | 181 | GDVHKIN FLG | 259 | WHRQAPGKE REKVA | 197 | HITIGD ATD | 280 | YADSAKGRFTISRDEAKNMV YLQMNSLKPEDTAVYFCRA | 220 | GSRIYPYDY | 321 | WGQGTQ VTVSS |
| 109 | T0170PMP 055G09 | 233 | EVQLVESGGGSVQP GGSLRLSCAAS | 182 | GSVHKIN FLG | 261 | WYRQAPGKE REVVA | 194 | TITIGD ATD | 284 | YADSAKGRFTISRDEAKNMV YLQMNSLSPEDTAVYFCRA | 219 | GSRLYPYNY | 321 | WGQGTQ VTVSS |
| 110 | T0170PMP 056A02 | 236 | EVQLVESGGGLVQP GGSARLSCVAS | 181 | GDVHKIN FLG | 251 | WYRQAPGKE REKVA | 207 | HITIGD QTD | 280 | YADSAKGRFTISRDEAKNMV YLQMNSLKPEDTAVYFCRA | 222 | GSRIWPYDY | 321 | WGQGTQ VTVSS |
| 111 | T0170PMP 056A08 | 227 | EVQLVESGGGLVQP GGSLRLSCAAS | 183 | GSVHLLN FLG | 254 | WYRQAPGKE REMVA | 195 | HITIAD ATD | 281 | YSHFAKGRFTISRDEAKNMV YLQMNSLRPEDTAVYFCRA | 220 | GSRIYPYDY | 320 | WGQGTL VTVSS |
| 112 | T0170PMP 056A10 | 229 | EVQLVESGGGLVQP GGSLRLSCAVS | 183 | GSVHLLN FLG | 262 | WYRQAPGKE RGVVA | 195 | HITIAD ATD | 281 | YSHFAKGRFTISRDEAKNMV YLQMNSLRPEDTAVYFCRA | 220 | GSRIYPYDY | 321 | WGQGTQ VTVSS |
| 113 | T0170PMP 056B11 | 237 | EVQLVESGGGLVQA GGSLTLSCAAS | 185 | GDVHKIN ILG | 256 | WYRQAPGKE REMVA | 197 | HITIGD ATD | 280 | YADSAKGRFTISRDEAKNMV YLQMNSLKPEDTAVYFCRA | 221 | YSRIYPYNY | 320 | WGQGTL VTVSS |
| 114 | T0170PMP 056C01 | 227 | EVQLVESGGGLVQP GGSLRLSCAAS | 188 | GGVHKIN ILG | 256 | WYRQAPGKE REMVA | 197 | HITIGD ATD | 280 | YADSAKGRFTISRDEAKNMV YLQMNSLKPEDTAVYFCRA | 221 | YSRIYPYNY | 320 | WGQGTL VTVSS |
| 115 | T0170PMP 056C02 | 227 | EVQLVESGGGLVQP GGSLRLSCAAS | 187 | GEVYKIN FLG | 251 | WYRQAPGKE REKVA | 204 | HITIAD VAD | 295 | YADFAQGRFTISRDEAKNMV YLQMNSLKPEDTAVYFCRA | 222 | GSRIWPYDY | 321 | WGQGTQ VTVSS |
| 116 | T0170PMP 056C03 | 227 | EVQLVESGGGLVQP GGSLRLSCAAS | 185 | GDVHKIN ILG | 256 | WYRQAPAKE REMVA | 208 | HITIGD TTD | 280 | YADSAKGRFTISRDEAKNMV YLQMNSLKPEDTAVYFCRA | 221 | YSRIYPYNY | 321 | WGQGTQ VTVSS |
| 117 | T0170PMP 056C04 | 227 | EVQLVESGGGLVQP GGSLRLSCAAS | 183 | GSVHLLN FLG | 254 | WYRQAPGKE REMVA | 195 | HITIAD ATD | 281 | YSHFAKGRFTISRDEAKNMV YLQMNSLRPEDTAVYFCRA | 220 | GSRIYPYDY | 323 | WGHGTL VTVSS |
| 118 | T0170PMP 056C07 | 226 | EVQLVESGGGLVQP GGSLRLSCVAS | 181 | GDVHKIN FLG | 251 | WYRQAPGKE REKVA | 198 | HITIGD QAD | 280 | YADSAKGRFTISRDEAKNMV YLQMNSLKPEDTAVYFCRA | 220 | GSRIYPYDY | 324 | WGRGTL VTVSS |
| 119 | T0170PMP 056C10 | 229 | EVQLVESGGGLVQP GGSLRLSCAVS | 183 | GSVHLLN FLG | 263 | WYRQAPGKE REMVT | 195 | HITIAD ATD | 281 | YSHFAKGRFTISRDEAKNMV YLQMNSLRPEDTAVYFCRA | 220 | GSRIYPYDY | 321 | WGQGTQ VTVSS |
| 120 | T0170PMP 056D01 | 238 | EVQLVESGGDLVQP GGSLRLSCAAS | 181 | GDVHKIN FLG | 254 | WYRQAPGKE REMVA | 195 | HITIAD ATD | 296 | YAEFAKGRFTISRDEPKNMV HLQMNSLKPEDTAVYLCRA | 223 | GSRIYPYNY | 321 | WGQGTQ VTVSS |
| 121 | T0170PMP 056D02 | 227 | EVQLVESGGGLVQP GGSLRLSCAAS | 185 | GDVHKIN ILG | 256 | WYRQAPAKE REMVA | 197 | HITIGD ATD | 280 | YADSAKGRFTISRDEAKNMV YLQMNSLKPEDTAVYFCRA | 221 | YSRIYPYNY | 322 | WGRGTQ VTVSS |

TABLE A-5-continued

CDRs and framework sequences of TCR binding building blocks, plus preferred combinations as provided in formula I, namely FR1-CDR1-FR2-CDR2-FR3-CDR3-FR4. "SEQ" refers to the given SEQ ID NO. The first column refers to the SEQ ID NO of the complete ISV, i.e. FR1-CDR1-FR2-CDR2-FR3-CDR3-FR4. CDR1, CDR2 and CDR3 were determined according to Kontermann, 2010.

| SEQ | Nanobody | SEQ | FR1 | SEQ | CDR1 | SEQ | FR2 | SEQ | CDR2 | SEQ | FR3 | SEQ | CDR3 | SEQ | FR4 |
|---|---|---|---|---|---|---|---|---|---|---|---|---|---|---|---|
| 122 | T0170PMP 056D11 | 226 | EVQLVESGGGLVQP GGSLRLSCVAS | 185 | GDVHKIN ILG | 251 | WYRQAPGKE REKVA | 209 | RISISD QTD | 293 | YAESAKGRFTISRDESKNMV YLQMNSLKPEDTAVYLCRA | 218 | FSRIYPYDY | 320 | WGQGTL VTVSS |
| 123 | T0170PMP 056E02 | 239 | EVQLVESGGGLVQP EGSLRLSCAAS | 187 | GEVYKIN FLG | 251 | WYRQAPGKE REKVA | 204 | HITIAD VAD | 297 | YADFAKGRLTISRDEAKNMV YLQMNSLKPEDTAVYFCRA | 222 | GSRIWPYDY | 320 | WGQGTL VTVSS |
| 124 | T0170PMP 056F01 | 240 | EVQLVESGGGLVQP GGSLKLPCAAS | 184 | GAVHKIN FLG | 255 | WYRQTPEKE REMVA | 205 | TITIGD EVD | 282 | YADSAKGRFTISRDEAKNMV YLQMTSLKPEDTAVYVCRA | 219 | GSRLYPYNY | 320 | WGQGTL VTVSS |
| 125 | T0170PMP 056F08 | 241 | EVQLVESGGGLVQP GGSLGLSCAAS | 183 | GSVHLLN FLG | 254 | WYRQAPGKE REMVA | 195 | HITIAD ATD | 285 | YAHFAKGRFTISRDEAKNMV YLQMNSLRPEDTAVYFCRA | 220 | GSRIYPYDY | 320 | WGQGTL VTVSS |
| 126 | T0170PMP 056G02 | 242 | EVQLVESGGGLAQP GGSLRLSCAAS | 185 | GDVHKIN ILG | 256 | WYRQAPAKE REMVA | 197 | HITIGD ATD | 280 | YADSAKGRFTISRDEAKNMV YLQMNSLKPEDTAVYFCRA | 221 | YSRIYPYNY | 320 | WGQGTL VTVSS |
| 127 | T0170PMP 056G11 | 227 | EVQLVESGGGLVQP GGSLRLSCAAS | 187 | GEVYKIN FLG | 251 | WYRQAPGKE REKVA | 210 | HITIAD AAD | 298 | YADFAKGRFTISRDGAKNMV YLQMNSLKPEDTAVYFCRA | 222 | GSRIWPYDY | 321 | WGQGTQ VTVSS |
| 128 | T0170PMP 057B02 | 243 | EVQLVESGGGWVQP GGSLRLSCAAS | 189 | GSVYKIN FLS | 264 | WYRQAPGHE RELVA | 211 | TITIGD AAD | 299 | YADSAKGRFTISRDEARNMV YLQMNSLKPEDTALYFCHA | 219 | GSRLYPYNY | 321 | WGQGTQ VTVSS |
| 129 | T0170PMP 057D06 | 227 | EVQLVESGGGLVQP GGSLRLSCAAS | 183 | GSVHLLN FLG | 254 | WYRQAPGKE REMVA | 195 | HITIAD ATD | 281 | YSHFAKGRFTISRDEAKNMV YLQMNSLRPEDTAVYFCRA | 220 | GSRIYPYDY | 321 | WGQGTQ VTVSS |
| 130 | T0170PMP 061A02 | 226 | EVQLVESGGGLVQP GGSLRLSCVAS | 185 | GDVHKIN ILG | 251 | WYRQAPGKE REKVA | 212 | HIAISD QTD | 293 | YAESAKGRFTISRDESKNMV YLQMNSLKPEDTAVYLCRA | 218 | FSRIYPYDY | 320 | WGQGTL VTVSS |
| 131 | T0170PMP 061B04 | 227 | EVQLVESGGGLVQP GGSLRLSCAAS | 185 | GDVHKIN ILG | 256 | WYRQAPAKE REMVA | 197 | HITIGD ATD | 300 | YADSAKGRFTISRDEAKNMV YLQMNSLKPEDTAAYFCRA | 221 | YSRIYPYNY | 320 | WGQGTL VTVSS |
| 132 | T0170PMP 067A01 | 227 | EVQLVESGGGLVQP GGSLRLSCAAS | 185 | GDVHKIN ILG | 265 | WYRQAPAKE RGMVA | 197 | HITIGD ATD | 280 | YADSAKGRFTISRDEAKNMV YLQMNSLKPEDTAVYFCRA | 221 | YSRIYPYNY | 321 | WGQGTQ VTVSS |
| 133 | T0170PMP 067A03 | 227 | EVQLVESGGGLVQP GGSLRLSCAAS | 185 | GDVHKIN ILG | 266 | WYRQAPAKE HEMVA | 197 | HITIGD ATD | 280 | YADSAKGRFTISRDEAKNMV YLQMNSLKPEDTAVYFCRA | 221 | YSRIYPYNY | 320 | WGQGTL VTVSS |
| 134 | T0170PMP 067B06 | 227 | EVQLVESGGGLVQP GGSLRLSCAAS | 185 | GDVHKIN ILG | 267 | WYRQAPARE REMVA | 197 | HITIGD ATD | 280 | YADSAKGRFTISRDEAKNMV YLQMNSLKPEDTAVYFCRA | 221 | YSRIYPYNY | 321 | WGQGTQ VTVSS |
| 135 | T0170PMP 067C09 | 227 | EVQLVESGGGLVQP GGSLRLSCAAS | 185 | GDVHKIN ILG | 256 | WYRQAPAKE REMVA | 197 | HITIGD ATD | 301 | YADSAKGRFTISRDEAENMV YLQMNSLKPEDTAVYFCRA | 221 | YSRIYPYNY | 320 | WGQGTL VTVSS |
| 136 | T0170PMP 067D01 | 230 | EVQLVESGGGLVQP GGSLKLSCAAS | 184 | GAVHKIN FLG | 255 | WYRQTPEKE REMVA | 205 | TITIGD EVD | 282 | YADSAKGRFTISRDEAKNMV YLQMTSLKPEDTAVYVCRA | 219 | GSRLYPYNY | 320 | WGQGTL VTVSS |

TABLE A-5-continued

CDRs and framework sequences of TCR binding building blocks, plus preferred combinations as
provided in formula I, namely FR1-CDR1-FR2-CDR2-FR3-CDR3-FR4. "SEQ" refers to the given SEQ ID
NO. The first column refers to the SEQ ID NO of the complete ISV, i.e. FR1-CDR1-FR2-CDR2-FR3-CDR3-FR4.
CDR1, CDR2 and CDR3 were determined according to Kontermann, 2010.

| SEQ | Nanobody | SEQ | FR1 | SEQ | CDR1 | SEQ | FR2 | SEQ | CDR2 | SEQ | FR3 | SEQ | CDR3 | SEQ | FR4 |
|---|---|---|---|---|---|---|---|---|---|---|---|---|---|---|---|
| 137 | T0170PMP 067D06 | 230 | EVQLVESGGGLVQP GGSLRLSCAAS | 184 | GAVHKIN FLG | 260 | WYRQAPEKE REMVA | 205 | TITIGD EVD | 302 | YADSAKGRFTISRDEATNMV YLQMTSLKPEDTAVYFCRA | 223 | GSRIYPYNY | 321 | WGQGTQ VTVSS |
| 138 | T0170PMP 067D09 | 227 | EVQLVESGGGLVQP GGSLRLSCAAS | 185 | GDVHKIN ILG | 256 | WYRQAPAKE REMVA | 213 | HITIGD ATS | 303 | YAGSAKGRFTISRDEAKNMV YLQLNNLKPEDTAVYFCRA | 221 | YSRIYPYNY | 320 | WGQGTL VTVSS |
| 139 | T0170PMP 067E03 | 227 | EVQLVESGGGLVQP GGSLRLSCAAS | 185 | GDVHKIN ILG | 256 | WYRQAPAKE REMVA | 213 | HITIGD ATS | 304 | YADSAKGRFTISRDEAKNMV YLQLNNLKPEDTAVYFCRA | 221 | YSRIYPYNY | 320 | WGQGTL VTVSS |
| 140 | T0170PMP 067E06 | 238 | EVQLVESGGDLVQP GGSLRLSCAAS | 181 | GDVHKIN FLG | 254 | WYRQAPGKE REMVA | 195 | HITIAD ATD | 305 | YAEFAKGRFTISRDEPKNMV YLQMNSLKPEDTAVYLCRA | 223 | GSRIYPYNY | 321 | WGQGTQ VTVSS |
| 141 | T0170PMP 067F02 | 230 | EVQLVESGGGLVQP GGSLKLSCAAS | 184 | GAVHKIN FLG | 255 | WYRQTPEKE REMVA | 205 | TITIGD EVD | 306 | YAHSAKGRFTISRDEAKNMV YLQMTSLKPEDTAVYVCRA | 219 | GSRLYPYNY | 321 | WGQGTQ VTVSS |
| 142 | T0170PMP 068C03 | 230 | EVQLVESGGGLVQP GGSLKLSCAAS | 184 | GAVHKIN FLG | 255 | WYRQTPEKE REMVA | 214 | TITIGD EVA | 282 | YADSAKGRFTISRDEAKNMV YLQMTSLKPEDTAVYVCRA | 219 | GSRLYPYNY | 321 | WGQGTQ VTVSS |
| 143 | T0170PMP 068C07 | 227 | EVQLVESGGGLVQP GGSLRLSCAAS | 187 | GEVYKIN FLG | 251 | WYRQAPGKE REKVA | 210 | HITIAD AAD | 291 | YADFAKGRFTISRDEAKNMV YLQMNSLKPEDTAVYFCRA | 222 | GSRIWPYDY | 321 | WGQGTQ VTVSS |
| 144 | T0170PMP 068C11 | 227 | EVQLVESGGGLVQP GGSLRLSCAAS | 187 | GEVYKIN FLG | 251 | WYRQAPGKE REKVA | 210 | HITIAD AAD | 291 | YADFAKGRFTISRDEAKNMV YLQMNSLKPEDTAVYFCRA | 220 | GSRIYPYDY | 321 | WGQGTQ VTVSS |
| 145 | T0170PMP 068D05 | 244 | EVQLVESGGGSVQP GGSLRPSCAAS | 182 | GSVHKIN FLG | 254 | WYRQAPGKE REMVA | 194 | TITIGD ATD | 284 | YADSAKGRFTISRDEAKNMV YLQMNSLSPEDTAVYFCRA | 219 | GSRLYPYNY | 321 | WGQGTQ VTVSS |
| 146 | T0170PMP 068D07 | 227 | EVQLVESGGGLVQP GGSLRLSCAAS | 187 | GEVYKIN FLG | 251 | WYRQAPGKE REKVA | 204 | HITIAD VAD | 307 | YADFAKGRFTISRDEVKNMV YLQMNSLKPEDTAVYFCRA | 222 | GSRIWPYDY | 320 | WGQGTL VTVSS |
| 147 | T0170PMP 068E01 | 245 | EVQLVESGGGLVQP GESLRLSCAAS | 185 | GDVHKIN ILG | 256 | WYRQAPAKE REMVA | 197 | HITIGD ATD | 280 | YADSAKGRFTISRDEAKNMV YLQMNSLKPEDTAVYFCRA | 221 | YSRIYPYNY | 320 | WGQGTL VTVSS |
| 148 | T0170PMP 068E08 | 227 | EVQLVESGGGLVQP GGSLRLSCAAS | 187 | GEVYKIN FLG | 251 | WYRQAPGKE REKVA | 210 | HITIAD AAD | 308 | YADFAKGRFTISRDEAKNMV YLQMNSLRPEDTAVYFCRA | 222 | GSRIWPYDY | 321 | WGQGTQ VTVSS |
| 149 | T0170PMP 068F04 | 227 | EVQLVESGGGLVQP GGSLRLSCAAS | 183 | GSVHLLN FLG | 254 | WYRQAPGKE REMVA | 215 | HITIAD VTD | 309 | YSYFAKGRFTISRDEAKNMV YLQMNSLRPEDTAVYFCRA | 220 | GSRIYPYDY | 321 | WGQGTQ VTVSS |
| 150 | T0170PMP 068F06 | 227 | EVQLVESGGGLVQP GGSLRLSCAAS | 185 | GDVHKIN ILG | 256 | WYRQAPAKE REMVA | 197 | HITIGD ATD | 310 | YADSAKGRFTISRDEAKNVV YLQMNSLKPEDTAVYFCRA | 221 | YSRIYPYNY | 320 | WGQGTL VTVSS |
| 151 | T0170PMP 068F08 | 233 | EVQLVESGGGSVQP GGSLRLSCAAS | 182 | GSVHKIN FLG | 268 | WYRQAPGKE RGMVA | 194 | TITIGD ATD | 284 | YADSAKGRFTISRDEAKNMV YLQMNSLSPEDTAVYFCRA | 219 | GSRLYPYNY | 321 | WGQGTQ VTVSS |

TABLE A-5-continued

CDRs and framework sequences of TCR binding building blocks, plus preferred combinations as provided in formula I, namely FR1-CDR1-FR2-CDR2-FR3-CDR3-FR4. "SEQ" refers to the given SEQ ID NO. The first column refers to the SEQ ID NO of the complete ISV, i.e. FR1-CDR1-FR2-CDR2-FR3-CDR3-FR4. CDR1, CDR2 and CDR3 were determined according to Kontermann, 2010.

| SEQ | Nanobody | SEQ | FR1 | SEQ | CDR1 | SEQ | FR2 | SEQ | CDR2 | SEQ | FR3 | SEQ | CDR3 | SEQ | FR4 |
|---|---|---|---|---|---|---|---|---|---|---|---|---|---|---|---|
| 152 | T0170PMP069A06 | 230 | EVQLVESGGGLVQPGGSLKLSCAAS | 184 | GAVHKINFLG | 255 | WYRQTPEKEREMVA | 205 | TITIGDEVD | 311 | YAEDSAKGRFTISRDEAKNMVYLQMTGLKPEDTAVYFCRA | 219 | GSRLYPYNY | 320 | WGQGTLVTVSS |
| 153 | T0170PMP069B02 | 246 | EVQLVESGGGLVRPGGSLRLSCVAS | 185 | GDVHKINILG | 251 | WYRQAPGKEREKVA | 206 | HISISDQTD | 293 | YAESAKGRFTISRDESKNMVYLQMNSLKPEDTAVYLCRA | 218 | FSRIYPYDY | 321 | WGQGTQVTVSS |
| 154 | T0170PMP069B08 | 227 | EVQLVESGGGLVQPGGSLRLSCAAS | 190 | GDVYKINFLG | 259 | WHRQAPGKEREKVA | 197 | HITIGDATD | 280 | YADSAKGRFTISRDEAKNMVYLQMNSLKPEDTAVYFCRA | 220 | GSRIYPYDY | 320 | WGQGTLVTVSS |
| 155 | T0170PMP069C01 | 231 | EVQLVESGGGLVQPGGSLRLSCRAS | 185 | GDVHKINILG | 269 | WYRQAPAKEREMIA | 197 | HITIGDATD | 283 | YAESAKGRFTISRDEAKNMVYLQMNSLKPEDTAVYFCRA | 221 | YSRIYPYNY | 321 | WGQGTQVTVSS |
| 156 | T0170PMP069C04 | 227 | EVQLVESGGGLVQPGGSLRLSCAAS | 185 | GDVHKINILG | 270 | WYRQAPAKGREMVA | 197 | HITIGDATD | 280 | YADSAKGRFTISRDEAKNMVYLQMNSLKPEDTAVYFCRA | 221 | YSRIYPYNY | 321 | WGQGTQVTVSS |
| 157 | T0170PMP069C05 | 238 | EVQLVESGGGLVQPGGSLRLSCAAS | 181 | GDVHKINFLG | 254 | WYRQAPGKEREMVA | 195 | HITIADATD | 305 | YAEFAKGRFTISRDEPKNMVYLQMNSLKPEDTAVYLCRA | 224 | GSRIYPYSY | 321 | WGQGTQVTVSS |
| 158 | T0170PMP069D02 | 247 | EVQLVESGGGMVQPGGSLRLSCAAS | 185 | GDVHKINILG | 256 | WYRQAPAKEREMVA | 197 | HITIGDATD | 280 | YADSAKGRFTISRDEAKNMVYLQMNSLKPEDTAVYFCRA | 221 | YSRIYPYNY | 320 | WGQGTLVTVSS |
| 159 | T0170PMP069D07 | 227 | EVQLVESGGGLVQPGGSLRLSCAAS | 185 | GDVHKINILG | 271 | WYRQVPAKEREMVA | 197 | HITIGDATD | 300 | YADSAKGRFTISRDEAKNMVYLQMNSLKPEDTAAYFCRA | 221 | YSRIYPYNY | 320 | WGQGTLVTVSS |
| 160 | T0170PMP069E02 | 227 | EVQLVESGGGLVQPGGSLRLSCAAS | 187 | GEVYKINFLG | 251 | WYRQAPGKEREKVA | 210 | HITIADAAD | 291 | YADFAKGRFTISRDEAKNMVYLQMNSLKPEDTAVYFCRA | 222 | GSRIWPYDY | 320 | WGQGTLVTVSS |
| 161 | T0170PMP069E07 | 227 | EVQLVESGGGLVQPGGSLRLSCAAS | 183 | GSVHLLNFLG | 254 | WYRQAPGKEREMVA | 195 | HITIADATD | 312 | YSHFAKGRFTISRDEAKNMVYLQMNGLRPEDTAVYFCRA | 220 | GSRIYPYDY | 320 | WGQGTLVTVSS |
| 162 | T0170PMP069E09 | 227 | EVQLVESGGGLVQPGGSLRLSCAAS | 181 | GDVHKINFLG | 254 | WYRQAPGKEREMVA | 195 | HITIADATD | 305 | YAEFAKGRFTISRDEPKNMVYLQMNSLKPEDTAVYLCRA | 223 | GSRIYPYNY | 321 | WGQGTQVTVSS |
| 163 | T0170PMP069E11 | 227 | EVQLVESGGGLVQPGGSLRLSCAAS | 191 | GEVHKINILG | 272 | WYRQCPGKERDMVA | 194 | TITIGDATD | 280 | YADSAKGRFTISRDEAKNMVYLQMNSLKPEDTAVYFCRA | 225 | LSRLYPYNY | 320 | WGQGTLVTVSS |
| 164 | T0170PMP069F05 | 227 | EVQLVESGGGLVQPGGSLRLSCAAS | 185 | GDVHKINILG | 256 | WYRQAPAKEREMVA | 197 | HITIGDATD | 313 | YADSAKGRFTISRDEAKNMVYLQMNSLKPEDTAVYLCRA | 221 | YSRIYPYNY | 321 | WGQGTQVTVSS |
| 165 | T0170PMP069G08 | 227 | EVQLVESGGGLVQPGGSLRLSCAAS | 187 | GEVYKINFLG | 273 | WQRQAPAKEREKVA | 204 | HITIADVAD | 291 | YADFAKGRFTISRDEAKNMVYLQMNSLKPEDTAVYFCRA | 222 | GSRIWPYDY | 320 | WGQGTLVTVSS |
| 166 | T0170PMP070B08 | 238 | EVQLVESGGDLVQPGGSLRLSCAAS | 181 | GDVHKINFLG | 254 | WYRQAPGKEREMVA | 195 | HITIADATD | 314 | YAEFAKGRFTISRDEPKNMVYLQMNSLKPVDTAVYLCRA | 223 | GSRIYPYNY | 320 | WGQGTLVTVSS |

TABLE A-5-continued

CDRs and framework sequences of TCR binding building blocks, plus preferred combinations as provided in formula I, namely FR1-CDR1-FR2-CDR2-FR3-CDR3-FR4. "SEQ" refers to the given SEQ ID NO. The first column refers to the SEQ ID NO of the complete ISV, i.e. FR1-CDR1-FR2-CDR2-FR3-CDR3-FR4. CDR1, CDR2 and CDR3 were determined according to Kontermann, 2010.

| SEQ | Nanobody | SEQ | FR1 | SEQ | CDR1 | SEQ | FR2 | SEQ | CDR2 | SEQ | FR3 | SEQ | CDR3 | SEQ | FR4 |
|---|---|---|---|---|---|---|---|---|---|---|---|---|---|---|---|
| 167 | T0170PMP 070B09 | 227 | EVQLVESGGGLVQP GGSLRLSCAAS | 183 | GSVHLLN FLG | 251 | WYRQAPGKE REKVA | 195 | HITIAD ATD | 315 | YSHFAKGRFTISRDEAKNMV YLQMNNLRPEDTAVYFCRA | 220 | GSRIYPYDY | 320 | WGQGTL VTVSS |
| 168 | T0170PMP 070C09 | 248 | EVQLVESGGGLVQP GGSPRLSCVAS | 181 | GDVHKIN FLG | 251 | WYRQAPGKE REKVA | 198 | HITIGD QAD | 280 | YADSAKGRFTISRDEAKNMV YLQMNSLKPEDTAVYFCRA | 220 | GSRIYPYDY | 320 | WGQGTL VTVSS |
| 169 | T0170PMP 070D07 | 227 | EVQLVESGGGLVQP GGSLRLSCAAS | 185 | GDVHKIN ILG | 256 | WYRQAPAKE REMVA | 197 | HITIGD ATD | 316 | YADSAKGRFTISRDEAKNMV YLQMNSLKPEDAAVYFCRA | 221 | YSRIYPYNY | 320 | WGQGTL VTVSS |
| 170 | T0170PMP 070E07 | 227 | EVQLVESGGGLVQP GGSLRLSCAAS | 187 | GEVYKIN FLG | 251 | WYRQAPGKE REMVA | 204 | HITIAD VAD | 298 | YADFAKGRFTISRDGAKNMV YLQMNSLKPEDTAVYFCRA | 222 | GSRIWPYDY | 320 | WGQGTL VTVSS |
| 171 | T0170PMP 070F11 | 233 | EVQLVESGGGSVQP GGSLRLSCAAS | 182 | GSVHKIN FLG | 274 | WYCQAPGKE REMVA | 194 | TITIGD ATD | 284 | YADSAKGRFTISRDEAKNMV YLQMNSLSPEDTAVYFCRA | 219 | GSRLYPYNY | 321 | WGQGTQ VTVSS |
| 172 | T0170PMP 070G02 | 226 | EVQLVESGGGLVQP GGSLRLSCVAS | 185 | GDVHKIN ILG | 251 | WYRQAPGKE REKVA | 206 | HISISD QTD | 317 | YAESAKGRFTISRDESKNMV YLQMNSLKPEDAAVYLCRA | 218 | FSRIYPYDY | 321 | WGQGTQ VTVSS |
| 173 | T0170PMP 070G06 | 234 | EVQLVESGGGLVQP GGSLRPSCAAS | 187 | GEVYKIN FLG | 251 | WYRQAPGKE REKVA | 204 | HITIAD VAD | 291 | YADFAKGRFTISRDEAKNMV YLQMNSLKPEDTAVYFCRA | 222 | GSRIWPYDY | 320 | WGQGTL VTVSS |
| 174 | T0170PMP 082B04 | 249 | EVQLVESGGGLVQP GGSLRPSCVAS | 181 | GDVHKIN FLG | 251 | WYRQAPGKE REKVA | 216 | HITIAD QAD | 280 | YADSAKGRFTISRDEAKNMV YLQMNSLKPEDTAVYFCRA | 220 | GSRIYPYDY | 320 | WGQGTL VTVSS |
| 175 | T0170PMP 084B07 | 227 | EVQLVESGGGLVQP GGSLRLSCAAS | 191 | GEVHKIN ILG | 275 | WYRQAPGKE RDMVA | 217 | TITIGD ETQ | 280 | YADSAKGRFTISRDEAKNMV YLQMNSLKPEDTAVYFCRA | 225 | LSRLYPYNY | 320 | WGQGTL VTVSS |
| 176 | T0170PMP 084C02 | 227 | EVQLVESGGGLVQP GGSLRLSCAAS | 185 | GDVHKIN ILG | 256 | WYRQAPAKE REMVA | 197 | HITIGD ATD | 318 | YADSAKGRFTISRDEAKNMV YLQMDSLKPGDTAVYFCRA | 221 | YSRIYPYNY | 320 | WGQGTL VTVSS |
| 177 | T0170PMP 084E03 | 227 | EVQLVESGGGLVQP GGSLRLSCAAS | 185 | GDVHKIN ILG | 256 | WYRQAPAKE REMVA | 197 | HITIGD ATD | 319 | YADSAKGRFTISRDEAKNMV YLQMNSLKPGDTAVYFCRA | 221 | YSRIYPYNY | 320 | WGQGTL VTVSS |
| 178 | T0170PMP 084E05 | 227 | EVQLVESGGGLVQP GGSLRLSCAAS | 185 | GDVHKIN ILG | 276 | WHRQAPAKE REMVA | 197 | HITIGD ATD | 280 | YADSAKGRFTISRDEAKNMV YLQMNSLKPEDTAVYFCRA | 221 | YSRIYPYNY | 320 | WGQGTL VTVSS |
| 179 | T0170PMP 084F04 | 227 | EVQLVESGGGLVQP GGSLRLSCAAS | 185 | GDVHKIN ILG | 276 | WHRQAPAKE REMVA | 197 | HITIGD ATD | 300 | YADSAKGRFTISRDEAKNMV YLQMNSLKPEDTAAYFCRA | 221 | YSRIYPYNY | 321 | WGQGTQ VTVSS |
| 180 | T0170PMP 084F10 | 250 | EVQLVESGGGWVQA GGSLRLSCAAS | 185 | GDVHKIN ILG | 256 | WYRQAPAKE REMVA | 197 | HITIGD ATD | 280 | YADSAKGRFTISRDEAKNMV YLQMNSLKPEDTAVYFCRA | 221 | YSRIYPYNY | 320 | WGQGTL VTVSS |

TABLE A-6

Sequences of control Nanobodies. "SEQ" refers to a given SEQ ID NO; "ID" refers to identification name; "Sequence" denotes amino acid sequence

| SEQ | ID | Sequence |
|---|---|---|
| 44 | RSV7B2 (Q108L) | EVQLVESGGGLVQAGDSLRLSCAASGRTFSSYAMGWFRQAPGKEREFVAAISWSDGSTYYADSVKGRFT ISRDNAKNTVYLQMNSLKPEDTAVYYCAADLTSTNPGSYIYIWAYDYWGQGTLVTVSS |
| 45 | cAbLys3 D1E, Q5V, A6E, Q108L) | EVQLVESGGGSVQAGGSLRLSCAASGYTIGPYCMGWFRQAPGKEREGVAAINMGGGITYYADSVKGRFT ISQDNAKNTVYLLMNSLEPEDTAIYYCAADSTIYASYYECGHGLSTGGYGYDSWGQGTLVTVSS |

TABLE A-7

Sequences of multispecific polypeptides. "SEQ" refers to the given SEQ ID NO; "ID" refers to identification name; "Sequence" denotes amino acid sequence.

| SEQ | ID | Sequence |
|---|---|---|
| 46 | T017000113 | EVQLVESGGGLVQAGGPLRLSCAASGRTFSSYVMGWFRQAPGKEREFVAAIYWSNGKTQYTDSVKGRFTISGDNAKNTVYLQMNSLNPEDTAVYYCV ADKDETGFRTLPIAYDYWGQGTLVTVSSGGGGSGGGGSGGGGSGGGGSEVQLVESGGGSGGGGSEVQLVESGGGSVQAGGSLRLSCAASGYTIGPYCM GWFRQAPGKEREGVAAINMGGGITYYADSVKGRFTISQDNAKNTVYLLMNSLEPEDTAIYYCAADSTIYASYYECGHGLSTGGYGYDSWGQGTLVTV SSGGGGSGGGGSGGGGSGGGGSEVQLVESGGGLVQPGGSLRLSCVASGDVHKINFLGWYRQAPGKEREKVAHISIGDQTDYA DSAKGRFTISRDESKNMVYLQMNSLKPEDTAVYFCRAFSRIYPYDYWGQGTLVTVSS |
| 47 | T017000114 | EVQLVESGGGLVQAGGPLRLSCAASGRTFSSYVMGWFRQAPGKEREFVAAIYWSNGKTQYTDSVKGRFTISGDNAKNTVYLQMNSLNPEDTAVYYCV ADKDETGFRTLPIAYDYWGQGTLVTVSSGGGGSGGGGSGGGGSGGGGSEVQLVESGGGSGGGGSEVQLVESGGGSLRLSCAASGITSKINDM GWYRQTPGNYREWVASITATGTTNYRDSVKGRFTISRDNAKSTVYLQMNSLKPEDTTVYCNTFPPISNFWGQGTLVTVSSGGGGSGGGGSGGGGSG GGGSGGGGSGGGGSGGGGSEVQLVESGGGLVQPGGSLRLSCVASGDVHKINFLGWYRQAPGKEREKVAHISIGDQTDYADSAKGRFTISRDESKNMV YLQMNSLKPEDTAVYFCRAFSRIYPYDYWGQGTLVTVSS |
| 48 | T017000115 | EVQLVESGGGLVQAGGSLRLSCAASGITSKINDMGWYRQTPGNYREWVASITATGTTNYRDSVKGRFTISRDNAKSTVYLQMNSLKPEDTTVYCNT FPPISNFWGQGTLVTVSSGGGGSGGGGSGGGGSGGGGSEVQLVESGGGSGGGGSEVQLVESGGGSVQAGGSLRLSCAASGYTIGPYCMGWFRQAPGKE REGVAAINMGGGITYYADSVKGRFTISQDNAKNTVYLLMNSLEPEDTAIYYCAADSTIYASYYECGHGLSTGGYGYDSWGQGTLVTVSSGGGGSGGG GSGGGGSGGGGSEVQLVESGGGLVQPGGSLRLSCVASGDVHKINFLGWYRQAPGKEREKVAHISIGDQTDYADSAKGRFTIS RDESKNMVYLQMNSLKPEDTAVYFCRAFSRIYPYDYWGQGTLVTVSS |
| 49 | T017000116 | EVQLVESGGGLVQAGGSLRLSCAASGITSKINDMGWYRQTPGNYREWVASITATGTTNYRDSVKGRFTISRDNAKSTVYLQMNSLKPEDTTVYCNT FPPISNFWGQGTLVTVSSGGGGSGGGGSGGGGSGGGGSEVQLVESGGGSGGGGSEVQLVESGGGLVQAGGPLRLSCAASGRTFSSYVMGWFRQAPGKE REFVAAIYWSNGKTQYTDSVKGRFTISGDNAKNTVYLQMNSLNPEDTAVYYCVADKDETGFRTLPIAYDYWGQGTLVTVSSGGGGSGGGGSGGGGSG GGGSGGGGSGGGGSEVQLVESGGGLVQPGGSLRLSCVASGDVHKINFLGWYRQAPGKEREKVAHISIGDQTDYADSAKGRFTISRDESKNMV YLQMNSLKPEDTAVYFCRAFSRIYPYDYWGQGTLVTVSS |
| 50 | T017000120 | EVQLVESGGGSVQAGGSLRLSCAASGYTIGPYCMGWFRQAPGKEREGVAAINMGGGITYYADSVKGRFTISQDNAKNTVYLLMNSLEPEDTAIYYCA ADSTIYASYYECGHGLSTGGYGYDSWGQGTLVTVSSGGGGSGGGGSGGGGSGGGGSEVQLVESGGGLVQAGGPLRLSCAASG RTFSSYVMGWFRQAPGKEREFVAAIYWSNGKTQYTDSVKGRFTISGDNAKNTVYLQMNSLNPEDTAVYYCVADKDETGFRTLPIAYDYWGQGTLVTV SSGGGGSGGGGSGGGGSGGGGSEVQLVESGGGLVQPGGSLRLSCVASGDVHKINFLGWYRQAPGKEREKVAHISIGDQTDYA DSAKGRFTISRDESKNMVYLQMNSLKPEDTAVYFCRAFSRIYPYDYWGQGTLVTVSS |
| 51 | T017000121 | EVQLVESGGGSVQAGGSLRLSCAASGYTIGPYCMGWFRQAPGKEREGVAAINMGGGITYYADSVKGRFTISQDNAKNTVYLLMNSLEPEDTAIYYCA ADSTIYASYYECGHGLSTGGYGYDSWGQGTLVTVSSGGGGSGGGGSGGGGSGGGGSEVQLVESGGGSLRLSCAASG ITSKINDMGWYRQTPGNYREWVASITATGTTNYRDSVKGRFTISRDNAKSTVYLQMNSLKPEDTTVYCNTFPPISNFWGQGTLVTVSSGGGGSGGGG GSGGGGSGGGGSGGGGSEVQLVESGGGLVQPGGSLRLSCVASGDVHKINFLGWYRQAPGKEREKVAHISIGDQTDYADSAKGRFTIS RDESKNMVYLQMNSLKPEDTAVYFCRAFSRIYPYDYWGQGTLVTVSS |
| 52 | T017000126 | DVQLVESGGGLVQAGGPLRLSCAASGRTFSSYVMGWFRQAPGKEREFVAAIYWSNGKTQYTDSVKGRFTISGDNAKNTVYLQMNSLNPEDTAVYYCV ADKDETGFRTLPIAYDYWGQGTLVTVSSGGGGSGGGGSGGGGSGGGGSEVQLVESGGGSGGGGSEVQLVESGGGSLRLSCAASGITSKINDM GWYRQTPGNYREWVASITATGTTNYRDSVKGRFTISRDNAKSTVYLQMNSLKPEDTTVYCNTFPPISNFWGQGTLVTVSSGGGGSGGGGSGGGGSG GGGSGGGGSGGGGSEVQLVESGGGLVQPGGSLRLSCVASGDVHKINFLGWYRQAPGKEREKVAHISIGDQTDYADSAKGRFTISRDESKNMV YLQMNSLKPEDTAVYFCRAFSRIYPYDYWGQGTLVTVSS |
| 53 | T017000128 | DVQLVESGGGLVQPGGSLRLSCVASGDVHKINFLGWYRQAPGKEREKVAHISIGDQTDYADSAKGRFTISRDESKNMVYLQMNSLKPEDTAVYFCRA FSRIYPYDYWGQGTLVTVSSGGGGSGGGGSGGGGSGGGGSEVQLVESGGGSGGGGSEVQLVESGGGSLRDNAKSTVYLQMNSLKPEDTTVYCNTFPPISNFWGQGTLVTVSS NYREWVASITATGTTNYRDSVKGRFTISRDNAKSTVYLQMNSLKPEDTTVYCNTFPPISNFWGQGTLVTVSS |

TABLE A-7-continued

Sequences of multispecific polypeptides. "SEQ" refers to the given SEQ ID NO; "ID" refers to identification name; "sequence" denotes amino acid sequence.

| SEQ | ID | Sequence |
|---|---|---|
| 54 | T017000129 | DVQLVESGGGLVQPGGSLRLSCVASGDVHKINFLGWYRQAPGKEREKVAHISIGDQTDYADSAKGRFTISRDESKNMVLQMNSLKPEDTAVYFCRA FSRIYPYDYWGQGTLVTVSSGGGGSGGGGSGGGGSGGGGSEVQLVESGGGLVQAGDSLRLSCAASGRTFSSYAMGWFRQAPG KEREFVAAISWSDGSTYYADSVKGRFTISRDNAKNTVYLQMNSLKPEDTAVYYCAADLTSNPGSYIYIWAYDYWGQGTLVTVSS |
| 55 | T017000130 | DVQLVESGGGLVQAGGSLRLSCAASGITSKINDMGWYRQTPGNYREWVASITATGTTNYRDSVKGRFTISRDNAKSTVYLQMNSLKPEDTTVYYCNT FPPISNFWGQGTLVTVSSGGGGSGGGGSGGGGSGGGGSEVQLVESGGGLVQAGGPLRLSCAASGRTFSSYVMGWFRQAPGKE REFVAAIYWSNGKTQYTDSVKGRFTISGDNAKNTVYLQMNSLNPEDTAVYYCVADKDETGFRTLPIAYDYWGQGTLVTVSSGGGGSGGGGSG GGGSGGGGSGGGGSGGGGSEVQLVESGGGLVQPGGSLRLSCVASGDVHKINFLGWYRQAPGKEREKVAHISIGDQTDYADSAKGRFTISRDESKNMV YLQMNSLKPEDTAVYFCRAPSRIYPYDYWGQGTLVTVSS |
| 56 | T017000131 | DVQLVESGGGLVQAGGSLRLSCAASGITSKINDMGWYRQTPGNYREWVASITATGTTNYRDSVKGRFTISRDNAKSTVYLQMNSLKPEDTTVYYCNT FPPISNFWGQGTLVTVSSGGGGSGGGGSGGGGSGGGGSEVQLVESGGGLVQPGGSLRLSCVASGDVHKINFLGWYRQAPGKE REKVAHISIGDQTDYADSAKGRFTISRDESKNMVLQMNSLKPEDTAVYFCRAFSRIYPYDYWGQGTLVTVSS |
| 57 | T017000132 | DVQLVESGGGLVQAGDSLRLSCAASGRTFSSYAMGWFRQAPGKEREFVAAISWSDGSTYYADSVKGRFTISRDNAKNTVYLQMNSLKPEDTAVYYCA ADLTSNPGSYIYIWAYDYWGQGTLVTVSSGGGGSGGGGSGGGGSGGGGSEVQLVESGGGLVQPGGSLRLSCVASGDVHKIN FLGWYRQAPGKEREKVAHISIGDQTDYADSAKGRFTISRDESKNMVLQMNSLKPEDTAVYFCRAFSRIYPYDYWGQGTLVTVSS |
| 58 | T017000134 | VQLVESGGGLVQAGGSLRLSCAASGITSKINDMGWYRQTPGNYREWVASITATGTTNYRDSVKGRFTISRDNAKSTVYLQMNSLKPEDTTVYYCNTF PPISNFWGQGTLVTVSSGGGGSGGGGSGGGGSGGGGSEVQLVESGGGLVQPGGSLRLSCVASGDVHKINFLGWYRQAPGKER EKVAHISIGDQTDYADSAKGRFTISRDESKNMVLQMNSLKPEDTAVYFCRAFSRIYPYDYWGQGTLVTVSSGGGGSGGGGSGGGGS GGGGSGGGGSGGGGSEVQLVESGGGLVQAGGPLRLSCAASGRTFSSYVMGWFRQAPGKEREFVAAIYWSNGKTQYTDSVKGRFTISGDNAKNTVYLQMNSLN PEDTAVYYCVADKDETGFRTLPIAYDYWGQGTLVTVSS |
| 59 | T017000135 | DVQLVESGGGLVQAGGPLRLSCAASGRTFSSYVMGWFRQAPGKEREFVAAIYWSNGKTQYTDSVKGRFTISGDNAKNTVYLQMNSLNPEDTAVYYCV ADKDETGFRTLPIAYDYWGQGTLVTVSSGGGGSGGGGSGGGGSGGGGSEVQLVESGGGLVQPGGSLRLSCVASGDVHKINFL GWYRQAPGKEREKVAHISIGDQTDYADSAKGRFTISRDESKNMVLQMNSLKPEDTAVYFCRAFSRIYPYDYWGQGTLVTVSSGGGGSGGGGSGGGGS SGGGGSGGGGSGGGGSEVQLVESGGGLVQAGGSLRLSCAASGITSKINDMGWYRQTPGNYREWVASITATGTTNYRDSVKGRFTISRDNAKS TVYLQMNSLKPEDTTVYYCNTFPPISNFWGQGTLVTVSS |
| 60 | T017000138 | DVQLVESGGGLVQPGGSLRLSCVASGDVHKINFLGWYRQAPGKEREKVAHISIGDQTDYADSAKGRFTISRDESKNMVLQMNSLKPEDTAVYFCRA FSRIYPYDYWGQGTLVTVSSGGGGSGGGGSGGGGSGGGGSEVQLVESGGGLVQAGGSLRLSCAASGITSKINDMGWYRQTPG NYREWVASITATGTTNYRDSVKGRFTISRDNAKSTVYLQMNSLKPEDTTVYYCNTFPPISNFWGQGTLVTVSSGGGGSGGGGSGGGGSGGGGSGGGG SGGGGSGGGGSEVQLVESGGGLVQAGGPLRLSCAASGRTFSSYVMGWFRQAPGKEREFVAAIYWSNGKTQYTDSVKGRFTISGDNAKNTVYLQMNSL NPEDTAVYYCVADKDETGFRTLPIAYDYWGQGTLVTVSS |
| 61 | T017000139 | DVQLVESGGGLVQPGGSLRLSCVASGDVHKINFLGWYRQAPGKEREKVAHISIGDQTDYADSAKGRFTISRDESKNMVLQMNSLKPEDTAVYFCRA FSRIYPYDYWGQGTLVTVSSGGGGSGGGGSGGGGSGGGGSEVQLVESGGGLVQAGGPLRLSCAASGRTFSSYVMGWFRQAPG KEREFVAAIYWSNGKTQYTDSVKGRFTISGDNAKNTVYLQMNSLNPEDTAVYYCVADKDETGFRTLPIAYDYWGQGTLVTVSSGGGGSGGGGSGGGG SGGGGSGGGGSGGGGSEVQLVESGGGLVQAGGSLRLSCAASGITSKINDMGWYRQTPGNYREWVASITATGTTNYRDSVKGRFTISRDNAKS TVYLQMNSLKPEDTTVYYCNTFPPISNFWGQGTLVTVSS |
| 62 | A022600009 | EVQLVESGGGLVQPGGSLRLSCVASGDVHKINFLGWYRQAPGKEREKVAHISIGDQTDYADSAKGRFTISRDESKNMVLQMNSLKPEDTAVYFCRA FSRIYPYDYWGQGTLVTVSSGGGGSGGGGSGGGGSGGGGSEVQLVESGGGLVQAGDSLRLSCAASGRTFSSYAMGWFRQAPG KEREFVAAISWSDGSTYYADSVKGRFTISRDNAKNTVYLQMNSLKPEDTAVYYCAADLTSNPGSYIYIWAYDYWGQGTLVTVSSGGGGSGGGGSGGG SGGGGSGGGGSGGGGSEVQLVESGGGLVQPGNSLRLSCAASGFTFSSFGMSWRQAPGKGLEWVSSISGSGSDTLYADSVKGRFTISRDN AKTTLYLQMNSLRPEDTAVYYCTIGGSLSRSSQGTLVTVSS |

TABLE A-7-continued

Sequences of multispecific polypeptides. "SEQ" refers to the given SEQ ID NO; "ID" refers to identification name; "sequence" denotes amino acid sequence.

| SEQ | ID | Sequence |
|---|---|---|
| 63 | T017000142 | DVQLVESGGGLVQPGGSLRLSCVASGDVHKINFLGWYRQAPGKEREKVAHISIGDQTDYADSAKGRFTISRDESKNMVLQMNSLKPEDTAVYFCRA FSRIYPYDYWGQGTLVTVSSGGGGSGGGGSGGGGSGGGGSGGGGSEVQLVESGGGLVQAGGSLRLSCAASGITSKINDMGWYRQTPG NYREWVASITATGTTNYRDSVKGRFTISRDNAKSTVYLQMNSLKPEDTTVYCNTFPPISNFWGQGTLVTVSSGGGGSGGGGSGGGGSGGGGGGG SGGGGSGGGGSEVQLVESGGGLVQPGNSLRLSCAASGFTFSSFGMSWVRQAPGKGLEWVSSISGSGSDTLYADSVKGRFTISRDNAKTTLYLQMNSL RPEDTAVYYCTIGGSLSRSSQGTLVTVSS |
| 64 | T017000143 | DVQLVESGGGLVQPGGSLRLSCVASGDVHKINFLGWYRQAPGKEREKVAHISIGDQTDYADSAKGRFTISRDESKNMVLQMNSLKPEDTAVYFCRA FSRIYPYDYWGQGTLVTVSSGGGGSGGGGSGGGGSGGGGSGGGGSEVQLVESGGGLVQAGGSLRLSCAASGITSKINDMGWYRQTPG NYREWVASITATGTTNYRDSVKGRFTISRDNAKSTVYLQMNSLKPEDTTVYCNTFPPISNFWGQGTLVTVSSGGGGSGGGGSGGGGSGGGGSGGG SGGGGSGGGGSEVQLVESGGGLVQAGGPLRLSCAASGRTFSSYVMGWFRQAPGKEREFVAAIYWSNGKTQYTDSVKGRFTISGDNAKNTVYLQMNSL NPEDTAVYYCVADKDETGFRTLPIAYDYWGQGTLVTVSSGSDTLYADSVKGRFTISRDNAKTTLYLQMNSLRPEDTAVYYCTIGGSLVQPGNSLRLSCA ASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 65 | T017000144 | DVQLVESGGGLVQPGGSLRLSCVASGDVHKINFLGWYRQAPGKEREKVAHISIGDQTDYADSAKGRFTISRDESKNMVLQMNSLKPEDTAVYFCRA FSRIYPYDYWGQGTLVTVSSGGGGSGGGGSGGGGSGGGGSGGGGSEVQLVESGGGLVQAGGSLRLSCAASGITSKINDMGWYRQTPG NYREWVASITATGTTNYRDSVKGRFTISRDNAKSTVYLQMNSLKPEDTTVYCNTFPPISNFWGQGTLVTVSSGGGGSGGGGSGGGGSGGGGSGGG RPEDTAVYYCTIGGSLSRSSQGTLVTVSSGGGGSGGGGSGGGGSGGGGSGGGGSEVQLVESGGGLVQAGGPLRLSCAASGRTFSSYV MGWFRQAPGKEREFVAAIYWSNGKTQYTDSVKGRFTISGDNAKNTVYLQMNSLNPEDTAVYYCVADKDETGFRTLPIAYDYWGQGTLVTVSS |
| 66 | T017000145 | DVQLVESGGGLVQPGGSLRLSCVASGDVHKINFLGWYRQAPGKEREKVAHISIGDQTDYADSAKGRFTISRDESKNMVLQMNSLKPEDTAVYFCRA FSRIYPYDYWGQGTLVTVSSGGGGSGGGGSGGGGSGGGGSGGGGSEVQLVESGGGLVQAGGPLRLSCAASGRTFSSYVMGWFRQAPG KEREFVAAIYWSNGKTQYTDSVKGRFTISGDNAKNTVYLQMNSLNPEDTAVYYCVADKDETGFRTLPIAYDYWGQGTLVTVSSGGGGSGGGGSGGGG SGGGGSGGGGSGGGGSEVQLVESGGGLVQPGNSLRLSCAASGFTFSSFGMSWVRQAPGKGLEWVSSISGSGSDTLYADSVKGRFTISRDNAKS TVYLQMNSLKPEDTTVYCNTFPPISNFWGQGTLVTVSSGSDTLYADSVKGRFTISRDNAKTTLYLQMNSLRPEDTAVYYCTIGGSLVQPGNSLRLSCA ASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 67 | T017000146 | DVQLVESGGGLVQPGGSLRLSCVASGDVHKINFLGWYRQAPGKEREKVAHISIGDQTDYADSAKGRFTISRDESKNMVLQMNSLKPEDTAVYFCRA FSRIYPYDYWGQGTLVTVSSGGGGSGGGGSGGGGSGGGGSGGGGSEVQLVESGGGLVQAGGPLRLSCAASGRTFSSYVMGWFRQAPG KEREFVAAIYWSNGKTQYTDSVKGRFTISGDNAKNTVYLQMNSLNPEDTAVYYCVADKDETGFRTLPIAYDYWGQGTLVTVSSGGGGSGGGGSGGGG SGGGGSGGGGSGGGGSEVQLVESGGGLVQPGNSLRLSCAASGFTFSSFGMSWVRQAPGKGLEWVSSISGSGSDTLYADSVKGRFTISRDNAK TTLYLQMNSLRPEDTAVYYCTIGGSLSRSSQGTLVTVSSISGSGSDTLYADSVKGRFTISRDNAKTTVYLQMNSLKPEDTTVYYCNTFPPISNFWGQGTLVTVSS ASGITSKINDMGWYRQTPGNYREWVASITATGTTNYRDSVKGRFTISRDNAKSTVYLQMNSLKPEDTTVYYCNTFPPISNFWGQGTLVTVSS |
| 337 | T017000099 | EVQLVESGGGLVQPGGSLRLSCVASGDVHKINFLGWYRQAPGKEREKVAHISIGDQTDYADSAKGRFTISRDESKNMVLQMNSLKPEDTAVYFCRA FSRIYPYDYWGQGTLVTVSSGGGGSGGGGSGGGGSGGGGSGGGGSEVQLVESGGGLVQPGGSLRLSCVASGDVHKINFLGWYRQAPG KEREKVAHISIGDQTDYADSAKGRFTISRDESKNMVLQMNSLKPEDTAVYFCRAFSRIYPYDYWGQGTLVTVSSGAADYKDHDGDYKDHDIDYKDD DDKGAAHHHHHH |
| 338 | T017000142 | DVQLVESGGGLVQPGGSLRLSCVASGDVHKINFLGWYRQAPGKEREKVAHISIGDQTDYADSAKGRFTISRDESKNMVLQMNSLKPEDTAVYFCRA FSRIYPYDYWGQGTLVTVSSGGGGSGGGGSGGGGSGGGGSGGGGSEVQLVESGGGLVQAGGSLRLSCAASGITSKINDMGWYRQTPG NYREWVASITATGTTNYRDSVKGRFTISRDNAKSTVYLQMNSLEPEDTTVYYCNTEPPISNFWGQGTLVTVSSGGGGSGGGGSGGGGSGGGGSGGG SGGGGSGGGGSEVQLVESGGGLVQPGNSLRLSCAASGFTFSSFGMSWVRQAPGEGLEWVSSISGSGSDTLYADSVKGRFTISRDNAKTTLYLQMNSL RPEDTAVYYCTIGGSLSRSSQGTLVTVSS |
| 339 | T017000143 | DVQLVESGGGLVQPGGSLRLSCVASGDVHKINFLGWYRQAPGKEREKVAHISIGDQTDYADSAKGRFTISRDESKNMVLQMNSLKPEDTAVYFCRA FSRIYPYDYWGQGTLVTVSSGGGGSGGGGSGGGGSGGGGSGGGGSEVQLVESGGGLVQAGGSLRLSCAASGITSKINDMGWYRQTPG NYREWVASITATGTTNYRDSVKGRFTISRDNAKSTVYLQMNSLEPEDTTVYYCNTEPPISNFWGQGTLVTVSSGGGGSGGGGSGGGGSGGGGGGG |

TABLE A-7-continued

Sequences of multispecific polypeptides. "SEQ" refers to the given SEQ ID NO; "ID" refers to identification name; "sequence" denotes amino acid sequence.

| SEQ | ID | Sequence |
|---|---|---|
| 340 | T017000144 | SGGGGSGGGGSEVQLVESGGGLVQAGGPLRLSCAASGRTFSSYVMGWFRQAPGKEREFVAAIYWSNGETQYTDSVEGRFTISGDNAKNTVYLQMNSL NPEDTAVYYCVADEDTGERTLPIAYDYWGQGTLVTVSSGGGGSGGGGSGGGGSGGGGSEVQLVESGGGLVQPGNSLRLSCA ASGFTESSEGMSWVRQAPGEGLEWVSISGSGSDTLYADSVKGRFTISRDNAKTTLYLQMNSLRPEDTAVYYCTIGGSLSRSSQGTLVTVSSA |
| 341 | T017000145 | DVQLVESGGGLVQPGGSLRLSCVASGDVHKINFLGWYRQAPGKEREKVAHISIGDQTDYADSAKGRFTISRDESKNMVYLQMNSLKPEDTAVYFCRA FSRIYPYDYWGQGTLVTVSSGGGGSGGGGSGGGGSGGGGSEVQLVESGGGLVQAGGSLRLSCAASGITSKINDMGWYRQTPG NYREWVASITATGTTNYRDSVKGRFTISRDNAKTVYLQMNSLEPEDTTVYYCNTEPPISNFWGQGTLVTVSSGGGGSGGGGG SGGGGSGGGGSEVQLVESGGGLVQPGNSLRLSCAASGFTESSEGMSWVRQAPGEGLEWVSISGSGSDTLYADSVKGRFTISRDNAKTTLYLQMNSL RPEDTAVYYCTIGGSLSRSSQGTLVTVSSGGGGSGGGGSEVQLVESGGGLVQAGGPLRLSCAASGRTFSSYV MGWFRQAPGKEREFVAAIYWSNGKTQYTDSVKGRFTISGDNAKNTVYLQMNSLNPEDTAVYYCVADEDTGERTLPIAYDYWGQGTLVTVSSA |
| 342 | T017000146 | DVQLVESGGGLVQPGGSLRLSCVASGDVHKINFLGWYRQAPGKEREKVAHISIGDQTDYADSAKGRFTISRDESKNMVYLQMNSLKPEDTAVYFCRA FSRIYPYDYWGQGTLVTVSSGGGGSGGGGSGGGGSGGGGSEVQLVESGGGLVQAGGPLRLSCAASGRTFSSYVMGWFRQAPG KEREFVAAIYWSNGETQYTDSVEGRFTISGDNAKNTVYLQMNSLNPEDTAVYYCVADEDTGERTLPIAYDYWGQGTLVTVSSGGGGSGGGGGGGG SGGGGSGGGGSEVQLVESGGGLVQPGNSLRLSCAASGFTESSEGMSWVRQAPGEGLEWVSISGSGSDTLYADSVKGRFTISRDNAK TTLYLQMNSLRPEDTAVYYCTIGGSLSRSSQGTLVTVSSGGGGSGGGGSEVQLVESGGGLVQAGGSLRLSCA ASGITSKINDMGWYRQTPGNYREWVASITATGTTNYRDSVKGRFTISRDNAKTVYLQMNSLEPEDTTVYYCNTEPPISNFWGQGTLVTVSSA |

TABLE A-8

Sequences of CD123 and components of TCR complex. "SEQ" refers to the given SEQ ID NO; "ID" refers to identification name; "sequence" denotes amino acid sequence

| SEQ | ID | Sequence |
|---|---|---|
| 68 | Human CD123 (NP_002174) | MVLLWLTLLLIALPCLLQTKEDPNPPITNLRMKAKAQQLTWDLNRNVTDIECVKDADYSMPAVNNSYCQFGAISLCEVTNYTVRVANPPFSTWILF<br>PENSGKPWAGAENLTCWIHDVDFLSCSWAVGPGAPADVQVYDLYLNVANRRQQYECLHYKTDAQGTRIGCRFDDISRLSSGSQSSHILVRGRSAAFG<br>IPCTDKFVVFSQIEILTPPNMTAKCNKTHSFMHWKMRSHFNRKFRYELQIQKRMQPVITEQVRDTSFQLLNPGTYTVQTRARERVYEFLSAWSTP<br>QRFECDQEEGANTRAWRTSLLIALGTLLALVCVFVICRRYLVMQRLFPRIPHMKDPIGDSFQNDKLVVWEAGKAGLEECLVTEVQVVQKT |
| 69 | Cyno CD123 (EHH61867.1) | MTLLWLTLLLVATPCLLRTKEDPNAPIRNLRMKEKAQQLMWDLNRNVTDVECIKGTDYSMPAMNNSYCQFGAISLCEVTNYTVRVASPPFSTWILF<br>PENSGTPRAGAENLTCWVHDVDFLSCSWVVGPAAPADVQVYDLYLNNPNSHEQYRCLHYKTDARGTQIGCRFDDIAPLSRGSQSSHILVRGRSAAVS<br>IPCTDKFVFFSQIERLTPPNMTGECNETHSFMHWKMKSHFNRKFRYELRIQKRMQPVRTEQVRDTTSFQLPNPGTYTVQTRARETVYEFLSAWSTP<br>QRFECDQEEGASSRAWRTSLLIALGTLLALLCVFLICRRYLVMQRLFPRIPHMKDPIGDTFQQDKLVVWEAGKAGLEECLVSEVQVVEKT |
| 70 | Human CD3 delta (P04234) | MEHSTELSGLVLATLLSQVSPFKIPIEELEDRVEVNCNTSITWVEGTVGTLLSDITRLDLGKRILDPRGIYRCNGTDIYKDKESTVQVHYRMCQSC<br>VELDPATVAGIIVTDVIATLLLALGVFCFAGHETGRLSGAADTQALLRNDQVYQPLRDRDDAQYSHLGGNWARNK |
| 71 | Human CD3 gamma (P09693) | MEQGKGLAVLILAIILLQGTLAQSIKGNHLVKVYDYQEDGSVLLTCDAEAKNITWFKDGKMIGFLTEDKKKWNLGSNAKDPRGMYQCKGSQNKSKP<br>LQVYYRMCQNCIELNAATISGFLFAEIVSIFVLAVGVYFIAGQDGVRQSRASDKQTLLPNDQLYQPLKDREDDQYSHLQGNQLRRN |
| 72 | Human CD3 epsilon (P07766) | MQSGTHWRVLGLCLLSVGVWGQDGNEEMGGITQTPYKVSISGTTVILTCPQYPGSEILWQHNDKNIGGDEDDKNIGSDEDHLSLKEFSELEQSGYY<br>VCYPRGSKPEDANFYLYLRARVCENCMEMDVMSVATIVIVDICITGGLLLLVYYWSKNRKAKAKPVTRGAGAGGRQRGQNKERPPPVPNPDYEPIR<br>KGQRDLYSGLNQRRI |
| 73 | Human CD3 zeta (P20963) | MKWKALFTAAILQAQLPITEAQSFGLLDPKLCYLLDGILFIYGVILTALFLRVKFSRSADAPAYQQGQNQLYNELNLGRREEYDVLDKRRGRDPEM<br>GGKPQRRKNPQEGLYNELQKDKMAEAYSEIGMKGERRRGKGHDGLYQGLSTATKDTYDALHMQALPPR |
| 74 | Human TCR alpha constant domain (P01848) | PNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSC<br>DVKLVEKSFETDTNLNFQNLSVIGFRILLLKVAGFNLLMTLRLWSS |
| 75 | Human TCR beta constant domain | EDLNKVFPPEVAVFEPSEAEISHTQKATLVCLATGFFPDHVELSWWVNGKEVHSGVSTDPQPLKEQPALNDSRYCLSSRLRVSATFWQNPRNHFRC<br>QVQFYGLSENDEWTQDRAKPVTQIVSAEAWGRADCGFTSVSYQQGVLSATILYEILLGKATLYAVLVSALVLMAVKRKDF |
| 76 | Human TCR alpha variable domain derived from 2XN9 | QLLEQSPQFLSIQEGENLTVYCNSSSVFSSLQWYRQEPGEGPVLLVTVTGGEVKKLKRLTFQFGDARKDSSLHITAAQPGDTGLYLCAGAGSQGN<br>LIFGKGTKLSVK |

TABLE A-8-continued

Sequences of CD123 and components of TCR complex. "SEQ" refers to the given SEQ ID NO; "ID" refers to identification name; "Sequence"
denotes amino acid sequence

| SEQ | ID | Sequence |
|---|---|---|
| 77 | Human TCR beta variable domain derived from 2XN9 | DGGITQSPKYLFRKEGQNVTLSCEQNLNHDAMYWYRQDPGQGLRLIYYSQIVNDFQKGDIAEGYSVSREKKESFPLTVTSAQKNPTAFYLCASSSR SSYEQYFGPGTRLTVT |
| 343 | Human TCR alpha variable domain derived from 2IAN | IQVEQSPPDLILQEGANSTLRCNFSDSVNNLQWFHQNPWGQLINLFYIPSGTKQNGRLSATTVATERYSLLYISSQTTDSGVYFCAALIQGAQKL VFGQGTRLTIN |
| 344 | Human TCR beta variable domain derived from 2IAN | NAGVTQTPKFRILKIGQSWTLQCTQDMNHNYMYWYRQDPGMGLKLIYYSVGAGITDKGEVPNGYNVSRSTTEDFPLRLELAAPSQTSVYFCASTYH GTGYFGEGSWLTVV |
| 345 | Human TCR alpha variable domain derived from 3TOE | GDAKTTQPNSMESNEEPVHLPCNHSTISGTDYIHWYRQLPSQGPEYVIHGLTSNVNNRMASLAIAEDRKSSTLILHRATLRDAAVYYCTVYGGAT NKLIFGTGTLLAVQ |
| 346 | Human TCR beta variable domain derived from 3TOE | VVSQHPSWVIAKSGTSVKIECRSLDFQATTMFWYRQFPKQSLMLMATSNEGSKATYEQGVEKDKFLINHASLTLSTLTVTSAHPEDSSFYICSARG GSYNSPLHFGNGTRLTVT |

TABLE A-8-continued

Sequences of CD123 and components of TCR complex. "SEQ" refers to the given SEQ ID NO; "ID" refers to identification name; "Sequence"
denotes amino acid sequence

| SEQ ID | | Sequence |
|---|---|---|
| 347 | Cyno TCR alpha constant domain | PYIQNPDPAVYQLRGSKSNDTSVCLFTDFDSVMNVSQSKDSDVHITDKTVLDMRSMDFKSNGAVAWSNKSDFACTSAFKDSVIPADTFFPSPESSC |
| 348 | Rhesus TCR beta constant domain | EDLKKVFPPKVAVFEPSEAEISHTQKATLVCLATGFYPDHVELSWWVNGKEVHSGVSTDPQPLKEQPALEDSRYSLSSRLRVSATFWHNPRNHFRC QVQFYGLSEDDEWTEDRDKPITQKISAEAWGRADC |
| 349 | Rhesus TCR alpha variable domain | QQIMQIPQYQHVQEGEDFTTYCNSSTTLSNIQWYKQRPGGHPVFLIMLVKSGEVKKQKRLIFQFGEAKKNSSLHITATQTTDVGTYFCATTGVNNL FFGTGTRLTVL |
| 350 | Rhesus TCR beta variable domain | AGPVNAGVTQTPKFQVLKTGQSMTLQCAQDMNHDYMYWYRQDPGMGLRLIHYSVGEGSTEKGEVPDGYNVTRSNTEDFPLRLESAAPSQTSVFCA SSYWTGRSYEQYFGPGTRLTVI |

The invention claimed is:

1. A nucleic acid encoding a polypeptide comprising a first immunoglobulin single variable domain (ISV) and a second ISV, wherein the first ISV specifically binds TCR and essentially consists of 4 framework regions (FR1 to FR4, respectively) and 3 complementarity determining regions (CDR1 to CDR3, respectively), in which:

i) CDR1 is chosen from the group consisting of:
  a) SEQ ID NO: 181; and
  b) amino acid sequences that have 3, 2 or 1 amino acid(s) difference with the amino acid sequence of SEQ ID NO: 181, wherein
    at position 2 the D has been changed into A, S, E, or G;
    at position 4 the H has been changed into Y;
    at position 5 the K has been changed into L;
    at position 6 the I has been changed into L;
    at position 8 the F has been changed into I or V; and/or
    at position 10 the G has been changed into S; and ii) CDR2 is chosen from the group consisting of:
  c) SEQ ID NO: 192; and
  d) amino acid sequences that have 3, 2 or 1 amino acid(s) difference with the amino acid sequence of SEQ ID NO: 192, wherein
    at position 1 the D has been changed into T or R;
    at position 3 the S has been changed into T or A;
    at position 5 the G has been changed into S or A;
    at position 7 the Q has been changed into D, E, T, A or V;
    at position 8 the T has been changed into A or V; and/or
    at position 9 the D has been changed into A, Q, N, V or S;

and iii) CDR3 is chosen from the group consisting of:
  e) SEQ ID NO: 218; and
  f) amino acid sequences that have 3, 2 or 1 amino acid(s) difference with the amino acid sequence of SEQ ID NO: 218, wherein
    at position 1 the F has been changed into Y, L or G;
    at position 4 the I has been changed into L;
    at position 5 the Y has been changed into W; and/or
    at position 8 the D has been changed into N or S;

and wherein the second ISV specifically binds CD123 and essentially consists of 4 framework regions (FR1 to FR4, respectively) and 3 complementarity determining regions (CDR1 to CDR3, respectively), in which:

i) CDR1 is chosen from the group consisting of:
  a) SEQ ID NO: 11; and
  b) amino acid sequences that have 3, 2 or 1 amino acid(s) difference with the amino acid sequence of SEQ ID NO: 11, wherein
    at position 3 the T has been changed into S or P;
    at position 6 the I has been changed into S;
    at position 7 the N has been changed into D; and/or
    at position 8 the D has been changed into V or A;

and ii) CDR2 is SEQ ID NO: 17;

and iii) CDR3 is chosen from the group consisting of:
  c) SEQ ID NO: 21; and
  d) amino acid sequences that have 1 amino acid(s) difference with the amino acid sequence of SEQ ID NO: 21, wherein at position 3 the P has been changed into A.

2. The nucleic acid according to claim 1, which is in the form of a genetic construct.

3. An expression vector comprising the nucleic acid according to claim 1.

4. A host or host cell comprising the nucleic acid according to claim 1.

5. A method for the production of a polypeptide, said method at least comprising the steps of:
  a) expressing, in a suitable host cell or in another suitable expression system, the nucleic acid according to claim 1; optionally followed by
  b) isolating and/or purifying the polypeptide.

6. A composition comprising the nucleic acid according to claim 1.

7. The composition according to claim 6, which is a pharmaceutical composition.

8. The composition according to claim 7, which further comprises at least one pharmaceutically acceptable carrier, diluent or excipient and/or adjuvant.

9. A kit comprising the nucleic acid according to claim 1.

10. The nucleic acid of claim 1, wherein the first ISV essentially consists of 4 framework regions (FR1 to FR4, respectively) and 3 complementarity determining regions (CDR1 to CDR3, respectively), in which CDR1 is SEQ ID NO: 181, CDR2 is SEQ ID NO: 192, and CDR3 is SEQ ID NO: 218.

11. The nucleic acid of claim 1, wherein the first ISV is chosen from the group consisting of SEQ ID NOs: 42 and 78-180 and an amino acid sequence having a sequence identity of more than 90% with one of SEQ ID NOs: 42 and 78-180.

12. The nucleic acid of claim 1, comprising a third ISV, wherein the third ISV specifically binds CD123 and essentially consists of 4 framework regions (FR1 to FR4, respectively) and 3 complementarity determining regions (CDR1 to CDR3, respectively), in which:

i) CDR1 is SEQ ID NO: 16; and ii) CDR2 is chosen from the group consisting of:
    a) SEQ ID NO: 18; and
    b) amino acid sequences that have 3, 2 or 1 amino acid(s) difference with the amino acid sequence of SEQ ID NO: 18, wherein
      at position 3 the Y has been changed into W;
      at position 6 the N has been changed into S; and/or
      at position 10 the Q has been changed into E; and iii) CDR3 is chosen from the group consisting of:
    c) SEQ ID NO: 23; and
    d) amino acid sequences that have 2 or 1 amino acid(s) difference with the amino acid sequence of SEQ ID NO: 23, wherein
      at position 4 the E has been changed into R; and/or
      at position 5 the T has been changed into D or Y.

13. The nucleic acid of claim 1, wherein the second ISV essentially consists of 4 framework regions (FR1 to FR4, respectively) and 3 complementarity determining regions (CDR1 to CDR3, respectively), in which CDR1 is SEQ ID NO: 11, CDR2 is SEQ ID NO: 17, and CDR3 is SEQ ID NO: 21.

14. The nucleic acid of claim 1, wherein the second ISV is chosen from the group consisting of SEQ ID NOs: 1-6 and an amino acid sequence having a sequence identity of more than 90% with one of SEQ ID NOs: 1-6.

15. The nucleic acid of claim 1, further comprising a third ISV, wherein the third ISV specifically binds CD123, wherein the second ISV binds to an epitope on CD123 that is different from the epitope on CD123 bound by the third ISV.

16. The nucleic acid of claim 15, wherein the second ISV is chosen from the group consisting of SEQ ID NOs: 1-6 and an amino acid sequence having more than 90% identity with one of SEQ ID NOs: 1-6, and wherein the third ISV is chosen from the group consisting of SEQ ID NOs: 7-10 and an amino acid sequence having more than 90% identity with one of SEQ ID NOs: 7-10.

17. The nucleic acid of claim 1, wherein each of the first ISV and the second ISV essentially consist of a single domain antibody, a dAb, a Nanobody, a VHH, a humanized VHH, a camelized VH or a VHH which has been obtained by affinity maturation.

18. The nucleic acid of claim 1, wherein the polypeptide is chosen from the group consisting of SEQ ID NOs: 47, 49, 52, 53, 55, 56 and 58-61 and an amino acid sequence having a sequence identity of more than 90% with one of SEQ ID NOs: 47, 49, 52, 53, 55, 56 and 58-61.

19. A nucleic acid encoding a polypeptide comprising a first immunoglobulin single variable domain (ISV) and a second ISV, wherein the first ISV specifically binds TCR and essentially consists of 4 framework regions (FR1 to FR4, respectively) and 3 complementarity determining regions (CDR1 to CDR3, respectively), in which:

i) CDR1 is chosen from the group consisting of:
    a) SEQ ID NO: 181; and
    b) amino acid sequences that have 1 amino acid difference with the amino acid sequence of SEQ ID NO: 181; and ii) CDR2 is chosen from the group consisting of:
    c) SEQ ID NO: 192; and
    d) amino acid sequences that have 1 amino acid difference with the amino acid sequence of SEQ ID NO: 192; and iii) CDR3 is chosen from the group consisting of:
    e) SEQ ID NO: 218; and
    f) amino acid sequences that have 1 amino acid difference with the amino acid sequence of SEQ ID NO: 218;

and wherein the second ISV specifically binds CD123 and essentially consists of 4 framework regions (FR1 to FR4, respectively) and 3 complementarity determining regions (CDR1 to CDR3, respectively), in which:

i) CDR1 is chosen from the group consisting of:
    a) SEQ ID NO: 11; and
    b) amino acid sequences that have 1 amino acid difference with the amino acid sequence of SEQ ID NO: 11; and ii) CDR2 is chosen from the group consisting of:
    c) SEQ ID NO: 17; and
    d) amino acid sequences that have 1 amino acid difference with the amino acid sequence of SEQ ID NO: 17; and iii) CDR3 is chosen from the group consisting of:
    e) SEQ ID NO: 21; and
    f) amino acid sequences that have 1 amino acid difference with the amino acid sequence of SEQ ID NO: 21.

\* \* \* \* \*

SEQUENCE LISTING

Sequence total quantity: 382
SEQ ID NO: 1                    moltype = AA   length = 115
FEATURE                         Location/Qualifiers
REGION                          1..115
                                note = Nanobody Sequence
source                          1..115
                                mol_type = protein
                                organism = synthetic construct
SEQUENCE: 1
EVQLVKSGGG LVQAGGSLRL SCAASGITSK INDMGWYRQT PGNYREWVAS ITATGTTNYR   60
DSVKGRFTIS RDNAKSTVYL QMNSLKPEDT TVYYCNTFPP ISNFWGQGTL VTVSS        115

SEQ ID NO: 2                    moltype = AA   length = 115
FEATURE                         Location/Qualifiers
REGION                          1..115
                                note = Nanobody Sequence
source                          1..115
                                mol_type = protein
                                organism = synthetic construct
SEQUENCE: 2
EVQLVESGGG LVQAGGSLRL SCAANGISSK SDAMGWYRQT PGKYREWVAS ITATGTTNYR   60
DSVKGRFTIS RDNAKNTVYL QMNSLKPEDT TVYYCNTFPA ISNFWGQGTQ VTVSS        115

SEQ ID NO: 3                    moltype = AA   length = 115
FEATURE                         Location/Qualifiers
REGION                          1..115
                                note = Nanobody Sequence
source                          1..115
                                mol_type = protein
                                organism = synthetic construct
SEQUENCE: 3
EVQLVESGGG LVQAGGSLRL SCAANGITSK SNAMGWYRQT PGKYREWVAS ITATGTTNYR   60
DSVKGRFTIS RDNAKNTVYL QMNSLKPEDT TVYYCNTFPA ISNFWGQGTQ VTVSS        115

SEQ ID NO: 4                    moltype = AA   length = 115
FEATURE                         Location/Qualifiers
REGION                          1..115
                                note = Nanobody Sequence
source                          1..115
                                mol_type = protein
                                organism = synthetic construct
SEQUENCE: 4
EVQLVESGGG LVQAGGSLRL SCAASGIPSK INDMGWFRQT PGNYREWVAS ITATGTTNYR   60
DSVKGRFTIS RDNAKNTVYL QMNSLKPEDT TVYYCNTFPP ISNFWGQGTL VTVSS        115

SEQ ID NO: 5                    moltype = AA   length = 115
FEATURE                         Location/Qualifiers
REGION                          1..115
                                note = Nanobody Sequence
source                          1..115
                                mol_type = protein
                                organism = synthetic construct
SEQUENCE: 5
EVQLVESGGG LVQAGGSLRL SCAASGITSK INDMGWYRQT PGNYREWVAS ITATGTTNYR   60
DSVKGRFTIS RDNAKSTVYL QMNSLKPEDT TVYYCNTFPP ISNFWGQGTL VTVSS        115

SEQ ID NO: 6                    moltype = AA   length = 115
FEATURE                         Location/Qualifiers
REGION                          1..115
                                note = Nanobody Sequence
source                          1..115
                                mol_type = protein
                                organism = synthetic construct
SEQUENCE: 6
EVQLVESGGG LVQAGGSLRL SCAASGITSK SNVMGWYRQT PGKYREWVAS ITATGTTNYR   60
DSVKGRFTIS RDNAKNTVYL QMNSLKPEDT TVYYCNTFPA ISNFWGQGTQ VTVSS        115

SEQ ID NO: 7                    moltype = AA   length = 125
FEATURE                         Location/Qualifiers
REGION                          1..125
                                note = Nanobody Sequence
source                          1..125
                                mol_type = protein
                                organism = synthetic construct
SEQUENCE: 7
EVQLVESGGG LVQAGGPLRL SCAASGRTFS SYVMGWFRQA PGKEREFVAA IYWSNGKTQY   60
TDSVKGRFTI SGDNAKNTVY LQMNSLNPED TAVYYCVADK DETGFRTLPI AYDYWGQGTQ   120
VTVSS                                                              125

-continued

```
SEQ ID NO: 8               moltype = AA   length = 125
FEATURE                    Location/Qualifiers
REGION                     1..125
                           note = Nanobody Sequence
source                     1..125
                           mol_type = protein
                           organism = synthetic construct
SEQUENCE: 8
EVQLVESGGG LVQAGGSLRL SCAASGRTFS SYVMGWFRQA PGKEREFVAA IYWSSGKTEY  60
TDSVKGRFTL SGDNAKNTVY LQMNSLNPED TAVYYCVADK DRDGFRTLPI AYDYWGQGTQ 120
VTVSS                                                             125

SEQ ID NO: 9               moltype = AA   length = 125
FEATURE                    Location/Qualifiers
REGION                     1..125
                           note = Nanobody Sequence
source                     1..125
                           mol_type = protein
                           organism = synthetic construct
SEQUENCE: 9
EVQLVESGGG LVQAGGSLRL SCAASGRTFS SYVMGWFRQA PGKEREFVAA IYWSSGKTEY  60
TESVKGRFTL SGDNAKNTVY LQMNSLNPED TAVYYCVADK DRYGFRTLPI AYDYWGQGTQ 120
VTVSS                                                             125

SEQ ID NO: 10              moltype = AA   length = 125
FEATURE                    Location/Qualifiers
REGION                     1..125
                           note = Nanobody Sequence
source                     1..125
                           mol_type = protein
                           organism = synthetic construct
SEQUENCE: 10
EVQLVESGGG LVQAGGSLRL SCAASGRTFS SYVMGWFRQA PGKEREFVAA IWWSSGKTEY  60
TDSVKGRFTL SGDNAKNTVY LQMNNLNPED TAVYYCVADK DRDGFRTLPI AYDYWGQGTQ 120
VTVSS                                                             125

SEQ ID NO: 11              moltype = AA   length = 10
FEATURE                    Location/Qualifiers
REGION                     1..10
                           note = CDR1
source                     1..10
                           mol_type = protein
                           organism = synthetic construct
SEQUENCE: 11
GITSKINDMG                                                         10

SEQ ID NO: 12              moltype = AA   length = 10
FEATURE                    Location/Qualifiers
REGION                     1..10
                           note = CDR1
source                     1..10
                           mol_type = protein
                           organism = synthetic construct
SEQUENCE: 12
GISSKSDAMG                                                         10

SEQ ID NO: 13              moltype = AA   length = 10
FEATURE                    Location/Qualifiers
REGION                     1..10
                           note = CDR1
source                     1..10
                           mol_type = protein
                           organism = synthetic construct
SEQUENCE: 13
GITSKSNAMG                                                         10

SEQ ID NO: 14              moltype = AA   length = 10
FEATURE                    Location/Qualifiers
REGION                     1..10
                           note = CDR1
source                     1..10
                           mol_type = protein
                           organism = synthetic construct
SEQUENCE: 14
GIPSKINDMG                                                         10

SEQ ID NO: 15              moltype = AA   length = 10
FEATURE                    Location/Qualifiers
```

```
REGION                    1..10
                          note = CDR1
source                    1..10
                          mol_type = protein
                          organism = synthetic construct
SEQUENCE: 15
GITSKSNVMG                                                                          10

SEQ ID NO: 16             moltype = AA   length = 10
FEATURE                   Location/Qualifiers
REGION                    1..10
                          note = CDR1
source                    1..10
                          mol_type = protein
                          organism = synthetic construct SEQUENCE: 16
GRTFSSYVMG                                                                          10

SEQ ID NO: 17             moltype = AA   length = 9
FEATURE                   Location/Qualifiers
REGION                    1..9
                          note = CDR2
source                    1..9
                          mol_type = protein
                          organism = synthetic construct SEQUENCE: 17
SITATGTTN                                                                           9

SEQ ID NO: 18             moltype = AA   length = 10
FEATURE                   Location/Qualifiers
REGION                    1..10
                          note = CDR2
source                    1..10
                          mol_type = protein
                          organism = synthetic construct SEQUENCE: 18
AIYWSNGKTQ                                                                          10

SEQ ID NO: 19             moltype = AA   length = 10
FEATURE                   Location/Qualifiers
REGION                    1..10
                          note = CDR2
source                    1..10
                          mol_type = protein
                          organism = synthetic construct SEQUENCE: 19
AIYWSSGKTE                                                                          10

SEQ ID NO: 20             moltype = AA   length = 10
FEATURE                   Location/Qualifiers
REGION                    1..10
                          note = CDR2
source                    1..10
                          mol_type = protein
                          organism = synthetic construct
SEQUENCE: 20
AIWWSSGKTE                                                                          10

SEQ ID NO: 21             moltype = AA   length = 7
FEATURE                   Location/Qualifiers
REGION                    1..7
                          note = CDR3
source                    1..7
                          mol_type = protein
                          organism = synthetic construct SEQUENCE: 21
FPPISNF                                                                             7

SEQ ID NO: 22             moltype = AA   length = 7
FEATURE                   Location/Qualifiers
REGION                    1..7
                          note = CDR3
source                    1..7
                          mol_type = protein
                          organism = synthetic construct SEQUENCE: 22
FPAISNF                                                                             7

SEQ ID NO: 23             moltype = AA   length = 16
```

-continued

```
FEATURE              Location/Qualifiers
REGION               1..16
                     note = CDR3
source               1..16
                     mol_type = protein
                     organism = synthetic construct
SEQUENCE: 23
DKDETGFRTL PIAYDY                                            16

SEQ ID NO: 24        moltype = AA   length = 16
FEATURE              Location/Qualifiers
REGION               1..16
                     note = CDR3
source               1..16
                     mol_type = protein
                     organism = synthetic construct
SEQUENCE: 24
DKDRDGFRTL PIAYDY                                            16

SEQ ID NO: 25        moltype = AA   length = 16
FEATURE              Location/Qualifiers
REGION               1..16
                     note = CDR3
source               1..16
                     mol_type = protein
                     organism = synthetic construct
SEQUENCE: 25
DKDRYGFRTL PIAYDY                                            16

SEQ ID NO: 26        moltype = AA   length = 25
FEATURE              Location/Qualifiers
REGION               1..25
                     note = FR1
source               1..25
                     mol_type = protein
                     organism = synthetic construct
SEQUENCE: 26
EVQLVKSGGG LVQAGGSLRL SCAAS                                  25

SEQ ID NO: 27        moltype = AA   length = 25
FEATURE              Location/Qualifiers
REGION               1..25
                     note = FR1
source               1..25
                     mol_type = protein
                     organism = synthetic construct
SEQUENCE: 27
EVQLVESGGG LVQAGGSLRL SCAAN                                  25

SEQ ID NO: 28        moltype = AA   length = 25
FEATURE              Location/Qualifiers
REGION               1..25
                     note = FR1
source               1..25
                     mol_type = protein
                     organism = synthetic construct
SEQUENCE: 28
EVQLVESGGG LVQAGGSLRL SCAAS                                  25

SEQ ID NO: 29        moltype = AA   length = 25
FEATURE              Location/Qualifiers
REGION               1..25
                     note = FR1
source               1..25
                     mol_type = protein
                     organism = synthetic construct
SEQUENCE: 29
EVQLVESGGG LVQAGGPLRL SCAAS                                  25

SEQ ID NO: 30        moltype = AA   length = 14
FEATURE              Location/Qualifiers
REGION               1..14
                     note = FR2
source               1..14
                     mol_type = protein
                     organism = synthetic construct
SEQUENCE: 30
WYRQTPGNYR EWVA                                              14
```

-continued

```
SEQ ID NO: 31                moltype = AA   length = 14
FEATURE                      Location/Qualifiers
REGION                       1..14
                             note = FR2
source                       1..14
                             mol_type = protein
                             organism = synthetic construct
SEQUENCE: 31
WYRQTPGKYR EWVA                                                  14

SEQ ID NO: 32                moltype = AA   length = 14
FEATURE                      Location/Qualifiers
REGION                       1..14
                             note = FR2
source                       1..14
                             mol_type = protein
                             organism = synthetic construct
SEQUENCE: 32
WFRQTPGNYR EWVA                                                  14

SEQ ID NO: 33                moltype = AA   length = 14
FEATURE                      Location/Qualifiers
REGION                       1..14
                             note = FR2
source                       1..14
                             mol_type = protein
                             organism = synthetic construct
SEQUENCE: 33
WFRQAPGKER EFVA                                                  14

SEQ ID NO: 34                moltype = AA   length = 39
FEATURE                      Location/Qualifiers
REGION                       1..39
                             note = FR3
source                       1..39
                             mol_type = protein
                             organism = synthetic construct
SEQUENCE: 34
YRDSVKGRFT ISRDNAKSTV YLQMNSLKPE DTTVYYCNT                       39

SEQ ID NO: 35                moltype = AA   length = 39
FEATURE                      Location/Qualifiers
REGION                       1..39
                             note = FR3
source                       1..39
                             mol_type = protein
                             organism = synthetic construct
SEQUENCE: 35
YRDSVKGRFT ISRDNAKNTV YLQMNSLKPE DTTVYYCNT                       39

SEQ ID NO: 36                moltype = AA   length = 39
FEATURE                      Location/Qualifiers
REGION                       1..39
                             note = FR3
source                       1..39
                             mol_type = protein
                             organism = synthetic construct
SEQUENCE: 36
YTDSVKGRFT ISGDNAKNTV YLQMNSLNPE DTAVYYCVA                       39

SEQ ID NO: 37                moltype = AA   length = 39
FEATURE                      Location/Qualifiers
REGION                       1..39
                             note = FR3
source                       1..39
                             mol_type = protein
                             organism = synthetic construct
SEQUENCE: 37
YTDSVKGRFT LSGDNAKNTV YLQMNSLNPE DTAVYYCVA                       39

SEQ ID NO: 38                moltype = AA   length = 39
FEATURE                      Location/Qualifiers
REGION                       1..39
                             note = FR3
source                       1..39
                             mol_type = protein
                             organism = synthetic construct
SEQUENCE: 38
YTESVKGRFT LSGDNAKNTV YLQMNSLNPE DTAVYYCVA                       39
```

```
SEQ ID NO: 39            moltype = AA  length = 39
FEATURE                  Location/Qualifiers
REGION                   1..39
                         note = FR3
source                   1..39
                         mol_type = protein
                         organism = synthetic construct
SEQUENCE: 39
YTDSVKGRFT LSGDNAKNTV YLQMNNLNPE DTAVYYCVA                        39

SEQ ID NO: 40            moltype = AA  length = 11
FEATURE                  Location/Qualifiers
REGION                   1..11
                         note = FR4
source                   1..11
                         mol_type = protein
                         organism = synthetic construct
SEQUENCE: 40
WGQGTLVTVS S                                                      11

SEQ ID NO: 41            moltype = AA  length = 11
FEATURE                  Location/Qualifiers
REGION                   1..11
                         note = FR4
source                   1..11
                         mol_type = protein
                         organism = synthetic construct
SEQUENCE: 41
WGQGTQVTVS S                                                      11

SEQ ID NO: 42            moltype = AA  length = 117
FEATURE                  Location/Qualifiers
REGION                   1..117
                         note = Nanobody sequence
source                   1..117
                         mol_type = protein
                         organism = synthetic construct
SEQUENCE: 42
EVQLVESGGG LVQPGGSLRL SCVASGDVHK INFLGWYRQA PGKEREKVAH ISIGDQTDYA  60
DSAKGRFTIS RDESKNMVYL QMNSLKPEDT AVYFCRAFSR IYPYDYWGQG TLVTVSS     117

SEQ ID NO: 43            moltype = AA  length = 115
FEATURE                  Location/Qualifiers
REGION                   1..115
                         note = Nanobody Sequence
source                   1..115
                         mol_type = protein
                         organism = synthetic construct
SEQUENCE: 43
EVQLVESGGG LVQPGNSLRL SCAASGFTFS SFGMSWVRQA PGKGLEWVSS ISGSGSDTLY  60
ADSVKGRFTI SRDNAKTTLY LQMNSLRPED TAVYYCTIGG SLSRSSQGTL VTVSS       115

SEQ ID NO: 44            moltype = AA  length = 127
FEATURE                  Location/Qualifiers
REGION                   1..127
                         note = Nanobody Sequence
source                   1..127
                         mol_type = protein
                         organism = synthetic construct
SEQUENCE: 44
EVQLVESGGG LVQAGDSLRL SCAASGRTFS SYAMGWFRQA PGKEREFVAA ISWSDGSTYY  60
ADSVKGRFTI SRDNAKNTVY LQMNSLKPED TAVYYCAADL TSTNPGSYIY IWAYDYWGQG  120
TLVTVSS                                                            127

SEQ ID NO: 45            moltype = AA  length = 133
FEATURE                  Location/Qualifiers
REGION                   1..133
                         note = Nanobody Sequence
source                   1..133
                         mol_type = protein
                         organism = synthetic construct
SEQUENCE: 45
EVQLVESGGG SVQAGGSLRL SCAASGYTIG PYCMGWFRQA PGKEREGVAA INMGGGITYY  60
ADSVKGRFTI SQDNAKNTVY LLMNSLEPED TAIYYCAADS TIYASYYECG HGLSTGGYGY  120
DSWGQGTLVT VSS                                                     133

SEQ ID NO: 46            moltype = AA  length = 445
FEATURE                  Location/Qualifiers
```

-continued

```
REGION                    1..445
                          note = Nanobody Sequence
source                    1..445
                          mol_type = protein
                          organism = synthetic construct
SEQUENCE: 46
EVQLVESGGG LVQAGGPLRL SCAASGRTFS SYVMGWFRQA PGKEREFVAA IYWSNGKTQY   60
TDSVKGRFTI SGDNAKNTVY LQMNSLNPED TAVYYCVADK DETGFRTLPI AYDYWGQGTL  120
VTVSSGGGGS GGGGSGGGGS GGGGSGGGGS EVQLVESGGG SVQAGGSLRL             180
SCAASGYTIG PYCMGWFRQA PGKEREGVAA INMGGGITYY ADSVKGRFTI SQDNAKNTVY  240
LLMNSLEPED TAIYYCAADS TIYASYYECG HGLSTGGYGY DSWGQGTLVT VSSGGGGSGG  300
GGSGGGGSGG GGSGGGGSGG GGSGGGGSEV QLVESGGGLV QPGGSLRLSC VASGDVHKIN  360
FLGWYRQAPG KEREKVAHIS IGDQTDYADS AKGRFTISRD ESKNMVYLQM NSLKPEDTAV  420
YFCRAFSRIY PYDYWGQGTL VTVSS                                        445

SEQ ID NO: 47             moltype = AA   length = 427
FEATURE                   Location/Qualifiers
REGION                    1..427
                          note = Nanobody Sequence
source                    1..427
                          mol_type = protein
                          organism = synthetic construct
SEQUENCE: 47
EVQLVESGGG LVQAGGPLRL SCAASGRTFS SYVMGWFRQA PGKEREFVAA IYWSNGKTQY   60
TDSVKGRFTI SGDNAKNTVY LQMNSLNPED TAVYYCVADK DETGFRTLPI AYDYWGQGTL  120
VTVSSGGGGS GGGGSGGGGS GGGGSGGGGS EVQLVESGGG LVQAGGSLRL             180
SCAASGITSK INDMGWYRQT PGNYREWVAS ITATGTTNYR DSVKGRFTIS RDNAKSTVYL  240
QMNSLKPEDT TVYYCNTFPP ISNFWGQGTL VTVSSGGGGS GGGGSGGGGS GGGGSGGGGS  300
GGGGSGGGGS EVQLVESGGG LVQPGGSLRL SCVASGDVHK INFLGWYRQA PGKEREKVAH  360
ISIGDQTDYA DSAKGRFTIS RDESKNMVYL QMNSLKPEDT AVYFCRAFSR IYPYDYWGQG  420
TLVTVSS                                                            427

SEQ ID NO: 48             moltype = AA   length = 435
FEATURE                   Location/Qualifiers
REGION                    1..435
                          note = Nanobody Sequence
source                    1..435
                          mol_type = protein
                          organism = synthetic construct
SEQUENCE: 48
EVQLVESGGG LVQAGGSLRL SCAASGITSK INDMGWYRQT PGNYREWVAS ITATGTTNYR   60
DSVKGRFTIS RDNAKSTVYL QMNSLKPEDT TVYYCNTFPP ISNFWGQGTL VTVSSGGGGS  120
GGGGSGGGGS GGGGSGGGGS EVQLVESGGG SVQAGGSLRL SCAASGYTIG             180
PYCMGWFRQA PGKEREGVAA INMGGGITYY ADSVKGRFTI SQDNAKNTVY LLMNSLEPED  240
TAIYYCAADS TIYASYYECG HGLSTGGYGY DSWGQGTLVT VSSGGGGSGG GGSGGGGSGG  300
GGSGGGGSGG GGSGGGGSEV QLVESGGGLV QPGGSLRLSC VASGDVHKIN FLGWYRQAPG  360
KEREKVAHIS IGDQTDYADS AKGRFTISRD ESKNMVYLQM NSLKPEDTAV YFCRAFSRIY  420
PYDYWGQGTL VTVSS                                                   435

SEQ ID NO: 49             moltype = AA   length = 427
FEATURE                   Location/Qualifiers
REGION                    1..427
                          note = Nanobody Sequence
source                    1..427
                          mol_type = protein
                          organism = synthetic construct
SEQUENCE: 49
EVQLVESGGG LVQAGGSLRL SCAASGITSK INDMGWYRQT PGNYREWVAS ITATGTTNYR   60
DSVKGRFTIS RDNAKSTVYL QMNSLKPEDT TVYYCNTFPP ISNFWGQGTL VTVSSGGGGS  120
GGGGSGGGGS GGGGSGGGGS EVQLVESGGG LVQAGGPLRL SCAASGRTFS             180
SYVMGWFRQA PGKEREFVAA IYWSNGKTQY TDSVKGRFTI SGDNAKNTVY LQMNSLNPED  240
TAVYYCVADK DETGFRTLPI AYDYWGQGTL VTVSSGGGGS GGGGSGGGGS GGGGSGGGGS  300
GGGGSGGGGS EVQLVESGGG LVQPGGSLRL SCVASGDVHK INFLGWYRQA PGKEREKVAH  360
ISIGDQTDYA DSAKGRFTIS RDESKNMVYL QMNSLKPEDT AVYFCRAFSR IYPYDYWGQG  420
TLVTVSS                                                            427

SEQ ID NO: 50             moltype = AA   length = 445
FEATURE                   Location/Qualifiers
REGION                    1..445
                          note = Nanobody Sequence
source                    1..445
                          mol_type = protein
                          organism = synthetic construct
SEQUENCE: 50
EVQLVESGGG SVQAGGSLRL SCAASGYTIG PYCMGWFRQA PGKEREGVAA INMGGGITYY   60
ADSVKGRFTI SQDNAKNTVY LLMNSLEPED TAIYYCAADS TIYASYYECG HGLSTGGYGY  120
DSWGQGTLVT VSSGGGGSGG GGSGGGGSGG GGSGGGGSGG GGSGGGGSEV QLVESGGGLV  180
QAGGPLRLSC AASGRTFSSY VMGWFRQAPG KEREFVAAIY WSNGKTQYTD SVKGRFTISG  240
DNAKNTVYLQ MNSLNPEDTA VYYCVADKDE TGFRTLPIAY DYWGQGTLVT VSSGGGGSGG  300
```

```
GGSGGGGSGG GGSGGGGSGG GGSGGGGSEV QLVESGGGLV QPGGSLRLSC VASGDVHKIN    360
FLGWYRQAPG KEREKVAHIS IGDQTDYADS AKGRFTISRD ESKNMVYLQM NSLKPEDTAV    420
YFCRAFSRIY PYDYWGQGTL VTVSS                                          445

SEQ ID NO: 51              moltype = AA   length = 435
FEATURE                    Location/Qualifiers
REGION                     1..435
                           note = Nanobody Sequence
source                     1..435
                           mol_type = protein
                           organism = synthetic construct
SEQUENCE: 51
EVQLVESGGG SVQAGGSLRL SCAASGYTIG PYCMGWFRQA PGKEREGVAA INMGGGITYY    60
ADSVKGRFTI SQDNAKNTVY LLMNSLEPED TAIYYCAADS TIYASYYECG HGLSTGGYGY    120
DSWGQGTLVT VSSGGGGSGG GGSGGGGSGG GGSGGGGSGG GGSGGGGSEV QLVESGGGLV    180
QAGGSLRLSC AASGITSKIN DMGWYRQTPG NYREWVASIT ATGTTNYRDS VKGRFTISRD    240
NAKSTVYLQM NSLKPEDTTV YYCNTFPPIS NFWGQGTLVT VSSGGGGSGG GGSGGGGSGG    300
GGSGGGGSGG GGSGGGGSEV QLVESGGGLV QPGGSLRLSC VASGDVHKIN FLGWYRQAPG    360
KEREKVAHIS IGDQTDYADS AKGRFTISRD ESKNMVYLQM NSLKPEDTAV YFCRAFSRIY    420
PYDYWGQGTL VTVSS                                                     435

SEQ ID NO: 52              moltype = AA   length = 427
FEATURE                    Location/Qualifiers
REGION                     1..427
                           note = Nanobody Sequence
source                     1..427
                           mol_type = protein
                           organism = synthetic construct
SEQUENCE: 52
DVQLVESGGG LVQAGGPLRL SCAASGRTFS SYVMGWFRQA PGKEREFVAA IYWSNGKTQY    60
TDSVKGRFTI SGDNAKNTVY LQMNSLNPED TAVYYCVADK DETGFRTLPI AYDYWGQGTL    120
VTVSSGGGGS GGGGSGGGGS GGGGSGGGGS GGGGSGGGGS EVQLVESGGG LVQAGGSLRL    180
SCAASGITSK INDMGWYRQT PGNYREWVAS ITATGTTNYR DSVKGRFTIS RDNAKSTVYL    240
QMNSLKPEDT TVYYCNTFPP ISNFWGQGTL VTVSSGGGGS GGGGSGGGGS GGGGSGGGGS    300
GGGGSGGGGS EVQLVESGGG LVQPGGSLRL SCVASGDVHK INFLGWYRQA PGKEREKVAH    360
ISIGDQTDYA DSAKGRFTIS RDESKNMVYL QMNSLKPEDT AVYFCRAFSR IYPYDYWGQG    420
TLVTVSS                                                              427

SEQ ID NO: 53              moltype = AA   length = 267
FEATURE                    Location/Qualifiers
REGION                     1..267
                           note = Nanobody Sequence
source                     1..267
                           mol_type = protein
                           organism = synthetic construct
SEQUENCE: 53
DVQLVESGGG LVQPGGSLRL SCVASGDVHK INFLGWYRQA PGKEREKVAH ISIGDQTDYA    60
DSAKGRFTIS RDESKNMVYL QMNSLKPEDT AVYFCRAFSR IYPYDYWGQG TLVTVSSGGG    120
GSGGGGSGGG GSGGGGSGGG GSGGGGSGGG GSEVQLVESG GGLVQAGGSL RLSCAASGIT    180
SKINDMGWYR QTPGNYREWV ASITATGTTN YRDSVKGRFT ISRDNAKSTV YLQMNSLKPE    240
DTTVYYCNTF PPISNFWGQG TLVTVSS                                        267

SEQ ID NO: 54              moltype = AA   length = 279
FEATURE                    Location/Qualifiers
REGION                     1..279
                           note = Nanobody Sequence
source                     1..279
                           mol_type = protein
                           organism = synthetic construct
SEQUENCE: 54
DVQLVESGGG LVQPGGSLRL SCVASGDVHK INFLGWYRQA PGKEREKVAH ISIGDQTDYA    60
DSAKGRFTIS RDESKNMVYL QMNSLKPEDT AVYFCRAFSR IYPYDYWGQG TLVTVSSGGG    120
GSGGGGSGGG GSGGGGSGGG GSGGGGSGGG GSEVQLVESG GGLVQAGDSL RLSCAASGRT    180
FSSYAMGWFR QAPGKEREFV AAISWSDGST YYADSVKGRF TISRDNAKNT VYLQMNSLKP    240
EDTAVYYCAA DLTSTNPGSY IYIWAYDYWG QGTLVTVSS                           279

SEQ ID NO: 55              moltype = AA   length = 427
FEATURE                    Location/Qualifiers
REGION                     1..427
                           note = Nanobody Sequence
source                     1..427
                           mol_type = protein
                           organism = synthetic construct
SEQUENCE: 55
DVQLVESGGG LVQAGGSLRL SCAASGITSK INDMGWYRQT PGNYREWVAS ITATGTTNYR    60
DSVKGRFTIS RDNAKSTVYL QMNSLKPEDT TVYYCNTFPP ISNFWGQGTL VTVSSGGGGS    120
GGGGSGGGGS GGGGSGGGGS GGGGSGGGGS EVQLVESGGG LVQAGGPLRL SCAASGRTFS    180
SYVMGWFRQA PGKEREFVAA IYWSNGKTQY TDSVKGRFTI SGDNAKNTVY LQMNSLNPED    240
TAVYYCVADK DETGFRTLPI AYDYWGQGTL VTVSSGGGGS GGGGSGGGGS GGGGSGGGGS    300
```

```
GGGGSGGGGS EVQLVESGGG LVQPGGSLRL SCVASGDVHK INFLGWYRQA PGKEREKVAH   360
ISIGDQTDYA DSAKGRFTIS RDESKNMVYL QMNSLKPEDT AVYFCRAFSR IYPYDYWGQG   420
TLVTVSS                                                             427

SEQ ID NO: 56           moltype = AA  length = 267
FEATURE                 Location/Qualifiers
REGION                  1..267
                        note = Nanobody Sequence
source                  1..267
                        mol_type = protein
                        organism = synthetic construct
SEQUENCE: 56
DVQLVESGGG LVQAGGSLRL SCAASGITSK INDMGWYRQT PGNYREWVAS ITATGTTNYR   60
DSVKGRFTIS RDNAKSTVYL QMNSLKPEDT TVYYCNTFPP ISNFWGQGTL VTVSSGGGGS   120
GGGGSGGGGS GGGGSGGGGS GGGGSGGGGS EVQLVESGGG LVQPGGSLRL SCVASGDVHK   180
INFLGWYRQA PGKEREKVAH ISIGDQTDYA DSAKGRFTIS RDESKNMVYL QMNSLKPEDT   240
AVYFCRAFSR IYPYDYWGQG TLVTVSS                                       267

SEQ ID NO: 57           moltype = AA  length = 279
FEATURE                 Location/Qualifiers
REGION                  1..279
                        note = Nanobody Sequence
source                  1..279
                        mol_type = protein
                        organism = synthetic construct
SEQUENCE: 57
DVQLVESGGG LVQAGDSLRL SCAASGRTFS SYAMGWFRQA PGKEREFVAA ISWSDGSTYY   60
ADSVKGRFTI SRDNAKNTVY LQMNSLKPED TAVYYCAADL TSTNPGSYIY IWAYDYWGQG   120
TLVTVSSGGG GSGGGGSGGG GSGGGGSGGG GSGGGGSGGG GSEVQLVESG GGLVQPGGSL   180
RLSCVASGDV HKINFLGWYR QAPGKEREKV AHISIGDQTD YADSAKGRFT ISRDESKNMV   240
YLQMNSLKPE DTAVYFCRAF SRIYPYDYWG QGTLVTVSS                          279

SEQ ID NO: 58           moltype = AA  length = 426
FEATURE                 Location/Qualifiers
REGION                  1..426
                        note = Nanobody Sequence
source                  1..426
                        mol_type = protein
                        organism = synthetic construct
SEQUENCE: 58
VQLVESGGGL VQAGGSLRLS CAASGITSKI NDMGWYRQTP GNYREWVASI TATGTTNYRD   60
SVKGRFTISR DNAKSTVYLQ MNSLKPEDTT VYYCNTFPPI SNFWGQGTLV TVSSGGGGSG   120
GGGSGGGGSG GGGSGGGGSE VQLVESGGGL VQPGGSLRLS CVASGDVHKI   180
NFLGWYRQAP GKEREKVAHI SIGDQTDYAD SAKGRFTISR DESKNMVYLQ MNSLKPEDTA   240
VYFCRAFSRI YPYDYWGQGT LVTVSSGGGG SGGGGSGGGG SGGGGSGGGG SGGGGSGGGG   300
SEVQLVESGG GLVQAGGPLR LSCAASGRTF SSYVMGWFRQ APGKEREFVA AIYWSNGKTQ   360
YTDSVKGRFT ISGDNAKNTV YLQMNSLNPE DTAVYYCVAD KDETGFRTLP IAYDYWGQGT   420
LVTVSS                                                             426

SEQ ID NO: 59           moltype = AA  length = 427
FEATURE                 Location/Qualifiers
REGION                  1..427
                        note = Nanobody Sequence
source                  1..427
                        mol_type = protein
                        organism = synthetic construct
SEQUENCE: 59
DVQLVESGGG LVQAGGPLRL SCAASGRTFS SYVMGWFRQA PGKEREFVAA IYWSNGKTQY   60
TDSVKGRFTI SGDNAKNTVY LQMNSLNPED TAVYYCVADK DETGFRTLPI AYDYWGQGTL   120
VTVSSGGGGS GGGGSGGGGS GGGGSGGGGS EVQLVESGGG LVQPGGSLRL   180
SCVASGDVHK INFLGWYRQA PGKEREKVAH ISIGDQTDYA DSAKGRFTIS RDESKNMVYL   240
QMNSLKPEDT AVYFCRAFSR IYPYDYWGQG TLVTVSSGGG GSGGGGSGGG GSGGGGSGGG   300
GSGGGGSGGG GSEVQLVESG GGLVQAGGSL RLSCAASGIT SKINDMGWYR QTPGNYREWV   360
ASITATGTTN YRDSVKGRFT ISRDNAKSTV YLQMNSLKPE DTTVYYCNTF PPISNFWGQG   420
TLVTVSS                                                             427

SEQ ID NO: 60           moltype = AA  length = 427
FEATURE                 Location/Qualifiers
REGION                  1..427
                        note = Nanobody Sequence
source                  1..427
                        mol_type = protein
                        organism = synthetic construct
SEQUENCE: 60
DVQLVESGGG LVQPGGSLRL SCVASGDVHK INFLGWYRQA PGKEREKVAH ISIGDQTDYA   60
DSAKGRFTIS RDESKNMVYL QMNSLKPEDT AVYFCRAFSR IYPYDYWGQG TLVTVSSGGG   120
GSGGGGSGGG GSGGGGSGGG GSGGGGSGGG GSEVQLVESG GGLVQAGGSL RLSCAASGIT   180
SKINDMGWYR QTPGNYREWV ASITATGTTN YRDSVKGRFT ISRDNAKSTV YLQMNSLKPE   240
DTTVYYCNTF PPISNFWGQG TLVTVSSGGG GSGGGGSGGG GSGGGGSGGG GSGGGGSGGG   300
```

```
GSEVQLVESG GGLVQAGGPL RLSCAASGRT FSSYVMGWFR QAPGKEREFV AAIYWSNGKT    360
QYTDSVKGRF TISGDNAKNT VYLQMNSLNP EDTAVYYCVA DKDETGFRTL PIAYDYWGQG    420
TLVTVSS                                                             427

SEQ ID NO: 61              moltype = AA   length = 427
FEATURE                    Location/Qualifiers
REGION                     1..427
                           note = Nanobody Sequence
source                     1..427
                           mol_type = protein
                           organism = synthetic construct
SEQUENCE: 61
DVQLVESGGG LVQPGGSLRL SCVASGDVHK INFLGWYRQA PGKEREKVAH ISIGDQTDYA    60
DSAKGRFTIS RDESKNMVYL QMNSLKPEDT AVYFCRAFSR IYPYDYWGQG TLVTVSSGGG    120
GSGGGGSGGG GSGGGGSGGG GSGGGGSGGG GSEVQLVESG GGLVQAGGPL RLSCAASGRT    180
FSSYVMGWFR QAPGKEREFV AAIYWSNGKT QYTDSVKGRF TISGDNAKNT VYLQMNSLNP    240
EDTAVYYCVA DKDETGFRTL PIAYDYWGQG TLVTVSSGGG GSGGGGSGGG GSGGGGSGGG    300
GSGGGGSGGG GSEVQLVESG GGLVQAGGSL RLSCAASGIT SKINDMGWYR QTPGNYREWV    360
ASITATGTTN YRDVKGRFT ISRDNAKSTV YLQMNSLKPE DTTVYYCNTF PPISNFWGQG    420
TLVTVSS                                                             427

SEQ ID NO: 62              moltype = AA   length = 429
FEATURE                    Location/Qualifiers
REGION                     1..429
                           note = Nanobody Sequence
source                     1..429
                           mol_type = protein
                           organism = synthetic construct
SEQUENCE: 62
EVQLVESGGG LVQPGGSLRL SCVASGDVHK INFLGWYRQA PGKEREKVAH ISIGDQTDYA    60
DSAKGRFTIS RDESKNMVYL QMNSLKPEDT AVYFCRAFSR IYPYDYWGQG TLVTVSSGGG    120
GSGGGGSGGG GSGGGGSGGG GSGGGGSGGG GSEVQLVESG GGLVQAGDSL RLSCAASGRT    180
FSSYAMGWFR QAPGKEREFV AAISWSDGST YYADSVKGRF TISRDNAKNT VYLQMNSLKP    240
EDTAVYYCAA DLTSTNPGSY IYIWAYDYWG QGTLVTVSSG GGSGGGGSGG GGSGGGGSGG    300
GGGSGGGGSG GGGSEVQLVE SGGGLVQPGN SLRLSCAASG FTFSSFGMSW VRQAPGKGLE    360
WVSSISGSGS DTLYADSVKG RFTISRDNAK TTLYLQMNSL RPEDTAVYYC TIGGSLSRSS    420
QGTLVTVSS                                                          429

SEQ ID NO: 63              moltype = AA   length = 417
FEATURE                    Location/Qualifiers
REGION                     1..417
                           note = Nanobody Sequence
source                     1..417
                           mol_type = protein
                           organism = synthetic construct
SEQUENCE: 63
DVQLVESGGG LVQPGGSLRL SCVASGDVHK INFLGWYRQA PGKEREKVAH ISIGDQTDYA    60
DSAKGRFTIS RDESKNMVYL QMNSLKPEDT AVYFCRAFSR IYPYDYWGQG TLVTVSSGGG    120
GSGGGGSGGG GSGGGGSGGG GSGGGGSGGG GSEVQLVESG GGLVQAGGSL RLSCAASGIT    180
SKINDMGWYR QTPGNYREWV ASITATGTTN YRDVKGRFT ISRDNAKSTV YLQMNSLKPE    240
DTTVYYCNTF PPISNFWGQG TLVTVSSGGG GSGGGGSGGG GSGGGGSGGG GSGGGGSGGG    300
GSEVQLVESG GGLVQPGNSL RLSCAASGFT FSSFGMSWVR QAPGKGLEWV SSISGSGSDT    360
LYADSVKGRF TISRDNAKTT LYLQMNSLRP EDTAVYYCTI GGSLSRSSQG TLVTVSS      417

SEQ ID NO: 64              moltype = AA   length = 577
FEATURE                    Location/Qualifiers
REGION                     1..577
                           note = Nanobody Sequence
source                     1..577
                           mol_type = protein
                           organism = synthetic construct
SEQUENCE: 64
DVQLVESGGG LVQPGGSLRL SCVASGDVHK INFLGWYRQA PGKEREKVAH ISIGDQTDYA    60
DSAKGRFTIS RDESKNMVYL QMNSLKPEDT AVYFCRAFSR IYPYDYWGQG TLVTVSSGGG    120
GSGGGGSGGG GSGGGGSGGG GSGGGGSGGG GSEVQLVESG GGLVQAGGSL RLSCAASGIT    180
SKINDMGWYR QTPGNYREWV ASITATGTTN YRDVKGRFT ISRDNAKSTV YLQMNSLKPE    240
DTTVYYCNTF PPISNFWGQG TLVTVSSGGG GSGGGGSGGG GSGGGGSGGG GSGGGGSGGG    300
GSEVQLVESG GGLVQAGGPL RLSCAASGRT FSSYVMGWFR QAPGKEREFV AAIYWSNGKT    360
QYTDSVKGRF TISGDNAKNT VYLQMNSLNP EDTAVYYCVA DKDETGFRTL PIAYDYWGQG    420
TLVTVSSGGG GSGGGGSGGG GSGGGGSGGG GSGGGGSGGG GSEVQLVESG GGLVQPGNSL    480
RLSCAASGFT FSSFGMSWVR QAPGKGLEWV SSISGSGSDT LYADSVKGRF TISRDNAKTT    540
LYLQMNSLRP EDTAVYYCTI GGSLSRSSQG TLVTVSS                            577

SEQ ID NO: 65              moltype = AA   length = 577
FEATURE                    Location/Qualifiers
REGION                     1..577
                           note = Nanobody Sequence
source                     1..577
                           mol_type = protein
``` organism = synthetic construct
SEQUENCE: 65
DVQLVESGGG LVQPGGSLRL SCVASGDVHK INFLGWYRQA PGKEREKVAH ISIGDQTDYA   60
DSAKGRFTIS RDESKNMVYL QMNSLKPEDT AVYFCRAFSR IYPYDYWGQG TLVTVSSGGG  120
GSGGGGSGGG GSGGGGSGGG GSGGGGSGGG GSEVQLVESG GGLVQAGGSL RLSCAASGIT  180
SKINDMGWYR QTPGNYREWV ASITATGTTN YRDSVKGRFT ISRDNAKSTV YLQMNSLKPE  240
DTTVYYCNTF PPISNFWGQG TLVTVSSGGG GSGGGGSGGG GSGGGGSGGG GSGGGGSGGG  300
GSEVQLVESG GGLVQPGNSL RLSCAASGFT FSSFGMSWVR QAPGKGLEWV SSISGSGSDT  360
LYADSVKGRF TISRDNAKTT LYLQMNSLRP EDTAVYYCTI GGSLSRSSQG TLVTVSSGGG  420
GSGGGGSGGG GSGGGGSGGG GSGGGGSGGG GSEVQLVESG GGLVQAGGPL RLSCAASGRT  480
FSSYVMGWFR QAPGKEREFV AAIYWSNGKT QYTDSVKGRF TISGDNAKNT VYLQMNSLNP  540
EDTAVYYCVA DKDETGFRTL PIAYDYWGQG TLVTVSS                          577

SEQ ID NO: 66            moltype = AA  length = 577
FEATURE                  Location/Qualifiers
REGION                   1..577
                         note = Nanobody Sequence
source                   1..577
                         mol_type = protein
                         organism = synthetic construct
SEQUENCE: 66
DVQLVESGGG LVQPGGSLRL SCVASGDVHK INFLGWYRQA PGKEREKVAH ISIGDQTDYA   60
DSAKGRFTIS RDESKNMVYL QMNSLKPEDT AVYFCRAFSR IYPYDYWGQG TLVTVSSGGG  120
GSGGGGSGGG GSGGGGSGGG GSGGGGSGGG GSEVQLVESG GGLVQAGGPL RLSCAASGRT  180
FSSYVMGWFR QAPGKEREFV AAIYWSNGKT QYTDSVKGRF TISGDNAKNT VYLQMNSLNP  240
EDTAVYYCVA DKDETGFRTL PIAYDYWGQG TLVTVSSGGG GSGGGGSGGG GSGGGGSGGG  300
GSGGGGSGGG GSEVQLVESG GGLVQAGGSL RLSCAASGIT SKINDMGWYR QTPGNYREWV  360
ASITATGTTN YRDSVKGRFT ISRDNAKSTV YLQMNSLKPE DTTVYYCNTF PPISNFWGQG  420
TLVTVSSGGG GSGGGGSGGG GSGGGGSGGG GSGGGGSGGG GSEVQLVESG GGLVQPGNSL  480
RLSCAASGFT FSSFGMSWVR QAPGKGLEWV SSISGSGSDT LYADSVKGRF TISRDNAKTT  540
LYLQMNSLRP EDTAVYYCTI GGSLSRSSQG TLVTVSS                          577

SEQ ID NO: 67            moltype = AA  length = 577
FEATURE                  Location/Qualifiers
REGION                   1..577
                         note = Nanobody Sequence
source                   1..577
                         mol_type = protein
                         organism = synthetic construct
SEQUENCE: 67
DVQLVESGGG LVQPGGSLRL SCVASGDVHK INFLGWYRQA PGKEREKVAH ISIGDQTDYA   60
DSAKGRFTIS RDESKNMVYL QMNSLKPEDT AVYFCRAFSR IYPYDYWGQG TLVTVSSGGG  120
GSGGGGSGGG GSGGGGSGGG GSGGGGSGGG GSEVQLVESG GGLVQAGGPL RLSCAASGRT  180
FSSYVMGWFR QAPGKEREFV AAIYWSNGKT QYTDSVKGRF TISGDNAKNT VYLQMNSLNP  240
EDTAVYYCVA DKDETGFRTL PIAYDYWGQG TLVTVSSGGG GSGGGGSGGG GSGGGGSGGG  300
GSGGGGSGGG GSEVQLVESG GGLVQPGNSL RLSCAASGFT FSSFGMSWVR QAPGKGLEWV  360
SSISGSGSDT LYADSVKGRF TISRDNAKTT LYLQMNSLRP EDTAVYYCTI GGSLSRSSQG  420
TLVTVSSGGG GSGGGGSGGG GSGGGGSGGG GSGGGGSGGG GSEVQLVESG GGLVQAGGSL  480
RLSCAASGIT SKINDMGWYR QTPGNYREWV ASITATGTTN YRDSVKGRFT ISRDNAKSTV  540
YLQMNSLKPE DTTVYYCNTF PPISNFWGQG TLVTVSS                          577

SEQ ID NO: 68            moltype = AA  length = 378
FEATURE                  Location/Qualifiers
source                   1..378
                         mol_type = protein
                         organism = Homo sapiens
SEQUENCE: 68
MVLLWLTLLL IALPCLLQTK EDPNPPITNL RMKAKAQQLT WDLNRNVTDI ECVKDADYSM   60
PAVNNSYCQF GAISLCEVTN YTVRVANPPF STWILFPENS GKPWAGAENL TCWIHDVDFL  120
SCSWAVGPGA PADVQYDLYL NVANRRQQYE CLHYKTDAQG TRIGCRFDDI SRLSSGSQSS  180
HILVRGRSAA FGIPCTDKFV VFSQIEILTP PNMTAKCNKT HSFMHWKMRS HFNRKFRYEL  240
QIQKRMQPVI TEQVRDRTSF QLLNPGTYTV QIRARERVYE FLSAWSTPQR FECDQEEGAN  300
TRAWRTSLLI ALGTLLALVC VFVICRRYLV MQRLFPRIPH MKDPIGDSFQ NDKLVVWEAG  360
KAGLEECLVT EVQVVQKT                                               378

SEQ ID NO: 69            moltype = AA  length = 378
FEATURE                  Location/Qualifiers
source                   1..378
                         mol_type = protein
                         organism = Macaca fascicularis
SEQUENCE: 69
MTLLWLTLLL VATPCLLRTK EDPNAPIRNL RMKEKAQQLM WDLNRNVTDV ECIKGTDYSM   60
PAMNNSYCQF GAISLCEVTN YTVRVASPPF STWILFPENS GTPRAGAENL TCWVHDVDFL  120
SCSWVVGPAA PADVQYDLYL NNPNSHEQRY CLHYKTDARG TQIGCRFDDI APLSRGSQSS  180
HILVRGRSAA VSIPCTDKFV FFSQIERLTP PNMTGECNET HSFMHWKMKS HFNRKFRYEL  240
RIQKRMQPVR TEQVRDTTSF QLPNPGTYTV QIRARETVYE FLSAWSTPQR FECDQEEGAS  300
SRAWRTSLLI ALGTLLALLC VFLICRRYLV MQRLFPRIPH MKDPIGDTFQ QDKLVVWEAG  360
KAGLEECLVS EVQVVEKT                                               378

-continued

```
SEQ ID NO: 70          moltype = AA  length = 171
FEATURE                Location/Qualifiers
source                 1..171
                       mol_type = protein
                       organism = Homo sapiens
SEQUENCE: 70
MEHSTFLSGL VLATLLSQVS PFKIPIEELE DRVFVNCNTS ITWVEGTVGT LLSDITRLDL   60
GKRILDPRGI YRCNGTDIYK DKESTVQVHY RMCQSCVELD PATVAGIIVT DVIATLLLAL  120
GVFCFAGHET GRLSGAADTQ ALLRNDQVYQ PLRDRDDAQY SHLGGNWARN K           171

SEQ ID NO: 71          moltype = AA  length = 182
FEATURE                Location/Qualifiers
source                 1..182
                       mol_type = protein
                       organism = Homo sapiens
SEQUENCE: 71
MEQGKGLAVL ILAIILLQGT LAQSIKGNHL VKVYDYQEDG SVLLTCDAEA KNITWFKDGK   60
MIGFLTEDKK KWNLGSNAKD PRGMYQCKGS QNKSKPLQVY YRMCQNCIEL NAATISGFLF  120
AEIVSIFVLA VGVYFIAGQD GVRQSRASDK QTLLPNDQLY QPLKDREDDQ YSHLQGNQLR  180
RN                                                                 182

SEQ ID NO: 72          moltype = AA  length = 207
FEATURE                Location/Qualifiers
source                 1..207
                       mol_type = protein
                       organism = Homo sapiens
SEQUENCE: 72
MQSGTHWRVL GLCLLSVGVW GQDGNEEMGG ITQTPYKVSI SGTTVILTCP QYPGSEILWQ   60
HNDKNIGGDE DDKNIGSDED HLSLKEFSEL EQSGYYVCYP RGSKPEDANF YLYLRARVCE  120
NCMEMDVMSV ATIVIVDICI TGGLLLLVYY WSKNRKAKAK PVTRGAGAGG RQRGQNKERP  180
PPVPNPDYEP IRKGQRDLYS GLNQRRI                                      207

SEQ ID NO: 73          moltype = AA  length = 164
FEATURE                Location/Qualifiers
source                 1..164
                       mol_type = protein
                       organism = Homo sapiens
SEQUENCE: 73
MKWKALFTAA ILQAQLPITE AQSFGLLDPK LCYLLDGILF IYGVILTALF LRVKFSRSAD   60
APAYQQGQNQ LYNELNLGRR EEYDVLDKRR GRDPEMGGKP QRRKNPQEGL YNELQKDKMA  120
EAYSEIGMKG ERRRGKGHDG LYQGLSTATK DTYDALHMQA LPPR                    164

SEQ ID NO: 74          moltype = AA  length = 142
FEATURE                Location/Qualifiers
source                 1..142
                       mol_type = protein
                       organism = Homo sapiens
SEQUENCE: 74
PNIQNPDPAV YQLRDSKSSD KSVCLFTDFD SQTNVSQSKD SDVYITDKTV LDMRSMDFKS   60
NSAVAWSNKS DFACANAFNN SIIPEDTFFP SPESSCDVKL VEKSFETDTN LNFQNLSVIG  120
FRILLLKVAG FNLLMTLRLW SS                                           142

SEQ ID NO: 75          moltype = AA  length = 177
FEATURE                Location/Qualifiers
source                 1..177
                       mol_type = protein
                       organism = Homo sapiens
SEQUENCE: 75
EDLNKVFPPE VAVFEPSEAE ISHTQKATLV CLATGFFPDH VELSWWVNGK EVHSGVSTDP   60
QPLKEQPALN DSRYCLSSRL RVSATFWQNP RNHFRCQVQF YGLSENDEWT QDRAKPVTQI  120
VSAEAWGRAD CGFTSVSYQQ GVLSATILYE ILLGKATLYA VLVSALVLMA MVKRKDF     177

SEQ ID NO: 76          moltype = AA  length = 108
FEATURE                Location/Qualifiers
source                 1..108
                       mol_type = protein
                       organism = Homo sapiens
SEQUENCE: 76
QLLEQSPQFL SIQEGENLTV YCNSSSVFSS LQWYRQEPGE GPVLLVTVVT GGEVKKLKRL   60
TFQFGDARKD SSLHITAAQP GDTGLYLCAG AGSQGNLIFG KGTKLSVK              108

SEQ ID NO: 77          moltype = AA  length = 112
FEATURE                Location/Qualifiers
source                 1..112
                       mol_type = protein
                       organism = Homo sapiens
SEQUENCE: 77
DGGITQSPKY LFRKEGQNVT LSCEQNLNHD AMYWYRQDPG QGLRLIYYSQ IVNDFQKGDI   60
AEGYSVSREK KESFPLTVTS AQKNPTAFYL CASSSRSSYE QYFGPGTRLT VT          112
```

```
SEQ ID NO: 78          moltype = AA  length = 117
FEATURE                Location/Qualifiers
REGION                 1..117
                       note = Nanobody Sequence
source                 1..117
                       mol_type = protein
                       organism = synthetic construct
SEQUENCE: 78
EVQLVESGGG LVQPGGSLRL SCAASGSVHK INFLGWYRQA PGKERELVAT ITIGDTTDYA  60
DSAKGRFTIS RDEAKNMVYL QMNSLKPEDT AVHFCRAGSR LYPYNYWGQG TQVTVSS     117

SEQ ID NO: 79          moltype = AA  length = 117
FEATURE                Location/Qualifiers
REGION                 1..117
                       note = Nanobody Sequence
source                 1..117
                       mol_type = protein
                       organism = synthetic construct
SEQUENCE: 79
EVQLVESGGG LVQPGGSLRL SCAASGSVHK INFLGWYRQA PGKERGLVAT ITIGDTTDYA  60
DYAKGRFTIS RDEARNMVYL QMNSLKPEDT AVFCRAGSR LYPYNYWGQG TQVTVSS      117

SEQ ID NO: 80          moltype = AA  length = 117
FEATURE                Location/Qualifiers
REGION                 1..117
                       note = Nanobody Sequence
source                 1..117
                       mol_type = protein
                       organism = synthetic construct
SEQUENCE: 80
EVQLVESGGG LVQPGRSLRL PCAASGSVHK INFLGWYRQA PGKEREMVAT ITIGDATDYA  60
DSAKGRFTIS RDEAKNMVYL QMNSLKPEDT AVFCRAGSR LYPYNYWGQG TQVTVSS      117

SEQ ID NO: 81          moltype = AA  length = 117
FEATURE                Location/Qualifiers
REGION                 1..117
                       note = Nanobody Sequence
source                 1..117
                       mol_type = protein
                       organism = synthetic construct
SEQUENCE: 81
EVQLVESGGG LVQPGGSLRL SCAASGSVHK INFLGWYRQA PGKERELVAT ITIGDTTDYA  60
DYAKGRFTIS RDEARNMVYL QMNSLKPEDT AVYFCRAGSR LYPYNYWGQG TLVTVSS     117

SEQ ID NO: 82          moltype = AA  length = 117
FEATURE                Location/Qualifiers
REGION                 1..117
                       note = Nanobody Sequence
source                 1..117
                       mol_type = protein
                       organism = synthetic construct
SEQUENCE: 82
EVQLVESGGG LVQPGGSLRL SCAASGSVHK INFLGWYRQA PGKEREMVAT ITIGDATDYA  60
DSAKGRFTIS RDEAKNMVYL QMNSLKPEDT AVYFCRAGSR LYPYNYWGQG TLVTVSS     117

SEQ ID NO: 83          moltype = AA  length = 117
FEATURE                Location/Qualifiers
REGION                 1..117
                       note = Nanobody Sequence
source                 1..117
                       mol_type = protein
                       organism = synthetic construct
SEQUENCE: 83
EVQLVESGGG LVQPGGSLRL SCAASGSVHK INFLGWYRQA PGKERELVAT ITIGDTTDYA  60
DSAKGRFTIS RDEAKNMVYL QMNSLKPEDT AVYFCRAGSR LYPYNYWGQG TQVTVSS     117

SEQ ID NO: 84          moltype = AA  length = 117
FEATURE                Location/Qualifiers
REGION                 1..117
                       note = Nanobody Sequence
source                 1..117
                       mol_type = protein
                       organism = synthetic construct
SEQUENCE: 84
EVQLVESGGG LVQPGGSLRL SCAVSGSVHL LNFLGWYRQA PGKEREMVAH ITIADATDYS  60
HFAKGRFTIS RDEAKNMVYL QMNSLRPEDT AVYFCRAGSR IYPYDYWGQG TLVTVSS     117

SEQ ID NO: 85          moltype = AA  length = 117
```

```
FEATURE                Location/Qualifiers
REGION                 1..117
                       note = Nanobody Sequence
source                 1..117
                       mol_type = protein
                       organism = synthetic construct
SEQUENCE: 85
EVQLVESGGG LVQPGGSLKL SCAASGAVHK INFLGWYRQT PEKEREMVAT ITIGDDVDYA  60
DSAKGRFTIS RDEAKNMVYL QMTSLKPEDT AVYVCRAGSR LYPYNYWGQG TLVTVSS    117

SEQ ID NO: 86          moltype = AA  length = 117
FEATURE                Location/Qualifiers
REGION                 1..117
                       note = Nanobody Sequence
source                 1..117
                       mol_type = protein
                       organism = synthetic construct
SEQUENCE: 86
EVQLVESGGG LVQPGGSLRL SCRASGDVHK INILGWYRQA PAKEREMVAH ITIGDATDYA  60
ESAKGRFTIS RDEAKNMVYL QMNSLKPEDT AVYFCRAYSR IYPYNYWGQG TQVTVSS    117

SEQ ID NO: 87          moltype = AA  length = 117
FEATURE                Location/Qualifiers
REGION                 1..117
                       note = Nanobody Sequence
source                 1..117
                       mol_type = protein
                       organism = synthetic construct
SEQUENCE: 87
EVQLVESGGG LVRPGGSLRL SCAASGDVHK INILGWYRQA PAKEREMVAH ITIGDATDYA  60
DSAKGRFTIS RDEAKNMVYL QMNSLKPEDT AVYFCRAYSR IYPYNYWGQG TLVTVSS    117

SEQ ID NO: 88          moltype = AA  length = 117
FEATURE                Location/Qualifiers
REGION                 1..117
                       note = Nanobody Sequence
source                 1..117
                       mol_type = protein
                       organism = synthetic construct
SEQUENCE: 88
EVQLVESGGG LVQPGGSLRL SCAASGDVHK INILGWYRQA PAKEREMVAH ITIGDATDYA  60
DSAKGRFTIS RDEAKNMVYL QMNSLKPEDT AVYFCRAYSR IYPYNYWGQG TLVTVSS    117

SEQ ID NO: 89          moltype = AA  length = 117
FEATURE                Location/Qualifiers
REGION                 1..117
                       note = Nanobody Sequence
source                 1..117
                       mol_type = protein
                       organism = synthetic construct
SEQUENCE: 89
EVQLVESGGG LVQPGGSLRL SCVASGDVHK INFLGWYRQA PGKEREKVAH ITIGDQADYA  60
DSAKGRFTIS RDEAKNMVYL QMNSLKPEDT AVYFCRAGSR IYPYDYWGQG TQVTVSS    117

SEQ ID NO: 90          moltype = AA  length = 117
FEATURE                Location/Qualifiers
REGION                 1..117
                       note = Nanobody Sequence
source                 1..117
                       mol_type = protein
                       organism = synthetic construct
SEQUENCE: 90
EVQLVESGGG SVQPGGSLRL SCAASGSVHK INFLGWYRQA PGKEREMVAT ITIGDATDYA  60
DSAKGRFTIS RDEAKNMVYL QMNSLSPEDT AVYFCRAGSR LYPYNYWGQG TLVTVSS    117

SEQ ID NO: 91          moltype = AA  length = 117
FEATURE                Location/Qualifiers
REGION                 1..117
                       note = Nanobody Sequence
source                 1..117
                       mol_type = protein
                       organism = synthetic construct
SEQUENCE: 91
EVQLVESGGG LVQPGGSLRL SCAASGSVHL LNFLGWYRQA PGKEREMVAH ISIADATDYA  60
HFAKGRFTIS RDEAKNMVYL QMNSLRPEDT AVYFCRAGSR IYPYDYWGRG TQVTVSS    117

SEQ ID NO: 92          moltype = AA  length = 117
FEATURE                Location/Qualifiers
REGION                 1..117
```

-continued

```
                              note = Nanobody Sequence
source                        1..117
                              mol_type = protein
                              organism = synthetic construct
SEQUENCE: 92
EVQLVESGGG LVQPGGSLRL SCRASGDVHK INILGWYRQA PAKEREMVAH ITIGDATVYA 60
ESAKGRFTIS RDEAKNMVYL QMNSLKPEDT AVYFCRAYSR IYPYNYWGQG TQVTVSS     117

SEQ ID NO: 93                 moltype = AA   length = 117
FEATURE                       Location/Qualifiers
REGION                        1..117
                              note = Nanobody Sequence
source                        1..117
                              mol_type = protein
                              organism = synthetic construct
SEQUENCE: 93
EVQLVESGGG LVQPGGSLRL SCAASGSVHL LNFLGWYRQC PGKEREMVAH ITIADATDYS 60
HFAKGRFTIS RDEAKNMVYL QMNSLRPEDT AVYFCRAGSR IYPYDYWGQG TLVTVSS     117

SEQ ID NO: 94                 moltype = AA   length = 117
FEATURE                       Location/Qualifiers
REGION                        1..117
                              note = Nanobody Sequence
source                        1..117
                              mol_type = protein
                              organism = synthetic construct
SEQUENCE: 94
EVQLVESGGG LVQPGGSLRP SCAASGSVHL LNFLGWYRQA PGKEREMVAH ITIADATDYA 60
HFAKGRFTIS RDEAKNMVYL QMNSLRPEDT AVYFCRAGSR IYPYDYWGQG TQVTVSS     117

SEQ ID NO: 95                 moltype = AA   length = 117
FEATURE                       Location/Qualifiers
REGION                        1..117
                              note = Nanobody Sequence
source                        1..117
                              mol_type = protein
                              organism = synthetic construct
SEQUENCE: 95
EVQLVESGGG LVQPGGSLRL SCAASGSVHL LNFLGWYRQA PGKEREMVAH ITIADATDYA 60
HFAKGRFTIS RDEAKNMVYL QMNSLRPEDT AVYFCRAGSR IYPYDYWGQG TLVTVSS     117

SEQ ID NO: 96                 moltype = AA   length = 117
FEATURE                       Location/Qualifiers
REGION                        1..117
                              note = Nanobody Sequence
source                        1..117
                              mol_type = protein
                              organism = synthetic construct
SEQUENCE: 96
EVQLVESGGG LVQPGGSLKL SCAASGAVHK INFLGWYRQT PEKEREMVAH ITIGDEVDYA 60
DSAKGRFTIS RDEAKNMVYL QMTSLTPEDT AVYVCRAGSR LYPYNYWGQG TQVTVSS     117

SEQ ID NO: 97                 moltype = AA   length = 117
FEATURE                       Location/Qualifiers
REGION                        1..117
                              note = Nanobody Sequence
source                        1..117
                              mol_type = protein
                              organism = synthetic construct
SEQUENCE: 97
EVQLVESGGG LVHPGGSLRL SCAASGDVHK INFLGWHRQP PGKEREKVAH ITIGDVTDYA 60
DSAKGRFTIS RDEAKNMVYL QMNNLKPEDT AVYFCRAGSR IYPYDYWGQG TQVTVSS     117

SEQ ID NO: 98                 moltype = AA   length = 117
FEATURE                       Location/Qualifiers
REGION                        1..117
                              note = Nanobody Sequence
source                        1..117
                              mol_type = protein
                              organism = synthetic construct
SEQUENCE: 98
EVQLVESGGG LVQPGGSLRL SCAASGDVHK INVLGWYRQA PAKEREMVAH ITIGDATDYA 60
DSAKGRFTIS RDEAKNMVHL QMNSLKPEDT AVYFCRAYSR IYPYNYWGQG TQVTVSS     117

SEQ ID NO: 99                 moltype = AA   length = 117
FEATURE                       Location/Qualifiers
REGION                        1..117
                              note = Nanobody Sequence
source                        1..117
```

-continued

```
                              mol_type = protein
                              organism = synthetic construct
SEQUENCE: 99
EVQLVESGGG LVQPGGSLRL SCAASGDVHK INILGWYRQA PAKEREMVAH ITIGDATNYA   60
DSAKGRFTIS RDEAKNMVYL QMNSLKPEDT AVYFCRAYSR IYPYNYWGQG TLVTVSS      117

SEQ ID NO: 100          moltype = AA   length = 117
FEATURE                 Location/Qualifiers
REGION                  1..117
                        note = Nanobody Sequence
source                  1..117
                        mol_type = protein
                        organism = synthetic construct
SEQUENCE: 100
EVQLVESGGG LVQPGGSLRL SCAASGDVHK INFLGWHRQA PGKEREKVAH ITIGDVTDYA   60
DSAKGRFTIS RDEAKNMVFL QMNNLKPEDT AVYFCRAGSR IYPYDYWGQG TQVTVSS      117

SEQ ID NO: 101          moltype = AA   length = 117
FEATURE                 Location/Qualifiers
REGION                  1..117
                        note = Nanobody Sequence
source                  1..117
                        mol_type = protein
                        organism = synthetic construct
SEQUENCE: 101
EVQLVESGGG LVQPGGSLRL SCAASGDVHK INILGWYRQA PAKEREMVAH ITIGDATDYA   60
GSAKGRFTIS RDEAKNMVYL QMNSLKPEDT AVYFCRAYSR IYPYNYWGQG TLVTVSS      117

SEQ ID NO: 102          moltype = AA   length = 117
FEATURE                 Location/Qualifiers
REGION                  1..117
                        note = Nanobody Sequence
source                  1..117
                        mol_type = protein
                        organism = synthetic construct
SEQUENCE: 102
EVQLVESGGG LVQPGGSLRL SCAASGEVYK INFLGWYRQA PGKEREKVAH ITIADVADYA   60
DFAKGRFTIS RDEAKNMVYL QMNSLKPEDT AVYFCRAGSR IWPYDYWGQG TQVTVSS      117

SEQ ID NO: 103          moltype = AA   length = 117
FEATURE                 Location/Qualifiers
REGION                  1..117
                        note = Nanobody Sequence
source                  1..117
                        mol_type = protein
                        organism = synthetic construct
SEQUENCE: 103
EVQLVESGGG LVQPGGSLKL SCAASGAVHK INFLGWYRQA PEKEREMVAT ITIGDEVDYA   60
DSAKGRFTIS RDEAKNMVYL QMTSLKPEDT TVYVCRAGSR LYPYNYWGQG TQVTVSS      117

SEQ ID NO: 104          moltype = AA   length = 117
FEATURE                 Location/Qualifiers
REGION                  1..117
                        note = Nanobody Sequence
source                  1..117
                        mol_type = protein
                        organism = synthetic construct
SEQUENCE: 104
EVQLVESGGG LVQPGGSLRL SCAASGEVYK INFLGWYRQA PGKEREKVAH ITIADVADYA   60
DFAKGRFTIS RDEAKNMVYL QMNSLKPEDT AVYFCRAGSR IWPYDYWGQG TLVTVSS      117

SEQ ID NO: 105          moltype = AA   length = 117
FEATURE                 Location/Qualifiers
REGION                  1..117
                        note = Nanobody Sequence
source                  1..117
                        mol_type = protein
                        organism = synthetic construct
SEQUENCE: 105
EVQLVESGGG LVQPGGSLRL SCVASGDVHK INILGWYRQA PGKEREKVAH ISISDQTDYA   60
ESAKGRFTIS RDESKNMVYL QMNSLKPEDT AVYLCRAFSR IYPYDYWGQG TLVTVSS      117

SEQ ID NO: 106          moltype = AA   length = 117
FEATURE                 Location/Qualifiers
REGION                  1..117
                        note = Nanobody Sequence
source                  1..117
                        mol_type = protein
                        organism = synthetic construct
```

```
SEQUENCE: 106
EVQLVESGGG LVQPGGSLRL SCAASGSVHK INFLGWYRQA PGKERELVAT ITIGDATDYA   60
DYAKGRFTIS RDEARNMVYL QMNSLKPEDT AVYFCRAGSR LYPYNYWGQG TLVTVSS      117

SEQ ID NO: 107          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 107
EVQLVESGGG LVQPGGSLRL SCAASGDVHK INILGWYRQA PAKEREMVAH ITIGDATDYA   60
DSAKGRFAIS RDEAKNMVYL QMNSLKPEDT AVYFCRAYSR IYPYNYWGQG TLVTVSS      117

SEQ ID NO: 108          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 108
EVQLVESGGG LVQPGGSLRL SCAASGDVHK INFLGWHRQA PGKEREKVAH ITIGDATDYA   60
DSAKGRFTIS RDEAKNMVYL QMNSLKPEDT AVYFCRAGSR IYPYDYWGQG TQVTVSS      117

SEQ ID NO: 109          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 109
EVQLVESGGG SVQPGGSLRL SCAASGSVHK INFLGWYRQA PGKEREVVAT ITIGDATDYA   60
DSAKGRFTIS RDEAKNMVYL QMNSLSPEDT AVYFCRAGSR LYPYNYWGQG TQVTVSS      117

SEQ ID NO: 110          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 110
EVQLVESGGG LVQPGGSARL SCVASGDVHK INFLGWYRQA PGKEREKVAH ITIGDQTDYA   60
DSAKGRFTIS RDEAKNMVYL QMNSLKPEDT AVYFCRAGSR IWPYDYWGQG TQVTVSS      117

SEQ ID NO: 111          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 111
EVQLVESGGG LVQPGGSLRL SCAASGSVHL LNFLGWYRQA PGKEREMVAH ITIADATDYS   60
HFAKGRFTIS RDEAKNMVYL QMNSLRPEDT AVYFCRAGSR IYPYDYWGQG TLVTVSS      117

SEQ ID NO: 112          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 112
EVQLVESGGG LVQPGGSLRL SCAVSGSVHL LNFLGWYRQA PGKERGVVAH ITIADATDYS   60
HFAKGRFTIS RDEAKNMVYL QMNSLRPEDT AVYFCRAGSR IYPYDYWGQG TQVTVSS      117

SEQ ID NO: 113          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 113
EVQLVESGGG LVQAGGSLTL SCAASGDVHK INILGWYRQA PAKEREMVAH ITIGDATDYA   60
```

```
DSAKGRFTIS RDEAKNMVYL QMNSLKPEDT AVYFCRAYSR IYPYNYWGQG TLVTVSS      117

SEQ ID NO: 114          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 114
EVQLVESGGG LVQPGGSLRL SCAASGGVHK INILGWYRQA PAKEREMVAH ITIGDATDYA   60
DSAKGRFTIS RDEAKNMVYL QMNSLKPEDT AVYFCRAYSR IYPYNYWGQG TLVTVSS      117

SEQ ID NO: 115          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 115
EVQLVESGGG LVQPGGSLRL SCAASGEVYK INFLGWYRQA PGKEREKVAH ITIADVADYA   60
DFAQGRFTIS RDEAKNMVYL QMNSLKPEDT AVYFCRAGSR IWPYDYWGQG TQVTVSS      117

SEQ ID NO: 116          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 116
EVQLVESGGG LVQPGGSLRL SCAASGDVHK INILGWYRQA PAKEREMVAH ITIGDTTDYA   60
DSAKGRFTIS RDEAKNMVYL QMNSLKPEDT AVYFCRAYSR IYPYNYWGQG TQVTVSS      117

SEQ ID NO: 117          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 117
EVQLVESGGG LVQPGGSLRL SCAASGSVHL LNFLGWYRQA PGKEREMVAH ITIADATDYS   60
HFAKGRFTIS RDEAKNMVYL QMNSLRPEDT AVYFCRAGSR IYPYDYWGHG TLVTVSS      117

SEQ ID NO: 118          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 118
EVQLVESGGG LVQPGGSLRL SCVASGDVHK INFLGWYRQA PGKEREKVAH ITIGDQADYA   60
DSAKGRFTIS RDEAKNMVYL QMNSLKPEDT AVYFCRAGSR IYPYDYWGRG TLVTVSS      117

SEQ ID NO: 119          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 119
EVQLVESGGG LVQPGGSLRL SCAVSGSVHL LNFLGWYRQA PGKEREMVTH ITIADATDYS   60
HFAKGRFTIS RDEAKNMVYL QMNSLRPEDT AVYFCRAGSR IYPYDYWGQG TQVTVSS      117

SEQ ID NO: 120          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 120
EVQLVESGGD LVQPGGSLRL SCAASGDVHK INFLGWYRQA PGKEREMVAH ITIADATDYA   60
EFAKGRFTIS RDEPKNMVHL QMNSLKPEDT AVYLCRAGSR IYPYNYWGQG TQVTVSS      117
```

-continued

```
SEQ ID NO: 121          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 121
EVQLVESGGG LVQPGGSLRL SCAASGDVHK INILGWYRQA PAKEREMVAH ITIGDATDYA  60
DSAKGRFTIS RDEAKNMVYL QMNSLKPEDT AVYFCRAYSR IYPYNYWGRG TQVTVSS     117

SEQ ID NO: 122          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 122
EVQLVESGGG LVQPGGSLRL SCVASGDVHK INILGWYRQA PGKEREKVAR ISISDQTDYA  60
ESAKGRFTIS RDESKNMVYL QMNSLKPEDT AVYLCRAFSR IYPYDYWGQG TLVTVSS     117

SEQ ID NO: 123          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 123
EVQLVESGGG LVQPEGSLRL SCAASGEVYK INFLGWYRQA PGKEREKVAH ITIADVADYA  60
DFAKGRLTIS RDEAKNMVYL QMNSLKPEDT AVYFCRAGSR IWPYDYWGQG TLVTVSS     117

SEQ ID NO: 124          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 124
EVQLVESGGG LVQPGGSLKL PCAASGAVHK INFLGWYRQT PEKEREMVAT ITIGDEVDYA  60
DSAKGRFTIS RDEAKNMVYL QMTSLKPEDT AVYVCRAGSR LYPYNYWGQG TLVTVSS     117

SEQ ID NO: 125          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 125
EVQLVESGGG LVQPGGSLGL SCAASGSVHL LNFLGWYRQA PGKEREMVAH ITIADATDYA  60
HFAKGRFTIS RDEAKNMVYL QMNSLRPEDT AVYFCRAGSR IYPYDYWGQG TLVTVSS     117

SEQ ID NO: 126          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 126
EVQLVESGGG LAQPGGSLRL SCAASGDVHK INILGWYRQA PAKEREMVAH ITIGDATDYA  60
DSAKGRFTIS RDEAKNMVYL QMNSLKPEDT AVYFCRAYSR IYPYNYWGQG TLVTVSS     117

SEQ ID NO: 127          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 127
EVQLVESGGG LVQPGGSLRL SCAASGEVYK INFLGWYRQA PGKEREKVAH ITIADAADYA  60
DFAKGRFTIS RDGAKNMVYL QMNSLKPEDT AVYFCRAGSR IWPYDYWGQG TQVTVSS     117

SEQ ID NO: 128          moltype = AA  length = 117
FEATURE                 Location/Qualifiers
```

-continued

```
REGION                    1..117
                          note = Nanobody Sequence
source                    1..117
                          mol_type = protein
                          organism = synthetic construct
SEQUENCE: 128
EVQLVESGGG WVQPGGSLRL SCAASGSVYK INFLSWYRQA PGHERELVAT ITIGDAADYA    60
DSAKGRFTIS RDEARNMVYL QMNSLKPEDT ALYFCHAGSR LYPYNYWGQG TQVTVSS      117

SEQ ID NO: 129           moltype = AA  length = 117
FEATURE                  Location/Qualifiers
REGION                   1..117
                         note = Nanobody Sequence
source                   1..117
                         mol_type = protein
                         organism = synthetic construct
SEQUENCE: 129
EVQLVESGGG LVQPGGSLRL SCAASGSVHL LNFLGWYRQA PGKEREMVAH ITIADATDYS    60
HFAKGRFTIS RDEAKNMVYL QMNSLRPEDT AVYFCRAGSR IYPYDYWGQG TQVTVSS      117

SEQ ID NO: 130           moltype = AA  length = 117
FEATURE                  Location/Qualifiers
REGION                   1..117
                         note = Nanobody Sequence
source                   1..117
                         mol_type = protein
                         organism = synthetic construct
SEQUENCE: 130
EVQLVESGGG LVQPGGSLRL SCVASGDVHK INILGWYRQA PGKEREKVAH IAISDQTDYA    60
ESAKGRFTIS RDESKNMVYL QMNSLKPEDT AVYLCRAFSR IYPYDYWGQG TLVTVSS      117

SEQ ID NO: 131           moltype = AA  length = 117
FEATURE                  Location/Qualifiers
REGION                   1..117
                         note = Nanobody Sequence
source                   1..117
                         mol_type = protein
                         organism = synthetic construct
SEQUENCE: 131
EVQLVESGGG LVQPGGSLRL SCAASGDVHK INILGWYRQA PAKEREMVAH ITIGDATDYA    60
DSAKGRFTIS RDEAKNMVYL QMNSLKPEDT AAYFCRAYSR IYPYNYWGQG TLVTVSS      117

SEQ ID NO: 132           moltype = AA  length = 117
FEATURE                  Location/Qualifiers
REGION                   1..117
                         note = Nanobody Sequence
source                   1..117
                         mol_type = protein
                         organism = synthetic construct
SEQUENCE: 132
EVQLVESGGG LVQPGGSLRL SCAASGDVHK INILGWYRQA PAKERGMVAH ITIGDATDYA    60
DSAKGRFTIS RDEAKNMVYL QMNSLKPEDT AVYFCRAYSR IYPYNYWGQG TQVTVSS      117

SEQ ID NO: 133           moltype = AA  length = 117
FEATURE                  Location/Qualifiers
REGION                   1..117
                         note = Nanobody Sequence
source                   1..117
                         mol_type = protein
                         organism = synthetic construct
SEQUENCE: 133
EVQLVESGGG LVQPGGSLRL SCAASGDVHK INILGWYRQA PAKEHEMVAH ITIGDATDYA    60
DSAKGRFTIS RDEAKNMVYL QMNSLKPEDT AVYFCRAYSR IYPYNYWGQG TLVTVSS      117

SEQ ID NO: 134           moltype = AA  length = 117
FEATURE                  Location/Qualifiers
REGION                   1..117
                         note = Nanobody Sequence
source                   1..117
                         mol_type = protein
                         organism = synthetic construct
SEQUENCE: 134
EVQLVESGGG LVQPGGSLRL SCAASGDVHK INILGWYRQA PAREREMVAH ITIGDATDYA    60
DSAKGRFTIS RDEAKNMVYL QMNSLKPEDT AVYFCRAYSR IYPYNYWGQG TQVTVSS      117

SEQ ID NO: 135           moltype = AA  length = 117
FEATURE                  Location/Qualifiers
REGION                   1..117
                         note = Nanobody Sequence
```

-continued

```
source                  1..117
                        mol_type = protein
                        organism = synthetic construct
SEQUENCE: 135
EVQLVESGGG LVQPGGSLRL SCAASGDVHK INILGWYRQA PAKEREMVAH ITIGDATDYA   60
DSAKGRFTIS RDEAENMVYL QMNSLKPEDT AVYFCRAYSR IYPYNYWGQG TLVTVSS      117

SEQ ID NO: 136          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 136
EVQLVESGGG LVQPGGSLKL SCAASGAVHK INFLGWYRQT PEKEREMVAT ITIGDEVDYA   60
DSAKGRFTIS RDEAKNMVYL QMTSLKPEDT AVYVCRAGSR LYPYNYWGQG TLVTVSS      117

SEQ ID NO: 137          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 137
EVQLVESGGG LVQPGGSLKL SCAASGAVHK INFLGWYRQA PEKEREMVAT ITIGDEVDYA   60
DSAKGRFTIS RDEATNMVYL QMTSLKPEDT AVYFCRAGSR IYPYNYWGQG TQVTVSS      117

SEQ ID NO: 138          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 138
EVQLVESGGG LVQPGGSLRL SCAASGDVHK INILGWYRQA PAKEREMVAH ITIGDATSYA   60
GSAKGRFTIS RDEAKNMVYL QLNNLKPEDT AVYFCRAYSR IYPYNYWGQG TLVTVSS      117

SEQ ID NO: 139          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 139
EVQLVESGGG LVQPGGSLRL SCAASGDVHK INILGWYRQA PAKEREMVAH ITIGDATSYA   60
DSAKGRFTIS RDEAKNMVYL QLNNLKPEDT AVYFCRAYSR IYPYNYWGQG TLVTVSS      117

SEQ ID NO: 140          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 140
EVQLVESGGD LVQPGGSLRL SCAASGDVHK INFLGWYRQA PGKEREMVAH ITIADATDYA   60
EFAKGRFTIS RDEPKNMVYL QMNSLKPEDT AVLCRAGSR IYPYNYWGQG TQVTVSS       117

SEQ ID NO: 141          moltype = AA  length = 117
FEATURE                 Location/Qualifiers
REGION                  1..117
                        note = Nanobody Sequence
source                  1..117
                        mol_type = protein
                        organism = synthetic construct
SEQUENCE: 141
EVQLVESGGG LVQPGGSLKL SCAASGAVHK INFLGWYRQT PEKEREMVAT ITIGDEVDYA   60
HSAKGRFTIS RDEAKNMVYL QMTSLKPEDT AVYVCRAGSR LYPYNYWGQG TQVTVSS      117

SEQ ID NO: 142          moltype = AA  length = 117
FEATURE                 Location/Qualifiers
REGION                  1..117
                        note = Nanobody Sequence
source                  1..117
                        mol_type = protein
```

```
                            organism = synthetic construct
SEQUENCE: 142
EVQLVESGGG LVQPGGSLKL SCAASGAVHK INFLGWYRQT PEKEREMVAT ITIGDEVAYA   60
DSAKGRFTIS RDEAKNMVYL QMTSLKPEDT AVYVCRAGSR LYPYNYWGQG TQVTVSS      117

SEQ ID NO: 143             moltype = AA   length = 117
FEATURE                    Location/Qualifiers
REGION                     1..117
                           note = Nanobody Sequence
source                     1..117
                           mol_type = protein
                           organism = synthetic construct
SEQUENCE: 143
EVQLVESGGG LVQPGGSLRL SCAASGEVYK INFLGWYRQA PGKEREKVAH ITIADAADYA   60
DFAKGRFTIS RDEAKNMVYL QMNSLKPEDT AVYFCRAGSR IWPYDYWGQG TQVTVSS      117

SEQ ID NO: 144             moltype = AA   length = 117
FEATURE                    Location/Qualifiers
REGION                     1..117
                           note = Nanobody Sequence
source                     1..117
                           mol_type = protein
                           organism = synthetic construct
SEQUENCE: 144
EVQLVESGGG LVQPGGSLRL SCAASGEVYK INFLGWYRQA PGKEREKVAH ITIADAADYA   60
DFAKGRFTIS RDEAKNMVYL QMNSLKPEDT AVYFCRAGSR IYPYDYWGQG TQVTVSS      117

SEQ ID NO: 145             moltype = AA   length = 117
FEATURE                    Location/Qualifiers
REGION                     1..117
                           note = Nanobody Sequence
source                     1..117
                           mol_type = protein
                           organism = synthetic construct
SEQUENCE: 145
EVQLVESGGG SVQPGGSLRP SCAASGSVHK INFLGWYRQA PGKEREMVAT ITIGDATDYA   60
DSAKGRFTIS RDEAKNMVYL QMNSLSPEDT AVYFCRAGSR LYPYNYWGQG TQVTVSS      117

SEQ ID NO: 146             moltype = AA   length = 117
FEATURE                    Location/Qualifiers
REGION                     1..117
                           note = Nanobody Sequence
source                     1..117
                           mol_type = protein
                           organism = synthetic construct
SEQUENCE: 146
EVQLVESGGG LVQPGGSLRL SCAASGEVYK INFLGWYRQA PGKEREKVAH ITIADVADYA   60
DFAKGRFTIS RDEVKNMVYL QMNSLKPEDT AVYFCRAGSR IWPYDYWGQG TLVTVSS      117

SEQ ID NO: 147             moltype = AA   length = 117
FEATURE                    Location/Qualifiers
REGION                     1..117
                           note = Nanobody Sequence
source                     1..117
                           mol_type = protein
                           organism = synthetic construct
SEQUENCE: 147
EVQLVESGGG LVQPGESLRL SCAASGDVHK INILGWYRQA PAKEREMVAH ITIGDATDYA   60
DSAKGRFTIS RDEAKNMVYL QMNSLKPEDT AVYFCRAYSR IYPYNYWGQG TLVTVSS      117

SEQ ID NO: 148             moltype = AA   length = 117
FEATURE                    Location/Qualifiers
REGION                     1..117
                           note = Nanobody Sequence
source                     1..117
                           mol_type = protein
                           organism = synthetic construct
SEQUENCE: 148
EVQLVESGGG LVQPGGSLRL SCAASGEVYK INFLGWYRQA PGKEREKVAH ITIADAADYA   60
DFAKGRFTIS RDEAKNMVYL QMNSLRPEDT AVYFCRAGSR IWPYDYWGQG TQVTVSS      117

SEQ ID NO: 149             moltype = AA   length = 117
FEATURE                    Location/Qualifiers
REGION                     1..117
                           note = Nanobody Sequence
source                     1..117
                           mol_type = protein
                           organism = synthetic construct
SEQUENCE: 149
```

```
EVQLVESGGG LVQPGGSLRL SCAASGSVHL LNFLGWYRQA PGKEREMVAH ITIADVTDYS 60
YFAKGRFTIS RDEAKNMVYL QMNSLRPEDT AVYFCRAGSR IYPYDYWGQG TQVTVSS   117

SEQ ID NO: 150         moltype = AA  length = 117
FEATURE                Location/Qualifiers
REGION                 1..117
                       note = Nanobody Sequence
source                 1..117
                       mol_type = protein
                       organism = synthetic construct
SEQUENCE: 150
EVQLVESGGG LVQPGGSLRL SCAASGDVHK INILGWYRQA PAKEREMVAH ITIGDATDYA 60
DSAKGRFTIS RDEAKNVVYL QMNSLKPEDT AVYFCRAYSR IYPYNYWGQG TLVTVSS   117

SEQ ID NO: 151         moltype = AA  length = 117
FEATURE                Location/Qualifiers
REGION                 1..117
                       note = Nanobody Sequence
source                 1..117
                       mol_type = protein
                       organism = synthetic construct
SEQUENCE: 151
EVQLVESGGG SVQPGGSLRL SCAASGSVHK INFLGWYRQA PGKERGMVAT ITIGDATDYA 60
DSAKGRFTIS RDEAKNMVYL QMNSLSPEDT AVYFCRAGSR LYPYNYWGQG TQVTVSS   117

SEQ ID NO: 152         moltype = AA  length = 117
FEATURE                Location/Qualifiers
REGION                 1..117
                       note = Nanobody Sequence
source                 1..117
                       mol_type = protein
                       organism = synthetic construct
SEQUENCE: 152
EVQLVESGGG LVQPGGSLKL SCAASGAVHK INFLGWYRQT PEKEREMVAT ITIGDEVDYE 60
DSAKGRFTIS RDEAKNMVYL QMTGLKPEDT AVYVCRAGSR LYPYNYWGQG TLVTVSS   117

SEQ ID NO: 153         moltype = AA  length = 117
FEATURE                Location/Qualifiers
REGION                 1..117
                       note = Nanobody Sequence
source                 1..117
                       mol_type = protein
                       organism = synthetic construct
SEQUENCE: 153
EVQLVESGGG LVRPGGSLRL SCVASGDVHK INILGWYRQA PGKEREKVAH ISISDQTDYA 60
ESAKGRFTIS RDESKNMVYL QMNSLKPEDT AVYLCRAFSR IYPYDYWGQG TQVTVSS   117

SEQ ID NO: 154         moltype = AA  length = 117
FEATURE                Location/Qualifiers
REGION                 1..117
                       note = Nanobody Sequence
source                 1..117
                       mol_type = protein
                       organism = synthetic construct
SEQUENCE: 154
EVQLVESGGG LVQPGGSLRL SCAASGDVYK INFLGWHRQA PGKEREKVAH ITIGDATDYA 60
DSAKGRFTIS RDEAKNMVYL QMNSLKPEDT AVYFCRAGSR IYPYDYWGQG TLVTVSS   117

SEQ ID NO: 155         moltype = AA  length = 117
FEATURE                Location/Qualifiers
REGION                 1..117
                       note = Nanobody Sequence
source                 1..117
                       mol_type = protein
                       organism = synthetic construct
SEQUENCE: 155
EVQLVESGGG LVQPGGSLRL SCRASGDVHK INILGWYRQA PAKEREMIAH ITIGDATDYA 60
ESAKGRFTIS RDEAKNMVYL QMNSLKPEDT AVYFCRAYSR IYPYNYWGQG TQVTVSS   117

SEQ ID NO: 156         moltype = AA  length = 117
FEATURE                Location/Qualifiers
REGION                 1..117
                       note = Nanobody Sequence
source                 1..117
                       mol_type = protein
                       organism = synthetic construct
SEQUENCE: 156
EVQLVESGGG LVQPGGSLRL SCAASGDVHK INILGWYRQA PAKGREMVAH ITIGDATDYA 60
DSAKGRFTIS RDEAKNMVYL QMNSLKPEDT AVYFCRAYSR IYPYNYWGQG TQVTVSS   117
```

```
SEQ ID NO: 157            moltype = AA   length = 117
FEATURE                   Location/Qualifiers
REGION                    1..117
                          note = Nanobody Sequence
source                    1..117
                          mol_type = protein
                          organism = synthetic construct
SEQUENCE: 157
EVQLVESGGD LVQPGGSLRL SCAASGDVHK INFLGWYRQA PGKEREMVAH ITIADATDYA  60
EFAKGRFTIS RDEPKNMVYL QMNSLKPEDT AVYLCRAGSR IYPYSYWGQG TQVTVSS     117

SEQ ID NO: 158            moltype = AA   length = 117
FEATURE                   Location/Qualifiers
REGION                    1..117
                          note = Nanobody Sequence
source                    1..117
                          mol_type = protein
                          organism = synthetic construct
SEQUENCE: 158
EVQLVESGGG MVQPGGSLRL SCAASGDVHK INILGWYRQA PAKEREMVAH ITIGDATDYA  60
DSAKGRFTIS RDEAKNMVYL QMNSLKPEDT AVYFCRAYSR IYPYNYWGQG TLVTVSS     117

SEQ ID NO: 159            moltype = AA   length = 117
FEATURE                   Location/Qualifiers
REGION                    1..117
                          note = Nanobody Sequence
source                    1..117
                          mol_type = protein
                          organism = synthetic construct
SEQUENCE: 159
EVQLVESGGG LVQPGGSLRL SCAASGDVHK INILGWYRQV PAKEREMVAH ITIGDATDYA  60
DSAKGRFTIS RDEAKNMVYL QMNSLKPEDT AAYFCRAYSR IYPYNYWGQG TLVTVSS     117

SEQ ID NO: 160            moltype = AA   length = 117
FEATURE                   Location/Qualifiers
REGION                    1..117
                          note = Nanobody Sequence
source                    1..117
                          mol_type = protein
                          organism = synthetic construct
SEQUENCE: 160
EVQLVESGGG LVQPGGSLRL SCAASGEVYK INFLGWYRQA PGKEREKVAH ITIADAADYA  60
DFAKGRFTIS RDEAKNMVYL QMNSLKPEDT AVYFCRAGSR IWPYDYWGQG TLVTVSS     117

SEQ ID NO: 161            moltype = AA   length = 117
FEATURE                   Location/Qualifiers
REGION                    1..117
                          note = Nanobody Sequence
source                    1..117
                          mol_type = protein
                          organism = synthetic construct
SEQUENCE: 161
EVQLVESGGG LVQPGGSLRL SCAASGSVHL LNFLGWYRQA PGKEREMVAH ITIADATDYS  60
HFAKGRFTIS RDEAKNMVYL QMNGLRPEDT AVYFCRAGSR IYPYDYWGQG TLVTVSS     117

SEQ ID NO: 162            moltype = AA   length = 117
FEATURE                   Location/Qualifiers
REGION                    1..117
                          note = Nanobody Sequence
source                    1..117
                          mol_type = protein
                          organism = synthetic construct
SEQUENCE: 162
EVQLVESGGG LVQPGGSLRL SCAASGDVHK INFLGWYRQA PGKEREMVAH ITIADATDYA  60
EFAKGRFTIS RDEPKNMVYL QMNSLKPEDT AVYLCRAGSR IYPYNYWGQG TQVTVSS     117

SEQ ID NO: 163            moltype = AA   length = 117
FEATURE                   Location/Qualifiers
REGION                    1..117
                          note = Nanobody Sequence
source                    1..117
                          mol_type = protein
                          organism = synthetic construct
SEQUENCE: 163
EVQLVESGGG LVQPGGSLRL SCAASGEVHK INILGWYRQC PGKERDMVAT ITIGDATDYA  60
DSAKGRFTIS RDEAKNMVYL QMNSLKPEDT AVYFCRALSR LYPYNYWGQG TLVTVSS     117

SEQ ID NO: 164            moltype = AA   length = 117
```

-continued

```
FEATURE                   Location/Qualifiers
REGION                    1..117
                          note = Nanobody Sequence
source                    1..117
                          mol_type = protein
                          organism = synthetic construct
SEQUENCE: 164
EVQLVESGGG LVQPGGSLRL SCAASGDVHK INILGWYRQA PAKEREMVAH ITIGDATDYA   60
DSAKGRFTIS RDEAKNMVYL QMNSLKPEDT AVYLCRAYSR IYPYNYWGQG TQVTVSS      117

SEQ ID NO: 165           moltype = AA  length = 117
FEATURE                   Location/Qualifiers
REGION                    1..117
                          note = Nanobody Sequence
source                    1..117
                          mol_type = protein
                          organism = synthetic construct
SEQUENCE: 165
EVQLVESGGG LVQPGGSLRL SCAASGEVYK INFLGWQRQA PGKEREKVAH ITIADVADYA   60
DFAKGRFTIS RDEAKNMVYL QMNSLKPEDT AVYFCRAGSR IWPYDYWGQG TLVTVSS      117

SEQ ID NO: 166           moltype = AA  length = 117
FEATURE                   Location/Qualifiers
REGION                    1..117
                          note = Nanobody Sequence
source                    1..117
                          mol_type = protein
                          organism = synthetic construct
SEQUENCE: 166
EVQLVESGGD LVQPGGSLRL SCAASGDVHK INFLGWYRQA PGKEREMVAH ITIADATDYA   60
EFAKGRFTIS RDEPKNMVYL QMNSLKPVDT AVYLCRAGSR IYPYNYWGQG TLVTVSS      117

SEQ ID NO: 167           moltype = AA  length = 117
FEATURE                   Location/Qualifiers
REGION                    1..117
                          note = Nanobody Sequence
source                    1..117
                          mol_type = protein
                          organism = synthetic construct
SEQUENCE: 167
EVQLVESGGG LVQPGGSLRL SCAASGSVHL LNFLGWYRQA PGKEREKVAH ITIADATDYS   60
HFAKGRFTIS RDEAKNMVYL QMNNLRPEDT AVYFCRAGSR IYPYDYWGQG TLVTVSS      117

SEQ ID NO: 168           moltype = AA  length = 117
FEATURE                   Location/Qualifiers
REGION                    1..117
                          note = Nanobody Sequence
source                    1..117
                          mol_type = protein
                          organism = synthetic construct
SEQUENCE: 168
EVQLVESGGG LVQPGGSPRL SCVASGDVHK INFLGWYRQA PGKEREKVAH ITIGDQADYA   60
DSAKGRFTIS RDEAKNMVYL QMNSLKPEDT AVYFCRAGSR IYPYDYWGQG TLVTVSS      117

SEQ ID NO: 169           moltype = AA  length = 117
FEATURE                   Location/Qualifiers
REGION                    1..117
                          note = Nanobody Sequence
source                    1..117
                          mol_type = protein
                          organism = synthetic construct
SEQUENCE: 169
EVQLVESGGG LVQPGGSLRL SCAASGDVHK INILGWYRQA PAKEREMVAH ITIGDATDYA   60
DSAKGRFTIS RDEAKNMVYL QMNSLKPEDA AVYFCRAYSR IYPYNYWGQG TLVTVSS      117

SEQ ID NO: 170           moltype = AA  length = 117
FEATURE                   Location/Qualifiers
REGION                    1..117
                          note = Nanobody Sequence
source                    1..117
                          mol_type = protein
                          organism = synthetic construct
SEQUENCE: 170
EVQLVESGGG LVQPGGSLRL SCAASGEVYK INFLGWYRQA PGKEREKVAH ITIADVADYA   60
DFAKGRFTIS RDGAKNMVYL QMNSLKPEDT AVYFCRAGSR IWPYDYWGQG TLVTVSS      117

SEQ ID NO: 171           moltype = AA  length = 117
FEATURE                   Location/Qualifiers
REGION                    1..117
```

-continued

```
                              note = Nanobody Sequence
source                        1..117
                              mol_type = protein
                              organism = synthetic construct
SEQUENCE: 171
EVQLVESGGG SVQPGGSLRL SCAASGSVHK INFLGWYCQA PGKEREMVAT ITIGDATDYA  60
DSAKGRFTIS RDEAKNMVYL QMNSLSPEDT AVYFCRAGSR LYPYNYWGQG TQVTVSS     117

SEQ ID NO: 172               moltype = AA   length = 117
FEATURE                      Location/Qualifiers
REGION                       1..117
                              note = Nanobody Sequence
source                        1..117
                              mol_type = protein
                              organism = synthetic construct
SEQUENCE: 172
EVQLVESGGG LVQPGGSLRL SCVASGDVHK INILGWYRQA PGKEREKVAH ISISDQTDYA  60
ESAKGRFTIS RDESKNMVYL QMNSLKPEDA AVYLCRAFSR IYPYDYWGQG TQVTVSS     117

SEQ ID NO: 173               moltype = AA   length = 117
FEATURE                      Location/Qualifiers
REGION                       1..117
                              note = Nanobody Sequence
source                        1..117
                              mol_type = protein
                              organism = synthetic construct
SEQUENCE: 173
EVQLVESGGG LVQPGGSLRP SCAASGEVYK INFLGWYRQA PGKEREKVAH ITIADVADYA  60
DFAKGRFTIS RDEAKNMVYL QMNSLKPEDT AVYFCRAGSR IWPYDYWGQG TQVTVSS     117

SEQ ID NO: 174               moltype = AA   length = 117
FEATURE                      Location/Qualifiers
REGION                       1..117
                              note = Nanobody Sequence
source                        1..117
                              mol_type = protein
                              organism = synthetic construct
SEQUENCE: 174
EVQLVESGGG LVQPGGSLRP SCVASGDVHK INFLGWYRQA PGKEREKVAH ITIADQADYA  60
DSAKGRFTIS RDEAKNMVYL QMNSLKPEDT AVYFCRAGSR IYPYDYWGQG TLVTVSS     117

SEQ ID NO: 175               moltype = AA   length = 117
FEATURE                      Location/Qualifiers
REGION                       1..117
                              note = Nanobody Sequence
source                        1..117
                              mol_type = protein
                              organism = synthetic construct
SEQUENCE: 175
EVQLVESGGG LVQPGGSLRL SCAASGEVHK INILGWYRQA PGKERDMVAT ITIGDETQYA  60
DSAKGRFTIS RDEAKNMVYL QMNSLKPEDT AVYFCRALSR LYPYNYWGQG TLVTVSS     117

SEQ ID NO: 176               moltype = AA   length = 117
FEATURE                      Location/Qualifiers
REGION                       1..117
                              note = Nanobody Sequence
source                        1..117
                              mol_type = protein
                              organism = synthetic construct
SEQUENCE: 176
EVQLVESGGG LVQPGGSLRL SCAASGDVHK INILGWYRQA PAKEREMVAH ITIGDATDYA  60
DSAKGRFTIS RDEAKNMVYL QMDSLKPEDT AVYFCRAYSR IYPYNYWGQG TLVTVSS     117

SEQ ID NO: 177               moltype = AA   length = 117
FEATURE                      Location/Qualifiers
REGION                       1..117
                              note = Nanobody Sequence
source                        1..117
                              mol_type = protein
                              organism = synthetic construct
SEQUENCE: 177
EVQLVESGGG LVQPGGSLRL SCAASGDVHK INILGWYRQA PAKEREMVAH ITIGDATDYA  60
DSAKGRFTIS RDEAKNMVYL QMNSLKPGDT AVYFCRAYSR IYPYNYWGQG TLVTVSS     117

SEQ ID NO: 178               moltype = AA   length = 117
FEATURE                      Location/Qualifiers
REGION                       1..117
                              note = Nanobody Sequence
source                        1..117
```

```
                              mol_type = protein
                              organism = synthetic construct
SEQUENCE: 178
EVQLVESGGG LVQPGGSLRL SCAASGDVHK INILGWHRQA PAKEREMVAH ITIGDATDYA   60
DSAKGRFTIS RDEAKNMVYL QMNSLKPEDT AVYFCRAYSR IYPYNYWGQG TLVTVSS      117

SEQ ID NO: 179            moltype = AA  length = 117
FEATURE                   Location/Qualifiers
REGION                    1..117
                          note = Nanobody Sequence
source                    1..117
                          mol_type = protein
                          organism = synthetic construct
SEQUENCE: 179
EVQLVESGGG LVQPGGSLRL SCAASGDVHK INILGWHRQA PAKEREMVAH ITIGDATDYA   60
DSAKGRFTIS RDEAKNMVYL QMNSLKPEDT AAYFCRAYSR IYPYNYWGQG TQVTVSS      117

SEQ ID NO: 180            moltype = AA  length = 117
FEATURE                   Location/Qualifiers
REGION                    1..117
                          note = Nanobody Sequence
source                    1..117
                          mol_type = protein
                          organism = synthetic construct
SEQUENCE: 180
EVQLVESGGG WVQAGGSLRL SCAASGDVHK INILGWYRQA PAKEREMVAH ITIGDATDYA   60
DSAKGRFTIS RDEAKNMVYL QMNSLKPEDT AVYFCRAYSR IYPYNYWGQG TLVTVSS      117

SEQ ID NO: 181            moltype = AA  length = 10
FEATURE                   Location/Qualifiers
REGION                    1..10
                          note = CDR1
source                    1..10
                          mol_type = protein
                          organism = synthetic construct
SEQUENCE: 181
GDVHKINFLG                                                          10

SEQ ID NO: 182            moltype = AA  length = 10
FEATURE                   Location/Qualifiers
REGION                    1..10
                          note = CDR1
source                    1..10
                          mol_type = protein
                          organism = synthetic construct
SEQUENCE: 182
GSVHKINFLG                                                          10

SEQ ID NO: 183            moltype = AA  length = 10
FEATURE                   Location/Qualifiers
REGION                    1..10
                          note = CDR1
source                    1..10
                          mol_type = protein
                          organism = synthetic construct
SEQUENCE: 183
GSVHLLNFLG                                                          10

SEQ ID NO: 184            moltype = AA  length = 10
FEATURE                   Location/Qualifiers
REGION                    1..10
                          note = CDR1
source                    1..10
                          mol_type = protein
                          organism = synthetic construct
SEQUENCE: 184
GAVHKINFLG                                                          10

SEQ ID NO: 185            moltype = AA  length = 10
FEATURE                   Location/Qualifiers
REGION                    1..10
                          note = CDR1
source                    1..10
                          mol_type = protein
                          organism = synthetic construct
SEQUENCE: 185
GDVHKINILG                                                          10

SEQ ID NO: 186            moltype = AA  length = 10
```

```
FEATURE                Location/Qualifiers
REGION                 1..10
                       note = CDR1
source                 1..10
                       mol_type = protein
                       organism = synthetic construct
SEQUENCE: 186
GDVHKINVLG                                                    10

SEQ ID NO: 187         moltype = AA  length = 10
FEATURE                Location/Qualifiers
REGION                 1..10
                       note = CDR1
source                 1..10
                       mol_type = protein
                       organism = synthetic construct
SEQUENCE: 187
GEVYKINFLG                                                    10

SEQ ID NO: 188         moltype = AA  length = 10
FEATURE                Location/Qualifiers
REGION                 1..10
                       note = CDR1
source                 1..10
                       mol_type = protein
                       organism = synthetic construct
SEQUENCE: 188
GGVHKINILG                                                    10

SEQ ID NO: 189         moltype = AA  length = 10
FEATURE                Location/Qualifiers
REGION                 1..10
                       note = CDR1
source                 1..10
                       mol_type = protein
                       organism = synthetic construct
SEQUENCE: 189
GSVYKINFLS                                                    10

SEQ ID NO: 190         moltype = AA  length = 10
FEATURE                Location/Qualifiers
REGION                 1..10
                       note = CDR1
source                 1..10
                       mol_type = protein
                       organism = synthetic construct
SEQUENCE: 190
GDVYKINFLG                                                    10

SEQ ID NO: 191         moltype = AA  length = 10
FEATURE                Location/Qualifiers
REGION                 1..10
                       note = CDR1
source                 1..10
                       mol_type = protein
                       organism = synthetic construct
SEQUENCE: 191
GEVHKINILG                                                    10

SEQ ID NO: 192         moltype = AA  length = 9
FEATURE                Location/Qualifiers
REGION                 1..9
                       note = CDR2
source                 1..9
                       mol_type = protein
                       organism = synthetic construct
SEQUENCE: 192
HISIGDQTD                                                     9

SEQ ID NO: 193         moltype = AA  length = 9
FEATURE                Location/Qualifiers
REGION                 1..9
                       note = CDR2
source                 1..9
                       mol_type = protein
                       organism = synthetic construct
SEQUENCE: 193
TITIGDTTD                                                     9
```

-continued

```
SEQ ID NO: 194        moltype = AA   length = 9
FEATURE               Location/Qualifiers
REGION                1..9
                      note = CDR2
source                1..9
                      mol_type = protein
                      organism = synthetic construct
SEQUENCE: 194
TITIGDATD                                                          9

SEQ ID NO: 195        moltype = AA   length = 9
FEATURE               Location/Qualifiers
REGION                1..9
                      note = CDR2
source                1..9
                      mol_type = protein
                      organism = synthetic construct
SEQUENCE: 195
HITIADATD                                                          9

SEQ ID NO: 196        moltype = AA   length = 9
FEATURE               Location/Qualifiers
REGION                1..9
                      note = CDR2
source                1..9
                      mol_type = protein
                      organism = synthetic construct
SEQUENCE: 196
TITIGDDVD                                                          9

SEQ ID NO: 197        moltype = AA   length = 9
FEATURE               Location/Qualifiers
REGION                1..9
                      note = CDR2
source                1..9
                      mol_type = protein
                      organism = synthetic construct
SEQUENCE: 197
HITIGDATD                                                          9

SEQ ID NO: 198        moltype = AA   length = 9
FEATURE               Location/Qualifiers
REGION                1..9
                      note = CDR2
source                1..9
                      mol_type = protein
                      organism = synthetic construct
SEQUENCE: 198
HITIGDQAD                                                          9

SEQ ID NO: 199        moltype = AA   length = 9
FEATURE               Location/Qualifiers
REGION                1..9
                      note = CDR2
source                1..9
                      mol_type = protein
                      organism = synthetic construct
SEQUENCE: 199
HISIADATD                                                          9

SEQ ID NO: 200        moltype = AA   length = 9
FEATURE               Location/Qualifiers
REGION                1..9
                      note = CDR2
source                1..9
                      mol_type = protein
                      organism = synthetic construct
SEQUENCE: 200
HITIGDATV                                                          9

SEQ ID NO: 201        moltype = AA   length = 9
FEATURE               Location/Qualifiers
REGION                1..9
                      note = CDR2
source                1..9
                      mol_type = protein
                      organism = synthetic construct
SEQUENCE: 201
HITIGDEVD                                                          9
```

-continued

```
SEQ ID NO: 202          moltype = AA   length = 9
FEATURE                 Location/Qualifiers
REGION                  1..9
                        note = CDR2
source                  1..9
                        mol_type = protein
                        organism = synthetic construct
SEQUENCE: 202
HITIGDVTD                                                                    9

SEQ ID NO: 203          moltype = AA   length = 9
FEATURE                 Location/Qualifiers
REGION                  1..9
                        note = CDR2
source                  1..9
                        mol_type = protein
                        organism = synthetic construct
SEQUENCE: 203
HITIGDATN                                                                    9

SEQ ID NO: 204          moltype = AA   length = 9
FEATURE                 Location/Qualifiers
REGION                  1..9
                        note = CDR2
source                  1..9
                        mol_type = protein
                        organism = synthetic construct
SEQUENCE: 204
HITIADVAD                                                                    9

SEQ ID NO: 205          moltype = AA   length = 9
FEATURE                 Location/Qualifiers
REGION                  1..9
                        note = CDR2
source                  1..9
                        mol_type = protein
                        organism = synthetic construct
SEQUENCE: 205
TITIGDEVD                                                                    9

SEQ ID NO: 206          moltype = AA   length = 9
FEATURE                 Location/Qualifiers
REGION                  1..9
                        note = CDR2
source                  1..9
                        mol_type = protein
                        organism = synthetic construct
SEQUENCE: 206
HISISDQTD                                                                    9

SEQ ID NO: 207          moltype = AA   length = 9
FEATURE                 Location/Qualifiers
REGION                  1..9
                        note = CDR2
source                  1..9
                        mol_type = protein
                        organism = synthetic construct
SEQUENCE: 207
HITIGDQTD                                                                    9

SEQ ID NO: 208          moltype = AA   length = 9
FEATURE                 Location/Qualifiers
REGION                  1..9
                        note = CDR2
source                  1..9
                        mol_type = protein
                        organism = synthetic construct
SEQUENCE: 208
HITIGDTTD                                                                    9

SEQ ID NO: 209          moltype = AA   length = 9
FEATURE                 Location/Qualifiers
REGION                  1..9
                        note = CDR2
source                  1..9
                        mol_type = protein
                        organism = synthetic construct
SEQUENCE: 209
```

-continued

```
RISISDQTD                                                          9

SEQ ID NO: 210            moltype = AA   length = 9
FEATURE                   Location/Qualifiers
REGION                    1..9
                          note = CDR2
source                    1..9
                          mol_type = protein
                          organism = synthetic construct
SEQUENCE: 210
HITIADAAD                                                          9

SEQ ID NO: 211            moltype = AA   length = 9
FEATURE                   Location/Qualifiers
REGION                    1..9
                          note = CDR2
source                    1..9
                          mol_type = protein
                          organism = synthetic construct
SEQUENCE: 211
TITIGDAAD                                                          9

SEQ ID NO: 212            moltype = AA   length = 9
FEATURE                   Location/Qualifiers
REGION                    1..9
                          note = CDR2
source                    1..9
                          mol_type = protein
                          organism = synthetic construct
SEQUENCE: 212
HIAISDQTD                                                          9

SEQ ID NO: 213            moltype = AA   length = 9
FEATURE                   Location/Qualifiers
REGION                    1..9
                          note = CDR2
source                    1..9
                          mol_type = protein
                          organism = synthetic construct
SEQUENCE: 213
HITIGDATS                                                          9

SEQ ID NO: 214            moltype = AA   length = 9
FEATURE                   Location/Qualifiers
REGION                    1..9
                          note = CDR2
source                    1..9
                          mol_type = protein
                          organism = synthetic construct
SEQUENCE: 214
TITIGDEVA                                                          9

SEQ ID NO: 215            moltype = AA   length = 9
FEATURE                   Location/Qualifiers
REGION                    1..9
                          note = CDR2
source                    1..9
                          mol_type = protein
                          organism = synthetic construct
SEQUENCE: 215
HITIADVTD                                                          9

SEQ ID NO: 216            moltype = AA   length = 9
FEATURE                   Location/Qualifiers
REGION                    1..9
                          note = CDR2
source                    1..9
                          mol_type = protein
                          organism = synthetic construct
SEQUENCE: 216
HITIADQAD                                                          9

SEQ ID NO: 217            moltype = AA   length = 9
FEATURE                   Location/Qualifiers
REGION                    1..9
                          note = CDR2
source                    1..9
                          mol_type = protein
                          organism = synthetic construct
```

```
SEQUENCE: 217
TITIGDETQ                                                            9

SEQ ID NO: 218        moltype = AA   length = 9
FEATURE               Location/Qualifiers
REGION                1..9
                      note = CDR3
source                1..9
                      mol_type = protein
                      organism = synthetic construct
SEQUENCE: 218
FSRIYPYDY                                                            9

SEQ ID NO: 219        moltype = AA   length = 9
FEATURE               Location/Qualifiers
REGION                1..9
                      note = CDR3
source                1..9
                      mol_type = protein
                      organism = synthetic construct
SEQUENCE: 219
GSRLYPYNY                                                            9

SEQ ID NO: 220        moltype = AA   length = 9
FEATURE               Location/Qualifiers
REGION                1..9
                      note = CDR3
source                1..9
                      mol_type = protein
                      organism = synthetic construct
SEQUENCE: 220
GSRIYPYDY                                                            9

SEQ ID NO: 221        moltype = AA   length = 9
FEATURE               Location/Qualifiers
REGION                1..9
                      note = CDR3
source                1..9
                      mol_type = protein
                      organism = synthetic construct
SEQUENCE: 221
YSRIYPYNY                                                            9

SEQ ID NO: 222        moltype = AA   length = 9
FEATURE               Location/Qualifiers
REGION                1..9
                      note = CDR3
source                1..9
                      mol_type = protein
                      organism = synthetic construct
SEQUENCE: 222
GSRIWPYDY                                                            9

SEQ ID NO: 223        moltype = AA   length = 9
FEATURE               Location/Qualifiers
REGION                1..9
                      note = CDR3
source                1..9
                      mol_type = protein
                      organism = synthetic construct
SEQUENCE: 223
GSRIYPYNY                                                            9

SEQ ID NO: 224        moltype = AA   length = 9
FEATURE               Location/Qualifiers
REGION                1..9
                      note = CDR3
source                1..9
                      mol_type = protein
                      organism = synthetic construct
SEQUENCE: 224
GSRIYPYSY                                                            9

SEQ ID NO: 225        moltype = AA   length = 9
FEATURE               Location/Qualifiers
REGION                1..9
                      note = CDR3
source                1..9
                      mol_type = protein
```

-continued

```
                              organism = synthetic construct
SEQUENCE: 225
LSRLYPYNY                                                       9

SEQ ID NO: 226            moltype = AA  length = 25
FEATURE                   Location/Qualifiers
REGION                    1..25
                          note = FR1
source                    1..25
                          mol_type = protein
                          organism = synthetic construct
SEQUENCE: 226
EVQLVESGGG LVQPGGSLRL SCVAS                                     25

SEQ ID NO: 227            moltype = AA  length = 25
FEATURE                   Location/Qualifiers
REGION                    1..25
                          note = FR1
source                    1..25
                          mol_type = protein
                          organism = synthetic construct
SEQUENCE: 227
EVQLVESGGG LVQPGGSLRL SCAAS                                     25

SEQ ID NO: 228            moltype = AA  length = 25
FEATURE                   Location/Qualifiers
REGION                    1..25
                          note = FR1
source                    1..25
                          mol_type = protein
                          organism = synthetic construct
SEQUENCE: 228
EVQLVESGGG LVQPGRSLRL PCAAS                                     25

SEQ ID NO: 229            moltype = AA  length = 25
FEATURE                   Location/Qualifiers
REGION                    1..25
                          note = FR1
source                    1..25
                          mol_type = protein
                          organism = synthetic construct
SEQUENCE: 229
EVQLVESGGG LVQPGGSLRL SCAVS                                     25

SEQ ID NO: 230            moltype = AA  length = 25
FEATURE                   Location/Qualifiers
REGION                    1..25
                          note = FR1
source                    1..25
                          mol_type = protein
                          organism = synthetic construct
SEQUENCE: 230
EVQLVESGGG LVQPGGSLKL SCAAS                                     25

SEQ ID NO: 231            moltype = AA  length = 25
FEATURE                   Location/Qualifiers
REGION                    1..25
                          note = FR1
source                    1..25
                          mol_type = protein
                          organism = synthetic construct
SEQUENCE: 231
EVQLVESGGG LVQPGGSLRL SCRAS                                     25

SEQ ID NO: 232            moltype = AA  length = 25
FEATURE                   Location/Qualifiers
REGION                    1..25
                          note = FR1
source                    1..25
                          mol_type = protein
                          organism = synthetic construct
SEQUENCE: 232
EVQLVESGGG LVRPGGSLRL SCAAS                                     25

SEQ ID NO: 233            moltype = AA  length = 25
FEATURE                   Location/Qualifiers
REGION                    1..25
                          note = FR1
source                    1..25
```

-continued

```
                             mol_type = protein
                             organism = synthetic construct
SEQUENCE: 233
EVQLVESGGG SVQPGGSLRL SCAAS                                     25

SEQ ID NO: 234          moltype = AA   length = 25
FEATURE                 Location/Qualifiers
REGION                  1..25
                        note = FR1
source                  1..25
                        mol_type = protein
                        organism = synthetic construct
SEQUENCE: 234
EVQLVESGGG LVQPGGSLRP SCAAS                                     25

SEQ ID NO: 235          moltype = AA   length = 25
FEATURE                 Location/Qualifiers
REGION                  1..25
                        note = FR1
source                  1..25
                        mol_type = protein
                        organism = synthetic construct
SEQUENCE: 235
EVQLVESGGG LVHPGGSLRL SCAAS                                     25

SEQ ID NO: 236          moltype = AA   length = 25
FEATURE                 Location/Qualifiers
REGION                  1..25
                        note = FR1
source                  1..25
                        mol_type = protein
                        organism = synthetic construct
SEQUENCE: 236
EVQLVESGGG LVQPGGSARL SCVAS                                     25

SEQ ID NO: 237          moltype = AA   length = 25
FEATURE                 Location/Qualifiers
REGION                  1..25
                        note = FR1
source                  1..25
                        mol_type = protein
                        organism = synthetic construct
SEQUENCE: 237
EVQLVESGGG LVQAGGSLTL SCAAS                                     25

SEQ ID NO: 238          moltype = AA   length = 25
FEATURE                 Location/Qualifiers
REGION                  1..25
                        note = FR1
source                  1..25
                        mol_type = protein
                        organism = synthetic construct
SEQUENCE: 238
EVQLVESGGD LVQPGGSLRL SCAAS                                     25

SEQ ID NO: 239          moltype = AA   length = 25
FEATURE                 Location/Qualifiers
REGION                  1..25
                        note = FR1
source                  1..25
                        mol_type = protein
                        organism = synthetic construct
SEQUENCE: 239
EVQLVESGGG LVQPEGSLRL SCAAS                                     25

SEQ ID NO: 240          moltype = AA   length = 25
FEATURE                 Location/Qualifiers
REGION                  1..25
                        note = FR1
source                  1..25
                        mol_type = protein
                        organism = synthetic construct
SEQUENCE: 240
EVQLVESGGG LVQPGGSLKL PCAAS                                     25

SEQ ID NO: 241          moltype = AA   length = 25
FEATURE                 Location/Qualifiers
REGION                  1..25
                        note = FR1
```

```
source                    1..25
                          mol_type = protein
                          organism = synthetic construct
SEQUENCE: 241
EVQLVESGGG LVQPGGSLGL SCAAS                                            25

SEQ ID NO: 242            moltype = AA   length = 25
FEATURE                   Location/Qualifiers
REGION                    1..25
                          note = FR1
source                    1..25
                          mol_type = protein
                          organism = synthetic construct
SEQUENCE: 242
EVQLVESGGG LAQPGGSLRL SCAAS                                            25

SEQ ID NO: 243            moltype = AA   length = 25
FEATURE                   Location/Qualifiers
REGION                    1..25
                          note = FR1
source                    1..25
                          mol_type = protein
                          organism = synthetic construct
SEQUENCE: 243
EVQLVESGGG WVQPGGSLRL SCAAS                                            25

SEQ ID NO: 244            moltype = AA   length = 25
FEATURE                   Location/Qualifiers
REGION                    1..25
                          note = FR1
source                    1..25
                          mol_type = protein
                          organism = synthetic construct
SEQUENCE: 244
EVQLVESGGG SVQPGGSLRP SCAAS                                            25

SEQ ID NO: 245            moltype = AA   length = 25
FEATURE                   Location/Qualifiers
REGION                    1..25
                          note = FR1
source                    1..25
                          mol_type = protein
                          organism = synthetic construct
SEQUENCE: 245
EVQLVESGGG LVQPGESLRL SCAAS                                            25

SEQ ID NO: 246            moltype = AA   length = 25
FEATURE                   Location/Qualifiers
REGION                    1..25
                          note = FR1
source                    1..25
                          mol_type = protein
                          organism = synthetic construct
SEQUENCE: 246
EVQLVESGGG LVRPGGSLRL SCVAS                                            25

SEQ ID NO: 247            moltype = AA   length = 25
FEATURE                   Location/Qualifiers
REGION                    1..25
                          note = FR1
source                    1..25
                          mol_type = protein
                          organism = synthetic construct
SEQUENCE: 247
EVQLVESGGG MVQPGGSLRL SCAAS                                            25

SEQ ID NO: 248            moltype = AA   length = 25
FEATURE                   Location/Qualifiers
REGION                    1..25
                          note = FR1
source                    1..25
                          mol_type = protein
                          organism = synthetic construct
SEQUENCE: 248
EVQLVESGGG LVQPGGSPRL SCVAS                                            25

SEQ ID NO: 249            moltype = AA   length = 25
FEATURE                   Location/Qualifiers
REGION                    1..25
```

-continued

```
                          note = FR1
source                    1..25
                          mol_type = protein
                          organism = synthetic construct
SEQUENCE: 249
EVQLVESGGG LVQPGGSLRP SCVAS                                            25

SEQ ID NO: 250            moltype = AA  length = 25
FEATURE                   Location/Qualifiers
REGION                    1..25
                          note = FR1
source                    1..25
                          mol_type = protein
                          organism = synthetic construct
SEQUENCE: 250
EVQLVESGGG WVQAGGSLRL SCAAS                                            25

SEQ ID NO: 251            moltype = AA  length = 14
FEATURE                   Location/Qualifiers
REGION                    1..14
                          note = FR2
source                    1..14
                          mol_type = protein
                          organism = synthetic construct
SEQUENCE: 251
WYRQAPGKER EKVA                                                        14

SEQ ID NO: 252            moltype = AA  length = 14
FEATURE                   Location/Qualifiers
REGION                    1..14
                          note = FR2
source                    1..14
                          mol_type = protein
                          organism = synthetic construct
SEQUENCE: 252
WYRQAPGKER ELVA                                                        14

SEQ ID NO: 253            moltype = AA  length = 14
FEATURE                   Location/Qualifiers
REGION                    1..14
                          note = FR2
source                    1..14
                          mol_type = protein
                          organism = synthetic construct
SEQUENCE: 253
WYRQAPGKER GLVA                                                        14

SEQ ID NO: 254            moltype = AA  length = 14
FEATURE                   Location/Qualifiers
REGION                    1..14
                          note = FR2
source                    1..14
                          mol_type = protein
                          organism = synthetic construct
SEQUENCE: 254
WYRQAPGKER EMVA                                                        14

SEQ ID NO: 255            moltype = AA  length = 14
FEATURE                   Location/Qualifiers
REGION                    1..14
                          note = FR2
source                    1..14
                          mol_type = protein
                          organism = synthetic construct
SEQUENCE: 255
WYRQTPEKER EMVA                                                        14

SEQ ID NO: 256            moltype = AA  length = 14
FEATURE                   Location/Qualifiers
REGION                    1..14
                          note = FR2
source                    1..14
                          mol_type = protein
                          organism = synthetic construct
SEQUENCE: 256
WYRQAPAKER EMVA                                                        14

SEQ ID NO: 257            moltype = AA  length = 14
FEATURE                   Location/Qualifiers
```

```
REGION                    1..14
                          note = FR2
source                    1..14
                          mol_type = protein
                          organism = synthetic construct
SEQUENCE: 257
WYRQCPGKER EMVA                                                                        14

SEQ ID NO: 258            moltype = AA  length = 14
FEATURE                   Location/Qualifiers
REGION                    1..14
                          note = FR2
source                    1..14
                          mol_type = protein
                          organism = synthetic construct
SEQUENCE: 258
WHRQPPGKER EKVA                                                                        14

SEQ ID NO: 259            moltype = AA  length = 14
FEATURE                   Location/Qualifiers
REGION                    1..14
                          note = FR2
source                    1..14
                          mol_type = protein
                          organism = synthetic construct
SEQUENCE: 259
WHRQAPGKER EKVA                                                                        14

SEQ ID NO: 260            moltype = AA  length = 14
FEATURE                   Location/Qualifiers
REGION                    1..14
                          note = FR2
source                    1..14
                          mol_type = protein
                          organism = synthetic construct
SEQUENCE: 260
WYRQAPEKER EMVA                                                                        14

SEQ ID NO: 261            moltype = AA  length = 14
FEATURE                   Location/Qualifiers
REGION                    1..14
                          note = FR2
source                    1..14
                          mol_type = protein
                          organism = synthetic construct
SEQUENCE: 261
WYRQAPGKER EVVA                                                                        14

SEQ ID NO: 262            moltype = AA  length = 14
FEATURE                   Location/Qualifiers
REGION                    1..14
                          note = FR2
source                    1..14
                          mol_type = protein
                          organism = synthetic construct
SEQUENCE: 262
WYRQAPGKER GVVA                                                                        14

SEQ ID NO: 263            moltype = AA  length = 14
FEATURE                   Location/Qualifiers
REGION                    1..14
                          note = FR2
source                    1..14
                          mol_type = protein
                          organism = synthetic construct
SEQUENCE: 263
WYRQAPGKER EMVT                                                                        14

SEQ ID NO: 264            moltype = AA  length = 14
FEATURE                   Location/Qualifiers
REGION                    1..14
                          note = FR2
source                    1..14
                          mol_type = protein
                          organism = synthetic construct
SEQUENCE: 264
WYRQAPGHER ELVA                                                                        14

SEQ ID NO: 265            moltype = AA  length = 14
```

-continued

```
FEATURE                 Location/Qualifiers
REGION                  1..14
                        note = FR2
source                  1..14
                        mol_type = protein
                        organism = synthetic construct
SEQUENCE: 265
WYRQAPAKER GMVA                                                          14

SEQ ID NO: 266          moltype = AA  length = 14
FEATURE                 Location/Qualifiers
REGION                  1..14
                        note = FR2
source                  1..14
                        mol_type = protein
                        organism = synthetic construct
SEQUENCE: 266
WYRQAPAKEH EMVA                                                          14

SEQ ID NO: 267          moltype = AA  length = 14
FEATURE                 Location/Qualifiers
REGION                  1..14
                        note = FR2
source                  1..14
                        mol_type = protein
                        organism = synthetic construct
SEQUENCE: 267
WYRQAPARER EMVA                                                          14

SEQ ID NO: 268          moltype = AA  length = 14
FEATURE                 Location/Qualifiers
REGION                  1..14
                        note = FR2
source                  1..14
                        mol_type = protein
                        organism = synthetic construct
SEQUENCE: 268
WYRQAPGKER GMVA                                                          14

SEQ ID NO: 269          moltype = AA  length = 14
FEATURE                 Location/Qualifiers
REGION                  1..14
                        note = FR2
source                  1..14
                        mol_type = protein
                        organism = synthetic construct
SEQUENCE: 269
WYRQAPAKER EMIA                                                          14

SEQ ID NO: 270          moltype = AA  length = 14
FEATURE                 Location/Qualifiers
REGION                  1..14
                        note = FR2
source                  1..14
                        mol_type = protein
                        organism = synthetic construct
SEQUENCE: 270
WYRQAPAKGR EMVA                                                          14

SEQ ID NO: 271          moltype = AA  length = 14
FEATURE                 Location/Qualifiers
REGION                  1..14
                        note = FR2
source                  1..14
                        mol_type = protein
                        organism = synthetic construct
SEQUENCE: 271
WYRQVPAKER EMVA                                                          14

SEQ ID NO: 272          moltype = AA  length = 14
FEATURE                 Location/Qualifiers
REGION                  1..14
                        note = FR2
source                  1..14
                        mol_type = protein
                        organism = synthetic construct
SEQUENCE: 272
WYRQCPGKER DMVA                                                          14
```

-continued

```
SEQ ID NO: 273        moltype = AA   length = 14
FEATURE               Location/Qualifiers
REGION                1..14
                      note = FR2
source                1..14
                      mol_type = protein
                      organism = synthetic construct
SEQUENCE: 273
WQRQAPGKER EKVA                                                14

SEQ ID NO: 274        moltype = AA   length = 14
FEATURE               Location/Qualifiers
REGION                1..14
                      note = FR2
source                1..14
                      mol_type = protein
                      organism = synthetic construct
SEQUENCE: 274
WYCQAPGKER EMVA                                                14

SEQ ID NO: 275        moltype = AA   length = 14
FEATURE               Location/Qualifiers
REGION                1..14
                      note = FR2
source                1..14
                      mol_type = protein
                      organism = synthetic construct
SEQUENCE: 275
WYRQAPGKER DMVA                                                14

SEQ ID NO: 276        moltype = AA   length = 14
FEATURE               Location/Qualifiers
REGION                1..14
                      note = FR2
source                1..14
                      mol_type = protein
                      organism = synthetic construct
SEQUENCE: 276
WHRQAPAKER EMVA                                                14

SEQ ID NO: 277        moltype = AA   length = 39
FEATURE               Location/Qualifiers
REGION                1..39
                      note = FR3
source                1..39
                      mol_type = protein
                      organism = synthetic construct
SEQUENCE: 277
YADSAKGRFT ISRDESKNMV YLQMNSLKPE DTAVYFCRA                     39

SEQ ID NO: 278        moltype = AA   length = 39
FEATURE               Location/Qualifiers
REGION                1..39
                      note = FR3
source                1..39
                      mol_type = protein
                      organism = synthetic construct
SEQUENCE: 278
YADSAKGRFT ISRDEAKNMV YLQMNSLKPE DTAVHFCRA                     39

SEQ ID NO: 279        moltype = AA   length = 39
FEATURE               Location/Qualifiers
REGION                1..39
                      note = FR3
source                1..39
                      mol_type = protein
                      organism = synthetic construct
SEQUENCE: 279
YADYAKGRFT ISRDEARNMV YLQMNSLKPE DTAVYFCRA                     39

SEQ ID NO: 280        moltype = AA   length = 39
FEATURE               Location/Qualifiers
REGION                1..39
                      note = FR3
source                1..39
                      mol_type = protein
                      organism = synthetic construct
SEQUENCE: 280
YADSAKGRFT ISRDEAKNMV YLQMNSLKPE DTAVYFCRA                     39
```

-continued

```
SEQ ID NO: 281          moltype = AA   length = 39
FEATURE                 Location/Qualifiers
REGION                  1..39
                        note = FR3
source                  1..39
                        mol_type = protein
                        organism = synthetic construct
SEQUENCE: 281
YSHFAKGRFT ISRDEAKNMV YLQMNSLRPE DTAVYFCRA                          39

SEQ ID NO: 282          moltype = AA   length = 39
FEATURE                 Location/Qualifiers
REGION                  1..39
                        note = FR3
source                  1..39
                        mol_type = protein
                        organism = synthetic construct
SEQUENCE: 282
YADSAKGRFT ISRDEAKNMV YLQMTSLKPE DTAVYVCRA                          39

SEQ ID NO: 283          moltype = AA   length = 39
FEATURE                 Location/Qualifiers
REGION                  1..39
                        note = FR3
source                  1..39
                        mol_type = protein
                        organism = synthetic construct
SEQUENCE: 283
YAESAKGRFT ISRDEAKNMV YLQMNSLKPE DTAVYFCRA                          39

SEQ ID NO: 284          moltype = AA   length = 39
FEATURE                 Location/Qualifiers
REGION                  1..39
                        note = FR3
source                  1..39
                        mol_type = protein
                        organism = synthetic construct
SEQUENCE: 284
YADSAKGRFT ISRDEAKNMV YLQMNSLSPE DTAVYFCRA                          39

SEQ ID NO: 285          moltype = AA   length = 39
FEATURE                 Location/Qualifiers
REGION                  1..39
                        note = FR3
source                  1..39
                        mol_type = protein
                        organism = synthetic construct
SEQUENCE: 285
YAHFAKGRFT ISRDEAKNMV YLQMNSLRPE DTAVYFCRA                          39

SEQ ID NO: 286          moltype = AA   length = 39
FEATURE                 Location/Qualifiers
REGION                  1..39
                        note = FR3
source                  1..39
                        mol_type = protein
                        organism = synthetic construct
SEQUENCE: 286
YADSAKGRFT ISRDEAKNMV YLQMTSLTPE DTAVYVCRA                          39

SEQ ID NO: 287          moltype = AA   length = 39
FEATURE                 Location/Qualifiers
REGION                  1..39
                        note = FR3
source                  1..39
                        mol_type = protein
                        organism = synthetic construct
SEQUENCE: 287
YADSAKGRFT ISRDEAKNMV YLQMNNLKPE DTAVYFCRA                          39

SEQ ID NO: 288          moltype = AA   length = 39
FEATURE                 Location/Qualifiers
REGION                  1..39
                        note = FR3
source                  1..39
                        mol_type = protein
                        organism = synthetic construct
SEQUENCE: 288
```

```
YADSAKGRFT ISRDEAKNMV HLQMNSLKPE DTAVYFCRA                              39

SEQ ID NO: 289          moltype = AA  length = 39
FEATURE                 Location/Qualifiers
REGION                  1..39
                        note = FR3
source                  1..39
                        mol_type = protein
                        organism = synthetic construct
SEQUENCE: 289
YADSAKGRFT ISRDEAKNMV FLQMNNLKPE DTAVYFCRA                              39

SEQ ID NO: 290          moltype = AA  length = 39
FEATURE                 Location/Qualifiers
REGION                  1..39
                        note = FR3
source                  1..39
                        mol_type = protein
                        organism = synthetic construct
SEQUENCE: 290
YAGSAKGRFT ISRDEAKNMV YLQMNSLKPE DTAVYFCRA                              39

SEQ ID NO: 291          moltype = AA  length = 39
FEATURE                 Location/Qualifiers
REGION                  1..39
                        note = FR3
source                  1..39
                        mol_type = protein
                        organism = synthetic construct
SEQUENCE: 291
YADFAKGRFT ISRDEAKNMV YLQMNSLKPE DTAVYFCRA                              39

SEQ ID NO: 292          moltype = AA  length = 39
FEATURE                 Location/Qualifiers
REGION                  1..39
                        note = FR3
source                  1..39
                        mol_type = protein
                        organism = synthetic construct
SEQUENCE: 292
YADSAKGRFT ISRDEAKNMV YLQMTSLKPE DTTVYVCRA                              39

SEQ ID NO: 293          moltype = AA  length = 39
FEATURE                 Location/Qualifiers
REGION                  1..39
                        note = FR3
source                  1..39
                        mol_type = protein
                        organism = synthetic construct
SEQUENCE: 293
YAESAKGRFT ISRDESKNMV YLQMNSLKPE DTAVYLCRA                              39

SEQ ID NO: 294          moltype = AA  length = 39
FEATURE                 Location/Qualifiers
REGION                  1..39
                        note = FR3
source                  1..39
                        mol_type = protein
                        organism = synthetic construct
SEQUENCE: 294
YADSAKGRFA ISRDEAKNMV YLQMNSLKPE DTAVYFCRA                              39

SEQ ID NO: 295          moltype = AA  length = 39
FEATURE                 Location/Qualifiers
REGION                  1..39
                        note = FR3
source                  1..39
                        mol_type = protein
                        organism = synthetic construct
SEQUENCE: 295
YADFAQGRFT ISRDEAKNMV YLQMNSLKPE DTAVYFCRA                              39

SEQ ID NO: 296          moltype = AA  length = 39
FEATURE                 Location/Qualifiers
REGION                  1..39
                        note = FR3
source                  1..39
                        mol_type = protein
                        organism = synthetic construct
```

```
SEQUENCE: 296
YAEFAKGRFT ISRDEPKNMV HLQMNSLKPE DTAVYLCRA                                39

SEQ ID NO: 297           moltype = AA  length = 39
FEATURE                  Location/Qualifiers
REGION                   1..39
                         note = FR3
source                   1..39
                         mol_type = protein
                         organism = synthetic construct
SEQUENCE: 297
YADFAKGRLT ISRDEAKNMV YLQMNSLKPE DTAVYFCRA                                39

SEQ ID NO: 298           moltype = AA  length = 39
FEATURE                  Location/Qualifiers
REGION                   1..39
                         note = FR3
source                   1..39
                         mol_type = protein
                         organism = synthetic construct
SEQUENCE: 298
YADFAKGRFT ISRDGAKNMV YLQMNSLKPE DTAVYFCRA                                39

SEQ ID NO: 299           moltype = AA  length = 39
FEATURE                  Location/Qualifiers
REGION                   1..39
                         note = FR3
source                   1..39
                         mol_type = protein
                         organism = synthetic construct
SEQUENCE: 299
YADSAKGRFT ISRDEARNMV YLQMNSLKPE DTALYFCHA                                39

SEQ ID NO: 300           moltype = AA  length = 39
FEATURE                  Location/Qualifiers
REGION                   1..39
                         note = FR3
source                   1..39
                         mol_type = protein
                         organism = synthetic construct
SEQUENCE: 300
YADSAKGRFT ISRDEAKNMV YLQMNSLKPE DTAAYFCRA                                39

SEQ ID NO: 301           moltype = AA  length = 39
FEATURE                  Location/Qualifiers
REGION                   1..39
                         note = FR3
source                   1..39
                         mol_type = protein
                         organism = synthetic construct
SEQUENCE: 301
YADSAKGRFT ISRDEAENMV YLQMNSLKPE DTAVYFCRA                                39

SEQ ID NO: 302           moltype = AA  length = 39
FEATURE                  Location/Qualifiers
REGION                   1..39
                         note = FR3
source                   1..39
                         mol_type = protein
                         organism = synthetic construct
SEQUENCE: 302
YADSAKGRFT ISRDEATNMV YLQMTSLKPE DTAVYFCRA                                39

SEQ ID NO: 303           moltype = AA  length = 39
FEATURE                  Location/Qualifiers
REGION                   1..39
                         note = FR3
source                   1..39
                         mol_type = protein
                         organism = synthetic construct
SEQUENCE: 303
YAGSAKGRFT ISRDEAKNMV YLQLNNLKPE DTAVYFCRA                                39

SEQ ID NO: 304           moltype = AA  length = 39
FEATURE                  Location/Qualifiers
REGION                   1..39
                         note = FR3
source                   1..39
                         mol_type = protein
```

-continued

```
                          organism = synthetic construct
SEQUENCE: 304
YADSAKGRFT ISRDEAKNMV YLQLNNLKPE DTAVYFCRA                    39

SEQ ID NO: 305           moltype = AA   length = 39
FEATURE                  Location/Qualifiers
REGION                   1..39
                         note = FR3
source                   1..39
                         mol_type = protein
                         organism = synthetic construct
SEQUENCE: 305
YAEFAKGRFT ISRDEPKNMV YLQMNSLKPE DTAVYLCRA                    39

SEQ ID NO: 306           moltype = AA   length = 39
FEATURE                  Location/Qualifiers
REGION                   1..39
                         note = FR3
source                   1..39
                         mol_type = protein
                         organism = synthetic construct
SEQUENCE: 306
YAHSAKGRFT ISRDEAKNMV YLQMTSLKPE DTAVYVCRA                    39

SEQ ID NO: 307           moltype = AA   length = 39
FEATURE                  Location/Qualifiers
REGION                   1..39
                         note = FR3
source                   1..39
                         mol_type = protein
                         organism = synthetic construct
SEQUENCE: 307
YADFAKGRFT ISRDEVKNMV YLQMNSLKPE DTAVYFCRA                    39

SEQ ID NO: 308           moltype = AA   length = 39
FEATURE                  Location/Qualifiers
REGION                   1..39
                         note = FR3
source                   1..39
                         mol_type = protein
                         organism = synthetic construct
SEQUENCE: 308
YADFAKGRFT ISRDEAKNMV YLQMNSLRPE DTAVYFCRA                    39

SEQ ID NO: 309           moltype = AA   length = 39
FEATURE                  Location/Qualifiers
REGION                   1..39
                         note = FR3
source                   1..39
                         mol_type = protein
                         organism = synthetic construct
SEQUENCE: 309
YSYFAKGRFT ISRDEAKNMV YLQMNSLRPE DTAVYFCRA                    39

SEQ ID NO: 310           moltype = AA   length = 39
FEATURE                  Location/Qualifiers
REGION                   1..39
                         note = FR3
source                   1..39
                         mol_type = protein
                         organism = synthetic construct
SEQUENCE: 310
YADSAKGRFT ISRDEAKNVV YLQMNSLKPE DTAVYFCRA                    39

SEQ ID NO: 311           moltype = AA   length = 39
FEATURE                  Location/Qualifiers
REGION                   1..39
                         note = FR3
source                   1..39
                         mol_type = protein
                         organism = synthetic construct
SEQUENCE: 311
YEDSAKGRFT ISRDEAKNMV YLQMTGLKPE DTAVYVCRA                    39

SEQ ID NO: 312           moltype = AA   length = 39
FEATURE                  Location/Qualifiers
REGION                   1..39
                         note = FR3
source                   1..39
```

-continued

```
                              mol_type = protein
                              organism = synthetic construct
SEQUENCE: 312
YSHFAKGRFT ISRDEAKNMV YLQMNGLRPE DTAVYFCRA                          39

SEQ ID NO: 313          moltype = AA   length = 39
FEATURE                 Location/Qualifiers
REGION                  1..39
                        note = FR3
source                  1..39
                        mol_type = protein
                        organism = synthetic construct
SEQUENCE: 313
YADSAKGRFT ISRDEAKNMV YLQMNSLKPE DTAVYLCRA                          39

SEQ ID NO: 314          moltype = AA   length = 39
FEATURE                 Location/Qualifiers
REGION                  1..39
                        note = FR3
source                  1..39
                        mol_type = protein
                        organism = synthetic construct
SEQUENCE: 314
YAEFAKGRFT ISRDEPKNMV YLQMNSLKPV DTAVYLCRA                          39

SEQ ID NO: 315          moltype = AA   length = 39
FEATURE                 Location/Qualifiers
REGION                  1..39
                        note = FR3
source                  1..39
                        mol_type = protein
                        organism = synthetic construct
SEQUENCE: 315
YSHFAKGRFT ISRDEAKNMV YLQMNNLRPE DTAVYFCRA                          39

SEQ ID NO: 316          moltype = AA   length = 39
FEATURE                 Location/Qualifiers
REGION                  1..39
                        note = FR3
source                  1..39
                        mol_type = protein
                        organism = synthetic construct
SEQUENCE: 316
YADSAKGRFT ISRDEAKNMV YLQMNSLKPE DAAVYFCRA                          39

SEQ ID NO: 317          moltype = AA   length = 39
FEATURE                 Location/Qualifiers
REGION                  1..39
                        note = FR3
source                  1..39
                        mol_type = protein
                        organism = synthetic construct
SEQUENCE: 317
YAESAKGRFT ISRDESKNMV YLQMNSLKPE DAAVYLCRA                          39

SEQ ID NO: 318          moltype = AA   length = 39
FEATURE                 Location/Qualifiers
REGION                  1..39
                        note = FR3
source                  1..39
                        mol_type = protein
                        organism = synthetic construct
SEQUENCE: 318
YADSAKGRFT ISRDEAKNMV YLQMDSLKPE DTAVYFCRA                          39

SEQ ID NO: 319          moltype = AA   length = 39
FEATURE                 Location/Qualifiers
REGION                  1..39
                        note = FR3
source                  1..39
                        mol_type = protein
                        organism = synthetic construct
SEQUENCE: 319
YADSAKGRFT ISRDEAKNMV YLQMNSLKPG DTAVYFCRA                          39

SEQ ID NO: 320          moltype = AA   length = 11
FEATURE                 Location/Qualifiers
REGION                  1..11
                        note = FR4
```

-continued

```
source                    1..11
                          mol_type = protein
                          organism = synthetic construct
SEQUENCE: 320
WGQGTLVTVS S                                                        11

SEQ ID NO: 321            moltype = AA  length = 11
FEATURE                   Location/Qualifiers
REGION                    1..11
                          note = FR4
source                    1..11
                          mol_type = protein
                          organism = synthetic construct
SEQUENCE: 321
WGQGTQVTVS S                                                        11

SEQ ID NO: 322            moltype = AA  length = 11
FEATURE                   Location/Qualifiers
REGION                    1..11
                          note = FR4
source                    1..11
                          mol_type = protein
                          organism = synthetic construct
SEQUENCE: 322
WGRGTQVTVS S                                                        11

SEQ ID NO: 323            moltype = AA  length = 11
FEATURE                   Location/Qualifiers
REGION                    1..11
                          note = FR4
source                    1..11
                          mol_type = protein
                          organism = synthetic construct
SEQUENCE: 323
WGHGTLVTVS S                                                        11

SEQ ID NO: 324            moltype = AA  length = 11
FEATURE                   Location/Qualifiers
REGION                    1..11
                          note = FR4
source                    1..11
                          mol_type = protein
                          organism = synthetic construct
SEQUENCE: 324
WGRGTLVTVS S                                                        11

SEQ ID NO: 325            moltype = AA  length = 5
FEATURE                   Location/Qualifiers
REGION                    1..5
                          note = Linker sequence
source                    1..5
                          mol_type = protein
                          organism = synthetic construct
SEQUENCE: 325
GGGGS                                                                5

SEQ ID NO: 326            moltype = AA  length = 7
FEATURE                   Location/Qualifiers
REGION                    1..7
                          note = Linker sequence
source                    1..7
                          mol_type = protein
                          organism = synthetic construct
SEQUENCE: 326
SGGSGGS                                                              7

SEQ ID NO: 327            moltype = AA  length = 9
FEATURE                   Location/Qualifiers
REGION                    1..9
                          note = Linker sequence
source                    1..9
                          mol_type = protein
                          organism = synthetic construct
SEQUENCE: 327
GGGGSGGGS                                                            9

SEQ ID NO: 328            moltype = AA  length = 10
FEATURE                   Location/Qualifiers
REGION                    1..10
```

```
                              note = Linker sequence
source                        1..10
                              mol_type = protein
                              organism = synthetic construct
SEQUENCE: 328
GGGGSGGGGS                                                                   10

SEQ ID NO: 329        moltype = AA  length = 15
FEATURE               Location/Qualifiers
REGION                1..15
                      note = Linker sequence
source                1..15
                      mol_type = protein
                      organism = synthetic construct
SEQUENCE: 329
GGGGSGGGGS GGGGS                                                             15

SEQ ID NO: 330        moltype = AA  length = 18
FEATURE               Location/Qualifiers
REGION                1..18
                      note = Linker sequence
source                1..18
                      mol_type = protein
                      organism = synthetic construct
SEQUENCE: 330
GGGGSGGGGS GGGGGGGS                                                          18

SEQ ID NO: 331        moltype = AA  length = 20
FEATURE               Location/Qualifiers
REGION                1..20
                      note = Linker sequence
source                1..20
                      mol_type = protein
                      organism = synthetic construct
SEQUENCE: 331
GGGGSGGGGS GGGGSGGGGS                                                        20

SEQ ID NO: 332        moltype = AA  length = 25
FEATURE               Location/Qualifiers
REGION                1..25
                      note = Linker sequence
source                1..25
                      mol_type = protein
                      organism = synthetic construct
SEQUENCE: 332
GGGGSGGGGS GGGGSGGGGS GGGGS                                                  25

SEQ ID NO: 333        moltype = AA  length = 30
FEATURE               Location/Qualifiers
REGION                1..30
                      note = Linker sequence
source                1..30
                      mol_type = protein
                      organism = synthetic construct
SEQUENCE: 333
GGGGSGGGGS GGGGSGGGGS GGGGSGGGGS                                             30

SEQ ID NO: 334        moltype = AA  length = 35
FEATURE               Location/Qualifiers
REGION                1..35
                      note = Linker sequence
source                1..35
                      mol_type = protein
                      organism = synthetic construct
SEQUENCE: 334
GGGGSGGGGS GGGGSGGGGS GGGGSGGGGS GGGGS                                       35

SEQ ID NO: 335        moltype = AA  length = 40
FEATURE               Location/Qualifiers
REGION                1..40
                      note = Linker sequence
source                1..40
                      mol_type = protein
                      organism = synthetic construct
SEQUENCE: 335
GGGGSGGGGS GGGGSGGGGS GGGGSGGGGS GGGGSGGGGS                                  40

SEQ ID NO: 336        moltype =   length =
SEQUENCE: 336
```

-continued

```
000

SEQ ID NO: 337          moltype = AA   length = 303
FEATURE                 Location/Qualifiers
REGION                  1..303
                        note = Nanobody Sequence
source                  1..303
                        mol_type = protein
                        organism = synthetic construct
SEQUENCE: 337
EVQLVESGGG LVQPGGSLRL SCVASGDVHK INFLGWYRQA PGKEREKVAH ISIGDQTDYA  60
DSAKGRFTIS RDESKNMVYL QMNSLKPEDT AVYFCRAFSR IYPYDYWGQG TLVTVSSGGG  120
GSGGGGSGGG GSGGGGSGGG GSGGGGSGGG GSEVQLVESG GGLVQPGGSL RLSCVASGDV  180
HKINFLGWYR QAPGKEREKV AHISIGDQTD YADSAKGRFT ISRDESKNMV YLQMNSLKPE  240
DTAVYFCRAF SRIYPYDYWG QGTLVTVSSG AADYKDHDGD YKDHDIDYKD DDDKGAAHHH  300
HHH                                                                303

SEQ ID NO: 338          moltype = AA   length = 418
FEATURE                 Location/Qualifiers
REGION                  1..418
                        note = Nanobody Sequence
source                  1..418
                        mol_type = protein
                        organism = synthetic construct
SEQUENCE: 338
DVQLVESGGG LVQPGGSLRL SCVASGDVHK INFLGWYRQA PGKEREKVAH ISIGDQTDYA  60
DSAKGRFTIS RDESKNMVYL QMNSLKPEDT AVYFCRAFSR IYPYDYWGQG TLVTVSSGGG  120
GSGGGGSGGG GSGGGGSGGG GSGGGGSGGG GSEVQLVESG GGLVQAGGSL RLSCAASGIT  180
SKINDMGWYR QTPGNYREWV ASITATGTTN YRDSVKGRFT ISRDNAKSTV YLQMNSLKPE  240
DTTVYYCNTF PPISNFWGQG TLVTVSSGGG GSGGGGSGGG GSGGGGSGGG GSGGGGSGGG  300
GSEVQLVESG GGLVQPGNSL RLSCAASGFT FSSFGMSWVR QAPGKGLEWV SSISGSGSDT  360
LYADSVKGRF TISRDNAKTT LYLQMNSLRP EDTAVYYCTI GGSLSRSSQG TLVTVSSA    418

SEQ ID NO: 339          moltype = AA   length = 578
FEATURE                 Location/Qualifiers
REGION                  1..578
                        note = Nanobody Sequence
source                  1..578
                        mol_type = protein
                        organism = synthetic construct
SEQUENCE: 339
DVQLVESGGG LVQPGGSLRL SCVASGDVHK INFLGWYRQA PGKEREKVAH ISIGDQTDYA  60
DSAKGRFTIS RDESKNMVYL QMNSLKPEDT AVYFCRAFSR IYPYDYWGQG TLVTVSSGGG  120
GSGGGGSGGG GSGGGGSGGG GSGGGGSGGG GSEVQLVESG GGLVQAGGSL RLSCAASGIT  180
SKINDMGWYR QTPGNYREWV ASITATGTTN YRDSVKGRFT ISRDNAKSTV YLQMNSLKPE  240
DTTVYYCNTF PPISNFWGQG TLVTVSSGGG GSGGGGSGGG GSGGGGSGGG GSGGGGSGGG  300
GSEVQLVESG GGLVQAGGPL RLSCAASGRT FSSYVMGWFR QAPGKEREFV AAIYWSNGKT  360
QYTDSVKGRF TISGDNAKNT VYLQMNSLNP EDTAVYYCVA DKDETGFRTL PIAYDYWGQG  420
TLVTVSSGGG GSGGGGSGGG GSGGGGSGGG GSGGGGSGGG GSEVQLVESG GGLVQPGNSL  480
RLSCAASGFT FSSFGMSWVR QAPGKGLEWV SSISGSGSDT LYADSVKGRF TISRDNAKTT  540
LYLQMNSLRP EDTAVYYCTI GGSLSRSSQG TLVTVSSA                          578

SEQ ID NO: 340          moltype = AA   length = 578
FEATURE                 Location/Qualifiers
REGION                  1..578
                        note = Nanobody Sequence
source                  1..578
                        mol_type = protein
                        organism = synthetic construct
SEQUENCE: 340
DVQLVESGGG LVQPGGSLRL SCVASGDVHK INFLGWYRQA PGKEREKVAH ISIGDQTDYA  60
DSAKGRFTIS RDESKNMVYL QMNSLKPEDT AVYFCRAFSR IYPYDYWGQG TLVTVSSGGG  120
GSGGGGSGGG GSGGGGSGGG GSGGGGSGGG GSEVQLVESG GGLVQAGGSL RLSCAASGIT  180
SKINDMGWYR QTPGNYREWV ASITATGTTN YRDSVKGRFT ISRDNAKSTV YLQMNSLKPE  240
DTTVYYCNTF PPISNFWGQG TLVTVSSGGG GSGGGGSGGG GSGGGGSGGG GSGGGGSGGG  300
GSEVQLVESG GGLVQPGNSL RLSCAASGFT FSSFGMSWVR QAPGKGLEWV SSISGSGSDT  360
LYADSVKGRF TISRDNAKTT LYLQMNSLRP EDTAVYYCTI GGSLSRSSQG TLVTVSSGGG  420
GSGGGGSGGG GSGGGGSGGG GSGGGGSGGG GSEVQLVESG GGLVQAGGPL RLSCAASGRT  480
FSSYVMGWFR QAPGKEREFV AAIYWSNGKT QYTDSVKGRF TISGDNAKNT VYLQMNSLNP  540
EDTAVYYCVA DKDETGFRTL PIAYDYWGQG TLVTVSSA                          578

SEQ ID NO: 341          moltype = AA   length = 578
FEATURE                 Location/Qualifiers
REGION                  1..578
                        note = Nanobody Sequence
source                  1..578
                        mol_type = protein
                        organism = synthetic construct
SEQUENCE: 341
```

-continued

```
DVQLVESGGG LVQPGGSLRL SCVASGDVHK INFLGWYRQA PGKEREKVAH ISIGDQTDYA    60
DSAKGRFTIS RDESKNMVYL QMNSLKPEDT AVYFCRAFSR IYPYDYWGQG TLVTVSSGGG   120
GSGGGGSGGG GSGGGGSGGG GSGGGGSGGG GSEVQLVESG GGLVQAGGPL RLSCAASGRT   180
FSSYVMGWFR QAPGKEREFV AAIYWSNGKT QYTDSVKGRF TISGDNAKNT VYLQMNSLNP   240
EDTAVYYCVA DKDETGFRTL PIAYDYWGQG TLVTVSSGGG GSGGGGSGGG GSGGGGSGGG   300
GSGGGGSGGG GSEVQLVESG GGLVQAGGSL RLSCAASGIT SKINDMGWYR QTPGNYREWV   360
ASITATGTTN YRDSVKGRFT ISRDNAKSTV YLQMNSLKPE DTTVYYCNTF PPISNFWGQG   420
TLVTVSSGGG GSGGGGSGGG GSGGGGSGGG GSGGGGSGGG GSEVQLVESG GGLVQPGNSL   480
RLSCAASGFT FSSFGMSWVR QAPGKGLEWV SSISGSGSDT LYADSVKGRF TISRDNAKTT   540
LYLQMNSLRP EDTAVYYCTI GGSLSRSSQG TLVTVSSA                          578

SEQ ID NO: 342         moltype = AA   length = 578
FEATURE                Location/Qualifiers
REGION                 1..578
                       note = Nanobody Sequence
source                 1..578
                       mol_type = protein
                       organism = synthetic construct
SEQUENCE: 342
DVQLVESGGG LVQPGGSLRL SCVASGDVHK INFLGWYRQA PGKEREKVAH ISIGDQTDYA    60
DSAKGRFTIS RDESKNMVYL QMNSLKPEDT AVYFCRAFSR IYPYDYWGQG TLVTVSSGGG   120
GSGGGGSGGG GSGGGGSGGG GSGGGGSGGG GSEVQLVESG GGLVQAGGPL RLSCAASGRT   180
FSSYVMGWFR QAPGKEREFV AAIYWSNGKT QYTDSVKGRF TISGDNAKNT VYLQMNSLNP   240
EDTAVYYCVA DKDETGFRTL PIAYDYWGQG TLVTVSSGGG GSGGGGSGGG GSGGGGSGGG   300
GSGGGGSGGG GSEVQLVESG GGLVQPGNSL RLSCAASGFT FSSFGMSWVR QAPGKGLEWV   360
SSISGSGSDT LYADSVKGRF TISRDNAKTT LYLQMNSLRP EDTAVYYCTI GGSLSRSSQG   420
TLVTVSSGGG GSGGGGSGGG GSGGGGSGGG GSGGGGSGGG GSEVQLVESG GGLVQAGGSL   480
RLSCAASGIT SKINDMGWYR QTPGNYREWV ASITATGTTN YRDSVKGRFT ISRDNAKSTV   540
YLQMNSLKPE DTTVYYCNTF PPISNFWGQG TLVTVSSA                          578

SEQ ID NO: 343         moltype = AA   length = 107
FEATURE                Location/Qualifiers
source                 1..107
                       mol_type = protein
                       organism = Homo sapiens
SEQUENCE: 343
IQVEQSPPDL ILQEGANSTL RCNFSDSVNN LQWFHQNPWG QLINLFYIPS GTKQNGRLSA    60
TTVATERYSL LYISSSQTTD SGVYFCAALI QGAQKLVFGQ GTRLTIN                107

SEQ ID NO: 344         moltype = AA   length = 110
FEATURE                Location/Qualifiers
source                 1..110
                       mol_type = protein
                       organism = Homo sapiens
SEQUENCE: 344
NAGVTQTPKF RILKIGQSMT LQCTQDMNHN YMYWYRQDPG MGLKLIYYSV GAGITDKGEV    60
PNGYNVSRST TEDFPLRLEL AAPSQTSVYF CASTYHGTGY FGEGSWLTVV              110

SEQ ID NO: 345         moltype = AA   length = 110
FEATURE                Location/Qualifiers
source                 1..110
                       mol_type = protein
                       organism = Homo sapiens
SEQUENCE: 345
GDAKTTQPNS MESNEEEPVH LPCNHSTISG TDYIHWYRQL PSQGPEYVIH GLTSNVNNRM    60
ASLAIAEDRK SSTLILHRAT LRDAAVYYCT VYGGATNKLI FGTGTLLAVQ              110

SEQ ID NO: 346         moltype = AA   length = 114
FEATURE                Location/Qualifiers
source                 1..114
                       mol_type = protein
                       organism = Homo sapiens
SEQUENCE: 346
VVSQHPSWVI AKSGTSVKIE CRSLDFQATT MFWYRQFPKQ SLMLMATSNE GSKATYEQGV    60
EKDKFLINHA SLTLSTLTVT SAHPEDSSFY ICSARGGSYN SPLHFGNGTR LTVT         114

SEQ ID NO: 347         moltype = AA   length = 96
FEATURE                Location/Qualifiers
source                 1..96
                       mol_type = protein
                       organism = Macaca fascicularis
SEQUENCE: 347
PYIQNPDPAV YQLRGSKSND TSVCLFTDFD SVMNVSQSKD SDVHITDKTV LDMRSMDFKS    60
NGAVAWSNKS DFACTSAFKD SVIPADTFFP SPESSC                            96

SEQ ID NO: 348         moltype = AA   length = 131
FEATURE                Location/Qualifiers
source                 1..131
                       mol_type = protein
```

```
                        organism = Macaca mulatta
SEQUENCE: 348
EDLKKVFPPK VAVFEPSEAE ISHTQKATLV CLATGFYPDH VELSWWVNGK EVHSGVSTDP    60
QPLKEQPALE DSRYSLSSRL RVSATFWHNP RNHFRCQVQF YGLSEDDEWT EDRDKPITQK   120
ISAEAWGRAD C                                                        131

SEQ ID NO: 349            moltype = AA   length = 107
FEATURE                   Location/Qualifiers
source                    1..107
                          mol_type = protein
                          organism = Macaca mulatta
SEQUENCE: 349
QQIMQIPQYQ HVQEGEDFTT YCNSSTTLSN IQWYKQRPGG HPVFLIMLVK SGEVKKQKRL    60
IFQFGEAKKN SSLHITATQT TDVGTYFCAT TGVNNLFFGT GTRLTVL                 107

SEQ ID NO: 350            moltype = AA   length = 118
FEATURE                   Location/Qualifiers
source                    1..118
                          mol_type = protein
                          organism = Macaca mulatta
SEQUENCE: 350
AGPVNAGVTQ TPKFQVLKTG QSMTLQCAQD MNHDYMYWYR QDPGMGLRLI HYSVGEGSTE    60
KGEVPDGYNV TRSNTEDFPL RLESAAPSQT SVYFCASSYW TGRSYEQYFG PGTRLTVI    118

SEQ ID NO: 351            moltype = AA   length = 115
FEATURE                   Location/Qualifiers
REGION                    1..115
                          note = Nanobody Sequence
source                    1..115
                          mol_type = protein
                          organism = synthetic construct
SEQUENCE: 351
EVQLLESGGG LVQPGGSLRL SCAASGFTFR SFGMSWVRQA PGKGPEWVSS ISGSGSDTLY    60
ADSVKGRFTI SRDNSKNTLY LQMNSLRPED TAVYYCTIGG SLSRSSQGTL VTVSS        115

SEQ ID NO: 352            moltype = AA   length = 116
FEATURE                   Location/Qualifiers
REGION                    1..116
                          note = Nanobody Sequence
source                    1..116
                          mol_type = protein
                          organism = synthetic construct
SEQUENCE: 352
EVQLVESGGG VVQPGNSLRL SCAASGFTFS SFGMSWVRQA PGKGLEWVSS ISGSGSDTLY    60
ADSVKGRFTI SRDNAKTTLY LQMNSLRPED TATYYCTIGG SLSRSSQGTL VTVSSA       116

SEQ ID NO: 353            moltype = AA   length = 116
FEATURE                   Location/Qualifiers
REGION                    1..116
                          note = Nanobody Sequence
source                    1..116
                          mol_type = protein
                          organism = synthetic construct
SEQUENCE: 353
EVQLVESGGG VVQPGGSLRL SCAASGFTFR SFGMSWVRQA PGKGPEWVSS ISGSGSDTLY    60
ADSVKGRFTI SRDNSKNTLY LQMNSLRPED TATYYCTIGG SLSRSSQGTL VTVSSA       116

SEQ ID NO: 354            moltype = AA   length = 115
FEATURE                   Location/Qualifiers
REGION                    1..115
                          note = Nanobody Sequence
source                    1..115
                          mol_type = protein
                          organism = synthetic construct
SEQUENCE: 354
EVQLVESGGG LVQPGNSLRL SCAASGFTFS SFGMSWVRQA PGKGLEWVSS ISGSGSDTLY    60
ADSVKGRFTI SRDNAKTTLY LQMNSLRPED TAVYYCTIGG SLSRSSQGTL VTVSS        115

SEQ ID NO: 355            moltype = AA   length = 116
FEATURE                   Location/Qualifiers
REGION                    1..116
                          note = Nanobody Sequence
source                    1..116
                          mol_type = protein
                          organism = synthetic construct
SEQUENCE: 355
EVQLVESGGG LVQPGNSLRL SCAASGFTFS SFGMSWVRQA PGKGLEWVSS ISGSGSDTLY    60
ADSVKGRFTI SRDNAKTTLY LQMNSLRPED TAVYYCTIGG SLSRSSQGTL VKVSSA       116
```

-continued

```
SEQ ID NO: 356          moltype = AA   length = 115
FEATURE                 Location/Qualifiers
REGION                  1..115
                        note = Nanobody Sequence
source                  1..115
                        mol_type = protein
                        organism = synthetic construct
SEQUENCE: 356
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VTVSS       115

SEQ ID NO: 357          moltype = AA   length = 116
FEATURE                 Location/Qualifiers
REGION                  1..116
                        note = Nanobody Sequence
source                  1..116
                        mol_type = protein
                        organism = synthetic construct
SEQUENCE: 357
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VTVSSA      116

SEQ ID NO: 358          moltype = AA   length = 117
FEATURE                 Location/Qualifiers
REGION                  1..117
                        note = Nanobody Sequence
source                  1..117
                        mol_type = protein
                        organism = synthetic construct
SEQUENCE: 358
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VTVSSAA     117

SEQ ID NO: 359          moltype = AA   length = 118
FEATURE                 Location/Qualifiers
REGION                  1..118
                        note = Nanobody Sequence
source                  1..118
                        mol_type = protein
                        organism = synthetic construct
SEQUENCE: 359
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VTVSSAAA    118

SEQ ID NO: 360          moltype = AA   length = 116
FEATURE                 Location/Qualifiers
REGION                  1..116
                        note = Nanobody Sequence
source                  1..116
                        mol_type = protein
                        organism = synthetic construct
SEQUENCE: 360
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VTVSSG      116

SEQ ID NO: 361          moltype = AA   length = 117
FEATURE                 Location/Qualifiers
REGION                  1..117
                        note = Nanobody Sequence
source                  1..117
                        mol_type = protein
                        organism = synthetic construct
SEQUENCE: 361
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VTVSSGG     117

SEQ ID NO: 362          moltype = AA   length = 118
FEATURE                 Location/Qualifiers
REGION                  1..118
                        note = Nanobody Sequence
source                  1..118
                        mol_type = protein
                        organism = synthetic construct
SEQUENCE: 362
EVQLVESGGG VVQPGNSLRL SCAASGFTFS SFGMSWVRQA PGKGLEWVSS ISGSGSDTLY  60
ADSVKGRFTI SRDNAKTTLY LQMNSLRPED TALYYCTIGG SLSRSSQGTL VTVSSGGG    118

SEQ ID NO: 363          moltype = AA   length = 10
FEATURE                 Location/Qualifiers
```

```
REGION                    1..10
                          note = CDR1
source                    1..10
                          mol_type = protein
                          organism = synthetic construct
SEQUENCE: 363
GFTFSSFGMS                                                                 10

SEQ ID NO: 364            moltype = AA  length = 10
FEATURE                   Location/Qualifiers
REGION                    1..10
                          note = CDR1
source                    1..10
                          mol_type = protein
                          organism = synthetic construct
SEQUENCE: 364
GFTFRSFGMS                                                                 10

SEQ ID NO: 365            moltype = AA  length = 10
FEATURE                   Location/Qualifiers
REGION                    1..10
                          note = CDR2
source                    1..10
                          mol_type = protein
                          organism = synthetic construct
SEQUENCE: 365
SISGSGSDTL                                                                 10

SEQ ID NO: 366            moltype = AA  length = 6
FEATURE                   Location/Qualifiers
REGION                    1..6
                          note = CDR3
source                    1..6
                          mol_type = protein
                          organism = synthetic construct
SEQUENCE: 366
GGSLSR                                                                     6

SEQ ID NO: 367            moltype = AA  length = 17
FEATURE                   Location/Qualifiers
REGION                    1..17
                          note = Myc-Tag
source                    1..17
                          mol_type = protein
                          organism = synthetic construct
SEQUENCE: 367
AAAEQKLISE EDLNGAA                                                         17

SEQ ID NO: 368            moltype = AA  length = 10
FEATURE                   Location/Qualifiers
REGION                    1..10
                          note = CDR1
VARIANT                   2
                          note = X may be D, A, S, E or G
VARIANT                   4
                          note = X may be H or Y
VARIANT                   5
                          note = X may be K or L
VARIANT                   6
                          note = X may be I or L
VARIANT                   8
                          note = X may be F, I or V
VARIANT                   10
                          note = X may be G or S
source                    1..10
                          mol_type = protein
                          organism = synthetic construct
SEQUENCE: 368
GXVXXXNXLX                                                                 10

SEQ ID NO: 369            moltype =    length =
SEQUENCE: 369
000

SEQ ID NO: 370            moltype = AA  length = 9
FEATURE                   Location/Qualifiers
REGION                    1..9
                          note = CDR3
VARIANT                   1
```

-continued

```
                        note = X may be F, Y, G, L or K
VARIANT                 4
                        note = X may be I or L
VARIANT                 5
                        note = X may be Y or W
VARIANT                 8
                        note = X may be D, N or S
source                  1..9
                        mol_type = protein
                        organism = synthetic construct
SEQUENCE: 370
XSRXXPYXY                                                                    9

SEQ ID NO: 371          moltype =   length =
SEQUENCE: 371
000

SEQ ID NO: 372          moltype = AA   length = 10
FEATURE                 Location/Qualifiers
REGION                  1..10
                        note = Synthetic
VARIANT                 2
                        note = X may be D, A, S, E or G
VARIANT                 4
                        note = X may be H or Y
VARIANT                 5
                        note = X may be K or L
VARIANT                 6
                        note = X may be I or L
VARIANT                 8
                        note = X may be F, I or V
VARIANT                 10
                        note = X may be G or S
source                  1..10
                        mol_type = protein
                        organism = synthetic construct
SEQUENCE: 372
GXVXXXNXLX                                                                   10

SEQ ID NO: 373          moltype = AA   length = 9
FEATURE                 Location/Qualifiers
REGION                  1..9
                        note = Synthetic
VARIANT                 1
                        note = X may be F, Y, G, L or K
VARIANT                 4
                        note = X may be I or L
VARIANT                 5
                        note = X may be Y or W
VARIANT                 8
                        note = X may be D, N or S
source                  1..9
                        mol_type = protein
                        organism = synthetic construct
SEQUENCE: 373
XSRXXPYXY                                                                    9

SEQ ID NO: 374          moltype = AA   length = 10
FEATURE                 Location/Qualifiers
REGION                  1..10
                        note = Synthetic
VARIANT                 2
                        note = X may be D, A, S, E, or G
VARIANT                 4
                        note = X may be H or Y
VARIANT                 5
                        note = X may be K or L
VARIANT                 6
                        note = X may be I or L
VARIANT                 8
                        note = X may be F, I, or V
VARIANT                 10
                        note = X may be G or S
source                  1..10
                        mol_type = protein
                        organism = synthetic construct
SEQUENCE: 374
GXVXXXNXLX                                                                   10
```

```
SEQ ID NO: 375           moltype =    length =
SEQUENCE: 375
000

SEQ ID NO: 376           moltype = AA   length = 9
FEATURE                  Location/Qualifiers
REGION                   1..9
                         note = Synthetic
VARIANT                  1
                         note = X may be F, Y, G, or L
VARIANT                  4
                         note = X may be I or L
VARIANT                  5
                         note = X may be Y or W
VARIANT                  8
                         note = X may be D, N, or S
source                   1..9
                         mol_type = protein
                         organism = synthetic construct
SEQUENCE: 376
XSRXXPYXY                                                              9

SEQ ID NO: 377           moltype = AA   length = 10
FEATURE                  Location/Qualifiers
REGION                   1..10
                         note = Synthetic
VARIANT                  3
                         note = X may be T, S, or P
VARIANT                  6
                         note = X may be I or S
VARIANT                  7
                         note = X may be N or D
VARIANT                  8
                         note = X may be D, V, or A
source                   1..10
                         mol_type = protein
                         organism = synthetic construct
SEQUENCE: 377
GIXSKXXXMG                                                            10

SEQ ID NO: 378           moltype = AA   length = 9
FEATURE                  Location/Qualifiers
REGION                   1..9
                         note = Synthetic
source                   1..9
                         mol_type = protein
                         organism = synthetic construct
SEQUENCE: 378
SITATGTTN                                                              9

SEQ ID NO: 379           moltype = AA   length = 7
FEATURE                  Location/Qualifiers
REGION                   1..7
                         note = Synthetic
VARIANT                  3
                         note = X may be P or A
source                   1..7
                         mol_type = protein
                         organism = synthetic construct
SEQUENCE: 379
FPXISNF                                                                7

SEQ ID NO: 380           moltype = AA   length = 10
FEATURE                  Location/Qualifiers
REGION                   1..10
                         note = Synthetic
source                   1..10
                         mol_type = protein
                         organism = synthetic construct
SEQUENCE: 380
GRTFSSYVMG                                                            10

SEQ ID NO: 381           moltype = AA   length = 10
FEATURE                  Location/Qualifiers
REGION                   1..10
                         note = Synthetic
VARIANT                  3
                         note = X may be Y or W
VARIANT                  6
```

-continued

```
                          note = X may be N or S
VARIANT                   10
                          note = X may be Q or E
source                    1..10
                          mol_type = protein
                          organism = synthetic construct
SEQUENCE: 381
AIXWSXGKTX                                                        10

SEQ ID NO: 382            moltype = AA  length = 16
FEATURE                   Location/Qualifiers
REGION                    1..16
                          note = Synthetic
VARIANT                   4
                          note = X may be E or R
VARIANT                   5
                          note = X may be T, D, or Y
source                    1..16
                          mol_type = protein
                          organism = synthetic construct
SEQUENCE: 382
DKDXXGFRTL PIAYDY                                                 16
```